United States Patent
Harrison et al.

(10) Patent No.: US 9,850,247 B2
(45) Date of Patent: Dec. 26, 2017

(54) PYRIMIDOPYRIMIDINONES USEFUL AS WEE-1 KINASE INHIBITORS

(71) Applicant: Almac Discovery Limited, Craigavon (GB)

(72) Inventors: Timothy Harrison, Craigavon Armagh (GB); Graham Trevitt, Craigavon Armagh (GB); Peter Robin Hewitt, Craigavon Armagh (GB); Colin Roderick O'Dowd, Craigavon Armagh (GB); Frank Burkamp, Craigavon Armagh (GB); Andrew John Wilkinson, Craigavon Armagh (GB); Steven D. Shepherd, Craigavon Armagh (GB); Hugues Miel, Craigavon Armagh (GB)

(73) Assignee: ALMAC HOUSE, Craigavon (GB)

( * ) Notice: Subject to any disclaimer, the term of this patent is extended or adjusted under 35 U.S.C. 154(b) by 0 days.

(21) Appl. No.: 15/105,869

(22) PCT Filed: Dec. 19, 2014

(86) PCT No.: PCT/GB2014/053793
§ 371 (c)(1),
(2) Date: Jun. 17, 2016

(87) PCT Pub. No.: WO2015/092431
PCT Pub. Date: Jun. 25, 2015

(65) Prior Publication Data
US 2016/0318936 A1    Nov. 3, 2016

(30) Foreign Application Priority Data
Dec. 19, 2013  (GB) .................... 1322602.2

(51) Int. Cl.
| | | |
|---|---|---|
| A01N 43/90 | (2006.01) | |
| A61K 31/519 | (2006.01) | |
| C07D 475/00 | (2006.01) | |
| C07D 487/04 | (2006.01) | |
| C07D 487/14 | (2006.01) | |
| C07D 519/00 | (2006.01) | |

(52) U.S. Cl.
CPC ......... *C07D 487/04* (2013.01); *C07D 475/00* (2013.01); *C07D 487/14* (2013.01); *C07D 519/00* (2013.01)

(58) Field of Classification Search
CPC .................................................. A61K 31/519
USPC ..................................................... 514/262.1
See application file for complete search history.

(56) References Cited

U.S. PATENT DOCUMENTS

| | | |
|---|---|---|
| 2005/0209221 A1 | 9/2005 | Nunes et al. |
| 2007/0254892 A1 | 11/2007 | Sagara et al. |
| 2009/0048277 A1 | 2/2009 | Perreaut et al. |
| 2010/0063024 A1 | 3/2010 | Sakamoto et al. |
| 2011/0135601 A1 | 6/2011 | Bamba |
| 2013/0018045 A1 | 1/2013 | Woods et al. |
| 2013/0102590 A1 | 4/2013 | Mastracchio et al. |

FOREIGN PATENT DOCUMENTS

| | | |
|---|---|---|
| EP | 2 168 966 A1 | 3/2010 |
| EP | 2 213 673 A1 | 8/2010 |
| WO | 2005/090344 A1 | 9/2005 |
| WO | 2007/126122 A1 | 11/2007 |
| WO | 2008/133866 A1 | 11/2008 |
| WO | 2010/067886 A1 | 6/2010 |
| WO | 2010/067888 A1 | 6/2010 |
| WO | 2012085167 A1 | 6/2012 |
| WO | 2012/161812 A1 | 11/2012 |
| WO | 2013/013031 A1 | 1/2013 |
| WO | 2013/059485 A1 | 4/2013 |
| WO | 2013/126656 A1 | 8/2013 |

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
Ashwell et al. (2012) "Checkpoint Kinase and Wee1 Inhibitors as Anticancer Therapeutics," Ch. 10 In; DNA Repair in Cancer Therapy: Molecular Targets and Clinical Applications. Ed.: Kelley. Elsevier Inc. pp. 211-234.
Caretti et al. (Dec. 27, 2012) "WEE1 Kinase Inhibition Enhances the Radiation Response of Diffuse Intrinsic Pontine Gliomas," Mol. Cancer Ther. 12(2)141-150.
Carrassa et al. (Jul. 1, 2012) "Combined inhibition of Chk1 and Wee1: in vitro synergistic effect translates to tumor growth inhibition in vivo," Cell Cycle. 11(13):2507-2517.
Cozzi et al. (Mar. 1, 2012) "Antitumor activity of new pyrazolo[3,4-d]pyrimidine SRC kinase inhibitors in Burkitt lymphoma cell lines and its enhancement by WEE1 inhibition," Cell Cycle. 11(5)1029-1039.

(Continued)

*Primary Examiner* — Jeffrey H Murray
(74) *Attorney, Agent, or Firm* — Brian C. Trinque; Lathrop Gage LLP

(57) ABSTRACT

The present invention relates to compounds that are useful as inhibitors of the activity of Wee-1 kinase. The present invention also relates to pharmaceutical compositions comprising these compounds and to methods of using these compounds in the treatment of cancer and methods of treating cancer.

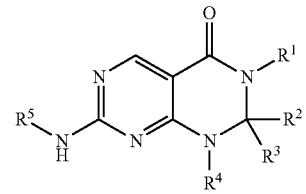

(I)

20 Claims, No Drawings

(56) References Cited

OTHER PUBLICATIONS

Do et al. (Aug. 26, 2013) "Wee1 kinase as a target for cancer therapy," Cell Cycle. 12(19):3159-3164.
Gottlieb et al. (1997) "NMR Chemical Shifts of Common Laboratory Solvents as Trace Impurities," J. Org. Chem. 62:7512-7515.
Guertin et al. (May 22, 2013) "Preclinical evaluation of the WEE1 inhibitor MK-1775 as single-agent anticancer therapy," Mol. Cancer Ther. 12(8):1442-1452.
Hirai et al. (2010) "MK-1775, a small molecule Wee1 inhibitor, enhances anti-tumor efficacy of various DNA-damaging agents, including 5-fluorouracil," Cancer Biol. Ther. 9(7):514-522.
Kreahling et al. (Nov. 14, 2011) "MK1775, a selective Wee1 inhibitor, shows single-agent antitumor activity against sarcoma cells," Mol. Cancer Ther. 11(1):174-182.
Magnussen et al. (Jun. 12, 2012) "High Expression of Wee1 Is Associated with Poor Disease-Free Survival in Malignant Melanoma: Potential for Targeted Therapy," PLoS One. 7(6):e38254. pp. 1-8.
Ohwada et al. (2011) "7-azabicyclo[2.2.1]heptane as a structural motif to block mutagenicity of nitrosamines," Bioorg. Med. Chem. Lett. 19(8):2726-2741.
Palmer et al. (2005) "Structure-activity relationships for 2-anilino-6-phenylpyrido[2,3-d]pyrimidin-7(8H)-ones as inhibitors of the cellular checkpoint kinase Wee1," Bioorg. Med. Chem. Lett. 15:1931-1935.
Russell et al. (Nov. 7, 2012) "Combination therapy targeting the Chk1 and Wee1 kinases shows therapeutic efficacy in neuroblastoma," Cancer Res. 73(2):776-784.
Safina et al. (May 24, 2012) "Discovery of novel PI3-kinase σ specific inhibitors for the treatment of rheumatoid arthritis: taming CYP3A4 time-dependent inhibition," J. Med. Chem. 55(12):5887-5900.
Tibes et al. (Jan. 20, 2012) "RNAi screening of the kinome with cytarabine in leukemias," Blood. 119(12)2863-2872.
Yang et al. (2004) "Knockdown of Chk1, Wee1 and Myt1 by RNA interference abrogates G2 checkpoint and induces apoptosis," Cancer Biol. Ther. 3(3):305-313.
William et al. (2011) "Discovery of the macrocycle 11-(2-pyrrolidin-1-yl-ethoxy)-14,19-dioxa-5,7,26-triaza-tetracyclo (19.3.1.1(2,6).1(8,12)]heptacosa-1(25),2(26),3,5,8,10,12(27),16,21,23-decaene (SB1518), a potent Janus kinase 2/fms-like tyrosine kinase-3 (JAK2/FLT3) inhibitor for the treatment of myelofibrosis and lymphoma," J. Med. Chem. 54 (13):4638-4658.
International Search Report with Written Opinion corresponding to Internatiobal Patent Application No. PCT/GB2014/053793, dated Feb. 12, 2015.

\* cited by examiner

US 9,850,247 B2

PYRIMIDOPYRIMIDINONES USEFUL AS WEE-1 KINASE INHIBITORS

RELATED APPLICATIONS

This application is a 35 U.S.C. §371 filing of International Application No. PCT/GB2014/053793, filed Dec. 19, 2014, which claims priority to Great Britain Patent Application No. 1322602.2, filed Dec. 19, 2013, each of which are incorporated herein by reference in their entireties.

The present invention relates to compounds that are useful as inhibitors of the activity of Wee-1 kinase. The present invention also relates to pharmaceutical compositions comprising these compounds and to methods of using these compounds in the treatment of cancer and methods of treating cancer.

BACKGROUND TO THE INVENTION

Cells are continually challenged on a daily basis, resulting in multiple lesions forming in DNA. The lesions, if not repaired, can lead to mutations or cell death, thus complex signalling networks exist which ensure that lesions are detected and repaired to maintain the integrity of DNA.

Detection of DNA damage initiates a series of events which are key in maintaining the genome. Cell cycle checkpoints are designed to stop the cell cycle and allow repair of the lesion before allowing the cell to continue into mitosis.

Two key checkpoints have been identified, one at the end of the G1 phase and the second at G2, working in tandem to ensure all lesions are identified and repaired. In 50% of human cancers the G1 checkpoint is non-functional due to mutations in the tumour suppressor gene p53. However, the G2 check-point is seldom mutated and often found to be activated in cancer cells. Cancer cells exploit this to confer resistance to treatment modalities, including DNA damaging agents and radiation.

Three kinases have been identified as key regulators of the G2 checkpoint, namely Chk1, Chk2 and Wee-1. Inhibitors for these kinases are currently being evaluated in clinical trials.

Wee-1 is a nuclear tyrosine kinase which negatively regulates entry into mitosis at the G2/M check-point by catalysing a phosphorylation of the cdc2/cyclin B kinase complex. The phosphorylation occurs on the tyrosine-15 residue and leads to the inactivation of the cdc2/cyclin B complex, ultimately preventing mitosis. Wee-1 function is intimately linked to that of Chk1 and Chk2 due to their phosphorylation and inactivation of cdc25 on serine-216, as well as the reported activation of Wee-1 by Chk 1 & 2 (Ashwell et al., 2012, *DNA Repair in Cancer Therapy, DOI:* 10.1016/B978-0-12-384999-1.10010-1).

Wee-1 is downstream of the Chk family and is a crucial component of the checkpoint signalling cascade as it prevents cells from entering mitosis if lesions are detected (Do et al., Cell Cycle 2013 12 (19) 3159-3164.

Commonly administered anti-cancer compounds induce DNA damage, including anti-metabolites, platinum agents, topoisomerase inhibitors and alkylating agents. However, their efficacy is limited due to excessive toxicity, resistance and lack of tumour selectivity. Compounds which work in combination with these agents to prevent DNA repair selectively in tumour cells would be extremely beneficial. As the tumour suppressor gene p53 is commonly mutated in tumour cell lines, the administration of a Wee-1 kinase inhibitor, abrogating the G2 check point, may lead to increased sensitivity to DNA damaging agents. The potential for this has been reported, as silencing of Wee-1 activity was sufficient to sensitize HeLa cells to doxorubicin due to abrogation of G2 arrest. By contrast, in normal breast epithelium due to the fully competent p53 protein, the removal of Wee-1 function had little additional effect compared to doxorubicin alone (Wang et al., 2004, Cancer Biology and Therapy, 3(3), 305-313).

It has been reported that cell lines harbouring mutations in the tumour suppressor gene p53 had increased sensitivity to DNA damaging agents when co-administered with Wee-1 small molecule inhibitors. Synergistic in vitro and in vivo efficacy has been reported when small molecule inhibitors were combined with gemcitabine, 5-fluorouracil, carboplatin, cisplatin (Hirai et al 2010, Cancer Biology & Therapy 9:7, 514-522), cytarabine (Tibes et al., 2012, Blood, 119(12), 2863-2872), Chk-1 inhibitors (Carrasa et al., 2012 Cell Cycle 1:11(13):2507-2517), (Russell et al., 2013 Cancer Res. 15; 73 (2) 776-784) and Src inhibitors (Cozzi et al., 2012, Cell Cycle 11(5), 1-11). Single agent apoptotic efficacy, independent of p53 status, has been reported in sarcoma cell lines and in patient derived sarcoma samples (Kreahling et al., 2012, Mol. Cancer Ther., 11(1), 174-182) and efficacy demonstrated in a panel of cancer cell lines in vivo (Guertin et al., 2013 Mol Cancer Ther, 12 (2) 141-151).

Irradiation is known to increase phosphorylation of the Tyr15 and Thr14 residues of cdc2, leading to a radioresistant phenotype. Inhibition of Wee-1 activity by small molecule inhibitors (Wang et al., 2004, Cancer Biology and Therapy 3(3), 305-313), (Caretti et al., 2013 Mol Cancer Ther. 12 (2) 141-150) lead to a reduction in phosphorylation and radiosensitization, with the effect being more pronounced in p53 mutant cell lines.

It has been reported in melanoma that over-expression of Wee-1 is correlated with poor clinical outcome (Magnusson et al., 2012 PLoS One 7; (6)e38254), indicating it may have a significant role as a biomarker and as a targeted therapy.

Compounds having a kinase inhibitory effect, for example a Wee-1 kinase inhibitory effect, are described in WO 2007/126122, US 2010/0063024, EP 2,213,673, WO 2008/133866, US 2007/0254892, WO 2012/161812, WO 2013/126656, US 2013/0102590, WO 2013/059485 and WO 2013/013031.

WO 2010/067886, WO 2010/067888, US 2011/0135601, EP 2,168,966, WO 2005/090344, US 2009/0048277 and Bioorg. Med. Chem. Lett., 2005, 15, 1931-1935 describe various compounds such as dihydropyrimidopyrimidine and pyridopyrimidinone derivatives having a kinase inhibitory effect. In particular, the compounds of WO 2005/090344 are said to show activity as protein kinase inhibitors, in particular Src family tyrosine kinase inhibitors. The compounds described in Bioorg. Med. Chem. Lett., 2005, 15, p 1931-1935 are said to be 10-100-fold more potent inhibitors of c-Src than Wee-1, and variation of substituents on the 6-phenyl ring does not markedly alter this preference. 5-Alkyl substituted analogues are said to be generally Wee-1 selective, but at the expense of binding potency.

WO 2013/013031 describes pyridazino[4,5-d]pyrimidin-(6H)-one inhibitors of Wee-1 kinase which are said to be useful for inhibiting kinases such as Wee-1 and in methods of treating diseases such as cancer. Compounds of WO 2013/013031 have a nitrogen atom at the '3-position' of the ring relative to the carbonyl group.

US 2013/0018045 describes various tricyclic-sulfonamide compounds which are useful for inhibiting kinases such as Wee-1 and methods of treating diseases such as cancer. Compounds of US 2013/0018045 have a sulfonamide group at the '1-position' on the ring and the atoms at the '3- and '4-positions' form part of a fused aryl or heteroaryl ring ("A").

It is one object of the present invention to overcome at least some of the disadvantages of the prior art or to provide a commercially useful alternative thereto.

It is a further object of the present invention to provide compounds with an improved selectivity towards Wee-1 kinase compared to known compounds or compositions.

It is a further object of the present invention to provide compounds with an improved stability in human microsomes, for example human liver microsomes, compared to known compounds or compositions.

It is a further object of the present invention to provide a compound having an enhanced or similar kinase-inhibitory effect compared to known compounds or compositions.

It is a further object of the present invention to provide compounds having an improved efficacy compared to known compounds or compositions.

It is a further object of the present invention to provide a compound having an improved efficacy and tolerability when administered in combination with other therapies compared to known compounds or compositions.

It is a further object of the present invention to provide a compound having an improved tolerability compared to known compounds or compositions.

SUMMARY OF THE INVENTION

In a first aspect the present invention provides a compound of Formula (I):

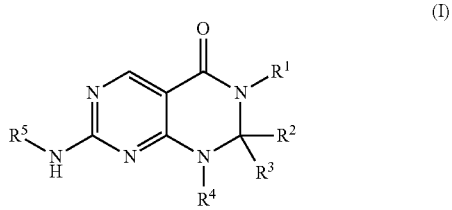

or a pharmaceutically acceptable salt or N-oxide derivative thereof, wherein:
  $R^1$ is an optionally substituted alkyl group, an optionally substituted alkenyl group, an optionally substituted aryl group or an optionally substituted heteroaryl group;
  $R^2$ and $R^3$ are independently selected from the group consisting of a hydrogen atom, a deuterium atom, an optionally substituted alkyl group, an optionally substituted cycloalkyl group, an optionally substituted alkoxy group, an optionally substituted amino group, an optionally substituted aryl group and an optionally substituted heteroaryl group; or $R^2$, $R^3$ and the carbon atom to which they are both attached, as taken together, form an optionally substituted cycloalkyl group or an optionally substituted heterocyclyl group;
  $R^4$ is a hydrogen atom, an optionally substituted alkyl group, an optionally substituted alkenyl group, an optionally substituted aryl group or an optionally substituted heteroaryl group;
  or $R^4$ and $R^2$ or $R^3$ and the ring atoms to which they are attached, as taken together, form an optionally substituted heterocyclyl group; and
  $R^5$ is an optionally substituted alkyl group, an optionally substituted aryl group or an optionally substituted heteroaryl group.

Each aspect or embodiment as defined herein may be combined with any other aspect(s) or embodiment(s) unless clearly indicated to the contrary. In particular any feature indicated as being preferred or advantageous may be combined with any other feature or features indicated as being preferred or advantageous.

In a second aspect the present invention provides a pharmaceutical composition comprising the compound of formula (I), or a pharmaceutically acceptable salt or N-oxide derivative thereof, and at least one pharmaceutically acceptable excipient.

In a third aspect the present invention provides the compound of formula (I), or a pharmaceutically acceptable salt or N-oxide derivative thereof, or a pharmaceutical composition comprising the compound of formula (I) for use in therapy.

In a fourth aspect the present invention provides the compound of formula (I) for use as a medicament.

In a fifth aspect the present invention provides the compound of formula (I) for use in treating or preventing cancer.

In a sixth aspect the present invention provides the use of the compound of formula (I) for the manufacture of a medicament for treating or preventing cancer.

In an seventh aspect the present invention provides a method of treating or preventing cancer in a human or animal patient comprising administering to a patient in need thereof an effective amount of the compound of formula (I) or a pharmaceutical composition comprising the compound of formula (I).

Other preferred embodiments of the compounds according to the invention appear throughout the specification and in particular in the examples. Particularly preferred are those named compounds having greater activity as tested. Compounds having higher activity are more preferred over those having lower activity.

The present inventors have surprisingly found that the compounds of the present invention, which contain an sp3 hybridised carbon atom in the carbonyl-containing fused ring, show an improved or similar kinase-inhibitory effect compared to known compounds or compositions. In particular, the compounds of the present invention preferably show an improved or similar Wee-1 kinase-inhibitory effect compared to known compounds or compositions. This is surprising because known compounds said to show high Wee-1 kinase inhibition typically comprise a planar ring system with one or more $sp^2$ hybridised carbon atoms and one or more nitrogen atoms, whereas the compounds of the present invention comprise an $sp^3$ hybridised carbon atom in which at least one of the substituents on the sp3 carbon is projected out of plane of the ring.

The present inventors have also surprisingly found that compounds of the present invention may show an improved or comparable selectivity towards Wee-1 kinase compared to compounds of the prior art. Preferably, in particular, the compounds of the invention are selective over members of the Src family of kinases, for example LCK (Lymphocyte specific protein tyrosine kinase) and c-Src.

The present inventors have surprisingly found that compounds as described herein may have superior physicochemical properties compared with those known in the prior art. For example, kinetic solubility of examples shown below is higher than the corresponding example claimed in WO 2013/126656.

Compounds of the present invention may also have superior metabolic stability compared with those known in the prior art. For example, the intrinsic clearance from human microsomes of examples shown below is lower than that of the corresponding compounds claimed in WO 2013/126656 and WO 2013/059485.

The present inventors have also surprisingly found that the compounds of the present invention may also show reduced or comparable hERG inhibition (see examples), improved or comparable human liver microsome stability and reduced or comparable CVS toxicity compared to the kinase inhibitors of the prior art.

As discussed above, without wishing to be bound by theory it is thought that the compounds of the present invention tend to show the advantageous effects discussed above due, at least in part, to the presence of the $sp^3$ hybridised carbon atom as shown in formula (I), that is, the carbon to which $R^2$ and $R^3$ are attached.

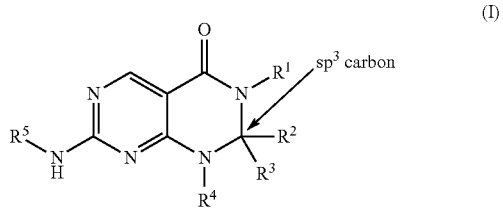

Further factors which result in the advantageous effects discussed above, include the structural relationship between the afore-mentioned $sp^3$ hybridised carbon atom at the '3-position', the carbonyl (C=O) group, the N—$R^1$ group at the '2-position' and the N—$R^4$ group at the '4-position'.

DETAILED DESCRIPTION OF THE INVENTION

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition.

As used in the specification and the appended claims, unless specified to the contrary, the following terms have the meaning indicated:

The term "alkyl group" (alone or in combination with another term(s)) means a straight- or branched-chain saturated hydrocarbyl substituent typically containing 1 to 15 carbon atoms, such as 1 to 10, 1 to 8, 1 to 6, or 1 to 4 carbon atoms. A "$C_n$ alkyl" group refers to an aliphatic group containing n carbon atoms. For example, a $C_1$-$C_{10}$ alkyl group contains 1, 2, 3, 4, 5, 6, 7, 8, 9 or 10 carbon atoms. Attachment to the alkyl group occurs through a carbon atom. Examples of such substituents include methyl, ethyl, n-propyl, isopropyl, n-butyl, isobutyl, sec-butyl, tert-butyl, pentyl (branched or unbranched), hexyl (branched or unbranched), heptyl (branched or unbranched), octyl (branched or unbranched), nonyl (branched or unbranched), and decyl (branched or unbranched).

The term "alkenyl group" (alone or in combination with another term(s)) means a straight- or branched-chain hydrocarbon substituent containing one or more double bonds and typically 2 to 15 carbon atoms; such as 2 to 10, 2 to 8, 2 to 6 or 2 to 4 carbon atoms. Examples of such substituents include ethenyl (vinyl), 1-propenyl, 3-propenyl, 1,4-pentadienyl, 1,4-butadienyl, 1-butenyl, 2-butenyl, 3-butenyl, pentenyl and hexenyl.

The term "alkynyl group" (alone or in combination with another term(s)) means a straight- or branched-chain hydrocarbon substituent containing one or more triple bonds and typically 2 to 15 carbon atoms; such as 2 to 10, 2 to 8, 2 to 6 or 2 to 4 carbon atoms. Examples of such substituents include ethynyl, 1-propynyl, 3-propynyl, 1-butynyl, 3-butynyl and 4-butynyl.

The term "carbocyclyl group" (alone or in combination with another term(s)) means a saturated cyclic (i.e. "cycloalkyl"), partially saturated cyclic (i.e. "cycloalkenyl"), or completely unsaturated (i.e. "aryl") hydrocarbon substituent containing from 3 to 14 carbon ring atoms ("ring atoms" are the atoms bound together to form the ring or rings of a cyclic substituent). A carbocyclyl may be a single-ring (monocyclic) or polycyclic ring structure.

A carbocyclyl may be a single ring structure, which typically contains 3 to 8 ring atoms, more typically 3 to 7 ring atoms, and more typically 5 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl. A carbocyclyl may alternatively be polycyclic (i.e., may contain more than one ring). Examples of polycyclic carbocyclyls include bridged, fused, and spirocyclic carbocyclyls. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl. In a fused-ring carbocyclyl system, two or more rings may be fused together, such that two rings share one common bond. Examples of two- or three-fused ring carbocyclyls include naphthalenyl, tetrahydronaphthalenyl (tetralinyl), indenyl, indanyl (dihydroindenyl), anthracenyl, phenanthrenyl, and decalinyl.

The term "cycloalkyl group" (alone or in combination with another term(s)) means a saturated cyclic hydrocarbon substituent containing 3 to 14 carbon ring atoms. A cycloalkyl may be a single carbon ring, which typically contains 3 to 8 carbon ring atoms and more typically 3 to 6 ring atoms. It is understood that attachment to a cycloalkyl group is via a ring atom of the cycloalkyl group. Examples of single-ring cycloalkyls include cyclopropyl, cyclobutyl, cyclopentyl, and cyclohexyl. A cycloalkyl may alternatively be polycyclic or contain more than one ring. Examples of polycyclic cycloalkyls include bridged, fused, and spirocyclic carbocyclyls.

The term "aryl group" (alone or in combination with another term(s)) means an aromatic carbocyclyl containing from 6 to 14 carbon ring atoms, or 3 to 8, 3 to 6 or 5 to 6 carbon ring atoms. An aryl may be monocyclic or polycyclic (i.e., may contain more than one ring). In the case of polycyclic aromatic rings, only one ring in the polycyclic system is required to be unsaturated while the remaining ring(s) may be saturated, partially saturated or unsaturated. Attachment to the aryl group occurs through a carbon atom contained in the ring. Examples of aryl groups include phenyl, naphthyl, acridinyl, indenyl, indanyl, and tetrahydronapthyl.

The term "heterocyclyl group" (alone or in combination with another term(s)) means a saturated (i.e. "heterocycloalkyl"), partially saturated (i.e. "heterocycloalkenyl"), or completely unsaturated (i.e. "heteroaryl") ring structure containing a total of 3 to 14 ring atoms, wherein at least one of the ring atoms is a heteroatom (i.e. oxygen, nitrogen, or sulfur), with the remaining ring atoms being carbon atoms.

A heterocyclyl group may, for example, contain one, two, three, four or five heteroatoms. Attachment to the heterocyclyl group may occur either through a carbon atom and/or one or more heteroatoms that are contained in the ring. A heterocyclyl may be a single-ring (monocyclic) or polycyclic ring structure.

A heterocyclyl group may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, triazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl (furazanyl) or 1,3,4-oxadiazolyl), oxatriazolyl (including 1,2,3,4-oxatriazolyl or 1,2,3,5-oxatriazolyl), dioxazolyl (including 1.2.3-dioxazolyl, 1,2,4-dioxazolyl, 1,3,2-dioxazolyl- or 1,3,4-dioxazolyl), oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl) or pyrazinyl (1,4-diazinyl)), piperazinyl, triazinyl (including 1,3,5-triazinyl, 1.2.4-triazinyl and 1,2,3-triazinyl)), oxazinyl (including 1,2-oxazinyl, 1,3-oxazinyl or 1,4-oxazinyl)), oxathiazinyl (including 1,2,3-oxathiazinyl, 1,2,4-oxathiazinyl, 1,2,5-oxathiazinyl or 1,2,6-oxathiazinyl)), oxadiazinyl (including 1,2,3-oxadiazinyl, 1,2,4-oxadiazinyl, 1,4,2-oxadiazinyl or 1,3,5-oxadiazinyl)), morpholinyl, azepinyl, oxepinyl, thiepinyl, and diazepinyl.

A heterocyclyl group may alternatively be polycyclic (i.e., may contain more than one ring). Examples of polycyclic heterocyclyl groups include bridged, fused, and spirocyclic heterocyclyl groups. In a spirocyclic heterocyclyl group, one atom is common to two different rings. In a bridged heterocyclyl group, the rings share at least two common non-adjacent atoms. In a fused-ring heterocyclyl group, two or more rings may be fused together, such that two rings share one common bond. Examples of fused ring heterocyclyl groups containing two or three rings include indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyl groups include benzo-fused heterocyclyl groups, such as indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl).

The term "heterocycloalkyl group" (alone or in combination with another term(s)) means a saturated heterocyclyl.

The term "heteroaryl group" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridyl, pyrazyl, pyrimidinyl, pyridazinyl, and 1,3,5-, 1,2,4- or 1,2,3-triazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, benzisoxazolyl, benzoxazolyl, purinyl, and anthranilyl; and 6/6-membered fused rings such as benzopyranyl, quinolinyl, isoquinolinyl, cinnolinyl, quinazolinyl, and benzoxazinyl.

The term "nitrogen-containing heterocyclyl group" refers to a monocyclic or bicyclic heterocyclyl group containing at least one nitrogen atom, in which each ring comprises from 3 to 7 ring atoms and optionally contains, in addition to the nitrogen atom, zero or one or two or more, the same or different hetero atoms, but preferably zero or one hetero atom selected from the group consisting of an oxygen atom, a nitrogen atom and a sulfur atom; and the heterocyclyl group may be saturated (i.e. "heterocycloalkyl"), partially saturated (i.e. "heterocycloalkenyl"), or completely unsaturated (i.e. "heteroaryl"). The bicyclic heterocyclyl group may have a spiro structure of which the two rings share one and the same ring atom, or may have a bicyclo structure of which the rings share two or more ring atoms. Examples of the nitrogen-containing heterocyclyl group include, for example, a pyrrolyl group, an imidazolyl group, a pyrazolyl group, a triazolyl group, an isothiazolyl group, an oxazolyl group, an isoxazolyl group, a triazolyl group, a tetrazolyl group, an oxadiazolyl group, a 1,2,3-thiadiazolyl group, a 1,2,4-thiadiazolyl group, a 1,3,4-thiadiazolyl group, a pyridyl group, a pyrazinyl group, a pyrimidinyl group, a pyridazinyl group, a 1,2,4-triazinyl group, a 1,3,5-triazinyl group, an indolyl group, a benzimidazolyl group, a benzoxazolyl group, a benzisoxazolyl group, a benzothiazolyl group, a benzisothiazolyl group, an indazolyl group, a purinyl group, a quinolyl group, an isoquinolyl group, a phthalazinyl group, a naphthyridinyl group, a quinoxalinyl group, a quinazolinyl group, a cinnolinyl group, a pteridinyl group, a pyrido[3,2-b]pyridyl group, an azetidinyl group, a pyrrolidinyl group, a dihydro-1,2,4-triazolyl group, a dihydro-1,2,4-oxadiazolyl group, a dihydro-1,3,4-oxadiazolyl group, a dihydro-1,2,4-thiadiazolyl group, a dihydro-1,2,3,5-oxathiadiazolyl group, a piperidinyl group, a piperazinyl group, a dihydropyridyl group, a morpholinyl group, a thiomorpholinyl group, a 2,6-diazaspiro[3.5]nonyl group, a 2,7-diazaspiro[3.5]nonyl group, a 2,7-diazaspiro[4.5]decyl group, or a 2,7-diazabicyclo[3.3.0]octyl group, a 3,6-diazabicyclo[3.3.0]octyl group.

The nitrogen-containing heterocyclyl group can be optionally substituted (a "substituted nitrogen-containing heterocyclyl group") with one or more substituents, which can be the same or different.

The term "amino group" refers to the —$NH_2$ group. The amino group can be optionally substituted (a "substituted amino") with one or more substituents, which can be the same or different. Amino group substituents may be, but are not limited to, an alkyl, alkenyl, alkanoyl, aryl and/or a heterocyclyl group.

The term "amido group" refers to the —C(=O)—NR— group. Attachment may be through the carbon and/or nitrogen atom. For example, the amido group may be attached as a substituent via the carbon atom only, in which case the nitrogen atom has two R groups attached (—C(=O)—$NR_2$). The amido group may be attached by the nitrogen atom only, in which case the carbon atom has an R group attached (—NR—C(=O)R.

The term "iminyl" group refers to the —C(=NR)— group. Attachment may be through the carbon atom.

The group "=N—R" refers to a substituent nitrogen-R group connected to another atom by a double bond. For example, an iminyl group (—C(=NR)— group) is a nitrogen atom) connected by a double bond to carbon atom, the nitrogen atom also being connected to an R group by a single bond.

The term "alkoxy group" refers to an —O-alkyl group. The alkoxy group can refer to linear, branched, or cyclic, saturated or unsaturated oxo-hydrocarbon chains, including, for example, methoxyl, ethoxyl, propoxyl, isopropoxyl, butoxyl, t-butoxyl and pentoxyl. The alkoxy group can be optionally substituted (a "substituted alkoxy") with one or more alkoxy group substituents.

The term "hydroxyl" refers to an —OH group.

The term "alkanoyl group" (i.e. acyl group) refers to an organic acid group wherein the —OH of the carboxyl group has been replaced with another substituent. Thus, the alkanoyl group can be represented by the formula RC(=O)—, wherein R includes but is not limited to an alkyl, aralkyl, or aryl group, which in turn may be optionally substituted by one or more substituents. Examples of alkanoyl groups include an acetyl group, a propionyl group, a butyryl group, an isobutyryl group, a valeryl group, an isovaleryl group and a pivaloyl group.

The term "sulfonyl group" refers to a sulfonic acid group wherein the wherein the —OH of the sulfonyl group has been replaced with another substituent. For example, the substituent may be an alkyl group ("an alkylsulfonyl group"). An alkylsulfonyl group can be represented by the formula RS(O)$_2$—, wherein R is an alkyl group, optionally substituted by one or more substituent. Examples of alkylsulfonyl groups include a methylsulfonyl group, an ethylsulfonyl group, a propylsulfonyl group, an isopropylsulfonyl group, a butylsulfonyl group, a sec-butylsulfonyl group, an isobutylsulfonyl group, a tert-butylsulfonyl group, a pentylsulfonyl group, an isopentylsulfonyl group, a hexylsulfonyl group and an isohexylsulfonyl group.

The term "sulfinyl group" refers to the bivalent —S(=O) group.

The term "sulfoximinyl group" refers to a "—S(=O)(=NR)(R)—" group.

The term "thiomorpholine sulfoximinyl" group refers to a group of the formula (h):

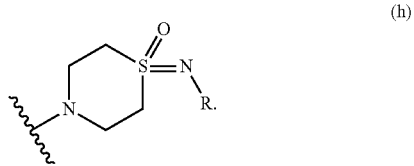

(h)

The term "oxo group" refers to the (=O) group, i.e. a substituent oxygen atom connected to another atom by a double bond. For example, a carbonyl group (—C(=O)— is a carbon atom connected by a double bond to an oxygen atom, i.e. an oxo group attached to a carbon atom.

The term "halo group" refers to a group selected from chlorine, fluorine, bromine and iodine. Preferably, the halo group is selected from chlorine and fluorine.

An alkyl, alkenyl, alkynyl, amino, amido, iminyl, alkoxy, carbocyclyl (including cycloalkyl, cycloalkenyl and aryl), heterocyclyl (including heterocycloalkyl, heterocyloalkenyl and heteroaryl), sulfonyl, sulfinyl, sulfoximinyl and nitrogen-containing heterocyclyl group can be optionally substituted with one or more substituents, which can be the same or different. A substituent can be attached through a carbon atom and/or a heteroatom in the alkyl, alkenyl, alkynyl, amino, amido, iminyl, alkoxy, carbocyclyl (including cycloalkyl, cycloalkenyl and aryl), heterocyclyl (including heterocycloalkyl, heterocyloalkenyl and heteroaryl), sulfonyl, sulfinyl, sulfoximinyl and nitrogen-containing heterocyclyl group. The term "substituent" (or "radical") includes but is not limited to alkyl, substituted alkyl, aralkyl, substituted aralkyl, alkenyl, substituted alkenyl, alkynyl, substituted alkynyl, halo, cyano, amino, amido, alkylamino, arylamino, carbocyclyl, cycloalkyl, substituted cycloalkyl, cycloalkenyl, substituted cycloalkenyl, aryl, substituted aryl, nitro, thio, alkanoyl, hydroxyl, aryloxyl, alkoxyl, alkylthio, arylthio, aralkyloxyl, aralkylthio, carboxyl, alkoxycarbonyl, oxo, alkylsulfonyl and arylsulfonyl.

If a group, for example an alkyl group, is "optionally substituted", it is understood that the group has one or more substituents attached (substituted) or does not have any substituents attached (unsubstituted).

For completeness, it is also noted that certain chemical formulae used herein define delocalized systems. This definition is known in the art as a definition of aromaticity and may indicate the presence of, for example, a mono-, di- or tri-cyclic system that contains (4n+2) electrons where n is an integer. In other words, these systems may display Hückel aromaticity.

In whatever aspect, the compounds of the present invention may possess some aspect of stereochemistry. For example, the compounds may possess chiral centres and/or planes and/or axes of symmetry. As such, the compounds may be provided as single stereoisomers, single diastereomers, mixtures of stereoisomers or as racemic mixtures. Stereoisomers are known in the art to be molecules that have the same molecular formula and sequence of bonded atoms, but which differ in their spatial orientations of their atoms and/or groups.

In addition, the compounds of the present invention may possess tautomerism. Each tautomeric form is intended to fall within the scope of the invention.

In addition, the compounds of the present invention may be provided as a pro-drug. Pro-drugs are transformed, generally in vivo, from one form to the active forms of the drugs described herein. For example, a pro-drug may be formed by protecting the —N—H group to which R$^3$ is attached with a hydrolyzable group that gives —NH on hydrolysis. Alternatively or additionally, any —NH group within the compound may be protected as a physiological hydrolyzable amide.

In addition, it will be understood that the elements described herein may be the common isotope or an isotope other than the common isotope. For example, a hydrogen atom may be $^1$H, $^2$H (deuterium) or $^3$H (tritium).

In addition, the compounds of the present invention may be provided in the form of their pharmaceutically acceptable salts or as co-crystals. For example, the compounds may be provided having protonated amine groups.

The term "pharmaceutically acceptable salt" refers to ionic compounds formed by the addition of an acid to a base. The term refers to such salts that are considered in the art as being suitable for use in contact with a patient, for example in vivo and pharmaceutically acceptable salts are generally chosen for their non-toxic, non-irritant characteristics.

The term "co-crystal" refers to a multi-component molecular crystal, which may comprise non-ionic interactions.

Pharmaceutically acceptable salts and co-crystals may be prepared by ion exchange chromatography or by reacting the free base or acidic form of a compound with stoichiometric amounts or with an excess of the desired salt-forming inorganic or organic acid or base in one or more suitable solvents, or by mixing the compound with another pharmaceutically acceptable compound capable of forming a co-crystal.

Salts known in the art to be generally suitable for use in contact with a patient include salts derived from inorganic and/or organic acids, including the hydrobromide, hydrochloride, sulfate, bisulfate, nitrate, acetate, oxalate, oleate, palmitate, stearate, laurate, benzoate, lactate, phosphate, tosylate, citrate, maleate, fumarate, succinate and tartrate. These may include cations based on the alkali and alkaline earth metals, such as sodium, potassium, calcium and magnesium, as well as ammonium, tetramethylammonium, tetraethylammonium. Further reference is made to the number of literature sources that survey suitable pharmaceutically acceptable salts, for example the Handbook of pharmaceutical salts published by IUPAC.

In addition, the compounds of the present invention may sometimes exist as zwitterions, which are considered as part of the invention.

The present inventors have discovered that the compounds of the present invention are useful in the treatment of medical conditions associated with disordered cell growth, including, but not restricted to, cancer, in particular cancers associated with mutations in the tumour suppressor gene p53.

For example, cancers include cardiac cancers, lung cancers, gastrointestinal cancers, genitourinary tract cancers, liver cancers, bone cancers, nervous system cancers, gynecological cancers, hematologic cancers, skin cancers and adrenal gland cancers.

For example, cancers include adrenal tumors, bile duct, bladder, blood, bone and connective tissue, brain and central nervous system, breast, cervical, colon and rectal (colorectal), endometrial, esophageal, gallbladder, head and neck, Hodgkin's Lymphoma, hypopharangeal, kidney, laryngeal, leukemias, liver, lung, lymphoma, mediastinal tumors, melanoma (malignant melanoma), mesothelioma, multiple myeloma, nasal cavity, nasopharyngeal, neuroendocrine tumors, non-Hodgkin's lymphoma, oral, oesophagus, oropharyngeal, ovarian, pancreas, paranasal sinus, parathyroid, penis, pituitary tumors, prostate, salivary gland, sarcoma, skin, spine, stomach, testicular, thyroid, urethra, uterine, vaginal and vulvar.

The compounds of the present invention are also useful in preparing a medicament that is useful in treating the diseases described above, in particular cancer.

The present invention is further directed to a method of inhibiting Wee-1 activity which comprises administering to a mammal in need thereof a pharmaceutically effective amount of the compound of the present invention.

The compounds of this invention may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The present invention also includes within its scope the use of the compounds of the present invention in combination with a second or further drug in the treatment of cancer. The second or further drug may be a drug that is already known in the art in the treatment of cancer.

The present invention also includes the use of the compounds of the invention in a regime including the step of radiotherapy. The radiotherapy maybe an ordinary method of treatment by x-ray, γ-ray, neutron, α-particle proton or electron beam irradiation. The co-administration of compounds contained in this invention may lead to the potentiation of the radiation therapy, thus classifying them as radio-sensitizers.

In particular, cancers often become resistant to therapy. The development of resistance may be delayed or overcome by the administration of a combination of drugs that includes the compounds of the present invention for example in cancers which are known to be resistant to DNA damaging agents or radiotherapy.

For example, drugs that may be used in combination with the compounds of the present invention may target the same or a similar biological pathway to that targeted by the compounds of the present invention or may act on a different or unrelated pathway.

Depending on the disease to be treated, a variety of combination partners may be co-administered with the compounds of the present invention. The second active ingredient may include, but is not restricted to: alkylating agents, including cyclophosphamide, ifosfamide, thiotepa, melphalan, chloroethylnitrosourea and bendamustine; platinum derivatives, including cisplatin, oxaliplatin, carboplatin and satraplatin; antimitotic agents, including vinca alkaloids (vincristine, vinorelbine and vinblastine), taxanes (paclitaxel, docetaxel), epothilones and inhibitors of mitotic kinases including aurora and polo kinases; topoisomerase inhibitors, including anthracyclines, epipodophyllotoxins, camptothecin and analogues of camptothecin; antimetabolites, including 5-fluorouracil, capecitabine, cytarabine, gemcitabine, 6-mercaptopurine, 6-thioguanine, fludarabine, methotrexate and premetrexed; protein kinase inhibitors, including imatinib, gefitinib, sorafenib, sunitinib, erlotinib, dasatinib, and lapatinib; proteasome inhibitors, including bortezomib; histone deacetylase inhibitors, including valproate and SAHA; antiangiogenic drugs, including bevacizumab; monoclonal antibodies, including trastuzumab, rituximab, alemtuzumab, tositumomab, cetuximab, panitumumab; conjugates of myoclonal antibodies, including Gemtuzumab ozogamicin, Ibritumomab tiuxetan; hormonal therapies, including antiestrogens (tamoxifen, raloxifen, anastrazole, letrozole, examestane) antiandrogens (flutamide, bicalutamide) and luteinising Hormone analogues or antagonists.

With regard to combination therapy the compounds of the present invention may be administered separately, sequentially, simultaneously, concurrently or may be chronologically staggered with one or more standard therapeutics such as any of those mentioned above.

Preferably, the present invention provides a compound of Formula (I):

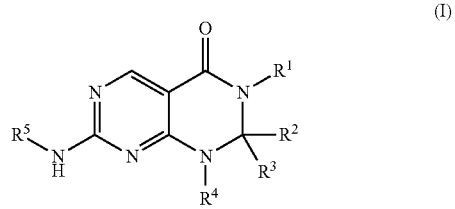

(I)

or a pharmaceutically acceptable salt or N-oxide derivative thereof, wherein:

$R^1$ is an optionally substituted alkyl group, an optionally substituted alkenyl group, an optionally substituted aryl group or an optionally substituted heteroaryl group;

$R^2$ and $R^3$ are independently selected from the group consisting of a hydrogen atom, a deuterium atom, an optionally substituted alkyl group, an optionally substituted cycloalkyl group, an optionally substituted alkoxy group, an optionally substituted amino group, an optionally substituted aryl group and an optionally substituted heteroaryl group; or $R^2$, $R^3$ and the carbon atom to which they are both attached, as taken together, form an optionally substituted cycloalkyl group or an optionally substituted heterocyclyl group;

$R^4$ is a hydrogen atom, an optionally substituted alkyl group, an optionally substituted alkenyl group, an optionally substituted aryl group or an optionally substituted heteroaryl group;

or $R^4$ and $R^2$ or $R^3$ and the ring atoms to which they are attached, as taken together, form an optionally substituted heterocyclyl group; and $R^5$ is an optionally substituted alkyl group, an optionally substituted aryl group or an optionally substituted heteroaryl group.

Preferably, $R^2$ and $R^3$ are independently selected from the group consisting of a hydrogen atom, a deuterium atom, an optionally substituted alkyl group, an optionally substituted cycloalkyl group, an optionally substituted alkoxy group, an optionally substituted amino group, an optionally substituted aryl group and an optionally substituted heteroaryl group; and $R^4$ is a hydrogen atom, an optionally substituted alkyl group, an optionally substituted alkenyl group, an optionally substituted aryl group or an optionally substituted heteroaryl group;

or $R^4$ and $R^2$ or $R^3$ and the ring atoms to which they are attached, as taken together, form an optionally substituted heterocyclyl group.

Alternatively, preferably, $R^2$ and $R^3$ are independently selected from the group consisting of a hydrogen atom, a deuterium atom, an optionally substituted alkyl group, an optionally substituted cycloalkyl group, an optionally substituted alkoxy group, an optionally substituted amino group, an optionally substituted aryl group and an optionally substituted heteroaryl group; and $R^4$ is a hydrogen atom, an optionally substituted alkyl group, an optionally substituted alkenyl group, an optionally substituted aryl group or an optionally substituted heteroaryl group.

Preferably, $R^1$ is an optionally substituted aryl group or optionally substituted heteroaryl group. Preferably, $R^1$ is a substituted aryl or substituted heteroaryl group.

More preferably, $R^1$ is a substituted aryl group. More preferably still, $R^1$ is a substituted six-membered aryl group.

Preferably, $R^1$ is a group represented by the formula (a):

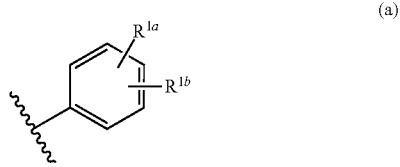

(a)

wherein $R^{1a}$ and $R^{1b}$ are each independently selected from the group consisting of a hydrogen atom, a halo group, a hydroxyl group, a cyano group, an amino group, a $C_1$-$C_6$ alkyl group, a $C_1$-$C_6$ alkoxy group and a $C_1$-$C_6$ alkoxy-$C_1$-$C_6$ alkyl group. Preferably, $R^{1a}$ and $R^{1b}$ are each independently selected from the group consisting of a hydrogen atom and a halo group. More preferably, $R^{1a}$ and $R^{1b}$ are each independently a halo group. More preferably still, $R^{1a}$ and $R^{1b}$ are each independently selected from the group consisting of a chlorine atom and a fluorine atom.

Preferably, $R^1$ is a group represented by the formula (b):

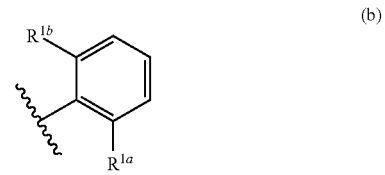

(b)

wherein $R^{1a}$ and $R^{1b}$ are each independently selected from the group consisting of a hydrogen atom, a halo group, a hydroxyl group, a cyano group, an amino group, a $C_1$-$C_6$ alkyl group, a $C_1$-$C_6$ alkoxy group and a $C_1$-$C_6$ alkoxy-$C_1$-$C_6$ alkyl group. Preferably, $R^{1a}$ and $R^{1b}$ are each independently selected from the group consisting of a hydrogen atom and a halo group. More preferably, $R^{1a}$ and $R^{1b}$ are each independently a halo group. More preferably still, $R^{1a}$ and $R^{1b}$ are each independently selected from the group consisting of a chlorine atom and a fluorine atom.

Preferably, in formula (a) and/or (b), $R^{1a}$ is a hydrogen atom, a halo group, a cyano group, a methyl group or a methoxy group; and $R^{1b}$ is a halo group.

Preferably, in formula (a) and/or (b), $R^{1a}$ is a hydrogen atom or a halo group; and $R^{1b}$ is a halo group.

Preferably, in formula (a) and/or (b), $R^{1a}$ is selected from the group consisting of a chlorine atom and a fluorine atom; and $R^{1b}$ is a chlorine atom.

Preferably, $R^1$ is a 2-chlorophenyl group.

Alternatively, preferably, $R^1$ is a 2,6-dichlorophenyl group.

Alternatively, preferably, $R^1$ is a 2-chloro-6-fluorophenyl group.

Alternatively, preferably, $R^1$ is an optionally substituted alkyl group or an optionally substituted alkenyl group. More preferably, $R^1$ is an optionally substituted $C_1$-$C_6$ alkyl group or an optionally substituted $C_1$-$C_6$ alkenyl group. More preferably still, $R^1$ is an optionally substituted $C_1$-$C_3$ alkyl group or an optionally substituted $C_1$-$C_3$ alkenyl group.

Preferably, $R^2$ and $R^3$ are independently selected from the group consisting of a hydrogen atom, a deuterium atom, an optionally substituted alkyl group, an optionally substituted cycloalkyl group, an optionally substituted alkoxy group, an optionally substituted amino group, an optionally substituted aryl group and an optionally substituted heteroaryl group. More preferably, $R^2$ and $R^3$ are independently selected from the group consisting of a hydrogen atom, a deuterium atom, an optionally substituted $C_1$-$C_6$ or $C_1$-$C_3$ alkyl group, an optionally substituted $C_3$-$C_6$ cycloalkyl group, an optionally substituted $C_1$-$C_6$ or $C_1$-$C_3$ alkoxy group, an optionally substituted amino group, an optionally substituted six-membered aryl group and an optionally substituted five- to seven-membered heteroaryl group. More preferably still, $R^2$ and $R^3$ are independently selected from the group consisting of a hydrogen atom, a deuterium atom, an optionally substituted methyl group, an optionally substituted six-membered aryl group and an optionally substituted five- to seven-membered heteroaryl group. More preferably still, $R^2$ and $R^3$ are independently selected from the group consisting of a hydrogen atom, a deuterium atom, a methyl group, an optionally substituted six-membered aryl group and an optionally substituted five- to six-membered heteroaryl group.

Preferably, $R^2$ and $R^3$ is each independently a hydrogen atom.

Alternatively, preferably, $R^2$ and/or $R^3$ are/is a deuterium atom.

Alternatively, preferably, $R^2$ is selected from the group consisting of an optionally substituted alkyl group and an optionally substituted $C_{3-6}$ cycloalkyl group; and $R^3$ is selected from the group consisting of a hydrogen atom, an optionally substituted alkyl group and an optionally substituted $C_{3-6}$ cycloalkyl group. More preferably, $R^2$ is an optionally substituted methyl group; and $R^3$ is selected from the group consisting of a hydrogen atom and a methyl group. More preferably still, $R^2$ is a methyl group; and $R^3$ is a hydrogen atom.

Alternatively, preferably, $R^2$ is selected from the group consisting of an optionally substituted six-membered aryl group and an optionally substituted five- to seven- or five- to six-membered heteroaryl group; and $R^3$ is a hydrogen atom. More preferably, $R^2$ is selected from the group consisting of an optionally substituted pyrrolyl group, an optionally substituted pyrazolyl group and an optionally substituted imidazolyl group; and $R^3$ is a hydrogen atom.

Alternatively, preferably, $R^2$ is selected from the group consisting of an optionally substituted phenyl group and an optionally substituted pyridinyl group; and $R^3$ is a hydrogen atom. More preferably, $R^2$ is selected from the group consisting of a phenyl group and a pyridinyl group; and $R^3$ is a hydrogen atom.

Alternatively, $R^1$ is selected from the group consisting of a $C_{2-3}$ alkenyl group and a methyl group substituted by a cyclopropanyl group; and $R^2$ is selected from the group consisting of an optionally substituted phenyl group and an optionally substituted pyridinyl group; and $R^3$ is a hydrogen atom.

Preferably, $R^4$ is a hydrogen atom, an optionally substituted $C_{1-6}$ alkyl group, an optionally substituted $C_{1-6}$ alkenyl group, an optionally substituted six-membered aryl group or an optionally substituted five- to seven-membered heteroaryl group.

Preferably, $R^4$ is an optionally substituted $C_{1-6}$ alkyl group. More preferably, $R^4$ is an optionally substituted $C_{1-3}$ alkyl group. More preferably still, $R^4$ is a methyl group.

Alternatively, preferably, $R^4$ is an optionally substituted heteroaryl group. Preferably, $R^4$ is an optionally substituted five- to seven- or five- to six-membered heteroaryl group. More preferably, $R^4$ is selected from the group consisting of an optionally substituted pyrazolyl group, an optionally substituted imidazolyl group, an optionally substituted triazolyl group, an optionally substituted oxazolyl group, an optionally substituted triazolyl group and an optionally substituted pyridinyl group.

Alternatively, $R^4$ and $R^2$ or $R^3$ and the ring atoms to which they are attached, as taken together, form an optionally substituted heterocyclyl group. Preferably, $R^4$ and $R^2$ or $R^3$ and the ring atoms to which they are attached, as taken together, form an optionally substituted four- to seven-membered, or five- to seven-membered, or five- to six-membered heterocyclyl group. More preferably still, $R^4$ and $R^2$ or $R^3$ and the ring atoms to which they are attached, as taken together, form an optionally substituted five-membered heterocyclyl group.

Preferably, $R^4$ and $R^2$ or $R^3$ and the ring atoms to which they are attached, as taken together, form an optionally substituted heterocycloalkyl group. More preferably, $R^4$ and $R^2$ or $R^3$ and the ring atoms to which they are attached, as taken together, form an optionally substituted four- to seven-membered, or five- to seven-membered, or five- to six-membered heterocycloalkyl group. More preferably still, $R^4$ and $R^2$ or $R^3$ and the ring atoms to which they are attached, as taken together, form an optionally substituted five-membered heterocycloalkyl group.

Most preferably, the heterocyclyl group is a pyrrolidinyl group, i.e. $R^4$ and $R^2$ or $R^3$ and the ring atoms to which they are attached, as taken together, form an optionally substituted pyrrolidinyl group.

Alternatively, when $R^4$ and $R^2$ or $R^3$ and the ring atoms to which they are attached, as taken together, form an optionally substituted heterocyclyl/heterocycloalyl group, $R^1$ is an optionally substituted alkyl group or an optionally substituted alkenyl group. Preferably, $R^1$ is an optionally substituted alkenyl group, more preferably $R^1$ is an optionally substituted $C_2$-$C_3$ alkenyl group, most preferably $R^1$ is

The heterocyclyl/heterocycloalkyl group may be substituted with one or more substituents selected from the group consisting of a hydroxyl group, a $C_{1-3}$ alkoxy group, an optionally substituted amino group, an oxo group and an optionally substituted $C_{1-3}$ alkyl group. In one embodiment, the heterocyclyl/heterocycloalkyl group is substituted with one or more substituents selected from the group consisting of an oxo group and an optionally substituted $C_{1-3}$ alkyl group.

Preferably, the optionally substituted heterocycloalkyl group is a substituted pyrrolidinyl group.

Preferably, $R^4$ and $R^2$ and the ring atoms to which they are attached, as taken together, form an optionally substituted heterocyclyl/heterocycloalkyl group; and $R^3$ is selected from the group consisting of a hydrogen atom and a $C_{1-3}$ alkyl group. More preferably, $R^4$ and $R^2$ and the ring atoms to which they are attached, as taken together, form an optionally substituted four- to seven-membered, or five- to seven-membered, or five- to six-membered heterocyclyl/heterocycloalkyl group; and $R^3$ is selected from the group consisting of a hydrogen atom and a methyl group. More preferably still, $R^4$ and $R^2$ and the ring atoms to which they are attached, as taken together, form an optionally substituted five-membered heterocyclyl/heterocycloalkyl group; and $R^3$ is a hydrogen atom. Most preferably, the optionally substituted heterocyclyl/heterocycloalkyl group is a substituted pyrrolidinyl group, i.e. $R^4$ and $R^2$ and the ring atoms to which they are attached, as taken together, form a substituted pyrrolidinyl group; and $R^3$ is a hydrogen atom.

Preferably, when $R^4$ and $R^2$ and the ring atoms to which they are attached, as taken together, form an optionally substituted heterocyclyl/heterocycloalyl group, $R^1$ is an optionally substituted alkyl group or an optionally substituted alkenyl group; and $R^3$ is a hydrogen atom.

Preferably, $R^5$ is an optionally substituted $C_1$-$C_6$ or $C_1$-$C_3$ alkyl group, an optionally substituted six-membered aryl group or an optionally substituted five- to seven-membered heteroaryl group.

Preferably, $R^5$ is an optionally substituted aryl group or an optionally substituted heteroaryl group. More preferably, $R^5$ is an optionally substituted six-membered aryl group or an optionally substituted five- to seven-membered heteroaryl group. More preferably still, $R^5$ is an optionally substituted six-membered aryl group or an optionally substituted six-membered heteroaryl group.

More preferably still, $R^5$ is a substituted phenyl group or a substituted pyridinyl group.

Preferably, $R^5$ is a group represented by the formula (c):

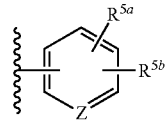

(c)

wherein Z is a nitrogen atom or an optionally substituted methine group;

$R^{5a}$ and $R^{5b}$ are independently selected from the group consisting of a hydrogen atom, a halo group, an optionally substituted $C_1$-$C_6$ alkyl group, an optionally substituted $C_1$-$C_6$ nitrile group, an optionally substituted amino group, an optionally substituted $C_1$-$C_6$ alkoxy group, an optionally substituted sulfanyl group, an optionally substituted sulfonyl group, an optionally substituted sulfoximinyl group and an optionally substituted four- to seven-membered nitrogen-containing heterocyclyl group;

wherein the optionally substituted four- to seven-membered nitrogen-containing heterocyclyl group is optionally substituted with one or more substituents selected from the group consisting of a halo group, an optionally substituted $C_1$-$C_6$ alkyl group, an oxo group, a hydroxyl group, an optionally substituted amino group and a group of =N—$R^{5g}$;

or, in formula (c), $R^{5a}$ and $R^{5b}$ exist on adjacent ring atoms and $R^{5a}$ and $R^{5b}$ and the ring atoms to which they are attached may form, as taken together, a three- to seven-membered cycloalkyl group or three- to seven-membered heterocyclyl group, wherein one or two of the ring atoms constituting the three- to seven-membered heterocyclyl group is optionally independently replaced by an oxygen atom, a nitrogen atom, a group of —N($R^{5c}$)—, a sulfinyl group, a sulfonyl group and a sulfoximinyl group, wherein the three- to seven-membered cycloalkyl or three- to seven-membered heterocyclyl group may be substituted with one or more substituents selected from the group consisting of a halo group and a $C_1$-$C_6$ alkyl group;

or $R^{5a}$ and $R^{5b}$ and the ring atoms to which they are attached may form, as taken together, a spirocyclic group or a bicyclic group formed of a five- to seven-membered aliphatic ring and any other three- to seven-membered aliphatic ring, in which one or two or more methylene groups constituting the spirocyclic group or the bicyclic group may be each independently replaced by an oxygen atom, a sulphur atom, a sulfinyl group, a sulfonyl, a sulfoximinyl group, an oxo group or a group of —N($R^{5d}$)—, and the spirocyclic group or the bicyclic group may be each independently substituted with a substituent selected from the group consisting of a halo group, a hydroxyl group or a $C_1$-$C_6$ alkyl group; wherein $R^{5c}$, $R^{5d}$ and $R^{5g}$ are each independently a hydrogen atom or a $C_1$-$C_6$ alkyl group optionally substituted with a substituent selected from the group consisting of a halo group, a hydroxyl group, a cyano group, an oxo group, a $C_1$-$C_6$ alkyl group, a $C_1$-$C_6$ alkoxy group, an amino group, a substituted amino group and a nitrogen-containing heterocyclyl group.

More preferably, $R^5$ is a group represented by the formula (d):

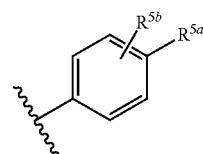

(d)

$R^{5a}$ and $R^{5b}$ are independently selected from the group consisting of a hydrogen atom, a halo group, an optionally substituted $C_1$-$C_6$ alkyl group, an optionally substituted $C_1$-$C_6$ nitrile group, an optionally substituted amino group, an optionally substituted $C_1$-$C_6$ alkoxy group, an optionally substituted sulfanyl group, an optionally substituted sulfonyl group, an optionally substituted sulfoximinyl group and an optionally substituted four- to seven-membered nitrogen-containing heterocyclyl group;

wherein the optionally substituted four- to seven-membered nitrogen-containing heterocyclyl group is optionally substituted with one or more substituents selected from the group consisting of a halo group, an optionally substituted $C_1$-$C_6$ alkyl group, an oxo group, a hydroxyl group, a group of =N—$R^{5g}$ and a group of -Q-N($R^{5e}$)$R^{5e'}$;

$R^{5e}$, $R^{5e'}$ and $R^{5g}$ each independently is a hydrogen atom or a $C_1$-$C_6$ alkyl group, or, $R^{5e}$ and $R^{5e'}$ and the nitrogen atom to which they are attached, as taken together, may form an optionally substituted six-membered heterocyclyl group; and Q is a single bond or a $C_1$-$C_3$ alkyl group.

Preferably, the four- to seven-membered nitrogen-containing heterocyclyl group is a four- to seven-membered nitrogen-containing hetercycloalkyl group.

More preferably, the four- to seven-membered nitrogen-containing heterocyclyl group is selected from the group consisting of an azetidinyl group, a pyrrolidinyl group, a piperidinyl group, a morpholinyl group, a thiomorpholinyl group, a thiomorpholine-S,S-dioxide group, a thiomorpholine-S-Oxo-S-iminyl sulfoximinyl group and a homopiperazinyl group, each of which can be optionally substituted.

Preferably, $R^{5a}$ is a $C_1$-$C_3$ alkoxy group substituted with an amino group, or $R^{5a}$ is a $C_1$-$C_3$ alkyl group substituted by an optionally substituted five- to seven-membered heterocyclyl group, or $R^{5a}$ is a five- to seven-membered nitrogen-containing heterocyclyl group optionally substituted with one or more substituents selected from the group consisting of a $C_1$-$C_3$ alkyl group and a $C_1$-$C_3$ alkyl group substituted with one or more substituents selected from the group consisting of a hydroxyl group, a carboxyl group, an oxo group and an amino group; and $R^{5b}$ is a hydrogen atom, a halo group, a $C_{1-3}$ nitrile group, a $C_{1-3}$ alkoxy group or a $C_1$-$C_3$ alkyl group substituted with a substituent selected from the group consisting of an amino group and a hydroxyl group.

Preferably, $R^{5a}$ is a nitrogen-containing heterocyclyl group optionally substituted with a methyl group; and $R^{5b}$ is a hydrogen atom, a methyl group, a methoxy group or a methyl group substituted by a hydroxyl group. Alternatively, preferably, $R^{5a}$ and/or $R^{5b}$ are independently selected from the group consisting of an optionally substituted sulfanyl group, an optionally substituted sulfonyl group, an optionally substituted sulfoximinyl group and an optionally substituted thiomorpholine sulfoximinyl group.

More preferably, $R^{5a}$ is an optionally substituted sulfoximinyl group.

Preferably, the optionally substituted sulfoximinyl group is a group of the formula (g):

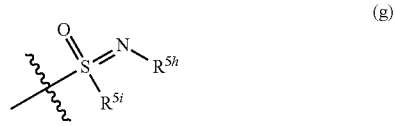

wherein $R^{5h}$ is selected from the group consisting of a hydrogen atom, an optionally substituted $C_1$-$C_6$ or $C_1$-$C_3$ alkyl group, an optionally substituted cyano group, an optionally substituted acyl group, an optionally substituted $C_1$-$C_6$ or $C_1$-$C_3$ alkoxycarbonyl group and an optionally substituted heterocyclyl group;

$R^{5i}$ is selected from the group consisting of an optionally substituted $C_1$-$C_6$ or $C_1$-$C_3$ alkyl group and an optionally substituted heterocyclyl group;

or $R^{5h}$ and $R^{5i}$ and the ring atoms to which they are attached may form, as taken together, a five- to seven-membered heterocyclyl group, wherein the five- to seven-membered heterocyclyl group may be substituted with one or more substituents selected from the group consisting of a hydroxyl group, a $C_1$-$C_6$ or $C_1$-$C_3$ alkyl group, an optionally substituted amino group and an oxo group.

Preferably, $R^{5h}$ and/or $R^{5i}$ is independently a $C_1$-$C_6$ or $C_1$-$C_3$ alkyl group optionally substituted with a group selected from the group consisting of a hydroxyl group and an optionally substituted amino group.

Preferably, $R^{5h}$ is selected from the group consisting of a hydrogen atom, an optionally substituted $C_1$-$C_6$ or $C_1$-$C_3$ alkyl group, an optionally substituted cyano group, an optionally substituted acyl group, an optionally substituted $C_1$-$C_6$ or $C_1$-$C_3$ alkoxycarbonyl group and an optionally substituted heterocyclyl group; and $R^{5i}$ is a methyl group.

Alternatively, preferably, $R^{5i}$ is selected from the group consisting of an optionally substituted $C_1$-$C_6$ or $C_1$-$C_3$ alkyl group and an optionally substituted heterocyclyl group; and $R^{5h}$ is a methyl group.

Alternatively, preferably, $R^5$ is a group represented by the formula (f):

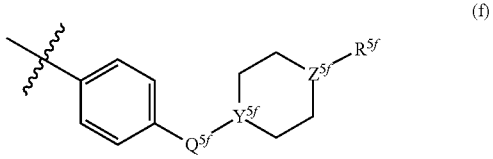

wherein $R^{5f}$ is selected from the group consisting of a hydrogen atom and an optionally substituted $C_1$-$C_6$ alkyl group; $Q^{5f}$ is selected from the group consisting of a single bond and a $C_1$-$C_3$ alkyl group; $Y^{5f}$ is selected from the group consisting of a nitrogen atom and a C—H group (i.e. a carbon atom connected to a hydrogen atom); and $Z^{5f}$ is selected from the group consisting of a nitrogen atom and an oxygen atom. More preferably, $R^{5f}$ is selected from the group consisting of a hydrogen atom and an optionally substituted $C_1$-$C_4$ or $C_1$-$C_3$ alkyl group; $Q^{5f}$ is selected from the group consisting of a single bond and a methylene group (i.e. a —C(H)$_2$— group); $Y^{5f}$ is selected from the group consisting of a nitrogen atom and a C—H group (i.e. a carbon atom connected to a hydrogen atom); and $Z^{5f}$ is selected from the group consisting of a nitrogen atom and an oxygen atom. More preferably still, $R^{5f}$ is selected from the group consisting of a hydrogen atom, a methyl group and a $C_1$-$C_3$ alkyl group optionally substituted with a group selected from the group consisting of a hydroxyl group and a $C_1$-$C_3$ alkyl group; $Q^{5f}$ is selected from the group consisting of a single bond and a methylene group (i.e. a —C(H)$_2$— group); $Y^{5f}$ is selected from the group consisting of a nitrogen atom and a C—H group (i.e. a carbon atom connected to a hydrogen atom); and $Z^{5f}$ is selected from the group consisting of a nitrogen atom and an oxygen atom. Most preferably, $R^{5f}$ is selected from the group consisting of a hydrogen atom, a methyl group and a $C_1$-$C_3$ alkyl group optionally substituted with a group selected from the group consisting of a hydroxyl group and a $C_1$-$C_3$ alkyl group; $Q^{5f}$ is selected from the group consisting of a single bond and a methylene group (i.e. a —C(H)$_2$— group); $Y^{5f}$ is a nitrogen atom; and $Z^{5f}$ is selected from the group consisting of a nitrogen atom and an oxygen atom.

Alternatively, preferably, $R^5$ is a group represented by the formula (e):

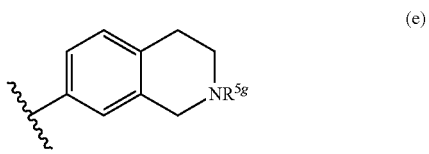

wherein $R^{5g}$ is selected from the group consisting of a hydrogen atom and an optionally substituted $C_1$-$C_3$ alkyl group. More preferably, $R^{5g}$ is selected from the group consisting of a hydrogen atom and a methyl group.

Preferably, in the compound of Formula (I), $R^1$ is a group represented by the formula (a) as defined above; and/or $R^2$ and $R^3$ are independently selected from the group consisting of a hydrogen atom, a deuterium atom, an optionally substituted methyl group, an optionally substituted six-membered aryl group and an optionally substituted five- to seven-membered heteroaryl group; and/or $R^4$ is a hydrogen atom, an optionally substituted $C_{1-6}$ alkyl group, an optionally substituted $C_{1-6}$ alkenyl group, an optionally substituted six-membered aryl group or an optionally substituted five- to seven-membered heteroaryl group; and/or $R^5$ is a group represented by the formula (c) as defined above.

More preferably, $R^1$ is a group represented by the formula (a) as defined above; and/or $R^2$ and $R^3$ are independently selected from the group consisting of a hydrogen atom, a deuterium atom, a methyl group, an optionally substituted six-membered aryl group and an optionally substituted five- to six-membered heteroaryl group; and/or $R^4$ is a hydrogen atom, an optionally substituted $C_{1-6}$ alkyl group, an optionally substituted $C_{1-6}$ alkenyl group, an optionally substituted six-membered aryl group or an optionally substituted five- to seven-membered heteroaryl group; and/or $R^5$ is a group represented by the formula (d) or formula (f) as defined above.

Preferably, $R^1$ is a group represented by the formula (b) as defined above; and/or $R^2$ and $R^3$ are independently selected from the group consisting of a hydrogen atom, a deuterium atom, a methyl group, an optionally substituted six-membered aryl group and an optionally substituted five- to six-membered heteroaryl group; and/or $R^4$ is a hydrogen atom or methyl group; and/or $R^5$ is a group represented by the formula (d) or formula (f) as defined above.

Preferably, $R^1$ is a 2-chlorophenyl group, a 2,6-dichlorophenyl group or a 2-chloro-6-fluorophenyl group and/or $R^2$ is selected from the group consisting of a hydrogen atom, a deuterium atom, a methyl group and a phenyl group; and/or $R^3$ is selected from the group consisting of a hydrogen atom and a deuterium atom; and/or $R^5$ is a group represented by the formula (d) or formula (f) as defined above.

Alternatively, $R^1$ is an optionally substituted $C_1$-$C_3$ alkyl group or an optionally substituted $C_1$-$C_3$ alkenyl group; and/or $R^4$ and $R^2$ and the ring atoms to which they are attached, as taken together, form an optionally substituted four- to seven-membered, or five- to seven-membered, or five- to six-membered heterocyclyl group; and/or $R^3$ is a hydrogen atom; and/or $R^5$ is a group represented by the formula (f) as defined above.

Preferably, the compound of formula (I) is selected from the following:
(1) 3-(2,6-dichlorophenyl)-1-methyl-7-((4-(piperazin-1-yl)phenyl)amino)-2,3-dihydropyrimido[4,5-d]pyrimidin-4(1H)-one;
(2) 3-(2,6-dichlorophenyl)-1-methyl-7-((4-(2-(methylamino)ethoxy)phenyl)amino)-2,3-dihydropyrimido[4,5-d]pyrimidin-4(1H)-one;
(3) 3-(2,6-dichlorophenyl)-7-((3-methoxy-4-(piperazin-1-yl)phenyl)amino)-1-methyl-2,3-dihydropyrimido[4,5-d]pyrimidin-4(1H)-one;
(4) 2-(4-(4-((6-(2,6-dichlorophenyl)-8-methyl-5-oxo-5,6,7,8-tetrahydropyrimido[4,5-d]pyrimidin-2-yl)amino)phenyl)piperazin-1-yl)acetic acid hydrochloride;
(5) 3-(2,6-dichlorophenyl)-1-methyl-7-((3-((methylamino)methyl)-4-morpholinophenyl)amino)-2,3-dihydropyrimido[4,5-d]pyrimidin-4(1H)-one;
(6) 3-(2,6-dichlorophenyl)-1-methyl-7-((3-methyl-4-(piperazin-1-yl)phenyl)amino)-2,3-dihydropyrimido[4,5-d]pyrimidin-4(1H)-one;
(7) 3-(2,6-dichlorophenyl)-7-((3-fluoro-4-(piperazin-1-yl)phenyl)amino)-1-methyl-2,3-dihydropyrimido[4,5-d]pyrimidin-4(1H)-one;
(8) 3-(2,6-dichlorophenyl)-1-(4-methoxybenzyl)-7-((4-(piperazin-1-yl)phenyl)amino)-2,3-dihydropyrimido[4,5-d]pyrimidin-4(1H)-one;
(9) 3-(2,6-dichlorophenyl)-7-((4-(piperazin-1-yl)phenyl)amino)-2,3-dihydropyrimido[4,5-d]pyrimidin-4(1H)-one;
(10) 3-(2,6-dichlorophenyl)-7-((3-(hydroxymethyl)-4-(piperazin-1-yl)phenyl)amino)-1-methyl-2,3-dihydropyrimido[4,5-d]pyrimidin-4(1H)-one;
(11) 3-(2,6-dichlorophenyl)-7-((3-cyano-4-(piperazin-1-yl)phenyl)amino)-1-methyl-2,3-dihydropyrimido[4,5-d]pyrimidin-4(1H)-one;
(12) 3-(2,6-dichlorophenyl)-1-methyl-7-((4-(piperazin-1-ylmethyl)phenyl)amino)-2,3-dihydropyrimido[4,5-d]pyrimidin-4(1H)-one;
(13) 7-((4-(4-(2-aminoacetyl)piperazin-1-yl)phenyl)amino)-3-(2,6-dichlorophenyl)-1-methyl-2,3-dihydropyrimido[4,5-d]pyrimidin-4(1H)-one;
(14) 3-(2,6-dichlorophenyl)-1-methyl-7-((1,2,3,4-tetrahydroisoquinolin-7-yl)amino)-2,3-dihydropyrimido[4,5-d]pyrimidin-4(1H)-one;
(15) 3-(2,6-dichlorophenyl)-2,2-dideutero-1-methyl-7-((4-(piperazin-1-yl)phenyl)amino)-2,3-dihydropyrimido[4,5-d]pyrimidin-4(1H)-one;
(16) (R)-3-(2,6-dichlorophenyl)-1-methyl-7-((4-(3-methylpiperazin-1-yl)phenyl)amino)-2,3-dihydropyrimido[4,5-d]pyrimidin-4(1H)-one;
(17) (S)-3-(2,6-dichlorophenyl)-1-methyl-7-((4-(3-methylpiperazin-1-yl)phenyl)amino)-2,3-dihydropyrimido[4,5-d]pyrimidin-4(1H)-one;
(18) 3-(2,6-dichlorophenyl)-1-methyl-7-((3-methyl-4-(piperidin-4-yl)phenyl)amino)-2,3-dihydropyrimido[4,5-d]pyrimidin-4(1H)-one;
(19) (R)-3-(2,6-dichlorophenyl)-7-((4-(3-(hydroxymethyl)piperazin-1-yl)phenyl)amino)-1-methyl-2,3-dihydropyrimido[4,5-d]pyrimidin-4(1H)-one;
(20) (S)-3-(2,6-dichlorophenyl)-7-((4-(3-(hydroxymethyl)piperazin-1-yl)phenyl)amino)-1-methyl-2,3-dihydropyrimido[4,5-d]pyrimidin-4(1H)-one;
(21) 3-(2,6-dichlorophenyl)-7-((3-(hydroxymethyl)-4-(4-isopropylpiperazin-1-yl)phenyl)amino)-1-methyl-2,3-dihydropyrimido[4,5-d]pyrimidin-4(1H)-one;
(22) 3-(2,6-dichlorophenyl)-1-methyl-7-((2-methyl-1,2,3,4-tetrahydroisoquinolin-7-yl)amino)-2,3-dihydropyrimido[4,5-d]pyrimidin-4(1H)-one;
(23) (rac)-3-(2,6-dichlorophenyl)-1-methyl-2-phenyl-7-((1,2,3,4-tetrahydroisoquinolin-7-yl)amino)-2,3-dihydropyrimido[4,5-d]pyrimidin-4(1H)-one;
(24) 3-(2-chlorophenyl)-1-methyl-7-((4-(piperazin-1-yl)phenyl)amino)-2,3-dihydropyrimido[4,5-d]pyrimidin-4(1H)-one;
(25) 3-(2-chloro-6-fluorophenyl)-1-methyl-7-((4-(piperazin-1-yl)phenyl)amino)-2,3-dihydropyrimido[4,5-d]pyrimidin-4(1H)-one;
(26) 3-(2,6-dichlorophenyl)-1,2-dimethyl-7-((4-(piperazin-1-yl)phenyl)amino)-2,3-dihydropyrimido[4,5-d]pyrimidin-4(1H)-one;
(27) 3-(2,6-dichlorophenyl)-1-methyl-7-((4-(morpholinomethyl)phenyl)amino)-2,3-dihydropyrimido[4,5-d]pyrimidin-4(1H)-one;
(28) 6-(2,6-dichlorophenyl)-2-((4-(piperazin-1-yl)phenyl)amino)-6a,7,8,9-tetrahydropyrimido[5,4-e]pyrrolo[1,2-a]pyrimidin-5(6H)-one;
(29) 3-(2,6-dichlorophenyl)-1-methyl-7-((4-((4-methylpiperazin-1-yl)methyl)phenyl)amino)-2,3-dihydropyrimido[4,5-d]pyrimidin-4(1H)-one; and
(30) (rac)-3-(2,6-dichlorophenyl)-1-methyl-7-((4-(S-methylsulfonimidoyl)phenyl)amino)-2,3-dihydropyrimido[4,5-d]pyrimidin-4(1H)-one.

Preferably, there is provided the compound of formula (I), or a pharmaceutically acceptable salt or N-oxide derivative thereof, and at least one pharmaceutically acceptable excipient.

Suitable pharmaceutically acceptable excipients would be known by the person skilled in the art, for example, fats, water, physiological saline, alcohol (e.g., ethanol), glycerol, polyols, aqueous glucose solution, extending agent, disintegrating agent, binder, lubricant, wetting agent, stabilizer, emulsifier, dispersant, preservative, sweetener, colorant, seasoning agent or aromatizer, concentrating agent, diluent, buffer substance, solvent or solubilizing agent, chemical for achieving storage effect, salt for modifying osmotic pressure, coating agent or antioxidant, saccharides such as lactose or glucose; starch of corn, wheat or rice; fatty acids such as stearic acid; inorganic salts such as magnesium metasilicate aluminate or anhydrous calcium phosphate; synthetic polymers such as polyvinylpyrrolidone or polyalkylene glycol; alcohols such as stearyl alcohol or benzyl alcohol; synthetic cellulose derivatives such as methylcellulose, carboxymethylcellulose, ethylcellulose or hydroxypropylmethylcellulose; and other conventionally used additives such as gelatin, talc, plant oil and gum arabic.

Preferably, there is provided a pharmaceutical composition comprising the compound of formula (I), or a pharmaceutically acceptable salt or N-oxide derivative thereof, and at least one pharmaceutically acceptable excipient.

Preferably, there is provided a pharmaceutical composition comprising the compound of formula (I) comprising one or more further pharmaceutically active agents.

Preferably, there is provided the compound of formula (I), or a pharmaceutically acceptable salt or N-oxide derivative thereof, or a pharmaceutical composition comprising the compound of formula (I) for use in therapy.

Preferably, there is provided the compound of formula (I) for use as a medicament.

Preferably, there is provided the compound of formula (I) for use in treating or preventing cancer.

Preferably, there is provided the compound of formula (I), or a pharmaceutically acceptable salt or N-oxide derivative thereof, or a pharmaceutical composition comprising the compound of formula (I) for use as a medicament and/or for use in treating or preventing cancer.

Preferably, there is provided the use of the compound of formula (I) for the manufacture of a medicament for treating or preventing cancer.

Preferably, there is provided a method of treating or preventing cancer in a human or animal patient comprising administering to a patient in need thereof an effective amount of a compound of formula (I) or a pharmaceutical composition comprising formula (I).

Preferably, the compounds of the present invention have an $IC_{50}$ value for Wee-1 kinase of about 1 nM to about 1,000 nM, more preferably from about 1 nM to about 500 nM, or from about 1 nM to about 300 nM, or from about 1 nM to about 100 nM, or from about 1 nM to about 50 nM, or from about 1 nM to about 30 nM, or from about 1 nM to about 15 nM, or from about 1 nM to about 10 nM, most preferably less than 10 nM. A method for determining the $IC_{50}$ value of a compound for Wee-1 kinase is described below (see examples).

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

The foregoing detailed description has been provided by way of explanation and illustration, and is not intended to limit the scope of the appended claims. Many variations in the presently preferred embodiments illustrated herein will be apparent to one of ordinary skill in the art, and remain within the scope of the appended claims and their equivalents.

The following non-limiting examples further illustrate the present invention.

EXAMPLES

The present invention will now be described in relation to several examples.

Examples 1 to 185 were synthesised according to the methods described subsequently. Wee-1 $IC_{50}$ values and other values were determined as described below and are represented in the following table.

TABLE 1

| Ex | STRUCTURE | Wee-1 | HT29 pCDC2 method 2 | HT29 pCDC2 method 3 | Mics - CLint |
|---|---|---|---|---|---|
| 1 | 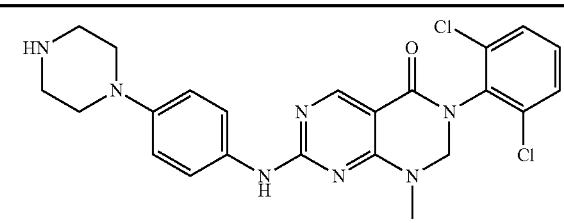 | * |  |  |  |
| 2 | 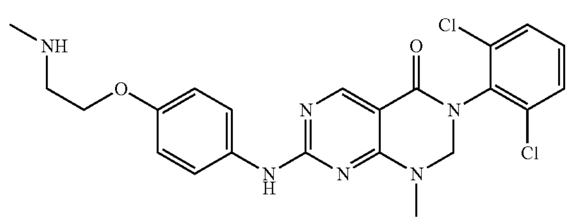 [SMILES: CNCCOc1ccc(Nc2ncc3c(n2)N(C)CN(c2c(Cl)cccc2Cl)C3=O)cc1] | * |  |  | * |
| 3 | 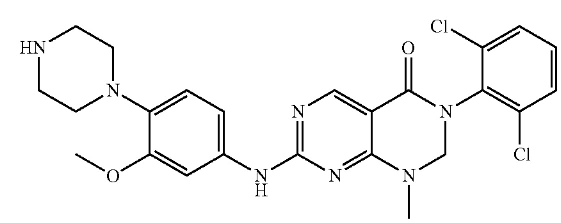 [SMILES: COc1cc(Nc2ncc3c(n2)N(C)CN(c2c(Cl)cccc2Cl)C3=O)ccc1N1CCNCC1] | * |  |  |  |

TABLE 1-continued

| Ex | STRUCTURE | Wee-1 | HT29 pCDC2 method 2 | HT29 pCDC2 method 3 | Mics - CLint |
|---|---|---|---|---|---|
| 4 | 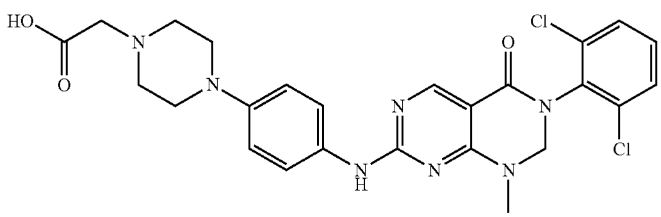 [SMILES: CN1CN(c2c(Cl)cccc2Cl)C(=O)c2cnc(Nc3ccc(N4CCN(CC(=O)O)CC4)cc3)nc21] | ** | * | | *** |
| 5 | 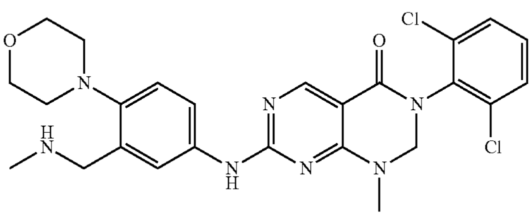 [SMILES: CNCc1cc(Nc2ncc3c(n2)N(C)CN(c2c(Cl)cccc2Cl)C3=O)ccc1N1CCOCC1] | * |  |  | * |
| 6 | 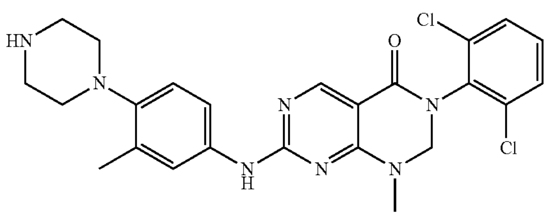 [SMILES: Cc1cc(Nc2ncc3c(n2)N(C)CN(c2c(Cl)cccc2Cl)C3=O)ccc1N1CCNCC1] | * | * |  |  |
| 7 | 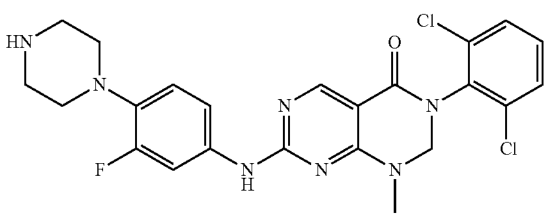 [SMILES: CN1CN(c2c(Cl)cccc2Cl)C(=O)c2cnc(Nc3ccc(N4CCNCC4)c(F)c3)nc21] |  |  | | *** |
| 8 | 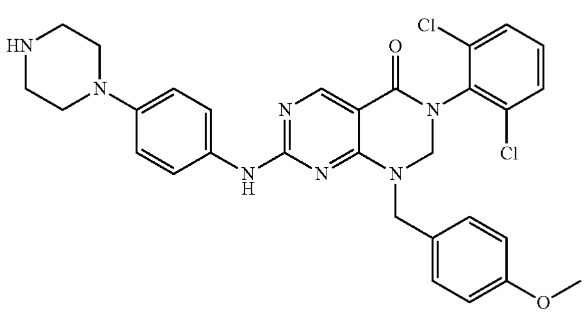 [SMILES: COc1ccc(CN2CN(c3c(Cl)cccc3Cl)C(=O)c3cnc(Nc4ccc(N5CCNCC5)cc4)nc32)cc1] | | * | | |
| 9 | 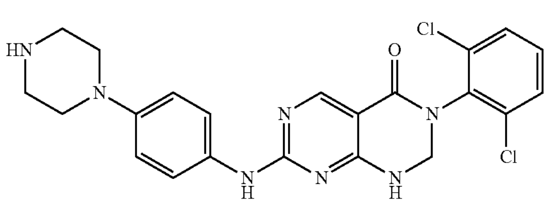 [SMILES: O=C1c2cnc(Nc3ccc(N4CCNCC4)cc3)nc2NCN1c1c(Cl)cccc1Cl] |  |  | | *** |

TABLE 1-continued

| Ex | STRUCTURE | Wee-1 | HT29 pCDC2 method 2 | HT29 pCDC2 method 3 | Mics - CLint |
|---|---|---|---|---|---|
| 10 | 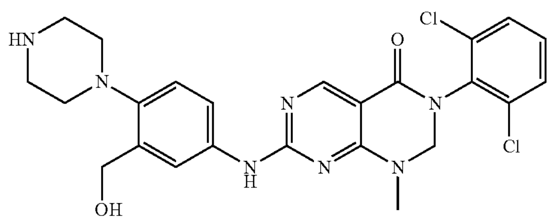 [SMILES: CN1CN(c2c(Cl)cccc2Cl)C(=O)c2cnc(Nc3ccc(N4CCNCC4)c(CO)c3)nc21] | * |  | | *** |
| 11 | 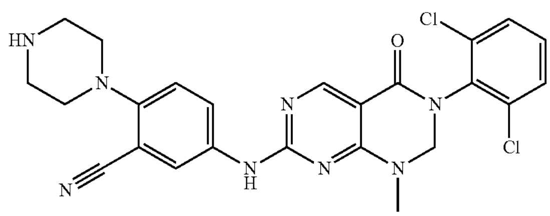 [SMILES: CN1CN(c2c(Cl)cccc2Cl)C(=O)c2cnc(Nc3ccc(N4CCNCC4)c(C#N)c3)nc21] | * |  |  | * |
| 12 | 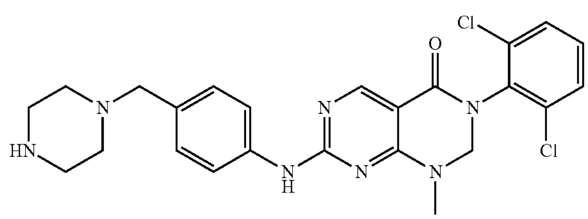 [SMILES: CN1CN(c2c(Cl)cccc2Cl)C(=O)c2cnc(Nc3ccc(CN4CCNCC4)cc3)nc21] |  |  | | *** |
| 13 | 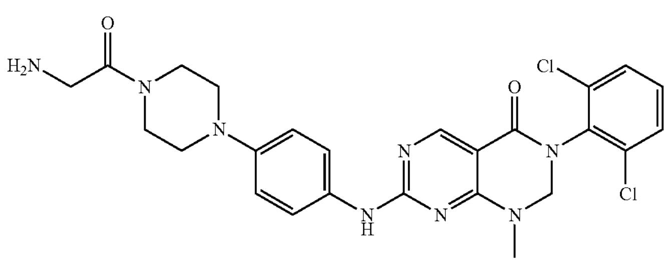 [SMILES: CN1CN(c2c(Cl)cccc2Cl)C(=O)c2cnc(Nc3ccc(N4CCN(C(=O)CN)CC4)cc3)nc21] | * |  |  | * |
| 14 | 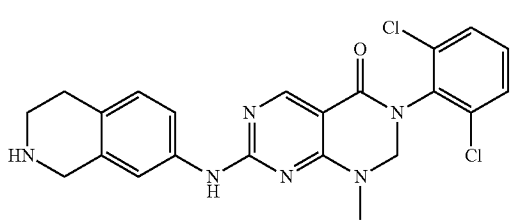 [SMILES: CN1CN(c2c(Cl)cccc2Cl)C(=O)c2cnc(Nc3ccc4c(c3)CNCC4)nc21] | * | * |  | * |
| 15 | 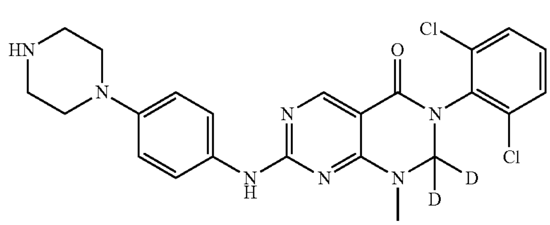 [SMILES: [2H]C1([2H])N(C)c2nc(Nc3ccc(N4CCNCC4)cc3)ncc2C(=O)N1c1c(Cl)cccc1Cl] | * | * |  | * |

TABLE 1-continued
| Ex | STRUCTURE | Wee-1 | HT29 pCDC2 method 2 | HT29 pCDC2 method 3 | Mics - CLint |
|---|---|---|---|---|---|
| 16 | 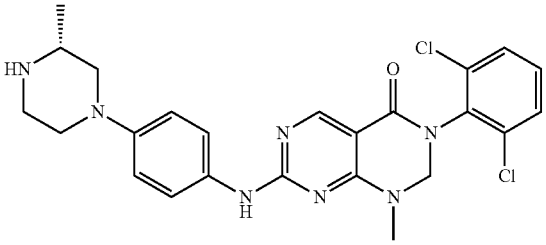 [SMILES: C[C@@H]1CN(c2ccc(Nc3ncc4c(n3)N(C)CN(c3c(Cl)cccc3Cl)C4=O)cc2)CCN1] | * | * |  | * |
| 17 | 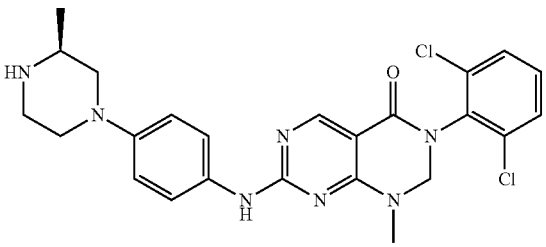 [SMILES: C[C@H]1CN(c2ccc(Nc3ncc4c(n3)N(C)CN(c3c(Cl)cccc3Cl)C4=O)cc2)CCN1] |  | * |  |  |
| 18 | 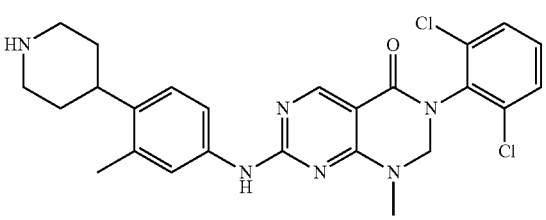 [SMILES: Cc1cc(Nc2ncc3c(n2)N(C)CN(c2c(Cl)cccc2Cl)C3=O)ccc1C1CCNCC1] | * |  |  | * |
| 19 | 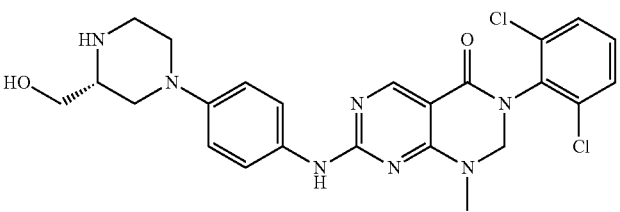 [SMILES: CN1CN(c2c(Cl)cccc2Cl)C(=O)c2cnc(Nc3ccc(N4CCN[C@@H](CO)C4)cc3)nc21] | * |  |  | * |
| 20 | 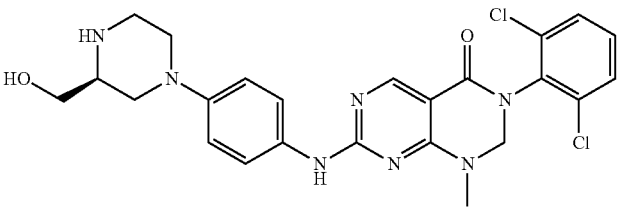 [SMILES: CN1CN(c2c(Cl)cccc2Cl)C(=O)c2cnc(Nc3ccc(N4CCN[C@H](CO)C4)cc3)nc21] | * |  |  | ** |
| 21 | 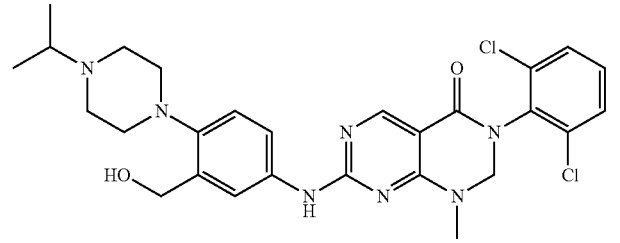 [SMILES: CC(C)N1CCN(c2ccc(Nc3ncc4c(n3)N(C)CN(c3c(Cl)cccc3Cl)C4=O)cc2CO)CC1] |  | * |  |  |

TABLE 1-continued

| Ex | STRUCTURE | Wee-1 | HT29 pCDC2 method 2 | HT29 pCDC2 method 3 | Mics - CLint |
|---|---|---|---|---|---|
| 22 | 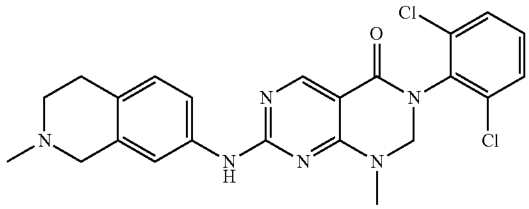 [SMILES: CN1CCc2ccc(Nc3ncc4c(n3)N(C)CN(c3c(Cl)cccc3Cl)C4=O)cc2C1] | * | * |  |  |
| 23 | 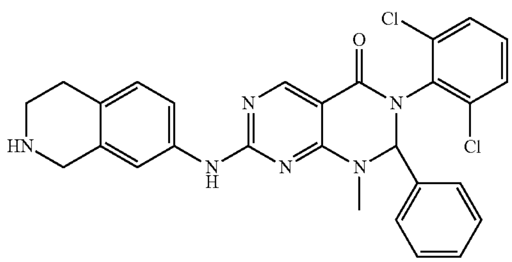 [SMILES: CN1c2nc(Nc3ccc4c(c3)CNCC4)ncc2C(=O)N(c2c(Cl)cccc2Cl)C1c1ccccc1] | * | * | | ** |
| 24 | 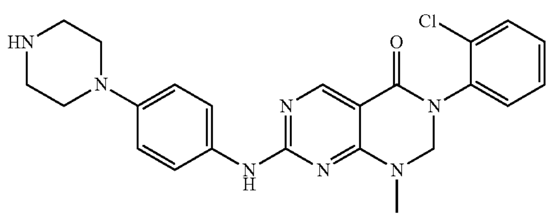 [SMILES: CN1CN(c2ccccc2Cl)C(=O)c2cnc(Nc3ccc(N4CCNCC4)cc3)nc21] | ** | | | |
| 25 | 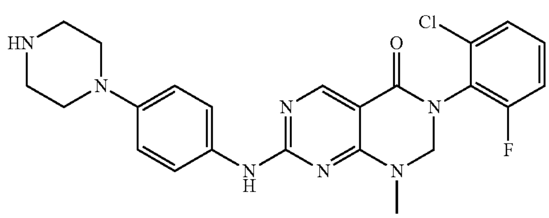 |  | * |  | * |
| 26 | 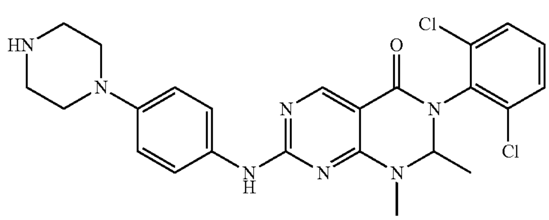 [SMILES: CC1N(C)c2nc(Nc3ccc(N4CCNCC4)cc3)ncc2C(=O)N1c1c(Cl)cccc1Cl] | ** | * | | *** |
| 27 | 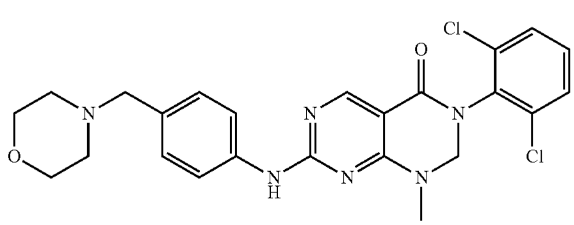 [SMILES: CN1CN(c2c(Cl)cccc2Cl)C(=O)c2cnc(Nc3ccc(CN4CCOCC4)cc3)nc21] |  |  | | * |
| 28 | 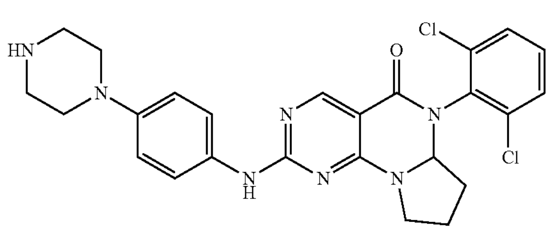 [SMILES: O=C1c2cnc(Nc3ccc(N4CCNCC4)cc3)nc2N2CCCC2N1c1c(Cl)cccc1Cl] |  |  | | *** |

TABLE 1-continued
| Ex | STRUCTURE | Wee-1 | HT29 pCDC2 method 2 | HT29 pCDC2 method 3 | Mics - CLint |
|---|---|---|---|---|---|
| 29 | 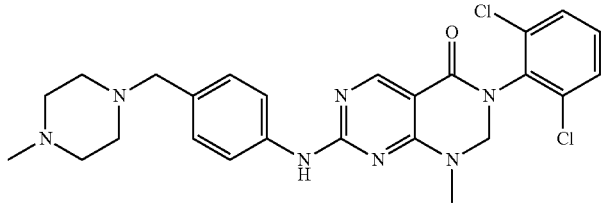 [SMILES: CN1CCN(Cc2ccc(Nc3ncc4c(n3)N(C)CN(c3c(Cl)cccc3Cl)C4=O)cc2)CC1] |  |  |  | * |
| 30 | 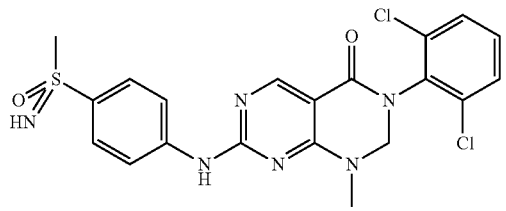 [SMILES: CN1CN(c2c(Cl)cccc2Cl)C(=O)c2cnc(Nc3ccc(S(C)(=N)=O)cc3)nc21] | ** | * |  |  |
| 31 | 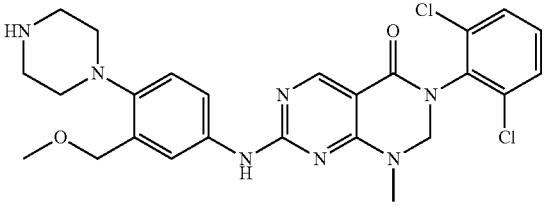 [SMILES: COCc1cc(Nc2ncc3c(n2)N(C)CN(c2c(Cl)cccc2Cl)C3=O)ccc1N1CCNCC1] |  |  |  | * |
| 32 | 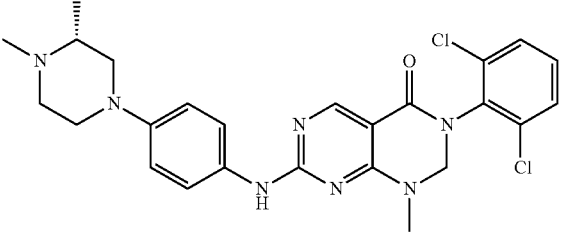 |  |  |  |  |
| 33 | 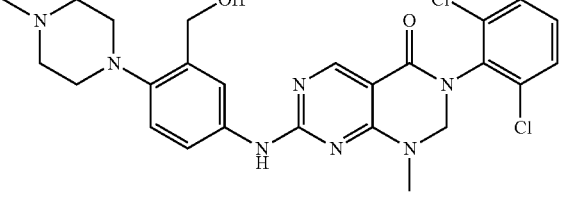 | * |  |  | ** |
| 34 | 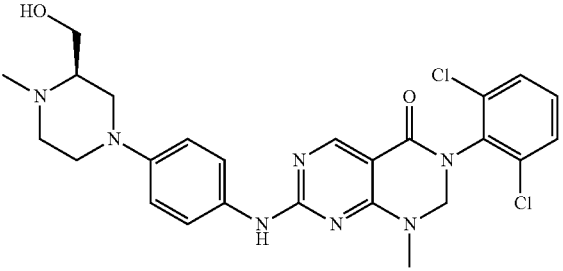 [SMILES: CN1CN(c2c(Cl)cccc2Cl)C(=O)c2cnc(Nc3ccc(N4CCN(C)[C@@H](CO)C4)cc3)nc21] |  |  |  |  |

TABLE 1-continued

| Ex | STRUCTURE | Wee-1 | HT29 pCDC2 method 2 | HT29 pCDC2 method 3 | Mics - CLint |
|---|---|---|---|---|---|
| 35 | 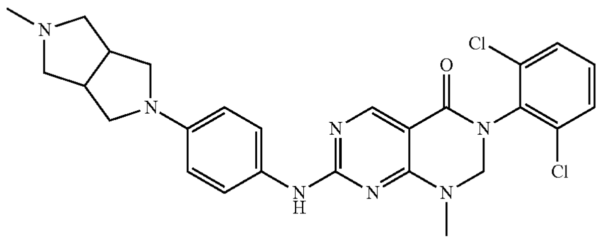 [SMILES: CN1CC2CN(c3ccc(Nc4ncc5c(n4)N(C)CN(c4c(Cl)cccc4Cl)C5=O)cc3)CC2C1] |  | | |  |
| 36 | 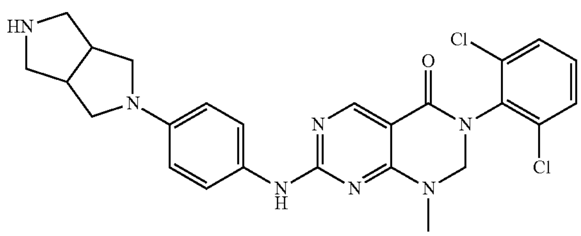 [SMILES: CN1CN(c2c(Cl)cccc2Cl)C(=O)c2cnc(Nc3ccc(N4CC5CNCC5C4)cc3)nc21] |  | | |  |
| 37 | 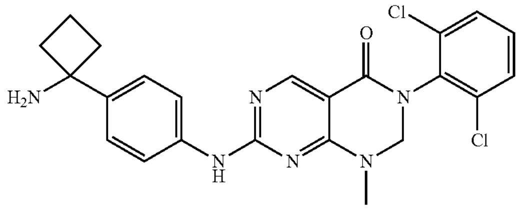 [SMILES: CN1CN(c2c(Cl)cccc2Cl)C(=O)c2cnc(Nc3ccc(C4(N)CCC4)cc3)nc21] |  | | |  |
| 38 | 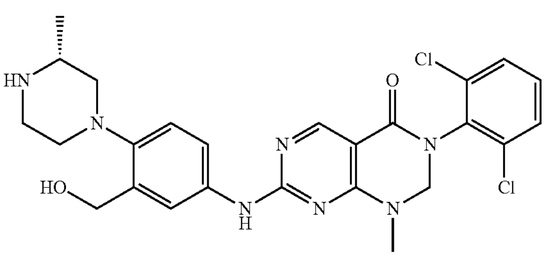 [SMILES: C[C@@H]1CN(c2ccc(Nc3ncc4c(n3)N(C)CN(c3c(Cl)cccc3Cl)C4=O)cc2CO)CCN1] | * | |  | *** |
| 39 | 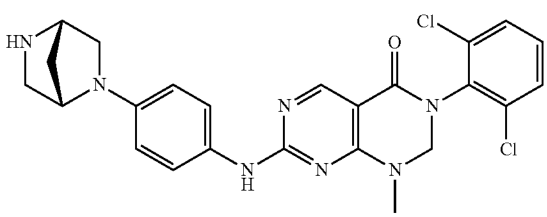 [SMILES: CN1CN(c2c(Cl)cccc2Cl)C(=O)c2cnc(Nc3ccc(N4C[C@@H]5C[C@H]4CN5)cc3)nc21] |  | | | * |
| 40 | 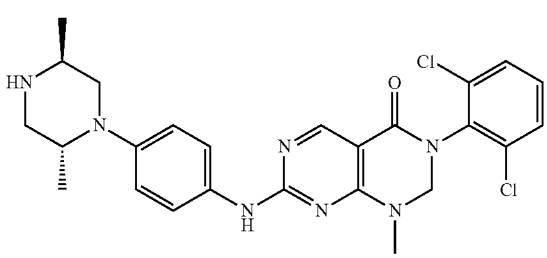 [SMILES: C[C@@H]1CN[C@@H](C)CN1c1ccc(Nc2ncc3c(n2)N(C)CN(c2c(Cl)cccc2Cl)C3=O)cc1] | * | * |  | * |

TABLE 1-continued

| Ex | STRUCTURE | Wee-1 | HT29 pCDC2 method 2 | HT29 pCDC2 method 3 | Mics - CLint |
|---|---|---|---|---|---|
| 41 | 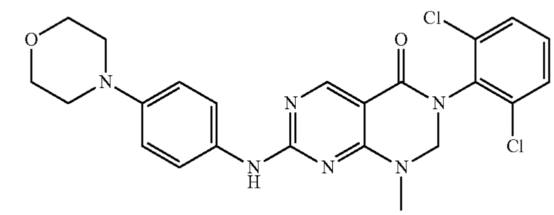 [SMILES: CN1CN(c2c(Cl)cccc2Cl)C(=O)c2cnc(Nc3ccc(N4CCOCC4)cc3)nc21] |  | | |  |
| 42 | 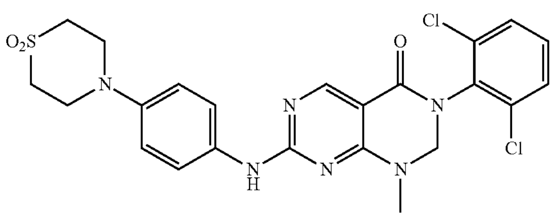 [SMILES: CN1CN(c2c(Cl)cccc2Cl)C(=O)c2cnc(Nc3ccc(N4CCS(=O)(=O)CC4)cc3)nc21] |  | | |  |
| 43 | 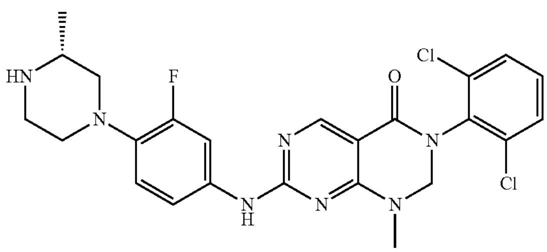 [SMILES: C[C@@H]1CN(c2ccc(Nc3ncc4c(n3)N(C)CN(c3c(Cl)cccc3Cl)C4=O)cc2F)CCN1] | * |  |  | * |
| 44 | 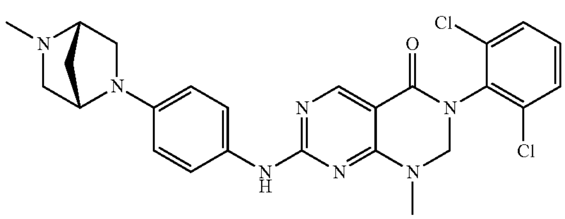 [SMILES: CN1CN(c2c(Cl)cccc2Cl)C(=O)c2cnc(Nc3ccc(N4C[C@@H]5C[C@H]4CN5C)cc3)nc21] |  | | | * |
| 45 | 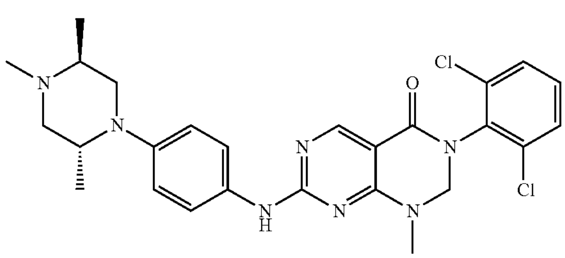 [SMILES: C[C@@H]1CN(C)[C@@H](C)CN1c1ccc(Nc2ncc3c(n2)N(C)CN(c2c(Cl)cccc2Cl)C3=O)cc1] | ** | | | |
| 46 | 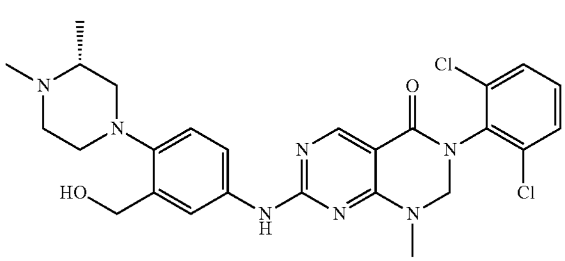 [SMILES: C[C@@H]1CN(c2ccc(Nc3ncc4c(n3)N(C)CN(c3c(Cl)cccc3Cl)C4=O)cc2CO)CCN1C] | * | |  | *** |

TABLE 1-continued
| Ex | STRUCTURE | Wee-1 | HT29 pCDC2 method 2 | HT29 pCDC2 method 3 | Mics - CLint |
|---|---|---|---|---|---|
| 47 | 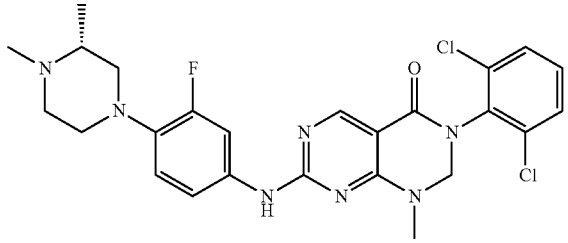 | ** | | | |
| 48 | 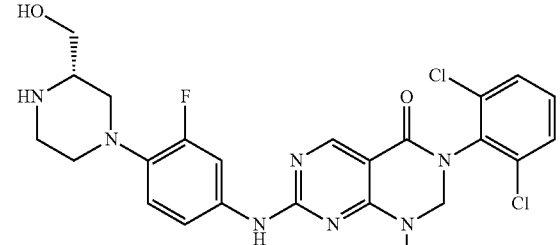 |  | | | * |
| 49 | 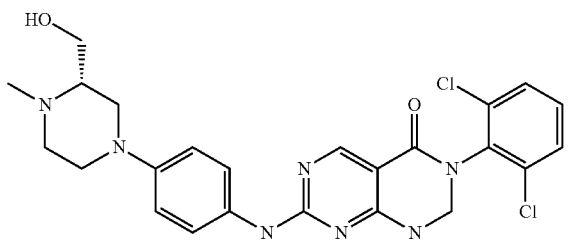 |  | | |  |
| 50 | 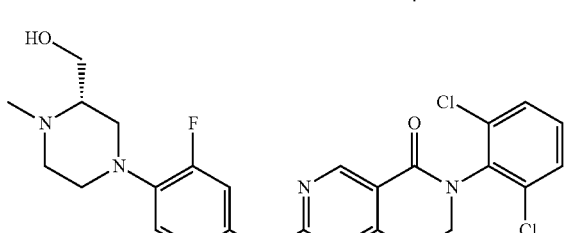 | ** | | | |
| 51 | 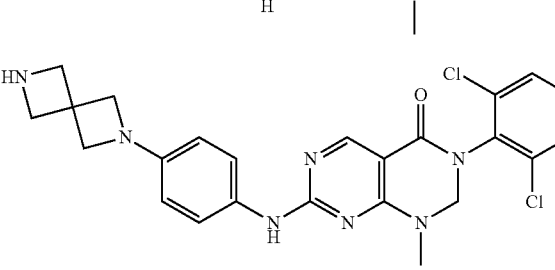 | ** | | | |
| 52 | 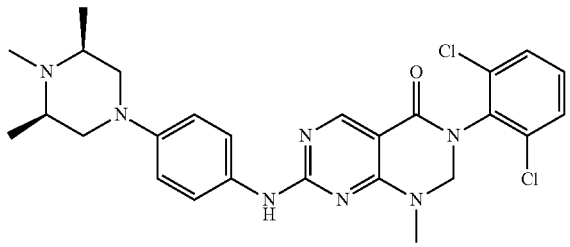 [SMILES: C[C@@H]1CN(c2ccc(Nc3ncc4c(n3)N(C)CN(c3c(Cl)cccc3Cl)C4=O)cc2)C[C@H](C)N1C] | ** | | | |

TABLE 1-continued

| Ex | STRUCTURE | Wee-1 | HT29 pCDC2 method 2 | HT29 pCDC2 method 3 | Mics - CLint |
|----|-----------|-------|---------------------|---------------------|--------------|
| 53 | 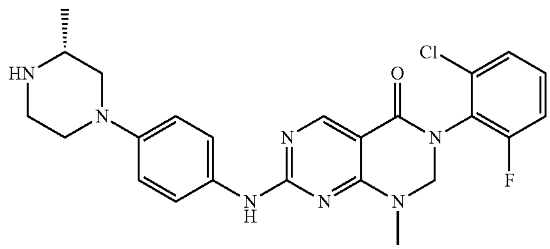 |  | * |  | * |
| 54 | 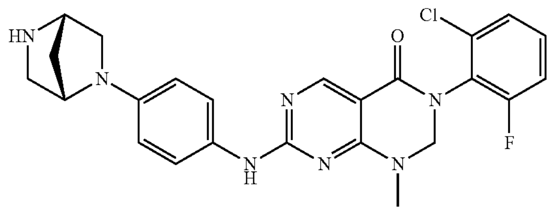 [SMILES: CN1CN(c2c(F)cccc2Cl)C(=O)c2cnc(Nc3ccc(N4C[C@@H]5C[C@H]4CN5)cc3)nc21] | ** | | | |
| 55 | 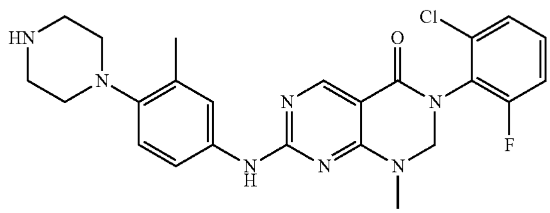 [SMILES: Cc1cc(Nc2ncc3c(n2)N(C)CN(c2c(F)cccc2Cl)C3=O)ccc1N1CCNCC1] | * | |  | *** |
| 56 | 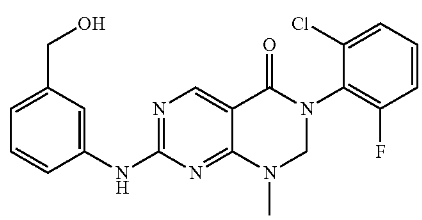 [SMILES: CN1CN(c2c(F)cccc2Cl)C(=O)c2cnc(Nc3cccc(CO)c3)nc21] | * | | | |
| 57 | 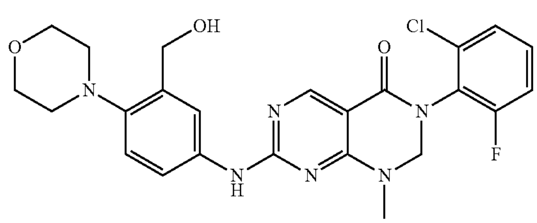 [SMILES: CN1CN(c2c(F)cccc2Cl)C(=O)c2cnc(Nc3ccc(N4CCOCC4)c(CO)c3)nc21] | ** | | | |
| 58 | 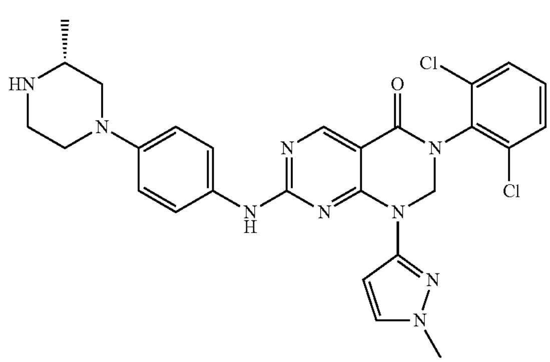 [SMILES: C[C@@H]1CN(c2ccc(Nc3ncc4c(n3)N(c3ccn(C)n3)CN(c3c(Cl)cccc3Cl)C4=O)cc2)CCN1] | * | | | * |

TABLE 1-continued
| Ex | STRUCTURE | Wee-1 | HT29 pCDC2 method 2 | HT29 pCDC2 method 3 | Mics - CLint |
|---|---|---|---|---|---|
| 59 | 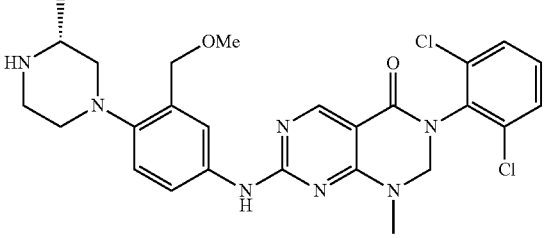 |  |  |  | * |
| 60 | 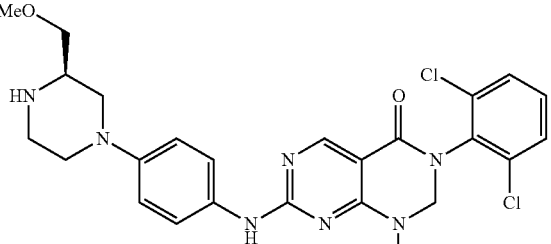 |  | * |  | * |
| 61 | 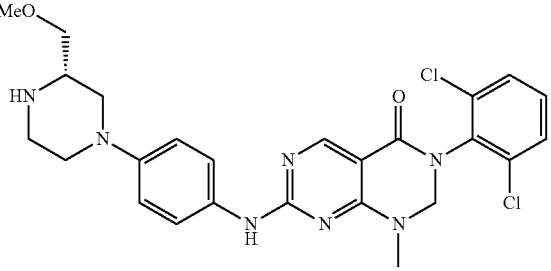 |  |  |  | *** |
| 62 | 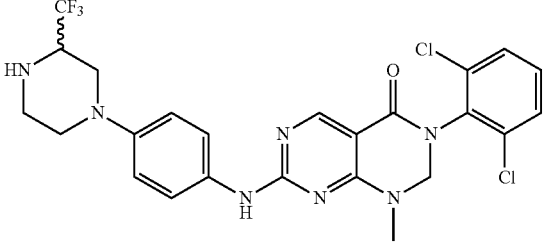 [SMILES: CN1CN(c2c(Cl)cccc2Cl)C(=O)c2cnc(Nc3ccc(N4CCNC(C(F)(F)F)C4)cc3)nc21] | ** |  |  |  |
| 63 | 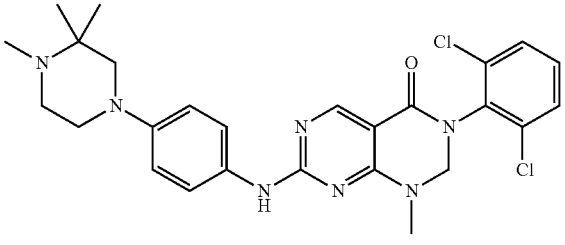 [SMILES: CN1CN(c2c(Cl)cccc2Cl)C(=O)c2cnc(Nc3ccc(N4CCN(C)C(C)(C)C4)cc3)nc21] | * |  | ** |  |
| 64 | 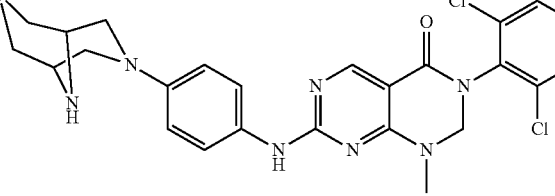 |  |  |  | * |

TABLE 1-continued
| Ex | STRUCTURE | Wee-1 | HT29 pCDC2 method 2 | HT29 pCDC2 method 3 | Mics - CLint |
|---|---|---|---|---|---|
| 65 | 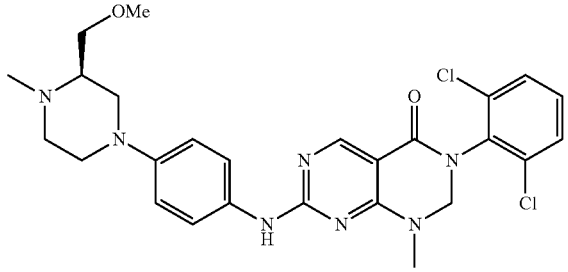 [SMILES: COC[C@H]1CN(c2ccc(Nc3ncc4c(n3)N(C)CN(c3c(Cl)cccc3Cl)C4=O)cc2)CCN1C] | ** | | | |
| 66 | 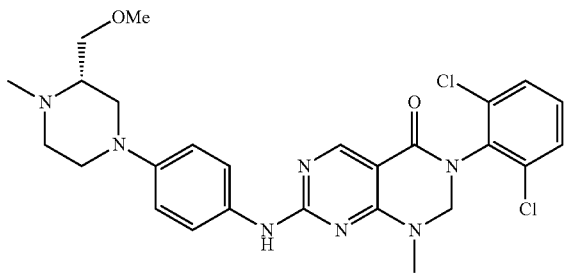 [SMILES: COC[C@@H]1CN(c2ccc(Nc3ncc4c(n3)N(C)CN(c3c(Cl)cccc3Cl)C4=O)cc2)CCN1C] |  | | |  |
| 67 | 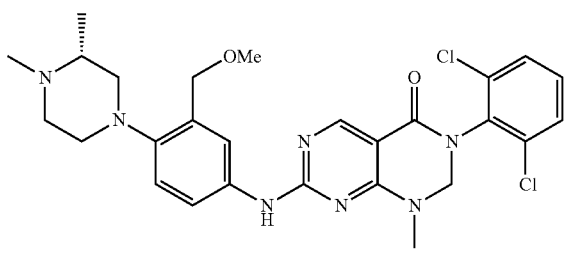 [SMILES: COCc1cc(Nc2ncc3c(n2)N(C)CN(c2c(Cl)cccc2Cl)C3=O)ccc1N1CCN(C)[C@H](C)C1] |  | | | * |
| 68 | 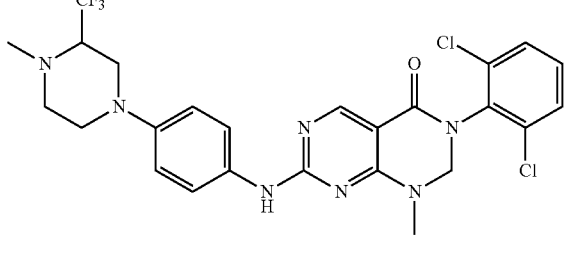 | * | | | |
| 69 | 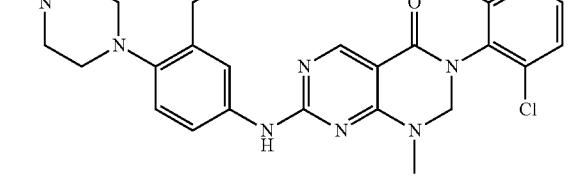 | ** | | | |
| 70 | 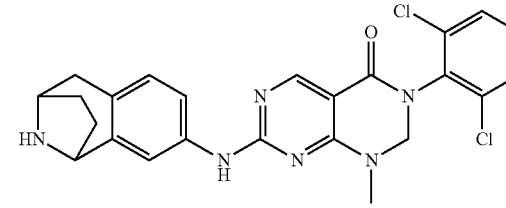 | ** | | | |

TABLE 1-continued

| Ex | STRUCTURE | Wee-1 | HT29 pCDC2 method 2 | HT29 pCDC2 method 3 | Mics - CLint |
|----|-----------|-------|---------------------|---------------------|--------------|
| 71 | 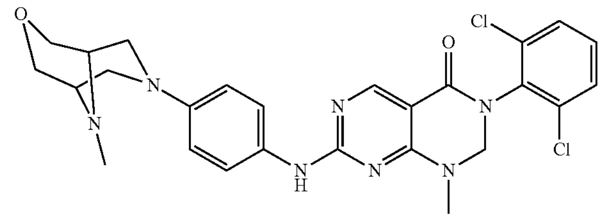 [SMILES: CN1CN(c2c(Cl)cccc2Cl)C(=O)c2cnc(Nc3ccc(N4CC5COCC(C4)N5C)cc3)nc21] | ** | | | |
| 72 | 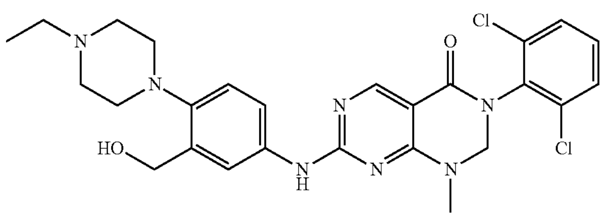 [SMILES: CCN1CCN(c2ccc(Nc3ncc4c(n3)N(C)CN(c3c(Cl)cccc3Cl)C4=O)cc2CO)CC1] | * | |  | *** |
| 73 | 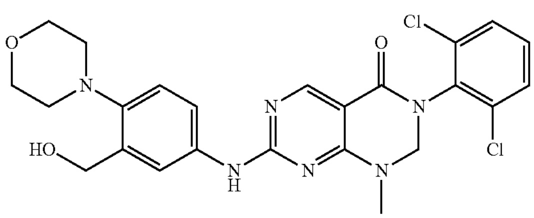 [SMILES: CN1CN(c2c(Cl)cccc2Cl)C(=O)c2cnc(Nc3ccc(N4CCOCC4)c(CO)c3)nc21] | ** | | | |
| 74 | 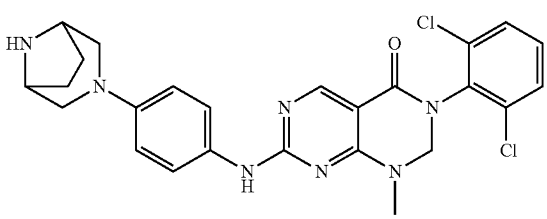 [SMILES: CN1CN(c2c(Cl)cccc2Cl)C(=O)c2cnc(Nc3ccc(N4CC5CCC(C4)N5)cc3)nc21] |  |  |  | * |
| 75 | 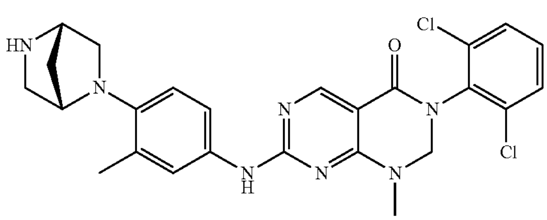 [SMILES: Cc1cc(Nc2ncc3c(n2)N(C)CN(c2c(Cl)cccc2Cl)C3=O)ccc1N1C[C@@H]2C[C@H]1CN2] | * | | | * |
| 76 | 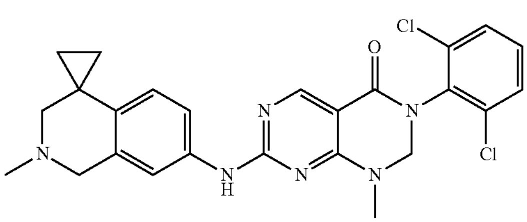 [SMILES: CN1Cc2cc(Nc3ncc4c(n3)N(C)CN(c3c(Cl)cccc3Cl)C4=O)ccc2C2(CC2)C1] | * | |  | * |
| 77 | 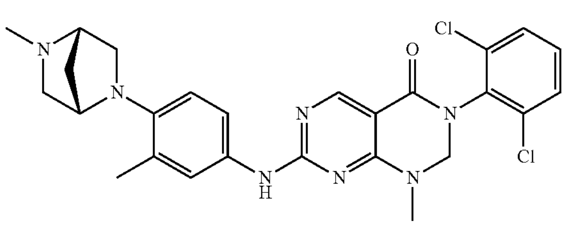 [SMILES: Cc1cc(Nc2ncc3c(n2)N(C)CN(c2c(Cl)cccc2Cl)C3=O)ccc1N1C[C@@H]2C[C@H]1CN2C] | * | |  | ** |

TABLE 1-continued

| Ex | STRUCTURE | Wee-1 | HT29 pCDC2 method 2 | HT29 pCDC2 method 3 | Mics - CLint |
|---|---|---|---|---|---|
| 78 | 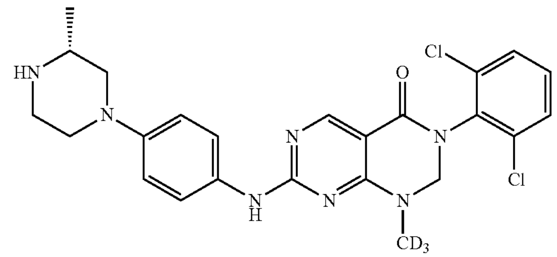 [SMILES: [2H]C([2H])([2H])N1CN(c2c(Cl)cccc2Cl)C(=O)c2cnc(Nc3ccc(N4CCN[C@H](C)C4)cc3)nc21] | * | |  | *** |
| 79 | 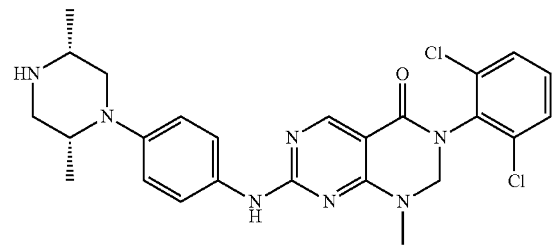 [SMILES: C[C@@H]1CN(c2ccc(Nc3ncc4c(n3)N(C)CN(c3c(Cl)cccc3Cl)C4=O)cc2)[C@H](C)CN1] |  | | |  |
| 80 | 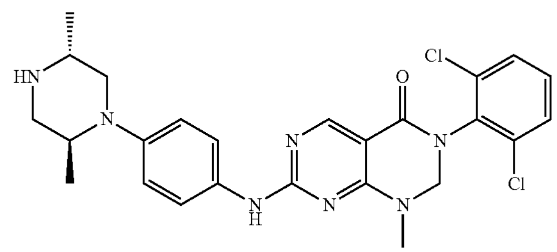 [SMILES: C[C@@H]1CN(c2ccc(Nc3ncc4c(n3)N(C)CN(c3c(Cl)cccc3Cl)C4=O)cc2)[C@@H](C)CN1] | * | * |  |  |
| 81 | 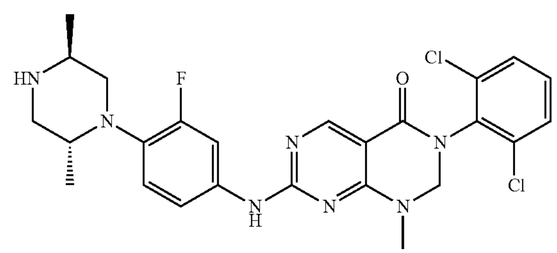 [SMILES: C[C@@H]1CN[C@@H](C)CN1c1ccc(Nc2ncc3c(n2)N(C)CN(c2c(Cl)cccc2Cl)C3=O)cc1F] | ** | | | |
| 82 | 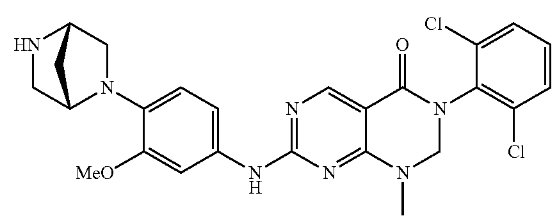 [SMILES: COc1cc(Nc2ncc3c(n2)N(C)CN(c2c(Cl)cccc2Cl)C3=O)ccc1N1C[C@@H]2C[C@H]1CN2] | ** | | | |
| 83 | 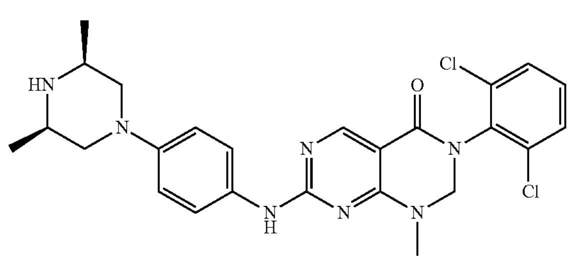 [SMILES: C[C@@H]1CN(c2ccc(Nc3ncc4c(n3)N(C)CN(c3c(Cl)cccc3Cl)C4=O)cc2)C[C@H](C)N1] | * | |  | ** |

TABLE 1-continued
| Ex | STRUCTURE | Wee-1 | HT29 pCDC2 method 2 | HT29 pCDC2 method 3 | Mics - CLint |
|---|---|---|---|---|---|
| 84 | 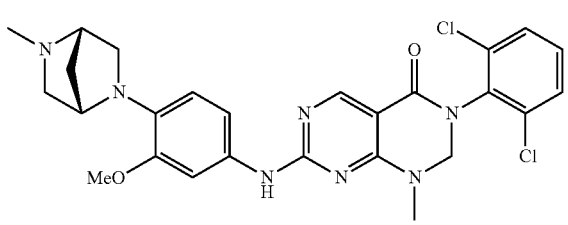 [SMILES: COc1cc(Nc2ncc3c(n2)N(C)CN(c2c(Cl)cccc2Cl)C3=O)ccc1N1C[C@@H]2C[C@H]1CN2C] |  | | |  |
| 85 | 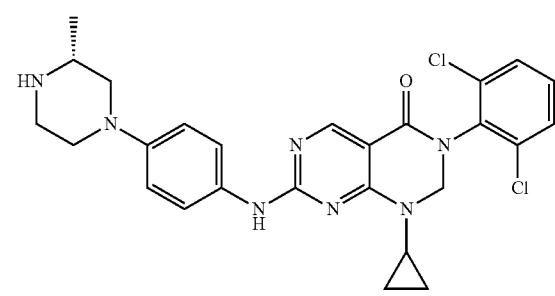 [SMILES: C[C@@H]1CN(c2ccc(Nc3ncc4c(n3)N(C3CC3)CN(c3c(Cl)cccc3Cl)C4=O)cc2)CCN1] | ** | | | |
| 86 | 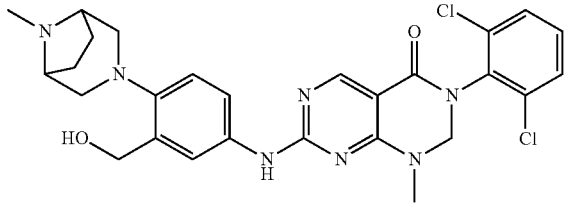 [SMILES: CN1CN(c2c(Cl)cccc2Cl)C(=O)c2cnc(Nc3ccc(N4CC5CCC(C4)N5C)c(CO)c3)nc21] | * | * |  | * |
| 87 | 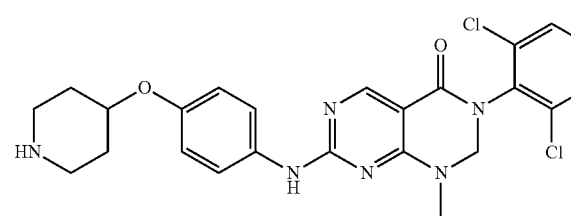 |  | | | * |
| 88 | 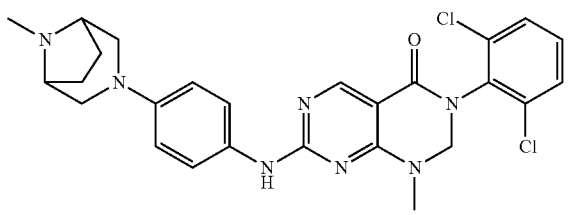 [SMILES: CN1CN(c2c(Cl)cccc2Cl)C(=O)c2cnc(Nc3ccc(N4CC5CCC(C4)N5C)cc3)nc21] | * | |  | ** |
| 89 | 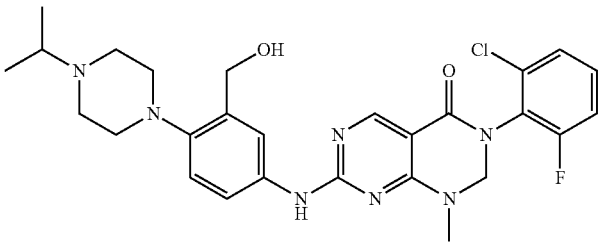 [SMILES: CC(C)N1CCN(c2ccc(Nc3ncc4c(n3)N(C)CN(c3c(F)cccc3Cl)C4=O)cc2CO)CC1] | * | |  | *** |

TABLE 1-continued

| Ex | STRUCTURE | Wee-1 | HT29 pCDC2 method 2 | HT29 pCDC2 method 3 | Mics - CLint |
|---|---|---|---|---|---|
| 90 | 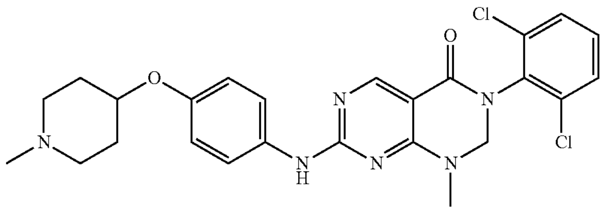 [SMILES: CN1CCC(Oc2ccc(Nc3ncc4c(n3)N(C)CN(c3c(Cl)cccc3Cl)C4=O)cc2)CC1] |  | | |  |
| 91 | 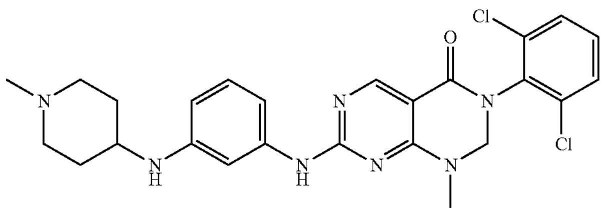 [SMILES: CN1CCC(Nc2cccc(Nc3ncc4c(n3)N(C)CN(c3c(Cl)cccc3Cl)C4=O)c2)CC1] |  | | | * |
| 92 | 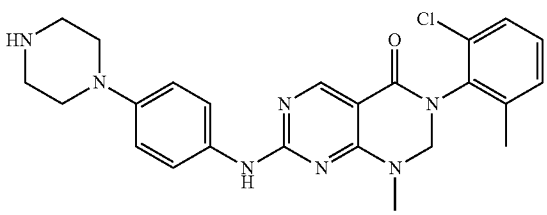 [SMILES: Cc1cccc(Cl)c1N1CN(C)c2nc(Nc3ccc(N4CCNCC4)cc3)ncc2C1=O] | ** | | | |
| 93 | 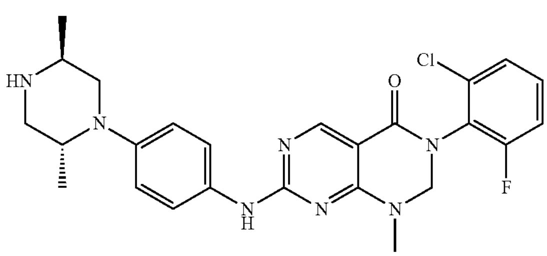 | ** | | | |
| 94 | 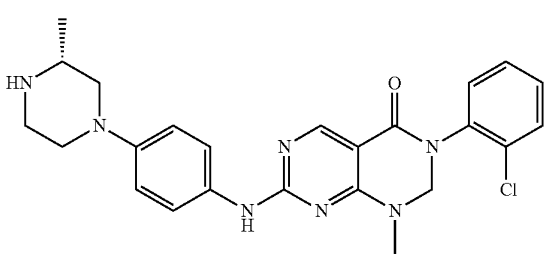 [SMILES: C[C@@H]1CN(c2ccc(Nc3ncc4c(n3)N(C)CN(c3ccccc3Cl)C4=O)cc2)CCN1] | ** | | | |
| 95 | 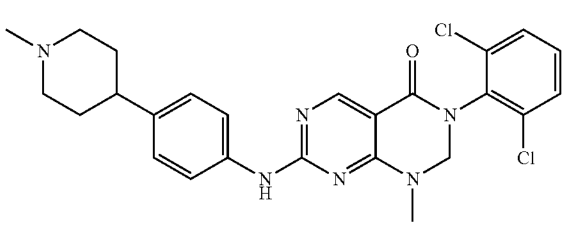 | * |  | | *** |

TABLE 1-continued

| Ex | STRUCTURE | Wee-1 | HT29 pCDC2 method 2 | HT29 pCDC2 method 3 | Mics - CLint |
|---|---|---|---|---|---|
| 96 | 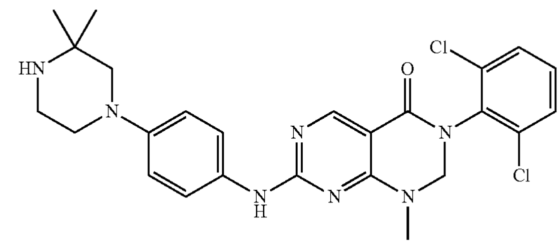 [SMILES: CN1CN(c2c(Cl)cccc2Cl)C(=O)c2cnc(Nc3ccc(N4CCNC(C)(C)C4)cc3)nc21] | * | |  | ** |
| 97 | 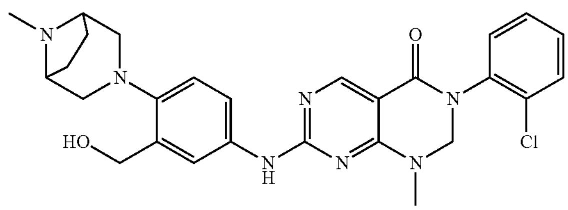 [SMILES: CN1CN(c2ccccc2Cl)C(=O)c2cnc(Nc3ccc(N4CC5CCC(C4)N5C)c(CO)c3)nc21] |  | | | * |
| 98 | 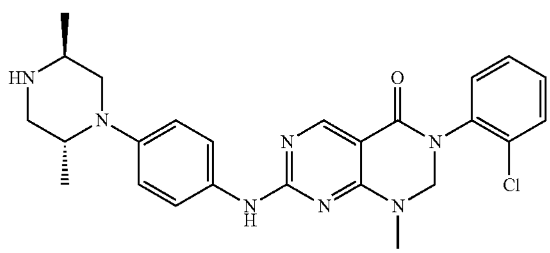 [SMILES: C[C@@H]1CN[C@@H](C)CN1c1ccc(Nc2ncc3c(n2)N(C)CN(c2ccccc2Cl)C3=O)cc1] | ** | | | |
| 99 | 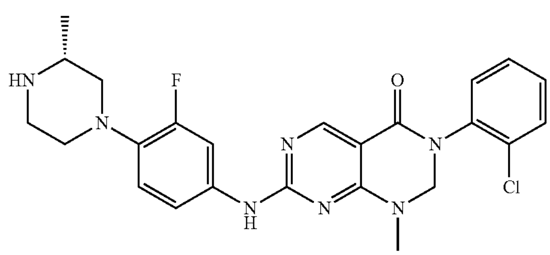 [SMILES: C[C@@H]1CN(c2ccc(Nc3ncc4c(n3)N(C)CN(c3ccccc3Cl)C4=O)cc2F)CCN1] | ** | | | |
| 100 | 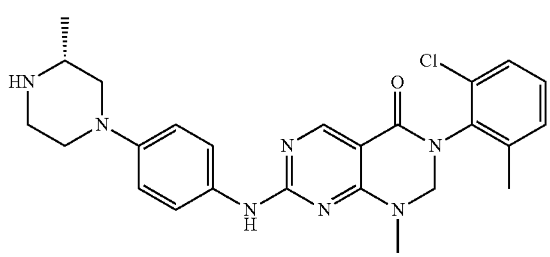 [SMILES: Cc1cccc(Cl)c1N1CN(C)c2nc(Nc3ccc(N4CCN[C@H](C)C4)cc3)ncc2C1=O] | ** | | | |
| 101 | 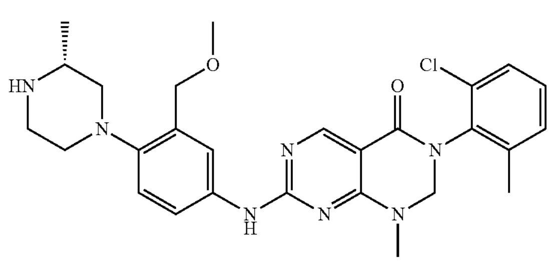 [SMILES: COCc1cc(Nc2ncc3c(n2)N(C)CN(c2c(C)cccc2Cl)C3=O)ccc1N1CCN[C@H](C)C1] | ** | | | |

TABLE 1-continued

| Ex | STRUCTURE | Wee-1 | HT29 pCDC2 method 2 | HT29 pCDC2 method 3 | Mics - CLint |
|---|---|---|---|---|---|
| 102 | 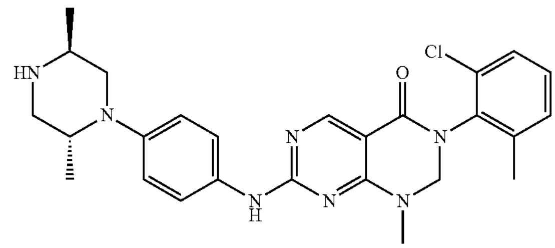 [SMILES: Cc1cccc(Cl)c1N1CN(C)c2nc(Nc3ccc(N4C[C@H](C)NC[C@H]4C)cc3)ncc2C1=O] |  | | | * |
| 103 | 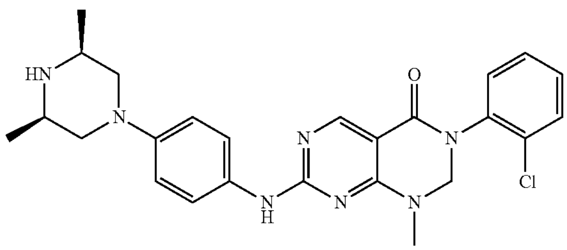 [SMILES: C[C@@H]1CN(c2ccc(Nc3ncc4c(n3)N(C)CN(c3ccccc3Cl)C4=O)cc2)C[C@H](C)N1] |  | |  | |
| 104 | 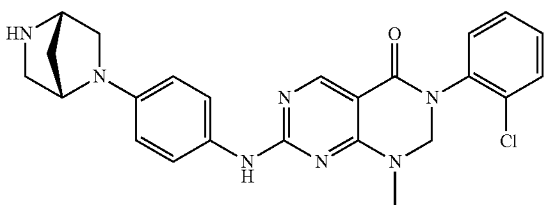 [SMILES: CN1CN(c2ccccc2Cl)C(=O)c2cnc(Nc3ccc(N4C[C@@H]5C[C@H]4CN5)cc3)nc21] | * | | | |
| 105 | 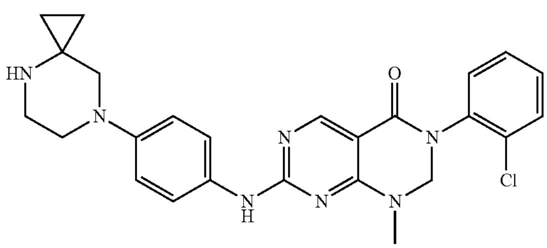 [SMILES: CN1CN(c2ccccc2Cl)C(=O)c2cnc(Nc3ccc(N4CCNC5(CC5)C4)cc3)nc21] | ** | | | |
| 106 | 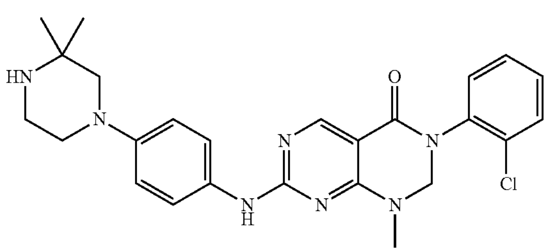 [SMILES: CN1CN(c2ccccc2Cl)C(=O)c2cnc(Nc3ccc(N4CCNC(C)(C)C4)cc3)nc21] |  | | | * |
| 107 | 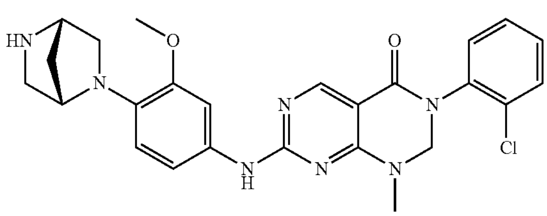 [SMILES: COc1cc(Nc2ncc3c(n2)N(C)CN(c2ccccc2Cl)C3=O)ccc1N1C[C@@H]2C[C@H]1CN2] | ** | | | |

TABLE 1-continued
| Ex | STRUCTURE | Wee-1 | HT29 pCDC2 method 2 | HT29 pCDC2 method 3 | Mics - CLint |
|---|---|---|---|---|---|
| 108 | 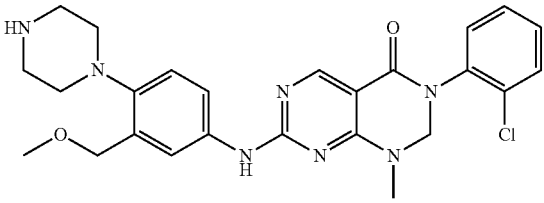 [SMILES: COCc1cc(Nc2ncc3c(n2)N(C)CN(c2ccccc2Cl)C3=O)ccc1N1CCNCC1] |  | | | * |
| 109 | 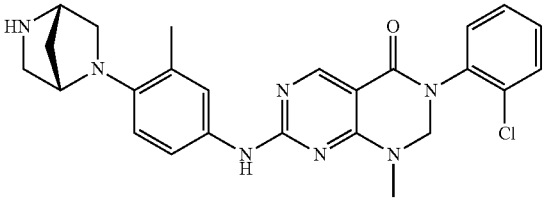 [SMILES: Cc1cc(Nc2ncc3c(n2)N(C)CN(c2ccccc2Cl)C3=O)ccc1N1C[C@@H]2C[C@H]1CN2] |  | | | * |
| 110 | 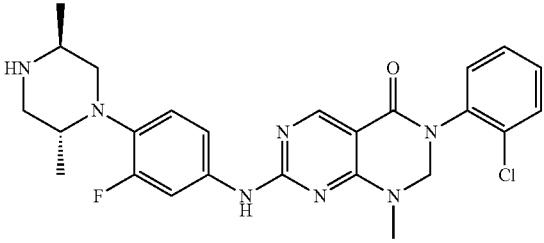 [SMILES: C[C@@H]1CN[C@@H](C)CN1c1ccc(Nc2ncc3c(n2)N(C)CN(c2ccccc2Cl)C3=O)cc1F] | ** | | | |
| 111 | 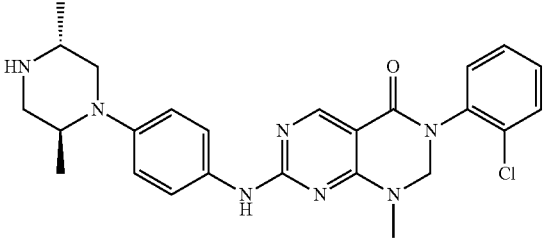 [SMILES: C[C@@H]1CN(c2ccc(Nc3ncc4c(n3)N(C)CN(c3ccccc3Cl)C4=O)cc2)[C@@H](C)CN1] |  | | | * |
| 112 | 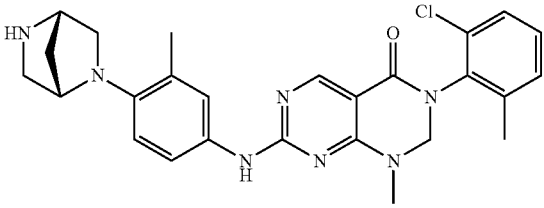 [SMILES: Cc1cc(Nc2ncc3c(n2)N(C)CN(c2c(C)cccc2Cl)C3=O)ccc1N1C[C@@H]2C[C@H]1CN2] |  | | | * |
| 113 | 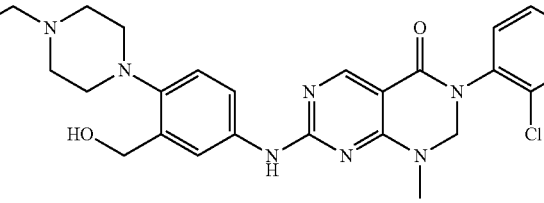 |  | | |  |
| 114 | 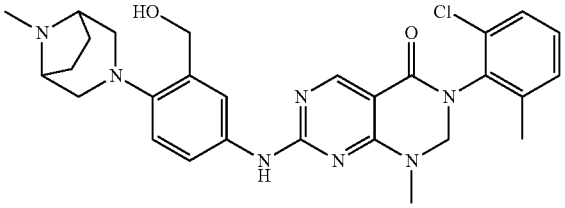 [SMILES: Cc1cccc(Cl)c1N1CN(C)c2nc(Nc3ccc(N4CC5CCC(C4)N5C)c(CO)c3)ncc2C1=O] | * | |  | *** |

TABLE 1-continued

| Ex | STRUCTURE | Wee-1 | HT29 pCDC2 method 2 | HT29 pCDC2 method 3 | Mics - CLint |
|---|---|---|---|---|---|
| 115 | 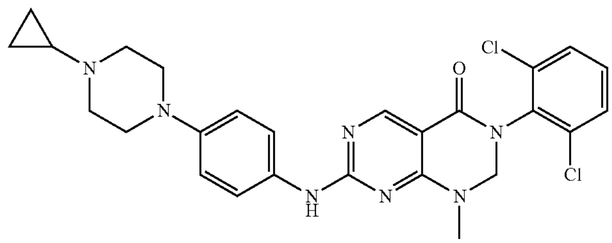 [SMILES: CN1CN(c2c(Cl)cccc2Cl)C(=O)c2cnc(Nc3ccc(N4CCN(C5CC5)CC4)cc3)nc21] | * | | | ** |
| 116 | 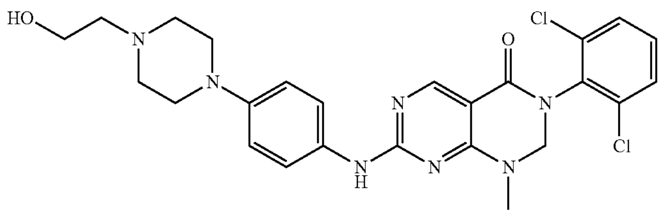 [SMILES: CN1CN(c2c(Cl)cccc2Cl)C(=O)c2cnc(Nc3ccc(N4CCN(CCO)CC4)cc3)nc21] |  | | |  |
| 117 | 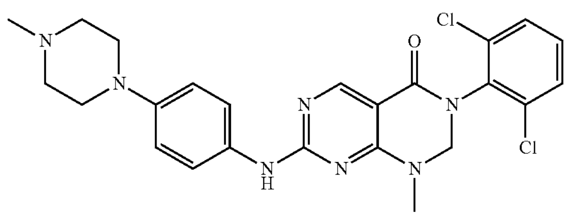 [SMILES: CN1CCN(c2ccc(Nc3ncc4c(n3)N(C)CN(c3c(Cl)cccc3Cl)C4=O)cc2)CC1] |  | |  | ** |
| 118 | 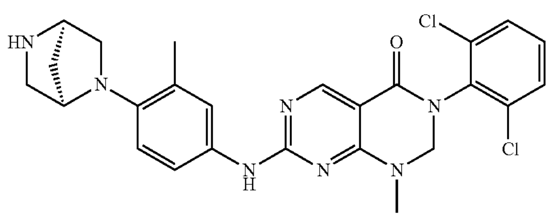 |  | | | * |
| 119 | 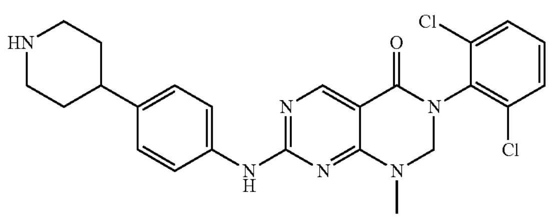 [SMILES: CN1CN(c2c(Cl)cccc2Cl)C(=O)c2cnc(Nc3ccc(C4CCNCC4)cc3)nc21] |  | | | * |
| 120 | 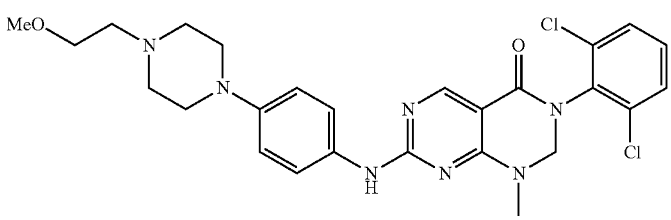 [SMILES: COCCN1CCN(c2ccc(Nc3ncc4c(n3)N(C)CN(c3c(Cl)cccc3Cl)C4=O)cc2)CC1] | * | | | ** |
| 121 | 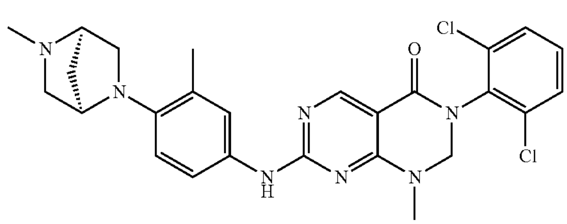 |  | | |  |

TABLE 1-continued

| Ex | STRUCTURE | Wee-1 | HT29 pCDC2 method 2 | HT29 pCDC2 method 3 | Mics - CLint |
|---|---|---|---|---|---|
| 122 | 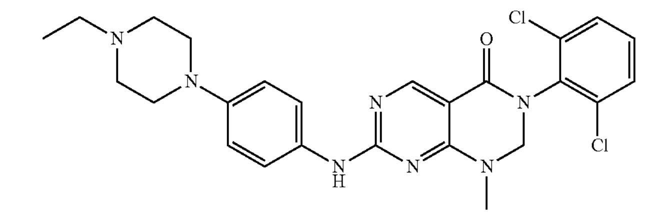 [SMILES: CCN1CCN(c2ccc(Nc3ncc4c(n3)N(C)CN(c3c(Cl)cccc3Cl)C4=O)cc2)CC1] |  | | |  |
| 123 | 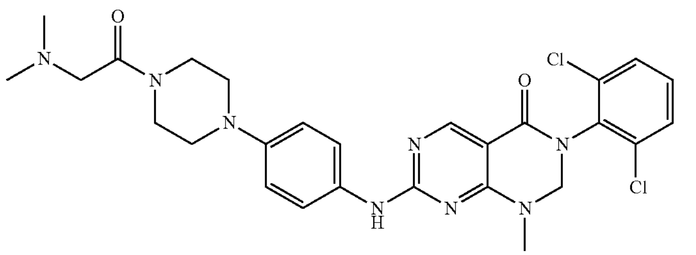 [SMILES: CN(C)CC(=O)N1CCN(c2ccc(Nc3ncc4c(n3)N(C)CN(c3c(Cl)cccc3Cl)C4=O)cc2)CC1] | * |  | | * |
| 124 | 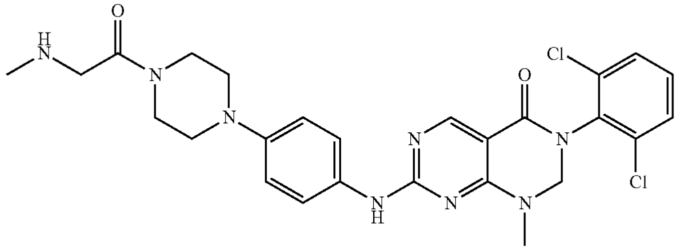 [SMILES: CNCC(=O)N1CCN(c2ccc(Nc3ncc4c(n3)N(C)CN(c3c(Cl)cccc3Cl)C4=O)cc2)CC1] | * |  | | *** |
| 125 | 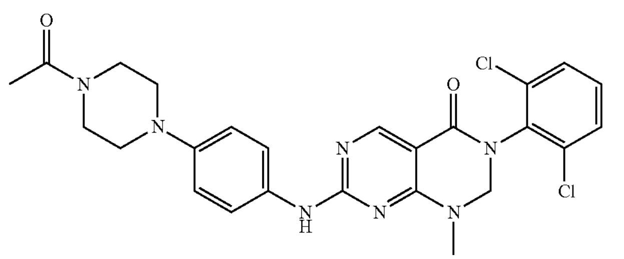 [SMILES: CC(=O)N1CCN(c2ccc(Nc3ncc4c(n3)N(C)CN(c3c(Cl)cccc3Cl)C4=O)cc2)CC1] | ** | | | |
| 126 | 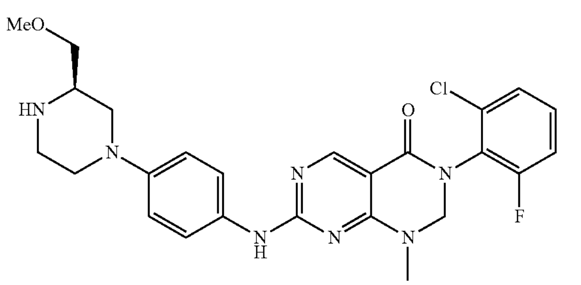 [SMILES: COC[C@H]1CN(c2ccc(Nc3ncc4c(n3)N(C)CN(c3c(F)cccc3Cl)C4=O)cc2)CCN1] | ** | * | | *** |
| 127 | 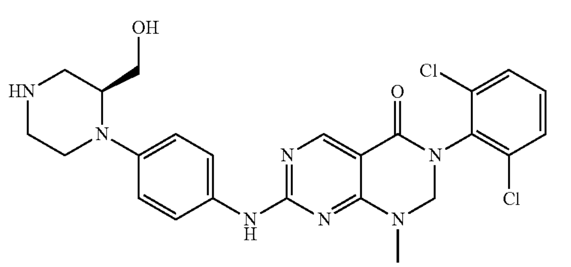 [SMILES: CN1CN(c2c(Cl)cccc2Cl)C(=O)c2cnc(Nc3ccc(N4CCNC[C@H]4CO)cc3)nc21] | *** | * | | *** |

TABLE 1-continued

| Ex | STRUCTURE | Wee-1 | HT29 pCDC2 method 2 | HT29 pCDC2 method 3 | Mics - CLint |
|---|---|---|---|---|---|
| 128 | 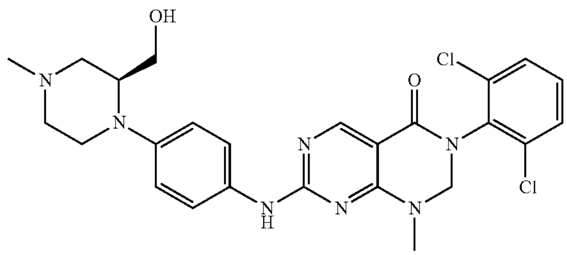 [SMILES: CN1CCN(c2ccc(Nc3ncc4c(n3)N(C)CN(c3c(Cl)cccc3Cl)C4=O)cc2)[C@H](CO)C1] |  | |  | ** |
| 129 | 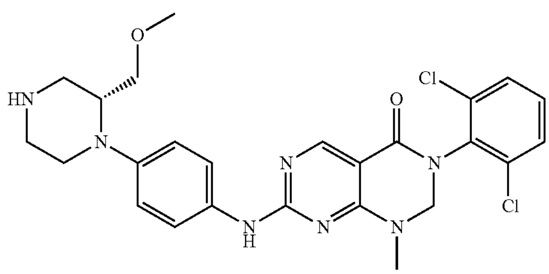 [SMILES: COC[C@H]1CNCCN1c1ccc(Nc2ncc3c(n2)N(C)CN(c2c(Cl)cccc2Cl)C3=O)cc1] | * | | | * |
| 130 | 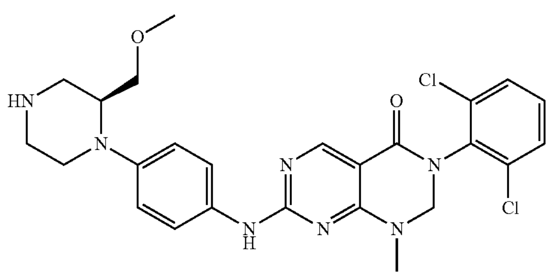 [SMILES: COC[C@@H]1CNCCN1c1ccc(Nc2ncc3c(n2)N(C)CN(c2c(Cl)cccc2Cl)C3=O)cc1] |  | | |  |
| 131 | 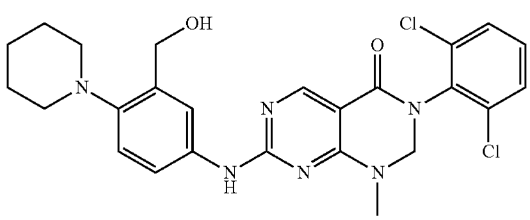 [SMILES: CN1CN(c2c(Cl)cccc2Cl)C(=O)c2cnc(Nc3ccc(N4CCCCC4)c(CO)c3)nc21] | * | | | * |
| 132 | 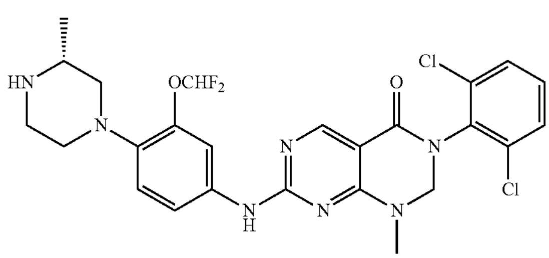 [SMILES: C[C@@H]1CN(c2ccc(Nc3ncc4c(n3)N(C)CN(c3c(Cl)cccc3Cl)C4=O)cc2OC(F)F)CCN1] |  | | | * |
| 133 | 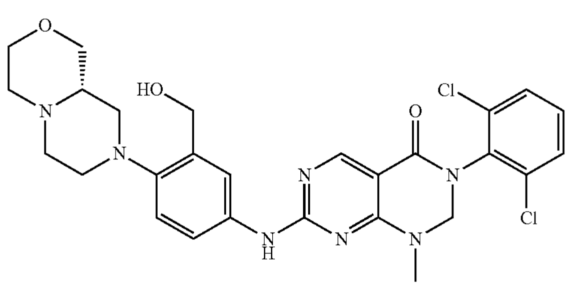 [SMILES: CN1CN(c2c(Cl)cccc2Cl)C(=O)c2cnc(Nc3ccc(N4CCN5CCOC[C@@H]5C4)c(CO)c3)nc21] |  | | |  |

TABLE 1-continued
| Ex | STRUCTURE | Wee-1 | HT29 pCDC2 method 2 | HT29 pCDC2 method 3 | Mics - CLint |
|---|---|---|---|---|---|
| 134 | 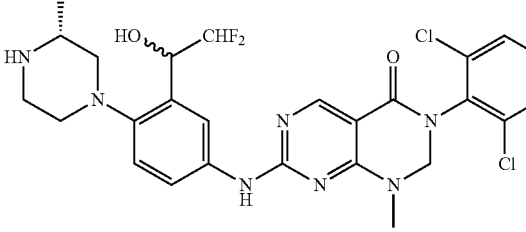 | * |  |  | *** |
| 135 | 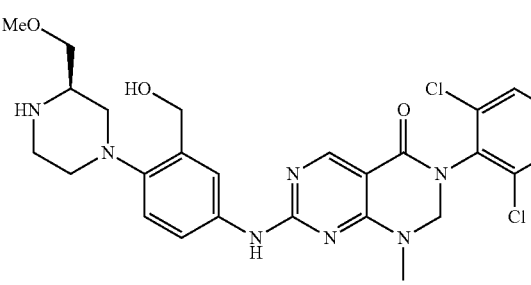 | * |  |  | *** |
| 136 | 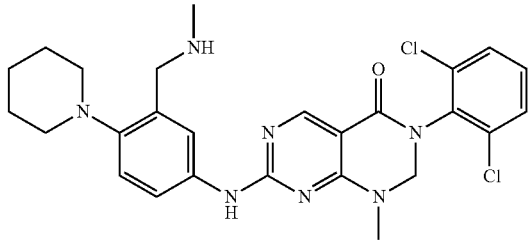 [SMILES: CNCc1cc(Nc2ncc3c(n2)N(C)CN(c2c(Cl)cccc2Cl)C3=O)ccc1N1CCCCC1] | ** |  |  | * |
| 137 | 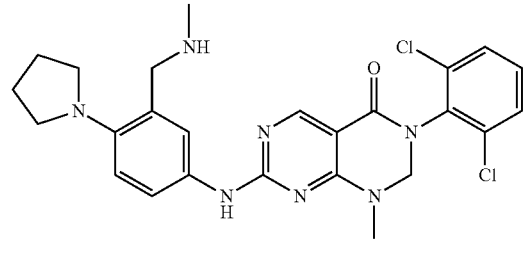 [SMILES: CNCc1cc(Nc2ncc3c(n2)N(C)CN(c2c(Cl)cccc2Cl)C3=O)ccc1N1CCCC1] |  |  |  | * |
| 138 | 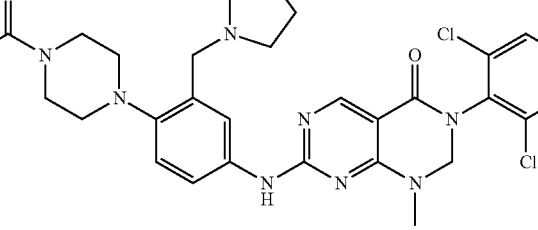 | * |  |  | * |

TABLE 1-continued

| Ex | STRUCTURE | Wee-1 | HT29 pCDC2 method 2 | HT29 pCDC2 method 3 | Mics - CLint |
|---|---|---|---|---|---|
| 139 | 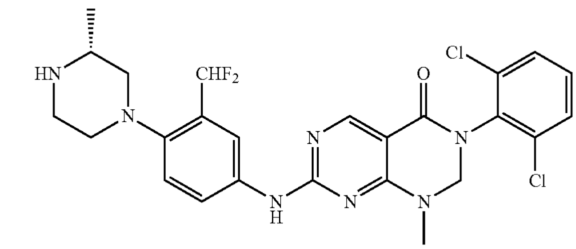 [SMILES: C[C@@H]1CN(c2ccc(Nc3ncc4c(n3)N(C)CN(c3c(Cl)cccc3Cl)C4=O)cc2C(F)F)CCN1] |  | | |  |
| 140 | 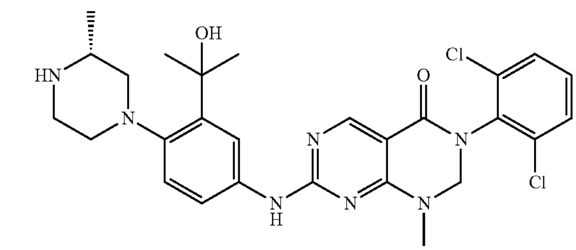 [SMILES: C[C@@H]1CN(c2ccc(Nc3ncc4c(n3)N(C)CN(c3c(Cl)cccc3Cl)C4=O)cc2C(C)(C)O)CCN1] | ** | | * | ** |
| 141 | 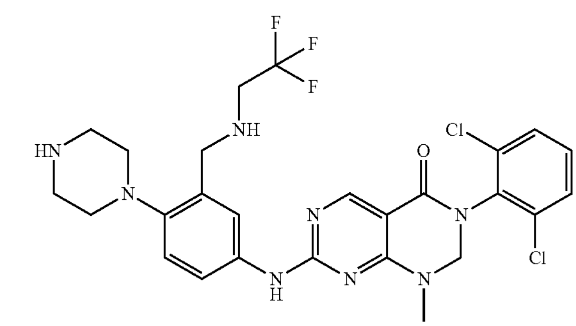 [SMILES: CN1CN(c2c(Cl)cccc2Cl)C(=O)c2cnc(Nc3ccc(N4CCNCC4)c(CNCC(F)(F)F)c3)nc21] | *** | | * | *** |
| 142 | 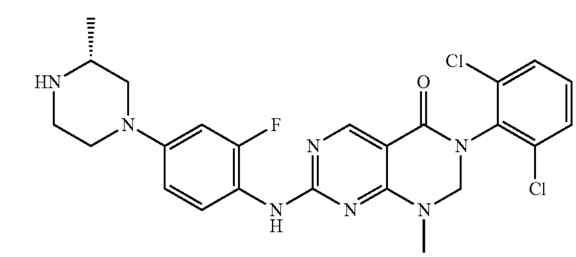 [SMILES: C[C@@H]1CN(c2ccc(Nc3ncc4c(n3)N(C)CN(c3c(Cl)cccc3Cl)C4=O)c(F)c2)CCN1] | * | | | ** |
| 143 | 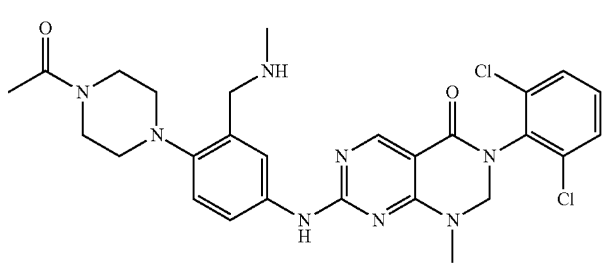 [SMILES: CNCc1cc(Nc2ncc3c(n2)N(C)CN(c2c(Cl)cccc2Cl)C3=O)ccc1N1CCN(C(C)=O)CC1] | *** | | * | *** |

TABLE 1-continued

| Ex | STRUCTURE | Wee-1 | HT29 pCDC2 method 2 | HT29 pCDC2 method 3 | Mics - CLint |
|---|---|---|---|---|---|
| 144 | 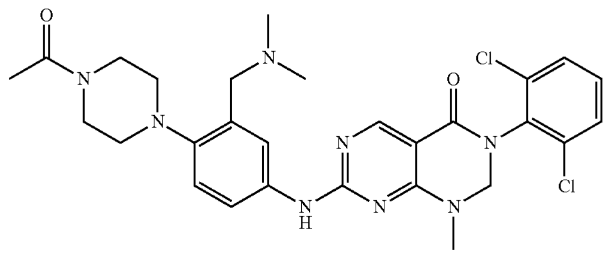 [SMILES: CC(=O)N1CCN(c2ccc(Nc3ncc4c(n3)N(C)CN(c3c(Cl)cccc3Cl)C4=O)cc2CN(C)C)CC1] | * | |  | ** |
| 145 | 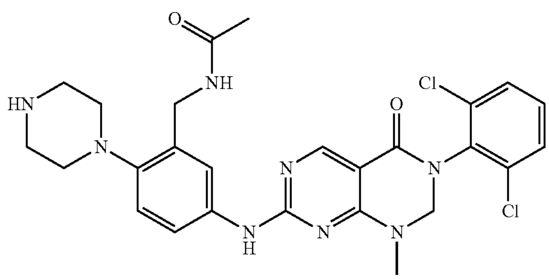 [SMILES: CC(=O)NCc1cc(Nc2ncc3c(n2)N(C)CN(c2c(Cl)cccc2Cl)C3=O)ccc1N1CCNCC1] |  | | | * |
| 146 | 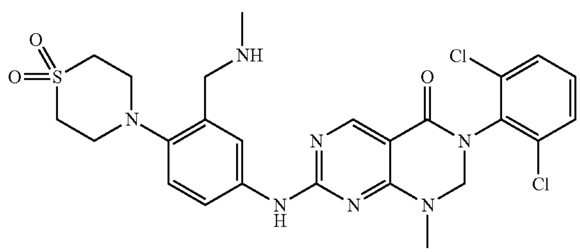 [SMILES: CNCc1cc(Nc2ncc3c(n2)N(C)CN(c2c(Cl)cccc2Cl)C3=O)ccc1N1CCS(=O)(=O)CC1] | *** | | * | *** |
| 147 | 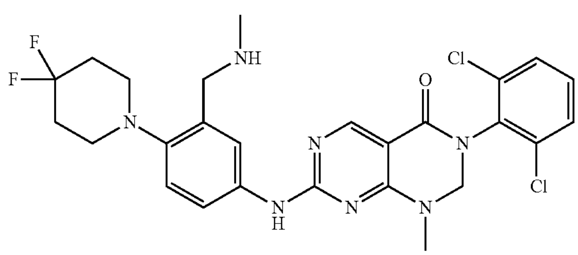 [SMILES: CNCc1cc(Nc2ncc3c(n2)N(C)CN(c2c(Cl)cccc2Cl)C3=O)ccc1N1CCC(F)(F)CC1] | * | |  | *** |
| 148 | 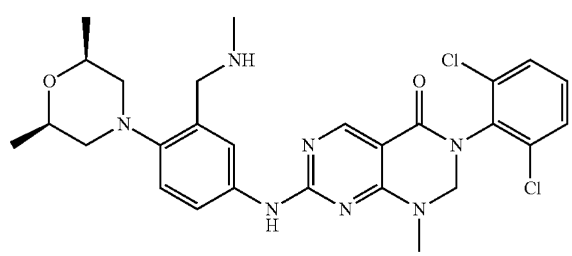 [SMILES: CNCc1cc(Nc2ncc3c(n2)N(C)CN(c2c(Cl)cccc2Cl)C3=O)ccc1N1C[C@@H](C)O[C@@H](C)C1] | * | |  | ** |
| 149 | 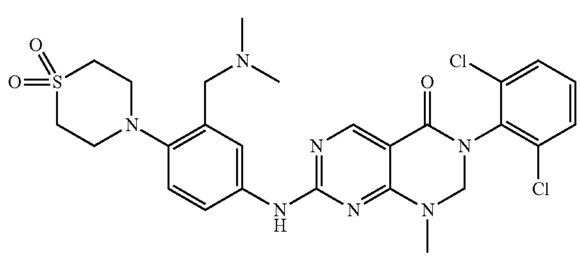 [SMILES: CN(C)Cc1cc(Nc2ncc3c(n2)N(C)CN(c2c(Cl)cccc2Cl)C3=O)ccc1N1CCS(=O)(=O)CC1] | * | |  | *** |

TABLE 1-continued
| Ex | STRUCTURE | Wee-1 | HT29 pCDC2 method 2 | HT29 pCDC2 method 3 | Mics - CLint |
|---|---|---|---|---|---|
| 150 | 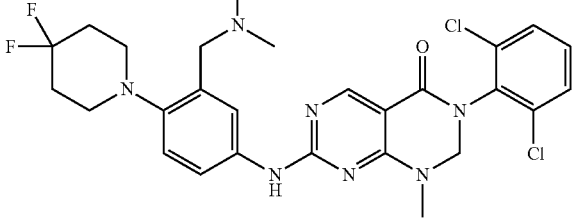 |  | |  | * |
| 151 | 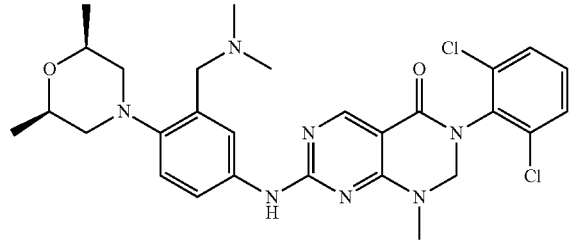 [SMILES: C[C@@H]1CN(c2ccc(Nc3ncc4c(n3)N(C)CN(c3c(Cl)cccc3Cl)C4=O)cc2CN(C)C)C[C@H](C)O1] | * | |  | * |
| 152 | 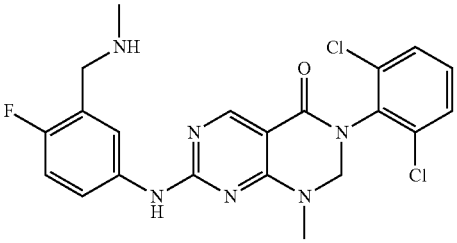 [SMILES: CNCc1cc(Nc2ncc3c(n2)N(C)CN(c2c(Cl)cccc2Cl)C3=O)ccc1F] | * | | | *** |
| 153 | 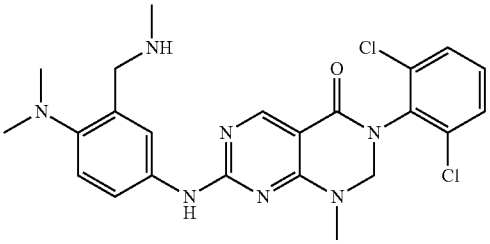 [SMILES: CNCc1cc(Nc2ncc3c(n2)N(C)CN(c2c(Cl)cccc2Cl)C3=O)ccc1N(C)C] | * | |  | ** |
| 154 | 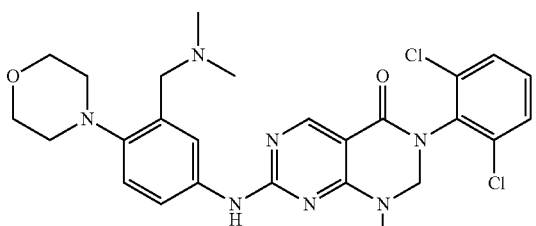 | * | |  | ** |
| 155 | 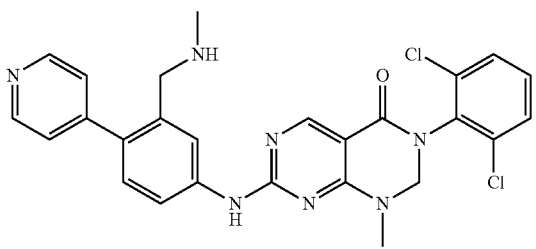 [SMILES: CNCc1cc(Nc2ncc3c(n2)N(C)CN(c2c(Cl)cccc2Cl)C3=O)ccc1-c1ccncc1] |  | | | * |

TABLE 1-continued

| Ex | STRUCTURE | Wee-1 | HT29 pCDC2 method 2 | HT29 pCDC2 method 3 | Mics - CLint |
|---|---|---|---|---|---|
| 156 | 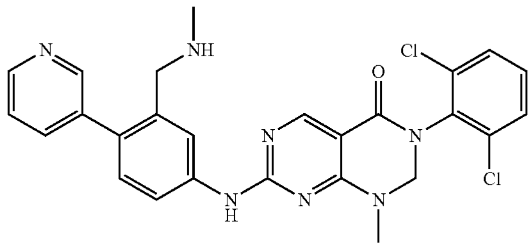 [SMILES: CNCc1cc(Nc2ncc3c(n2)N(C)CN(c2c(Cl)cccc2Cl)C3=O)ccc1-c1cccnc1] |  | | |  |
| 157 | 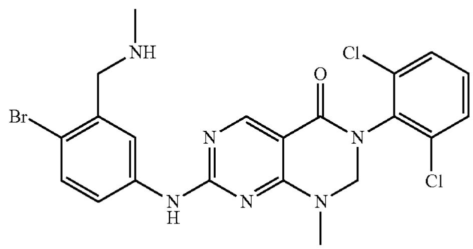 [SMILES: CNCc1cc(Nc2ncc3c(n2)N(C)CN(c2c(Cl)cccc2Cl)C3=O)ccc1Br] |  | | | * |
| 158 | 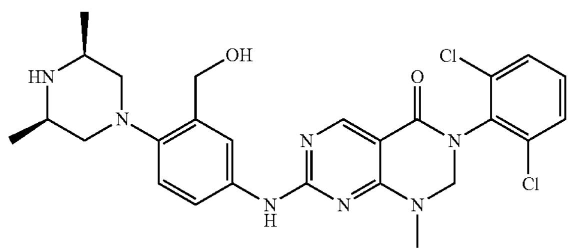 [SMILES: C[C@@H]1CN(c2ccc(Nc3ncc4c(n3)N(C)CN(c3c(Cl)cccc3Cl)C4=O)cc2CO)C[C@H](C)N1] | * |  | | *** |
| 159 | 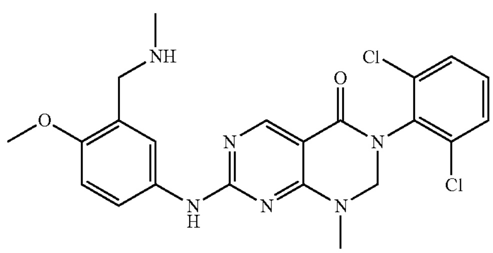 [SMILES: CNCc1cc(Nc2ncc3c(n2)N(C)CN(c2c(Cl)cccc2Cl)C3=O)ccc1OC] |  | | | * |
| 160 | 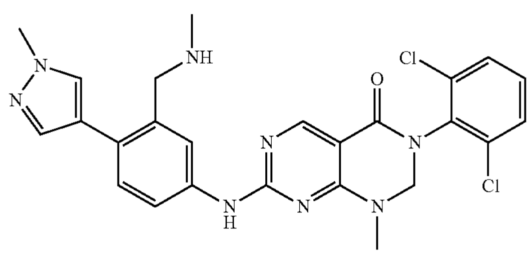 [SMILES: CNCc1cc(Nc2ncc3c(n2)N(C)CN(c2c(Cl)cccc2Cl)C3=O)ccc1-c1cnn(C)c1] | ** | * | | |
| 161 | 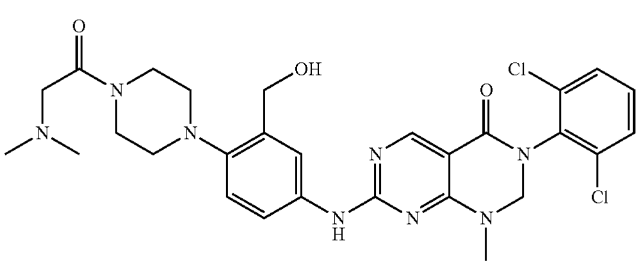 [SMILES: CN(C)CC(=O)N1CCN(c2ccc(Nc3ncc4c(n3)N(C)CN(c3c(Cl)cccc3Cl)C4=O)cc2CO)CC1] | * |  | | ** |

TABLE 1-continued
| Ex | STRUCTURE | Wee-1 | HT29 pCDC2 method 2 | HT29 pCDC2 method 3 | Mics - CLint |
|---|---|---|---|---|---|
| 162 | 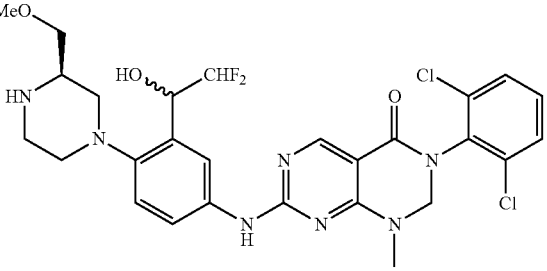 Diastereoisomer 1 | * |  | ** | |
| 163 | 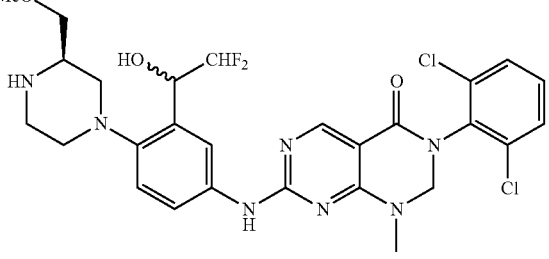 Diastereoisomer 2 | * |  | ** | |
| 164 | 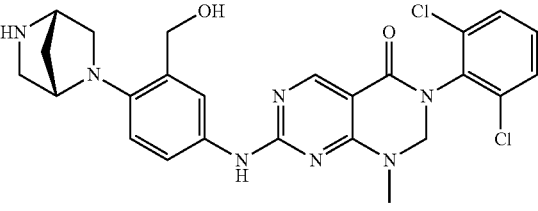 [SMILES: CN1CN(c2c(Cl)cccc2Cl)C(=O)c2cnc(Nc3ccc(N4C[C@@H]5C[C@H]4CN5)c(CO)c3)nc21] | *** | * | | |
| 165 | 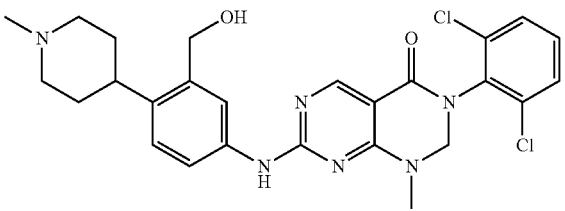 | * |  | *** | |
| 166 | 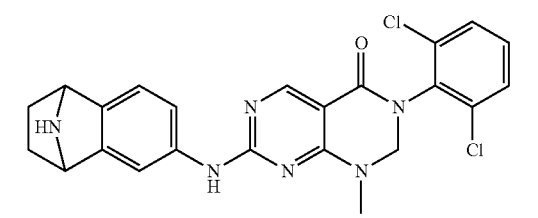 [SMILES: CN1CN(c2c(Cl)cccc2Cl)C(=O)c2cnc(Nc3ccc4c(c3)C3CCC4N3)nc21] | ** | * | | |
| 167 | 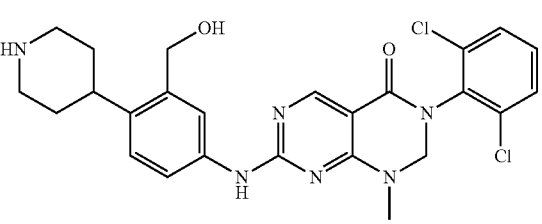 [SMILES: CN1CN(c2c(Cl)cccc2Cl)C(=O)c2cnc(Nc3ccc(C4CCNCC4)c(CO)c3)nc21] | *** | * | *** | |

TABLE 1-continued
| Ex | STRUCTURE | Wee-1 | HT29 pCDC2 method 2 | HT29 pCDC2 method 3 | Mics - CLint |
|---|---|---|---|---|---|
| 168 | 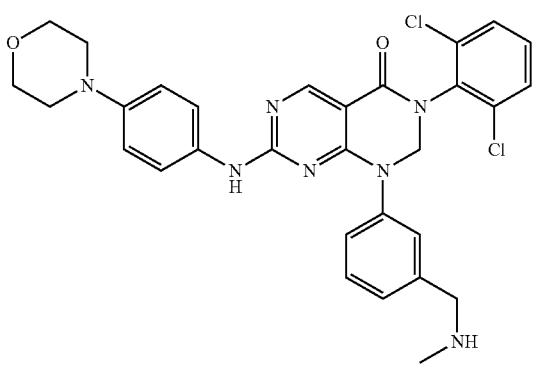 [SMILES: CNCc1cccc(N2CN(c3c(Cl)cccc3Cl)C(=O)c3cnc(Nc4ccc(N5CCOCC5)cc4)nc32)c1] | * |  |  | *** |
| 169 | 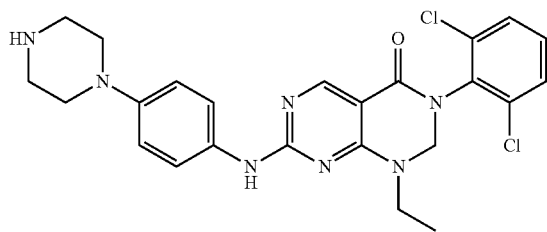 [SMILES: CCN1CN(c2c(Cl)cccc2Cl)C(=O)c2cnc(Nc3ccc(N4CCNCC4)cc3)nc21] | ** |  | * | *** |
| 170 | 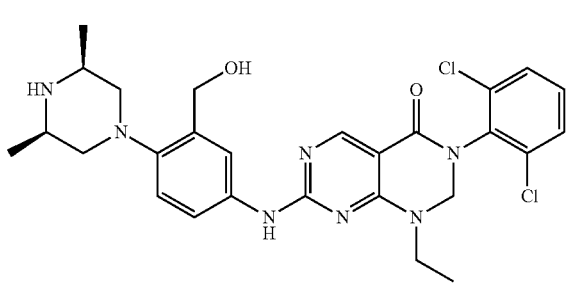 [SMILES: CCN1CN(c2c(Cl)cccc2Cl)C(=O)c2cnc(Nc3ccc(N4C[C@@H](C)N[C@@H](C)C4)c(CO)c3)nc21] | * |  |  | ** |
| 171 | 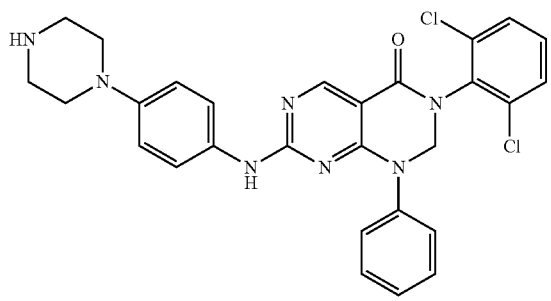 [SMILES: O=C1c2cnc(Nc3ccc(N4CCNCC4)cc3)nc2N(c2ccccc2)CN1c1c(Cl)cccc1Cl] | * |  |  |  |
| 172 | 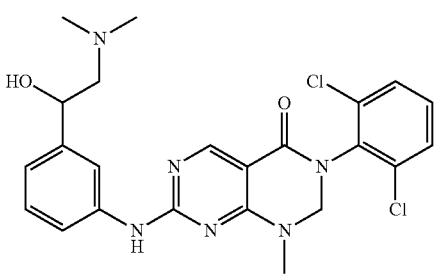 [SMILES: CN(C)CC(O)c1cccc(Nc2ncc3c(n2)N(C)CN(c2c(Cl)cccc2Cl)C3=O)c1] | ** |  | * |  |

TABLE 1-continued

| Ex | STRUCTURE | Wee-1 | HT29 pCDC2 method 2 | HT29 pCDC2 method 3 | Mics - CLint |
|---|---|---|---|---|---|
| 173 | 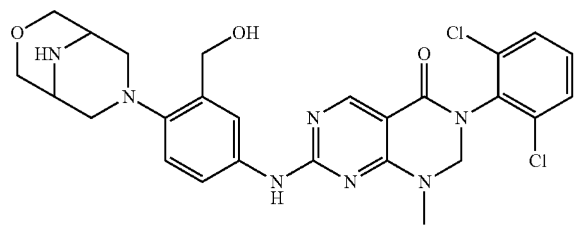 [SMILES: CN1CN(c2c(Cl)cccc2Cl)C(=O)c2cnc(Nc3ccc(N4CC5COCC(C4)N5)c(CO)c3)nc21] | |  |  | |
| 174 | 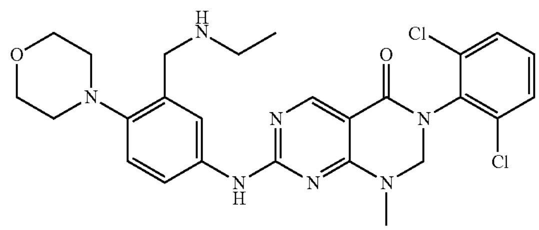 [SMILES: CCNCc1cc(Nc2ncc3c(n2)N(C)CN(c2c(Cl)cccc2Cl)C3=O)ccc1N1CCOCC1] | | ** | * | |
| 175 | 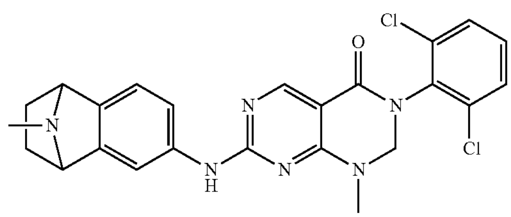 [SMILES: CN1CN(c2c(Cl)cccc2Cl)C(=O)c2cnc(Nc3ccc4c(c3)C3CCC4N3C)nc21] | | * |  | |
| 176 | 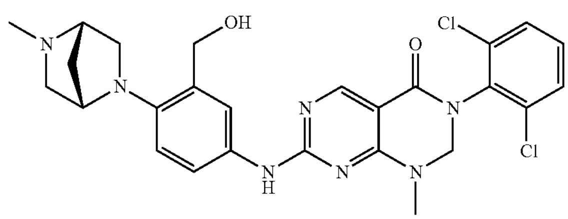 [SMILES: CN1CN(c2c(Cl)cccc2Cl)C(=O)c2cnc(Nc3ccc(N4C[C@@H]5C[C@H]4CN5C)c(CO)c3)nc21] | | * |  | |
| 177 | 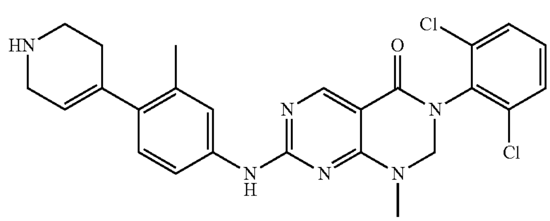 [SMILES: Cc1cc(Nc2ncc3c(n2)N(C)CN(c2c(Cl)cccc2Cl)C3=O)ccc1C1=CCNCC1] | | * |  | |
| 178 | 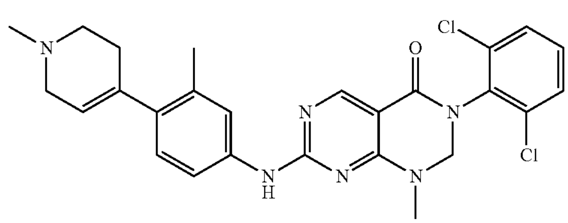 [SMILES: Cc1cc(Nc2ncc3c(n2)N(C)CN(c2c(Cl)cccc2Cl)C3=O)ccc1C1=CCN(C)CC1] | | * |  | |
| 179 | 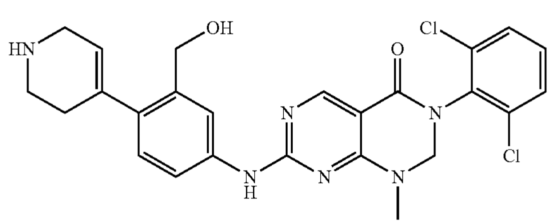 [SMILES: CN1CN(c2c(Cl)cccc2Cl)C(=O)c2cnc(Nc3ccc(C4=CCNCC4)c(CO)c3)nc21] | | *** | * | |

TABLE 1-continued

| Ex | STRUCTURE | Wee-1 | HT29 pCDC2 method 2 | HT29 pCDC2 method 3 | Mics - CLint |
|---|---|---|---|---|---|
| 180 | 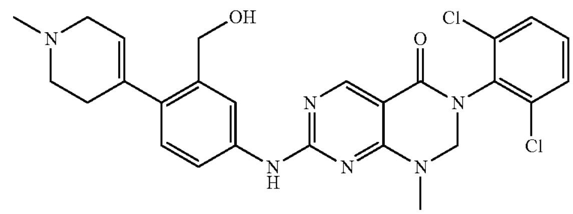 | * | |  | |
| 181 | 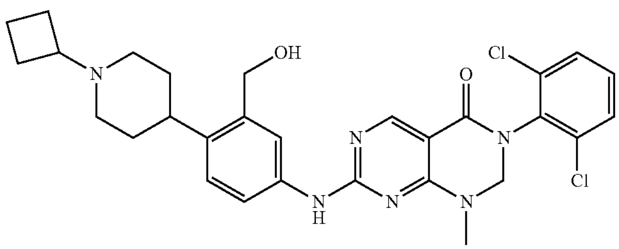 [SMILES: CN1CN(c2c(Cl)cccc2Cl)C(=O)c2cnc(Nc3ccc(C4CCN(C5CCC5)CC4)c(CO)c3)nc21] | * | |  | |
| 182 | 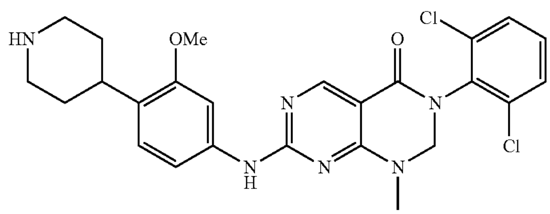 [SMILES: COc1cc(Nc2ncc3c(n2)N(C)CN(c2c(Cl)cccc2Cl)C3=O)ccc1C1CCNCC1] | *** | | | |
| 183 | 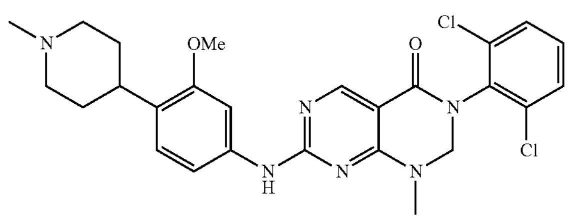 [SMILES: COc1cc(Nc2ncc3c(n2)N(C)CN(c2c(Cl)cccc2Cl)C3=O)ccc1C1CCN(C)CC1] | *** | | | |
| 184 | Diastereoisomer 1 | *** | | * | |
| 185 | Diastereoisomer 2 | *** | | ** | |

For representative examples in Table 1, Wee-1, HT29 pCDC2 and HLM activities are classified as the following:

|  | *** | ** | * |
|---|---|---|---|
| Wee-1 IC$_{50}$ [nM] | ≤10 | 10-100 | ≥100 |
| pCDC2/HT29 [nM] | ≤100 | 100-1000 | ≥1000 |
| HLM CLint [μL/min/mg] | ≤15 | 15-50 | ≥50 |

Experimental Section

Abbreviations aq: aqueous; Boc: Cert-butoxycarbonyl; c-hex: cyclohexane; cv: column volumes; dba: dibenzylideneacetone; DCM: dichloromethane; DIPEA: diisopropylethylamine; DMF: N,N-dimethylformamide; DMSO: dimethylsulfoxide; dppf: 1,1'-bis(diphenylphosphino)ferrocene; EtOAc: ethyl acetate; ESI: electrospray ionisation; h: hour; HATU: 1-[bis(dimethylamino)methylene]-1H-1,2,3-triazolo[4,5-b]pyridinium 3-oxid hexafluorophosphate; HPLC: high pressure liquid chromatography; LC: liquid chromatography; LCMS: liquid chromatography mass spectrometry; M: molar; m/z: mass-to-charge ratio; mCPBA: 3-chloroperbenzoic acid; MeOH: methanol; min: minutes; MS: mass spectrometry; NBS: N-bromosuccinimide; NMR: nuclear magnetic resonance; R$_T$: retention time; RT: room temperature; sat.: saturated; SM: starting material; TFA: trifluoroacetic acid; THF: tetrahydrofuran.

General Experimental Conditions

Solvents and Reagents

Common organic solvents that were used in reactions (e.g. THF, DMF, DCM, and methanol) were purchased anhydrous from Sigma-Aldrich® in Sure/Seal™ bottles and were handled appropriately under nitrogen. Water was deionised using an Elga PURELAB Option-Q. All other solvents used (i.e. for work-up procedures and purification) were generally HPLC grade and were used as supplied from various commercial sources. Unless otherwise stated, all starting materials used were purchased from commercial suppliers and used as supplied.

Microwave Synthesis

Unless quoted otherwise, microwave experiments were carried out using a CEM Discover™/Explorer24™ system controlled by Synergy 1.5 software. In other cases a Biotage Initiator™ Eight was used. Both machines give good reproducibility and control at temperature ranges from 60-250° C. and pressures of up to maximum of 20 bar.

Flash Chromatography

Purification of compounds by flash chromatography was achieved using a Biotage Isolera Four system. Unless otherwise stated, Biotage KP-Sil SNAP or Grace Resolv cartridge columns (10-340 g) were used along with the stated solvent system and an appropriate solvent gradient depending on compound polarity. In the case of more polar and basic compounds, Biotage KP-NH SNAP cartridge columns (11-28 g) were used.

NMR Spectroscopy $^1$H NMR spectra were recorded at ambient temperature using a Bruker Avance (500 MHz) or a Bruker Avance (400 MHz) or a Bruker Avance (300 MHz) spectrometer. All chemical shifts (δ) are expressed in ppm. Residual solvent signals were used as an internal standard and the characteristic solvent peaks were corrected to the reference data outlined in *J. Org. Chem.*, 1997, 62, p 7512-7515; in other cases, NMR solvents contained tetramethylsilane, which was used as an internal standard.

High Pressure Liquid Chromatography

Liquid Chromatography Mass Spectrometry (LCMS) experiments to determine retention times (R$_T$) and associated mass ions were performed using one of the following methods.

Method A:

The system consists of an Agilent Technologies 6140 single quadrupole mass spectrometer linked to an Agilent Technologies 1290 Infinity LC system with UV diode array detector and autosampler. The spectrometer consists of a multimode ionization source (electrospray and atmospheric pressure chemical ionizations) operating in positive and negative ion mode. LCMS experiments were performed on each sample submitted using the following conditions: LC Column: Zorbax Eclipse Plus C18 RRHD 1.8 micron 50×2.1 mm maintained at 40° C. Mobile phases: A) 0.1% (v/v) formic acid in water; B) 0.1% (v/v) formic acid in acetonitrile.

| Gradient Time (min) | Flow (mL/min) | % A | % B |
|---|---|---|---|
| 0.00 | 1.0 | 95 | 5 |
| 1.80 | 1.0 | 0 | 100 |
| 2.20 | 1.0 | 0 | 100 |
| 2.21 | 1.0 | 95 | 5 |
| 2.50 | 1.0 | 95 | 5 |

Method B:

The system consists of a Varian Prostar 1200 LC-MS system using a Phenomenex 50×4.6 mm ID 3 μM C18(2) Luna column. UV detection is carried out at two wavelengths (214 and 254 nM), with mass spectra analysis in positive ionisation mode. Mobile phases: A) 0.05% (v/v) formic acid in water; B) 0.05% (v/v) formic acid in acetonitrile.

| Gradient Time (min) | Flow (mL/min) | % A | % B |
|---|---|---|---|
| 0.00 | 1.0 | 95 | 5 |
| 0.50 | 1.0 | 95 | 5 |
| 4.50 | 1.0 | 0 | 100 |
| 5.50 | 1.0 | 0 | 100 |

Method C:

The system consists of an Agilent Technologies 6130 quadrupole mass spectrometer linked to an Agilent Technologies 1290 Infinity LC system with UV diode array detector and autosampler. The spectrometer consists of an electrospray ionization source operating in positive and negative ion mode. LCMS experiments were performed on each sample submitted using the following conditions: LC Column: Agilent Eclipse Plus C18 RRHD 1.8 micron 50×2.1 mm maintained at 40° C. Mobile phases: A) 0.1% (v/v) formic acid in water; B) 0.1% (v/v) formic acid in acetonitrile.

| Gradient Time (min) | Flow (mL/min) | % A | % B |
|---|---|---|---|
| 0.00 | 0.5 | 80 | 20 |
| 1.80 | 0.5 | 0 | 100 |

-continued

| Gradient Time (min) | Flow (mL/min) | % A | % B |
|---|---|---|---|
| 2.20 | 0.5 | 0 | 100 |
| 2.50 | 0.5 | 80 | 20 |
| 3.00 | 0.5 | 80 | 20 |

Preparative High Pressure Liquid Chromatography

The system consists of an Agilent Technologies 6120 single quadrupole mass spectrometer linked to an Agilent Technologies 1200 Preparative LC system with Multiple Wavelength detector and autosampler. The mass spectrometer uses a multimode ionization source (electrospray and atmospheric pressure chemical ionizations) operating in positive and negative ion mode. Fraction collection was mass-triggered (multimode positive and negative ion). Purification experiments, unless otherwise stated, were performed under basic conditions at an appropriate solvent gradient that was typically determined by the retention time found using HPLC Method A. In cases where the basic conditions were unsuccessful, acidic conditions were employed.

Basic Conditions:

LC Column: Waters XBridge™ Prep C18 5 μm OBD™ 19×50 mm column at RT or Water XBridge™ Prep C18 5 μM OBD™ 30×100 mm column at RT. Mobile phase: A) 0.1% (v/v) ammonium hydroxide in water; B) 0.1% (v/v) ammonium hydroxide in 95:5, acetonitrile/water. Total experiment time was ca. 10 or 20 min and an example method is given:

| Gradient Time (min) | Flow (mL/min) | % A | % B |
|---|---|---|---|
| 0.00 | 20.0 | 50 | 50 |
| 3.00 | 20.0 | 12 | 88 |
| 5.00 | 20.0 | 12 | 88 |
| 7.00 | 20.0 | 0 | 100 |
| 8.0 | 20.0 | 0 | 100 |
| 8.20 | 20.0 | 50 | 50 |

Acidic Conditions:

LC Column: Waters XBridge™ Prep C18 5 μm OBD™ 19×50 mm column at RT or Water XBridge™ Prep C18 5 μM OBD™ 30×100 mm column at RT. Mobile phase: A) Water 0.1% (v/v) formic acid in water; B) 0.1% (v/v) formic acid in 95:5, acetonitrile/water. Total experiment time was ca. 10 or 20 min and an example method is given:

| Gradient Time (min) | Flow (mL/min) | % A | % B |
|---|---|---|---|
| 0.00 | 20.0 | 95 | 5 |
| 7.00 | 20.0 | 0 | 100 |
| 9.00 | 20.0 | 0 | 100 |
| 9.20 | 20.0 | 95 | 5 |

The pure fractions were combined and concentrated using a Genevac EZ-2 Elite, unless stated otherwise.

Nomenclature

Unless otherwise indicated, the nomenclature of structures was determined using the 'Convert Structure to Name' function of ChemBioDraw Ultra 12.0.2 (CambridgeSoft/PerkinElmer).

Mass Ions

For compounds containing chlorine atoms, the ions reported are those containing only the isotope $^{35}$Cl.

Example 1: 3-(2,6-Dichlorophenyl)-1-methyl-7-((4-(piperazin-1-yl)phenyl)amino)-2,3-dihydropyrimido[4,5-d]pyrimidin-4(1H)-one

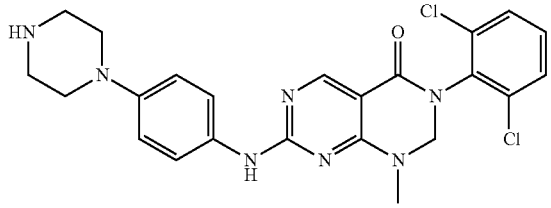 [SMILES: CN1CN(c2c(Cl)cccc2Cl)C(=O)c2cnc(Nc3ccc(N4CCNCC4)cc3)nc21]

Step 1: N-(2,6-Dichlorophenyl)-4-(methylamino)-2-(methylthio)pyrimidine-5-carboxamide 4-(Methylamino)-2-(methylthio)pyrimidine-5-carboxylic acid [*Bioorg. Med. Chem.* 2005, 13 (16), 4936] (0.5 g, 2.51 mmol) was suspended in chlorobenzene (10 mL) and 2,6-dichloroaniline (0.407 g, 2.51 mmol) was added. Phosphorous trichloride (0.220 mL, 2.51 mmol) was added and the mixture was stirred at 120° C. for 16 h. The reaction was quenched with 2 M aqueous $Na_2CO_3$, then extracted with ethyl acetate (×2). The combined organic extracts were washed with brine then dried ($MgSO_4$), filtered and concentrated (azeotroped with toluene). The residue was triturated with diethyl ether and the title compound was collected by filtration to give the title compound as a slightly yellow solid (180 mg, 21%). The mother liquor was concentrated to give a further, slightly less pure sample of the title compound (300 mg; overall yield 56%). $^1$H NMR (500 MHz, DMSO-$d_6$): δ 10.27 (s, 1H), 8.72 (br s, 1H), 8.61 (br s, 1H), 7.60 (m, 2H), 7.45 (m, 1H), 2.96 (s, 3H), SMe peak presumably masked by solvent. LCMS (Method A): $R_T$=1.24 min, m/z=343 [M+H]$^+$.

Step 2: 3-(2,6-Dichlorophenyl)-1-methyl-7-(methylthio)-2,3-dihydropyrimido[4,5-d]pyrimidin-4(1H)-one N-(2,6-Dichlorophenyl)-4-(methylamino)-2-(methylthio)pyrimidine-5-carboxamide (500 mg, 1.46 mmol) was suspended in acetonitrile (10 mL) and cesium carbonate (1.90 g, 5.83 mmol) was added. Dibromomethane (0.304 mL, 4.37 mmol) was added and the reaction was stirred at 80° C. for 16 h. The mixture was diluted with water then extracted with ethyl acetate (×3). The combined organic extracts were washed with brine then dried ($Na_2SO_4$), filtered and concentrated. The residue was chromatographed (Isolera 10 g; eluted 0-70% EtOAc/c-hex over 20 cv) to give the title compound as a crystalline white solid (190 mg, 37%). $^1$H NMR (500 MHz, CDCl$_3$): δ 8.72 (s, 1H), 7.44 (d, 2H), 7.30 (t, 1H), 4.91 (s, 2H), 3.20 (s, 3H), 2.58 (s, 3H). LCMS (Method A): $R_T$=1.29 min, m/z=355 [M+H]$^+$.

Step 3: 3-(2,6-Dichlorophenyl)-1-methyl-7-((4-(piperazin-1-yl)phenyl)amino)-2,3-dihydropyrimido[4,5-d]pyrimidin-4(1H)-one 3-(2,6-Dichlorophenyl)-1-methyl-7-(methylthio)-2,3-dihydropyrimido[4,5-d]pyrimidin-4(1H)-one (30 mg, 0.084 mmol) was suspended in toluene (2 mL) and mCPBA (34.4 mg, 0.110 mmol) was added as a suspension in toluene (2 mL) at RT. After 15 minutes DIPEA (0.044 mL, 0.253 mmol) was added, followed by tert-butyl 4-(4-aminophenyl)piperazine-1-carboxylate [Activate Scientific] (23.4 mg, 0.084 mmol). The resulting mixture was heated at 80° C. for 1 h, then concentrated in vacuo and azeotroped with ethyl acetate. The residue was chromatographed (Isolera 10 g; eluted 0-90% EtOAc/c-hex over 20 cv) to give a semi-solid material. This was suspended in diethyl ether and a yellow solid was collected by filtration. The solid was dissolved in DCM (1 mL) and TFA (1 mL) was added. The mixture was stirred for 30 min then concentrated. The residue was dissolved in methanol and added to a 2 g SCX-2 cartridge. The column was washed with methanol then eluted with 2 M NH$_3$/MeOH. The basic fraction was concentrated to give a waxy solid. This was suspended in diethyl ether and the solid collected by filtration to give the title compound as a white solid (7 mg, 17%). $^1$H NMR (500 MHz, DMSO-d$_6$): δ 9.70 (s, 1H), 8.42 (s, 1H), 7.63 (m, 4H), 7.48 (m, 1H), 6.90 (d, 2H), 4.95 (s, 2H), 3.10 (s, 3H), 2.97 (m, 4H), 2.81 (m, 4H). LCMS (Method A): R$_T$=0.71 min, m/z=484 [M+H]$^+$.

Example 2: 3-(2,6-Dichlorophenyl)-1-methyl-7-((4-(2-(methylamino)ethoxy)phenyl)amino)-2,3-dihydropyrimido[4,5-d]pyrimidin-4(1H)-one

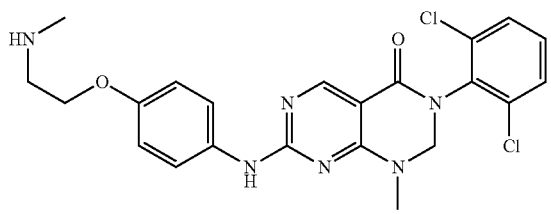 [SMILES: CNCCOc1ccc(Nc2ncc3c(n2)N(C)CN(c2c(Cl)cccc2Cl)C3=O)cc1]

3-(2,6-Dichlorophenyl)-1-methyl-7-(methylthio)-2,3-dihydropyrimido[4,5-d]pyrimidin-4(1H)-one (82 mg, 0.231 mmol) was reacted with tert-butyl (2-(4-aminophenoxy)ethyl)(methyl)carbamate (61.5 mg, 0.231 mmol) following the procedure for Example 1 to give the title compound as a white solid (27 mg, 24%). $^1$H NMR (500 MHz, DMSO-d$_6$): δ 9.71 (s, 1H), 8.45 (s, 1H), 7.69 (m, 4H), 7.47 (m, 1H), 6.89 (d, 2H), 4.88 (s, 2H), 3.97 (m, 2H), 3.10 (s, 3H), 2.81 (t, 2H), 2.32 (s, 3H). LCMS (Method A): R$_T$=0.77 min, m/z=473 [M+H]$^+$.

Example 3: 3-(2,6-Dichlorophenyl)-7-((3-methoxy-4-(piperazin-1-yl)phenyl)amino)-1-methyl-2,3-dihydropyrimido[4,5-d]pyrimidin-4(1H)-one

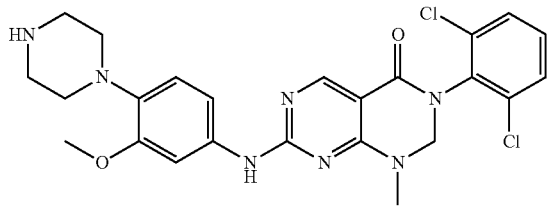 [SMILES: COc1cc(Nc2ncc3c(n2)N(C)CN(c2c(Cl)cccc2Cl)C3=O)ccc1N1CCNCC1]

3-(2,6-Dichlorophenyl)-1-methyl-7-(methylthio)-2,3-dihydropyrimido[4,5-d]pyrimidin-4(1H)-one (50 mg, 0.141 mmol) was reacted with tert-butyl 4-(4-amino-2-methoxyphenyl)piperazine-1-carboxylate (43 mg, 0.14 mmol) following the procedure for Example 1 to give the title compound as an off-white solid (34 mg, 47%). $^1$H NMR (500 MHz, DMSO-d$_6$): δ 9.75 (s, 1H), 8.48 (s, 1H), 7.65 (m, 3H), 7.47 (m, 1H), 7.21 (d, 1H), 6.85 (d, 1H), 4.97 (s, 2H), 3.69 (s, 3H), 3.13 (s, 3H), 2.92 (m, 8H). LCMS (Method A): R$_T$=0.75 min, m/z=514 [M+H]$^+$.

Example 4: 2-(4-(4-((6-(2,6-Dichlorophenyl)-8-methyl-5-oxo-5,6,7,8-tetrahydropyrimido[4,5-d]pyrimidin-2-yl)amino)phenyl)piperazin-1-yl)acetic acid hydrochloride

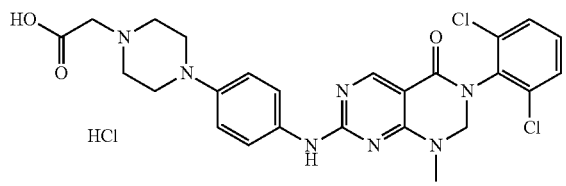 [SMILES: CN1CN(c2c(Cl)cccc2Cl)C(=O)c2cnc(Nc3ccc(N4CCN(CC(=O)O)CC4)cc3)nc21 ; Cl]

Step 1: tert-Butyl 2-(4-(4-nitrophenyl)piperazin-1-yl)acetate 1-(4-Nitrophenyl)piperazine (3 g, 14.5 mmol) was dissolved in acetonitrile (25 mL) and cesium carbonate (6.43 g, 19.7 mmol) was added, followed by tert-butyl 2-bromoacetate (1.95 mL, 13.2 mmol). The reaction mixture was stirred at room temperature for 1 h, then concentrated in vacuo. The residue was taken up in dichloromethane and washed sequentially with aqueous NaHCO3, water and brine. The organic component was dried using a phase separator cartridge then concentrated to give the title compound (3.5 g, 85%) which was used as obtained without further purification. LCMS (Method A): R$_T$=0.90 min, m/z=322 [M+H]$^+$.

Step 2: tert-Butyl 2-(4-(4-aminophenyl)piperazin-1-yl)acetate tert-Butyl 2-(4-(4-nitrophenyl)piperazin-1-yl)acetate (1.5 g, 4.67 mmol) was dissolved in ethanol (50 mL) and 10% palladium on carbon (0.497 g, 0.467 mmol) was added under a nitrogen atmosphere. Ammonium formate (2.94 g, 46.7 mmol) was added and the mixture was heated to 40° C. An additional portion of ammonium formate (2.94 g, 46.7 mmol) was added and the resulting mixture stirred at 40° C. for 16 h. The mixture was filtered through Celite® and concentrated in vacuo. The residue was taken up in aqueous sodium bicarbonate and extracted with dichloromethane (×3). The combined organic extracts were dried over Na$_2$SO$_4$ then filtered and concentrated in vacuo. The residue was chromatographed (Isolera 50 g Si; eluted 1:1 CH$_2$Cl$_2$:EtOAc) to give the title compound (1.2 g, 88%) which was used without further purification.

Step 3: 2-(4-(4-((6-(2,6-Dichlorophenyl)-8-methyl-5-oxo-5,6,7,8-tetrahydropyrimido[4,5-d]pyrimidin-2-yl)amino)phenyl)piperazin-1-yl)acetic acid hydrochloride 3-(2,6-Dichlorophenyl)-1-methyl-7-(methylthio)-2,3-dihydropyrimido[4,5-d]pyrimidin-4(1H)-one (50 mg, 0.141 mmol) was suspended in toluene (1 mL) and mCPBA (57.4 mg, 0.183 mmol) was added as a suspension in toluene (1 mL) at RT. The mixture was stirred at RT for 15 minutes. DIPEA (0.074 mL, 0.422 mmol) was added, followed by tert-butyl 2-(4-(4-aminophenyl)piperazin-1-yl)acetate (41 mg, 0.141 mmol). The resulting mixture was heated at 80° C. for 16 h then concentrated in vacuo. The residue was chromatographed (Isolera 10 g Si; eluted 0-90% EtOAc/C-hex over 20 cv) to give a yellow oil. This was triturated with diethyl ether to give an off-white solid, which was suspended in 1 mL 4 M HCl in dioxane and heated at 70° C. for 16 h. The mixture was concentrated in vacuo, at which point NMR indicated deprotection was not complete. The residue was dissolved in 2 mL 2 M HCl in water and heated at 60° C. for 3 h, then concentrated in vacuo and azeotroped with toluene (×3). The residual glass was dissolved in acetonitrile/water and lyophilized to give the title compound as a yellow solid (24 mg, 32%). $^1$H NMR (500 MHz, DMSO-d$_6$): δ 10.40 (s, 1H), 10.05 (s, 1H), 8.46 (s, 1H), 7.77 (m, 4H), 7.50 (t, 1H), 7.00 (d, 2H), 5.01 (s, 2H), 4.22 (s, 2H), 3.85 (m, 8H), 3.12 (s, 3H). LCMS (Method A): R$_T$=0.74 min, m/z=542 [M+H]$^+$.

Example 5: 3-(2,6-Dichlorophenyl)-1-methyl-7-((3-((methylamino)methyl)-4-morpholinophenyl)amino)-2,3-dihydropyrimido[4,5-d]pyrimidin-4(1H)-one

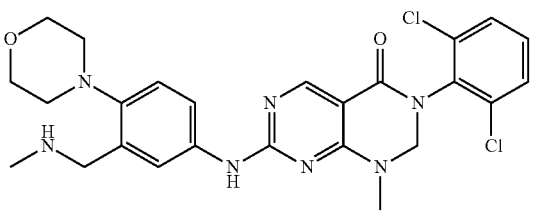 [SMILES: CNCc1cc(Nc2ncc3c(n2)N(C)CN(c2c(Cl)cccc2Cl)C3=O)ccc1N1CCOCC1]

Step 1: 2-Morpholino-5-nitrobenzaldehyde

To a solution of 2-chloro-5-nitrobenzaldehyde (3.00 g, 16.2 mmol) in DMF (20 mL) was added DIPEA (4.24 mL, 24.3 mmol) and morpholine (1.55 g, 17.8 mmol). The reaction mixture was stirred at 90° C. for 4 h. The reaction was cooled to RT and water was added. The mixture was extracted with EtOAc. The organic layer was washed with brine, dried over Na$_2$SO$_4$, filtered, and the solvents were removed in vacuo to give the title compound (crude 3.2 g, 85%), which was used in the next step without further purification. LCMS (Method A): R$_T$=0.99 min, m/z=237 [M+H]$^+$.

Step 2: N-Methyl-1-(2-morpholino-5-nitrophenyl)methanamine

To a suspension of sodium bicarbonate (0.356 g, 4.23 mmol) in MeOH (6 mL) was added 2-morpholino-5-nitrobenzaldehyde (0.5 g, 2.12 mmol) and methylamine (2 M in MeOH) (1.27 mL, 2.54 mmol). The reaction mixture was stirred at 70° C. After 4 h, the reaction was cooled to 0° C. and sodium borohydride (0.096 g, 2.54 mmol) was added. The reaction was stirred at RT for 2 h. A few drops of water were added and the solvents were removed in vacuo. The remaining residue was partitioned between DCM and brine, separated, extracted using further DCM, dried over Na$_2$SO$_4$, filtered, and the solvents were removed in vacuo to give the title compound (crude, 450 mg, 85%), which was used in the next step without further purification. LCMS (Method A): R$_T$=0.47 min, m/z=221 [M+H−30(CH$_3$NH)]$^+$.

Step 3: tert-Butyl methyl(2-morpholino-5-nitrobenzyl)carbamate

To a solution of N-methyl-1-(2-morpholino-5-nitrophenyl)methanamine (450 mg, 1.79 mmol) in THF (5 mL) was added triethylamine (0.50 mL, 3.58 mmol) and Boc$_2$O (0.46 mL, 1.97 mmol). The reaction mixture was stirred at RT for 16 h. Water was added and the reaction mixture was extracted using EtOAc. The combined organic phase was washed using water and brine, dried over Na$_2$SC$_4$, filtered, and the solvents were removed in vacuo to give the title compound (crude, 622 mg, 99%), which was used in the next step without further purification. LCMS (Method A): R$_T$=1.39 min, m/z=296 [M+H−56($^t$Bu)]$^+$.

Step 4: tert-Butyl 5-amino-2-morpholinobenzyl(methyl)carbamate

To a solution of tert-butyl methyl(2-morpholino-5-nitrobenzyl)carbamate (640 mg, 1.82 mmol) in ethanol (4 mL) was added 10% palladium on carbon (194 mg, 0.182 mmol) and ammonium formate (230 mg, 3.64 mmol). The reaction mixture was stirred at 60° C. for 3 h. The mixture was filtered through Celite® and the filtrate was concentrated in vacuo. The remaining residue was partitioned between EtOAc and sat. sodium bicarbonate (aq) solution, the organic phase was washed using brine, dried over Na$_2$SO$_4$, filtered, and the solvents were removed in vacuo to give the title compound (crude, 580 mg, 99%), which was used in the next step without further purification. LCMS (Method A): R$_T$=0.83 min, m/z=322 [M+H]$^+$.

Step 5: 3-(2,6-Dichlorophenyl)-1-methyl-7-((3-((methylamino)methyl)-4-morpholinophenyl)amino)-2,3-dihydropyrimido[4,5-d]pyrimidin-4(1H)-one 3-(2,6-Dichlorophenyl)-1-methyl-7-(methylthio)-2,3-dihydropyrimido[4,5-d]pyrimidin-4(1H)-one (50 mg, 0.141 mmol) was reacted with tert-butyl 5-amino-2-morpholinobenzyl(methyl)carbamate (45.2 mg, 0.141 mmol) following the procedure for Example 1 to give the title compound as a white solid (6 mg, 8%). $^1$H NMR (500 MHz, DMSO-d$_6$): δ 9.49 (s, 1H), 8.45 (s, 1H), 7.85 (s, 1H), 7.65 (m, 2H), 7.57 (d, 1H), 7.47 (t, 1H), 7.05 (d, 1H), 4.96 (s, 2H), 3.97 (m, 4H), 3.69 (s, 2H), 3.12 (s, 3H), 2.82 (m, 4H), 2.31 (s, 3H). LCMS (Method A): R$_T$=0.85 min, m/z=528 [M+H]$^+$.

Example 6: 3-(2,6-Dichlorophenyl)-1-methyl-7-((3-methyl-4-(piperazin-1-yl)phenyl)amino)-2,3-dihydropyrimido[4,5-d]pyrimidin-4(1H)-one

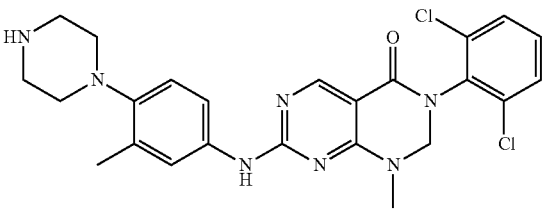 [SMILES: Cc1cc(Nc2ncc3c(n2)N(C)CN(c2c(Cl)cccc2Cl)C3=O)ccc1N1CCNCC1]

3-(2,6-Dichlorophenyl)-1-methyl-7-(methylthio)-2,3-dihydropyrimido[4,5-d]pyrimidin-4(1H)-one (50 mg, 0.141 mmol) was reacted with tert-butyl 4-(4-amino-2-methylphenyl)piperazine-1-carboxylate (41 mg, 0.141 mmol) following the procedure for Example 1 to give the title compound as an off-white solid (14 mg, 20%). $^1$H NMR (500 MHz, DMSO-$d_6$): δ 9.70 (s, 1H), 8.46 (s, 1H), 7.68 (m, 2H), 7.56 (m, 2H), 7.47 (m, 2H), 6.97 (d, 2H), 4.96 (s, 2H), 3.08 (s, 3H), 2.81 (m, 4H), 2.72 (m, 4H), 2.23 (s, 3H). LCMS (Method A): $R_T$=0.78 min, m/z=499 [M+H]$^+$.

Example 7: 3-(2,6-Dichlorophenyl)-7-((3-fluoro-4-(piperazin-1-yl)phenyl)amino)-1-methyl-2,3-dihydropyrimido[4,5-d]pyrimidin-4(1H)-one

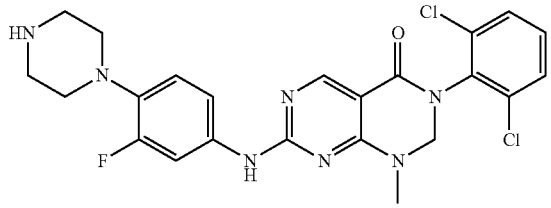

3-(2,6-Dichlorophenyl)-1-methyl-7-(methylthio)-2,3-dihydropyrimido[4,5-d]pyrimidin-4(1H)-one (50 mg, 0.141 mmol) was reacted with tert-butyl 4-(4-amino-2-fluorophenyl)piperazine-1-carboxylate (42 mg, 0.141 mmol) following the procedure for Example 1 to give the title compound as an off-white solid (22 mg, 31%). $^1$H NMR (500 MHz, DMSO-$d_6$): δ 9.87 (s, 1H), 8.48 (s, 1H), 7.74 (m, 3H), 7.45 (m, 2H), 6.96 (t, 1H), 4.96 (s, 2H), 3.11 (s, 3H), 2.85 (m, 8H). LCMS (Method A): $R_T$=0.76 min, m/z=503 [M+H]$^+$.

Example 8: 3-(2,6-Dichlorophenyl)-1-(4-methoxybenzyl)-7-((4-(piperazin-1-yl)phenyl)amino)-2,3-dihydropyrimido[4,5-d]pyrimidin-4(1H)-one

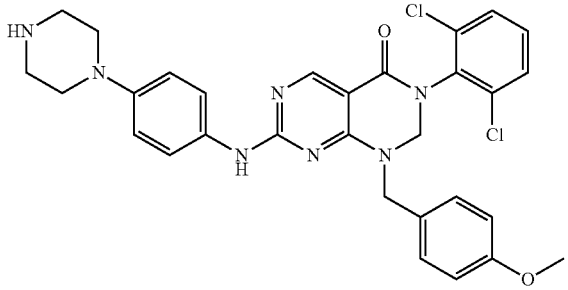 [SMILES: COc1ccc(CN2CN(c3c(Cl)cccc3Cl)C(=O)c3cnc(Nc4ccc(N5CCNCC5)cc4)nc32)cc1]

Step 1: 4-((4-Methoxybenzyl)amino)-2-(methylthio)pyrimidine-5-carboxylic acid

Ethyl 4-chloro-2-(methylthio)pyrimidine-5-carboxylate (3 g, 12.9 mmol) was dissolved in DMF (10 mL) and cooled to 0° C. A solution of triethylamine (2 mL, 14.4 mmol) and (4-methoxyphenyl)methanamine (1.85 mL, 14.2 mmol) in DMF (10 mL) was added slowly. The mixture was stirred for 1 h then poured into ice/10% citric acid solution. The mixture was extracted with ethyl acetate (×2). The combined organic layers were washed with citric acid solution then brine, then dried with MgSO$_4$, filtered and concentrated in vacuo. The residue was azeotroped with cyclohexane/DCM to give a syrup which crystallised to yield 5.20 g of a white solid on standing. This was dissolved in ethanol (25 mL) and 2 M NaOH (25 mL) and the solution was stirred overnight. The mixture was concentrated in vacuo, then acidified (2 M HCl). The precipitated solid was collected by filtration, then dried in vacuo to give the title compound as a white solid (4.1 g, quantitative). $^1$H NMR (500 MHz, DMSO-$d_6$): δ 13.30 (br s, 1H), 8.85 (t, 1H), 8.53 (s, 1H), 7.29 (t, 2H), 6.90 (t, 2H), 4.63 (d, 2H), 3.74 (s, 3H), 2.45 (s, 3H). LCMS (Method A): $R_T$=1.05 min, m/z=306 [M+H]$^+$.

Step 2: N-(2,6-Dichlorophenyl)-4-((4-methoxybenzyl)amino)-2-(methylthio)pyrimidine-5-carboxamide 4-((4-Methoxybenzyl)amino)-2-(methylthio)pyrimidine-5-carboxylic acid (4.1 g, 13.4 mmol) was suspended in chlorobenzene (30 mL). 2,6-Dichloroaniline (2.18 g, 13.4 mmol) was added followed by phosphorous trichloride (1.18 mL, 13.4 mmol). The mixture was stirred at 120° C. for 60 h. The reaction was quenched with Na$_2$CO$_3$ and ethyl acetate was added. The insoluble solid was collected by filtration. The biphasic mother liquor was extracted with DCM (×3). The combined organic layers were dried (MgSO$_4$), filtered and concentrated to a syrup which solidified on standing overnight. This was combined with the solid collected by filtration. The combined material was suspended in diethyl ether and sonicated, then the solid was collected by filtration to give the title compound (3.19 g, 53%) as an off-white solid which was used without further purification. $^1$H NMR (500 MHz, DMSO-$d_6$): δ 9.05 (s, 1H), 8.77 (s, 1H), 7.58 (d, 2H), 7.41 (m, 2H), 7.27 (d, 2H), 6.88 (d, 2H), 4.60 (d, 2H), 3.72 (s, 3H). LCMS (Method A): $R_T$=1.49 min, m/z=449 [M+H]$^+$.

Step 3: 3-(2,6-Dichlorophenyl)-1-(4-methoxybenzyl)-7-(methylthio)-2,3-dihydropyrimido[4,5-d]pyrimidin-4(1H)-one N-(2,6-Dichlorophenyl)-4-((4-methoxybenzyl)amino)-2-(methylthio)pyrimidine-5-carboxamide (760 mg, 1.69 mmol) was suspended in acetonitrile (20 mL) and cesium carbonate (2.76 g, 8.46 mmol) was added. The mixture was stirred at RT for 10 min. Diiodomethane (0.341 mL, 4.23 mmol) was added and the mixture stirred for 1 h at 70° C. A further portion of diiodomethane (0.341 mL, 4.23 mmol) was added and the mixture was stirred a further 1 h at 80° C. The mixture was diluted with water and extracted with dichloromethane (×2). The combined organic layers were washed with brine then dried (MgSO$_4$), filtered and concentrated in vacuo. The residue was chromatographed (Isolera 25 g; eluted 0-80% EtOAc/c-hex) to give the title compound as a sticky glass (125 mg, 16%) which was used directly without further purification. LCMS (Method A): $R_T$=1.48 min, m/z=461 [M+H]$^+$.

Step 4: 3-(2,6-Dichlorophenyl)-1-(4-methoxybenzyl)-7-((4-(piperazin-1-yl)phenyl)amino)-2,3-dihydropyrimido[4,5-d]pyrimidin-4(1H)-one 3-(2,6-Dichlorophenyl)-1-(4-methoxybenzyl)-7-(methylthio)-2,3-dihydropyrimido[4,5-d]pyrimidin-4(1H)-one (123 mg, 0.267 mmol) was suspended in toluene (1 mL) and mCPBA (109 mg, 0.347 mmol) was added as a suspension in toluene (1 mL). The mixture was stirred at RT for 15 minutes, then DIPEA (0.140 mL, 0.800 mmol) was added followed by tert-butyl 4-(4-aminophenyl)piperazine-1-carboxylate (73.9 mg, 0.267 mmol). The mixture was heated at 80° C. for 4 h, then cooled and concentrated in vacuo. The residue was chromatographed (Isolera 10 g; eluted 0-80% EtOAc/c-hex over 20 cv) to give a yellow glass. This was dissolved in DCM (1 mL) and TFA (1 mL) and stirred for 1 h at RT, then concentrated in vacuo. The residue was dissolved in methanol and added to a 2 g SCX-2 cartridge. The column was washed with methanol, then eluted with 2 M $NH_3$/MeOH and the solvent was concentrated in vacuo to give a yellow glass. This was triturated with ethyl acetate to give the title compound as an orange solid (43 mg, 27%). $^1$H NMR (500 MHz, DMSO-$d_6$): δ 9.70 (s, 1H), 8.49 (s, 1H), 7.62 (d, 2H), 7.54 (d, 2H), 7.45 (m, 1H), 7.35 (d, 2H), 6.87 (m, 4H), 4.90 (s, 2H), 4.77 (s, 2H), 3.71 (s, 3H), 2.96 (m, 4H), 2.80 (m, 4H). LCMS (Method A): $R_T$=0.97 min, m/z=590 $[M+H]^+$.

Example 9: 3-(2,6-Dichlorophenyl)-7-((4-(piperazin-1-yl)phenyl)amino)-2,3-dihydropyrimido[4,5-d]pyrimidin-4(1H)-one

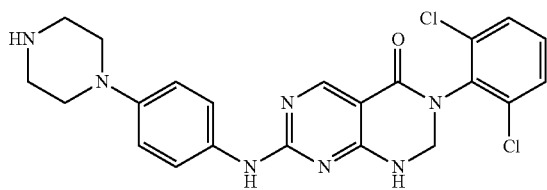 [SMILES: O=C1c2cnc(Nc3ccc(N4CCNCC4)cc3)nc2NCN1c1c(Cl)cccc1Cl]

3-(2,6-Dichlorophenyl)-1-(4-methoxybenzyl)-7-((4-(piperazin-1-yl)phenyl)amino)-2,3-dihydropyrimido[4,5-d]pyrimidin-4(1H)-one (35 mg, 0.059 mmol) was dissolved in TFA (2 mL, 26.0 mmol) in a microwave tube. The tube was sealed and heated at 150° C. for 20 min in the microwave. The mixture was concentrated in vacuo. The residue was dissolved in methanol and added to a 5 g SCX-2 cartridge. The column was washed with methanol then eluted with 2 M $NH_3$/MeOH and concentrated in vacuo. The residue was chromatographed (Isolera KP-NH 11 g; eluted 0-100% EtOAc/c-hex; then 0-25% MeOH/EtOAc over 25 cv) to give a glassy solid. This was triturated with diethyl ether to give the title compound as an off-white solid (6 mg, 21%). $^1$H NMR (500 MHz, DMSO-$d_6$): δ 9.52 (s, 1H), 8.46 (m, 1H), 8.25 (m, 1H), 7.57 (m, 4H), 7.46 (t, 1H), 6.87 (d, 1H), 4.89 (s, 2H), 2.98 (m, 4H), 2.83 (m, 4H). LCMS (Method A): $R_T$=0.62 min, m/z=470 $[M+H]^+$.

Example 10: 3-(2,6-Dichlorophenyl)-7-((3-(hydroxymethyl)-4-(piperazin-1-yl)phenyl)amino)-1-methyl-2,3-dihydropyrimido[4,5-d]pyrimidin-4(1H)-one

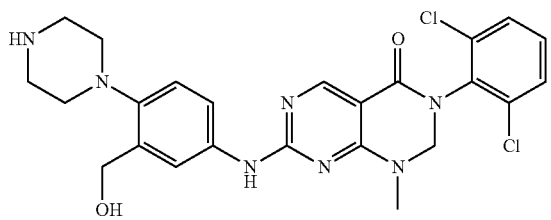 [SMILES: CN1CN(c2c(Cl)cccc2Cl)C(=O)c2cnc(Nc3ccc(N4CCNCC4)c(CO)c3)nc21]

Step 1: tert-Butyl 4-(4-amino-2-(hydroxymethyl)phenyl)piperazine-1-carboxylate

Ammonium formate (1.47 g, 23.2 mmol) was added carefully [Note: exothermic] to a stirred solution of tert-butyl 4-(2-(hydroxymethyl)-4-nitrophenyl)piperazine-1-carboxylate (1.57 g, 4.65 mmol) [J. Med. Chem., 2011, 54(13), 4638-4658] and 10% palladium on carbon (0.247 g, 0.232 mmol) in ethanol (15 mL) in a 100 mL round-bottomed flask at RT under nitrogen. After 16 h, the reaction mixture was filtered through Celite® and the solvents were removed in vacuo. The remaining residue was partitioned between sat. sodium bicarbonate (aq) solution (30 mL) and DCM (30 mL), separated, and extracted using further DCM (2×15 mL). The combined organic phase was dried (Phase Separator) and the solvents were removed in vacuo to give the title compound (1.40 g, 98%) as a pale brown foam. LCMS (Method A): $R_T$=0.72 min, m/z=308 $[M+H]^+$.

Step 2: 3-(2,6-Dichlorophenyl)-7-((3-(hydroxymethyl)-4-(piperazin-1-yl)phenyl)amino)-1-methyl-2,3-dihydropyrimido[4,5-d]pyrimidin-4(1H)-one 3-(2,6-Dichlorophenyl)-1-methyl-7-(methylthio)-2,3-dihydropyrimido[4,5-d]pyrimidin-4(1H)-one (58 mg, 0.163 mmol) was reacted with tert-butyl 4-(4-amino-2-(hydroxymethyl)phenyl)piperazine-1-carboxylate (55.2 mg, 0.180 mmol) following the procedure for Example 1 to give the title product (10 mg, 12%) as a beige solid. $^1$H NMR (400 MHz, DMSO-$d_6$): δ 9.80 (s, 1H), 8.46 (s, 1H), 7.99 (s, 1H), 7.65 (d, 2H), 7.57 (d, 1H), 7.48 (t, 1H), 7.01 (d, 1H), 5.07 (t, 1H), 4.98 (s, 2H), 4.66 (d, 2H), 3.14 (s, 3H), 2.78 (m, 4H), 2.70 (m, 4H). LCMS (Method B): $R_T$=2.20 min, m/z=514 $[M+H]^+$.

Example 11: 3-(2,6-Dichlorophenyl)-7-((3-cyano-4-(piperazin-1-yl)phenyl)amino)-1-methyl-2,3-dihydropyrimido[4,5-d]pyrimidin-4(1H)-one

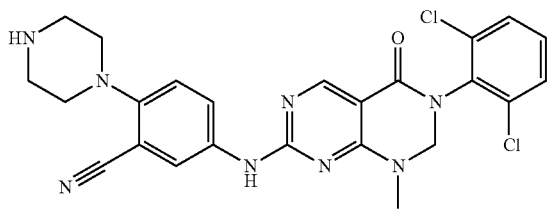 [SMILES: CN1CN(c2c(Cl)cccc2Cl)C(=O)c2cnc(Nc3ccc(N4CCNCC4)c(C#N)c3)nc21]

3-(2,6-Dichlorophenyl)-1-methyl-7-(methylthio)-2,3-dihydropyrimido[4,5-d]pyrimidin-4(1H)-one (75 mg, 0.211 mmol) was reacted with tert-butyl 4-(4-amino-2-cyanophenyl)piperazine-1-carboxylate (70.2 mg, 0.232 mmol) following the procedure for Example 1 to give the title compound as a white solid (15 mg, 14%). $^1$H NMR (400 MHz, DMSO-$d_6$): δ 10.05 (s, 1H), 8.51 (s, 1H), 8.15 (s, 1H), 7.94 (d, 1H), 7.68 (d, 2H), 7.52 (t, 1H), 7.16 (d, 1H), 5.01 (s, 2H), 3.13 (s, 3H), 2.99 (m, 4H), 2.85 (m, 4H). LCMS (Method B): $R_T$=3.35 min, m/z=509 $[M+H]^+$.

Example 12: 3-(2,6-Dichlorophenyl)-1-methyl-7-((4-(piperazin-1-ylmethyl)phenyl)amino)-2,3-dihydropyrimido[4,5-d]pyrimidin-4(1H)-one

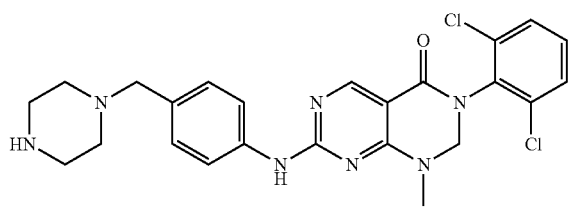

3-(2,6-Dichlorophenyl)-1-methyl-7-(methylthio)-2,3-dihydropyrimido[4,5-d]pyrimidin-4(1H)-one (75 mg, 0.211 mmol) was reacted with tert-butyl 4-(4-aminobenzyl)piperazine-1-carboxylate (67.7 mg, 0.232 mmol) following the procedure for Example 1 to give the title compound as a white solid (15 mg, 14%). ¹H NMR (400 MHz, CDCl₃): δ 8.73 (s, 1H), 7.61 (d, 2H), 7.44 (d, 2H), 7.31 (m, 4H), 4.90 (s, 2H), 3.48 (s, 2H), 3.20 (s, 3H), 2.90 (m, 4H), 2.44 (m, 4H). LCMS (Method B): $R_T$=3.38 min, m/z=498 [M+H]⁺.

Example 13: 7-((4-(4-(2-Aminoacetyl)piperazin-1-yl)phenyl)amino)-3-(2,6-dichlorophenyl)-1-methyl-2,3-dihydropyrimido[4,5-d]pyrimidin-4(1H)-one

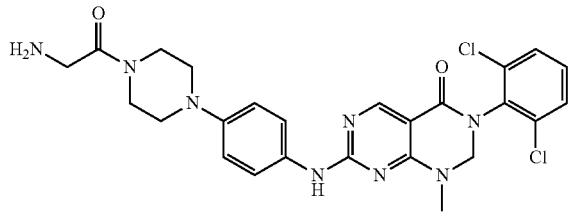 [SMILES: CN1CN(c2c(Cl)cccc2Cl)C(=O)c2cnc(Nc3ccc(N4CCN(C(=O)CN)CC4)cc3)nc21]

3-(2,6-Dichlorophenyl)-1-methyl-7-((4-(piperazin-1-yl)phenyl)amino)-2,3-dihydropyrimido[4,5-d]pyrimidin-4(1H)-one (85 mg, 0.175 mmol) was suspended in THF (1 mL) and pyridine (0.1 mL, 1.24 mmol). N-Boc-glycine (32.3 mg, 0.184 mmol) was added, followed by HATU (73.4 mg, 0.193 mmol) and the mixture was stirred at RT for 16 h then concentrated in vacuo. The residue was chromatographed (Isolera 10 g; eluted 0-100% EtOAc/c-hex then 0-15% MeOH/EtOAc) to give a yellow glass. This was dissolved in DCM (1 mL) and TFA (1 mL) and stirred at RT for 30 min, then concentrated in vacuo. The residue was dissolved in MeOH and added to a 5 g SCX-2 cartridge. The column was washed with methanol then eluted with 2 M NH₃/MeOH and the solvent was concentrated in vacuo to give a yellow glass. This was triturated with ethyl acetate and the solid collected by filtration and dried in vacuo to give the title compound as a beige solid (54 mg, 57%). ¹H NMR (400 MHz, DMSO-d₆): δ 9.72 (s, 1H), 8.45 (s, 1H), 7.65 (m, 4H), 7.49 (t, 1H), 6.93 (d, 2H), 4.95 (s, 2H), 3.62 (m 3H), 3.10 (m, 8H), several peaks hidden by broad water signal. LCMS (Method A): $R_T$=0.70 min, m/z=541 [M+H]⁺.

Example 14: 3-(2,6-Dichlorophenyl)-1-methyl-7-((1,2,3,4-tetrahydroisoquinolin-7-yl)amino)-2,3-dihydropyrimido[4,5-d]pyrimidin-4(1H)-one

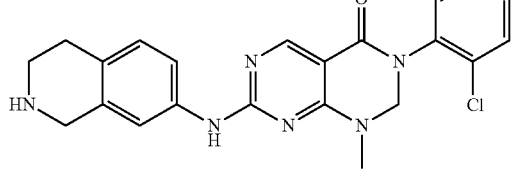

3-(2,6-Dichlorophenyl)-1-methyl-7-(methylthio)-2,3-dihydropyrimido[4,5-d]pyrimidin-4(1H)-one (80 mg, 0.225 mmol) was reacted with tert-butyl 7-amino-3,4-dihydroisoquinoline-2(1H)-carboxylate (61.5 mg, 0.248 mmol) following the procedure for Example 1 to give the title compound as a white solid (8 mg, 8%). ¹H NMR (400 MHz, DMSO-d₆): δ 9.76 (s, 1H), 8.46 (s, 1H), 7.64 (d, 2H), 7.48 (m, 4H), 6.97 (m, 1H), 4.98 (d, 2H), 3.83 (m 2H), 3.11 (s, 3H), 2.95 (m, 2H), 2.65 (m, 2H). LCMS (Method A): $R_T$=0.76 min, m/z=455 [M+H]⁺.

Example 15: 3-(2,6-Dichlorophenyl)-2,2-dideutero-1-methyl-7-((4-(piperazin-1-yl)phenyl)amino)-2,3-dihydropyrimido[4,5-d]pyrimidin-4(1H)-one

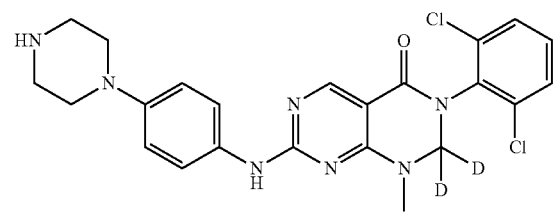 [SMILES: [2H]C1([2H])N(C)c2nc(Nc3ccc(N4CCNCC4)cc3)ncc2C(=O)N1c1c(Cl)cccc1Cl]

Step 1: 3-(2,6-Dichlorophenyl)-2,2-dideutero-1-methyl-7-(methylthio)-2,3-dihydropyrimido[4,5-d]pyrimidin-4(1H)-one N-(2,6-Dichlorophenyl)-4-(methylamino)-2-(methylthio)pyrimidine-5-carboxamide (500 mg, 1.46 mmol) was suspended in acetonitrile (10 mL) and cesium carbonate (1.90 g, 5.83 mmol) was added. Dibromomethane-d2 (0.307 mL, 4.37 mmol) was added and the mixture was stirred at 80° C. for 16 h, then concentrated in vacuo. The residue was diluted with water then extracted with ethyl acetate (×3). The combined organic layers were washed with brine then dried (Na₂SO₄), filtered and concentrated in vacuo. The residue was chromatographed (Isolera 10 g; eluted 0-90% EtOAc/c-hex over 20 cv) to give 3-(2,6-dichlorophenyl)-2,2-dideutero-1-methyl-7-(methylthio)-2,3-dihydropyrimido[4,5-d]pyrimidin-4(1H)-one as a crystalline white solid (85 mg, 16%). This was used directly without further purification.

Step 2: 3-(2,6-Dichlorophenyl)-2,2-dideutero-1-methyl-7-((4-(piperazin-1-yl)phenyl)amino)-2,3-dihydropyrimido[4,5-d]pyrimidin-4(1H)-one 3-(2,6-Dichlorophenyl)-2,2-dideutero-1-methyl-7-(methylthio)-2,3-dihydropyrimido[4,5-d]pyrimidin-4(1H)-one (80 mg, 0.224 mmol) was reacted with tert-butyl 4-(4-aminophenyl)piperazine-1-carboxylate (68.3 mg, 0.246 mmol) following the procedure for Example 1 to give the title compound as a pale brown solid (51 mg, 47%). $^1$H NMR (400 MHz, DMSO-$d_6$): δ 9.68 (s, 1H), 8.44 (s, 1H), 7.65 (m, 4H), 7.49 (t, 1H), 6.88 (d, 2H), 3.11 (s, 3H), 2.98 (m, 4H), 2.85 (m, 4H). LCMS (Method A): $R_T$=0.72 min, m/z=486 [M+H]$^+$.

Example 16: (R)-3-(2,6-Dichlorophenyl)-1-methyl-7-((4-(3-methylpiperazin-1-yl)phenyl)amino)-2,3-dihydropyrimido[4,5-d]pyrimidin-4(1H)-one

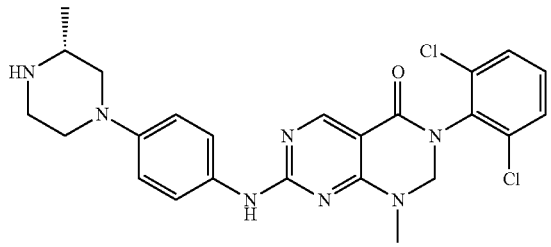 [SMILES: C[C@@H]1CN(c2ccc(Nc3ncc4c(n3)N(C)CN(c3c(Cl)cccc3Cl)C4=O)cc2)CCN1]

Step 1: (R)-tert-Butyl 2-methyl-4-(4-nitrophenyl)piperazine-1-carboxylate

A mixture of (R)-tert-butyl 2-methylpiperazine-1-carboxylate (1.42 g, 7.09 mmol), 1-fluoro-4-nitrobenzene (1 g, 7.09 mmol) and potassium carbonate (1.47 g, 10.6 mmol) in DMF (10 mL) was heated at 60° C. for 18 h. The reaction mixture was cooled to room temperature and diluted with water (120 mL) and stirred for 1 h. The resulting solid was collected by filtration and washed with water (3×40 mL), then dried in vacuo to give the title compound (1.9 g, 81%). LCMS (Method A): $R_T$=1.45 min, m/z=322 [M+H]$^+$.

Step 2: (R)-tert-Butyl 4-(4-aminophenyl)-2-methyl-piperazine-1-carboxylate

A mixture of (R)-tert-butyl 2-methyl-4-(4-nitrophenyl)piperazine-1-carboxylate (1.9 g, 5.91 mmol) and palladium on carbon (0.4 g, 0.376 mmol) in EtOH (50 mL) was heated to 50° C. Ammonium formate (2.2 g, 34.9 mmol) was added in one portion. The resulting reaction mixture was stirred at 50° C. for 2 h, then cooled and filtered through Celite®. The filtrate was concentrated and the residue was partitioned between ethyl acetate (80 mL) and sodium bicarbonate solution (70 mL). The organic phase was separated and concentrated to give the title compound (1.7 g, 98%). LCMS (Method A): $R_T$=0.77 min, m/z=236 [M−56]$^+$.

Step 3: (R)-3-(2,6-Dichlorophenyl)-1-methyl-7-((4-(3-methylpiperazin-1-yl)phenyl)amino)-2,3-dihydro-pyrimido[4,5-d]pyrimidin-4(1H)-one 3-(2,6-Dichlorophenyl)-1-methyl-7-(methylthio)-2,3-dihydropyrimido[4,5-d]pyrimidin-4(1H)-one (107 mg, 0.301 mmol) was reacted with (R)-tert-butyl 4-(4-aminophenyl)-2-methylpiperazine-1-carboxylate (88 mg, 0.301 mmol) following the procedure of Example 1 to give the title compound as an off-white solid (50 mg, 33%). $^1$H NMR (400 MHz, DMSO-$d_6$): δ 9.71 (s, 1H), 8.44 (s, 1H), 7.65 (m, 4H), 7.49 (t, 1H), 6.91 (d, 2H), 4.95 (s, 2H), 3.46 (m, 2H), 3.11 (s, 3H), 2.94 (m, 1H), 2.78 (m, 2H), 2.15 (t, 1H), 1.02 (d, 3H), one peak appears to be masked by solvent. LCMS (Method A): $R_T$=0.76 min, m/z=498 [M+H]$^+$.

Example 17: (S)-3-(2,6-Dichlorophenyl)-1-methyl-7-((4-(3-methylpiperazin-1-yl)phenyl)amino)-2,3-dihydropyrimido[4,5-d]pyrimidin-4(1H)-one

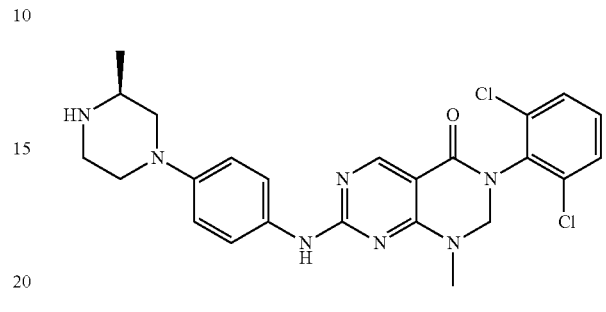

Step 1: (S)-tert-Butyl 2-methyl-4-(4-nitrophenyl)piperazine-1-carboxylate

A mixture of (S)-tert-butyl 2-methylpiperazine-1-carboxylate (1.42 g, 7.09 mmol), 1-fluoro-4-nitrobenzene (1 g, 7.09 mmol) and potassium carbonate (1.47 g, 10.6 mmol) in DMF (6 mL) was heated at 50° C. for 20 h. The reaction mixture was cooled to room temperature and diluted with water (50 mL). The resulting precipitate was collected by filtration and washed with water to give the title compound (1.83 g, 80%). LCMS (Method A): $R_T$=1.45 min, m/z=266 [M+H−tBu]$^+$.

Step 2: (S)-tert-Butyl 4-(4-aminophenyl)-2-methyl-piperazine-1-carboxylate

A mixture of (S)-tert-butyl 2-methyl-4-(4-nitrophenyl)piperazine-1-carboxylate (1.82 g, 5.66 mmol) and palladium on carbon (0.301 g, 0.283 mmol) in ethanol (30 mL) was warmed to 50° C. Ammonium formate (1.43 g, 22.7 mmol) was added portionwise and the mixture was heated at 50° C. for 1 h, then cooled. The mixture was filtered through Celite® and the filtrate was concentrated in vacuo to give the title compound (1.46 g, 88%). LCMS (Method A): $R_T$=0.77 min, m/z=236 [M+H-tBu]$^+$.

Step 3: (S)-3-(2,6-Dichlorophenyl)-1-methyl-7-((4-(3-methylpiperazin-1-yl)phenyl)amino)-2,3-dihydro-pyrimido[4,5-d]pyrimidin-4(1H)-one 3-(2,6-Dichlorophenyl)-1-methyl-7-(methylthio)-2,3-dihydropyrimido[4,5-d]pyrimidin-4(1H)-one (107 mg, 0.301 mmol) was reacted with (S)-tert-butyl 4-(4-aminophenyl)-2-methylpiperazine-1-carboxylate (88 mg, 0.301 mmol) following the procedure for Example 1 to give the title compound as an off-white solid (32 mg, 21%). $^1$H NMR (400 MHz, DMSO-$d_6$): δ 9.71 (s, 1H), 8.45 (s, 1H), 7.65 (m, 4H), 7.49 (t, 1H), 6.90 (d, 2H), 4.95 (s, 2H), 3.46 (m, 2H), 3.11 (s, 3H), 2.94 (m, 1H), 2.78 (m, 2H), 2.15 (t, 1H), 1.02 (d, 3H), one peak appears to be masked by solvent. LCMS (Method A): $R_T$=0.75 min, m/z=498 [M+H]$^+$.

Example 18: 3-(2,6-Dichlorophenyl)-1-methyl-7-((3-methyl-4-(piperidin-4-yl)phenyl)amino)-2,3-dihydropyrimido[4,5-d]pyrimidin-4(1H)-one

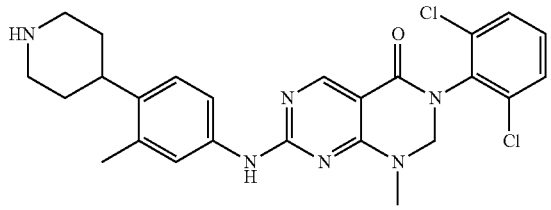

3-(2,6-Dichlorophenyl)-1-methyl-7-(methylthio)-2,3-dihydropyrimido[4,5-d]pyrimidin-4(1H)-one (80 mg, 0.225 mmol) was reacted with tert-butyl 4-(4-amino-2-methylphenyl)piperidine-1-carboxylate (78 mg, 0.270 mmol) following the procedure for Example 1 to give the title compound as an off-white solid (14 mg, 13%). $^1$H NMR (400 MHz, DMSO-$d_6$): δ 9.77 (s, 1H), 8.47 (s, 1H), 7.55 (m, 4H), 7.13 (m, 1H), 4.97 (s, 2H), 3.11 (s, 3H), 3.02 (m, 2H), 2.57 (m, 5H), 2.30 (s, 3H), 1.62 (m, 2H), 1.51 (m, 2H). LCMS (Method A): $R_T$=0.82 min, m/z=497 [M+H]$^+$.

Example 19: (R)-3-(2,6-Dichlorophenyl)-7-((4-(3-(hydroxymethyl)piperazin-1-yl)phenyl)amino)-1-methyl-2,3-dihydropyrimido[4,5-d]pyrimidin-4(1H)-one

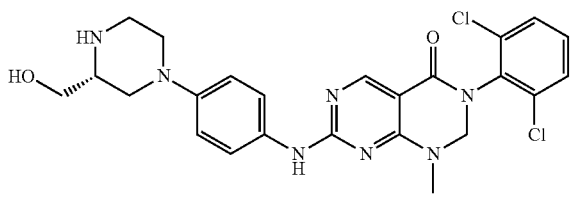 [SMILES: CN1CN(c2c(Cl)cccc2Cl)C(=O)c2cnc(Nc3ccc(N4CCN[C@@H](CO)C4)cc3)nc21]

3-(2,6-Dichlorophenyl)-1-methyl-7-(methylthio)-2,3-dihydropyrimido[4,5-d]pyrimidin-4(1H)-one (70 mg, 0.197 mmol) was reacted with (R)-tert-butyl 4-(4-aminophenyl)-2-(hydroxymethyl)piperazine-1-carboxylate [prepared from (R)-tert-butyl 2-(hydroxymethyl)piperazine-1-carboxylate and 1-fluoro-4-nitrobenzene in a manner similar to Example 17, Steps 1 and 2] (60 mg, 0.195 mmol) following the procedure for Example 1 to give the title compound as an orange solid (23 mg, 20%). $^1$H NMR (400 MHz, CDCl$_3$): δ 8.70 (s, 1H), 7.53 (d, 2H), 7.46 (d, 2H), 7.30 (m, 2H), 6.94 (m, 2H), 4.88 (s, 2H), 3.72 (dd, 1H), 3.64 (dd, 1H), 3.48 (d, 2H), 3.20 (m, 1H), 3.18 (s, 3H), 3.08 (m, 2H), 2.78 (t, 1H), 2.60 (t, 1H), 1.27 (m, 1H). LCMS (Method A): $R_T$=0.71 min, m/z=514 [M+H]$^+$.

Example 20: (S)-3-(2,6-Dichlorophenyl)-7-((4-(3-(hydroxymethyl)piperazin-1-yl)phenyl)amino)-1-methyl-2,3-dihydropyrimido[4,5-d]pyrimidin-4(1H)-one

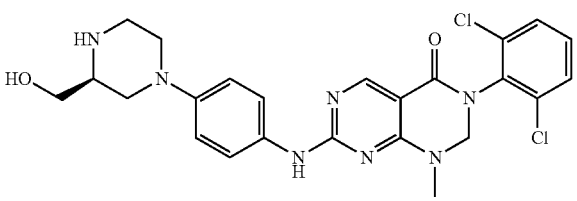 [SMILES: CN1CN(c2c(Cl)cccc2Cl)C(=O)c2cnc(Nc3ccc(N4CCN[C@H](CO)C4)cc3)nc21]

3-(2,6-Dichlorophenyl)-1-methyl-7-(methylthio)-2,3-dihydropyrimido[4,5-d]pyrimidin-4(1H)-one (80 mg, 0.225 mmol) was reacted with (S)-tert-butyl 4-(4-aminophenyl)-2-(hydroxymethyl)piperazine-1-carboxylate [prepared from (S)-tert-butyl 2-(hydroxymethyl)piperazine-1-carboxylate and 1-fluoro-4-nitrobenzene in a manner similar to Example 17, Steps 1 and 2] (83 mg, 0.270 mmol) following the procedure for Example 1 to give the title compound as a yellow solid (19 mg, 16%). $^1$H NMR (400 MHz, CDCl$_3$): δ 8.70 (s, 1H), 7.53 (d, 2H), 7.46 (d, 2H), 7.30 (m, 2H), 6.94 (m, 2H), 4.88 (s, 2H), 3.72 (dd, 1H), 3.64 (dd, 1H), 3.48 (d, 2H), 3.20 (m, 1H), 3.18 (s, 3H), 3.08 (m, 2H), 2.78 (t, 1H), 2.60 (t, 1H), 1.27 (m, 1H). LCMS (Method A): $R_T$=0.71 min, m/z=514 [M+H]$^+$.

Example 21: 3-(2,6-Dichlorophenyl)-7-((3-(hydroxymethyl)-4-(4-isopropylpiperazin-1-yl)phenyl)amino)-1-methyl-2,3-dihydropyrimido[4,5-d]pyrimidin-4(1H)-one

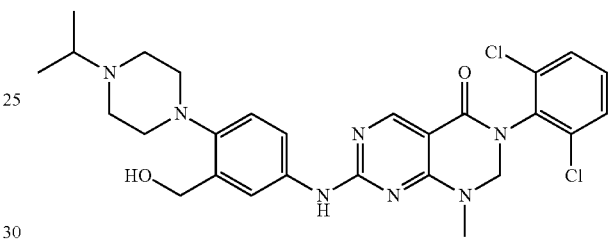

Step 1: 2-(4-Isopropylpiperazin-1-yl)-5-nitrobenzaldehyde

A mixture of 2-chloro-5-nitrobenzaldehyde (2 g, 10.8 mmol), 1-isopropylpiperazine (2.07 g, 16.2 mmol) and potassium carbonate (2.68 g, 19.4 mmol) in DMF (10 mL) was heated at 90° C. for 4 h. The reaction mixture was cooled to room temperature and diluted with water. The resulting precipitate was collected by filtration, then washed on the filter with water and dried in a vacuum oven to give the title compound (2.8 g, 96%). LCMS (Method A): $R_T$=0.49 min, m/z=278 [M+H]$^+$.

Step 2: (2-(4-Isopropylpiperazin-1-yl)-5-nitrophenyl)methanol

A solution of 2-(4-isopropylpiperazin-1-yl)-5-nitrobenzaldehyde (2.8 g, 10.1 mmol) in THF (25 mL) was cooled to 0° C. Sodium borohydride (0.382 g, 10.1 mmol) was added and the resulting suspension was stirred at 0° C. for 2 h. The reaction mixture was diluted with water and extracted with DCM (×3). The combined organic extracts were washed with water, dried, filtered and concentrated. The residue was chromatographed (Isolera KP-Sil 50 g, eluted with 0-100% ethyl acetate/cyclohexane) to give the title compound (1.5 g, 53%). LCMS (Method A): $R_T$=0.50 min, m/z=280 [M+H]$^+$.

Step 3: (5-Amino-2-(4-isopropylpiperazin-1-yl)phenyl)methanol

Palladium on carbon (0.419 g, 0.39 mmol) was added to a solution of (2-(4-isopropylpiperazin-1-yl)-5-nitrophenyl)methanol (1.1 g, 3.94 mmol) in ethanol (35 mL). The resulting solution was heated to 50° C. Ammonium formate (0.745 g, 11.8 mmol) was added and the mixture was stirred at 50° C. for 30 min. The mixture was cooled to RT and filtered through Celite®. The filtrate was concentrated in vacuo and the residue was partitioned between DCM and sodium bicarbonate (aq) solution. The organic phase was separated and concentrated in vacuo to give the title compound (0.65 g, 66%). LCMS (Method A): $R_T$=0.13 min, m/z=250 [M+H]$^+$.

Step 4: 3-(2,6-Dichlorophenyl)-7-((3-(hydroxymethyl)-4-(4-isopropylpiperazin-1-yl)phenyl)amino)-1-methyl-2,3-dihydropyrimido[4,5-d]pyrimidin-4 (1H)-one 3-(2,6-Dichlorophenyl)-1-methyl-7-(methylthio)-2,3-dihydropyrimido[4,5-d]pyrimidin-4(1H)-one (80 mg, 0.225 mmol) was reacted with (5-amino-2-(4-isopropylpiperazin-1-yl)phenyl)methanol (67.4 mg, 0.270 mmol) following the procedure for Example 1 to give the title compound as an off-white solid (11 mg, 8%). $^1$H NMR (400 MHz, DMSO-d$_6$): δ 9.82 (s, 1H), 8.47 (s, 1H), 8.01 (s, 1H), 7.66 (d, 2H), 7.55 (m, 1H), 7.50 (t, 1H), 7.01 (d, 1H), 5.08 (m, 1H), 4.97 (s, 2H), 4.55 (s, 2H), 3.12 (s, 3H), 2.79 (m, 4H), 2.70 (m, 1H), 2.58 (m, 4H), 1.03 (d, 6H). LCMS (Method A): $R_T$=0.76 min, m/z=556 [M+H]$^+$.

Example 22: 3-(2,6-Dichlorophenyl)-1-methyl-7-((2-methyl-1,2,3,4-tetrahydroisoquinolin-7-yl) amino)-2,3-dihydropyrimido[4,5-d]pyrimidin-4(1H)-one

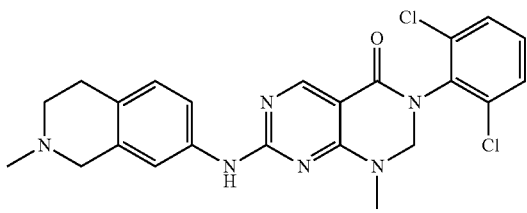 [SMILES: CN1CCc2ccc(Nc3ncc4c(n3)N(C)CN(c3c(Cl)cccc3Cl)C4=O)cc2C1]

3-(2,6-Dichlorophenyl)-1-methyl-7-((1,2,3,4-tetrahydroisoquinolin-7-yl)amino)-2,3-dihydropyrimido[4,5-d]pyrimidin-4(1H)-one (51 mg, 0.112 mmol) [Example 14] was dissolved in 1,2-dichloroethane (1 mL) and formalin (0.017 mL, 0.224 mmol) was added. The resulting mixture was stirred at RT for 15 min, then cooled to 0° C. Sodium triacetoxyborohydride (28.5 mg, 0.134 mmol) was added and the mixture was allowed to return to RT with stirring over 1 h. Further portions of formalin (0.1 mL) and sodium triacetoxyborohydride (28.5 mg, 0.134 mmol) were added and the mixture was stirred at RT for 16 h. 1,4-dioxane was added along with further portions of formalin (0.1 mL) and sodium triacetoxyborohydride (28.5 mg, 0.134 mmol). After a further 1 h, further portions of formalin (0.1 mL) and sodium triacetoxyborohydride (28.5 mg, 0.134 mmol) were added. After another 1 h of stirring, the reaction was quenched by addition of 1 N HCl (1 mL) and stirred for 20 min. The mixture was added to a 5 g SCX-2 cartridge. The column was washed with methanol then eluted with 2 M NH$_3$/MeOH and the basic fractions were concentrated in vacuo to yield a yellow glass. This was triturated with diethyl ether to give the title compound as an off-white solid (20 mg, 38%). $^1$H NMR (400 MHz, CDCl$_3$): δ 8.74 (s, 1H), 7.40 (m, 4H), 7.30 (m, 2H), 7.10-7.00 (m, 1H), 4.90 (s, 2H), 3.58 (s, 2H), 3.17 (s, 3H), 2.91 (m, 2H), 2.70 (m, 2H), 2.48 (s, 3H). LCMS (Method A): $R_T$=0.75 min, m/z=469 [M+H]$^+$.

Example 23: (rac)-3-(2,6-Dichlorophenyl)-1-methyl-2-phenyl-7-((1,2,3,4-tetrahydroisoquinolin-7-yl)amino)-2,3-dihydropyrimido[4,5-d]pyrimidin-4 (1H)-one

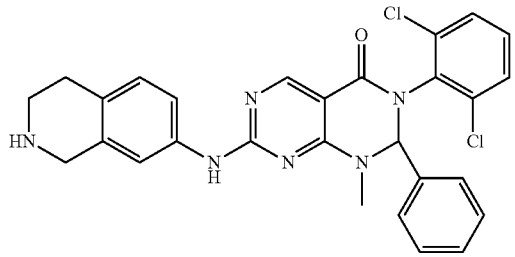 [SMILES: CN1c2nc(Nc3ccc4c(c3)CNCC4)ncc2C(=O)N(c2c(Cl)cccc2Cl)C1c1ccccc1]

Step 1: (rac)-3-(2,6-Dichlorophenyl)-1-methyl-7-(methylthio)-2-phenyl-2,3-dihydropyrimido[4,5-d] pyrimidin-4(1H)-one N-(2,6-Dichlorophenyl)-4-(methylamino)-2-(methylthio) pyrimidine-5-carboxamide (200 mg, 0.58 mmol) was dissolved in acetonitrile (10 mL) and benzaldehyde (0.25 mL, 2.47 mmol) was added, followed by p-toluenesulfonic acid hydrate (25 mg, 0.15 mmol). The tube was sealed and the mixture subjected to microwave heating at 220° C. for 16 h. The mixture was concentrated in vacuo and chromatographed (Isolera Si 10 g cartridge, eluted 0-600 EtOAc/c-hex), then chromatographed again (11 g KP-NH cartridge, eluted 0-70% DCM/c-hex) to give the title compound as a yellow foam (59 mg, 23%). $^1$H NMR (400 MHz, CDCl$_3$): δ 8.76 (s, 1H), 7.45 (m, 1H), 7.38 (m, 1H), 7.29 (m, 4H), 7.10 (d, 2H), 5.85 (s, 1H), 3.08 (s, 3H), 2.61 (s, 3H). LCMS (Method A): $R_T$=1.50 min, m/z=431 [M+H]$^+$.

Step 2: (rac)-3-(2,6-Dichlorophenyl)-1-methyl-2-phenyl-7-((1,2,3,4-tetrahydroisoquinolin-7-yl) amino)-2,3-dihydropyrimido[4,5-d]pyrimidin-4(1H)-one (rac)-3-(2,6-Dichlorophenyl)-1-methyl-7-(methylthio)-2-phenyl-2,3-dihydropyrimido[4,5-d]pyrimidin-4(1H)-one (57 mg, 0.132 mmol) was dissolved in toluene (2 mL) and mCPBA (49.8 mg, 0.159 mmol) was added. The mixture was stirred at RT for 20 min, then DIPEA (0.069 mL, 0.396 mmol) was added, followed by tert-butyl 7-amino-3,4-dihydroisoquinoline-2(1H)-carboxylate (32.8 mg, 0.132 mmol). The mixture was heated at 80° C. for 64 h, then concentrated in vacuo. The residue was chromatographed (Isolera 10 g GraceResolv; eluted 0-70% EtOAc/c-hex over 20 cv) to give a brown glass. This was dissolved in DCM (1 mL) and TFA (1 mL) and stirred for 30 min, then concentrated in vacuo. The residue was dissolved in methanol and added to a 2 g SCX-2 cartridge. The column was washed with methanol, then eluted with 2 M NH$_3$/MeOH and the solvent removed in vacuo to give a glass. The residue was chromatographed (Isolera KP-NH 11 g, eluted 0-100% EtOAc/c-hex then 0-10% MeOH/EtOAc) then triturated with diethyl ether to give the title compound as a white solid (11 mg, 16%). $^1$H NMR (400 MHz, CDCl$_3$): δ 8.77 (s, 1H), 7.37 (m, 6H), 7.15 (m, 6H), 5.83 (s, 1H), 4.02 (m, 2H), 3.15 (m, 2H), 3.07 (s, 3H), 2.79 (m, 2H). LCMS (Method A): $R_T$=0.90 min, m/z=531 [M+H]$^+$.

Example 24: 3-(2-Chlorophenyl)-1-methyl-7-((4-(piperazin-1-yl)phenyl)amino)-2,3-dihydropyrimido[4,5-d]pyrimidin-4(1H)-one

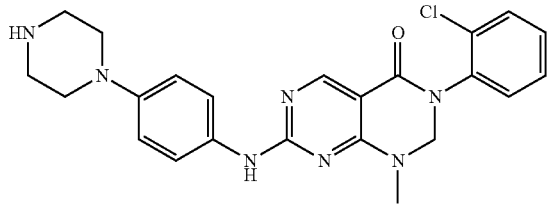 [SMILES: CN1CN(c2ccccc2Cl)C(=O)c2cnc(Nc3ccc(N4CCNCC4)cc3)nc21]

Step 1: N-(2-Chlorophenyl)-4-(methylamino)-2-(methylthio)pyrimidine-5-carboxamide 4-(Methylamino)-2-(methylthio)pyrimidine-5-carboxylic acid (400 mg, 2.01 mmol) was suspended in chlorobenzene (10 mL) and phosphorous trichloride (0.184 mL, 2.11 mmol) was added, followed by 2-chloroaniline (282 mg, 2.21 mmol). The mixture was stirred at 120° C. for 64 h, then concentrated in vacuo. The residue was taken up in aqueous Na$_2$CO$_3$ and extracted with ethyl acetate (×2). The organics were dried (Na$_2$SO$_4$), filtered and concentrated in vacuo to yield an off-white solid. This was triturated with diethyl ether to give the title compound as a white solid (460 mg, 74%). $^1$H NMR (400 MHz, CDCl$_3$): δ 8.53 (s, 1H), 8.42 (s, 1H), 8.32 (s, 1H), 8.21 (s, 1H), 7.42 (d, 1H), 7.31 (t, 1H), 7.10 (t, 1H), 3.10 (d, 3H), 2.57 (s, 3H). LCMS (Method A): $R_T$=0.58/0.65 min (split peak), m/z=450 [M+H]$^+$.

Step 2: 3-(2-Chlorophenyl)-1-methyl-7-(methylthio)-2,3-dihydropyrimido[4,5-d]pyrimidin-4(1H)-one N-(2-Chlorophenyl)-4-(methylamino)-2-(methylthio)pyrimidine-5-carboxamide (250 mg, 0.810 mmol) was dissolved in acetonitrile (10 mL) and cesium carbonate (1055 mg, 3.24 mmol) was added followed by dibromomethane (0.170 mL, 2.429 mmol). The mixture was heated at 80° C. for 1 h. A further 0.06 mL dibromomethane was added and the mixture heated at 90° C. for 16 h. A further 0.12 mL dibromomethane was added and the mixture was heated at 125° C. in the microwave for 1 h. The mixture was concentrated in vacuo and the residue was chromatographed (Isolera 25 g; eluted 0-100% EtOAc/c-hex over 20 cv) to give a semisolid material that was used without further purification (92 mg, 35%).

Step 3: 3-(2-Chlorophenyl)-1-methyl-7-((4-(piperazin-1-yl)phenyl)amino)-2,3-dihydropyrimido[4,5-d]pyrimidin-4(1H)-one 3-(2-Chlorophenyl)-1-methyl-7-(methylthio)-2,3-dihydropyrimido[4,5-d]pyrimidin-4(1H)-one (90 mg, 0.281 mmol) was dissolved in toluene (4 mL) and mCPBA (106 mg, 0.337 mmol) was added. The mixture was stirred for 15 min, then tert-butyl 4-(4-aminophenyl)piperazine-1-carboxylate (78 mg, 0.281 mmol) was added, followed by DIPEA (0.064 mL, 0.365 mmol), and the mixture was stirred at 80° C. for 16 h. The mixture was concentrated in vacuo then chromatographed (Isolera 10 g GraceResolv, eluted 0-100% EtOAc/c-hex over 20 cv) and the compound containing fractions were concentrated in vacuo to give a yellow glass. This was dissolved in DCM (1 mL) and TFA (1 mL) and stirred for 1 h then concentrated in vacuo. The residue was dissolved in methanol and added to a 2 g SCX-2 cartridge. The column was washed with methanol then eluted with 2 M NH$_3$/MeOH and the solvent concentrated in vacuo to give a yellow glass. This was chromatographed (Isolera 11 g KP-NH, eluted 0-100% EtOAc/c-hex then 0-15% MeOH/EtOAc over 20 cv) to give the title compound as a pale yellow solid (11 mg, 8%). $^1$H NMR (400 MHz, CDCl$_3$): δ 8.69 (s, 1H), 7.52 (m, 3H), 7.35 (m, 3H), 7.22 (s, 1H), 6.94 (d, 2H), 4.90 (br m, 2H), 3.15 (m, 7H), 3.06 (m, 4H). LCMS (Method A): $R_T$=0.65 min, m/z=450 [M+H]$^+$.

Example 25: 3-(2-Chloro-6-fluorophenyl)-1-methyl-7-((4-(piperazin-1-yl)phenyl)amino)-2,3-dihydropyrimido[4,5-d]pyrimidin-4(1H)-one

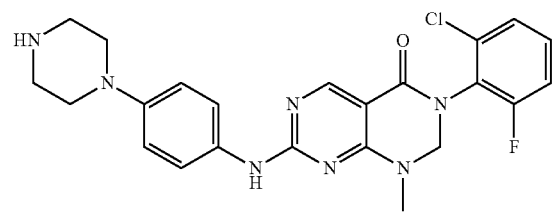 [SMILES: CN1CN(c2c(F)cccc2Cl)C(=O)c2cnc(Nc3ccc(N4CCNCC4)cc3)nc21]

Step 1: N-(2-Chloro-6-fluorophenyl)-4-(methylamino)-2-(methylthio)pyrimidine-5-carboxamide Prepared from 4-(methylamino)-2-(methylthio)pyrimidine-5-carboxylic acid and 2-chloro-6-fluoroaniline following the procedure described in Example 1, Step 1. $^1$H NMR (400 MHz, DMSO-d$_6$): δ 10.16 (s, 1H), 8.72 (s, 1H), 8.61 (br d, 1H), 7.41 (m, 3H), 2.95 (d, 3H), SMe signal presumably obscured by solvent. LCMS (Method A): $R_T$=1.17 min, m/z=327 [M+H]$^+$.

Step 2: 3-(2-Chloro-6-fluorophenyl)-1-methyl-7-(methylthio)-2,3-dihydropyrimido[4,5-d]pyrimidin-4(1H)-one Prepared from N-(2-chloro-6-fluorophenyl)-4-(methylamino)-2-(methylthio)pyrimidine-5-carboxamide following the procedure described in Example 1, Step 2. Obtained crude and used as such. LCMS (Method A): $R_T$=1.19 min, m/z=339 [M+H]$^+$.

Step 3: 3-(2-Chloro-6-fluorophenyl)-1-methyl-7-((4-(piperazin-1-yl)phenyl)amino)-2,3-dihydropyrimido[4,5-d]pyrimidin-4(1H)-one Prepared from 3-(2-chloro-6-fluorophenyl)-1-methyl-7-(methylthio)-2,3-dihydropyrimido[4,5-d]pyrimidin-4(1H)-one following the procedure described in Example 1, Step 3. $^1$H NMR (400 MHz, DMSO-d$_6$): δ 9.78 (s, 1H), 8.53 (s, 1H), 7.69 (d, 2H), 7.57 (m, 2H), 7.48 (m, 1H), 6.97 (d, 2H), 5.07 (d, 1H), 5.02 (d, 1H), 3.17 (s, 3H), 3.07 (m, 4H), 2.91 (m, 4H). LCMS (Method A): $R_T$=0.68 min, m/z=468 [M+H]$^+$.

Example 26: 3-(2,6-Dichlorophenyl)-1,2-dimethyl-7-((4-(piperazin-1-yl)phenyl)amino)-2,3-dihydropyrimido[4,5-d]pyrimidin-4(1H)-one

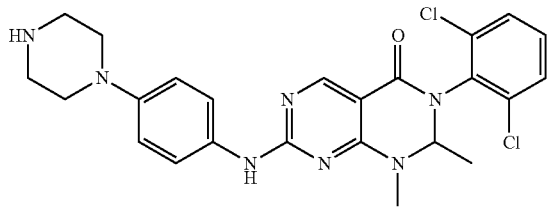 [SMILES: CC1N(C)c2nc(Nc3ccc(N4CCNCC4)cc3)ncc2C(=O)N1c1c(Cl)cccc1Cl]

Step 1: 3-(2,6-Dichlorophenyl)-1,2-dimethyl-7-(methylthio)-2,3-dihydropyrimido[4,5-d]pyrimidin-4(1H)-one N-(2,6-Dichlorophenyl)-4-(methylamino)-2-(methylthio)pyrimidine-5-carboxamide (200 mg) was suspended in acetaldehyde (1.5 mL). The mixture was heated in a microwave at 150° C. for 7 h. Water was added and the mixture extracted with ethyl acetate (×2). The combined organic extracts were dried over Na$_2$SO$_4$ and concentrated. The residue was chromatographed (Isolera 10 g Si, eluted 0-60% EtOAc/c-hex) to give the title compound as a yellow syrup (65 mg, 29%). $^1$H NMR (400 MHz, DMSO-d$_6$): δ 8.72 (s, 1H), 7.47 (t, 2H), 7.29 (d, 1H), 4.97 (q, 1H), 3.22 (s, 3H), 2.58 (s, 3H), 1.56 (d, 3H). LCMS (Method A): R$_T$=1.30 min, m/z=369 [M+H]$^+$.

Step 2: 3-(2,6-Dichlorophenyl)-1,2-dimethyl-7-((4-(piperazin-1-yl)phenyl)amino)-2,3-dihydropyrimido[4,5-d]pyrimidin-4(1H)-one Prepared from 3-(2,6-dichlorophenyl)-1,2-dimethyl-7-(methylthio)-2,3-dihydropyrimido[4,5-d]pyrimidin-4(1H)-one following the procedure described in Example 1, Step 3. $^1$H NMR (400 MHz, DMSO-d$_6$): δ 9.63 (s, 1H), 8.44 (s, 1H), 7.67 (m, 4H), 7.48 (t, 1H), 6.89 (d, 1H), 5.15 (q, 1H), 3.14 (s, 3H), 2.98 (m, 4H), 2.83 (m, 4H), 1.43 (d, 3H). LCMS (Method A): R$_T$=0.75 min, m/z=498 [M+H]$^+$.

Example 27: 3-(2,6-Dichlorophenyl)-1-methyl-7-((4-(morpholinomethyl)phenyl)amino)-2,3-dihydropyrimido[4,5-d]pyrimidin-4(1H)-one

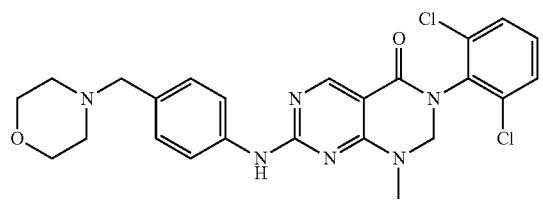 [SMILES: CN1CN(c2c(Cl)cccc2Cl)C(=O)c2cnc(Nc3ccc(CN4CCOCC4)cc3)nc21]

3-(2,6-Dichlorophenyl)-1-methyl-7-(methylthio)-2,3-dihydropyrimido[4,5-d]pyrimidin-4(1H)-one (60 mg, 0.17 mmol) was reacted with 4-(morpholinomethyl)aniline (36 mg, 0.19 mmol) following the procedure for Example 1 to give the title compound as a white solid (37 mg, 44%). $^1$H NMR (400 MHz, DMSO-d$_6$): δ 9.89 (s, 1H), 8.49 (s, 1H), 7.74 (d, 2H), 7.65 (d, 2H), 7.49 (m, 1H), 7.24 (d, 2H), 4.98 (s, 2H), 3.57 (m, 4H), 3.41 (s, 2H), 3.12 (s, 3H), 2.35 (m, 4H). LCMS (Method A): R$_T$=0.78 min, m/z=499 [M+H]$^+$.

Example 28: 6-(2,6-Dichlorophenyl)-2-((4-(piperazin-1-yl)phenyl)amino)-6a,7,8,9-tetrahydropyrimido[5,4-e]pyrrolo[1,2-a]pyrimidin-5(6H)-one

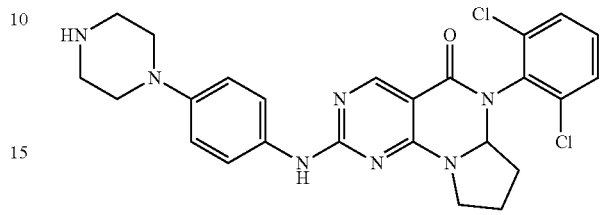

Step 1: 2-Chloro-1-(2,6-dichlorophenyl)-4-((4-hydroxybutyl)amino)pyrimidine-5-carboxamide To a solution of 2,4-dichloro-N-(2,6-dichlorophenyl)pyrimidine-5-carboxamide (350 mg, 1.04 mmol) (Prepared as described in US 2005/0209221) and DIPEA (0.200 mL, 1.14 mmol) in THF (5 mL) at 0° C. was added 4-aminobutan-1-ol (0.096 mL, 1.04 mmol) in THF (1 mL). The reaction was then stirred at RT for 30 min, concentrated in vacuo and the residue partitioned between water and DCM. The layers were then separated using a phase separator and the organic layer was concentrated in vacuo to afford the title compound (0.4 g, 1.03 mmol, 99%) as a white solid. LCMS (Method A): R$_T$=1.08 min, m/z=389 [M+H]$^+$.

Step 2: tert-Butyl 4-(4-((5-((2,6-dichlorophenyl)carbamoyl)-4-((4-hydroxybutyl)amino)pyrimidin-2-yl)amino)phenyl)piperazine-1-carboxylate A solution of 2-chloro-N-(2,6-dichlorophenyl)-4-((4-hydroxybutyl)amino)pyrimidine-5-carboxamide (401 mg, 1.03 mmol), tert-butyl 4-(4-aminophenyl)piperazine-1-carboxylate (400 mg, 1.44 mmol) and DIPEA (0.36 mL, 2.06 mmol) in anhydrous DMF (7 mL) was stirred at 90° C. for 60 h. The reaction mixture was diluted with EtOAc and water and the layers were separated, the aqueous layer was then extracted once more with EtOAc and the organic layers were combined, washed with water 4 times, dried (MgSO$_4$), filtered and concentrated in vacuo. The residue was purified by flash chromatography (SiO$_2$, 30-70% ethyl acetate in cyclohexane) to afford the title compound (480 mg, 74%) as a brown solid. LCMS (Method A): R$_T$=1.17 min, m/z=630 [M+H]$^+$.

Step 3: tert-Butyl 4-(4-((5-((2,6-dichlorophenyl)carbamoyl)-4-((4-oxobutyl)amino)pyrimidin-2-yl)amino)phenyl)piperazine-1-carboxylate To a solution of tert-butyl 4-(4-((5-((2,6-dichlorophenyl)carbamoyl)-4-((4-hydroxybutyl)amino)pyrimidin-2-yl)amino)phenyl)piperazine-1-carboxylate (480 mg, 0.761 mmol) in THF (10 mL) was charged 1,1,1-tris(acetyloxy)-1,1-dihydro-1,2-benziodoxol-3-(1H)-one [Dess-Martin periodinane] (517 mg, 1.218 mmol). The heterogeneous mixture was then stirred at 50° C. for 4 h. The reaction mixture was allowed to cool to RT, diluted with ethyl acetate and filtered, the filtrate was concentrated in vacuo and purified by flash chromatography (SiO$_2$, 30-65% ethyl acetate in cyclohexane) to afford the title compound (110 mg, 23%) as a brown gum. LCMS (Method A): $R_T$=1.27 min, m/z=628 [M+H]$^+$.

Step 4: tert-Butyl 4-(4-((6-(2,6-dichlorophenyl)-5-oxo-5,6,6a,7,8,9-hexahydropyrimido[5,4-e]pyrrolo[1,2-a]pyrimidin-2-yl)amino)phenyl)piperazine-1-carboxylate tert-Butyl 4-(4-((5-((2,6-dichlorophenyl)carbamoyl)-4-((4-oxobutyl)amino)pyrimidin-2-yl)amino)phenyl)piperazine-1-carboxylate (55 mg, 0.088 mmol) and p-toluenesulfonic acid monohydrate (1.7 mg, 8.75 µmol) in toluene (1 mL) was heated at 150° C. for 30 min in the microwave. The solvents were removed in vacuo and the residue purified by flash chromatography (SiO$_2$, 20-60% ethyl acetate in cyclohexane) to give the title compound (35 mg, 66%) LCMS (Method A): $R_T$=1.46 min, m/z=610 [M+H]$^+$.

Step 5: 6-(2,6-Dichlorophenyl)-2-((4-(piperazin-1-yl)phenyl)amino)-6a,7,8,9-tetrahydropyrimido[5,4-e]pyrrolo[1,2-a]pyrimidin-5(6H)-one To a solution of tert-butyl 4-(4-((6-(2,6-dichlorophenyl)-5-oxo-5,6,6a,7,8,9-hexahydropyrimido[5,4-e]pyrrolo[1,2-a]pyrimidin-2-yl)amino)phenyl)piperazine-1-carboxylate (70 mg, 0.115 mmol) in DCM was added TFA (8.8 µl, 0.115 mmol) at RT, the reaction was then stirred at RT for 30 min. The reaction mixture was then concentrated in vacuo and the residue triturated with ethyl acetate to form a brown solid. The solid was collected and dissolved in MeOH and loaded onto a Biotage SCX-2 cartridge, the cartridge was washed with MeOH and the product eluted with 2 M NH$_3$ in MeOH. The fractions containing product were concentrated in vacuo and the product dried (Genevac EZ-2) to afford the title compound (26 mg, 44%) as a brown solid. $^1$H NMR (400 MHz, DMSO-d$_6$): δ 9.72 (s, 1H), 8.43 (s, 1H), 7.66-7.63 (m, 4H), 7.49 (t, 1H), 6.90 (d, 2H), 5.63-5.60 (m, 1H), 4.77-3.64 (m, 2H), 3.08-3.05 (m, 4H), 2.95-2.93 (m, 4H), 2.10-1.91 (m, 2H), 1.86-1.71 (m, 2H). LCMS (Method A): $R_T$=0.79 min, m/z=510 [M+H]$^+$.

Example 29: 3-(2,6-Dichlorophenyl)-1-methyl-7-((4-((4-methylpiperazin-1-yl)methyl)phenyl)amino)-2,3-dihydropyrimido[4,5-d]pyrimidin-4(1H)-one

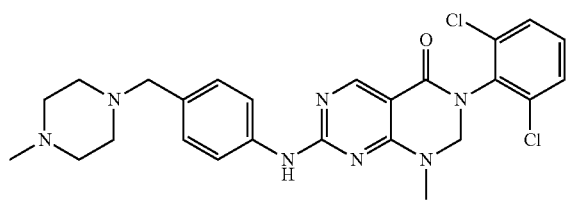 [SMILES: CN1CCN(Cc2ccc(Nc3ncc4c(n3)N(C)CN(c3c(Cl)cccc3Cl)C4=O)cc2)CC1]

3-(2,6-Dichlorophenyl)-1-methyl-7-((4-(piperazin-1-ylmethyl)phenyl)amino)-2,3-dihydropyrimido[4,5-d]pyrimidin-4(1H)-one (120 mg, 0.241 mmol) was heated at reflux in a mixture of formic acid (2 mL) and formaldehyde (37% wt in water, 2.5 mL) for 30 min. The reaction mixture was allowed to cool to RT, diluted with water and loaded onto a SCX-2 cartridge. The column was washed with methanol then eluted with 2 M NH$_3$/MeOH and the solvent was concentrated in vacuo. The remaining residue was purified by preparative HPLC to give the title compound (25 mg, 20%) as a white solid. $^1$H NMR (400 MHz, DMSO-d$_6$): δ 9.88 (s, 1H), 8.48 (s, 1H), 7.73 (d, 2H), 7.65 (d, 2H), 7.48 (m, 1H), 7.22 (d, 2H), 4.98 (s, 2H), 3.39 (s, 2H), 3.11 (s, 3H), 2.33 (br s, 8H), 2.14 (m, 3H). LCMS (Method A): $R_T$=0.74 min, m/z=512 (weak) [M+H]$^+$.

Example 30: (rac)-3-(2,6-Dichlorophenyl)-1-methyl-7-((4-(S-methylsulfonimidoyl)phenyl)amino)-2,3-dihydropyrimido[4,5-d]pyrimidin-4(1H)-one

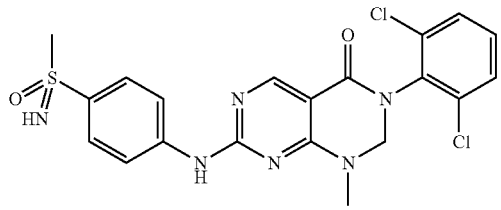 [SMILES: CN1CN(c2c(Cl)cccc2Cl)C(=O)c2cnc(Nc3ccc(S(C)(=N)=O)cc3)nc21]

Step 1: 3-(2,6-Dichlorophenyl)-1-methyl-7-((4-(methylthio)phenyl)amino)-2,3-dihydropyrimido[4,5-d]pyrimidin-4(1H)-one Prepared from 3-(2,6-dichlorophenyl)-1-methyl-7-(methylthio)-2,3-dihydropyrimido[4,5-d]pyrimidin-4(1H)-one following the procedure described in Example 1, Step 3. Obtained crude and used as such. LCMS (Method A): $R_T$=1.34 min, m/z=446 [M+H]$^+$.

Step 2: (rac)-3-(2,6-Dichlorophenyl)-1-methyl-7-((4-(methylsulfinyl)phenyl)amino)-2,3-dihydropyrimido[4,5-d]pyrimidin-4(1H)-one 3-(2,6-Dichlorophenyl)-1-methyl-7-((4-(methylthio)phenyl)amino)-2,3-dihydropyrimido[4,5-d]pyrimidin-4(1H)-one (148 mg, 0.332 mmol) was dissolved in acetonitrile (5 mL) and iron (III) chloride (1.6 mg, 0.001 mmol) was added, followed by periodic acid (79 mg, 0.348 mmol). The resulting mixture was stirred for 16 h and concentrated in vacuo. The residue was taken up in aqueous sodium thiosulfate and extracted with DCM (×2). The combined organic extracts were washed with brine then dried (Na$_2$SO$_4$), filtered and concentrated to give the title compound as a brown foam (150 mg) which was used crude as obtained. LCMS (Method A): $R_T$=0.91 min, m/z=462 [M+H]$^+$.

Step 3: (rac)-3-(2,6-Dichlorophenyl)-1-methyl-7-((4-(S-methylsulfonimidoyl)phenyl)amino)-2,3-dihydropyrimido[4,5-d]pyrimidin-4(1H)-one (rac)-3-(2,6-Dichlorophenyl)-1-methyl-7-((4-(methylsulfinyl)phenyl)amino)-2,3-dihydropyrimido[4,5-d]pyrimidin-4(1H)-one (100 mg, 0.216 mmol) was dissolved in DCM (3 mL) and rhodium (II) acetate dimer (5.0 mg, 1.13 µmol) was added, followed by magnesium oxide (52 mg, 1.30 mmol) and 2,2,2-trifluoroacetamide (74 mg, 0.65 mmol). Iodobenzene diacetate (157 mg, 0.49 mmol) was then added and the resulting mixture was stirred at 40° C. for 16 h. A further portion of rhodium (II) acetate dimer (5.0 mg, 1.13 µmol) was added followed by 2,2,2-trifluoroacetamide (37 mg, 0.32 mmol) and iodobenzene diacetate (78 mg, 0.24 mmol). The mixture was stirred at 40° C. a further 16 h, then filtered through Celite® and concentrated. The residue was chromatographed (Isolera 10 g; eluted 0-100% EtOAc/c-hex then 0-20% MeOH/EtOAc) to give a white solid. This was dissolved in methanol (2 mL) and potassium carbonate (30 mg, 0.217 mmol) was added and the mixture was stirred at RT for 16 h, then concentrated in vacuo. The residue was chromatographed (Isolera 12 g GraceResolv; eluted 0-100% EtOAc/c-hex then 0-25% MeOH/EtOAc) to give the title compound as a grey solid (5.3 mg, 5%). $^1$H NMR (400 MHz, DMSO-d$_6$): δ 10.31 (s, 1H), 8.55 (s, 1H), 8.00 (d, 2H), 7.87 (d, 2H), 7.68 (d, 2H), 7.65 (t, 1H), 5.03 (s, 2H), 4.05 (s, 1H), 3.16 (s, 3H), 3.04 (s, 3H). LCMS (Method A): R$_T$=0.91 min, m/z=477 [M+H]$^+$.

Example 31: 3-(2,6-dichlorophenyl)-7-((3-(methoxymethyl)-4-(piperazin-1-yl)phenyl)amino)-1-methyl-2,3-dihydropyrimido[4,5-d]pyrimidin-4(1H)-one

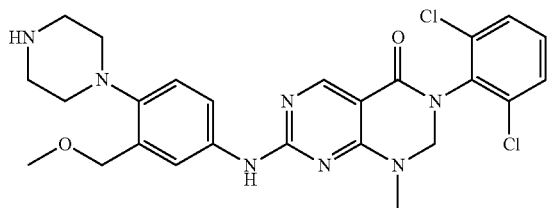 [SMILES: COCc1cc(Nc2ncc3c(n2)N(C)CN(c2c(Cl)cccc2Cl)C3=O)ccc1N1CCNCC1]

Step 1: tert-butyl 4-(2-formyl-4-nitrophenyl)piperazine-1-carboxylate

A suspension of 2-fluoro-5-nitrobenzaldehyde (3 g, 17.74 mmol), tert-butyl piperazine-1-carboxylate (3.30 g, 17.74 mmol) and potassium carbonate (3.68 g, 26.6 mmol) in anhydrous DMF (15 mL) was heated to 50° C. under a nitrogen atmosphere overnight. The reaction mixture was allowed to cool to room temperature, diluted with water (70 mL) and stirred at room temperature for 15 minutes. The precipitated solid was isolated by filtration, washed with water, sucked dry and freeze-dried overnight to give the title compound as a yellow solid (5.89 g, 99%). $^1$H NMR (300 MHz, CDCl$_3$): δ 10.11 (s, 1H), 8.65 (d, 1H), 8.33 (dd, 1H), 7.09 (d, 1H), 3.68 (t, 4H), 3.26 (t, 4H), 1.49 (s, 9H). LCMS (Method C) R$_T$=1.60 min, m/z=336 [M+H]$^+$.

Step 2: tert-butyl 4-(2-(hydroxymethyl)-4-nitrophenyl)piperazine-1-carboxylate

A solution of tert-butyl 4-(2-formyl-4-nitrophenyl)piperazine-1-carboxylate (5.89 g, 17.56 mmol) in anhydrous THF (32.5 mL) was cooled to 0° C. followed by the portionwise addition of sodium borohydride (0.664 g, 17.56 mmol). The reaction mixture was stirred at 0° C. for 90 minutes then quenched with water (50 mL) and extracted into dichloromethane (3×30 mL). The combined organic phases were dried over Na$_2$SO$_4$, filtered and concentrated to dryness under reduced pressure to give the title compound as a yellow solid (5.42 g, 91%). $^1$H NMR (300 MHz, CDCl$_3$): δ 8.32 (d, 1H), 8.13 (dd, 1H), 7.10 (d, 1H), 4.80 (d, 2H), 3.61 (t, 4H), 3.05 (t, 1H), 2.99 (t, 4H), 1.48 (s, 9H). LCMS (Method C): R$_T$=1.48 min, m/z=338 [M+H]$^+$.

Step 3: tert-butyl 4-(2-(methoxymethyl)-4-nitrophenyl)piperazine-1-carboxylate

A solution of tert-butyl 4-(2-(hydroxymethyl)-4-nitrophenyl)piperazine-1-carboxylate (2.00 g, 5.93 mmol) in anhydrous THF (19.7 mL) was cooled to 0° C. followed by the addition of sodium hydride (60% in mineral oil, 0.26 g, 6.52 mmol). After stirring at 0° C. under a nitrogen atmosphere for 10 minutes, methyl iodide (0.45 mL, 7.11 mmol) was added. The resulting mixture was allowed to warm to room temperature and stirred for 60 minutes. Further methyl iodide (0.13 mL, 2.08 mmol) was added and the mixture stirred for an additional 60 minutes. The reaction mixture was diluted with ammonium chloride solution (30 mL) and extracted into ethyl acetate (3×20 mL). The combined organic phases were dried over Na$_2$SO$_4$, filtered, concentrated to dryness under reduced pressure and chromatographed (silica 50 g cartridge, cyclohexane:ethyl acetate, gradient elution from 95:5 to 50:50) to give the title compound as a yellow solid (1.48 g, 71%). $^1$H NMR (300 MHz, CDCl$_3$): δ 8.35 (d, 1H), 8.13 (dd, 1H), 7.04 (d, 1H), 4.48 (s, 2H), 3.60 (t, 4H), 3.46 (s, 3H), 3.00 (t, 4H), 1.49 (s, 9H). LCMS (Method C) R$_T$=1.79 min, m/z=352 [M+H]$^+$.

Step 4: tert-butyl 4-(4-amino-2-(methoxymethyl)phenyl)piperazine-1-carboxylate

A solution of tert-butyl 4-(2-(methoxymethyl)-4-nitrophenyl)piperazine-1-carboxylate (1.48 g, 4.21 mmol) in methanol (100 mL) was hydrogenated by H-Cube (10% Pd/C cartridge, Full H$_2$, 25° C., 1 mL/min) with two passes. The reaction mixture was concentrated to dryness under reduced pressure to give the title compound as an off-white solid (1.33 g, 98%). $^1$H NMR (300 MHz, CDCl$_3$): δ 6.91 (d, 1H), 6.78 (d, 1H), 6.59 (dd, 1H), 4.49 (s, 2H), 3.47-3.61 (m, 6H), 3.42 (s, 3H), 2.77 (t, 4H), 1.48 (s, 9H). LCMS (Method C): R$_T$=0.94 min, m/z=322 [M+H]$^+$.

Step 5: tert-butyl 4-(4-((6-(2,6-dichlorophenyl)-8-methyl-5-oxo-5,6,7,8-tetrahydropyrimido[4,5-d]pyrimidin-2-yl)amino)-2-(methoxymethyl)phenyl)piperazine-1-carboxylate A solution of mCPBA, 50% purity (291 mg, 0.844 mmol) in dichloromethane (1.50 mL) was passed through a phase separator and washed through with further dichloromethane (0.750 mL). This solution was added to a stirring suspension of 3-(2,6-dichlorophenyl)-1-methyl-7-(methylthio)-2,3-dihydropyrimido[4,5-d]pyrimidin-4(1H)-one (250 mg, 0.704 mmol) in anhydrous toluene (7.5 mL) and the mixture stirred for 30 minutes. Hunig's Base (0.369 mL, 2.111 mmol) was added followed by tert-butyl 4-(4-amino-2-(methoxymethyl)phenyl)piperazine-1-carboxylate (215 mg, 0.669 mmol) and the mixture was heated to 75° C. for 40 h. After cooling, the reaction mixture was purified directly by flash chromatography (5-65% ethyl acetate in cyclohexane) to afford the title compound (360 mg, 81%). LCMS (Method C): R$_T$=1.81 min, m/z=628 [M+H]$^+$.

Step 6: 3-(2,6-dichlorophenyl)-7-((3-(methoxymethyl)-4-(piperazin-1-yl)phenyl)amino)-1-methyl-2,3-dihydropyrimido[4,5-d]pyrimidin-4(1H)-one To a stirring solution of tert-butyl 4-(4-((6-(2,6-dichlorophenyl)-8-methyl-5-oxo-5,6,7,8-tetrahydropyrimido[4,5-d]pyrimidin-2-yl)amino)-2-(methoxymethyl)phenyl)piperazine-1-carboxylate in anhydrous dichloromethane (6 mL) was added trifluoroacetic acid (1.5 mL, 19.5 mmol) and the solution stirred for 2 h. An SCX-2 silica cartridge (10 g) was pretreated with 20% v/v methanol in dichloromethane (100 mL). The reaction mixture was added to the SCX-2 column using dichloromethane (3×2 mL) to rinse the flask. After 5 mins the column was flushed with 20% v/v methanol in dichloromethane (100 mL) followed by 20% v/v (7 M ammonia in methanol) in dichloromethane (50 mL). The ammonia containing fraction was concentrated in vacuo. The residue was dissolved in methanol (3 mL) and water (12 mL) and freeze-dried to afford the title compound (260 mg, 86%). $^1$H NMR (400 MHz, MeOH-d$_4$): δ 8.55 (s, 1H), 7.84-8.01 (m, 1H), 7.53-7.64 (m, 3H), 7.44 (dd, 1H), 7.14 (d, 1H), 5.00 (s, 2H), 4.59 (s, 2H), 3.45 (s, 3H), 3.21 (s, 3H), 3.00 (t, 4H), 2.90 (t, 4H). LCMS (Method C): R$_T$=0.77 min, m/z=528 [M+H]$^+$.

Example 32: (R)-3-(2,6-dichlorophenyl)-7-((4-(3,4-dimethyl piperazin-1-yl)phenyl)amino)-1-methyl-2,3-dihydropyrimido[4,5-d]pyrimidin-4(1H)-one

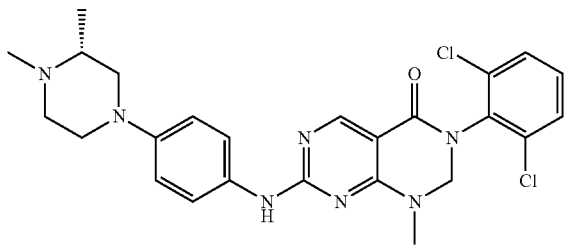 [SMILES: C[C@@H]1CN(c2ccc(Nc3ncc4c(n3)N(C)CN(c3c(Cl)cccc3Cl)C4=O)cc2)CCN1C]

Step 1: (R)-3-(2,6-dichlorophenyl)-1-methyl-7-((4-(3-methylpiperazin-1-yl)phenyl)amino)-2,3-dihydropyrimido[4,5-d]pyrimidin-4(1H)-one 3-(2,6-Dichlorophenyl)-1-methyl-7-(methylthio)-2,3-dihydropyrimido[4,5-d]pyrimidin-4(1H)-one (150 mg, 0.42 mmol) was reacted with (R)-tert-butyl 4-(4-aminophenyl)-2-methylpiperazine-1-carboxylate (123 mg, 0.422 mmol) following the procedure for Example 31 to give the title compound (120 mg, 41%) which was used without further purification.

Step 2: (R)-3-(2,6-dichlorophenyl)-7-((4-(3,4-dimethylpiperazin-1-yl)phenyl)amino)-1-methyl-2,3-dihydropyrimido[4,5-d]pyrimidin-4(1H)-one (R)-3-(2,6-dichlorophenyl)-1-methyl-7-((4-(3-methylpiperazin-1-yl)phenyl)amino)-2,3-dihydropyrimido[4,5-d]pyrimidin-4(1H)-one (60 mg, 0.12 mmol) was reacted with formaldehyde (0.018 mL, 0.24 mmol) following the procedure for example 35 to give the title compound (56 mg, 91%). $^1$H NMR (400 MHz, DMSO-d$_6$): δ 9.72 (s, 1H), 8.43 (s, 1H), 7.66 (m, 3H), 7.46 (m, 1H), 6.91 (d, 2H), 4.95 (s, 2H), 3.45 (m, 2H), 3.34 (s, 1H), 3.09 (s, 3H), 2.83 (m, 1H), 2.67 (m, 1H), 2.30 (m, 1H), 1.05 (d, 3H). LCMS (Method C): R$_T$=0.72 min, m/z=512 [M+H]$^+$.

Example 33: 3-(2,6-dichlorophenyl)-7-((3-(hydroxymethyl)-4-(4-methylpiperazin-1-yl)phenyl)amino)-1-methyl-2,3-dihydropyrimido[4,5-d]pyrimidin-4(1H)-one

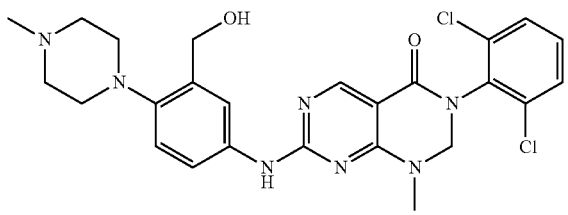 [SMILES: CN1CCN(c2ccc(Nc3ncc4c(n3)N(C)CN(c3c(Cl)cccc3Cl)C4=O)cc2CO)CC1]

3-(2,6-dichlorophenyl)-7-((3-(hydroxymethyl)-4-(piperazin-1-yl)phenyl)amino)-1-methyl-2,3-dihydropyrimido[4,5-d]pyrimidin-4(1H)-one (60 mg, 0.117 mmol) was reacted with formaldehyde (0.018 mL) following the procedure for Example 35 to give the title compound (59 mg, 96%). $^1$H NMR (400 MHz, DMSO-d$_6$): δ 9.82 (s, 1H), 8.45 (s, 1H), 8.12 (s, 1H), 7.99 (s, 1H), 7.65 (d, 2H), 7.48 (m, 1H), 7.01 (d, 1H), 5.09 (t, 1H), 4.97 (s, 2H), 4.54 (d, 2H), 3.17 (s, 3H), 2.80 (m, 4H), 2.4 (m, 4H), 2.25 (s, 3H). LCMS (Method C): R$_T$=0.69 min, m/z=528 [M+H]$^+$.

Example 34: (R)-3-(2,6-dichlorophenyl)-7-((4-(3-(hydroxymethyl)-4-methylpiperazin-1-yl)phenyl)amino)-1-methyl-2,3-dihydropyrimido[4,5-d]pyrimidin-4(1H)-one

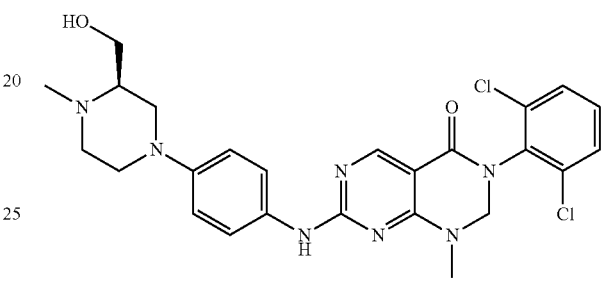

(R)-3-(2,6-dichlorophenyl)-7-((4-(3-(hydroxymethyl)piperazin-1-yl)phenyl)amino)-1-methyl-2,3-dihydropyrimido[4,5-d]pyrimidin-4(1H)-one (60 mg, 0.117 mmol) was reacted with formaldehyde (0.017 mL) following the procedure for Example 35 to give the title compound (60 mg, 97%). $^1$H NMR (400 MHz, DMSO-d$_6$): δ 9.72 (s, 1H), 8.44 (s, 1H), 7.7-7.6 (m, 4H), 7.48 (m, 1H), 6.91 (d, 2H), 4.95 (s, 2H), 3.65 (m, 2H), 3.43 (m, 1H), 3.17 (d, 1H), 3.09 (s, 3H), 2.80 (m, 1H), 2.65 (m, 1H), 2.45 (m, 1H), 2.31 (m, 1H), 2.25 (s, 3H), 2.13 (m, 1H). LCMS (Method C): R$_T$=0.69 min, m/z=528 [M+H]$^+$.

Example 35: 3-(2,6-dichlorophenyl)-1-methyl-7-((4-(5-methylhexahydropyrrolo[3,4-c]pyrrol-2(1H)-yl)phenyl)amino)-2,3-dihydropyrimido[4,5-d]pyrimidin-4(1H)-one

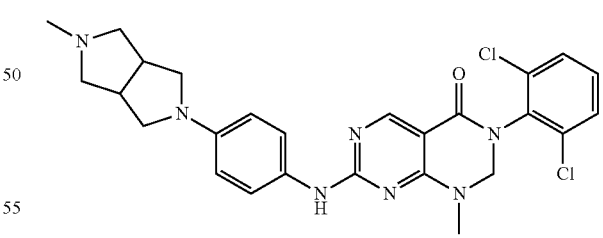

Step 1: tert-butyl 5-(4-nitrophenyl)hexahydropyrrolo[3,4-c]pyrrole-2(1H)-carboxylate A suspension of 1-fluoro-4-nitrobenzene (1.662 g, 11.78 mmol), tert-butyl hexahydropyrrolo[3,4-c]pyrrole-2(1H)-carboxylate (2.5 g, 11.78 mmol) and potassium carbonate (2.441 g, 17.66 mmol) in anhydrous DMF (5 mL) was heated to 50° C. under a nitrogen atmosphere overnight. Further DMF (5 mL) was added and the mixture heated at 50° C. for a further 24 hours. The reaction mixture was allowed to cool to room temperature, diluted with water (30 mL) and stirred at room temperature for 15 minutes. The precipitated solid was isolated by filtration, washed with water and sucked dry to give the title compound as a yellow solid (3.21 g, 82%). $^1$H NMR (300 MHz, CDCl$_3$): δ 8.13 (dt, 2H), 6.47 (dt, 2H), 3.59-3.74 (m, 4H), 3.21-3.43 (m, 4H), 2.98-3.14 (m, 2H), 1.45 (s, 9H). LCMS (Method C): R$_T$=1.66 min, m/z=334 [M+H]$^+$.

Step 2: tert-butyl 5-(4-aminophenyl)hexahydropyrrolo[3,4-c]pyrrole-2(1H)-carboxylate A solution of tert-butyl 5-(4-nitrophenyl)hexahydropyrrolo[3,4-c]pyrrole-2(1H)-carboxylate (2.3 g, 6.90 mmol) in methanol (500 mL) was hydrogenated by H-Cube (10% Pd/C cartridge, Full H$_2$, 25° C., 1.5 mL/min). The reaction mixture was concentrated to dryness under reduced pressure to give the title compound as a grey solid (1.35 g, 65%). $^1$H NMR (300 MHz, CDCl$_3$): δ 6.67 (d, 2H), 6.45 (d, 2H), 3.63 (dd, 2H), 2.87-3.55 (m, 10H), 1.45 (s, 9H). LCMS (Method C): R$_T$=0.76 min, m/z=304 [M+H]$^+$.

Step 3: 3-(2,6-dichlorophenyl)-1-methyl-7-((4-(5-methylhexahydropyrrolo[3,4-c]pyrrol-2(1H)-yl)phenyl)amino)-2,3-dihydropyrimido[4,5-d]pyrimidin-4(1H)-one A solution of tert-butyl 5-(4-aminophenyl hexahydropyrrolo[3,4-c]pyrrole-2(1H)-carboxylate (50 mg, 0.098 mmol), formaldehyde (37% in water, 0.015 mL, 0.196 mmol, 2 eq) and sodium triacetoxyborohydride (0.062 g, 0.294 mmol, 3 eq) was stirred at room temperature for 1 h. The solution was then loaded onto an SCX-2 column. The column was eluted with DCM/MeOH (20/80, 20 mL) then with a 7 N solution of ammonia in methanol. The ammonia fraction was concentrated in vacuo. The residue was diluted with methanol and water and freeze-dried to give the title compound (25 mg, 49%). $^1$H NMR (400 MHz, DMSO-d$_6$): δ 9.66 (br s, 1H), 8.43 (s, 1H), 7.64 (m, 2H), 7.56-7.45 (m, 3H), 6.62 (d, 2H), 4.94 (s, 2H), 3.34 (m, 3H), 3.08 (s, 3H), 3.02 (m, 2H), 2.85 (m, 2H), 2.56 (m, 1H), 2.37 (m, 2H). LCMS (Method C): R$_T$=0.72 min, m/z=524 [M+H]$^+$.

Example 36: 3-(2,6-dichlorophenyl)-7-((4-(hexahydropyrrolo [3,4-c]pyrrol-2(1H)-yl)phenyl)amino)-1-methyl-2,3-dihydropyrimido[4,5-d]pyrimidin-4(1H)-one

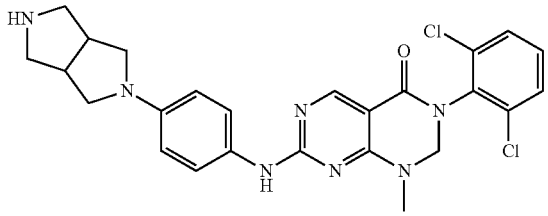 [SMILES: CN1CN(c2c(Cl)cccc2Cl)C(=O)c2cnc(Nc3ccc(N4CC5CNCC5C4)cc3)nc21]

3-(2,6-dichlorophenyl)-1-methyl-7-(methylthio)-2,3 dihydropyrimido [4,5-d]pyrimidin-4(1H)-one (150 mg, 0.422 mmol) was reacted with tert-butyl 5-(4-aminophenyl) hexahydropyrrolo [3,4-c]pyrrole-2(1H)-carboxylate (128 mg, 0.422 mmol) following the procedure for example 31 to give the title compound (120 mg, 56%). $^1$H NMR (400 MHz, DMSO-d$_6$): δ 9.66 (s, 1H), 8.43 (s, 1H), 7.64 (d, 2H), 7.56-7.45 (m, 3H), 6.62 (d, 2H), 4.94 (s, 2H), 3.40-3.32 (m, 3H), 3.08 (s, 3H), 3.10-2.95 (m, 3H), 2.85 (m, 2H), 2.66 (m, 2H). LCMS (Method C): R$_T$=0.72 min, m/z=510 [M+H]$^+$.

Example 37: 7-((4-(1-aminocyclobutyl)phenyl) amino)-3-(2,6-dichlorophenyl)-1-methyl-2,3-dihydropyrimido[4,5-d]pyrimidin-4(1H)-one

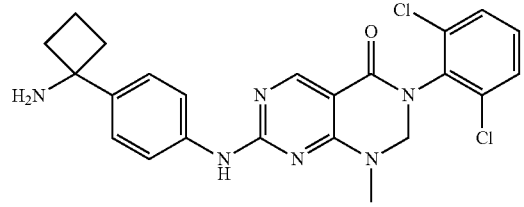 [SMILES: CN1CN(c2c(Cl)cccc2Cl)C(=O)c2cnc(Nc3ccc(C4(N)CCC4)cc3)nc21]

3-(2,6-Dichlorophenyl)-1-methyl-7-(methylthio)-2,3-dihydropyrimido[4,5-d]pyrimidin-4(1H)-one (150 mg, 0.422 mmol) was reacted with tert-butyl (1-(4-aminophenyl) cyclobutyl) carbamate (111 mg, 0.422 mmol) following the procedure for example 31 to give the title compound (45 mg, 83%). $^1$H NMR (400 MHz, DMSO-d$_6$): δ 9.89 (s, 1H), 8.49 (s, 1H), 7.73 (d, 2H), 7.65 (d, 2H), 7.48 (t, 1H), 7.40 (d, 2H), 4.98 (s, 2H), 3.12 (s, 3H), 2.38 (m, 2H), 2.07 (m, 2H), 1.95 (m, 1H), 1.60 (m, 1H). LCMS (Method A): R$_T$=0.81 min, m/z=469 [M+H]$^+$ Example 38: (R)-3-(2,6-dichlorophenyl)-7-((3-(hydroxymethyl)-4-(3-methylpiperazin-1-yl)phenyl) amino)-1-methyl-2,3-dihydropyrimido[4,5-d]pyrimidin-4(1H)-one

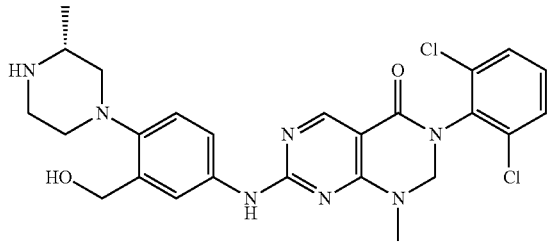 [SMILES: C[C@@H]1CN(c2ccc(Nc3ncc4c(n3)N(C)CN(c3c(Cl)cccc3Cl)C4=O)cc2CO)CCN1]

Step 1: (R)-tert-butyl 4-(2-formyl-4-nitrophenyl)-2-methylpiperazine-1-carboxylate A suspension of 2-fluoro-5-nitrobenzaldehyde (2.53 g, 14.98 mmol), (R)-tert-butyl 2-methylpiperazine-1-carboxylate (3 g, 14.98 mmol) and potassium carbonate (3.11 g, 22.47 mmol) in anhydrous DMF (10 mL) was heated to 50° C. under a nitrogen atmosphere overnight. The reaction mixture was allowed to cool to room temperature, diluted with water (70 mL) and stirred at room temperature for 15 minutes. The mixture was then extracted into ethyl acetate (100 mL) and washed with 50:50 water:brine. The organic phase was dried over Na$_2$SO$_4$, filtered and concentrated to dryness under reduced pressure to give the title compound as a yellow solid (4.72 g, 90%). $^1$H NMR (300 MHz, CDCl$_3$): δ 10.15 (s, 1H), 8.63 (d, 1H), 8.31 (dd, 1H), 7.08 (d, 1H), 4.41 (br s, 1H), 3.97 (dt, 1H), 3.20-3.53 (m, 4H), 3.08 (td, 1H), 1.48 (d, 9H), 1.31 (d, 3H). LCMS (Method C): R$_T$=1.68 min, m/z=350 [M+H]$^+$.

Step 2: (R)-tert-butyl 4-(2-(hydroxymethyl)-4-nitrophenyl)-2-methylpiperazine-1-carboxylate A solution of (R)-tert-butyl 4-(2-formyl-4-nitrophenyl)-2-methylpiperazine-1-carboxylate (4.72 g, 13.51 mmol) in anhydrous THF (25.02 mL) was cooled to 0° C. followed by the portionwise addition of sodium borohyride (0.511 g, 13.51 mmol). The reaction mixture was stirred at 0° C. for 90 minutes then quenched with water (50 mL) and extracted into dichloromethane (3×30 mL). The combined organic phases were dried over $Na_2SO_4$, filtered and concentrated to dryness under reduced pressure to give the title compound as a yellow solid (4.39 g, 92%). $^1$H NMR (300 MHz, $CDCl_3$): δ 8.34 (d, 1H), 8.12 (dd, 1H), 7.09 (d, 1H), 4.81 (br s, 2H), 4.37 (br s, 1H), 3.99 (dt, 1H), 3.27 (td, 1H), 3.12 (ddd, 1H), 3.05 (dt, 1H), 2.88-3.01 (m, 2H), 2.80 (td, 1H), 1.48 (s, 9H), 1.36 (d, 3H). LCMS (Method C): $R_T$=1.56 min, m/z=352 [M+H]$^+$.

Step 3: (R)-tert-butyl 4-(4-amino-2-(hydroxymethyl)phenyl)-2-methylpiperazine-1-carboxylate A solution of (R)-tert-butyl 4-(2-(hydroxymethyl)-4-nitrophenyl)-2-methylpiperazine-1-carboxylate (2.4 g, 6.83 mmol) in methanol (100 mL) was hydrogenated by H-Cube (10% Pd/C cartridge, Full $H_2$, 25° C., 1 mL/min). The reaction mixture was concentrated to dryness under reduced pressure to give the title compound as a yellow solid (2.05 g, 93%). $^1$H NMR (300 MHz, $CDCl_3$): δ 6.99 (d, 1H), 6.57 (dd, 1H), 6.53 (d, 1H), 4.96 (br s, 1H), 4.69 (s, 2H), 4.26-4.39 (m, 1H), 3.94 (br d, 1H), 3.62 (br s, 2H), 3.21 (td, 1H), 2.87-2.97 (m, 2H), 2.65-2.82 (m, 2H), 1.48 (s, 9H), 1.33 (d, 3H). LCMS (Method C): $R_T$=0.81 min, m/z=322 [M+H]$^+$.

Step 4: (R)-3-(2,6-dichlorophenyl)-7-((3-(hydroxymethyl)-4-(3-methylpiperazin-1-yl)phenyl)amino)-1-methyl-2,3-dihydropyrimido[4,5-d]pyrimidin-4(1H)-one 3-(2,6-Dichlorophenyl)-1-methyl-7-(methylthio)-2,3-dihydropyrimido[4,5-d]pyrimidin-4(1H)-one (120 mg, 0.338 mmol) was reacted with (R)-tert-butyl 4-(4-amino-2-(hydroxymethyl)phenyl)-2-methylpiperazine-1-carboxylate (109 mg, 0.338 mmol) following the procedure for Example 31 to give the title compound (57.5 mg, 76%). $^1$H NMR (400 MHz, MeOH-$d_4$): δ 8.55 (s, 1H), 7.90 (br s, 1H), 7.54-7.61 (m, 3H), 7.44 (dd, 1H), 7.15 (d, 1H), 5.00 (s, 2H), 4.77 (s, 2H), 3.21 (s, 3H), 2.94-3.06 (m, 5H), 2.77 (td, 1H), 2.46 (t, 1H), 1.13 (d, 3H). LCMS (Method C): $R_T$=0.71 min, m/z=528 [M+H]$^+$.

Example 39: 7-((4-((1S,4S)-2,5-diazabicyclo[2.2.1]heptan-2-yl)phenyl)amino)-3-(2,6-dichlorophenyl)-1-methyl-2,3-dihydropyrimido[4,5-d]pyrimidin-4(1H)-one

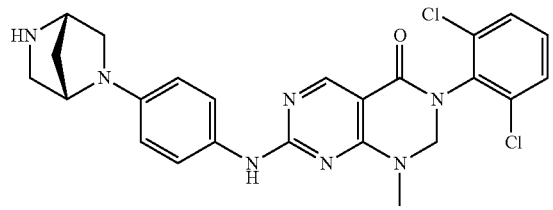 [SMILES: CN1CN(c2c(Cl)cccc2Cl)C(=O)c2cnc(Nc3ccc(N4C[C@@H]5C[C@H]4CN5)cc3)nc21]

Step 1: tert-butyl 5-(4-nitrophenyl)-2,5-diazabicyclo[2.2.1]heptane-2-carboxylate To a stirring suspension of 1-fluoro-4-nitrobenzene (1.294 g, 9.17 mmol) and potassium carbonate (5.07 g, 36.7 mmol) in anhydrous DMF (10 mL) was added tert-butyl 2,5-diazabicyclo[2.2.1]heptane-2-carboxylate (2 g, 10.09 mmol) and the mixture heated at 80° C. for 40 h. After cooling the mixture was partitioned between brine/water (100 mL) and ethyl acetate (50 mL). The aqueous layer was separated and extracted with ethyl acetate (3×50 mL). The combined ethyl acetate fractions were washed with brine/water (1:1, 4×25 mL), dried (anhydrous sodium sulfate), filtered and reduced in vacuo. The resulting residue was chromatographed (gradient 0-50% ethyl acetate in cyclohexane) to afford the title compound (2.11 g, 72.0%). $^1$H NMR (400 MHz, $CDCl_3$): δ 8.12 (d, 2H), 6.49 (d, 2H), 4.53-4.71 (m, 2H), 3.59 (d, 1H), 3.23-3.51 (m, 3H), 2.00 (m, 2H), 1.44 (d, 9H). LCMS (Method C): $R_T$=1.57 min, m/z=320 [M+H]$^+$.

Step 2: tert-butyl 5-(4-aminophenyl)-2,5-diazabicyclo[2.2.1]heptane-2-carboxylate A solution of tert-butyl 5-(4-nitrophenyl)-2,5-diazabicyclo[2.2.1]heptane-2-carboxylate (1.20 g, 3.76 mmol) in tetrahydrofuran (50 mL) was passed twice through an H-Cube apparatus fitted with a 10% Pd—C cartridge under the following settings [1.0 ml/min flow, 20° C., Full $H_2$ mode]. The solvent was removed in vacuo to afford the title compound which was used without further purification (1.03 g, 95%). LCMS (Method C): $R_T$=0.68 min, m/z=290 [M+H]$^+$.

Step 3: 7-((4-((1S,4S)-2,5-diazabicyclo[2.2.1]heptan-2-yl)phenyl)amino)-3-(2,6-dichlorophenyl)-1-methyl-2,3-dihydropyrimido[4,5-d]pyrimidin-4(1H)-one 3-(2,6-Dichlorophenyl)-1-methyl-7-(methylthio)-2,3-dihydropyrimido[4,5-d]pyrimidin-4(1H)-one (120 mg, 0.338 mmol) was reacted with (1S,4S)-tert-butyl 5-(4-aminophenyl)-2,5-diazabicyclo[2.2.1]heptane-2-carboxylate (98 mg, 0.338 mmol) following the procedure for Example 31 to give the title compound (84.0 mg, 100%). $^1$H NMR (400 MHz, MeOH-$d_4$): δ 8.50 (s, 1H), 7.57 (d, 2H), 7.49 (br s 2H), 7.43 (dd, 1H), 6.64 (d, 2H), 4.97 (s, 2H), 4.39 (s, 1H), 3.78 (s, 1H), 3.63 (dd, 1H), 3.16 (s, 3H), 3.06 (t, 2H), 2.97 (dd, 1H), 1.99 (d, 1H), 1.82 (d, 1H). LCMS (Method C): $R_T$=0.72 min, m/z=496 [M+H]$^+$.

Example 40: 3-(2,6-dichlorophenyl)-7-((4-((2R,5S)-2,5-dimethylpiperazin-1-yl)phenyl)amino)-1-methyl-2,3-dihydropyrimido[4,5-d]pyrimidin-4(1H)-one

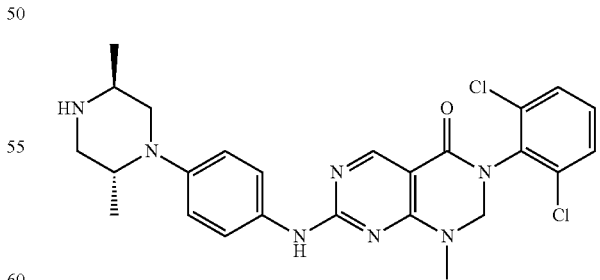

Step 1: (2S,5R)-tert-butyl 2,5-dimethyl-4-(4-nitrophenyl)piperazine-1-carboxylate To a stirring suspension of 1-fluoro-4-nitrobenzene (0.60 g, 4.24 mmol) and potassium carbonate (2.34 g, 16.97 mmol) in anhydrous DMF (5 mL) was added (2S,5R)-tert-butyl 2,5-dimethylpiperazine-1-carboxylate (1 g, 4.67 mmol) and the mixture heated at 90° C. for 120 h. After cooling the mixture was partitioned between brine/water (1:1, 50 mL) and ethyl acetate (25 mL). The aqueous layer was separated and extracted with ethyl acetate (3×25 mL). The combined ethyl acetate fractions were washed with brine/water (1:1, 4×12.5 mL), dried (anhydrous sodium sulfate), filtered and reduced in vacuo. The resulting residue was purified by silica gel chromatography (gradient 0-50% Ethyl Acetate in Cyclohexane) to afford the title compound (1.03 g, 72.4%). $^1$H NMR (400 MHz, CDCl$_3$): δ 8.12 (d, 2H), 6.77 (d, 2H), 4.24-4.58 (m, 1H), 4.03-4.16 (m, 1H), 3.73-3.93 (m, 1H), 3.31-3.49 (m, 3H), 1.49 (s, 9H), 1.24 (d, 3H), 1.18 (d, 3H). LCMS (Method C): R$_T$=1.80 min, m/z=336 [M+H]$^+$.

Step 2: (2S,5R)-tert-butyl 4-(4-aminophenyl)-2,5-dimethylpiperazine-1-carboxylate A solution of (2S,5R)-tert-butyl 2,5-dimethyl-4-(4-nitrophenyl)piperazine-1-carboxylate (1.03 g, 3.07 mmol) in methanol (100 mL) was passed through an H-Cube apparatus fitted with a 10% Pd—C cartridge under the following settings [1.0 ml/min flow, 40° C., Full H$_2$ mode]. The solvent was removed in vacuo to afford the title compound which was used without further purification (900 mg, 96%). $^1$H NMR (400 MHz, DMSO-d$_6$): δ 6.62 (d, 2H), 6.49 (d, 2H), 4.51 (s, 2H), 4.21-4.29 (m, 1H), 3.67-3.75 (m, 1H), 3.63 (d, 1H), 3.33 (dd, 1H), 3.04 (dd, 1H), 2.79 (d, 1H), 1.41 (s, 9H), 1.17 (d, 3H), 0.78 (d, 3H). LCMS (Method C): R$_T$=0.82 min, m/z=306 [M+H]$^+$.

Step 3: 3-(2,6-dichlorophenyl)-7-((4-((2R,5S)-2,5-dimethylpiperazin-1-yl)phenyl)amino)-1-methyl-2,3-dihydropyrimido[4,5-d]pyrimidin-4(1H)-one 3-(2,6-Dichlorophenyl)-1-methyl-7-(methylthio)-2,3-dihydropyrimido[4,5-d]pyrimidin-4(1H)-one (200 mg, 0.563 mmol) was reacted with (2S,5R)-tert-butyl 4-(4-aminophenyl)-2,5-dimethylpiperazine-1-carboxylate (163 mg, 0.535 mmol) following the procedure for Example 31 to give the title compound (151 mg, 92%). $^1$H NMR (300 MHz, MeOH-d$_4$): δ 8.56 (s, 1H), 7.69 (d, 2H), 7.57 (d, 2H), 7.43 (dd, 1H), 7.18 (d, 2H), 5.00 (s, 2H), 3.19 (s, 3H), 2.92-3.11 (m, 4H), 2.64 (dd, 1H), 2.50 (t, 1H), 1.09 (d, 3H), 0.90 (d, 3H). LCMS (Method C): R$_T$=0.79 min, m/z=512 [M+H]$^+$.

Example 41: 3-(2,6-dichlorophenyl)-1-methyl-7-((4-morpholinophenyl)amino)-2,3-dihydropyrimido[4,5-d]pyrimidin-4(1H)-one

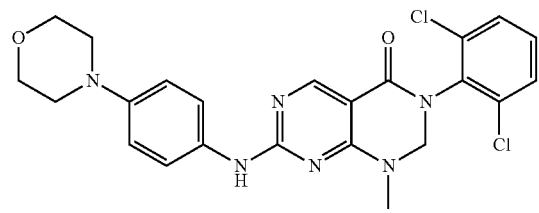 [SMILES: CN1CN(c2c(Cl)cccc2Cl)C(=O)c2cnc(Nc3ccc(N4CCOCC4)cc3)nc21]

3-(2,6-Dichlorophenyl)-1-methyl-7-(methylthio)-2,3-dihydropyrimido[4,5-d]pyrimidin-4(1H)-one (120 mg, 0.338 mmol) was reacted with 4-morpholinoaniline (60 mg, 0.338 mmol) following the procedure for example 31 to give the title compound as an off-white solid (67 mg, 41%). $^1$H NMR (400 MHz, DMSO-d$_6$): δ 9.74 (s, 1H), 8.45 (s, 1H), 7.64 (d, 4H), 7.50 (t, 1H), 6.91 (d, 2H),4.97 (s, 2H), 3.74 (m, 4H), 3.09 (s, 3H), 3.04 (m, 4H). LCMS (Method C): R$_T$=1.17 min, m/z=485 [M+H]$^+$.

Example 42: 3-(2,6-dichlorophenyl)-7-((4-(1,1-dioxidothiomorpholino) phenyl)amino)-1-methyl-2,3-dihydropyrimido[4,5-d]pyrimidin-4(1H)-one

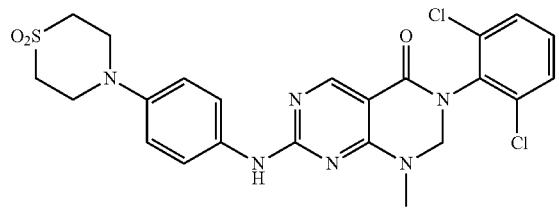 [SMILES: CN1CN(c2c(Cl)cccc2Cl)C(=O)c2cnc(Nc3ccc(N4CCS(=O)(=O)CC4)cc3)nc21]

3-(2,6-Dichlorophenyl)-1-methyl-7-(methylthio)-2,3-dihydropyrimido[4,5-d]pyrimidin-4(1H)-one (120 mg, 0.338 mmol) was reacted with tert-5 butyl 4-(4-amino-2-methoxyphenyl)piperazine-1-carboxylate (76 mg, 0.338 mmol) following the procedure for Example 31 to give the title compound (91 mg, 53%). $^1$H NMR (400 MHz, DMSO-d$_6$): δ 9.78 (s, 1H), 8.45 (s, 1H), 7.7-7.6 (m, 4H), 7.48 (m, 1H), 7.01 (d, 2H), 4.96 (s, 2H), 3.72 (m, 4H), 3.13 (m, 4H), 3.03 (s, 3H). LCMS (Method C): R$_T$=1.09 min, m/z=533 [M+H]$^+$.

Example 43: (R)-3-(2,6-dichlorophenyl)-7-((3-fluoro-4-(3-methylpiperazin-1-yl)phenyl)amino)-1-methyl-2,3-dihydropyrimido[4,5-d]pyrimidin-4(1H)-one

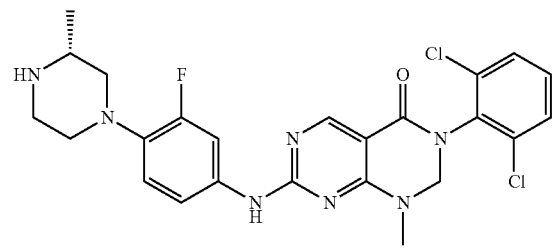 [SMILES: C[C@@H]1CN(c2ccc(Nc3ncc4c(n3)N(C)CN(c3c(Cl)cccc3Cl)C4=O)cc2F)CCN1]

Step 1: (R)-tert-butyl 4-(2-fluoro-4-nitrophenyl)-2-methylpiperazine-1-carboxylate To a stirring suspension of 1,2-difluoro-4-nitrobenzene (1.444 g, 9.08 mmol) and potassium carbonate (5.02 g, 36.3 mmol) in anhydrous DMF (10 mL) was added (R)-tert-butyl 2-methylpiperazine-1-carboxylate (2 g, 9.99 mmol) and the mixture heated at 90° C. for 21 h. After cooling the mixture was partitioned between brine/water (100 mL) and ethyl acetate (50 mL). The aqueous layer was separated and extracted with ethyl acetate (3×50 mL). The combined ethyl acetate fractions were washed with brine/water (1:1, 4×25 mL), dried (anhydrous sodium sulfate), filtered and reduced in vacuo. The resulting residue was chromatographed (gradient 0-30% ethyl acetate in cyclohexane) to afford the title compound (2.56 g, 83%). $^1$H NMR (400 MHz, CDCl$_3$): δ

7.98 (dd, 1H), 7.90 (dd, 1H), 6.89 (t, 1H), 4.30-4.40 (m, 1H), 3.97 (d, 1H), 3.44-3.56 (m, 2H), 3.28 (td, 1H), 3.07 (dd, 1H), 2.93 (td, 1H), 1.49 (s, 9H), 1.31 (d, 3H). LCMS (Method C): $R_T$=1.87 min, m/z=284 [M−butene]$^+$.

Step 2: (R)-tert-butyl 4-(4-amino-2-fluorophenyl)-2-methylpiperazine-1-carboxylate A solution of (R)-tert-butyl 4-(2-fluoro-4-nitrophenyl)-2-methylpiperazine-1-carboxylate (1.3 g, 3.83 mmol) in tetrahydrofuran (40 mL) was passed through an H-Cube apparatus fitted with a 10% Pd—C cartridge under the following settings [1.0 ml/min flow, 40° C., Full H$_2$ mode]. The solvent was removed in vacuo to afford the title compound which was used without further purification (1.17 g, 99%). $^1$H NMR (300 MHz, CDCl$_3$): δ 6.74 (dd, 1H), 6.32 (dd, 1H), 6.29 (dd, 1H), 5.01 (br s, 2H), 4.07-4.20 (m, 1H), 3.75 (d, 1H), 3.08 (td, 1H), 2.98 (d, 1H), 2.91 (d, 1H), 2.62 (dd, 1H), 2.55 (dd, 1H), 1.41 (s, 9H), 1.23 (d, 3H). LCMS (Method C): $R_T$=1.32 min, m/z=310 [M+H]$^+$.

Step 3: (R)-3-(2,6-dichlorophenyl)-7-((3-fluoro-4-(3-methylpiperazin-1-yl)phenyl)amino)-1-methyl-2,3-dihydropyrimido[4,5-d]pyrimidin-4(1H)-one 3-(2,6-Dichlorophenyl)-1-methyl-7-(methylthio)-2,3-dihydropyrimido[4,5-d]pyrimidin-4(1H)-one (250 mg, 0.704 mmol) was reacted with (R)-tert-butyl 4-(4-amino-2-fluorophenyl)-2-methylpiperazine-1-carboxylate (207 mg, 0.669 mmol) following the procedure for Example 31 to give the title compound (227 mg, 88%). $^1$H NMR (400 MHz, MeOH-d$_4$): δ 8.56 (s, 1H), 7.70 (dd, 1H), 7.58 (d, 2H), 7.44 (dd, 1H), 7.36 (d, 1H), 7.03 (t, 1H), 5.01 (s, 2H), 3.28 (d, 2H), 3.20 (s, 3H), 2.98-3.11 (m, 3H), 2.75 (td, 1H), 2.42 (t, 1H), 1.14 (d, 3H). LCMS (Method C): $R_T$=0.83 min, m/z=516 [M+H]$^+$.

Example 44: 3-(2,6-dichlorophenyl)-1-methyl-7-((4-((1S,4S)-5-methyl-2,5-diazabicyclo[2.2.1]heptan-2-yl)phenyl)amino)-2,3-dihydropyrimido[4,5-d]pyrimidin-4(1H)-one

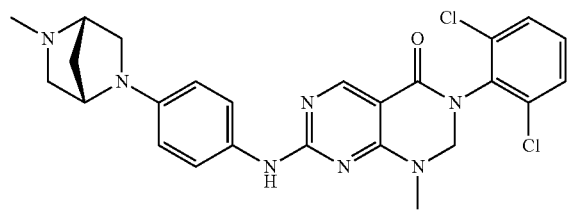

Step 1: 3-(2,6-dichlorophenyl)-1-methyl-7-((4-((1S,4S)-5-methyl-2,5-diazabicyclo[2.2.1]heptan-2-yl)phenyl)amino)-2,3-dihydropyrimido[4,5-d]pyrimidin-4(1H)-one 7-((4-(2,5-Diazabicyclo[2.2.1]heptan-2-yl)phenyl)amino)-3-(2,6-dichlorophenyl)-1-methyl-2,3-dihydropyrimido[4,5-d]pyrimidin-4(1H)-one (25 mg, 0.050 mmol) was methylated following the procedure in Example 35 to give the title compound (25.0 mg, 97%). $^1$H NMR (400 MHz, MeOH-d$_4$): δ 8.50 (s, 1H), 7.57 (d, 2H), 7.46-7.53 (m, 2H), 7.43 (dd, 1H), 6.64 (d, 2H), 4.97 (s, 2H), 4.32 (s, 1H), 3.54 (s, 1H), 3.46 (dd, 1H), 3.31 (d, 1H), 3.16 (s, 3H), 2.77-2.88 (m, 2H), 2.39 (s, 3H), 1.97 (q$_{AB}$, 2H). LCMS (Method C): $R_T$=0.72 min, m/z=510 [M+H]$^+$.

Example 45: 3-(2,6-dichlorophenyl)-1-methyl-7-((4-((2R,5S)-2,4,5-trimethylpiperazin-1-yl)phenyl)amino)-2,3-dihydropyrimido[4,5-d]pyrimidin-4(1H)-one

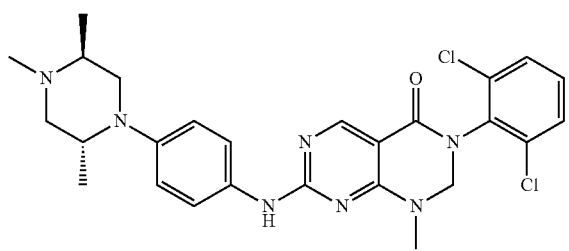 [SMILES: C[C@@H]1CN(C)[C@@H](C)CN1c1ccc(Nc2ncc3c(n2)N(C)CN(c2c(Cl)cccc2Cl)C3=O)cc1]

Step 1: 3-(2,6-dichlorophenyl)-1-methyl-7-((4-((2R,5S)-2,4,5-trimethylpiperazin-1-yl)phenyl)amino)-2,3-dihydropyrimido[4,5-d]pyrimidin-4(1H)-one 3-(2,6-dichlorophenyl)-7-((4-((2R,5S)-2,5-dimethylpiperazin-1-yl)phenyl)amino)-1-methyl-2,3-dihydropyrimido[4,5-d]pyrimidin-4(1H)-one (26 mg, 0.051 mmol) was methylated following the procedure in Example 35 to give the title compound (26.5 mg, 99%). $^1$H NMR (400 MHz, MeOH-d$_4$): δ 8.56 (s, 1H), 7.70 (d, 2H), 7.58 (d, 2H), 7.44 (dd, 1H), 7.18 (d, 2H), 5.00 (s, 2H), 3.20 (s, 3H), 3.13-3.19 (m, 1H), 3.01 (dd, 1H), 2.93 (dd, 1H), 2.66 (dd, 1H), 2.37-2.43 (m, 1H), 2.36 (s, 3H), 2.19 (dd, 1H), 1.11 (d, 3H), 0.92 (d, 3H). LCMS (Method C): $R_T$=0.84 min, m/z=526 [M+H]$^+$.

Example 46: (R)-3-(2,6-dichlorophenyl)-7-((4-(3,4-dimethylpiperazin-1-yl)-3-(hydroxymethyl)phenyl)amino)-1-methyl-2,3-dihydropyrimido[4,5-d]pyrimidin-4(1H)-one

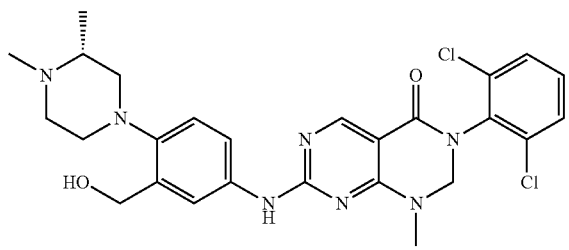 [SMILES: C[C@@H]1CN(c2ccc(Nc3ncc4c(n3)N(C)CN(c3c(Cl)cccc3Cl)C4=O)cc2CO)CCN1C]

Step 1: (R)-3-(2,6-dichlorophenyl)-7-((4-(3,4-dimethylpiperazin-1-yl)-3-(hydroxymethyl)phenyl)amino)-1-methyl-2,3-dihydropyrimido[4,5-d]pyrimidin-4(1H)-one (R)-3-(2,6-Dichlorophenyl)-7-((3-(hydroxymethyl)-4-(3-methylpiperazin-1-yl)phenyl)amino)-1-methyl-2,3-dihydropyrimido[4,5-d]pyrimidin-4(1H)-one (26 mg, 0.051 mmol) was methylated following the procedure in Example 35 to give the title compound (25.3 mg, 99%). $^1$H NMR (400 MHz, MeOH-d$_4$): δ 8.55 (s, 1H), 7.90 (s, 1H), 7.57-7.62 (m, 1H), 7.58 (d, 2H), 7.44 (dd, 1H), 7.15 (d, 1H), 5.00 (s, 2H), 4.76 (s, 2H), 3.21 (s, 3H), 2.88-3.02 (m, 4H), 2.61 (dd, 1H), 2.52 (td, 1H), 2.35-2.45 (m, 1H), 2.38 (s, 3H), 1.15 (d, 3H). LCMS (Method C): $R_T$=0.73 min, m/z=542 [M+H]$^+$.

Example 47: (R)-3-(2,6-dichlorophenyl)-7-((4-(3,4-dimethylpiperazin-1-yl)-3-fluorophenyl)amino)-1-methyl-2,3-dihydropyrimido[4,5-d]pyrimidin-4(1H)-one

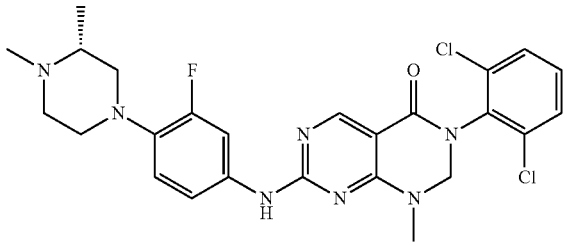

(R)-3-(2,6-dichlorophenyl)-7-((3-fluoro-4-(3-methylpiperazin-1-yl)phenyl)amino)-1-methyl-2,3-dihydropyrimido[4,5-d]pyrimidin-4(1H)-one (23 mg, 0.045 mmol) was methylated following the procedure for Example 35 to give the title compound as a white solid (20 mg, 85%). $^1$H NMR (400 MHz, DMSO-d$_6$): δ 9.91 (br s, 1H), 8.48 (s, 1H), 7.69 (dd, 1H), 7.65 (d, 2H), 7.43-7.52 (m, 2H), 6.98 (t, 1H), 4.98 (s, 2H), 3.07-3.20 (m, 5H), 2.73-2.82 (m, 2H), 2.42 (t, 1H), 2.29 (td, 1H), 2.14-2.24 (m, 4H), 1.01 (d, 3H). LCMS (Method C): $R_T$=0.87 min, m/z=530 [M+H]$^+$.

Example 48: (S)-3-(2,6-dichlorophenyl)-7-((3-fluoro-4-(3-(hydroxymethyl)piperazin-1-yl)phenyl) amino)-1-methyl-2,3-dihydropyrimido[4,5-d]pyrimidin-4(1H)-one

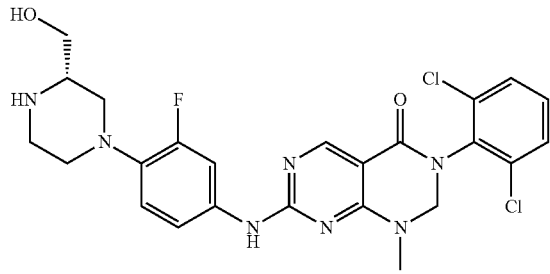 [SMILES: CN1CN(c2c(Cl)cccc2Cl)C(=O)c2cnc(Nc3ccc(N4CCN[C@H](CO)C4)c(F)c3)nc21]

Step 1: (S)-tert-butyl 4-(2-fluoro-4-nitrophenyl)-2-(hydroxymethyl)piperazine-1-carboxylate To a stirred suspension of 1,2-difluoro-4-nitrobenzene (0.464 mL, 4.20 mmol) and potassium carbonate (2.324 g, 16.81 mmol) in anhydrous DMF (5 mL) was added (S)-tert-butyl 2-(hydroxymethyl)piperazine-1-carboxylate (1 g, 4.62 mmol) and the mixture heated at 90° C. for 21 hours. After cooling the mixture was partitioned between brine/water (100 mL) and ethyl acetate (50 mL). The aqueous was separated and extracted with ethyl acetate (3×50 mL). The combined ethyl acetate fractions were washed with brine/water (1:1, 4×25 mL), dried (anhydrous sodium sulfate), filtered and reduced in vacuo. The resulting residue was purified by silica gel chromatography (gradient 20-100% Ethyl Acetate in Cyclohexane) to afford the title compound (1.14 g, 76%). $^1$H NMR (300 MHz, CDCl$_3$): δ 8.00 (ddd, 1H), 7.92 (dd, 1H), 6.94 (t, 1H), 4.22-4.35 (m, 1H), 4.03 (d, 1H), 3.90 (d, 2H), 3.74 (d, 1H), 3.50 (d, 1H), 3.30 (t, 1H), 3.05 (dd, 1H), 2.97 (td, 1H), 1.97 (br s, 1H), 1.49 (s, 9H). LCMS (Method C): $R_T$=1.48 min, m/z=356 [M+H]$^+$.

Step 2: (S)-tert-butyl 4-(4-amino-2-fluorophenyl)-2-(hydroxymethyl)piperazine-1-carboxylate A solution of (S)-tert-butyl 4-(2-fluoro-4-nitrophenyl)-2-(hydroxymethyl)piperazine-1-carboxylate (1.14 g, 3.21 mmol) in methanol (100 mL) was passed through an H-Cube apparatus fitted with a 10% Pd—C cartridge under the following settings [1.0 ml/min flow, 40° C., Full H$_2$ mode] as two portions. The solvent was removed in vacuo to afford the title compound which was used without further purification (1.04 g, 100%). $^1$H NMR (300 MHz, DMSO-d$_6$): δ 6.77 (t, 1H), 6.27-6.36 (m, 2H), 5.01 (br s, 2H), 4.72 (t, 1H), 3.90-4.02 (m, 1H), 3.67-3.93 (m, 2H), 3.42-3.54 (m, 1H), 3.17 (d, 1H), 2.92-3.09 (m, 2H), 2.57 (dd, 1H), 2.44-2.54 (m, 1H), 1.41 (s, 9H). LCMS (Method C): $R_T$=0.89 min, m/z=326 [M+H]$^+$.

Step 3: (S)-tert-butyl 4-(4-((6-(2,6-dichlorophenyl)-8-methyl-5-oxo-5,6,7,8-tetrahydropyrimido[4,5-d]pyrimidin-2-yl)amino)-2-fluorophenyl)-2-(hydroxymethyl)piperazine-1-carboxylate 3-(2,6-Dichlorophenyl)-1-methyl-7-(methylthio)-2,3-dihydropyrimido[4,5-d]pyrimidin-4(1H)-one (120 mg, 0.338 mmol) was reacted with (S)-tert-butyl 4-(4-amino-2-fluorophenyl)-2-(hydroxymethyl)piperazine-1-carboxylate (110 mg, 0.338 mmol) following the procedure for Example 31 to give the title compound (108 mg, 51%).

Step 4: (S)-3-(2,6-dichlorophenyl)-7-((3-fluoro-4-(3-(hydroxymethyl)piperazin-1-yl)phenyl)amino)-1-methyl-2,3-dihydropyrimido[4,5-d]pyrimidin-4(1H)-one (S)-tert-Butyl 4-(4-((6-(2,6-dichlorophenyl)-8-methyl-5-oxo-5,6,7,8-tetrahydropyrimido[4,5-d]pyrimidin-2-yl) amino)-2-fluorophenyl)-2-(hydroxymethyl)piperazine-1-carboxylate (108 mg, 0.171 mmol) was deprotected following the procedure for Example 31 to give the title compound as a pale yellow solid (41 mg, 45%). $^1$H NMR (400 MHz, DMSO-d$_6$): δ 9.91 (br s, 1H), 8.48 (s, 1H), 7.69 (dd, 1H), 7.65 (d, 2H), 7.42-7.52 (m, 2H), 6.97 (t, 1H), 4.98 (s, 2H), 4.60 (t, 1H), 3.30-3.38 (m, 1H), 3.22 (d, 1H), 3.07-3.16 (m, 4H), 2.94 (d, 1H), 2.76-2.88 (m, 2H), 2.61 (td, 1H), 2.26-2.33 (m, 1H), 2.18 (br s, 1H). LCMS (Method C): $R_T$=0.79 min, m/z=532 [M+H]$^+$.

Example 49: (S)-3-(2,6-dichlorophenyl)-7-((4-(3-(hydroxymethyl)-4-methylpiperazin-1-yl)phenyl) amino)-1-methyl-2,3-dihydropyrimido[4,5-d]pyrimidin-4(1H)-one

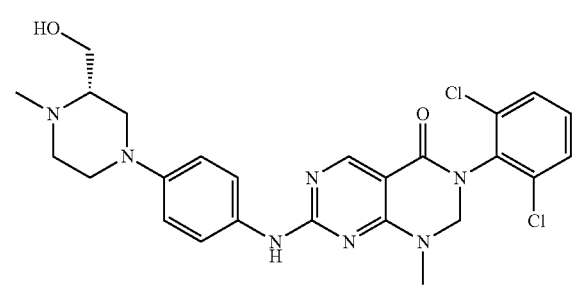 [SMILES: CN1CN(c2c(Cl)cccc2Cl)C(=O)c2cnc(Nc3ccc(N4CCN(C)[C@H](CO)C4)cc3)nc21]

(S)-3-(2,6-Dichlorophenyl)-7-((4-(3-(hydroxymethyl)piperazin-1-yl)phenyl)amino)-1-methyl-2,3-dihydropyrimido[4,5-d]pyrimidin-4(1H)-one (27 mg, 0.052 mmol) was methylated following the procedure for Example 35 to give the title compound as a pale yellow solid (27 mg, 97%). $^1$H NMR (400 MHz, DMSO-d$_6$): δ 9.69 (br s, 1H), 8.44 (s, 1H), 7.57-7.67 (br m, 4H), 7.48 (dd, 1H), 6.89 (d, 2H), 4.95 (s, 2H), 4.56 (t, 1H), 3.66 (ddd, 1H), 3.59 (br d, 1H), 3.44 (br d, 1H), 3.33-3.39 (m, 1H), 3.09 (s, 3H), 2.79 (dt, 1H), 2.65-2.73 (m, 1H), 2.41-2.48 (m, 1H), 2.21-2.33 (m, 4H), 2.07-2.16 (m, 1H). LCMS (Method C): R$_T$=0.70 min, m/z=528 [M+H]$^+$.

Example 50: (S)-3-(2,6-dichlorophenyl)-7-((3-fluoro-4-(3-(hydroxymethyl)-4-methylpiperazin-1-yl)phenyl)amino)-1-methyl-2,3-dihydropyrimido[4,5-d]pyrimidin-4(1H)-one

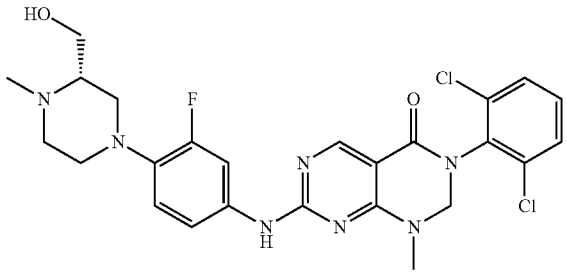

(S)-3-(2,6-dichlorophenyl)-7-((3-fluoro-4-(3-(hydroxymethyl)piperazin-1-yl)phenyl)amino)-1-methyl-2,3-dihydropyrimido[4,5-d]pyrimidin-4(1H)-one (19 mg, 0.036 mmol) was methylated following the procedure for Example 35 to give the title compound as a white solid (15 mg, 77%). $^1$H NMR (400 MHz, DMSO-d$_6$): δ 9.91 (br s, 1H), 8.48 (s, 1H), 7.70 (dd, 1H), 7.65 (d, 2H), 7.48 (dd, 2H), 6.98 (t, 1H), 4.98 (s, 2H), 4.53 (t, 1H), 3.61-3.69 (m, 1H), 3.26-3.38 (m, 2H), 3.07-3.17 (m, 4H), 2.71-2.81 (m, 2H), 2.44-2.51 (m, 1H), 2.28-2.36 (m, 1H), 2.25 (s, 3H), 2.13-2.21 (m, 1H). LCMS (Method C): R$_T$=0.81 min, m/z=546 [M+H]$^+$.

Example 51: 7-((4-(2,6-diazaspiro[3.3]heptan-2-yl)phenyl)amino)-3-(2,6-dichlorophenyl)-1-methyl-2,3-dihydropyrimido[4,5-d]pyrimidin-4(1H)-one

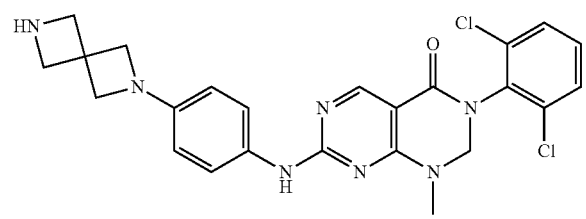 [SMILES: CN1CN(c2c(Cl)cccc2Cl)C(=O)c2cnc(Nc3ccc(N4CC5(CNC5)C4)cc3)nc21]

Step 1: tert-butyl 6-(4-nitrophenyl)-2,6-diazaspiro[3.3]heptane-2-carboxylate

A suspension of 1-fluoro-4-nitrobenzene (356 mg, 2.52 mmol), tert-butyl 2,6-diazaspiro[3.3]heptane-2-carboxylate (500 mg, 2.52 mmol) and potassium carbonate (523 mg, 3.78 mmol) in anhydrous DMF (3 mL) was heated to 50° C. under a nitrogen atmosphere overnight. The reaction mixture was allowed to cool to room temperature, diluted with water (30 mL) and stirred at room temperature for 15 minutes. The precipitated solid was isolated by filtration, washed with water, sucked dry and purified by Biotage chromatography (silica 25 g cartridge, cyclohexane:ethyl acetate, gradient elution from 90:10 to 20:80) to give the title compound as a yellow solid (400 mg, 50%). $^1$H NMR (300 MHz, CDCl$_3$): δ 8.10 (dt, 2H), 6.31 (dt, 2H), 4.15 (s, 4H), 4.13 (s, 4H), 1.45 (s, 9H). LCMS (Method C): R$_T$=1.64 min, m/z=320 [M+H]$^+$.

Step 2: tert-butyl 6-(4-aminophenyl)-2,6-diazaspiro[3.3]heptane-2-carboxylate

A solution of tert-butyl 6-(4-nitrophenyl)-2,6-diazaspiro[3.3]heptane-2-carboxylate (400 mg, 1.253 mmol) in methanol (100 mL) [NB: Poor solubility so high dilution required] was hydrogenated by H-Cube (10% Pd/C cartridge, Full H$_2$, 25° C., 1 mL/min). The reaction mixture was concentrated to dryness under reduced pressure to give the title compound as a pale brown solid (315 mg, 87%). $^1$H NMR (400 MHz, CDCl$_3$): δ 6.63 (dt, 2H), 6.35 (dt, 2H), 4.06 (s, 4H), 3.87 (s, 4H), 3.34 (br s, 2H), 1.44 (s, 9H). LCMS (Method C): R$_T$=0.76 min, m/z=290 [M+H]$^+$.

Step 3: 7-((4-(2,6-diazaspiro[3.3]heptan-2-yl)phenyl)amino)-3-(2,6-dichlorophenyl)-1-methyl-2,3-dihydropyrimido[4,5-d]pyrimidin-4(1H)-one 3-(2,6-Dichlorophenyl)-1-methyl-7-(methylthio)-2,3-dihydropyrimido[4,5-d]pyrimidin-4(1H)-one (120 mg, 0.338 mmol) was reacted with tert-butyl 6-(4-aminophenyl)-2,6-diazaspiro[3.3]heptane-2-carboxylate (98 mg, 0.338 mmol) following the procedure for Example 31 to give the title compound (71.6 mg, 81%). $^1$H NMR: (400 MHz, MeOH-d$_4$): δ 8.51 (s, 1H), 7.57 (d, 2H), 7.47-7.55 (m, 2H), 7.43 (dd, 1H), 6.53 (d, 2H), 4.97 (s, 2H), 3.94 (s, 4H), 3.82 (s, 4H), 3.15 (s, 3H). LCMS (Method C): R$_T$=0.68 min, m/z=496 [M+H]$^+$.

Example 52: 3-(2,6-dichlorophenyl)-1-methyl-7-((4-((3R,5S)-3,4,5-trimethylpiperazin-1-yl)phenyl)amino)-2,3-dihydropyrimido[4,5-d]pyrimidin-4(1H)-one

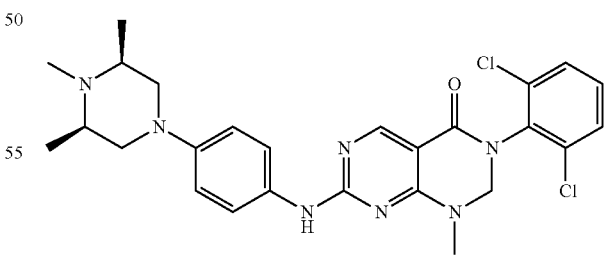

3-(2,6-Dichlorophenyl)-7-((4-((3R,5S)-3,5-dimethylpiperazin-1-yl)phenyl)amino)-1-methyl-2,3-dihydropyrimido[4,5-d]pyrimidin-4(1H)-one (57 mg, 0.111 mmol) was methylated following the procedure in Example 35 to give the title compound (33.6 mg, 57.4%). $^1$H NMR (400 MHz, MeOH-d$_4$): δ 8.53 (s, 1H), 7.53-7.65 (m, 4H), 7.44 (dd, 1H), 6.99 (d, 2H), 4.98 (s, 2H), 3.52 (d, 2H), 3.17 (s, 3H), 2.42-2.57 (m, 4H), 2.97 (s, 3H), 1.22 (d, 6H). LCMS (Method C): $R_T$=0.79 min, m/z=526 [M+H]$^+$.

Example 53: (R)-3-(2-chloro-6-fluorophenyl)-1-methyl-7-((4-(3-methylpiperazin-1-yl)phenyl)amino)-2,3-dihydropyrimido[4,5-d]pyrimidin-4(1H)-one

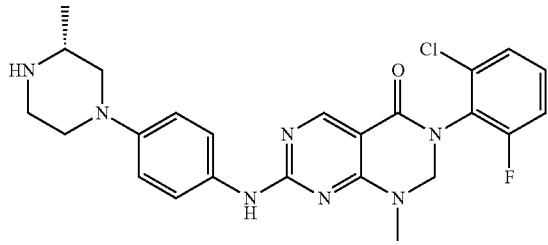

3-(2-Chloro-6-fluorophenyl)-1-methyl-7-(methylthio)-2,3-dihydropyrimido[4,5-d]pyrimidin-4(1H)-one (100 mg, 0.295 mmol) was reacted with (R)-tert-butyl 4-(4-aminophenyl)-2-methylpiperazine-1-carboxylate (86 mg, 0.295 mmol) following the procedure for example 31 to give the title compound (45 mg, 33%). $^1$H NMR (400 MHz, CDCl$_3$): δ 9.73 (s, 1H), 8.45 (s, 1H), 7.60 (d, 2H), 7.51 (m, 2H), 7.42-7.37 (m, 1H), 6.88 (d, 1H), 4.98 (d, 1H), 4.93 (d, 1H), 3.48 (m, 1H), 3.08 (s, 3H), 2.93 (m, 1H), 2.75 (m, 2H), 2.13 (m, 2H), 1.01 (d, 3H). LCMS (Method C): $R_T$=0.62 min, m/z=470 [M+H]$^+$.

Example 54: 7-((4-((1S,4S)-2,5-diazabicyclo[2.2.1]heptan-2-yl)phenyl)amino)-3-(2-chloro-6-fluorophenyl)-1-methyl-2,3-dihydropyrimido[4,5-d]pyrimidin-4(1H)-one

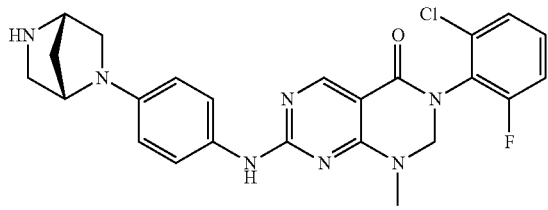

3-(2-Chloro-6-fluorophenyl)-1-methyl-7-(methylthio)-2,3-dihydropyrimido[4,5-d]pyrimidin-4(1H)-one (85 mg, 0.295 mmol) was reacted with tert-5 butyl 4-(4-amino-2-methoxyphenyl) piperazine-1-carboxylate (100 mg, 0.295 mmol) following the procedure for example 31 to give the title compound (36 mg, 27%). $^1$H NMR (400 MHz, CDCl$_3$): δ 8.69 (s, 1H), 7.44 (d, 2H), 7.31 (m, 2H), 7.13 (m, 1H), 6.55 (d, 2H), 4.91 (d, 1H), 4.80 (d, 1H), 4.29 (m, 1H), 3.80 (m, 1H), 3.66 (m, 1H), 3.14 (s, 3H), 3.05 (m, 1H), 2.95 (m, 1H), 2.00 (d, 1H), 1.84 (d, 1H). LCMS (Method C): $R_T$=0.67 min, m/z=480 [M+H]$^+$.

Example 55: 3-(2-chloro-6-fluorophenyl)-1-methyl-7-((3-methyl-4-(piperazin-1-yl)phenyl)amino)-2,3-dihydropyrimido[4,5-d]pyrimidin-4(1H)-one

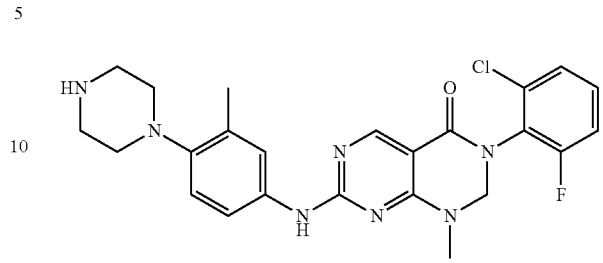

Step 1: tert-butyl 4-(2-methyl-4-nitrophenyl)piperazine-1-carboxylate

A suspension of 1-fluoro-2-methyl-4-nitrobenzene (2.00 g, 12.9 mmol), tert-butyl piperazine-1-carboxylate (2.40 g, 12.9 mmol) and potassium carbonate (2.67 g, 19.3 mmol) in anhydrous DMF (10 mL) was heated to 50° C. under a nitrogen atmosphere overnight. The reaction mixture was allowed to cool to room temperature, diluted with water (200 mL) and stirred at room temperature for 15 minutes. The precipitated solid was isolated by filtration, washed with water and sucked dry to give the title compound as a yellow solid (1.51 g, 36%). LCMS (Method A): $R_T$=1.52 min, m/z=222 [M−Boc+H]$^+$.

Step 2: tert-butyl 4-(4-amino-2-methylphenyl)piperazine-1-carboxylate

To a solution of tert-butyl 4-(2-methyl-4-nitrophenyl)piperazine-1-carboxylate (0.85 g, 2.64 mmol) in ethanol (10 mL) was added 10% palladium on carbon (0.141 g, 0.132 mmol). The reaction mixture was heated to 50° C. Under stirring, ammonium formate (0.667 g, 10.58 mmol) was added portionwise, then heated at 50° C. for 30 minutes. The reaction mixture was allowed to cool to room temperature overnight and filtered through Celite®. The filtrates were concentrated and the residue was partitioned between DCM and sodium bicarbonate solution. The organic phase was separated, dried (phase separator) and concentrated to give the title compound as an off-white solid (632 mg, 82%). LCMS (Method A): $R_T$=0.88 min, m/z=236 [M−$^t$Bu+H]$^+$.

Step 3: 3-(2-chloro-6-fluorophenyl)-1-methyl-7-((3-methyl-4-(piperazin-1-yl)phenyl)amino)-2,3-dihydropyrimido[4,5-d]pyrimidin-4(1H)-one 3-(2-Chloro-6-fluorophenyl)-1-methyl-7-(methylthio)-2,3-dihydropyrimido[4,5-d]pyrimidin-4(1H)-one) (100 mg, 0.295 mmol) was reacted with tert-butyl 4-(4-amino-2-methylphenyl)piperazine-1-carboxylate (86 mg, 0.295 mmol) following the procedure for Example 31 to give the title compound (56 mg, 39%). $^1$H NMR (400 MHz, CDCl$_3$): δ 8.71 (s, 1H), 7.48 (m, 1H), 7.43 (m, 1H), 7.33 (m, 2H), 7.15 (m, 1H), 6.92 (1, 2H), 4.93 (d, 1H), 4.83 (d, 1H), 3.18 (s, 3H), 3.06 (m, 4H), 2.90 (m, 4H), 2.33 (s, 3H). LCMS (Method C): $R_T$=0.75 min, m/z=482 [M+H]$^+$.

Example 56: 3-(2-chloro-6-fluorophenyl)-7-((3-(hydroxymethyl)phenyl)amino)-1-methyl-2,3-dihydropyrimido[4,5-d]pyrimidin-4(1H)-one

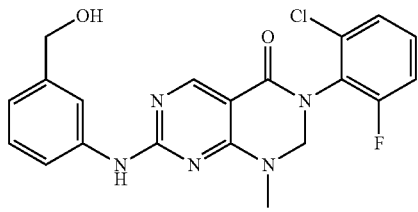 [SMILES: CN1CN(c2c(F)cccc2Cl)C(=O)c2cnc(Nc3cccc(CO)c3)nc21]

3-(2-chloro-6-fluorophenyl)-1-methyl-7-(methylthio)-2,3-dihydropyrimido[4,5-d]pyrimidin-4(1H)-one (100 mg, 0.295 mmol) was reacted with (3-aminophenyl)methanol (36 mg, 0.295 mmol) following the procedure for Example 31 to give the title compound (35 mg, 29%). $^1$H NMR (400 MHz, CDCl$_3$): δ8.65 (s, 1H), 7.81 (m, 1H), 7.67 (s, 1H), 7.49 (m, 1H), 7.28 (m, 1H), 7.10 (m, 1H), 6.98 (m, 1H), 4.93 (d, 1H), 4.86 (d, 1H), 4.78 (d, 1H), 4.53 (s, 3H). LCMS (Method C): R$_T$=0.93 min, m/z=414 [M+H]$^+$.

Example 57: 3-(2,6-dichlorophenyl)-7-((3-(hydroxymethyl)-4-morpholinophenyl)amino)-1-methyl-2,3-dihydropyrimido[4,5-d]pyrimidin-4(1H)-one

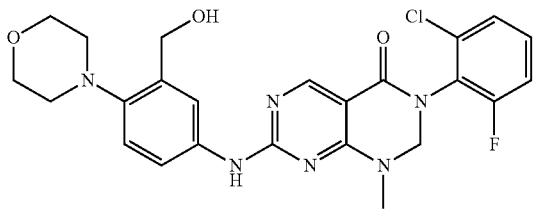

3-(2-chloro-6-fluorophenyl)-1-methyl-7-(methylthio)-2,3-dihydropyrimido[4,5-d]pyrimidin-4(1H)-one (100 mg, 0.295 mmol) was reacted with (5-amino-2-morpholinophenyl) methanol (61 mg, 0.295 mmol) following the procedure for example 31 to give the title compound (57 mg, 39%). $^1$H NMR (400 MHz, CDCl$_3$): δ 8.71 (s, 1H), 7.48 (m, 1H), 7.43 (m, 1H), 7.33 (m, 2H), 7.15 (m, 1H), 6.92 (1, 2H), 4.95 (d, 1H), 4.83 (d, 1H), 4.78 (s, 2H), 3.18 (s, 3H), 3.72 (m, 4H), 3.04 (m, 4H). LCMS (Method C): R$_T$=0.93 min, m/z=499 [M+H]$^+$.

Example 58: (R)-3-(2,6-dichlorophenyl)-1-(1-methyl-1H-pyrazol-3-yl)-7-((4-(3-methylpiperazin-1-yl)phenyl)amino)-2,3-dihydropyrimido[4,5-d]pyrimidin-4(1H)-one

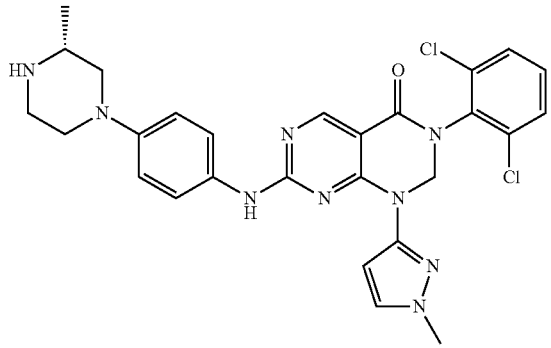 [SMILES: C[C@@H]1CN(c2ccc(Nc3ncc4c(n3)N(c3ccn(C)n3)CN(c3c(Cl)cccc3Cl)C4=O)cc2)CCN1]

Step 1: 4-chloro-N-(2,6-dichlorophenyl)-2-(methylthio)pyrimidine-5-carboxamide A mixture of 4-chloro-2-(methylthio)pyrimidine-5-carbonyl chloride (35 g, 157 mmol) and Amberlyst A21 (6 g, 149 mmol) in ethyl acetate (250 mL) was heated to 40° C. followed by the dropwise addition of a solution of 2,6-dichloroaniline (24.21 g, 149 mmol) in ethyl acetate (250 mL). The reaction mixture was heated at 40° C. under a nitrogen atmosphere overnight. The resulting suspension was allowed to cool to room temperature and filtered. The isolated solids were taken up in hot tetrahydrofuran (100 mL) and filtered, repeating the process with the undissolved solid a further two times until most of the solid was dissolved. The combined filtrates were concentrated to dryness under reduced pressure to give a pale yellow solid. This was slurried in dichloromethane (100 mL) to give the title compound as a white solid (22.1 g, 42%). $^1$H NMR (300 MHz, DMSO-d$_6$): δ 10.71 (s, 1H), 8.82 (s, 1H), 7.62 (d, 2H), 7.43 (t, 1H), 2.60 (s, 3H). LCMS (Method C): R$_T$=1.46 min, m/z=348 [M+H]$^+$.

Step 2: N-(2,6-dichlorophenyl)-4-((1-methyl-1H-pyrazol-3-yl)amino)-2-(methylthio)pyrimidine-5-carboxamide To a stirring solution of 4-chloro-N-(2,6-dichlorophenyl)-2-(methylthio)pyrimidine-5-carboxamide (218 mg, 0.625 mmol) and Hunig's base (0.328 mL, 1.876 mmol) in anhydrous tetrahydrofuran (4 mL) was added 1-methyl-1H-pyrazol-3-amine (0.052 mL, 0.657 mmol) and the mixture heated to 50° C. for 16 h. The solvent was removed in vacuo. The resulting residue was purified by silica gel chromatography (gradient 0-5% methanol in dichloromethane) to afford the title compound (117 mg, 45.6%). LCMS (Method C): R$_T$=1.45 min, m/z=409 [M+H]$^+$.

Step 3: 3-(2,6-dichlorophenyl)-1-(1-methyl-1H-pyrazol-3-yl)-7-(methylthio)-2,3-dihydropyrimido[4,5-d]pyrimidin-4(1H)-one In a 10 ml microwave vial was added N-(2,6-dichlorophenyl)-4-((1-methyl-1H-pyrazol-3-yl)amino)-2-(methylthio)pyrimidine-5-carboxamide (112 mg, 0.274 mmol) in anhydrous acetonitrile (3 mL) followed by cesium carbonate (535 mg, 1.642 mmol) and dibromomethane (0.058 mL, 0.821 mmol). The tube was sealed and the mixture was heated to 90° C. while stirring for 40 h. The solvent was removed in vacuo. The residue was partitioned between water (10 mL) and dichloromethane (20 mL). The aqueous was separated and extracted with dichloromethane (2×10 mL). The combined dichloromethane fractions were dried (phase separator) and reduced in vacuo. The resulting residue was purified by silica gel chromatography (gradient 0-50% ethyl acetate in cyclohexane) to afford the title compound (54.1 mg, 46.9%). LCMS (Method C): R$_T$=1.53 min, m/z=421 [M+H]$^+$.

Step 4: (R)-3-(2,6-dichlorophenyl)-1-(1-methyl-1H-pyrazol-3-yl)-7-((4-(3-methylpiperazin-1-yl)phenyl)amino)-2,3-dihydropyrimido [4,5-d]pyrimidin-4(1H)-one 3-(2,6-Dichlorophenyl)-1-(1-methyl-1H-pyrazol-3-yl)-7-(methylthio)-2,3-dihydropyrimido[4,5-d]pyrimidin-4(1H)-one (50 mg, 0.119 mmol) was reacted with (R)-tert-butyl 4-(4-aminophenyl)-2-methylpiperazine-1-carboxylate (38 mg, 0.131 mmol) following the procedure for example 31 to give the title compound as an off-white solid (25 mg, 37%). $^1$H NMR (400 MHz, methanol-$d_4$): δ 8.69 (s, 1H), 7.60-7.35 (m, 5H), 6.93 (d, 2H), 6.61 (brs, 1H), 5.49 (s, 2H), 3.82 (s, 3H), 3.50 (m, 2H), 3.15-2.9 (m, 3H), 2.67 (dt, 1H), 2.35 (m, 1H), 1.17 (d, 3H). LCMS (Method C): $R_T$=0.88 min, m/z=564 [M+H]$^+$.

Example 59: (R)-3-(2,6-dichlorophenyl)-7-((3-(methoxymethyl)-4-(3-methylpiperazin-1-yl)phenyl)amino)-1-methyl-2,3-dihydropyrimido[4,5-d]pyrimidin-4(1H)-one

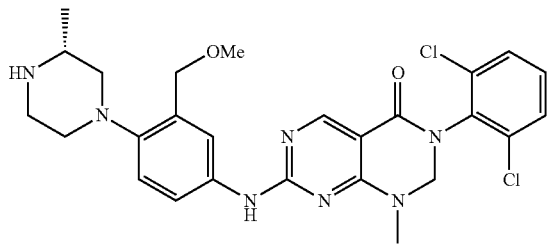 [SMILES: COCc1cc(Nc2ncc3c(n2)N(C)CN(c2c(Cl)cccc2Cl)C3=O)ccc1N1CCN[C@H](C)C1]

Step 1: (R)-tert-butyl 4-(2-(methoxymethyl)-4-nitrophenyl)-2-methylpiperazine-1-carboxylate A solution of (R)-tert-butyl 4-(2-(hydroxymethyl)-4-nitrophenyl)-2-methylpiperazine-1-carboxylate (1.00 g, 2.85 mmol) in anhydrous THF (9.49 mL) was cooled to 0° C. followed by the addition of sodium hydride (60% in mineral oil, 0.125 g, 3.13 mmol). After stirring at 0° C. under a nitrogen atmosphere for 10 minutes, methyl iodide (0.214 mL, 3.41 mmol) was added. The resulting mixture was allowed to warm to room temperature and stirred for 60 minutes. Further methyl iodide (0.071 mL, 1.138 mmol) was added and the mixture stirred for an additional 60 minutes. The reaction mixture was diluted with ammonium chloride solution (30 mL) and extracted into ethyl acetate (3×20 mL). The combined organic phases were dried over $Na_2SO_4$, filtered, concentrated to dryness under reduced pressure and purified by Biotage chromatography (silica 50 g cartridge, cyclohexane:ethyl acetate, gradient elution from 95:5 to 50:50) to give the title compound as a yellow oil that solidified upon standing (870 mg, 84%). $^1$H NMR (300 MHz, CDCl$_3$): δ 8.34 (d, 1H), 8.13 (dd, 1H), 7.04 (d, 1H), 4.56 (d, 1H), 4.50 (d, 1H), 4.36 (br s, 1H), 3.98 (dt, 1H), 3.47 (s, 3H), 3.29 (td, 1H), 3.18 (ddd, 1H), 3.10 (dt, 1H), 2.97 (dd, 1H), 2.80 (td, 1H), 1.49 (s, 9H), 1.37 (d, 3H). LCMS (Method C): $R_T$=1.87 min, m/z=366 [M+H]$^+$.

Step 2: (R)-tert-butyl 4-(4-amino-2-(methoxymethyl)phenyl)-2-methylpiperazine-1-carboxylate A solution of (R)-tert-butyl 4-(2-(methoxymethyl)-4-nitrophenyl)-2-methylpiperazine-1-carboxylate (870 mg, 2.381 mmol) in methanol (40 mL) was hydrogenated by H-Cube (10% Pd/C cartridge, Full $H_2$, 25° C., 1 mL/min) with three passes. The reaction mixture was concentrated to dryness under reduced pressure to give the title compound as a yellow oil (730 mg, 91%). $^1$H NMR (400 MHz, CDCl$_3$): δ 6.90 (d, 1H), 6.78 (d, 1H), 6.59 (dd, 1H), 4.55 (d, 1H), 4.51 (d, 1H), 4.28 (br s, 1H), 3.88 (d, 1H), 3.42 (s, 3H), 3.22 (td, 1H), 2.80-2.90 (m, 2H), 2.76 (dt, 1H), 2.66 (td, 1H), 1.48 (s, 9H), 1.36 (d, 3H). LCMS (Method C): $R_T$=1.05 min, m/z=336 [M+H]$^+$.

Step 3: (R)-tert-butyl 4-(4-((6-(2,6-dichlorophenyl)-8-methyl-5-oxo-5,6,7,8-tetrahydropyrimido[4,5-d]pyrimidin-2-yl)amino)-2-(methoxymethyl)phenyl)-2-methylpiperazine-1-carboxylate 3-(2,6-dichlorophenyl)-1-methyl-7-(methylthio)-2,3-dihydropyrimido[4,5-d]pyrimidin-4(1H)-one (100 mg, 0.283 mmol) was reacted with (R)-tert-butyl 4-(4-amino-2-(methoxymethyl)phenyl)-2-methylpiperazine-1-carboxylate (95 mg, 0.283 mmol) following the procedure for Example 31 to give the title compound as a pale yellow solid (98 mg, 54%). $^1$H NMR (300 MHz, CDCl$_3$) δ 8.72 (s, 1H), 7.73-7.93 (br m, 2H), 7.53 (dd, 1H), 7.43 (d, 2H), 7.27 (dd, 1H), 7.04 (d, 1H), 4.88 (s, 2H), 4.61 (d, 1H), 4.56 (d, 1H), 4.24-4.38 (m, 1H), 3.92 (br d, 1H), 3.44 (s, 3H), 3.25 (td, 1H), 3.19 (s, 3H), 2.96 (br d, 1H), 2.82-2.89 (m, 2H), 2.71 (td, 1H), 1.48 (s, 9H), 1.37 (d, 3H). LCMS (Method C): $R_T$=1.88 min, m/z=642 [M+H]$^+$.

Step 4: (R)-3-(2,6-dichlorophenyl)-7-((3-(methoxymethyl)-4-(3-methylpiperazin-1-yl)phenyl)amino)-1-methyl-2,3-dihydropyrimido[4,5-d]pyrimidin-4(1H)-one (R)-tert-Butyl 4-(4-((6-(2,6-dichlorophenyl)-8-methyl-5-oxo-5,6,7,8-tetrahydropyrimido[4,5-d]pyrimidin-2-yl)amino)-2-(methoxymethyl)phenyl)-2-methylpiperazine-1-carboxylate (98 mg, 0.153 mmol) was deprotected following the procedure for Example 31 to give the title compound as an off-white solid (70 mg, 85%). $^1$H NMR (400 MHz, MeOH-$d_4$): δ 8.53 (s, 1H), 7.90 (br s, 1H), 7.53-7.60 (m, 3H), 7.42 (dd, 1H), 7.11 (d, 1H), 4.98 (s, 2H), 4.56 (s, 2H), 3.43 (s, 3H), 3.19 (s, 3H), 2.92-3.05 (m, 5H), 2.69-2.78 (m, 1H), 2.42 (t, 1H), 1.11 (d, 3H). LCMS (Method C): $R_T$=0.82 min, m/z=542 [M+H]$^+$.

Example 60: (R)-3-(2,6-dichlorophenyl)-7-((4-(3-(methoxymethyl)piperazin-1-yl)phenyl)amino)-1-methyl-2,3-dihydropyrimido[4,5-d]pyrimidin-4(1H)-one

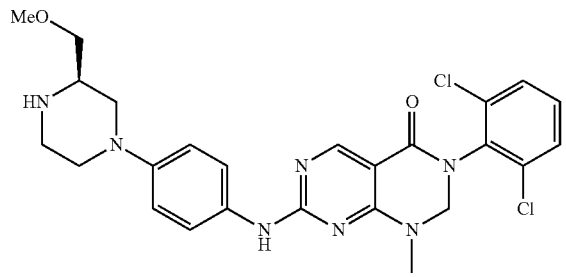 [SMILES: COC[C@H]1CN(c2ccc(Nc3ncc4c(n3)N(C)CN(c3c(Cl)cccc3Cl)C4=O)cc2)CCN1]

Step 1: (R)-tert-butyl 2-(hydroxymethyl)-4-(4-nitrophenyl)piperazine-1-carboxylate A suspension of 1-fluoro-4-nitrobenzene (2.86 g, 20.30 mmol), (R)-tert-butyl 2-(hydroxymethyl)piperazine-1-carboxylate (4.39 g, 20.30 mmol) and potassium carbonate (4.21 g, 30.4 mmol) in anhydrous DMF (10 mL) was heated to 50° C. under a nitrogen atmosphere overnight. The reaction mixture was allowed to cool to room temperature, diluted with water (30 mL) and stirred at room temperature for 15 minutes. The oily product was extracted into ethyl acetate (50 mL) and washed with 50:50 water:brine (3×50 mL). The organic phase was then dried over $Na_2SO_4$, filtered and concentrated to dryness under reduced pressure. The residue was slurried in a mixture of cyclohexane (20 mL) and diethyl ether (2 mL) to give the title compound as a yellow solid (4.78 g, 70%). $^1$H NMR (300 MHz, $CDCl_3$): δ 8.11 (dt, 2H), 6.78 (dt, 2H), 4.25 (br s, 1H), 3.87-4.03 (m, 2H), 3.62-3.80 (m, 3H), 3.26-3.42 (m, 2H), 3.18 (ddd, 1H), 1.49 (s, 9H). LCMS (Method C): $R_T$=1.39 min, m/z=338 $[M+H]^+$.

Step 2: (R)-tert-butyl 2-(methoxymethyl)-4-(4-nitrophenyl)piperazine-1-carboxylate A solution of (R)-tert-butyl 2-(hydroxymethyl)-4-(4-nitrophenyl)piperazine-1-carboxylate (500 mg, 1.482 mmol) in anhydrous THF (4.94 mL) was cooled to 0° C. followed by the addition of sodium hydride (60% in mineral oil, 65.2 mg, 1.630 mmol). After stirring at 0° C. under a nitrogen atmosphere for 10 minutes, methyl iodide (111 μl, 1.778 mmol) was added. The resulting mixture was allowed to warm to room temperature and stirred for 60 minutes. The reaction mixture was diluted with ammonium chloride solution (10 mL) and extracted into ethyl acetate (3×10 mL). The combined organic phases were dried over $Na_2SO_4$, filtered, concentrated to dryness under reduced pressure and purified by Biotage chromatography (silica 25 g cartridge, cyclohexane:ethyl acetate, gradient elution from 95:5 to 20:80) to give the title compound as a yellow oil (200 mg, 38% yield). $^1$H NMR (300 MHz, $CDCl_3$): δ 8.12 (d, 2H), 6.79 (d, 2H), 4.29 (br s, 1H), 4.04 (br d, 1H), 3.95 (br d, 1H), 3.73 (br d, 1H), 3.36-3.43 (m, 2H), 3.33 (s, 3H), 3.08-3.30 (m, 3H), 1.49 (s, 9H). LCMS (Method C): $R_T$=1.69 min, m/z=352 $[M+H]^+$.

Step 3: (R)-tert-butyl 4-(4-aminophenyl)-2-(methoxymethyl)piperazine-1-carboxylate A solution of (R)-tert-butyl 2-(methoxymethyl)-4-(4-nitrophenyl)piperazine-1-carboxylate (200 mg, 0.569 mmol) in methanol (30 mL) was hydrogenated by H-Cube (10% Pd/C cartridge, Full $H_2$, 25° C., 1 mL/min) with two passes. The reaction mixture was concentrated to dryness under reduced pressure to give the title compound as a brown oil (160 mg, 87% yield). $^1$H NMR (300 MHz, $CDCl_3$): δ 6.79 (dt, 2H), 6.65 (dt, 2H), 4.28 (br s, 1H), 3.97 (br d, 1H), 3.78 (t, 1H), 3.37-3.55 (m, 4H), 3.39 (s, 3H), 3.27 (dr d, 1H), 3.11 (td, 1H), 2.56-2.73 (m, 2H), 1.48 (s, 9H). LCMS (Method C): $R_T$=0.74 min, m/z=322 $[M+H]^+$.

Step 4: (R)-tert-butyl 4-(4-((6-(2,6-dichlorophenyl)-8-methyl-5-oxo-5,6,7,8-tetrahydropyrimido[4,5-d]pyrimidin-2-yl)amino)phenyl)-2-(methoxymethyl)piperazine-1-carboxylate 3-(2,6-dichlorophenyl)-1-methyl-7-(methylthio)-2,3-dihydropyrimido[4,5-d]pyrimidin-4(1H)-one (100 mg, 0.283 mmol) was reacted with (R)-tert-butyl 4-(4-aminophenyl)-2-(methoxymethyl)piperazine-1-carboxylate (91 mg, 0.283 mmol) following the procedure for Example 31 to give the title compound as a yellow solid (113 mg, 64%). $^1$H NMR (300 MHz, $CDCl_3$): δ 8.70 (s, 1H), 7.51 (d, 2H), 7.44 (d, 2H), 7.28 (dd, 1H), 6.92 (d, 2H), 4.87 (s, 2H), 4.31 (br s, 1H), 4.00 (br d, 1H), 3.65-3.80 (m, 2H), 3.40-3.50 (m, 2H), 3.40 (d, 3H), 3.07-3.20 (m, 4H), 2.80 (dd, 1H), 2.74 (td, 1H), 1.49 (s, 9H). LCMS (Method C): $R_T$=1.67 min, m/z=628 $[M+H]^+$.

Step 5: (R)-3-(2,6-dichlorophenyl)-7-((4-(3-(methoxymethyl)piperazin-1-yl)phenyl)amino)-1-methyl-2,3-dihydropyrimido[4,5-d]pyrimidin-4(1H)-one (R)-tert-Butyl 4-(4-((6-(2,6-dichlorophenyl)-8-methyl-5-oxo-5,6,7,8-tetrahydropyrimido[4,5-d]pyrimidin-2-yl)amino)phenyl)-2-(methoxymethyl)piperazine-1-carboxylate (113 mg, 0.180 mmol) was deprotected following the procedure for Example 31 to give the title compound as a pale yellow solid (83 mg, 87%). $^1$H NMR (400 MHz, MeOH-$d_4$): δ 8.51 (s, 1H), 7.52-7.61 (m, 4H), 7.42 (dd, 1H), 6.98 (d, 2H), 4.96 (s, 2H), 3.39-3.57 (m, 4H), 3.39 (s, 3H), 3.15 (s, 3H), 3.04-3.14 (m, 2H), 2.96 (td, 1H), 2.72 (td, 1H), 2.48 (t, 1H). LCMS (Method C): $R_T$=0.75 min, m/z=528 $[M+H]^+$.

Example 61: (S)-3-(2,6-dichlorophenyl)-7-((4-(3-(methoxymethyl)piperazin-1-yl)phenyl)amino)-1-methyl-2,3-dihydropyrimido[4,5-d]pyrimidin-4(1H)-one

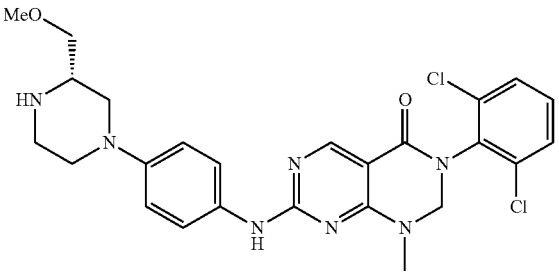 [SMILES: COC[C@@H]1CN(c2ccc(Nc3ncc4c(n3)N(C)CN(c3c(Cl)cccc3Cl)C4=O)cc2)CCN1]

Step 1: (S)-tert-butyl 2-(hydroxymethyl)-4-(4-nitrophenyl)piperazine-1-carboxylate A suspension of 1-fluoro-4-nitrobenzene (1.305 g, 9.25 mmol), (S)-tert-butyl 2-(hydroxymethyl)piperazine-1-carboxylate (2.00 g, 9.25 mmol) and potassium carbonate (1.917 g, 13.87 mmol) in anhydrous DMF (10 mL) was heated to 50° C. under a nitrogen atmosphere overnight. The reaction mixture was allowed to cool to room temperature, diluted with water (70 mL) and stirred at room temperature for 15 minutes. The precipitated solid was isolated by filtration, washed with water (50 mL), sucked dry and freeze-dried overnight to give the title compound as an orange solid (2.13 g, 68%). $^1$H NMR (300 MHz, $CDCl_3$): δ 8.11 (dt, 2H), 6.78 (dt, 2H), 4.25 (br s, 1H), 3.85-4.04 (m, 2H), 3.61-3.80 (m, 3H), 3.25-3.43 (m, 2H), 3.18 (ddd, 1H), 1.49 (s, 9H). LCMS (Method C): $R_T$=1.39 min, m/z=338 $[M+H]^+$.

Step 2: (S)-tert-butyl 2-(methoxymethyl)-4-(4-nitrophenyl)piperazine-1-carboxylate A solution of (S)-tert-butyl 2-(hydroxymethyl)-4-(4-nitrophenyl)piperazine-1-carboxylate (1.00 g, 2.96 mmol) in anhydrous THF (9.88 mL) was cooled to 0° C. followed by the addition of sodium hydride (60% in mineral oil, 0.130 g, 3.26 mmol). After stirring at 0° C. under a nitrogen atmosphere for 10 minutes, methyl iodide (0.222 mL, 3.56 mmol) was added. The resulting mixture was allowed to warm to room temperature and stirred for 60 minutes. The reaction mixture was diluted with ammonium chloride solution (20 mL) and extracted into ethyl acetate (3×10 mL). The combined organic phases were dried over Na$_2$SO$_4$, filtered, concentrated to dryness under reduced pressure and purified by Biotage chromatography (silica 50 g cartridge, cyclohexane:ethyl acetate, gradient elution from 95:5 to 20:80) to give the title compound as a yellow oil (282 mg, 27% yield). $^1$H NMR (300 MHz, CDCl$_3$): δ 8.13 (dt, 2H), 6.79 (dt, 2H), 4.29 (br s, 1H), 4.05 (dt, 1H), 3.95 (br d, 1H), 3.74 (br d, 1H), 3.37-3.43 (m, 2H), 3.33 (s, 3H), 3.08-3.28 (m, 3H), 1.49 (s, 9H). LCMS (Method C): R$_T$=1.69 min, m/z=352 [M+H]$^+$.

Step 3: (S)-tert-butyl 4-(4-aminophenyl)-2-(methoxymethyl)piperazine-1-carboxylate A solution of (S)-tert-butyl 2-(methoxymethyl)-4-(4-nitrophenyl)piperazine-1-carboxylate (282 mg, 0.803 mmol) in methanol (30 mL) was hydrogenated by H-Cube (10% Pd/C cartridge, Full H$_2$, 25° C., 1 mL/min) with two passes. The reaction mixture was concentrated to dryness under reduced pressure to give the title compound as an off-white solid (236 mg, 91% yield). $^1$H NMR (300 MHz, CDCl$_3$) δ 6.78 (dt, 2H), 6.65 (dt, 2H), 4.28 (br s, 1H), 3.98 (br d, 1H), 3.78 (t, 1H), 3.43-3.54 (m, 2H), 3.39 (s, 3H), 3.27 (dr d, 1H), 3.11 (td, 1H), 2.56-2.74 (m, 2H), 1.48 (s, 9H). LCMS (Method C): R$_T$=0.78 min, m/z=322 [M+H]$^+$.

Step 4: (S)-tert-butyl 4-(4-((6-(2,6-dichlorophenyl)-8-methyl-5-oxo-5,6,7,8-tetrahydropyrimido[4,5-d]pyrimidin-2-yl)amino)phenyl)-2-(methoxymethyl)piperazine-1-carboxylate 3-(2,6-Dichlorophenyl)-1-methyl-7-(methylthio)-2,3-dihydropyrimido[4,5-d]pyrimidin-4(1H)-one (200 mg, 0.563 mmol) was reacted with (S)-tert-butyl 4-(4-aminophenyl)-2-(methoxymethyl)piperazine-1-carboxylate (181 mg, 0.563 mmol) following the procedure for Example 31 to give the title compound as a yellow solid (190 mg, 54%). $^1$H NMR (300 MHz, CDCl$_3$): δ 8.70 (s, 1H), 7.51 (d, 2H), 7.44 (d, 2H), 7.41 (br s, 1H), 7.28 (dd, 1H), 6.91 (d, 2H), 4.87 (s, 2H), 4.32 (br s, 1H), 4.00 (br d, 1H), 3.64-3.80 (m, 2H), 3.39-3.52 (m, 2H), 3.39 (s, 3H), 3.06-3.21 (m, 4H), 2.67-2.85 (m, 2H), 1.49 (s, 9H). LCMS (Method C): R$_T$=1.66 min, m/z=628 [M+H]$^+$.

Step 5: (S)-3-(2,6-dichlorophenyl)-7-((4-(3-(methoxymethyl)piperazin-1-yl)phenyl)amino)-1-methyl-2,3-dihydropyrimido[4,5-d]pyrimidin-4(1H)-one (S)-tert-butyl 4-(4-((6-(2,6-dichlorophenyl)-8-methyl-5-oxo-5,6,7,8-tetrahydropyrimido[4,5-d]pyrimidin-2-yl)amino)phenyl)-2-(methoxymethyl)piperazine-1-carboxylate (190 mg, 0.302 mmol) was deprotected following the procedure for Example 31 to give the title compound as an off-white solid (135 mg, 85%). $^1$H NMR (400 MHz, MeOH-d$_4$): δ 8.51 (s, 1H), 7.51-7.62 (m, 4H), 7.42 (dd, 1H), 6.98 (d, 2H), 4.96 (s, 2H), 3.39-3.57 (m, 4H), 3.39 (s, 3H), 3.15 (s, 3H), 3.04-3.14 (m, 2H), 2.96 (td, 1H), 2.72 (td, 1H), 2.48 (t, 1H). LCMS (Method C): R$_T$=0.76 min, m/z=528 [M+H]$^+$.

Example 62: 3-(2,6-dichlorophenyl)-1-methyl-7-((4-(3-(trifluoromethyl)piperazin-1-yl)phenyl)amino)-2,3-dihydropyrimido[4,5-d]pyrimidin-4(1H)-one

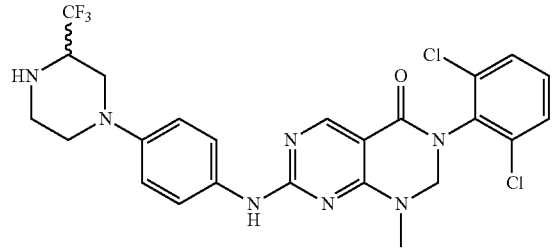 [SMILES: CN1CN(c2c(Cl)cccc2Cl)C(=O)c2cnc(Nc3ccc(N4CCNC(C(F)(F)F)C4)cc3)nc21]

Step 1: 1-(4-nitrophenyl)-3-(trifluoromethyl)piperazine

A suspension of 1-fluoro-4-nitrobenzene (0.915 g, 6.49 mmol), 2-(trifluoromethyl)piperazine (1.00 g, 6.49 mmol) and potassium carbonate (1.345 g, 9.73 mmol) in anhydrous DMF (5 mL) was heated to 50° C. under a nitrogen atmosphere overnight. The reaction mixture was allowed to cool to room temperature, diluted with water (30 mL) and stirred at room temperature for 15 minutes. The precipitated solid was isolated by filtration, washed with water and sucked dry to give the title compound as a yellow solid (1.47 g, 82%). $^1$H NMR (300 MHz, CDCl$_3$): δ 8.15 (dt, 2H), 6.87 (dt, 2H), 3.91 (br d, 1H), 3.74 (ddd, 1H), 3.39-3.54 (m, 1H), 3.25 (dd, 1H), 2.93-3.16 (m, 3H), 2.00 (br s, 1H). LCMS (Method C): R$_T$=1.12 min, m/z=276 [M+H]$^+$.

Step 2: tert-butyl 4-(4-nitrophenyl)-2-(trifluoromethyl)piperazine-1-carboxylate To a solution of 1-(4-nitrophenyl)-3-(trifluoromethyl)piperazine (1.20 g, 4.36 mmol) in anhydrous dichloromethane (14.53 mL) was added di-tert-butyl dicarbonate (2.025 mL, 8.72 mmol), DIPEA (1.904 mL, 10.90 mmol) and DMAP (0.053 g, 0.436 mmol) and the resulting mixture stirred at room temperature for 3 days. Further di-tert-butyl dicarbonate (2.025 mL, 8.72 mmol), DIPEA (1.904 mL, 10.90 mmol) and DMAP (0.053 g, 0.436 mmol) were added and the mixture stirred at room temperature for 24 hours. Further di-tert-butyl dicarbonate (2.025 mL, 8.72 mmol), DIPEA (1.904 mL, 10.90 mmol) and DMAP (0.053 g, 0.436 mmol) were added and the mixture stirred at room temperature for 24 hours. Further di-tert-butyl dicarbonate (2.025 mL, 8.72 mmol) was added and the mixture stirred at room temperature overnight. The reaction mixture was washed with saturated sodium bicarbonate solution (15 mL), dried over Na$_2$SO$_4$, filtered and concentrated to dryness under reduced pressure. The resulting residue was purified by Biotage chromatography (silica 100 g cartridge, cyclohexane:ethyl acetate, gradient elution from 95:5 to 60:40) to give the title compound as a yellow solid (1.49 g, 91%). $^1$H NMR (300 MHz, CDCl$_3$): δ 8.14 (dt, 2H), 6.82 (dt, 2H), 4.54-4.99 (br m, 1H), 3.97-4.27 (br m, 2H), 3.79 (d, 1H), 3.23-3.48 (br m, 2H), 3.10 (td, 1H), 1.49 (s, 9H). LCMS (Method C): R$_T$=1.78 min, m/z=376 [M+H]$^+$.

Step 3: tert-butyl 4-(4-aminophenyl)-2-(trifluoromethyl)piperazine-1-carboxylate A solution of tert-butyl 4-(4-nitrophenyl)-2-(trifluoromethyl)piperazine-1-carboxylate (1.49 g, 3.97 mmol) in methanol (50 mL) was hydrogenated by H-Cube (10% Pd/C cartridge, Full $H_2$, 25° C., 1 mL/min) with two passes. The reaction mixture was concentrated to dryness under reduced pressure to give the title compound as a yellow solid (1.34 g, 98%). $^1$H NMR (400 MHz, CDCl$_3$): δ 6.80 (dt, 2H), 6.65 (dt, 2H), 4.49-4.88 (br m, 1H), 4.10 (br s, 1H), 3.65 (d, 1H), 3.23-3.59 (br m, 4H), 2.85 (ddd, 1H), 2.66 (td, 1H), 1.49 (s, 9H). LCMS (Method C): $R_T$=0.99 min, m/z=346 [M+H]$^+$.

Step 4: tert-butyl 4-(4-((6-(2,6-dichlorophenyl)-8-methyl-5-oxo-5,6,7,8-tetrahydropyrimido[4,5-d]pyrimidin-2-yl)amino)phenyl)-2-(trifluoromethyl)piperazine-1-carboxylate 3-(2,6-Dichlorophenyl)-1-methyl-7-(methylthio)-2,3-dihydropyrimido[4,5-d]pyrimidin-4(1H)-one (100 mg, 0.283 mmol) was reacted with tert-butyl 4-(4-aminophenyl)-2-(trifluoromethyl)piperazine-1-carboxylate (98 mg, 0.283 mmol) following the procedure for Example 31 to give the title compound as a pale yellow solid (126 mg, 68%). $^1$H NMR (400 MHz, CDCl$_3$): δ 8.71 (s, 1H), 7.54 (d, 2H), 7.44 (d, 2H), 7.28 (dd, 1H), 7.24 (br s, 1H), 6.93 (d, 2H), 4.88 (s, 2H), 4.65 (br s, 1H), 4.13 (br s, 1H), 3.82 (d, 1H), 3.46 (d, 1H), 3.35 (br s, 1H), 3.17 (s, 3H), 2.97 (ddd, 1H), 2.76 (td, 1H), 1.50 (s, 9H). LCMS (Method C): $R_T$=1.80 min, m/z=652 [M+H]$^+$.

Step 5: 3-(2,6-dichlorophenyl)-1-methyl-7-((4-(3-(trifluoromethyl)piperazin-1-yl)phenyl)amino)-2,3-dihydropyrimido[4,5-d]pyrimidin-4(1H)-one tert-Butyl 4-(4-((6-(2,6-dichlorophenyl)-8-methyl-5-oxo-5,6,7,8-tetrahydropyrimido[4,5-d]pyrimidin-2-yl)amino)phenyl)-2-(trifluoromethyl)piperazine-1-carboxylate (126 mg, 0.193 mmol) was deprotected following the procedure for Example 31 to give the title compound as a yellow solid (92 mg, 86%). $^1$H NMR (400 MHz, MeOH-d$_4$): δ 8.51 (s, 1H), 7.60 (br d, 2H), 7.56 (d, 2H), 7.42 (dd, 1H), 7.00 (d, 2H), 4.97 (s, 2H), 3.66 (br d, 1H), 3.43-3.61 (m, 2H), 3.10-3.19 (m, 4H), 2.98 (td, 1H), 2.70-2.81 (m, 2H). LCMS (Method C): $R_T$=1.06 min, m/z=552 [M+H]$^+$.

Example 63: 3-(2,6-dichlorophenyl)-1-methyl-7-((4-(3,3,4-trimethylpiperazin-1-yl)phenyl)amino)-2,3-dihydropyrimido[4,5-d]pyrimidin-4(1H)-one

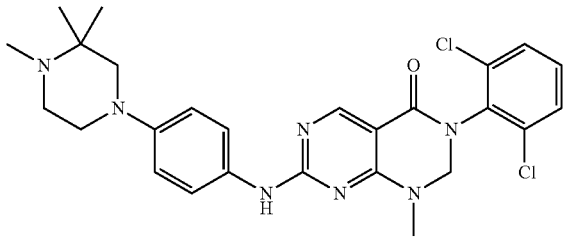 [SMILES: CN1CN(c2c(Cl)cccc2Cl)C(=O)c2cnc(Nc3ccc(N4CCN(C)C(C)(C)C4)cc3)nc21]

Step 1: 1,2,2-trimethyl-4-(4-nitrophenyl)piperazine

To a stirred suspension of 1-fluoro-4-nitrobenzene (0.668 g, 4.74 mmol) and potassium carbonate (3.27 g, 23.68 mmol) in anhydrous DMF (5 mL) was added 1,2,2-trimethylpiperazine.2HCl (1 g, 4.97 mmol) and the mixture heated at 90° C. for 21 hours. After cooling the mixture was partitioned between brine/water (100 mL) and ethyl acetate (50 mL). The aqueous layer was separated and extracted with ethyl acetate (3×50 mL). The combined ethyl acetate fractions were washed with brine/water (1:1, 4×25 mL), dried (anhydrous sodium sulfate), filtered and concentrated to dryness under reduced pressure. The resulting residue was purified by silica gel chromatography (gradient 50-100% ethyl acetate in cyclohexane then 0-20% methanol in ethyl acetate) to give the title compound (1.15 g, 97%). $^1$H NMR (400 MHz, CDCl$_3$): δ 8.10 (d, 2H), 6.78 (d, 2H), 3.46 (t, 2H), 3.18 (s, 2H), 2.67 (t, 2H), 2.29 (s, 3H), 1.08 (s, 6H). LCMS (Method C) $R_T$=0.48 min, m/z=250 [M+H]$^+$.

Step 2: 4-(3,3,4-trimethylpiperazin-1-yl)aniline

A solution of 1,2,2-trimethyl-4-(4-nitrophenyl)piperazine (1.15 g, 4.61 mmol) in methanol (30 mL) and tetrahydrofuran (5.00 mL) was passed twice through an H-Cube apparatus fitted with a 10% Pd—C cartridge under the following settings [1.0 ml/min flow, 40° C., Full $H_2$ mode]. The solvent was removed in vacuo to give the title compound (1.02 g, 101%). $^1$H NMR (400 MHz, DMSO-d$_6$): δ 6.64 (d, 2H), 6.48 (d, 2H), 4.54 (br s, 2H), 2.85 (t, 2H), 2.60 (s, 2H), 2.52 (t, 2H), 2.13 (s, 3H), 1.01 (s, 6H). LCMS (Method C) $R_T$=0.21 min, m/z=220 [M+H]$^+$.

Step 3: 3-(2,6-dichlorophenyl)-1-methyl-7-((4-(3,3,4-trimethylpiperazin-1-yl)phenyl)amino)-2,3-dihydropyrimido[4,5-d]pyrimidin-4(1H)-one 3-(2,6-Dichlorophenyl)-1-methyl-7-(methylthio)-2,3-dihydropyrimido[4,5-d]pyrimidin-4(1H)-one (100 mg, 0.283 mmol) was reacted with 4-(3,3,4-trimethylpiperazin-1-yl)aniline (62 mg, 0.283 mmol) following the procedure for Example 31 to give the title compound as an off-white solid (19 mg, 13%). $^1$H NMR (400 MHz, MeOH-d$_4$): δ 8.50 (s, 1H), 7.50-7.60 (m, 4H), 7.42 (dd, 1H), 6.93 (d, 2H), 4.96 (s, 2H), 3.12-3.19 (m, 5H), 2.91 (s, 2H), 2.73 (t, 2H), 2.29 (s, 3H), 1.16 (s, 6H). LCMS (Method C): $R_T$=0.80 min, m/z=526 [M+H]$^+$.

Example 64: 7-((4-(3-oxa-7,9-diazabicyclo[3.3.1]nonan-7-yl)phenyl)amino)-3-(2,6-dichlorophenyl)-1-methyl-2,3-dihydropyrimido[4,5-d]pyrimidin-4(1H)-one

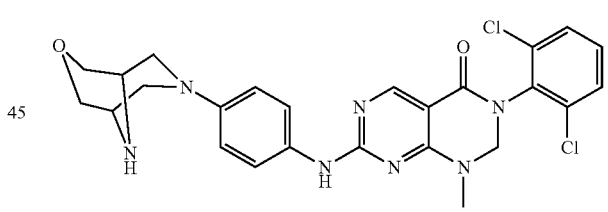

Step 1: tert-butyl 7-(4-nitrophenyl)-3-oxa-7,9-diazabicyclo[3.3.1]nonane-9-carboxylate To a stirred suspension of 1-fluoro-4-nitrobenzene (124 mg, 0.876 mmol) and potassium carbonate (484 mg, 3.50 mmol) in anhydrous DMF (2 mL) was added tert-butyl 3-oxa-7,9-diazabicyclo[3.3.1]nonane-9-carboxylate (200 mg, 0.876 mmol) and the mixture heated at 90° C. for 21 hours. After cooling the mixture was partitioned between brine/water (20 mL) and ethyl acetate (10 mL). The aqueous was separated and extracted with ethyl acetate (3×10 mL). The combined ethyl acetate fractions were washed with brine/water (1:1, 4×5 mL), dried (anhydrous sodium sulfate), filtered and concentrated to dryness under reduced pressure. The resulting residue was chromatographed (gradient 0-50% ethyl acetate in cyclohexane) to afford the title compound (237 mg, 77%). $^1$H NMR (400 MHz, CDCl$_3$): δ 8.15 (d, 2H), 6.78 (d, 2H), 4.24-4.31 (m, 1H), 4.11-4.18 (m, 1H), 3.95 (t, 2H), 3.84 (t, 4H), 3.37 (t, 2H), 1.49 (s, 9H). LCMS (Method C): R$_T$=1.54 min, m/z=350 [M-butene]$^+$.

Step 2: tert-butyl 7-(4-aminophenyl)-3-oxa-7,9-diazabicyclo[3.3.1]nonane-9-carboxylate A solution of tert-butyl 7-(4-nitrophenyl)-3-oxa-7,9-diazabicyclo[3.3.1]nonane-9-carboxylate (230 mg, 0.658 mmol) in methanol (30 mL) and tetrahydrofuran (5 mL) was passed through an H-Cube apparatus fitted with a 10% Pd—C cartridge under the following settings [1.0 ml/min flow, 40° C., Full H$_2$ mode]. The solvent was removed in vacuo to afford the title compound (208 mg, 99%). $^1$H NMR (400 MHz, DMSO-d$_6$): δ 6.62 (d, 2H), 6.50 (d, 2H), 4.67 (br s, 2H), 3.96 (d, 2H), 3.85 (d, 2H), 3.64 (d, 2H), 3.50 (t, 2H), 2.76 (d, 2H), 1.42 (s, 9H). LCMS (Method C) R$_T$=0.67 min, m/z=320 [M+H]$^+$.

Step 3: tert-butyl 7-(4-((6-(2,6-dichlorophenyl)-8-methyl-5-oxo-5,6,7,8-tetrahydropyrimido[4,5-d]pyrimidin-2-yl)amino)phenyl)-3-oxa-7,9-diazabicyclo[3.3.1]nonane-9-carboxylate 3-(2,6-Dichlorophenyl)-1-methyl-7-(methylthio)-2,3-dihydropyrimido[4,5-d]pyrimidin-4(1H)-one (100 mg, 0.283 mmol) was reacted with tert-butyl 7-(4-aminophenyl)-3-oxa-7,9-diazabicyclo[3.3.1]nonane-9-carboxylate (90 mg, 0.283 mmol) following the procedure for Example 31 to give the title compound as a yellow solid (108 mg, 61%). $^1$H NMR (300 MHz, CDCl$_3$): δ 8.69 (s, 1H), 7.50 (d, 2H), 7.44 (d, 2H), 7.28 (dd, 1H), 7.16 (br s, 1H), 6.87 (d, 2H), 4.87 (s, 2H), 4.22 (br s, 1H), 4.09 (br s, 1H), 4.00 (d, 1H), 3.96 (d, 1H), 3.87 (ddd, 2H), 3.71 (d, 2H), 3.09-3.21 (m, 5H), 1.49 (s, 9H). LCMS (Method C): R$_T$=1.46 min, m/z=626 [M+H]$^+$.

Step 4: 7-((4-(3-oxa-7,9-diazabicyclo[3.3.1]nonan-7-yl)phenyl)amino)-3-(2,6-dichlorophenyl)-1-methyl-2,3-dihydropyrimido[4,5-d]pyrimidin-4(1H)-one tert-Butyl 7-(4-((6-(2,6-dichlorophenyl)-8-methyl-5-oxo-5,6,7,8-tetrahydropyrimido[4,5-d]pyrimidin-2-yl)amino)phenyl)-3-oxa-7,9-diazabicyclo[3.3.1]nonane-9-carboxylate (108 mg, 0.172 mmol) was deprotected following the procedure for Example 31 to give the title compound as a yellow solid (60 mg, 66%). $^1$H NMR (400 MHz, MeOH-d$_4$): δ 8.50 (s, 1H), 7.49-7.62 (m, 4H), 7.41 (dd, 1H), 6.93 (d, 2H), 4.96 (s, 2H), 3.91-4.00 (m, 4H), 3.79 (d, 2H), 3.09-3.18 (m, 5H), 3.03 (s, 2H). LCMS (Method C): R$_T$=0.66 min, m/z=526 [M+H]$^+$.

Example 65: (R)-3-(2,6-dichlorophenyl)-7-((4-(3-(methoxymethyl)-4-methylpiperazin-1-yl)phenyl)amino)-1-methyl-2,3-dihydropyrimido[4,5-d]pyrimidin-4(1H)-one

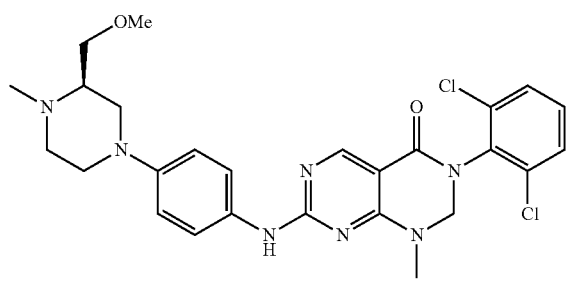 [SMILES: COC[C@H]1CN(c2ccc(Nc3ncc4c(n3)N(C)CN(c3c(Cl)cccc3Cl)C4=O)cc2)CCN1C]

(R)-3-(2,6-Dichlorophenyl)-7-((4-(3-(methoxymethyl)piperazin-1-yl)phenyl)amino)-1-methyl-2,3-dihydropyrimido[4,5-d]pyrimidin-4(1H)-one (46 mg, 0.087 mmol) was methylated following the procedure for Example 35 to give the title compound as a pale yellow solid (28 mg, 59%). $^1$H NMR (400 MHz, MeOH-d$_4$): δ 8.51 (s, 1H), 7.52-7.62 (m, 4H), 7.42 (dd, 1H), 6.97 (d, 2H), 4.96 (s, 2H), 3.54-3.62 (m, 2H), 3.44-3.54 (m, 2H), 3.38 (s, 3H), 3.16 (s, 3H), 2.93 (dt, 1H), 2.84 (td, 1H), 2.67 (dd, 1H), 2.41-2.55 (m, 2H), 2.39 (s, 3H). LCMS (Method C): R$_T$=0.78 min, m/z=542 [M+H]$^+$.

Example 66: (S)-3-(2,6-dichlorophenyl)-7-((4-(3-(methoxymethyl)-4-methylpiperazin-1-yl)phenyl)amino)-1-methyl-2,3-dihydropyrimido[4,5-d]pyrimidin-4(1H)-one

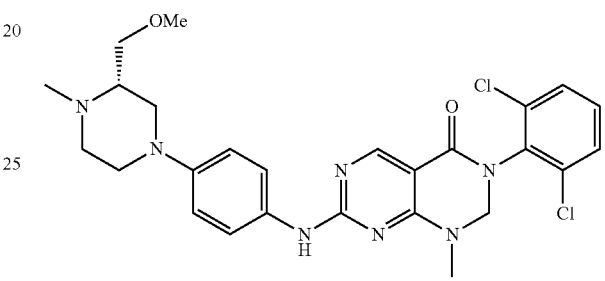

(S)-3-(2,6-Dichlorophenyl)-7-((4-(3-(methoxymethyl)piperazin-1-yl)phenyl)amino)-1-methyl-2,3-dihydropyrimido[4,5-d]pyrimidin-4(1H)-one (41 mg, 0.078 mmol) was methylated following the procedure for Example 35 to give the title compound as a pale yellow solid (28 mg, 67%). $^1$H NMR (400 MHz, MeOH-d$_4$): δ 8.51 (s, 1H), 7.50-7.62 (m, 4H), 7.42 (dd, 1H), 6.97 (d, 2H), 4.96 (s, 2H), 3.54-3.62 (m, 2H), 3.44-3.54 (m, 2H), 3.37 (s, 3H), 3.15 (s, 3H), 2.92 (dt, 1H), 2.84 (td, 1H), 2.67 (dd, 1H), 2.40-2.55 (m, 2H), 2.38 (s, 3H). LCMS (Method C): R$_T$=0.78 min, m/z=542 [M+H]$^+$.

Example 67: (R)-3-(2,6-dichlorophenyl)-7-((4-(3,4-dimethylpiperazin-1-yl)-3-(methoxymethyl)phenyl)amino)-1-methyl-2,3-dihydropyrimido[4,5-d]pyrimidin-4(1H)-one

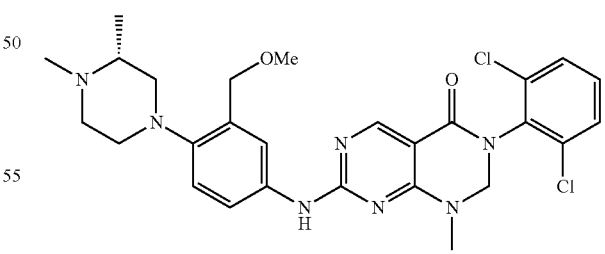

(R)-3-(2,6-dichlorophenyl)-7-((3-(methoxymethyl)-4-(3-methylpiperazin-1-yl)phenyl)amino)-1-methyl-2,3-dihydropyrimido[4,5-d]pyrimidin-4(1H)-one (40 mg, 0.074 mmol) was methylated following the procedure for Example 35 to give the title compound as a white solid (33 mg, 80%). $^1$H NMR (400 MHz, MeOH-d$_4$): δ 8.53 (s, 1H), 7.90 (br s, 1H), 7.52-7.60 (m, 3H), 7.42 (dd, 1H), 7.12 (d, 1H), 4.98 (s, 2H), 4.55 (s, 2H), 3.42 (s, 3H), 3.19 (s, 3H), 2.86-3.04 (m, 4H), 2.48-2.62 (m, 2H), 2.33-2.47 (m, 4H), 1.13 (d, 3H). LCMS (Method C): $R_T$=0.83 min, m/z=556 [M+H]$^+$.

Example 68: 3-(2,6-dichlorophenyl)-1-methyl-7-((4-(4-methyl-3-(trifluoromethyl)piperazin-1-yl)phenyl)amino)-2,3-dihydropyrimido[4,5-d]pyrimidin-4(1H)-one

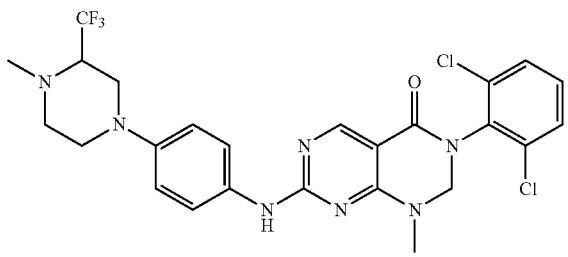 [SMILES: CN1CN(c2c(Cl)cccc2Cl)C(=O)c2cnc(Nc3ccc(N4CCN(C)C(C(F)(F)F)C4)cc3)nc21]

3-(2,6-Dichlorophenyl)-1-methyl-7-((4-(3-(trifluoromethyl)piperazin-1-yl)phenyl)amino)-2,3-dihydropyrimido[4,5-d]pyrimidin-4(1H)-one (57 mg, 0.103 mmol) was methylated following the procedure for Example 35 to give the title compound as a pale yellow solid (17 mg, 29%). $^1$H NMR (400 MHz, MeOH-d$_4$): δ 8.47 (s, 1H), 7.49-7.62 (m, 4H), 7.43 (dd, 1H), 6.99 (d, 2H), 5.01 (s, 2H), 3.58 (d, 1H), 3.33-3.42 (m, 1H), 3.19 (s, 3H), 3.08-3.17 (m, 1H), 2.97-3.09 (m, 3H), 2.61-2.71 (m, 1H), 2.53 (d, 3H). LCMS (Method C): $R_T$=1.46 min, m/z=566 [M+H]$^+$.

Example 69: 3-(2,6-dichlorophenyl)-7-((3-(methoxymethyl)-4-(piperazin-1-yl)phenyl)amino)-1-methyl-2,3-dihydropyrimido[4,5-d]pyrimidin-4(1H)-one

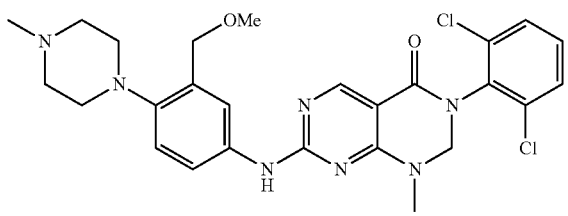 [SMILES: COCc1cc(Nc2ncc3c(n2)N(C)CN(c2c(Cl)cccc2Cl)C3=O)ccc1N1CCN(C)CC1]

3-(2,6-Dichlorophenyl)-7-((3-(methoxymethyl)-4-(piperazin-1-yl)phenyl)amino)-1-methyl-2,3-dihydropyrimido[4,5-d]pyrimidin-4(1H)-one (55 mg, 0.104 mmol) was methylated following the procedure for Example 35 to give the title compound as a white solid (29 mg, 51%). $^1$H NMR (400 MHz, DMSO-d$_6$): δ 9.81 (br s, 1H), 8.46 (s, 1H), 7.95 (br s, 1H), 7.64 (d, 2H), 7.60 (dd, 1H), 7.48 (dd, 1H), 7.06 (d, 1H), 4.97 (s, 2H), 4.45 (s, 2H), 3.34 (s, 3H), 3.12 (s, 3H), 2.84 (t, 4H), 2.54 (br s, 4H), 2.29 (s, 3H). LCMS (Method C): $R_T$=0.81 min, m/z=542 [M+H]$^+$.

Example 70: 3-(2,6-dichlorophenyl)-1-methyl-7-((6,7,8,9-tetrahydro-5H-5,8-epiminobenzo[7]annulen-3-yl)amino)-2,3-dihydropyrimido[4,5-d]pyrimidin-4(1H)-one

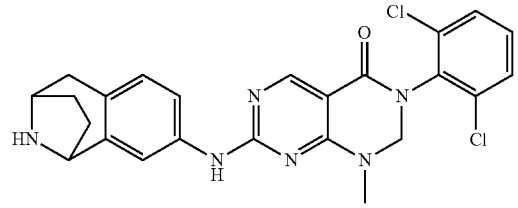 [SMILES: CN1CN(c2c(Cl)cccc2Cl)C(=O)c2cnc(Nc3ccc4c(c3)C3CCC(C4)N3)nc21]

Step 1: tert-butyl 3-amino-6,7,8,9-tetrahydro-5H-5,8-epiminobenzo[7]annulene-10-carboxylate A solution of 6,7,8,9-tetrahydro-5H-5,8-epiminobenzo[7]annulen-3-amine (WO 2008051547, 0.11 g, 0.631 mmol), di-tert-butyl dicarbonate (0.138 g, 0.631 mmol) and triethylamine (0.128 g, 1.26 mmol) was stirred at room temperature overnight then concentrated in vacuo. The residue was purified by Biotage chromatography to afford the title compound (0.137 g, 79%). LCMS (Method A): $R_T$=1.01 min, m/z=275 [M+H]$^+$ Step 2: 3-(2,6-dichlorophenyl)-1-methyl-7-((6,7,8,9-tetrahydro-5H-5,8-epiminobenzo[7]annulen-3-yl)amino)-2,3-dihydropyrimido[4,5-d]pyrimidin-4(1H)-one 3-(2,6-Dichlorophenyl)-1-methyl-7-(methylthio)-2,3-dihydropyrimido[4,5-d]pyrimidin-4(1H)-one (177 mg, 0.498 mmol) was reacted with tert-butyl 3-amino-6,7,8,9-tetrahydro-5H-5,8-epiminobenzo[7]annulene-10-carboxylate (130 mg, 0.474 mmol) following the procedure for example 31 to give the title compound (58 mg, 25%). $^1$H NMR (400 MHz, CDCl$_3$): δ 8.71 (s, 1H), 7.77 (brs, 1H), 7.44 (d, 2H), 7.36 (m, 2H), 7.28 (m, 1H), 7.02 (m, 1H), 4.90 (s, 2H), 4.20 (m, 1H), 3.91 (m, 1H), 3.18 (s, 3H), 3.10 (m, 1H), 2.55 (m, 1H), 2.11 (m, 2H), 1.92 (m, 1H), 1.62 (m, 1H). LCMS (Method C): $R_T$=0.79 min, m/z=481 [M+H]$^+$.

Example 71: 3-(2,6-dichlorophenyl)-1-methyl-7-((4-(9-methyl-3-oxa-7,9-diazabicyclo[3.3.1]nonan-7-yl)phenyl)amino)-2,3-dihydropyrimido[4,5-d]pyrimidin-4(1H)-one

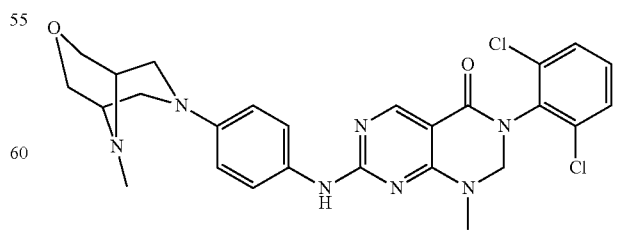

7-((4-(3-oxa-7,9-diazabicyclo[3.3.1]nonan-7-yl)phenyl)amino)-3-(2,6-dichlorophenyl)-1-methyl-2,3-dihydropyrimido[4,5-d]pyrimidin-4(1H)-one (30 mg, 0.057 mmol)

was methylated following the procedure for Example 35 to give the title compound as a yellow solid (13 mg, 42%). $^1$H NMR (400 MHz, DMSO-$d_6$): δ 9.64 (br s, 1H), 8.43 (s, 1H), 7.64 (d, 2H), 7.59 (br s, 2H), 7.47 (t, 1H), 6.80 (d, 2H), 4.94 (s, 2H), 3.84 (d, 2H), 3.74 (d, 2H), 3.41 (d, 2H), 3.20 (dd, 2H), 3.08 (s, 3H), 2.76 (br s, 2H), 2.46 (s, 3H). LCMS (Method C): $R_T$=0.69 min, m/z=540 [M+H]$^+$.

Example 72: 3-(2,6-dichlorophenyl)-7-((4-(4-ethyl-piperazin-1-yl)-3-(hydroxymethyl)phenyl)amino)-1-methyl-2,3-dihydropyrimido[4,5-d]pyrimidin-4(1H)-one

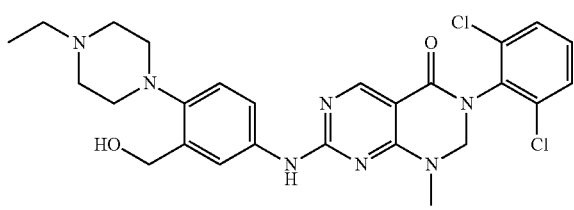 [SMILES: CCN1CCN(c2ccc(Nc3ncc4c(n3)N(C)CN(c3c(Cl)cccc3Cl)C4=O)cc2CO)CC1]

Step 1:
2-(4-ethylpiperazin-1-yl)-5-nitrobenzaldehyde

A suspension of 2-fluoro-5-nitrobenzaldehyde (3 g, 17.74 mmol), 1-ethylpiperazine (2.026 g, 17.74 mmol) and potassium carbonate (3.68 g, 26.6 mmol) in anhydrous DMF (15 mL) was heated to 50° C. under a nitrogen atmosphere overnight. The reaction mixture was allowed to cool to room temperature, diluted with water (70 mL) and stirred at room temperature for 15 minutes. The precipitated solid was isolated by filtration, washed with water, sucked dry and freeze-dried overnight to give the title compound as a yellow solid (4.38 g, 94%). $^1$H NMR (300 MHz, CDCl$_3$): δ 10.10 (s, 1H), 8.62 (d, 1H), 8.30 (dd, 1H), 7.09 (d, 1H), 3.35 (t, 4H), 2.68 (t, 4H), 2.52 (q, 2H), 1.14 (t, 3H). LCMS (Method C): $R_T$=0.38 min, m/z=264 [M+H]$^+$.

Step 2:
(2-(4-ethylpiperazin-1-yl)-5-nitrophenyl)methanol

A solution of 2-(4-ethylpiperazin-1-yl)-5-nitrobenzaldehyde (4.38 g, 16.64 mmol) in anhydrous THF (30.8 mL) was cooled to 0° C. followed by the portionwise addition of sodium borohyride (0.629 g, 16.64 mmol). The reaction mixture was stirred at 0° C. for 90 minutes. The reaction mixture was quenched with water (50 mL) and extracted into dichloromethane (3×30 mL). The combined organic phases were dried over Na$_2$SO$_4$, filtered, concentrated to dryness under reduced pressure and purified by Biotage chromatography (silica 100 g cartridge, dichloromethane:methanol, gradient elution from 100:0 to 85:15) to give the title compound as a yellow solid (1.70 g, 39%). $^1$H NMR (300 MHz, CDCl$_3$): δ 8.26 (d, 1H), 8.12 (dd, 1H), 7.14 (d, 1H), 4.79 (s, 2H), 3.61 (br s, 1H), 3.08 (t, 4H), 2.64 (br s, 4H), 2.50 (q, 2H), 1.12 (t, 3H). LCMS (Method C): $R_T$=0.37 min, m/z=266 [M+H]$^+$.

Step 3: (5-amino-2-(4-ethylpiperazin-1-yl)phenyl)methanol

A solution of (2-(4-ethylpiperazin-1-yl)-5-nitrophenyl)methanol (1.70 g, 6.41 mmol) in methanol (100 mL) was hydrogenated by H-Cube (10% Pd/C scale-up cartridge, Full H$_2$, 40° C., 1 mL/min) with two passes. The reaction mixture was concentrated to dryness under reduced pressure to give the title compound as an off-white solid (1.48 g, 98%). $^1$H NMR (300 MHz, DMSO-$d_6$): δ 6.80 (d, 1H), 6.66 (d, 1H), 6.39 (dd, 1H), 4.96 (t, 1H), 4.76 (br s, 2H), 4.45 (d, 2H), 2.70 (t, 4H), 2.44 (br s, 4H), 2.35 (q, 2H), 1.01 (t, 3H). LCMS (Method C): $R_T$=0.21 min, m/z=236 [M+H]$^+$.

Step 4: 3-(2,6-dichlorophenyl)-7-((4-(4-ethylpiperazin-1-yl)-3-(hydroxymethyl)phenyl)amino)-1-methyl-2,3-dihydropyrimido[4,5-d]pyrimidin-4(1H)-one 3-(2,6-Dichlorophenyl)-1-methyl-7-(methylthio)-2,3-dihydropyrimido[4,5-d]pyrimidin-4(1H)-one (100 mg, 0.283 mmol) was reacted with (5-amino-2-(4-ethylpiperazin-1-yl)phenyl)methanol (67 mg, 0.283 mmol) following the procedure for Example 31 to give the title compound as a white solid (24 mg, 16%). $^1$H NMR (400 MHz, DMSO-$d_6$): δ 9.81 (br s, 1H), 8.46 (s, 1H), 7.99 (br s, 1H), 7.64 (d, 2H), 7.56 (dd, 1H), 7.48 (dd, 1H), 7.01 (d, 1H), 5.06 (t, 1H), 4.96 (s, 2H), 4.54 (d, 2H), 3.11 (s, 3H), 2.81 (t, 4H), 2.50 (t, 4H), 2.38 (q, 2H), 1.02 (t, 3H). LCMS (Method C): $R_T$=0.71 min, m/z=542 [M+H]$^+$.

Example 73: 3-(2,6-dichlorophenyl)-7-((3-(hydroxymethyl)-4-morpholinophenyl)amino)-1-methyl-2,3-dihydropyrimido[4,5-d]pyrimidin-4(1H)-one

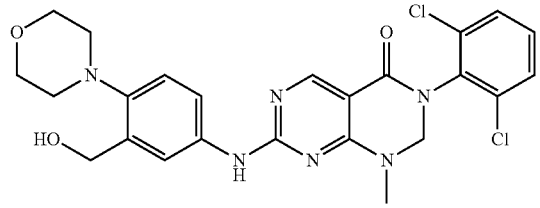

A solution of mCPBA, 50% purity (117 mg, 0.338 mmol) in dichloromethane (0.400 mL) was passed through a phase separator and washed through with further dichloromethane (0.400 mL). This solution was added to a stirring suspension of 3-(2,6-dichlorophenyl)-1-methyl-7-(methylthio)-2,3-dihydropyrimido[4,5-d]pyrimidin-4(1H)-one (100 mg, 0.281 mmol) in anhydrous toluene (2 mL) and the mixture stirred for 30 minutes. Hunig's base (0.147 mL, 0.844 mmol) followed by (5-amino-2-morpholinophenyl)methanol (58.6 mg, 0.281 mmol) were added and the mixture was heated to 75° C. for 30 min. DMF (0.5 mL) was added and heating was continued for 16 h. After cooling the reaction mixture was purified directly by flash chromatography (0-100%, ethyl acetate in cyclohexane, KP-NH column). The residue was dissolved in methanol (1 mL) and water (8 mL) then freeze-dried. The residue was stirred in diethyl ether (2 mL) for 20 mins. The diethyl ether was removed by decanting then the solid was dried in vacuo at 50° C. The solid was dissolved in methanol (0.5 mL) and water (1.5 mL) then freeze-dried to afford the title compound (40.8 mg, 28.1%). $^1$H NMR (400 MHz, DMSO-$d_6$): δ 9.83 (br s, 1H), 8.46 (s, 1H), 8.00 (br s, 1H), 7.65 (d, 2H), 7.58 (dd, 1H), 7.48 (dd, 1H), 7.03 (d, 1H), 5.06 (t, 1H), 4.96 (s, 2H), 4.56 (d, 2H), 3.71 (t, 4H), 3.12 (s, 3H), 2.80 (t, 4H). LCMS (Method C): $R_T$=1.08 min, m/z=515 [M+H]$^+$.

Example 74: 7-((4-(3,8-diazabicyclo[3.2.1]octan-3-yl)phenyl) amino)-3-(2,6-dichlorophenyl)-1-methyl-2,3-dihydropyrimido [4,5-d]pyrimidin-4(1H)-one

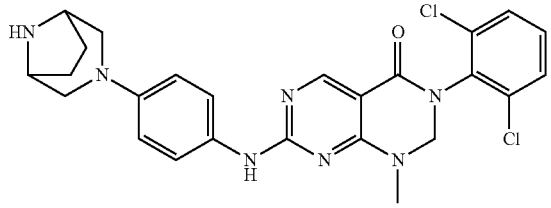 [SMILES: CN1CN(c2c(Cl)cccc2Cl)C(=O)c2cnc(Nc3ccc(N4CC5CCC(C4)N5)cc3)nc21]

Step 1: tert-butyl 3-(4-nitrophenyl)-3,8-diazabicyclo [3.2.1] octane-8-carboxylate A suspension of 1-fluoro-4-nitrobenzene (0.266 g, 1.884 mmol), tert-butyl 3,8-diazabicyclo[3.2.1]octane-8-carboxylate (0.4 g, 1.884 mmol) and potassium carbonate (0.39 g, 2.83 mmol) in anhydrous DMF (5 mL) was heated to 50° C. under a nitrogen atmosphere for 16 h. The reaction mixture was allowed to cool to room temperature, partitioned between water (50 mL) and ethyl acetate (50 ml). The ethyl acetate was separated and washed with water (3×20 ml), dried (anhydrous sodium sulfate), filtered and reduced in vacuo. The residue was purified by flash chromatography (0-100% ethyl acetate in cyclohexane) to afford the title compound (0.62 g, 100%). LCMS (Method A): $R_T$=1.61 min, m/z=334 [M+H]$^+$.

Step 2: tert-butyl 3-(4-aminophenyl)-3,8-diazabicyclo [3.2.1] octane-8-carboxylate A solution of tert-butyl 2,2-dimethyl-4-(4-nitrophenyl)piperazine-1-carboxylate (250 mg, 0.75 mmol) in methanol (10 ml) was passed through an H-Cube apparatus fitted with a 10% Pd—C cartridge under the following settings [1.0 ml/min flow, 40° C., Full H$_2$ mode)]. The solvent was removed in vacuo to afford the title compound which was used without further purification (230 mg, 100%). LCMS (Method C): $R_T$=0.84 min, m/z=304 [M+H]$^+$.

Step 3: 7-((4-(3,8-diazabicyclo[3.2.1]octan-3-yl)phenyl) amino)-3-(2,6-dichlorophenyl)-1-methyl-2,3-dihydropyrimido [4,5-d]pyrimidin-4(1H)-one 3-(2,6-Dichlorophenyl)-1-methyl-7-(methylthio)-2,3-dihydropyrimido[4,5-d]pyrimidin-4(1H)-one (250 mg, 0.704 mmol) was reacted with tert-butyl 3-(4-aminophenyl)-3,8-diazabicyclo[3.2.1]octane-8-carboxylate (203 mg, 0.67 mmol) following the procedure for Example 31 to give the title compound (168 mg, 41%). $^1$H NMR (400 MHz, DMSO-d$_6$): δ 9.65 (s, 1H), 8.43 (s, 1H), 7.64 (d, 2H), 7.56 (m, 1H), 7.47 (m, 1H), 6.76 (d, 2H), 4.91 (s, 2H), 3.48 (m, 2H), 3.31 (m, 1H), 3.08 (s, 3H), 2.70 (m, 2H), 2.33 (m, 1H), 1.69 (m, 4H). LCMS (Method C): $R_T$=0.77 min, m/z=510 [M+H]$^+$.

Example 75: 7-((4-((1S,4S)-2,5-diazabicyclo[2.2.1]heptan-2-yl)-3-methylphenyl)amino)-3-(2,6-dichlorophenyl)-1-methyl-2,3-dihydropyrimido[4,5-d]pyrimidin-4(1H)-one

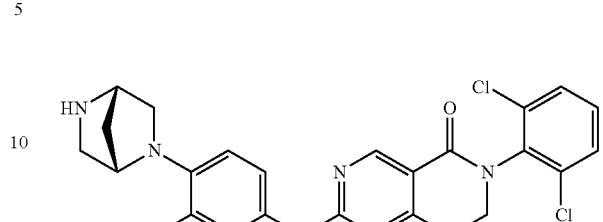

Step 1: (1S,4S)-tert-butyl 5-(2-methyl-4-nitrophenyl)-2,5-diazabicyclo[2.2.1]heptane-2-carboxylate A suspension of 2-fluoro-5-nitrotoluene (1.565 g, 10.09 mmol), (1S,4S)-tert-butyl 2,5-diazabicyclo[2.2.1]heptane-2-carboxylate (2.00 g, 10.09 mmol) and potassium carbonate (2.091 g, 15.13 mmol) in anhydrous DMF (8 mL) was heated to 50° C. under a nitrogen atmosphere for 2 days, then at 100° C. for 3 days. The reaction mixture was allowed to cool to room temperature, diluted with water (50 mL) and extracted into ethyl acetate (3×30 mL). The combined organic phases were dried over Na$_2$SO$_4$, filtered and concentrated to dryness under reduced pressure. The residue was purified by Biotage chromatography (silica 100 g cartridge, cyclohexane:ethyl acetate, gradient elution from 90:10 to 0:100) to give the title compound as a yellow solid (1.87 g, 56%). $^1$H NMR (300 MHz, CDCl$_3$): δ 7.92-8.02 (m, 2H), 6.60 (dd, 1H), 4.56 (d, 1H), 4.44 (s, 1H), 3.83 (d, 1H), 3.62 (dd, 1H), 3.47 (t, 1H), 3.32 (dd, 1H), 2.36 (s, 3H), 1.86-2.06 (m, 2H), 1.38-1.49 (m, 9H). LCMS (Method C): $R_T$=1.69 min, m/z=334 [M+H]$^+$.

Step 2: (1S,4S)-tert-butyl 5-(4-amino-2-methylphenyl)-2,5-diazabicyclo[2.2.1]heptane-2-carboxylate A solution of (1S,4S)-tert-butyl 5-(2-methyl-4-nitrophenyl)-2,5-diazabicyclo[2.2.1]heptane-2-carboxylate (1.87 g, 5.61 mmol) in THF (140 mL) was hydrogenated by H-Cube (10% Pd/C scale-up cartridge, Full H$_2$, 40° C., 1 mL/min) with three-passes. The reaction mixture was concentrated to dryness under reduced pressure, slurried in diethyl ether (25 mL), filtered and sucked dry to give the title compound as a tan solid (1.21 g, 71%). $^1$H NMR (400 MHz, CDCl$_3$): δ 6.71 (dd, 1H), 6.55 (s, 1H), 6.48 (d, 1H), 4.46 (d, 1H), 3.91 (s, 1H), 3.54 (dd, 1H), 3.19-3.47 (m, 5H), 2.21 (s, 3H), 1.96 (t, 1H), 1.82 (t, 1H), 1.42-1.52 (m, 9H). LCMS (Method C): $R_T$=0.81 min, m/z=304 [M+H]$^+$.

Step 3: (1S,4S)-tert-butyl 5-(4-((6-(2,6-dichlorophenyl)-8-methyl-5-oxo-5,6,7,8-tetrahydropyrimido[4,5-d]pyrimidin-2-yl)amino)-2-methylphenyl)-2,5-diazabicyclo[2.2.1]heptane-2-carboxylate 3-(2,6-Dichlorophenyl)-1-methyl-7-(methylthio)-2,3-dihydropyrimido[4,5-d]pyrimidin-4(1H)-one (100 mg, 0.283 mmol) was reacted with (1S,4S)-tert-butyl 5-(4-amino-2-methylphenyl)-2,5-diazabicyclo[2.2.1]heptane-2-carboxylate (86 mg, 0.283 mmol) following the procedure for Example 31 to give the title compound as a yellow solid (109 mg, 63%). $^1$H NMR (300 MHz, CDCl$_3$): δ 8.70 (s, 1H), 7.73 (br s, 1H), 7.43 (d, 2H), 7.32-7.42 (m, 2H), 7.27 (dd, 1H), 6.79 (dd, 1H), 4.86 (s, 2H), 4.50 (d, 1H), 4.10 (br s, 1H), 3.61 (dd, 1H), 3.19-3.50 (m, 3H), 3.16 (s, 3H), 2.28 (s, 3H), 1.75-2.01 (m, 2H), 1.41-1.50 (m, 9H). LCMS (Method C): $R_T$=1.65 min, m/z=610 [M+H]$^+$.

Step 4: 7-((4-((1S,4S)-2,5-diazabicyclo[2.2.1]heptan-2-yl)-3-methylphenyl)amino)-3-(2,6-dichlorophenyl)-1-methyl-2,3-dihydropyrimido[4,5-d]pyrimidin-4(1H)-one (1S,4S)-tert-Butyl 5-(4-((6-(2,6-dichlorophenyl)-8-methyl-5-oxo-5,6,7,8-tetrahydropyrimido[4,5-d]pyrimidin-2-yl)amino)-2-methylphenyl)-2,5-diazabicyclo[2.2.1]heptane-2-carboxylate (109 mg, 0.179 mmol) was deprotected following the procedure for Example 31 to give the title compound as a yellow solid (76 mg, 83%). $^1$H NMR (400 MHz, DMSO-d$_6$): δ 9.63 (br s, 1H), 8.43 (s, 1H), 7.64 (d, 2H), 7.39-7.53 (br m, 3H), 6.75 (d, 1H), 4.95 (s, 2H), 3.98 (s, 1H), 3.54 (s, 1H), 3.41 (dd, 1H), 3.09 (s, 3H), 3.04 (d, 1H), 2.95 (d, 1H), 2.84 (dd, 1H), 2.18 (s, 3H), 1.75 (d, 1H), 1.58 (d, 1H). LCMS (Method C): $R_T$=0.78 min, m/z=510 [M+H]$^+$.

Example 76: 3-(2,6-dichlorophenyl)-1-methyl-7-((2'-methyl-2',3'-dihydro-1'H-spiro[cyclopropane-1,4'-isoquinolin]-7'-yl)amino)-2,3-dihydropyrimido[4,5-d]pyrimidin-4(1H)-one

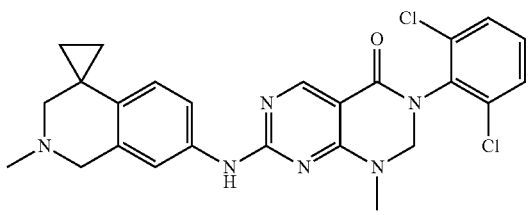 [SMILES: CN1Cc2cc(Nc3ncc4c(n3)N(C)CN(c3c(Cl)cccc3Cl)C4=O)ccc2C2(CC2)C1]

Step 1: 3-(2,6-dichlorophenyl)-1-methyl-7-((2'-methyl-2',3'-dihydro-1'H-spiro[cyclopropane-1,4'-isoquinolin]-7'-yl)amino)-2,3-dihydropyrimido[4,5-d]pyrimidin-4(1H)-one 3-(2,6-Dichlorophenyl)-1-methyl-7-(methylthio)-2,3-dihydropyrimido[4,5-d]pyrimidin-4(1H)-one (100 mg, 0.283 mmol) was reacted with 2'-methyl-2',3'-dihydro-1'H-spiro[cyclopropane-1,4'-isoquinolin]-7'-amine di-hydrochloride salt [WO 2009/151997] (74 mg, 0.283 mmol) following the procedure for Example 31 to give the title compound as an off-white solid (8 mg, 6%). $^1$H NMR (400 MHz, DMSO-d$_6$): δ 9.79 (br s, 1H), 8.47 (s, 1H), 7.64 (d, 2H), 2.43-7.56 (br m, 3H), 6.65 (d, 1H), 4.97 (s, 2H), 3.55 (s, 2H), 3.10 (s, 3H), 2.43 (s, 2H), 2.30 (s, 3H), 0.85 (dt, 4H). LCMS (Method C): $R_T$=0.84 min, m/z=495 [M+H]$^+$.

Example 77: 3-(2,6-dichlorophenyl)-1-methyl-7-((3-methyl-4-((1S,4S)-5-methyl-2,5-diazabicyclo[2.2.1]heptan-2-yl)phenyl)amino)-2,3-dihydropyrimido[4,5-d]pyrimidin-4(1H)-one

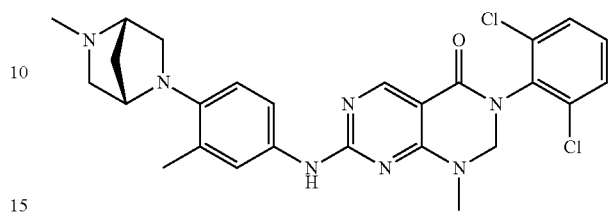

7-((4-((1S,4S)-2,5-diazabicyclo[2.2.1]heptan-2-yl)-3-methylphenyl)amino)-3-(2,6-dichlorophenyl)-1-methyl-2,3-dihydropyrimido[4,5-d]pyrimidin-4(1H)-one (41 mg, 0.080 mmol) was methylated following the procedure for Example 35 to give the title compound as a pale yellow solid (30 mg, 71%). $^1$H NMR (400 MHz, MeOH-d$_4$): δ 8.50 (s, 1H), 7.56 (d, 2H), 7.35-7.48 (m, 3H), 6.86 (d, 1H), 4.97 (s, 2H), 4.03 (s, 1H), 3.52 (s, 1H), 3.40 (d, 1H), 3.28 (dd, 1H), 3.17 (s, 3H), 3.01 (d, 1H), 2.85 (dd, 1H), 2.45 (s, 3H), 2.29 (s, 3H), 1.98 (d, 1H), 1.91 (d, 1H). LCMS (Method C): $R_T$=0.80 min, m/z=524 [M+H]$^+$.

Example 78: (R)-3-(2,6-dichlorophenyl)-1-d3-methyl-7-((4-(3-methylpiperazin-1-yl)phenyl)amino)-2,3-dihydropyrimido[4,5-d]pyrimidin-4(1H)-one

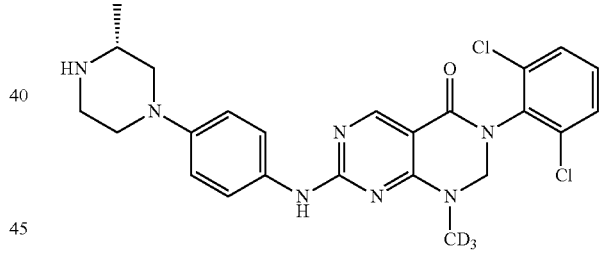

Step 1: N-(2,6-dichlorophenyl)-4-(d3-methylamino)-2-(methylthio)pyrimidine-5-carboxamide 4-chloro-N-(2,6-dichlorophenyl)-2-(methylthio)pyrimidine-5-carboxamide (3.1 g, 8.89 mmol) was suspended in anhydrous methanol (30 mL). Methyl-d$_3$-amine hydrochloride (0.627 g, 8.89 mmol) and Hunig's Base (4.66 mL, 26.7 mmol) were added. The mixture was split between two microwave vials which were sealed and heated to 50° C. for 1 h each. The combined mixture was partitioned between water (25 mL) and dichloromethane (50 mL). The aqueous layer was separated and extracted with dichloromethane (2×50 mL). The combined dichloromethane fractions were dried (phase separator) and reduced in vacuo to afford the title compound which was used without further purification (3.31 g, 108%). $^1$H NMR (400 MHz, CDCl$_3$): δ 8.49 (s, 1H), 8.45 (br s, 1H), 7.50 (br s, 1H), 7.42 (d, 2H), 7.22 (dd, 1H), 2.56 (s, 3H). LCMS (Method C): $R_T$=1.43 min, m/z=346 [M+H]$^+$.

Step 2: 3-(2,6-dichlorophenyl)-1-d3-methyl-7-(methylthio)-2,3-dihydropyrimido[4,5-d]pyrimidin-4(1H)-one N-(2,6-Dichlorophenyl)-4-(d$_3$-methylamino)-2-(methylthio)pyrimidine-5-carboxamide (3.31 g, 8.89 mmol) was suspended in anhydrous acetonitrile (70 mL) in a Schlenk tube. Cesium carbonate (11.59 g, 35.6 mmol) was added, followed by diiodomethane (1.434 mL, 17.78 mmol). The tube was sealed and the mixture was heated to 80° C. while stirring for 40 h. Further diiodomethane (1.434 mL, 17.78 mmol) was added and heating continued for 48 h. The solvent was removed in vacuo. The residue was partitioned between water (50 mL) and dichloromethane (100 mL). The aqueous layer was separated and extracted with dichloromethane (2×25 mL). The combined dichloromethane fractions were dried (phase separator) and reduced in vacuo. The resulting residue was purified by silica gel chromatography (gradient 0-50% ethyl acetate in cyclohexane). The resulting residue was purified further by silica gel chromatography (isocratic 25% ethyl acetate in cyclohexane) to afford the title compound (779 mg, 24.5%). $^1$H NMR (400 MHz, CDCl$_3$): δ 8.72 (s, 1H), 7.45 (d, 2H), 7.30 (dd, 1H), 4.91 (s, 2H), 2.57 (s, 3H). LCMS (Method C): R$_T$=1.44 min, m/z [M+H]$^+$.

Step 3

(R)-3-(2,6-dichlorophenyl)-1-d$_3$-methyl-7-((4-(3-methylpiperazin-1-yl)phenyl)amino)-2,3-dihydropyrimido[4,5-d]pyrimidin-4(1H)-one 3-(2,6-Dichlorophenyl)-1-methyl-7-(methylthio)-2,3-dihydropyrimido[4,5-d]pyrimidin-4(1H)-one (100 mg, 0.279 mmol) was reacted with (R)-tert-butyl 4-(4-aminophenyl)-2-methylpiperazine-1-carboxylate (81 mg, 0.279 mmol) following the procedure for Example 31 to give the title compound (84.4 mg, 96%). $^1$H NMR (400 MHz, DMSO-d$_6$): δ 9.68 (br s, 1H), 8.44 (s, 1H), 7.64 (d, 2H), 7.60 (br d, 2H), 7.48 (t, 1H), 6.88 (d, 2H), 4.95 (s, 2H), 3.44 (t, 2H), 2.93 (d, 1H), 2.71-2.84 (m, 2H), 2.23 (br s, 1H), 2.14 (t, 1H), 1.01 (d, 3H). LCMS (Method C): R$_T$=0.78 min, m/z=501 [M+H]$^+$.

Example 79: 3-(2,6-dichlorophenyl)-7-((4-((2R,5R)-2,5-dimethylpiperazin-1-yl)phenyl)amino)-1-methyl-2,3-dihydropyrimido[4,5-d]pyrimidin-4(1H)-one

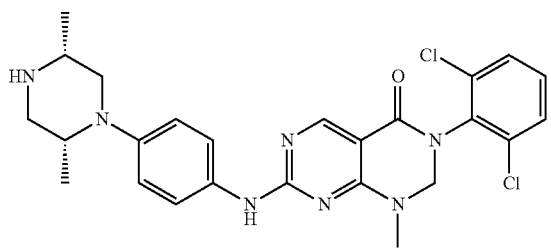

Step 1: (2R,5R)-tert-butyl 2,5-dimethyl-4-(4-nitrophenyl)piperazine-1-carboxylate A suspension of 1-fluoro-4-nitrobenzene (329 mg, 2.333 mmol), (2R,5R)-tert-butyl 2,5-dimethylpiperazine-1-carboxylate (500 mg, 2.333 mmol) and potassium carbonate (484 mg, 3.50 mmol) in anhydrous DMF (2 mL) was heated to 50° C. under a nitrogen atmosphere for 7 days. The reaction mixture was allowed to cool to room temperature, diluted with water (70 mL) and stirred at room temperature for 15 minutes. The mixture was extracted into ethyl acetate (3×20 mL), dried over Na$_2$SO$_4$, filtered and concentrated to dryness under reduced pressure. The residue was purified by two consecutive Biotage chromatography columns (silica 100 g cartridge, cyclohexane:ethyl acetate, gradient elution from 90:10 to 50:50) to give the title compound as a yellow solid (200 mg, 26%). $^1$H NMR (400 MHz, CDCl$_3$): δ 8.11 (d, 2H), 6.66 (d, 2H), 3.93-4.21 (m, 3H), 3.79 (dd, 1H), 3.08 (dd, 1H), 2.90 (dd, 1H), 1.41 (s, 9H), 1.20 (dd, 6H). LCMS (Method C): R$_T$=1.74 min, m/z=336 [M+H]$^+$.

Step 2: (2R,5R)-tert-butyl 4-(4-aminophenyl)-2,5-dimethylpiperazine-1-carboxylate A solution of (2R,5R)-tert-butyl 2,5-dimethyl-4-(4-nitrophenyl)piperazine-1-carboxylate (0.20 g, 0.596 mmol) in methanol (20 mL) was hydrogenated by H-Cube (10% Pd/C cartridge, Full H$_2$, 50° C., 1 mL/min). The reaction mixture was concentrated to dryness under reduced pressure to give the title compound as a grey solid (150 mg, 82%). $^1$H NMR (400 MHz, DMSO-d$_6$): δ 6.79 (d, 2H), 6.54 (d, 2H), 5.49 (br s, 2H), 4.08 (br s, 1H), 3.74 (dd, 1H), 2.92 (dd, 1H), 2.75-2.87 (m, 1H), 2.63-2.75 (m, 2H), 1.40 (s, 9H), 1.22 (d, 3H), 0.79 (d, 3H). LCMS (Method C): R$_T$=0.84 min, m/z=306 [M+H]$^+$.

Step 3: (2R,5R)-tert-butyl 4-(4-((6-(2,6-dichlorophenyl)-8-methyl-5-oxo-5,6,7,8-tetrahydropyrimido[4,5-d]pyrimidin-2-yl)amino)phenyl)-2,5-dimethylpiperazine-1-carboxylate 3-(2,6-Dichlorophenyl)-1-methyl-7-(methylthio)-2,3-dihydropyrimido[4,5-d]pyrimidin-4(1H)-one (100 mg, 0.283 mmol) was reacted with (2R,5R)-tert-butyl 4-(4-aminophenyl)-2,5-dimethylpiperazine-1-carboxylate (86 mg, 0.283 mmol) following the procedure for Example 31 to give the title compound as a yellow solid (105 mg, 61%). $^1$H NMR (400 MHz, CDCl$_3$): δ 8.71 (s, 1H), 7.64 (br s, 1H), 7.53 (d, 2H), 7.43 (d, 2H), 7.28 (dd, 1H), 6.98 (d, 2H), 4.87 (s, 2H), 4.20 (br s, 1H), 3.93 (d, 1H), 3.08-3.23 (m, 5H), 2.89 (dd, 1H), 2.83 (dd, 1H), 1.46 (s, 9H), 1.30 (d, 3H), 0.97 (d, 3H). LCMS (Method C): R$_T$=1.76 min, m/z=612 [M+H]$^+$.

Step 4: 3-(2,6-dichlorophenyl)-7-((4-((2R,5R)-2,5-dimethylpiperazin-1-yl)phenyl)amino)-1-methyl-2,3-dihydropyrimido[4,5-d]pyrimidin-4(1H)-one (2R,5R)-tert-Butyl 4-(4-((6-(2,6-dichlorophenyl)-8-methyl-5-oxo-5,6,7,8-tetrahydropyrimido[4,5-d]pyrimidin-2-yl)amino)phenyl)-2,5-dimethylpiperazine-1-carboxylate (105 mg, 0.171 mmol) was deprotected following the procedure for Example 31 to give the title compound as a yellow solid (50 mg, 57%). $^1$H NMR (400 MHz, DMSO-d$_6$): δ 9.65 (br s, 1H), 8.43 (s, 1H), 7.64 (d, 2H), 7.58 (br s, 2H), 7.47 (dd, 1H), 6.82 (d, 2H), 4.94 (s, 2H), 3.84-3.94 (m, 1H), 3.14 (dd, 1H), 3.08 (s, 3H), 2.97 (dd, 1H), 2.79 (d, 1H), 2.67-2.77 (m, 1H), 2.40 (t, 1H), 1.06 (d, 3H), 0.96 (d, 3H). LCMS (Method C): R$_T$=0.77 min, m/z=512 [M+H]$^+$.

Example 80: 3-(2,6-dichlorophenyl)-7-((4-((2S,5R)-2,5-dimethylpiperazin-1-yl)phenyl)amino)-1-methyl-2,3-dihydropyrimido[4,5-d]pyrimidin-4(1H)-one

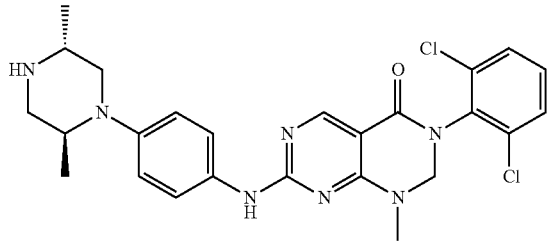

Step 1: (2R,5S)-tert-butyl 2,5-dimethyl-4-(4-nitrophenyl)piperazine-1-carboxylate A suspension of 1-fluoro-4-nitrobenzene (329 mg, 2.333 mmol), (2R,5S)-tert-butyl 2,5-dimethylpiperazine-1-carboxylate (500 mg, 2.333 mmol) and potassium carbonate (484 mg, 3.50 mmol) in anhydrous acetonitrile (3 mL) was heated to 100° C. under a nitrogen atmosphere for 11 days. The reaction mixture was allowed to cool to room temperature, diluted with water (30 mL) and extracted into ethyl acetate (3×10 mL). The combined organic phases were dried over $Na_2SO_4$, filtered and concentrated to dryness under reduced pressure. The residue was purified by Biotage chromatography (silica 50 g cartridge, cyclohexane:ethyl acetate, gradient elution from 95:5 to 60:40) to give the title compound as a yellow solid (530 mg, 68%). $^1$H NMR (400 MHz, CDCl$_3$): δ 8.12 (d, 2H), 6.77 (d, 2H), 4.42 (br d, 1H), 4.00-4.19 (m, 1H), 3.84 (dd, 1H), 3.29-3.50 (m, 3H), 1.24 (d, 3H), 1.49 (s, 9H), 1.19 (d, 3H). LCMS (Method C): $R_T$=1.80 min, m/z=336 [M+H]$^+$.

Step 2: (2R,5S)-tert-butyl 4-(4-aminophenyl)-2,5-dimethylpiperazine-1-carboxylate A solution of (2R,5S)-tert-butyl 2,5-dimethyl-4-(4-nitrophenyl)piperazine-1-carboxylate (0.53 g, 1.580 mmol) in methanol (50 mL) was hydrogenated by H-Cube (10% Pd/C cartridge, Full H$_2$, 50° C., 1 mL/min). The reaction mixture was concentrated to dryness under reduced pressure to give the title compound as a grey solid (480 mg, 99%). $^1$H NMR (400 MHz, CDCl$_3$): δ 6.72 (dt, 2H), 6.65 (dt, 2H), 4.39 (br s, 1H), 3.70-3.82 (m, 2H), 3.42 (dd, 1H), 3.39 (br s, 2H), 3.22 (dd, 1H), 2.85 (dd, 1H), 1.48 (s, 9H), 1.26 (d, 3H), 0.93 (d, 3H). LCMS (Method C): $R_T$=0.90 min, m/z=306 [M+H]$^+$.

Step 3: (2R,5S)-tert-butyl 4-(4-((6-(2,6-dichlorophenyl)-8-methyl-5-oxo-5,6,7,8-tetrahydropyrimido[4,5-d]pyrimidin-2-yl)amino)phenyl)-2,5-dimethylpiperazine-1-carboxylate 3-(2,6-Dichlorophenyl)-1-methyl-7-(methylthio)-2,3-dihydropyrimido[4,5-d]pyrimidin-4(1H)-one (100 mg, 0.283 mmol) was reacted with (2R,5S)-tert-butyl 4-(4-aminophenyl)-2,5-dimethylpiperazine-1-carboxylate (86 mg, 0.283 mmol) following the procedure for Example 31 to give the title compound as a yellow solid (133 mg, 77%). $^1$H NMR (400 MHz, CDCl$_3$): δ 8.70 (s, 1H), 8.13 (br s, 1H), 7.50 (d, 2H), 7.42 (d, 2H), 7.26 (dd, 1H), 6.84 (d, 2H), 4.86 (s, 2H), 4.41 (br s, 1H), 3.92 (br s, 1H), 3.79 (d, 1H), 3.42 (dd, 1H), 3.27 (dd, 1H), 3.15 (s, 3H), 3.05 (d, 1H), 1.48 (s, 9H), 1.27 (d, 3H), 1.02 (d, 3H). LCMS (Method C): $R_T$=1.78 min, m/z=612 [M+H]$^+$.

Step 4: 3-(2,6-dichlorophenyl)-7-((4-((2S,5R)-2,5-dimethylpiperazin-1-yl)phenyl)amino)-1-methyl-2,3-dihydropyrimido[4,5-d]pyrimidin-4(1H)-one (2R,5S)-tert-Butyl 4-(4-((6-(2,6-dichlorophenyl)-8-methyl-5-oxo-5,6,7,8-tetrahydropyrimido[4,5-d]pyrimidin-2-yl)amino)phenyl)-2,5-dimethylpiperazine-1-carboxylate (133 mg, 0.217 mmol) was deprotected following the procedure for Example 31 to give the title compound as a pale yellow solid (79 mg, 71%). $^1$H NMR (400 MHz, DMSO-d$_6$): δ 9.80 (br s, 1H), 8.47 (s, 1H), 7.68 (d, 2H), 7.64 (d, 2H), 7.48 (dd, 1H), 7.03 (d, 2H), 4.96 (s, 2H), 3.10 (s, 3H), 2.80-3.00 (m, 4H), 2.45 (dd, 1H), 2.33 (dd, 1H), 0.95 (d, 3H), 0.80 (d, 3H). LCMS (Method C): $R_T$=0.80 min, m/z=512 [M+H]$^+$.

Example 81: 3-(2,6-dichlorophenyl)-7-((4-((2R,5S)-2,5-dimethylpiperazin-1-yl)-3-fluorophenyl)amino)-1-methyl-2,3-dihydropyrimido[4,5-d]pyrimidin-4(1H)-one

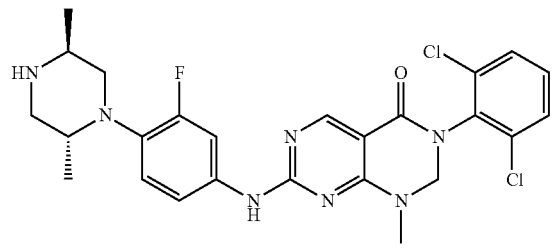 [SMILES: C[C@@H]1CN[C@@H](C)CN1c1ccc(Nc2ncc3c(n2)N(C)CN(c2c(Cl)cccc2Cl)C3=O)cc1F]

Step 1: (2S,5R)-tert-butyl 4-(2-fluoro-4-nitrophenyl)-2,5-dimethylpiperazine-1-carboxylate A suspension of 1,2-difluoro-4-nitrobenzene (371 mg, 2.333 mmol), (2S,5R)-tert-butyl 2,5-dimethylpiperazine-1-carboxylate (500 mg, 2.333 mmol) and potassium carbonate (484 mg, 3.50 mmol) in anhydrous acetonitrile (3 mL) was heated to 100° C. under a nitrogen atmosphere for 8 days. The reaction mixture was allowed to cool to room temperature, diluted with water (20 mL) and extracted into ethyl acetate (3×10 mL). The combined organic phases were dried over $Na_2SO_4$, filtered and concentrated to dryness under reduced pressure. The residue was purified by Biotage chromatography (silica 100 g cartridge, cyclohexane:ethyl acetate, gradient elution from 95:5 to 60:40) to give the title compound as a yellow oil (800 mg, 97%). $^1$H NMR (400 MHz, CDCl$_3$): δ 7.97 (dd, 1H), 7.90 (dd, 1H), 6.84 (t, 1H), 4.42 (br s, 1H), 4.00 (br s, 1H), 3.76 (d, 1H), 3.54 (dd, 1H), 3.46 (d, 1H), 3.16 (d, 1H), 1.49 (s, 9H), 1.28 (d, 3H), 1.15 (d, 3H). LCMS (Method C): $R_T$=1.92 min, m/z=376 [M+Na]$^+$.

Step 2: (2S,5R)-tert-butyl 4-(4-amino-2-fluorophenyl)-2,5-dimethylpiperazine-1-carboxylate A solution of (2S,5R)-tert-butyl 4-(2-fluoro-4-nitrophenyl)-2,5-dimethylpiperazine-1-carboxylate (800 mg, 2.264 mmol) in methanol (80 mL) was hydrogenated by H-Cube (10% Pd/C cartridge, Full H₂, 50° C., 1 mL/min). The reaction mixture was concentrated to dryness under reduced pressure to give the title compound as a grey solid (623 mg, 85%). ¹H NMR (300 MHz, CDCl₃) δ 6.61-6.71 (m, 1H), 6.34-6.45 (m, 2H), 4.37 (quin, 1H), 3.69 (d, 1H), 3.34-3.61 (m, 5H), 2.58 (dd, 1H), 1.47 (s, 9H), 1.29 (d, 3H), 0.91 (d, 3H). LCMS (Method C): R$_T$=1.37 min, m/z=324 [M+H]⁺.

Step 3: (2S,5R)-tert-butyl 4-(4-((6-(2,6-dichlorophenyl)-8-methyl-5-oxo-5,6,7,8-tetrahydropyrimido[4,5-d]pyrimidin-2-yl)amino)-2-fluorophenyl)-2,5-dimethylpiperazine-1-carboxylate 3-(2,6-Dichlorophenyl)-1-methyl-7-(methylthio)-2,3-dihydropyrimido[4,5-d]pyrimidin-4(1H)-one (100 mg, 0.283 mmol) was reacted with (2S,5R)-tert-butyl 4-(4-amino-2-fluorophenyl)-2,5-dimethylpiperazine-1-carboxylate (91 mg, 0.283 mmol) following the procedure for Example 31 to give the title compound as a yellow solid (86 mg, 48%). ¹H NMR (400 MHz, CDCl₃) δ 8.72 (s, 1H), 7.93 (br s, 1H), 7.65 (d, 1H), 7.43 (d, 2H), 7.28 (dd, 1H), 7.09 (dd, 1H), 6.80 (t, 1H), 4.89 (s, 2H), 4.40 (br s, 1H), 3.65-3.79 (m, 2H), 3.47 (ddd, 2H), 3.18 (s, 3H), 2.73 (d, 1H), 1.48 (s, 9H), 1.30 (d, 3H), 0.98 (d, 3H). LCMS (Method C): R$_T$=1.98 min, m/z=630 [M+H]⁺.

Step 4: 3-(2,6-dichlorophenyl)-7-((4-((2R,5S)-2,5-dimethylpiperazin-1-yl)-3-fluorophenyl)amino)-1-methyl-2,3-dihydropyrimido[4,5-d]pyrimidin-4(1H)-one (2S,5R)-tert-Butyl 4-(4-((6-(2,6-dichlorophenyl)-8-methyl-5-oxo-5,6,7,8-tetrahydropyrimido[4,5-d]pyrimidin-2-yl)amino)-2-fluorophenyl)-2,5-dimethylpiperazine-1-carboxylate (105 mg, 0.167 mmol) was deprotected following the procedure for Example 31 to give the title compound as an off-white solid (31 mg, 35%). ¹H NMR (400 MHz, DMSO-d₆): δ 10.01 (br s, 1H), 8.50 (s, 1H), 7.75 (dd, 1H), 7.65 (d, 2H), 7.43-7.53 (m, 2H), 7.18 (t, 1H), 4.99 (s, 2H), 3.12 (s, 3H), 2.80-2.99 (m, 4H), 2.46 (dd, 1H), 2.36 (t, 1H), 0.94 (d, 3H), 0.78 (d, 3H). LCMS (Method C): R$_T$=0.90 min, m/z=530 [M+H]⁺.

Example 82: 7-((4-((1S,4S)-2,5-diazabicyclo[2.2.1]heptan-2-yl)-3-methoxyphenyl)amino)-3-(2,6-dichlorophenyl)-1-methyl-2,3-dihydropyrimido[4,5-d]pyrimidin-4(1H)-one

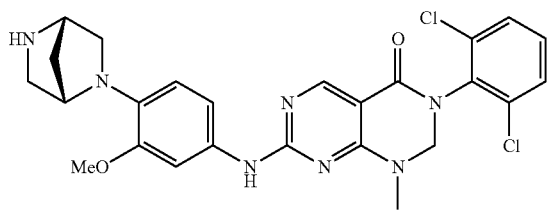 [SMILES: COc1cc(Nc2ncc3c(n2)N(C)CN(c2c(Cl)cccc2Cl)C3=O)ccc1N1C[C@@H]2C[C@H]1CN2]

Step 1: (1S,4S)-tert-butyl 5-(2-methoxy-4-nitrophenyl)-2,5-diazabicyclo[2.2.1]heptane-2-carboxylate A suspension of 1-fluoro-2-methoxy-4-nitrobenzene (2.59 g, 15.13 mmol), (1S,4S)-tert-butyl 2,5-diazabicyclo[2.2.1]heptane-2-carboxylate (3.00 g, 15.13 mmol) and potassium carbonate (3.14 g, 22.7 mmol) in anhydrous DMF (40 mL) was heated to 50° C. under a nitrogen atmosphere for 24 hours. The reaction mixture was allowed to cool to room temperature, diluted with water (120 mL) and stirred at room temperature for 15 minutes. The precipitated solid was isolated by filtration and dried under vacuum to give the title compound as a yellow solid (4.49 g, 85%). LCMS (Method C): R$_T$=1.44 min, m/z=294 [M–ᵗBu+H]⁺.

Step 2: (1S,4S)-tert-butyl 5-(4-amino-2-methoxyphenyl)-2,5-diazabicyclo[2.2.1]heptane-2-carboxylate A suspension of tert-butyl 4-(2-methoxy-4-nitrophenyl)piperazine-1-carboxylate (3.15 g, 9.34 mmol), iron powder (3.13 g, 56.0 mmol) and ammonium chloride (4.50 g, 84 mmol) in a mixture of methanol (38.6 mL) and water (8.12 mL) was heated to reflux under a nitrogen atmosphere for 1 hour. The reaction mixture was allowed to cool to room temperature and filtered through Celite®. The filtrates were diluted with ethyl acetate and washed with saturated sodium bicarbonate (×3). The combined organics were dried (Na₂SO₄) and concentrated to dryness under reduced pressure. The residue was diluted with ethyl acetate and the solid collected by filtration to give the title compound as a pink solid (2.78 g, 68%). LCMS (Method C): R$_T$=0.71 min, m/z=320 [M+H]⁺.

Step 3: (1S,4S)-tert-butyl 5-(4-((6-(2,6-dichlorophenyl)-8-methyl-5-oxo-5,6,7,8-tetrahydropyrimido[4,5-d]pyrimidin-2-yl)amino)-2-methoxyphenyl)-2,5-diazabicyclo[2.2.1]heptane-2-carboxylate 3-(2,6-Dichlorophenyl)-1-methyl-7-(methylthio)-2,3-dihydropyrimido[4,5-d]pyrimidin-4(1H)-one (100 mg, 0.283 mmol) was reacted with (1S,4S)-tert-butyl 5-(4-amino-2-methoxyphenyl)-2,5-diazabicyclo[2.2.1]heptane-2-carboxylate (90 mg, 0.283 mmol) following the procedure for Example 31 to give the title compound as a yellow solid (88 mg, 50%). ¹H NMR (400 MHz, CDCl₃): δ 8.71 (s, 1H), 7.75 (br s, 1H), 7.43 (d, 2H), 7.23-7.35 (m, 2H), 7.00 (dd, 1H), 6.61 (d, 1H), 4.87 (s, 2H), 4.48 (d, 1H), 4.40 (s, 1H), 3.83 (s, 3H), 3.71 (dd, 1H), 3.61 (dd, 1H), 3.30 (t, 1H), 3.26 (dd, 1H), 3.17 (s, 3H), 1.96 (d, 1H), 1.84 (dd, 1H), 1.43 (d, 9H). LCMS (Method C): R$_T$=1.53 min, m/z=626 [M+H]⁺.

Step 4: 7-((4-((1S,4S)-2,5-diazabicyclo[2.2.1]heptan-2-yl)-3-methoxyphenyl)amino)-3-(2,6-dichlorophenyl)-1-methyl-2,3-dihydropyrimido[4,5-d]pyrimidin-4(1H)-one (1S,4S)-tert-Butyl 5-(4-((6-(2,6-dichlorophenyl)-8-methyl-5-oxo-5,6,7,8-tetrahydropyrimido[4,5-d]pyrimidin-2-yl)amino)-2-methoxyphenyl)-2,5-diazabicyclo[2.2.1]heptane-2-carboxylate (88 mg, 0.140 mmol) was deprotected following the procedure for Example 31 to give the title compound as a yellow solid (36 mg, 49%). ¹H NMR (400 MHz, DMSO-d₆): δ 9.67 (br s, 1H), 8.44 (s, 1H), 7.64 (d, 2H), 7.57 (br s, 1H), 7.48 (dd, 1H), 7.11 (dd, 1H), 6.55 (d, 1H), 4.96 (s, 2H), 4.20 (s, 1H), 3.73 (s, 3H), 3.59 (dd, 1H), 3.48 (s, 1H), 3.11 (s, 3H), 2.99 (d, 1H), 2.88 (d, 1H), 2.81 (dd, 1H), 1.70 (d, 1H), 1.55 (d, 1H). LCMS (Method C): R$_T$=0.77 min, m/z=526 [M+H]⁺.

Example 83: 3-(2,6-dichlorophenyl)-7-((4-((3R,5S)-3,5-dimethylpiperazin-1-yl)phenyl)amino)-1-methyl-2,3-dihydropyrimido[4,5-d]pyrimidin-4(1H)-one

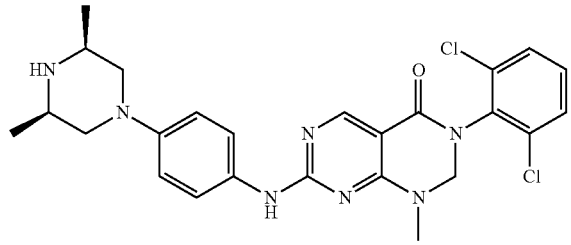 [SMILES: C[C@@H]1CN(c2ccc(Nc3ncc4c(n3)N(C)CN(c3c(Cl)cccc3Cl)C4=O)cc2)C[C@H](C)N1]

Step 1:
(3S,5R)-3,5-dimethyl-1-(4-nitrophenyl)piperazine

To a stirred suspension of 1-fluoro-4-nitrobenzene (562 mg, 3.98 mmol) and potassium carbonate (688 mg, 4.98 mmol) in anhydrous DMSO (2 mL) was added (2S,6R)-2,6-dimethylpiperazine (500 mg, 4.38 mmol) and the mixture heated at 100° C. for 16 h. After cooling the mixture was suspended in water (40 mL) and filtered under vacuum to afford the title compound (889 mg, 95%). $^1$H NMR (500 MHz, DMSO-$d_6$): δ 8.03 (d, 2H), 7.03 (d, 2H), 3.88 (dd, 2H), 2.75-2.79 (m, 2H), 2.37-2.42 (m, 2H), 2.28 (br s, 1H), 1.03 (d, 6H). LCMS (Method C): $R_T$=0.51 min, m/z=236 [M+H]$^+$.

Step 2:
4-((3S,5R)-3,5-dimethylpiperazin-1-yl)aniline

A stirred solution of (3S,5R)-3,5-dimethyl-1-(4-nitrophenyl)piperazine (888.8 mg, 3.78 mmol) in ethanol (15 mL) was heated to 50° C. Pd/C (201 mg, 0.189 mmol) was added followed by portionwise addition of ammonium formate (1191 mg, 18.89 mmol) and the suspension stirred for 10 min. The suspension was filtered washing with fresh ethanol (6 mL). The ethanol was removed in vacuo. The residue was partitioned between dichloromethane (15 mL) and water (10 mL). The aqueous was separated and extracted with dichloromethane (2×5 mL). The combined dichloromethane fractions were dried (phase separator) and reduced in vacuo to afford the title compound (111 mg, 14%). $^1$H NMR (500 MHz, DMSO-$d_6$): δ 6.66 (d, 2H), 6.47 (d, 2H), 4.49 (br s, 2H), 3.18 (dd, 2H), 2.81-2.84 (m, 2H), 1.82-2.10 (m, 1H), 1.96 (t, 2H), 0.98 (d, 6H). LCMS (Method C): $R_T$=0.12 min, m/z=206 [M+H]$^+$.

Step 3: 3-(2,6-dichlorophenyl)-7-((4-((3R,5S)-3,5-dimethylpiperazin-1-yl)phenyl)amino)-1-methyl-2,3-dihydropyrimido[4,5-d]pyrimidin-4(1H)-one 3-(2,6-Dichlorophenyl)-1-methyl-7-(methylthio)-2,3-dihydropyrimido[4,5-d]pyrimidin-4(1H)-one (100 mg, 0.283 mmol) was reacted with 4-((3R,5S)-3,5-dimethylpiperazin-1-yl)aniline (58 mg, 0.283 mmol) following the procedure for Example 31 to give the title compound as a white solid (44 mg, 30%). $^1$H NMR (400 MHz, DMSO-$d_6$): δ 9.68 (br s, 1H), 8.44 (s, 1H), 7.64 (d, 2H), 7.60 (br d, 2H), 7.47 (d, 1H), 6.88 (d, 2H), 4.95 (s, 2H), 3.45 (dd, 2H), 3.08 (s, 3H), 2.77-2.90 (m, 2H), 2.00-2.13 (m, 3H), 1.01 (d, 6H). LCMS (Method C): $R_T$=0.76 min, m/z=512 [M+H]$^+$.

Example 84: 3-(2,6-dichlorophenyl)-7-((3-methoxy-4-((1S,4S)-5-methyl-2,5-diazabicyclo[2.2.1]heptan-2-yl)phenyl)amino)-1-methyl-2,3-dihydropyrimido[4,5-d]pyrimidin-4(1H)-one

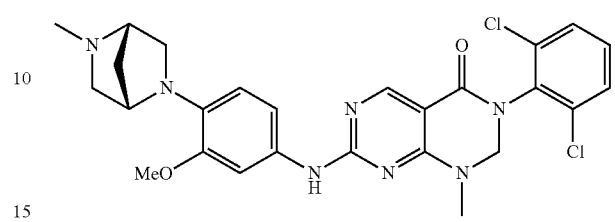

7-((4-((1S,4S)-2,5-diazabicyclo[2.2.1]heptan-2-yl)-3-methoxyphenyl)amino)-3-(2,6-dichlorophenyl)-1-methyl-2,3-dihydropyrimido[4,5-d]pyrimidin-4(1H)-one (21 mg, 0.040 mmol) was methylated following the procedure for Example 35 to give the title compound as a yellow solid (9 mg, 42%). $^1$H NMR (400 MHz, DMSO-$d_6$): δ 9.68 (br s, 1H), 8.44 (s, 1H), 7.64 (d, 2H), 7.58 (br s, 1H), 7.48 (dd, 1H), 7.12 (dd, 1H), 6.55 (d, 1H), 4.96 (s, 2H), 4.17 (s, 1H), 3.74 (s, 3H), 3.41 (dd, 1H), 3.28 (s, 1H), 3.05-3.17 (m, 4H), 2.71 (dd, 1H), 2.63 (d, 1H), 2.24 (s, 3H), 1.76 (d, 1H), 1.66 (d, 1H). LCMS (Method C): $R_T$=0.78 min, m/z=540 [M+H]$^+$.

Example 85: (R)-1-cyclopropyl-3-(2,6-dichlorophenyl)-7-((4-(3-methylpiperazin-1-yl)phenyl)amino)-2,3-dihydropyrimido[4,5-d]pyrimidin-4(1H)-one

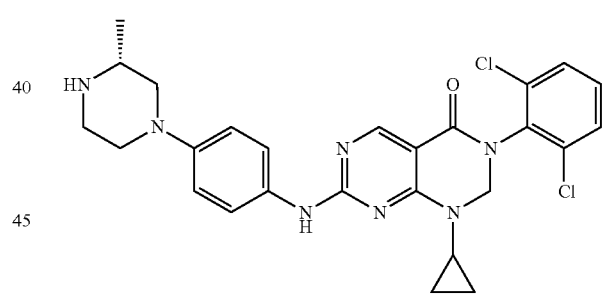

Step 1: 4-(cyclopropylamino)-N-(2,6-dichlorophenyl)-2-(methylthio)pyrimidine-5-carboxamide To a suspension of 4-chloro-N-(2,6-dichlorophenyl)-2-(methylthio)pyrimidine-5-carboxamide (2 g, 5.74 mmol) in tetrahydrofuran (20 mL) at 0° C. was charged Hunig's Base (2.004 mL, 11.47 mmol) followed by cyclopropanamine (0.437 mL, 6.31 mmol). The reaction was stirred at this temp for 15 min and at room temperature for 30 min. The reaction mixture was diluted with water and ethyl acetate and the layers separated, the aqueous was then extracted twice more with ethyl acetate and the combined organic extracts washed with brine, dried (anhydrous magnesium sulfate), filtered and concentrated in vacuo to afford the title compound (2.2 g) as a white solid. LCMS (Method C) $R_T$=1.65 min, m/z=369 [M+H]$^+$.

Step 2: 1-cyclopropyl-3-(2,6-dichlorophenyl)-7-(methylthio)-2,3-dihydropyrimido[4,5-d]pyrimidin-4(1H)-one 4-(cyclopropylamino)-N-(2,6-dichlorophenyl)-2-(methylthio)pyrimidine-5-carboxamide (2.2 g, 5.96 mmol) was suspended in anhydrous acetonitrile (25 mL) in a Schlenk tube. Cesium carbonate (11.65 g, 35.7 mmol) was added, followed by dibromomethane (1.254 mL, 17.87 mmol). The tube was sealed and the mixture was heated to 80° C. while stirring for 40 h. The solvent was removed in vacuo. The residue was partitioned between water (50 mL) and dichloromethane (100 mL). The aqueous was separated and extracted with dichloromethane (2×25 mL). The combined dichloromethane fractions were dried (phase separator) and reduced in vacuo. The resulting residue was purified by silica gel chromatography (gradient 0-40% ethyl acetate in cyclohexane) to afford the title compound (1.22 g, 53.7%). LCMS (Method C): $R_T$=1.63 min, m/z=381 [M+H]$^+$.

Step 3: (R)-1-cyclopropyl-3-(2,6-dichlorophenyl)-7-((4-(3-methylpiperazin-1-yl)phenyl)amino)-2,3-dihydropyrimido[4,5-d]pyrimidin-4(1H)-one 1-cyclopropyl-3-(2,6-dichlorophenyl)-7-(methylthio)-2,3-dihydropyrimido[4,5-d]pyrimidin-4(1H)-one (100 mg, 0.262 mmol) was reacted with (R)-tert-butyl 4-(4-aminophenyl)-2-methylpiperazine-1-carboxylate (76 mg, 0.262 mmol) following the procedure for Example 31 to give the title compound (47.2 mg, 47.5%). $^1$H NMR (400 MHz, MeOH-d$_4$): δ 8.56 (s, 1H), 7.64-7.90 (m, 2H), 7.57 (d, 2H), 7.43 (dd, 1H), 7.00 (d, 2H), 4.99 (s, 2H), 3.52 (t, 2H), 3.09 (dt, 1H), 2.91-3.04 (m, 2H), 2.63-2.77 (m, 2H), 2.34 (t, 1H), 1.17 (d, 3H), 1.02 (q, 2H), 0.83-0.89 (m, 2H). LCMS (Method C): $R_T$=0.88 min, m/z=524 [M+H]$^+$.

Example 86: 3-(2,6-dichlorophenyl)-7-((3-(hydroxymethyl)-4-(8-methyl-3,8-diazabicyclo[3.2.1]octan-3-yl)phenyl)amino)-1-methyl-2,3-dihydropyrimido[4,5-d]pyrimidin-4(1H)-one

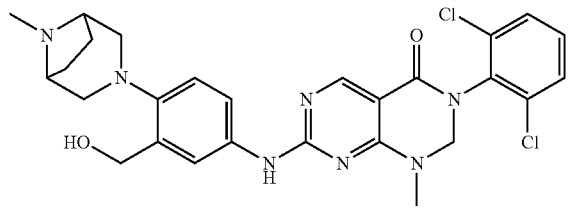 [SMILES: CN1CN(c2c(Cl)cccc2Cl)C(=O)c2cnc(Nc3ccc(N4CC5CCC(C4)N5C)c(CO)c3)nc21]

Step 1: tert-butyl 3-(2-formyl-4-nitrophenyl)-3,8-diazabicyclo[3.2.1]octane-8-carboxylate A suspension of 2-fluoro-5-nitrobenzaldehyde (0.358 g, 2.120 mmol) tert-butyl 3,8-diazabicyclo[3.2.1]octane-8-carboxylate (0.45 g, 2.120 mmol) and potassium carbonate (0.439 g, 3.18 mmol) in anhydrous DMF (2 mL) was heated to 50° C. under a nitrogen atmosphere for 16 h. The reaction mixture was allowed to cool to room temperature, partitioned between water (50 mL) and ethyl acetate (50 mL). The ethyl acetate was separated and washed with water (3×20 mL), dried (anhydrous sodium sulfate), filtered and reduced in vacuo. The residue was purified by flash chromatography (0-100% ethyl acetate in cyclohexane) to afford the title compound (360 mg, 0.996 mmol). LCMS (Method C): $R_T$=1.69 min, m/z=384 [M+Na]$^+$.

Step 2: tert-butyl 3-(2-(hydroxymethyl)-4-nitrophenyl)-3,8-diazabicyclo[3.2.1]octane-8-carboxylate To a stirring solution of tert-butyl 3-(2-formyl-4-nitrophenyl)-3,8-diazabicyclo[3.2.1]octane-8-carboxylate (360 mg, 0.996 mmol) in anhydrous tetrahydrofuran (4 mL) at 0° C. was added sodium borohydride (41.5 mg, 1.096 mmol). Stirring was continued for 3 h. The mixture was reduced in vacuo. The residue was partitioned between water (20 mL) and dichloromethane (10 mL). The aqueous was separated and extracted with dichloromethane (3×5 mL). The combined dichloromethane fractions were dried (phase separator), filtered and reduced in vacuo. The resulting residue was purified by silica gel chromatography (gradient 0-50% ethyl acetate in cyclohexane) to afford the title compound (343 mg, 95%). $^1$H NMR (400 MHz, CDCl$_3$): δ 8.34 (d, 1H), 8.12 (dd, 1H), 7.13 (d, 1H), 4.82 (d, 2H), 4.20-4.47 (m, 2H), 2.90-3.22 (m, 4H), 2.60 (t, 1H), 1.98-2.04 (m, 4H), 1.49 (s, 9H). LCMS (Method C): $R_T$=1.56 min, m/z=364 [M+H]$^+$.

Step 3: tert-butyl 3-(4-amino-2-(hydroxymethyl)phenyl)-3,8-diazabicyclo[3.2.1]octane-8-carboxylate A solution of tert-butyl 3-(2-(hydroxymethyl)-4-nitrophenyl)-3,8-diazabicyclo[3.2.1]octane-8-carboxylate (335 mg, 0.922 mmol) in methanol (10 mL) and tetrahydrofuran (2.000 mL) was passed through an H-Cube apparatus fitted with a 10% Pd—C cartridge under the following settings [1.0 ml/min flow, 40° C., Full H$_2$ mode)]. The solvent was removed in vacuo to afford the title compound which was used without further purification (295.6 mg, 96%). $^1$H NMR (400 MHz, DMSO-d$_6$): δ 6.79 (d, 1H), 6.67 (d, 1H), 6.38 (dd, 1H), 4.86 (t, 1H), 4.81 (br s, 2H), 4.04-4.13 (m, 2H), 4.53 (d, 2H), 2.75 (d, 2H), 2.59 (d, 2H), 1.93 (d, 2H), 1.72-1.84 (m, 2H), 1.43 (s, 9H). LCMS (Method C): $R_T$=0.84 min, m/z=334 [M+H]$^+$.

Step 4: 7-((4-(3,8-diazabicyclo[3.2.1]octan-3-yl)-3-(hydroxymethyl)phenyl)amino)-3-(2,6-dichlorophenyl)-1-methyl-2,3-dihydropyrimido[4,5-d]pyrimidin-4(1H)-one 3-(2,6-dichlorophenyl)-1-methyl-7-(methylthio)-2,3-dihydropyrimido[4,5-d]pyrimidin-4(1H)-one (100 mg, 0.281 mmol) was reacted with tert-butyl 3-(4-amino-2-(hydroxymethyl)phenyl)-3,8-diazabicyclo[3.2.1]octane-8-carboxylate (94 mg, 0.281 mmol) following the procedure for Example 31 to give the title compound (81.3 mg, 88%). $^1$H NMR (400 MHz, CDCl$_3$): δ 8.72 (s, 1H), 7.56-7.60 (m, 1H), 7.52 (dd, 1H), 7.44 (d, 2H), 7.28 (dd, 1H), 7.25 (d, 1H), 4.89 (s, 2H), 4.80 (s, 2H), 3.55-3.60 (m, 2H), 3.19 (s, 3H), 3.02 (d, 2H), 2.86 (dd, 2H), 1.99-2.08 (m, 2H), 1.83-1.89 (m, 2H). LCMS (Method C) $R_T$=0.73 min, m/z=540 [M+H]$^+$.

Step 5: 3-(2,6-dichlorophenyl)-7-((3-(hydroxymethyl)-4-(8-methyl-3,8-diazabicyclo[3.2.1]octan-3-yl)phenyl)amino)-1-methyl-2,3-dihydropyrimido[4,5-d]pyrimidin-4(1H)-one 7-((4-(3,8-diazabicyclo[3.2.1]octan-3-yl)-3-(hydroxymethyl)phenyl)amino)-3-(2,6-dichlorophenyl)-1-methyl-2,3-dihydropyrimido[4,5-d]pyrimidin-4(1H)-one (77 mg, 0.142 mmol) was methylated following the procedure in Example 35 to give the title compound (47.1 mg, 59.6%). $^1$H NMR (400 MHz, DMSO-d$_6$): δ 9.80 (br s, 1H), 8.46 (s, 1H), 8.00 (br s, 1H), 7.64 (d, 2H), 7.53 (dd, 1H), 7.48 (dd, 1H), 7.04 (d, 1H), 5.05 (br s, 1H), 4.96 (s, 2H), 4.60 (s, 2H), 3.12 (s, 3H), 3.04-3.10 (m, 2H), 2.88 (d, 2H), 2.62 (d, 2H), 2.20 (s, 3H), 1.88-1.98 (m, 2H), 1.80-1.98 (m, 2H). LCMS (Method C): R$_T$=0.72 min, m/z=554 [M+H]$^+$.

Example 87: 3-(2,6-dichlorophenyl)-1-methyl-7-((4-(piperidin-4-yloxy)phenyl)amino)-2,3-dihydropyrimido[4,5-d]pyrimidin-4(1H)-one

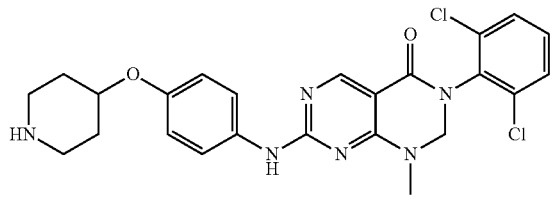

Step 1: tert-butyl 4-(4-nitrophenoxy)piperidine-1-carboxylate

To a suspension of tert-butyl 4-hydroxypiperidine-1-carboxylate (3.00 g, 14.91 mmol) and 1-fluoro-4-nitrobenzene (3.89 g, 27.6 mmol) in aqueous potassium hydroxide (25% solution by weight) (21.84 mL, 97 mmol) was added tetrabutylammonium bromide (0.625 g, 1.938 mmol) and the resulting mixture stirred at 35° C. overnight. The reaction mixture was allowed to cool to room temperature and the precipitated solid isolated by filtration, washed with water (2×20 mL) and sucked dry. The residue was purified by Biotage chromatography (silica 50 g cartridge, cyclohexane:ethyl acetate, gradient elution from 100:0 to 80:20) to give the title compound as an off-white solid (611 mg, 13%). $^1$H NMR (300 MHz, CDCl$_3$): δ 8.20 (dt, 2H), 6.95 (dt, 2H), (sep, 1H), 3.70 (ddd, 2H), 3.38 (ddd, 2H), 1.90-2.04 (m, 2H), 1.72-1.86 (m, 2H), 1.47 (s, 9H). LCMS (Method C): R$_T$=1.78 min, m/z=345 [M+Na]$^+$.

Step 2: tert-butyl 4-(4-aminophenoxy)piperidine-1-carboxylate

A solution of tert-butyl 4-(4-nitrophenoxy)piperidine-1-carboxylate (611 mg, 1.895 mmol) in methanol (60 mL) was hydrogenated by H-Cube (10% Pd/C cartridge, Full H$_2$, 50° C., 1 mL/min). The reaction mixture was concentrated to dryness under reduced pressure to give the title compound as a pale pink solid (517 mg, 93%). $^1$H NMR (300 MHz, CDCl$_3$): δ 6.76 (dt, 2H), 6.63 (dt, 2H), 4.26 (sep, 1H), 3.71 (ddd, 2H), 3.45 (br s, 2H), 3.26 (ddd, 2H), 1.80-1.95 (m, 2H), 1.61-1.78 (m, 2H), 1.46 (s, 9H). LCMS (Method C): R$_T$=0.85 min, m/z=237 [M-$^t$Bu+H]$^+$.

Step 3: tert-butyl 4-(4-((6-(2,6-dichlorophenyl)-8-methyl-5-oxo-5,6,7,8-tetrahydropyrimido[4,5-d]pyrimidin-2-yl)amino)phenoxy)piperidine-1-carboxylate 3-(2,6-dichlorophenyl)-1-methyl-7-(methylthio)-2,3-dihydropyrimido[4,5-d]pyrimidin-4(1H)-one (200 mg, 0.563 mmol) was reacted with tert-butyl 4-(4-aminophenoxy)piperidine-1-carboxylate (165 mg, 0.563 mmol) following the procedure for Example 31 to give the title compound as an off-white solid (190 mg, 56%). $^1$H NMR (300 MHz, CDCl$_3$): δ 8.71 (s, 1H), 7.52 (d, 2H), 7.44 (d, 2H), 7.38 (br s, 1H), 7.28 (dd, 1H), 6.91 (d, 2H), 4.88 (s, 2H), 4.43 (sep, 1H), 3.71 (ddd, 2H), 3.32 (ddd, 2H), 3.16 (s, 3H), 1.83-1.99 (m, 2H), 1.65-1.83 (m, 2H), 1.47 (s, 9H). LCMS (Method C): R$_T$=1.75 min, m/z=599 [M+H]$^+$.

Step 4: 3-(2,6-dichlorophenyl)-1-methyl-7-((4-(piperidin-4-yloxy)phenyl)amino)-2,3-dihydropyrimido[4,5-d]pyrimidin-4(1H)-one tert-butyl 4-(4-((6-(2,6-dichlorophenyl)-8-methyl-5-oxo-5,6,7,8-tetrahydropyrimido[4,5-d]pyrimidin-2-yl)amino)phenoxy)piperidine-1-carboxylate (150 mg, 0.250 mmol) was deprotected following the procedure for Example 31 to give the title compound as an off-white solid (123 mg, 98%). $^1$H NMR (400 MHz, DMSO-d$_6$): δ 9.74 (br s, 1H), 8.45 (s, 1H), 7.64 (d, 4H), 7.48 (dd, 1H), 6.90 (d, 2H), 4.95 (s, 2H), 4.31 (tt, 1H), 3.09 (s, 3H), 2.94 (dt, 2H), 2.55 (ddd, 2H), 1.84-1.95 (m, 2H), 1.36-1.49 (m, 2H). LCMS (Method C): R$_T$=0.76 min, m/z=499 [M+H]$^+$.

Example 88: 3-(2,6-dichlorophenyl)-1-methyl-7-((4-(8-methyl-3,8-diazabicyclo[3.2.1]octan-3-yl)phenyl)amino)-2,3-dihydropyrimido[4,5-d]pyrimidin-4(1H)-one

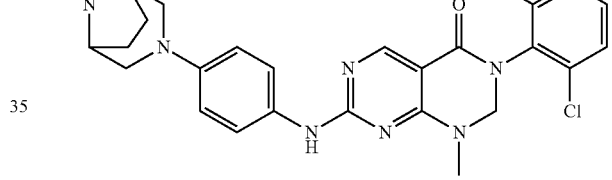

7-((4-(3,8-diazabicyclo[3.2.1]octan-3-yl)phenyl)amino)-3-(2,6-dichlorophenyl)-1-methyl-2,3-dihydropyrimido[4,5-d]pyrimidin-4(1H)-one (67 mg, 0.131 mmol) was reacted with formaldehyde (0.018 mL) following the procedure for example 35 to give the title compound (65 mg, 94%). $^1$H NMR (400 MHz, CDCl$_3$): δ 8.69 (s, 1H), 7.50-7.40 (m, 3H), 7.30 (d, 2H), 6.80 (d, 2H), 4.85 (s, 2H), 3.33 (m, 2H), 3.25 (m, 2H), 3.15 (s, 3H), 3.02 (m, 2H), 2.35 (s, 3H), 2.02 (m, 2H), 1.78 (m, 2H). LCMS (Method C): R$_T$=0.72 min, m/z=524 [M+H]$^+$.

Example 89: 3-(2-chloro-6-fluorophenyl)-7-((3-(hydroxymethyl)-4-(4-isopropylpiperazin-1-yl)phenyl)amino)-1-methyl-2,3-dihydropyrimido[4,5-d]pyrimidin-4(1H)-one

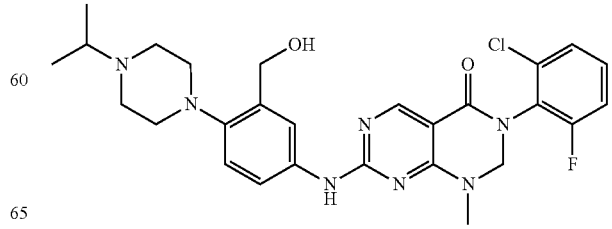

3-(2-chloro-6-fluorophenyl)-1-methyl-7-(methylthio)-2,3-dihydropyrimido[4,5-d]pyrimidin-4(1H)-one (150 mg, 0.443 mmol) was reacted with (5-amino-2-(4-isopropylpiperazin-1-yl)phenyl)methanol (105 mg, 0.422 mmol) following the procedure for Example 31 to give the title compound (109 mg, 48%). $^1$H NMR (400 MHz, CDCl$_3$): δ 8.72 (s, 1H), 7.51 (d, 2H), 7.40-7.3 (m, 3H), 7.23 (d, 1H), 7.15 (m, 1H), 4.94 (d, 1H), 4.85 (d, 1H), 4.81 (s, 2H), 3.19 (s, 3H), 3.03 (m, 4H), 2.73 (m, 4H), 2.78 (m, 1H), 1.11 (d, 3H). LCMS (Method C): R$_T$=0.709 min, m/z=540 [M+H]$^+$.

Example 90: 3-(2,6-dichlorophenyl)-1-methyl-7-((4-((1-methylpiperidin-4-yl)oxy)phenyl)amino)-2,3-dihydropyrimido[4,5-d]pyrimidin-4(1H)-one

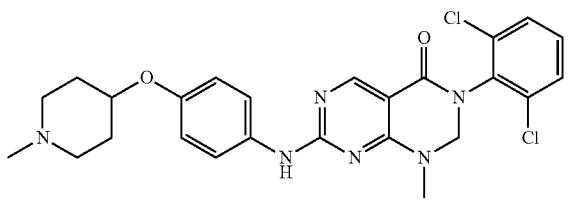

3-(2,6-dichlorophenyl)-1-methyl-7-((4-(piperidin-4-yloxy)phenyl)amino)-2,3-dihydropyrimido[4,5-d]pyrimidin-4(1H)-one (58 mg, 0.116 mmol) was methylated following the procedure for Example 35 to give the title compound as a white solid (54 mg, 91%). $^1$H NMR (400 MHz, DMSO-d$_6$) δ 9.74 (br s, 1H), 8.45 (s, 1H), 7.64 (d, 4H), 7.48 (dd, 1H), 6.91 (d, 2H), 4.95 (s, 2H), 4.28 (sep, 1H), 3.09 (s, 3H), 2.55-2.65 (m, 2H), 2.09-2.20 (m, 5H), 1.85-1.96 (m, 2H), 1.54-1.68 (m, 2H). LCMS (Method C): R$_T$=0.78 min, m/z=513 [M+H]$^+$.

Example 91: 3-(2,6-dichlorophenyl)-1-methyl-7-((3-((1-methylpiperidin-4-yl)amino)phenyl)amino)-2,3-dihydropyrimido[4,5-d]pyrimidin-4(1H)-one

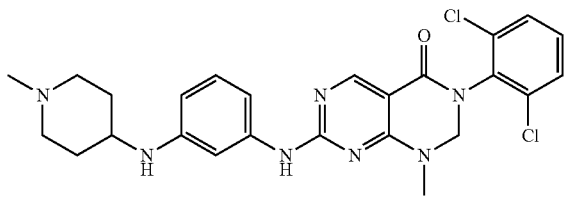 [SMILES: CN1CCC(Nc2cccc(Nc3ncc4c(n3)N(C)CN(c3c(Cl)cccc3Cl)C4=O)c2)CC1]

Step 1: tert-butyl 4-((3-nitrophenyl)amino)piperidine-1-carboxylate

To a stirring solution of 3-nitroaniline (2 g, 14.48 mmol) in anhydrous dichloromethane (40 mL) was added tert-butyl 4-oxopiperidine-1-carboxylate (5.77 g, 29.0 mmol) followed by sodium triacetoxyborohydride (9.21 g, 43.4 mmol). The mixture was stirred at room temperature for 40 h. The mixture was vigorously mixed with water (40 mL), then separated and dried (phase separator). The aqueous was washed with further dichloromethane (2×15 mL) which was separated and dried (phase separator). the combined dichloromethane fractions were reduced in vacuo. The resulting residue was purified by silica gel chromatography (gradient 10-15% ethyl acetate in cyclohexane) to afford the title compound (3.64 g, 78%). $^1$H NMR (400 MHz, CDCl$_3$): δ 7.51 (dd, 1H), 7.38 (t, 1H), 7.27 (t, 1H), 6.84 (dd, 1H), 3.97-4.17 (m, 2H), 3.90 (d, 1H), 3.44-3.53 (m, 1H), 2.95 (t, 2H), 2.05 (d, 2H), 1.47 (s, 9H), 1.31-1.41 (m, 2H). LCMS (Method C): R$_T$=1.74 min, m/z=266 [M-Butene]$^+$.

Step 2: tert-butyl 4-((3-aminophenyl)amino)piperidine-1-carboxylate

A solution of tert-butyl 4-((3-nitrophenyl)amino)piperidine-1-carboxylate (810 mg, 2.52 mmol) in methanol (50 mL) was passed through an H-Cube apparatus fitted with a 10% Pd—C cartridge under the following settings [1.0 ml/min flow, 40° C., Full H$_2$ mode)]. The solvent was removed in vacuo to afford the title compound which was used without further purification (735 mg, 100%). $^1$H NMR (400 MHz, DMSO-d$_6$): δ 6.70 (t, $^1$H), 5.84 (s, 1H), 5.81 (t, 2H), 5.05 (d, 1H), 4.68 (s, 2H), 3.86 (d, 2H), 3.54-3.60 (m, 1H), 3.37-3.47 (m, 1H), 3.22-3.31 (m, 1H), 1.85 (d, 2H), 1.41 (s, 9H), 1.21 (d, 2H). LCMS (Method C): R$_T$=0.82 min, m/z=292 [M+H]+.

Step 3: 3-(2,6-dichlorophenyl)-1-methyl-7-((3-(piperidin-4-ylamino)phenyl)amino)-2,3-dihydropyrimido[4,5-d]pyrimidin-4(1H)-one 3-(2,6-dichlorophenyl)-1-methyl-7-(methylthio)-2,3-dihydropyrimido[4,5-d]pyrimidin-4(1H)-one (100 mg, 0.281 mmol) was reacted with tert-butyl 4-((3-aminophenyl)amino)piperidine-1-carboxylate (82 mg, 0.281 mmol) following the procedure for Example 31 followed by purification by preparative HPLC to give the title compound (41.9 mg, 54.4%). LCMS (Method C): R$_T$=0.79 min, m/z=498 [M+H]$^+$.

Step 4: 3-(2,6-dichlorophenyl)-1-methyl-7-((3-((1-methylpiperidin-4-yl)amino)phenyl)amino)-2,3-dihydropyrimido[4,5-d]pyrimidin-4(1H)-one 3-(2,6-Dichlorophenyl)-1-methyl-7-((3-(piperidin-4-ylamino)phenyl)amino)-2,3-dihydropyrimido[4,5-d]pyrimidin-4(1H)-one (41.9 mg, 0.084 mmol) was methylated following the procedure in Example 35 to give the title compound (33.2 mg, 77%). $^1$H NMR (400 MHz, MeOH-d$_4$): δ 8.55 (s, 1H) 7.58 (d, 2H), 7.44 (dd, 1H), 7.05-7.13 (m, 2H), 6.99 (d, 1H), 6.43 (dd, 1H), 5.00 (s, 2H), 3.21 (s, 3H), 2.92 (d, 2H), 2.33 (s, 3H), 2.24 (t, 2H), 2.07 (d, 2H), 1.54 (q, 2H). LCMS (Method C): R$_T$=0.80 min, m/z=512 [M+H]$^+$.

Example 92: 3-(2-chloro-6-methylphenyl)-1-methyl-7-((4-(piperazin-1-yl)phenyl)amino)-2,3-dihydropyrimido[4,5-d]pyrimidin-4(1H)-one

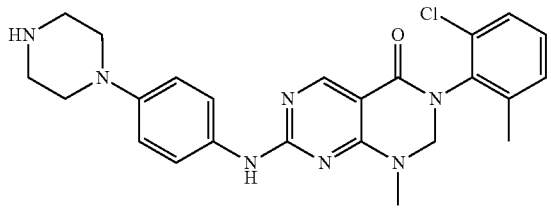 [SMILES: Cc1cccc(Cl)c1N1CN(C)c2nc(Nc3ccc(N4CCNCC4)cc3)ncc2C1=O]

Step 1: N-(2-chloro-6-methylphenyl)-4-(methylamino)-2-(methylthio)pyrimidine-5-carboxamide To a solution of 4-chloro-2-(methylthio)pyrimidine-5-carbonyl chloride (24.81 g, 111 mmol) in ethyl acetate (250 mL), Amberlyst A21 (7 g, 106 mmol) was added and the reaction mixture heated to 40° C. A solution of 2-chloro-6-methylaniline (15 g, 106 mmol) in ethyl acetate (250 mL) was then added and the reaction was stirred at 40° C. overnight. A white precipitate formed. It was filtered then taken up in dry THF (1 L) and heated at 60° C. for 15 min, then filtered again. The filtrate was concentrated in vacuo. The residue was slurried in DCM (200 mL) then filtered and dried. It was suspended in THF (1 L) and methylamine (2 M in THF, 50 mL) was added at 0° C. After stirring for 1 h at room temperature, the solution was filtered. The filtrate was concentrated in vacuo. The resulting oil was triturated in acetonitrile until formation of a white precipitate which was collected and dried at ambient temperature to give the title compound (3.5 g, 11%). LCMS (Method A): $R_T$=1.43 min, m/z=323 [M+H]$^+$ Step 2: 3-(2-chloro-6-methylphenyl)-1-methyl-7-(methylthio)-2,3-dihydropyrimido[4,5-d]pyrimidin-4(1H)-one A suspension of N-(2-chloro-6-methylphenyl)-4-(methylamino)-2-(methylthio)pyrimidine-5-carboxamide (3.5 g, 10.8 mmol), dibromomethane (2.3 mL, 32.5 mmol) and cesium carbonate (21 g, 65.1 mmol) in acetonitrile (120 mL) was heated at 80° C. in a sealed tube for 72 h. After cooling down, the reaction mixture was diluted with water and extracted three times with ethyl acetate. The combined organic extracts were washed with brine, dried (MgSO$_4$), filtered and concentrated in vacuo. The residue was purified by Biotage chromatography to afford the title compound (0.87 g, 24%). LCMS (Method A): $R_T$=1.48 min, m/z=335 [M+H]$^+$ Step 3: 3-(2-chloro-6-methylphenyl)-1-methyl-7-((4-(piperazin-1-yl)phenyl)amino)-2,3-dihydropyrimido[4,5-d]pyrimidin-4(1H)-one 3-(2-Chloro-6-methylphenyl)-1-methyl-7-(methylthio)-2,3-dihydropyrimido[4,5-d]pyrimidin-4(1H)-one (120 mg, 0.358 mmol) was reacted with tert-5 butyl 4-(4-amino-2-methoxyphenyl)piperazine-1-carboxylate (95 mg, 0.341 mmol) following the procedure for Example 31 to give the title compound (57 mg, 36%). $^1$H NMR (400 MHz, DMSO-d$_6$): δ 9.65 (s, 1H), 8.43 (s, 1H), 7.62 (m, 2H), 7.43 (m, 1H), 7.23 (m, 2H), 6.90 (d, 2H), 4.92 (d, 1H), 4.87 (d, 1H), 3.09 (s, 3H), 3.03 (m, 4H), 2.90 (m, 4H), 2.25 (s, 3H). LCMS (Method C): $R_T$=0.65 min, m/z=464 [M+H]$^+$.

Example 93: 3-(2-chloro-6-fluorophenyl)-7-((4-((2R,5S)-2,5-dimethylpiperazin-1-yl)phenyl)amino)-1-methyl-2,3-dihydropyrimido[4,5-d]pyrimidin-4(1H)-one

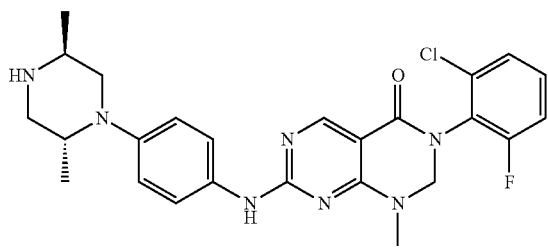

3-(2-Chloro-6-fluorophenyl)-1-methyl-7-(methylthio)-2,3-dihydropyrimido[4,5-d]pyrimidin-4(1H)-one (100 mg, 0.295 mmol) was reacted with (2S,5R)-tert-butyl 4-(4-aminophenyl)-2,5-dimethylpiperazine-1-carboxylate (86 mg, 0.281 mmol) following the procedure for Example 31 to give the title compound (42 mg, 36%). $^1$H NMR (400 MHz, CDCl$_3$): δ 8.72 (s, 1H), 7.57 (d, 2H), 7.32 (m, 2H), 7.13 (m, 3H), 4.93 (d, 1H), 4.85 (d, 1H), 3.18 (s, 3H), 3.09 (m, 3H), 2.94 (m, 1H), 2.71 (m, 1H), 2.47 (m, 1H), 1.07 (d, 3H), 0.91 (d, 3H). LCMS (Method C): $R_T$=0.74 min, m/z=496 [M+H]$^+$.

Example 94: (R)-3-(2-chlorophenyl)-1-methyl-7-((4-(3-methylpiperazin-1-yl)phenyl)amino)-2,3-dihydropyrimido[4,5-d]pyrimidin-4(1H)-one

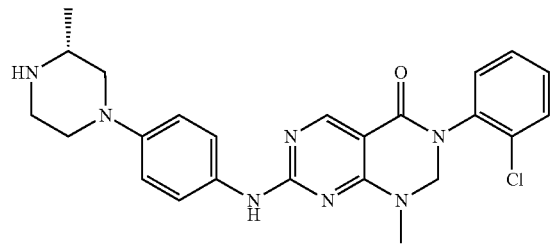 [SMILES: C[C@@H]1CN(c2ccc(Nc3ncc4c(n3)N(C)CN(c3ccccc3Cl)C4=O)cc2)CCN1]

Step 1: (R)-3-(2-chlorophenyl)-1-methyl-7-((4-(3-methylpiperazin-1-yl)phenyl)amino)-2,3-dihydropyrimido[4,5-d]pyrimidin-4(1H)-one 3-(2-chlorophenyl)-1-methyl-7-(methylthio)-2,3-dihydropyrimido[4,5-d]pyrimidin-4(1H)-one (200 mg, 0.623 mmol) was reacted with (R)-tert-butyl 4-(4-aminophenyl)-2-methylpiperazine-1-carboxylate (154 mg, 0.530 mmol) following the procedure for Example 31 to give the title compound (160 mg, 93%). $^1$H NMR (400 MHz, MeOH-d$_4$): δ 8.52 (s, 1H), 7.54-7.66 (m, 3H), 7.39-7.53 (m, 3H), 7.00 (d, 2H), 4.95-5.06 (m, 2H), 3.53 (t, 2H), 3.17 (s, 3H), 3.06-3.14 (m, 1H), 2.93-3.05 (m, 2H), 2.69 (td, 1H), 2.36 (dd, 1H), 1.17 (d, 3H). LCMS (Method C): $R_T$=0.63 min, m/z=464 [M+H]$^+$.

Example 95: 3-(2,6-dichlorophenyl)-1-methyl-7-((4-(1-methylpiperidin-4-yl)phenyl)amino)-2,3-dihydropyrimido[4,5-d]pyrimidin-4(1H)-one

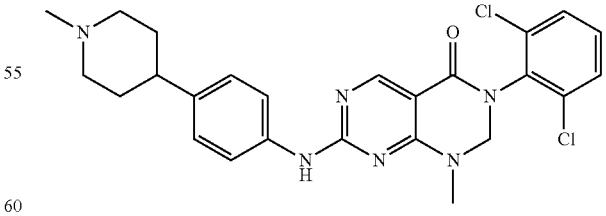

3-(2,6-Dichlorophenyl)-1-methyl-7-((4-(piperidin-4-yl)phenyl)amino)-2,3-dihydropyrimido[4,5-d]pyrimidin-4(1H)-one (54 mg, 0.112 mmol) was methylated following the procedure for Example 35 to give the title compound as an off-white solid (10 mg, 18%). $^1$H NMR (400 MHz, DMSO-d$_6$): δ 9.83 (br s, 1H), 8.47 (s, 1H), 7.71 (d, 2H), 7.65

(d, 2H), 7.48 (dd, 1H), 7.18 (d, 2H), 4.97 (s, 2H), 3.11 (s, 3H), 3.02 (d, 2H), 2.43-2.54 (m, 1H), 2.11-2.41 (m, 5H), 1.63-1.83 (m, 4H). LCMS (Method C): $R_T$=0.80 min, m/z=497 [M+H]$^+$.

Example 96: 3-(2,6-dichlorophenyl)-7-((4-(3,3-dimethylpiperazin-1-yl)phenyl)amino)-1-methyl-2,3-dihydropyrimido[4,5-d]pyrimidin-4(1H)-one

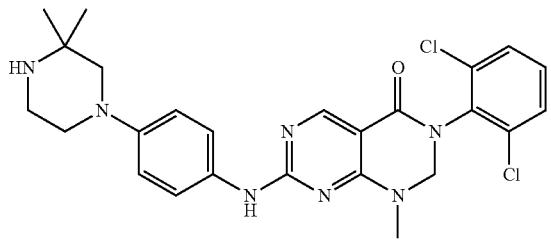 [SMILES: CN1CN(c2c(Cl)cccc2Cl)C(=O)c2cnc(Nc3ccc(N4CCNC(C)(C)C4)cc3)nc21]

Step 1: tert-butyl 2,2-dimethyl-4-(4-nitrophenyl)piperazine-1-carboxylate

A suspension of 1-fluoro-4-nitrobenzene (0.468 g, 3.32 mmol), tert-butyl 2,2-dimethylpiperazine-1-carboxylate hydrochloride (1.0 g, 3.48 mmol) and potassium carbonate (1.83 g, 13.26 mmol) in anhydrous DMF (5 mL) was heated to 50° C. under a nitrogen atmosphere for 16 h. The reaction mixture was allowed to cool to room temperature, partitioned between water (50 mL) and ethyl acetate (50 ml). The ethyl acetate was separated and washed with water (3×20 ml), dried (anhydrous sodium sulfate), filtered and reduced in vacuo. The residue was purified by flash chromatography (0-100% ethyl acetate in cyclohexane) to afford the title compound (1.15 g, 100%). LCMS (Method C): $R_T$=1.80 min, m/z=336 [M+H]$^+$.

Step 2: tert-butyl 4-(4-aminophenyl)-2,2-dimethylpiperazine-1-carboxylate

A solution of tert-butyl 2,2-dimethyl-4-(4-nitrophenyl)piperazine-1-carboxylate (150 mg, 0.447 mmol) in methanol (10 ml) was passed through an H-Cube apparatus fitted with a 10% Pd—C cartridge under the following settings [1.0 ml/min flow, 40° C., Full H$_2$ mode]. The solvent was removed in vacuo to afford the title compound which was used without further purification (137 mg, 100%). LCMS (Method C): $R_T$=0.94 min, m/z=306 [M+H]$^+$.

Step 3: 3-(2,6-dichlorophenyl)-7-((4-(3,3-dimethylpiperazin-1-yl)phenyl)amino)-1-methyl-2,3-dihydropyrimido[4,5-d]pyrimidin-4(1H)-one 3-(2,6-Dichlorophenyl)-1-methyl-7-(methylthio)-2,3-dihydropyrimido[4,5-d]pyrimidin-4(1H)-one (180 mg, 0.507 mmol) was reacted with tert-butyl 4-(4-aminophenyl)-2,2-dimethylpiperazine-1-carboxylate (147 mg, 0.483 mmol) following the procedure for Example 31 to give the title compound (87 mg, 34%). $^1$H NMR (400 MHz, CDCl$_3$): δ 8.70 (s, 1H), 7.71 (brs, 1H), 7.50 (d, 2H), 7.44 (d, 1H), 7.29 (m, 1H), 6.90 (d, 2H), 4.87 (s, 2H), 3.16 (s, 3H), 3.34 (s, 1H), 3.07 (m, 4H), 2.87 (m, 2H), 2.87 (m, 2H), 1.27 (s, 6H). LCMS (Method C): $R_T$=0.759 min, m/z=510 [M+H]$^+$.

Example 97: 3-(2-chlorophenyl)-7-((3-(hydroxymethyl)-4-(8-methyl-3,8-diazabicyclo[3.2.1]octan-3-yl)phenyl)amino)-1-methyl-2,3-dihydropyrimido[4,5-d]pyrimidin-4(1H)-one

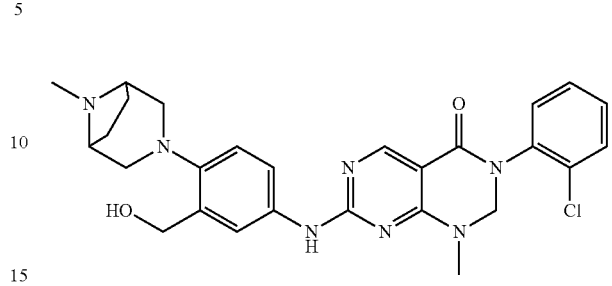

Step 1: 7-((4-(3,8-diazabicyclo[3.2.1]octan-3-yl)-3-(hydroxymethyl)phenyl)amino)-3-(2-chlorophenyl)-1-methyl-2,3-dihydropyrimido[4,5-d]pyrimidin-4(1H)-one 3-(2-Chlorophenyl)-1-methyl-7-(methylthio)-2,3-dihydropyrimido[4,5-d]pyrimidin-4(1H)-one (100 mg, 0.312 mmol) was reacted with tert-butyl 3-(4-amino-2-(hydroxymethyl)phenyl)-3,8-diazabicyclo[3.2.1]octane-8-carboxylate (88 mg, 0.265 mmol) following the procedure for Example 31 to give the title compound (76.4 mg, 83%). LCMS (Method C): $R_T$=0.63 min, m/z=506 [M+H]$^+$.

Step 2: 3-(2-chlorophenyl)-7-((3-(hydroxymethyl)-4-(8-methyl-3,8-diazabicyclo[3.2.1]octan-3-yl)phenyl)amino)-1-methyl-2,3-dihydropyrimido[4,5-d]pyrimidin-4(1H)-one 7-((4-(3,8-diazabicyclo[3.2.1]octan-3-yl)-3-(hydroxymethyl)phenyl)amino)-3-(2-chlorophenyl)-1-methyl-2,3-dihydropyrimido[4,5-d]pyrimidin-4(1H)-one (76.4 mg, 0.151 mmol) was methylated following the procedure in Example 35 to give the title compound (71.1 mg, 91%). $^1$H NMR (400 MHz, DMSO-d$_6$): δ 9.76 (s, 1H), 8.44 (s, 1H), 7.89-8.09 (m, 1H), 7.62 (dd, 1H), 7.49-7.57 (m, 2H), 7.38-7.48 (m, 2H), 7.04 (d, 1H), 5.04 (t, 1H), 4.83-5.13 (m, 2H), 4.60 (d, 2H), 3.11 (s, 3H), 3.04-3.10 (m, 2H), 2.89 (d, 2H), 2.62 (dd, 2H), 2.20 (s, 3H), 1.88-2.00 (m, 2H), 1.77-1.88 (m, 2H). LCMS (Method C): $R_T$=0.66 min, m/z=520 [M+H]$^+$.

Example 98: 3-(2-chlorophenyl)-7-((4-((2R,5S)-2,5-dimethylpiperazin-1-yl)phenyl)amino)-1-methyl-2,3-dihydropyrimido[4,5-d]pyrimidin-4(1H)-one

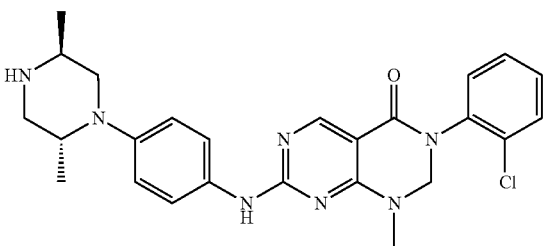 [SMILES: C[C@@H]1CN[C@@H](C)CN1c1ccc(Nc2ncc3c(n2)N(C)CN(c2ccccc2Cl)C3=O)cc1]

Step 1: (2S,5R)-tert-butyl 4-(4-((6-(2-chlorophenyl)-8-methyl-5-oxo-5,6,7,8-tetrahydropyrimido[4,5-d]pyrimidin-2-yl)amino)phenyl)-2,5-dimethylpiperazine-1-carboxylate 3-(2-Chlorophenyl)-1-methyl-7-(methylthio)-2,3-dihydropyrimido[4,5-d]pyrimidin-4(1H)-one (80 mg, 0.249 mmol) was reacted with (2S,5R)-tert-butyl 4-(4-aminophenyl)-2,5-dimethylpiperazine-1-carboxylate (76 mg, 0.249 mmol) following the procedure for Example 31 to give the title compound as a yellow solid (74 mg, 51%). $^1$H NMR (400 MHz, CDCl$_3$): δ 8.70 (s, 1H), 7.29-7.54 (m, 7H), 6.84 (d, 2H), 4.88 (br d, 2H), 4.42 (br s, 1H), 3.93 (br s, 1H), 3.80 (d, 1H), 3.43 (dd, 1H), 3.28 (dd, 1H), 3.16 (s, 3H), 3.05 (dd, 1H), 1.49 (s, 9H), 1.27 (d, 3H), 1.02 (d, 3H). LCMS (Method C): R$_T$=1.63 min, m/z=578 [M+H]$^+$.

Step 2: 3-(2-chlorophenyl)-7-((4-((2R,5S)-2,5-dimethylpiperazin-1-yl)phenyl)amino)-1-methyl-2,3-dihydropyrimido[4,5-d]pyrimidin-4(1H)-one (2S,5R)-tert-Butyl 4-(4-((6-(2-chlorophenyl)-8-methyl-5-oxo-5,6,7,8-tetrahydropyrimido[4,5-d]pyrimidin-2-yl)amino)phenyl)-2,5-dimethylpiperazine-1-carboxylate (74 mg, 0.128 mmol) was deprotected following the procedure for Example 31 to give the title compound as a pale yellow solid (61 mg, 100%). $^1$H NMR (400 MHz, DMSO-d$_6$): δ 9.77 (br s, 1H), 8.45 (s, 1H), 7.68 (d, 2H), 7.62 (dd, 1H), 7.52 (dd, 1H), 7.39-7.48 (m, 2H), 7.03 (d, 2H), 5.07 (d, 1H), 4.90 (d, 1H), 3.10 (s, 3H), 2.79-2.98 (m, 4H), 2.45 (dd, 1H), 2.32 (dd, 1H), 2.19 (br s, 1H), 0.94 (d, 3H), 0.80 (d, 3H). LCMS (Method C): R$_T$=0.72 min, m/z=478 [M+H]$^+$.

Example 99: (R)-3-(2-chlorophenyl)-7-((3-fluoro-4-(3-methylpiperazin-1-yl)phenyl)amino)-1-methyl-2,3-dihydropyrimido[4,5-d]pyrimidin-4(1H)-one

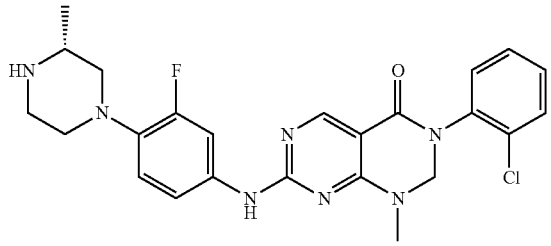 [SMILES: C[C@@H]1CN(c2ccc(Nc3ncc4c(n3)N(C)CN(c3ccccc3Cl)C4=O)cc2F)CCN1]

Step 1: (R)-tert-butyl 4-(4-((6-(2-chlorophenyl)-8-methyl-5-oxo-5,6,7,8-tetrahydropyrimido[4,5-d]pyrimidin-2-yl)amino)-2-fluorophenyl)-2-methylpiperazine-1-carboxylate 3-(2-Chlorophenyl)-1-methyl-7-(methylthio)-2,3-dihydropyrimido[4,5-d]pyrimidin-4(1H)-one (80 mg, 0.249 mmol) was reacted with (R)-tert-butyl 4-(4-amino-2-fluorophenyl)-2-methylpiperazine-1-carboxylate (77 mg, 0.249 mmol) following the procedure for Example 31 to give the title compound as an off-white solid (64 mg, 44%). $^1$H NMR (400 MHz, CDCl$_3$): δ 8.71 (s, 1H), 7.68 (d, 1H), 7.65 (br s, 1H), 7.52 (dd, 1H), 7.30-7.43 (m, 3H), 7.10 (dd, 1H), 6.88 (t, 1H), 4.91 (br d, 2H), 4.31 (br s, 1H), 3.94 (d, 1H), 3.15-3.33 (m, 6H), 2.83 (dd, 1H), 2.73 (td, 1H), 1.49 (s, 9H), 1.36 (d, 3H). LCMS (Method C): R$_T$=1.83 min, m/z=582 [M+H]$^+$.

Step 2: (R)-3-(2-chlorophenyl)-7-((3-fluoro-4-(3-methylpiperazin-1-yl)phenyl)amino)-1-methyl-2,3-dihydropyrimido[4,5-d]pyrimidin-4(1H)-one (R)-tert-Butyl 4-(4-((6-(2-chlorophenyl)-8-methyl-5-oxo-5,6,7,8-tetrahydropyrimido[4,5-d]pyrimidin-2-yl)amino)-2-fluorophenyl)-2-methylpiperazine-1-carboxylate (64 mg, 0.110 mmol) was deprotected following the procedure for Example 31 to give the title compound as an off-white solid (41 mg, 77%). $^1$H NMR (400 MHz, DMSO-d$_6$): δ 9.88 (br s, 1H), 8.47 (s, 1H), 7.69 (dd, 1H), 7.62 (dd, 1H), 7.52 (dd, 1H), 7.39-7.49 (m, 3H), 6.97 (t, 1H), 5.09 (d, 1H), 4.91 (d, 1H), 3.06-3.16 (m, 5H), 2.78-2.95 (m, 3H), 2.57 (td, 1H), 2.24 (t, 1H), 0.99 (d, 3H). LCMS (Method C): R$_T$=0.77 min, m/z=482 [M+H]$^+$.

Example 100: (R)-3-(2-chloro-6-methylphenyl)-1-methyl-7-((4-(3-methylpiperazin-1-yl)phenyl)amino)-2,3-dihydropyrimido[4,5-d]pyrimidin-4(1H)-one

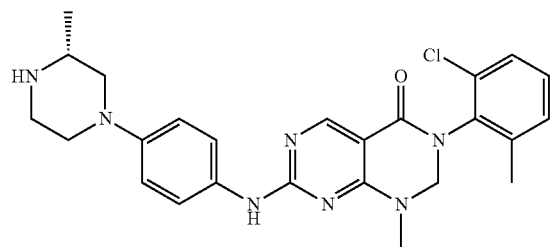

3-(2-Chloro-6-methylphenyl)-1-methyl-7-(methylthio)-2,3-dihydropyrimido[4,5-d]pyrimidin-4(1H)-one (120 mg, 0.358 mmol) was reacted with (R)-4-(3-methylpiperazin-1-yl)aniline (99 mg, 0.341 mmol) following the procedure for Example 31 to give the title compound (39 mg, 24%). $^1$H NMR (400 MHz, CDCl$_3$): δ 8.70 (s, 1H), 7.51 (d, 1H), 7.35 (m, 1H), 7.22 (m, 2H), 6.94 (d, 2H), 5.01 (d, 1H), 4.65 (d, 1H), 3.50 (m, 2H), 3.14 (s, 3H), 3.12-2.95 (m, 3H), 2.70 (m, 1H), 2.37 (m, 1H), 2.32 (s, 3H), 1.13 (d, 3H). LCMS (Method C): R$_T$=0.67 min, m/z=478 [M+H]$^+$.

Example 101: (R)-3-(2-chloro-6-methylphenyl)-7-((3-(methoxymethyl)-4-(3-methylpiperazin-1-yl)phenyl)amino)-1-methyl-2,3-dihydropyrimido[4,5-d]pyrimidin-4(1H)-one

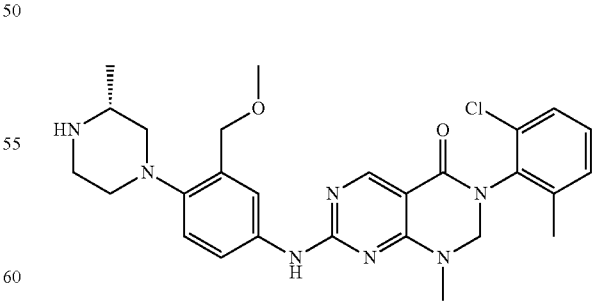

3-(2-Chloro-6-methylphenyl)-1-methyl-7-(methylthio)-2,3-dihydropyrimido[4,5-d]pyrimidin-4(1H)-one (120 mg, 0.358 mmol) was reacted with (R)-tert-butyl 4-(4-amino-2-(methoxymethyl) phenyl)-2-methylpiperazine-1-carboxylate (114 mg, 0.341 mmol) following the procedure for Example 31 to give the title compound (30 mg, 17%). ¹H NMR (400 MHz, CDCl₃): δ 8.71 (s, 1H), 7.78 (s, 1H), 7.53 (m, 1H), 7.35 (m, 1H), 7.23 (m, 2H), 7.08 (d, 1H), 5.03 (d, 1H), 4.66 (d, 1H), 4.56 (s, 2H), 3.44 (s, 3H), 3.19 (s, 3H), 3.02 (m, 3H), 2.92 (m, 2H), 2.71 (m, 1H), 2.45 (m, 1H), 2.23 (s, 3H). LCMS (Method C): R$_T$=0.77 min, m/z=522 [M+H]⁺.

Example 102: 3-(2-chloro-6-methylphenyl)-7-((4-((2R,5S)-2,5-dimethylpiperazin-1-yl)phenyl)amino)-1-methyl-2,3-dihydropyrimido[4,5-d]pyrimidin-4(1H)-one

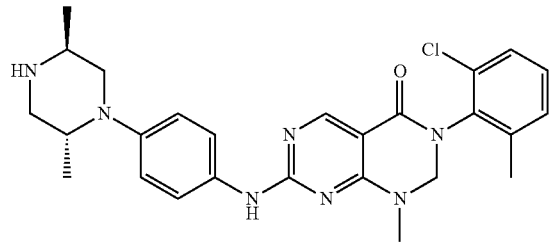

Step 1: (2S,5R)-tert-butyl 4-(4-((6-(2-chloro-6-methylphenyl)-8-methyl-5-oxo-5,6,7,8-tetrahydropyrimido[4,5-d]pyrimidin-2-yl)amino)phenyl)-2,5-dimethylpiperazine-1-carboxylate 3-(2-Chloro-6-methylphenyl)-1-methyl-7-(methylthio)-2,3-dihydropyrimido[4,5-d]pyrimidin-4(1H)-one (60 mg, 0.180 mmol) was reacted with (2S,5R)-tert-butyl 4-(4-aminophenyl)-2,5-dimethylpiperazine-1-carboxylate (55 mg, 0.180 mmol) following the procedure for Example 31 to give the title compound as a yellow solid (85 mg, 80%). ¹H NMR (400 MHz, CDCl₃): δ 8.70 (s, 1H), 7.54 (br s, 1H), 7.50 (d, 2H), 7.30-7.37 (m, 1H), 7.18-7.23 (m, 2H), 6.84 (d, 2H), 5.01 (d, 1H), 4.64 (d, 1H), 4.42 (br s, 1H), 3.93 (br s, 1H), 3.80 (d, 1H), 3.43 (dd, 1H), 3.27 (dd, 1H), 3.14 (s, 3H), 3.05 (dd, 1H), 2.32 (s, 3H), 1.49 (s, 9H), 1.27 (d, 3H), 1.02 (d, 3H). LCMS (Method C): R$_T$=1.73 min, m/z=592 [M+H]⁺.

Step 2: 3-(2-chloro-6-methylphenyl)-7-((4-((2R,5S)-2,5-dimethylpiperazin-1-yl)phenyl)amino)-1-methyl-2,3-dihydropyrimido[4,5-d]pyrimidin-4(1H)-one (2S,5R)-tert-Butyl 4-(4-((6-(2-chloro-6-methylphenyl)-8-methyl-5-oxo-5,6,7,8-tetrahydropyrimido[4,5-d]pyrimidin-2-yl)amino)phenyl)-2,5-dimethylpiperazine-1-carboxylate (85 mg, 0.144 mmol) was deprotected following the procedure for Example 31 to give the title compound as a pale yellow solid (60 mg, 85%). ¹H NMR (400 MHz, DMSO-d₆): δ 9.76 (br s, 1H), 8.45 (s, 1H), 7.68 (d, 2H), 7.41-7.48 (m, 1H), 7.30-7.37 (m, 2H), 7.03 (d, 2H), 4.92 (dd, 2H), 3.10 (s, 3H), 2.80-2.98 (m, 4H), 2.45 (dd, 1H), 2.33 (dd, 1H), 2.26 (s, 3H), 0.95 (d, 3H), 0.80 (d, 3H). LCMS (Method C): R$_T$=0.78 min, m/z=492 [M+H]⁺.

Example 103: 3-(2-chlorophenyl)-7-((4-((3S,5R)-3,5-dimethylpiperazin-1-yl)phenyl)amino)-1-methyl-2,3-dihydropyrimido[4,5-d]pyrimidin-4(1H)-one

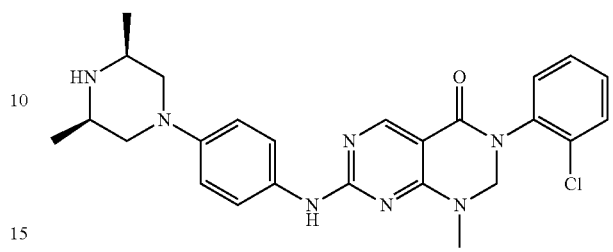

Step 1: 3-(2-chlorophenyl)-7-((4-((3S,5R)-3,5-dimethylpiperazin-1-yl)phenyl)amino)-1-methyl-2,3-dihydropyrimido[4,5-d]pyrimidin-4(1H)-one A solution of mCPBA, 50% purity (103 mg, 0.299 mmol) in dichloromethane (0.400 mL) was passed through a phase separator and washed through with further dichloromethane (0.200 mL). This solution was added to a stirring suspension of 3-(2-chlorophenyl)-1-methyl-7-(methylthio)-2,3-dihydropyrimido[4,5-d]pyrimidin-4(1H)-one (80 mg, 0.249 mmol) in anhydrous toluene (2 mL) and the mixture was stirred for 30 minutes. Hunig's Base (0.131 mL, 0.748 mmol) was added, followed by 4-((3S,5R)-3,5-dimethylpiperazin-1-yl)aniline (43.5 mg, 0.212 mmol), and the mixture was heated to 80° C. for 16 h. After cooling the reaction mixture was purified directly by flash chromatography (0-100%, ethyl acetate in cyclohexane, KP-NH). The residue was dissolved in methanol (1 mL) and water (10 mL) and freeze-dried to afford the title compound (29.6 mg, 24.83%). ¹H NMR (400 MHz, DMSO-d₆): δ 9.64 (br s, 1H), 8.43 (s, 1H), 7.55-7.67 (m, 3H), 7.51 (dd, 1H), 7.44 (dtd, 2H), 6.88 (d, 2H), 4.80-5.15 (m, 2H), 3.45 (d, 2H), 3.08 (s, 3H), 2.78-2.90 (m, 2H), 2.12 (br s, 1H), 2.06 (t, 2H), 1.01 (d, 6H). LCMS (Method C): R$_T$=0.67 min, m/z=478 [M+H]⁺.

Example 104: 7-((4-((1S,4R)-2,5-diazabicyclo[2.2.1]heptan-2-yl)phenyl)amino)-3-(2-chlorophenyl)-1-methyl-2,3-dihydropyrimido[4,5-d]pyrimidin-4(1H)-one

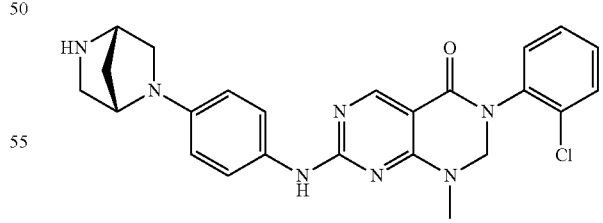

3-(2-Chlorophenyl)-1-methyl-7-(methylthio)-2,3-dihydropyrimido[4,5-d]pyrimidin-4(1H)-one (60 mg, 0.187 mmol) was reacted with (1R,4S)-tert-butyl 5-(4-aminophenyl)-2,5-diazabicyclo[2.2.1]heptane-2-carboxylate (46.0 mg, 0.159 mmol) following the procedure for Example 31 to give the title compound (42.0 mg, 88%). ¹H NMR (400 MHz, MeOH-d₄): δ 8.49 (s, 1H), 7.57-7.62 (m, 1H), 7.46-7.57 (m, 3H), 7.40-7.46 (m, 2H), 6.63 (d, 2H), 4.92-5.03 (m, 2H), 4.39 (s, 1H), 3.79 (s, 1H), 3.63 (dd, 1H), 3.15 (s, 3H), 3.05 (t, 2H), 2.98 (dd, 1H), 1.99 (d, 1H), 1.81 (d, 1H). LCMS (Method C): $R_T$=0.60 min, m/z=462 [M+H]$^+$.

Example 105: 7-((4-(4,7-diazaspiro[2.5]octan-7-yl)phenyl)amino)-3-(2-chlorophenyl)-1-methyl-2,3-dihydropyrimido[4,5-d]pyrimidin-4(1H)-one

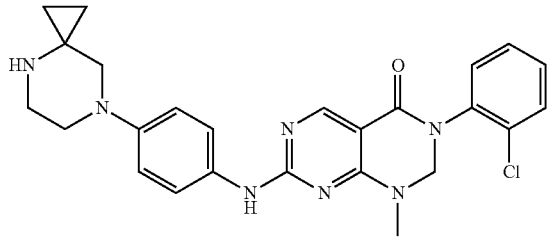 [SMILES: CN1CN(c2ccccc2Cl)C(=O)c2cnc(Nc3ccc(N4CCNC5(CC5)C4)cc3)nc21]

Step 1: tert-butyl 7-(4-nitrophenyl)-4,7-diazaspiro[2.5]octane-4-carboxylate A suspension of 1-fluoro-4-nitrobenzene (0.166 g, 1.177 mmol), tert-butyl 4,7-diazaspiro[2.5]octane-7-carboxylate (0.25 g, 1.178 mmol) and potassium carbonate (0.642 g, 4.64 mmol) in anhydrous DMF (5 mL) was heated to 50° C. under a nitrogen atmosphere for 16 h. The reaction mixture was allowed to cool to room temperature, then partitioned between water (50 mL) and ethyl acetate (50 mL). The ethyl acetate was separated and washed with water (3×20 mL), dried (anhydrous sodium sulfate), filtered and reduced in vacuo. The residue was purified by flash chromatography (0-100% ethyl acetate in cyclohexane) to afford the title compound (0.334 g, 85%). LCMS (Method C): $R_T$=1.78 min, m/z=334 [M+H]$^+$.

Step 2: tert-butyl 7-(4-aminophenyl)-4,7-diazaspiro[2.5]octane-4-carboxylate A solution of tert-butyl 7-(4-nitrophenyl)-4,7-diazaspiro[2.5]octane-4-carboxylate (149 mg, 0.447 mmol) in methanol (10 mL) was passed through an H-Cube apparatus fitted with a 10% Pd—C cartridge under the following settings [1.0 ml/min flow, 40° C., Full H$_2$ mode]. The solvent was removed in vacuo to afford the title compound which was used without further purification (136 mg, 100%). LCMS (Method C): $R_T$=0.82 min, m/z=304 [M+H]$^+$.

Step 3: 7-((4-(4,7-diazaspiro[2.5]octan-7-yl)phenyl)amino)-3-(2-chlorophenyl)-1-methyl-2,3-dihydropyrimido[4,5-d]pyrimidin-4(1H)-one 3-(2-Chlorophenyl)-1-methyl-7-(methylthio)-2,3-dihydropyrimido[4,5-d]pyrimidin-4(1H)-one (80 mg, 0.249 mmol) was reacted with tert-butyl 7-(4-aminophenyl)-4,7-diazaspiro[2.5]octane-4-carboxylate (64.3 mg, 0.212 mmol) following the procedure for Example 31 to give the title compound (25.7 mg, 93%). $^1$H NMR (400 MHz, MeOH-d$_4$): δ 8.52 (s, 1H), 7.53-7.66 (m, 3H), 7.38-7.52 (m, 3H), 6.98 (d, 2H), 4.93-5.06 (m, 2H), 3.11-3.21 (m, 5H), 3.05-3.11 (m, 2H), 2.97-3.02 (m, 2H), 0.63-0.75 (m, 4H). LCMS (Method C): $R_T$=0.67 min, m/z=476 [M+H]$^+$.

Example 106: 3-(2-chlorophenyl)-7-((4-(3,3-dimethylpiperazin-1-yl)phenyl)amino)-1-methyl-2,3-dihydropyrimido[4,5-d]pyrimidin-4(1H)-one

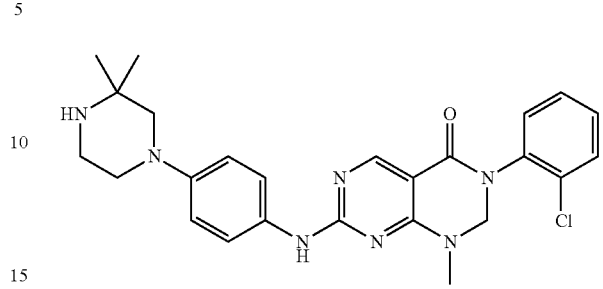

Step 1: 3-(2-chlorophenyl)-7-((4-(3,3-dimethylpiperazin-1-yl)phenyl)amino)-1-methyl-2,3-dihydropyrimido[4,5-d]pyrimidin-4(1H)-one 3-(2-chlorophenyl)-1-methyl-7-(methylthio)-2,3-dihydropyrimido[4,5-d]pyrimidin-4(1H)-one (80 mg, 0.249 mmol) was reacted with tert-butyl 4-(4-aminophenyl)-2,2-dimethylpiperazine-1-carboxylate (64.7 mg, 0.212 mmol) following the procedure for Example 31 to give the title compound (71.2 mg, 90%). $^1$H NMR (400 MHz, MeOH-d$_4$): δ 8.52 (s, 1H), 7.52-7.65 (m, 3H), 7.39-7.52 (m, 3H), 6.95 (d, 2H), 4.93-5.04 (m, 2H), 3.16 (s, 3H), 3.00-3.09 (m, 4H), 2.89 (s, 2H), 1.26 (s, 6H). LCMS (Method C): $R_T$=0.70 min, m/z=478 [M+H]$^+$.

Example 107: 7-((4-((1S,4S)-2,5-diazabicyclo[2.2.1]heptan-2-yl)-3-methoxyphenyl)amino)-3-(2-chlorophenyl)-1-methyl-2,3-dihydropyrimido[4,5-d]pyrimidin-4(1H)-one

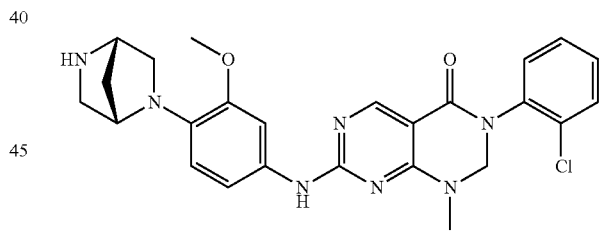

Step 1: 7-((4-((1S,4S)-2,5-diazabicyclo[2.2.1]heptan-2-yl)-3-methoxyphenyl)amino)-3-(2-chlorophenyl)-1-methyl-2,3-dihydropyrimido[4,5-d]pyrimidin-4(1H)-one 3-(2-chlorophenyl)-1-methyl-7-(methylthio)-2,3-dihydropyrimido[4,5-d]pyrimidin-4(1H)-one (80 mg, 0.249 mmol) was reacted with (1S,4S)-tert-butyl 5-(4-amino-2-methoxyphenyl)-2,5-diazabicyclo[2.2.1]heptane-2-carboxylate (67.7 mg, 0.212 mmol) following the procedure for Example 31 to give the title compound (68.5 mg, 86%). $^1$H NMR (400 MHz, MeOH-d$_4$): δ 8.49 (s, 1H), 7.54-7.61 (m, 1H), 7.35-7.50 (m, 4H), 7.11 (d, 1H), 6.70 (d, 1H), 4.90-5.03 (m, 2H), 4.33 (s, 1H), 3.82 (s, 3H), 3.63-3.70 (m, 2H), 3.12-3.22 (m, 4H), 3.05 (s, 1H), 2.91 (dd, 1H), 1.91 (d, 1H), 1.71 (d, 1H). LCMS (Method C): $R_T$=0.69 min, m/z=492 [M+H]$^+$.

Example 108: 3-(2-chlorophenyl)-7-((3-(methoxymethyl)-4-(piperazin-1-yl)phenyl)amino)-1-methyl-2,3-dihydropyrimido[4,5-d]pyrimidin-4(1H)-one

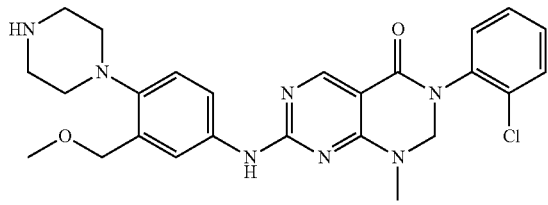 [SMILES: COCc1cc(Nc2ncc3c(n2)N(C)CN(c2ccccc2Cl)C3=O)ccc1N1CCNCC1]

Step 1: 3-(2-chlorophenyl)-7-((3-(methoxymethyl)-4-(piperazin-1-yl)phenyl)amino)-1-methyl-2,3-dihydropyrimido[4,5-d]pyrimidin-4(1H)-one 3-(2-Chlorophenyl)-1-methyl-7-(methylthio)-2,3-dihydropyrimido[4,5-d]pyrimidin-4(1H)-one (80 mg, 0.249 mmol) was reacted with tert-butyl 4-(4-amino-2-(methoxymethyl)phenyl)piperazine-1-carboxylate (68.1 mg, 0.212 mmol) following the procedure for Example 31 to give the title compound (46.6 mg, 96%). $^1$H NMR (400 MHz, MeOH-d$_4$): δ 8.54 (s, 1H), 7.92 (br s, 1H), 7.55-7.63 (m, 2H), 7.40-7.52 (m, 3H), 7.14 (d, 1H), 4.93-5.07 (m, 2H), 4.59 (s, 2H), 3.45 (s, 3H), 3.20 (s, 3H), 2.97-3.03 (m, 4H), 2.87-2.93 (m, 4H). LCMS (Method C): R$_T$=0.70 min, m/z=494 [M+H]$^+$.

Example 109: 7-((4-((1S,4S)-2,5-diazabicyclo[2.2.1]heptan-2-yl)-3-methylphenyl)amino)-3-(2-chlorophenyl)-1-methyl-2,3-dihydropyrimido[4,5-d]pyrimidin-4(1H)-one

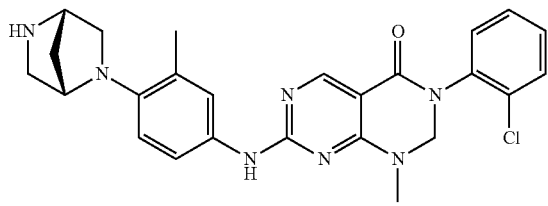 [SMILES: Cc1cc(Nc2ncc3c(n2)N(C)CN(c2ccccc2Cl)C3=O)ccc1N1C[C@@H]2C[C@H]1CN2]

Step 1: 7-((4-((1S,4S)-2,5-diazabicyclo[2.2.1]heptan-2-yl)-3-methylphenyl)amino)-3-(2-chlorophenyl)-1-methyl-2,3-dihydropyrimido[4,5-d]pyrimidin-4(1H)-one 3-(2-Chlorophenyl)-1-methyl-7-(methylthio)-2,3-dihydropyrimido[4,5-d]pyrimidin-4(1H)-one (80 mg, 0.249 mmol) was reacted with (1S,4S)-tert-butyl 5-(4-amino-2-methylphenyl)-2,5-diazabicyclo[2.2.1]heptane-2-carboxylate (64.3 mg, 0.212 mmol) following the procedure for Example 31 to give the title compound (58.8 mg, 83%). $^1$H NMR (400 MHz, MeOH-d$_4$): δ 8.51 (s, 1H), 7.57-7.63 (m, 1H), 7.36-7.54 (m, 5H), 6.90 (d, 1H), 4.92-5.05 (m, 2H), 4.10 (s, 1H), 3.74 (s, 1H), 3.45 (d, 1H), 3.23 (d, 1H), 3.13-3.20 (m, 4H), 2.98 (dd, 1H), 2.96 (s, 3H), 1.98 (d, 1H), 1.76 (d, 1H). LCMS (Method C): R$_T$=0.68 min, m/z=476 [M+H]$^+$.

Example 110: 3-(2-chlorophenyl)-7-((4-((2R,5S)-2,5-dimethylpiperazin-1-yl)-3-fluorophenyl)amino)-1-methyl-2,3-dihydropyrimido[4,5-d]pyrimidin-4(1H)-one

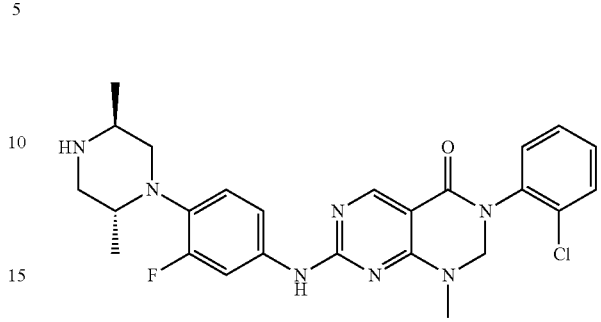

Step 1: 3-(2-chlorophenyl)-7-((4-((2R,5S)-2,5-dimethylpiperazin-1-yl)-3-fluorophenyl)amino)-1-methyl-2,3-dihydropyrimido[4,5-d]pyrimidin-4(1H)-one 3-(2-chlorophenyl)-1-methyl-7-(methylthio)-2,3-dihydropyrimido[4,5-d]pyrimidin-4(1H)-one (80 mg, 0.249 mmol) was reacted with (2S,5R)-tert-butyl 4-(4-amino-2-fluorophenyl)-2,5-dimethylpiperazine-1-carboxylate (68.6 mg, 0.212 mmol) following the procedure for Example 31 to give the title compound (49.7 mg, 92%). $^1$H NMR (400 MHz, MeOH-d$_4$): δ 8.57 (s, 1H), 7.77 (dd, 1H), 7.57-7.64 (m, 1H), 7.41-7.53 (m, 3H), 7.38 (dd, 1H), 7.21 (t, 1H), 4.95-5.10 (m, 2H), 3.21 (s, 3H), 3.06-3.14 (m, 1H), 2.96-3.06 (m, 3H), 2.63 (dd, 1H), 2.58 (t, 1H), 1.08 (d, 3H), 0.89 (d, 3H). LCMS (Method C): R$_T$=0.81 min, m/z=496 [M+H]$^+$.

Example 111: 3-(2-chlorophenyl)-7-((4-((2S,5R)-2,5-dimethylpiperazin-1-yl)phenyl)amino)-1-methyl-2,3-dihydropyrimido[4,5-d]pyrimidin-4(1H)-one

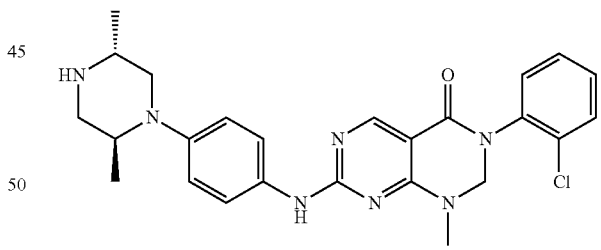

Step 1: 3-(2-chlorophenyl)-7-((4-((2S,5R)-2,5-dimethylpiperazin-1-yl)phenyl)amino)-1-methyl-2,3-dihydropyrimido[4,5-d]pyrimidin-4(1H)-one 3-(2-Chlorophenyl)-1-methyl-7-(methylthio)-2,3-dihydropyrimido[4,5-d]pyrimidin-4(1H)-one (80 mg, 0.249 mmol) was reacted with (2R,5S)-tert-butyl 4-(4-aminophenyl)-2,5-dimethylpiperazine-1-carboxylate (64.7 mg, 0.212 mmol) following the procedure for Example 31 to give the title compound (66.1 mg, 100%). $^1$H NMR (400 MHz, MeOH-d$_4$): δ 8.55 (s, 1H), 7.70 (d, 2H), 7.57-7.64 (m, 1H), 7.40-7.53 (m, 3H), 7.18 (d, 2H), 4.95-5.07 (m, 2H), 3.19 (s, 3H), 2.93-3.09 (m, 4H), 2.64 (dd, 1H), 2.51 (dd, 1H), 1.10 (d, 3H), 0.90 (d, 3H). LCMS (Method C): $R_T$=0.71 min, m/z=478 [M+H]$^+$.

Example 112: 7-((4-((1S,4S)-2,5-diazabicyclo[2.2.1]heptan-2-yl)-3-methylphenyl)amino)-3-(2-chloro-6-methylphenyl)-1-methyl-2,3-dihydropyrimido[4,5-d]pyrimidin-4(1H)-one

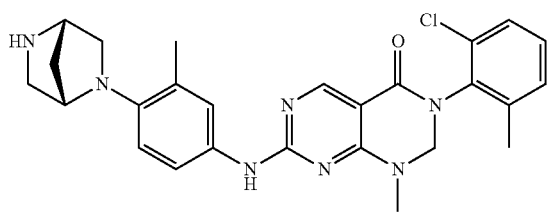 [SMILES: Cc1cc(Nc2ncc3c(n2)N(C)CN(c2c(C)cccc2Cl)C3=O)ccc1N1C[C@@H]2C[C@H]1CN2]

Step 1: (1S,4S)-tert-butyl 5-(4-((6-(2-chloro-6-methylphenyl)-8-methyl-5-oxo-5,6,7,8-tetrahydropyrimido[4,5-d]pyrimidin-2-yl)amino)-2-methylphenyl)-2,5-diazabicyclo[2.2.1]heptane-2-carboxylate 3-(2-Chloro-6-methylphenyl)-1-methyl-7-(methylthio)-2,3-dihydropyrimido[4,5-d]pyrimidin-4(1H)-one (60 mg, 0.180 mmol) was reacted with (1S,4S)-tert-butyl 5-(4-amino-2-methylphenyl)-2,5-diazabicyclo[2.2.1]heptane-2-carboxylate (55 mg, 0.180 mmol) following the procedure for Example 31 to give the title compound as a yellow solid (65 mg, 61%). $^1$H NMR (400 MHz, CDCl$_3$): δ 8.70 (s, 1H), 7.30-7.55 (m, 4H), 7.18-7.24 (m, 2H), 6.80 (t, 1H), 5.01 (d, 1H), 4.65 (d, 1H), 4.50 (d, 1H), 4.11 (br s, 1H), 3.62 (dd, 1H), 3.45 (t, 1H), 3.20-3.40 (m, 2H), 3.15 (s, 3H), 2.32 (s, 3H), 2.28 (s, 3H), 1.98 (d, 1H), 1.86 (t, 1H), 1.42-1.50 (m, 9H). LCMS (Method C): $R_T$=1.62 min, m/z=590 [M+H]$^+$.

Step 2: 7-((4-((1S,4S)-2,5-diazabicyclo[2.2.1]heptan-2-yl)-3-methylphenyl)amino)-3-(2-chloro-6-methylphenyl)-1-methyl-2,3-dihydropyrimido[4,5-d]pyrimidin-4(1H)-one (1S,4S)-tert-Butyl 5-(4-((6-(2-chloro-6-methylphenyl)-8-methyl-5-oxo-5,6,7,8-tetrahydropyrimido[4,5-d]pyrimidin-2-yl)amino)-2-methylphenyl)-2,5-diazabicyclo[2.2.1]heptane-2-carboxylate (65 mg, 0.110 mmol) was deprotected following the procedure for Example 31 to give the title compound as a yellow solid (36 mg, 67%). $^1$H NMR (400 MHz, DMSO-d$_6$): δ 9.57 (br s, 1H), 8.42 (s, 1H), 7.39-7.58 (m, 3H), 7.29-7.37 (m, 2H), 6.76 (d, 1H), 4.90 (dd, 2H), 3.99 (s, 1H), 3.56 (s, 1H), 3.41 (dd, 1H), 3.08 (s, 3H), 3.05 (d, 1H), 2.96 (d, 1H), 2.85 (dd, 1H), 2.25 (d, 3H), 2.18 (s, 3H), 1.75 (d, 1H), 1.59 (d, 1H). LCMS (Method C): $R_T$=0.75 min, m/z=490 [M+H]$^+$.

Example 113: 3-(2-chlorophenyl)-7-((4-(4-ethylpiperazin-1-yl)-3-(hydroxymethyl)phenyl)amino)-1-methyl-2,3-dihydropyrimido[4,5-d]pyrimidin-4(1H)-one

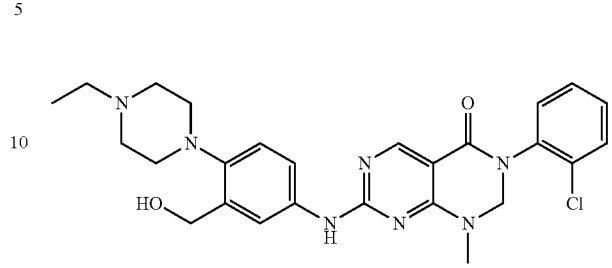

Step 1: 3-(2-chlorophenyl)-7-((4-(4-ethylpiperazin-1-yl)-3-(hydroxymethyl)phenyl)amino)-1-methyl-2,3-dihydropyrimido[4,5-d]pyrimidin-4(1H)-one A solution of mCPBA, 50% purity (103 mg, 0.299 mmol) in dichloromethane (0.400 mL) was passed through a phase separator and washed through with further dichloromethane (0.200 mL). This solution was added to a stirring suspension of 3-(2-chlorophenyl)-1-methyl-7-(methylthio)-2,3-dihydropyrimido[4,5-d]pyrimidin-4(1H)-one (80 mg, 0.249 mmol) in anhydrous toluene (2 mL) and the mixture was stirred for 30 minutes. Hunig's base (0.131 mL, 0.748 mmol) was added, followed by (5-amino-2-(4-ethylpiperazin-1-yl)phenyl)methanol (49.9 mg, 0.212 mmol), and the mixture was heated to 80° C. for 16 h. After cooling the reaction mixture was purified directly by flash chromatography (0-100%, ethyl acetate in cyclohexane, KP-NH). The residue was suspended in dichloromethane (4 mL). The solid was collected by filtration and washed with fresh dichloromethane (3 mL). The residue was suspended in methanol (1 mL) and water (10 mL) and freeze-dried to afford the title compound (58.3 mg, 46.0%). $^1$H NMR (400 MHz, DMSO-d$_6$): δ 9.77 (s, 1H), 8.45 (s, 1H), 7.99 (br s, 1H), 7.62 (dd, 1H), 7.56 (dd, 1H), 7.52 (dd, 1H), 7.38-7.48 (m, 2H), 7.01 (d, 1H), 4.85-5.12 (m, 3H), 4.54 (d, 2H), 3.12 (s, 3H), 2.76-2.88 (m, 4H), 2.40 (q, 2H), 1.03 (t, 3H). $^1$H NMR (300 MHz, MeOH-d$_4$): δ 8.54 (s, 1H), 7.90 (s, 1H), 7.54-7.68 (m, 2H), 7.39-7.53 (m, 3H), 7.18 (d, 1H), 4.97-5.07 (m, 2H), 4.76 (s, 2H), 3.21 (s, 3H), 2.95-3.06 (m, 4H), 4.64-2.82 (m, 4H), 2.59 (q, 2H), 1.19 (t, 3H). LCMS (Method C): $R_T$=0.61 min, m/z=508 [M+H]$^+$.

Example 114: 3-(2-chloro-6-methylphenyl)-7-((3-(hydroxymethyl)-4-(8-methyl-3,8-diazabicyclo[3.2.1]octan-3-yl)phenyl)amino)-1-methyl-2,3-dihydropyrimido[4,5-d]pyrimidin-4(1H)-one

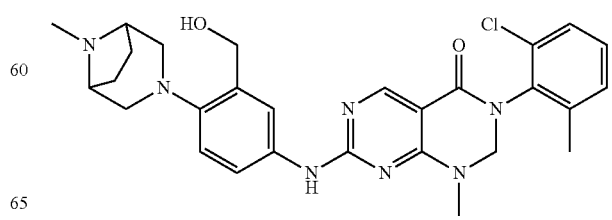

Step 1: tert-butyl 3-(4-((6-(2-chloro-6-methylphenyl)-8-methyl-5-oxo-5,6,7,8-tetrahydropyrimido[4,5-d]pyrimidin-2-yl)amino)-2-(hydroxymethyl)phenyl)-3,8-diazabicyclo[3.2.1]octane-8-carboxylate 3-(2-Chloro-6-methylphenyl)-1-methyl-7-(methylthio)-2,3-dihydropyrimido[4,5-d]pyrimidin-4(1H)-one (60 mg, 0.180 mmol) was reacted with tert-butyl 3-(4-amino-2-(hydroxymethyl)phenyl)-3,8-diazabicyclo[3.2.1]octane-8-carboxylate (60 mg, 0.180 mmol) following the procedure for Example 31 to give the title compound as an off-white solid (42 mg, 38%). $^1$H NMR (400 MHz, CDCl$_3$): δ 8.73 (s, 1H), 7.69 (br s, 1H), 7.61 (d, 1H), 7.56 (dd, 1H), 7.31-7.38 (m, 1H), 7.16-7.24 (m, 3H), 5.03 (d, 1H), 4.81 (d, 2H), 4.67 (d, 1H), 4.19-4.42 (m, 3H), 3.17 (s, 3H), 2.94-3.14 (m, 2H), 2.82 (d, 2H), 2.32 (s, 3H), 2.00 (br s, 4H), 1.50 (s, 9H). LCMS (Method C): R$_T$=1.54 min, m/z=620 [M+H]$^+$.

Step 2: 7-((4-(3,8-diazabicyclo[3.2.1]octan-3-yl)-3-(hydroxymethyl)phenyl)amino)-3-(2-chloro-6-methylphenyl)-1-methyl-2,3-dihydropyrimido[4,5-d]pyrimidin-4(1H)-one tert-Butyl 3-(4-((6-(2-chloro-6-methylphenyl)-8-methyl-5-oxo-5,6,7,8-tetrahydropyrimido[4,5-d]pyrimidin-2-yl)amino)-2-(hydroxymethyl)phenyl)-3,8-diazabicyclo[3.2.1]octane-8-carboxylate (42 mg, 0.068 mmol) was deprotected following the procedure for Example 31 to give the title compound as an off-white solid (32 mg, 91%). $^1$H NMR (400 MHz, DMSO-d$_6$): δ 9.76 (br s, 1H), 8.44 (s, 1H), 8.00 (br s, 1H), 7.54 (dd, 1H), 7.41-7.48 (m, 1H), 7.30-7.37 (m, 2H), 7.03 (d, 1H), 5.05 (t, 1H), 4.91 (dd, 2H), 4.61 (d, 2H), 3.41 (br s, 2H), 3.11 (s, 3H), 2.82 (d, 2H), 2.67 (dd, 2H), 2.26 (s, 3H), 1.91 (dd, 2H), 1.67 (dd, 2H). LCMS (Method C): R$_T$=0.71 min, m/z=520 [M+H]$^+$.

Step 3: 3-(2-chloro-6-methylphenyl)-7-((3-(hydroxymethyl)-4-(8-methyl-3,8-diazabicyclo[3.2.1]octan-3-yl)phenyl)amino)-1-methyl-2,3-dihydropyrimido[4,5-d]pyrimidin-4(1H)-one 7-((4-(3,8-Diazabicyclo[3.2.1]octan-3-yl)-3-(hydroxymethyl)phenyl)amino)-3-(2-chloro-6-methylphenyl)-1-methyl-2,3-dihydropyrimido[4,5-d]pyrimidin-4(1H)-one (32 mg, 0.062 mmol) was methylated following the procedure for Example 35 to give the title compound as a white solid (15 mg, 46%). $^1$H NMR (400 MHz, DMSO-d$_6$): δ 9.69 (br s, 1H), 8.37 (s, 1H), 7.93 (br s, 1H), 7.46 (dd, 1H), 7.35-7.40 (m, 1H), 7.24-7.30 (m, 2H), 6.98 (d, 1H), 4.98 (t, 1H), 4.87 (d, 1H), 4.82 (d, 1H), 4.54 (d, 2H), 3.04 (s, 3H), 3.01 (br s, 2H), 2.82 (d, 2H), 2.55 (dd, 2H), 2.19 (s, 3H), 2.13 (s, 3H), 1.71-1.92 (m, 4H). LCMS (Method C): R$_T$=0.71 min, m/z=534 [M+H]$^+$.

Example 115: 7-((4-(4-cyclopropylpiperazin-1-yl)phenyl)amino)-3-(2,6-dichlorophenyl)-1-methyl-2,3-dihydropyrimido[4,5-d]pyrimidin-4(1H)-one Step 1: 1-cyclopropyl-4-(4-nitrophenyl)piperazine A suspension of 1-fluoro-4-nitrobenzene (1.096 g, 7.77 mmol), 1-cyclopropylpiperazine (1.00 g, 7.92 mmol) and potassium carbonate (1.61 g, 11.65 mmol) in anhydrous DMF (10 mL) was heated to 50° C. under a nitrogen atmosphere overnight. The reaction mixture was allowed to cool to room temperature and poured into ice-water (50 mL). The precipitated solid was isolated by filtration, washed with water and sucked dry to give the title compound as a yellow solid (1.11 g, 58%). $^1$H NMR (500 MHz, CDCl$_3$): δ 8.12 (d, 2H), 7.01 (d, 2H), 3.47 (t, 4H), 2.80 (t, 4H), 1.70-1.80 (m, 1H), 0.45-0.60 (m, 4H). LCMS (Method C): R$_T$=0.51 min, m/z=248 [M+H]$^+$.

Step 2: 4-(4-cyclopropylpiperazin-1-yl)aniline

A suspension of 1-cyclopropyl-4-(4-nitrophenyl)piperazine (1.11 g, 4.49 mmol), iron powder (1.504 g, 26.9 mmol) and ammonium chloride (2.161 g, 40.4 mmol) in a mixture of methanol (18.54 mL) and water (3.90 mL) was heated to reflux under a nitrogen atmosphere for 1 hour. The reaction mixture was allowed to cool to room temperature, filtered through Celite® and concentrated to dryness under reduced pressure. The residue was taken up in ethyl acetate (100 mL) and washed with saturated sodium bicarbonate solution (3×70 mL). The organic phase was dried over Na$_2$SO$_4$, filtered and concentrated to dryness under reduced pressure to give the title compound as a brown oil that solidified upon standing (910 mg, 93%). $^1$H NMR (500 MHz, CDCl$_3$): δ 6.81 (d, 2H), 6.64 (d, 2H), 3.41 (br s, 2H), 3.02 (t, 4H), 2.77 (t, 4H), 1.64-1.69 (m, 1H), 0.40-0.51 (m, 4H). LCMS (Method C): R$_T$=0.13 min, m/z=218 [M+H]$^+$.

Step 3: 7-((4-(4-cyclopropylpiperazin-1-yl)phenyl)amino)-3-(2,6-dichlorophenyl)-1-methyl-2,3-dihydropyrimido[4,5-d]pyrimidin-4(1H)-one 3-(2,6-Dichlorophenyl)-1-methyl-7-(methylthio)-2,3-dihydropyrimido[4,5-d]pyrimidin-4(1H)-one (100 mg, 0.283 mmol) was reacted with 4-(4-cyclopropylpiperazin-1-yl)aniline (62 mg, 0.283 mmol) following the procedure for Example 31 to give the title compound as a pale yellow solid (60 mg, 41%). $^1$H NMR (400 MHz, DMSO-d$_6$): δ 9.70 (br s, 1H), 8.44 (s, 1H), 7.64 (d, 2H), 7.60 (br d, 2H), 7.48 (t, 1H), 6.89 (d, 2H), 4.95 (s, 2H), 3.08 (s, 3H), 3.04 (t, 4H), 2.67 (t, 4H), 1.65 (sep, 1H), 0.39-0.48 (m, 2H), 0.29-0.39 (m, 2H). LCMS (Method C): R$_T$=0.79 min, m/z=524 [M+H]$^+$.

Example 116: 3-(2,6-dichlorophenyl)-7-((4-(4-(2-hydroxyethyl)piperazin-1-yl)phenyl)amino)-1-methyl-2,3-dihydropyrimido[4,5-d]pyrimidin-4(1H)-one

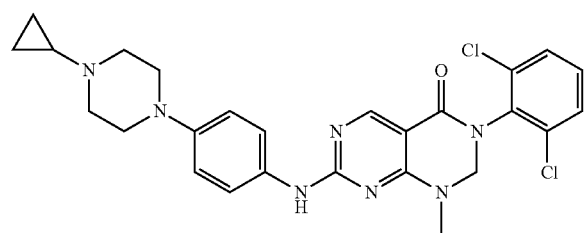 [SMILES: CN1CN(c2c(Cl)cccc2Cl)C(=O)c2cnc(Nc3ccc(N4CCN(C5CC5)CC4)cc3)nc21]

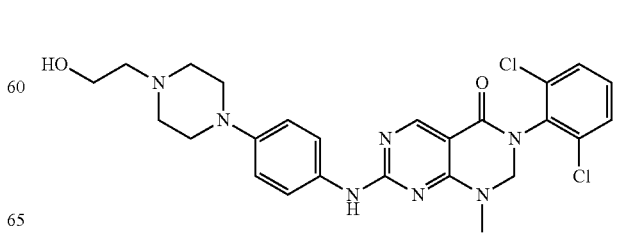

Step 1: 2-(4-(4-nitrophenyl)piperazin-1-yl)ethanol

To a stirred suspension of 1-fluoro-4-nitrobenzene (2 g, 14.17 mmol) and potassium carbonate (3.92 g, 28.3 mmol) in anhydrous dimethyl sulfoxide (10 mL) was added 2-(piperazin-1-yl)ethanol (2.089 mL, 17.01 mmol) and the mixture was heated at 80° C. for 16 hours. After cooling the mixture was partitioned between water (100 mL) and ethyl acetate (30 mL). The aqueous layer was separated and extracted with ethyl acetate (2×30 mL). The combined organic fractions were reduced in vacuo. The residue was triturated in water (100 mL). The solid was collected by filtration under vacuum and dried for 16 hours under vacuum and flowing nitrogen to give the title compound (3.45 g, 97%). $^1$H NMR (400 MHz, CDCl$_3$): δ 8.11 (d, 2H), 6.82 (d, 2H), 3.68 (t, 2H), 3.44 (t, 4H), 2.67 (t, 4H), 2.62 (t, 2H), 2.55 (br s, 1H). LCMS (Method C): $R_T$=0.45 min, m/z=252 [M+H]$^+$.

Step 2: 2-(4-(4-aminophenyl)piperazin-1-yl)ethanol

A stirred solution of 2-(4-(4-nitrophenyl)piperazin-1-yl)ethanol (1.2 g, 4.78 mmol) in ethanol (20 mL) was heated to 50° C. 10% palladium on carbon (0.254 g, 0.239 mmol) was added followed by portionwise addition of ammonium formate (1.506 g, 23.88 mmol) and the suspension was stirred for 1 hour. The suspension was filtered through Celite® washing with fresh ethanol (20 mL). The ethanol was removed in vacuo to give the title compound (1.10 g, 104%). $^1$H NMR (400 MHz, CDCl$_3$): δ 6.81 (d, 2H), 6.66 (d, 2H), 3.69 (t, 2H), 3.09 (t, 4H), 3.02 (br s, 3H), 2.74 (t, 4H), 2.66 (t, 2H). LCMS (Method C): $R_T$=0.13 min, m/z=222 [M+H]$^+$.

Step 3: 3-(2,6-dichlorophenyl)-7-((4-(4-(2-hydroxyethyl)piperazin-1-yl)phenyl)amino)-1-methyl-2,3-dihydropyrimido[4,5-d]pyrimidin-4(1H)-one 3-(2,6-Dichlorophenyl)-1-methyl-7-(methylthio)-2,3-dihydropyrimido[4,5-d]pyrimidin-4(1H)-one (100 mg, 0.283 mmol) was reacted with 2-(4-(4-aminophenyl)piperazin-1-yl)ethanol (63 mg, 0.283 mmol) following the procedure for Example 31 to give the title compound as a yellow solid (67 mg, 45%). $^1$H NMR (400 MHz, DMSO-d$_6$): δ 9.70 (br s, 1H), 8.44 (s, 1H), 7.64 (d, 2H), 7.61 (br d, 2H), 7.48 (dd, 1H), 6.90 (d, 2H), 4.95 (s, 2H), 4.42 (t, 1H), 3.53 (q, 2H), 3.02-3.14 (m, 7H), 2.55 (t, 4H), 2.43 (t, 2H). LCMS (Method C): $R_T$=0.71 min, m/z=528 [M+H]$^+$.

Example 117: 3-(2,6-dichlorophenyl)-1-methyl-7-((4-(4-methylpiperazin-1-yl)phenyl)amino)-2,3-dihydropyrimido[4,5-d]pyrimidin-4(1H)-one

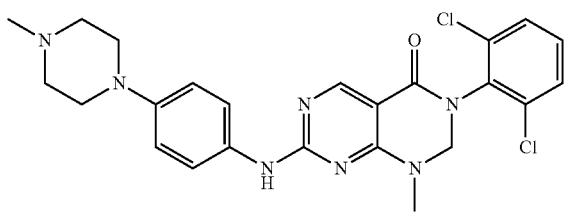 [SMILES: CN1CCN(c2ccc(Nc3ncc4c(n3)N(C)CN(c3c(Cl)cccc3Cl)C4=O)cc2)CC1]

Step 1: 3-(2,6-dichlorophenyl)-1-methyl-7-((4-(piperazin-1-yl)phenyl)amino)-2,3-dihydropyrimido[4,5-d]pyrimidin-4(1H)-one 3-(2,6-Dichlorophenyl)-1-methyl-7-(methylthio)-2,3-dihydropyrimido[4,5-d]pyrimidin-4(1H)-one (150 mg, 0.422 mmol) was reacted with tert-butyl 4-(4-aminophenyl)piperazine-1-carboxylate (100 mg, 0.359 mmol) following the procedure for Example 31 to give the title compound (143.5 mg, 86%). LCMS (Method C): $R_T$=0.71 min, m/z=484 [M+H]$^+$.

Step 2: 3-(2,6-dichlorophenyl)-1-methyl-7-((4-(4-methylpiperazin-1-yl)phenyl)amino)-2,3-dihydropyrimido[4,5-d]pyrimidin-4(1H)-one 3-(2,6-Dichlorophenyl)-1-methyl-7-((4-(piperazin-1-yl)phenyl)amino)-2,3-dihydropyrimido[4,5-d]pyrimidin-4(1H)-one (44 mg, 0.091 mmol) was methylated following the procedure in Example 35 to give the title compound (41.2 mg, 91%). $^1$H NMR (400 MHz, MeOH-d$_4$): δ 9.70 (br s, 1H), 8.44 (s, 1H), 7.53-7.72 (m, 3H), 7.47 (1H), 6.90 (d, 2H), 4.95 (s, 1H), 3.01-3.14 (m, 7H), 2.41-2.48 (m, 4H), 2.23 (m, 3H). LCMS (Method C): $R_T$=0.72 min, m/z=498 [M+H]$^+$.

Example 118: 7-((4-((1R,4R)-2,5-diazabicyclo[2.2.1]heptan-2-yl)-3-methylphenyl)amino)-3-(2,6-dichlorophenyl)-1-methyl-2,3-dihydropyrimido[4,5-d]pyrimidin-4(1H)-one

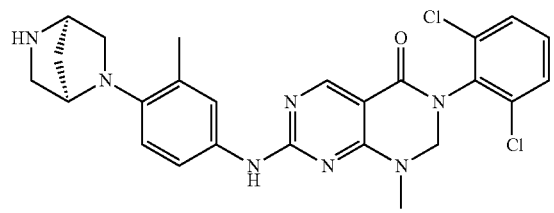 [SMILES: Cc1cc(Nc2ncc3c(n2)N(C)CN(c2c(Cl)cccc2Cl)C3=O)ccc1N1C[C@H]2C[C@@H]1CN2]

Step 1: (1R,4R)-tert-butyl 5-(2-methyl-4-nitrophenyl)-2,5-diazabicyclo[2.2.1]heptane-2-carboxylate A suspension of 2-fluoro-5-nitrotoluene (391 mg, 2.52 mmol), (1R,4R)-tert-butyl 2,5-diazabicyclo[2.2.1]heptane-2-carboxylate (500 mg, 2.52 mmol) and potassium carbonate (523 mg, 3.78 mmol) in anhydrous DMF (2 mL) was heated to 100° C. under a nitrogen atmosphere for 5 days. The reaction mixture was allowed to cool to room temperature, diluted with water (20 mL) and extracted into ethyl acetate (3×10 mL). The combined organic phases were dried over Na$_2$SO$_4$, filtered and concentrated to dryness under reduced pressure. The residue was purified by Biotage chromatography (silica 50 g cartridge, cyclohexane:ethyl acetate, gradient elution from 90:10 to 30:70) to give the title compound as a yellow solid (503 mg, 60%). $^1$H NMR (300 MHz, CDCl$_3$): δ 7.97 (br s, 2H), 6.60 (d, 1H), 4.56 (d, 1H), 4.44 (s, 1H), 3.83 (d, 1H), 3.62 (dd, 1H), 3.47 (t, 1H), 3.32 (dd, 1H), 2.36 (s, 3H), 1.86-2.06 (m, 2H), 1.34-1.57 (m, 9H). LCMS (Method C): $R_T$=1.68 min, m/z=334 [M+H]$^+$.

Step 2: (1R,4R)-tert-butyl 5-(4-amino-2-methylphenyl)-2,5-diazabicyclo[2.2.1]heptane-2-carboxylate A solution of (1R,4R)-tert-butyl 5-(2-methyl-4-nitrophenyl)-2,5-diazabicyclo[2.2.1]heptane-2-carboxylate (503 mg, 1.509 mmol) in methanol (75 mL) was hydrogenated by H-Cube (10% Pd/C cartridge, Full H$_2$, room temperature, 1 mL/min) with two-passes. The reaction mixture was concentrated to dryness under reduced pressure and purified by Biotage chromatography (silica 50 g cartridge, cyclohexane: ethyl acetate, gradient elution from 90:10 to 0:100) to give the title compound as a brown solid (319 mg, 70%). $^1$H NMR (300 MHz, CDCl$_3$): δ 6.71 (dd, 1H), 6.55 (s, 1H), 6.48 (d, 1H), 4.46 (d, 1H), 3.91 (s, 1H), 3.13-3.67 (m, 6H), 2.20 (s, 3H), 1.96 (d, 1H), 1.82 (dd, 1H), 1.46 (d, 9H). LCMS (Method C): R$_T$=0.78 min, m/z=304 [M+H]$^+$.

Step 3: (1R,4R)-tert-butyl 5-(4-((6-(2,6-dichlorophenyl)-8-methyl-5-oxo-5,6,7,8-tetrahydropyrimido [4,5-d]pyrimidin-2-yl)amino)-2-methylphenyl)-2,5-diazabicyclo[2.2.1]heptane-2-carboxylate 3-(2,6-Dichlorophenyl)-1-methyl-7-(methylthio)-2,3-dihydropyrimido[4,5-d]pyrimidin-4(1H)-one (100 mg, 0.283 mmol) was reacted with (1R,4R)-tert-butyl 5-(4-amino-2-methylphenyl)-2,5-diazabicyclo[2.2.1]heptane-2-carboxylate (86 mg, 0.283 mmol) following the procedure for Example 31 to give the title compound as a yellow solid (95 mg, 55%). $^1$H NMR (400 MHz, CDCl$_3$): δ 8.70 (s, 1H), 7.44 (d, 2H), 7.32-7.42 (m, 2H), 7.28 (dd, 1H), 7.11 (br s, 1H), 6.80 (t, 1H), 4.87 (s, 2H), 4.50 (d, 1H), 4.11 (s, 1H), 3.62 (dd, 1H), 3.46 (t, 1H), 3.20-3.41 (m, 2H), 3.17 (s, 3H), 2.29 (s, 3H), 1.98 (d, 1H), 1.87 (t, 1H), 1.40-1.51 (m, 9H). LCMS (Method C): R$_T$=1.68 min, m/z=610 [M+H]$^+$.

Step 4: 7-((4-((1R,4R)-2,5-diazabicyclo[2.2.1]heptan-2-yl)-3-methylphenyl)amino)-3-(2,6-dichlorophenyl)-1-methyl-2,3-dihydropyrimido[4,5-d]pyrimidin-4(1H)-one (1R,4R)-tert-butyl 5-(4-((6-(2,6-dichlorophenyl)-8-methyl-5-oxo-5,6,7,8-tetrahydropyrimido[4,5-d]pyrimidin-2-yl)amino)-2-methylphenyl)-2,5-diazabicyclo[2.2.1]heptane-2-carboxylate (95 mg, 0.156 mmol) was deprotected following the procedure for Example 31 to give the title compound as a pale yellow solid (16 mg, 20%). $^1$H NMR (400 MHz, DMSO-d$_6$): δ 9.62 (br s, 1H), 8.43 (s, 1H), 7.64 (d, 2H), 7.37-7.55 (m, 3H), 6.75 (d, 1H), 4.95 (s, 2H), 3.98 (s, 1H), 3.52 (s, 1H), 3.41 (dd, 1H), 3.09 (s, 3H), 3.04 (d, 1H), 2.94 (d, 1H), 2.83 (dd, 1H), 2.18 (s, 3H), 1.74 (d, 1H), 1.57 (d, 1H). LCMS (Method C): R$_T$=0.80 min, m/z=510 [M+H]$^+$.

Example 119: 3-(2,6-dichlorophenyl)-1-methyl-7-((4-(piperidin-4-yl)phenyl)amino)-2,3-dihydropyrimido[4,5-d]pyrimidin-4(1H)-one

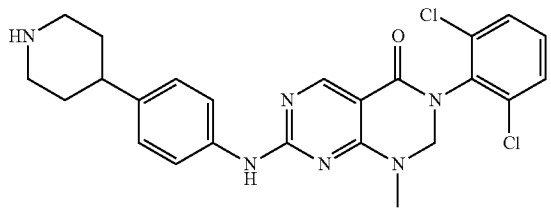 [SMILES: CN1CN(c2c(Cl)cccc2Cl)C(=O)c2cnc(Nc3ccc(C4CCNCC4)cc3)nc21]

Step 1: tert-butyl 4-(4-nitrophenyl)-5,6-dihydropyridine-1(2H)-carboxylate

A suspension of 1-bromo-4-nitrobenzene (0.205 g, 1.012 mmol), tert-butyl 4-(4,4,5,5-tetramethyl-1,3,2-dioxaborolan-2-yl)-5,6-dihydropyridine-1(2H)-carboxylate (0.36 g, 1.164 mmol) and sodium carbonate (0.322 g, 3.04 mmol) in a mixture of 1,4-dioxane (3.5 mL) and water (0.700 mL) was de-gassed with N$_2$ for 5 mins. To the mixture was then added PdCl$_2$(dppf)-dichloromethane adduct (0.083 g, 0.101 mmol) and the reaction mixture de-gassed with N$_2$ for 5 mins before heating in a microwave reactor at 100° C. for 10 mins. The heating was repeated a further five times. After cooling, the mixture was partitioned between saturated sodium hydrogen carbonate (25 mL) and dichloromethane (25 mL). The layers were separated and the aqueous phase was extracted with dichloromethane (3×25 mL). The combined organic phases were dried, filtered, concentrated to dryness under reduced pressure and purified by silica gel chromatography (gradient 0-15% ethyl acetate in cyclohexane) to give the title compound (303 mg, 98%). LCMS (Method C): R$_T$=1.53 min, m/z=304 [M]$^-$.

Step 2: tert-butyl 4-(4-aminophenyl)-5,6-dihydropyridine-1(2H)-carboxylate

To a stirred solution of tert-butyl 4-(4-nitrophenyl)-5,6-dihydropyridine-1(2H)-carboxylate (303.1 mg, 0.996 mmol) in ethanol (3.5 mL) was added tin(II) chloride (944 mg, 4.98 mmol) and the mixture was heated at 55° C. for 3 h. The mixture was concentrated to dryness under reduced pressure and the residue partitioned between 4 M sodium hydroxide solution (50 mL) and ethyl acetate (15 mL). The aqueous phase was separated and extracted with ethyl acetate (3×15 mL). The combined ethyl acetate fractions were dried (anhydrous sodium sulfate), filtered and concentrated to dryness under reduced pressure to give the title compound (310 mg, 100%). $^1$H NMR (400 MHz, DMSO-d6): δ 7.11 (d, 2H), 6.52 (d, 2H), 5.88 (br s, 1H), 5.08 (br s, 2H), 3.91-3.96 (m, 2H), 3.49 (t, 2H), 2.34-2.39 (m, 2H), 1.42 (s, 9H). LCMS (Method C): R$_T$=1.07 min, m/z=275 [M+H]$^+$.

Step 3: tert-butyl 4-(4-aminophenyl)piperidine-1-carboxylate

A stirred suspension of tert-butyl 4-(4-aminophenyl)-5,6-dihydropyridine-1(2H)-carboxylate (79 mg, 0.253 mmol) and 10% Pd/C (33.7 mg, 0.032 mmol) in ethanol (2 mL) was sealed then placed under vacuum and backfilled with nitrogen. This was repeated twice further before placing under vacuum and backfilling with hydrogen (from balloon). The suspension was stirred for 5 h. Remaining hydrogen was removed under vacuum. The mixture was filtered through Celite® washing with ethanol (5 mL) and the filtrate was concentrated to dryness under reduced pressure. The residue was purified by flash chromatography (0-10% Methanol in Dichloromethane) to give the title compound (51.3 mg, 73.3%). LCMS (Method C): R$_T$=0.92 min, m/z=221 [M–Butene]$^+$.

Step 4: tert-butyl 4-(4-((6-(2,6-dichlorophenyl)-8-methyl-5-oxo-5,6,7,8-tetrahydropyrimido[4,5-d] pyrimidin-2-yl)amino)phenyl)piperidine-1-carboxylate 3-(2,6-Dichlorophenyl)-1-methyl-7-(methylthio)-2,3-dihydropyrimido[4,5-d]pyrimidin-4(1H)-one (200 mg, 0.563 mmol) was reacted with tert-butyl 4-(4-aminophenyl)piperidine-1-carboxylate (156 mg, 0.563 mmol) following the procedure for Example 31 to give the title compound as a pale yellow solid (182 mg, 55%). $^1$H NMR (300 MHz, CDCl$_3$): δ 8.72 (s, 1H), 7.58 (br d, 3H), 7.44 (d, 2H), 7.28 (dd, 1H), 7.18 (d, 2H), 4.88 (s, 2H), 4.24 (br s, 2H), 3.18 (s, 3H), 2.80 (br t, 2H), 2.63 (tt, 1H), 1.83 (br d, 2H), 1.54-1.71 (m, 2H), 1.49 (s, 9H). LCMS (Method C): $R_T$=1.82 min, m/z=583 [M+H]$^+$.

Step 5: 3-(2,6-dichlorophenyl)-1-methyl-7-((4-(piperidin-4-yl)phenyl)amino)-2,3-dihydropyrimido[4,5-d]pyrimidin-4(1H)-one tert-Butyl 4-(4-((6-(2,6-dichlorophenyl)-8-methyl-5-oxo-5,6,7,8-tetrahydropyrimido[4,5-d]pyrimidin-2-yl)amino)phenyl)piperidine-1-carboxylate (182 mg, 0.312 mmol) was deprotected following the procedure for Example 31 to give the title compound as a white solid (24 mg, 16%). $^1$H NMR (400 MHz, MeOH-d$_4$) δ 8.54 (s, 1H), 7.66 (d, 2H), 7.58 (d, 2H), 7.44 (dd, 1H), 7.22 (d, 2H), 4.99 (s, 2H), 3.12-3.22 (m, 5H), 2.75 (td, 2H), 2.67 (tt, 1H), 1.84 (d, 2H), 1.68 (qt, 2H). LCMS (Method C): $R_T$=0.80 min, m/z=483 [M+H]$^+$.

Example 120: 3-(2,6-dichlorophenyl)-7-((4-(4-(2-methoxyethyl)piperazin-1-yl)phenyl)amino)-1-methyl-2,3-dihydropyrimido[4,5-d]pyrimidin-4(1H)-one

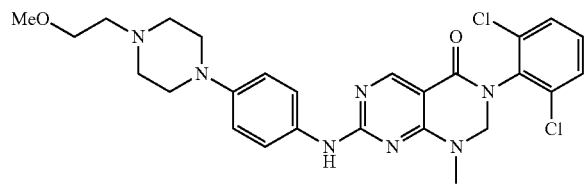 [SMILES: COCCN1CCN(c2ccc(Nc3ncc4c(n3)N(C)CN(c3c(Cl)cccc3Cl)C4=O)cc2)CC1]

Step 1: 1-(2-methoxyethyl)-4-(4-nitrophenyl)piperazine

A suspension of 1-fluoro-4-nitrobenzene (1.00 g, 7.09 mmol), 1-(2-methoxyethyl)piperazine (1.02 g, 7.09 mmol) and potassium carbonate (1.47 g, 10.63 mmol) in anhydrous DMF (10 mL) was heated to 50° C. under a nitrogen atmosphere overnight. The reaction mixture was allowed to cool to room temperature, diluted with water (50 mL) and extracted into ethyl acetate (3×10 mL). The combined organic phases were washed with water (5×20 mL) dried over Na$_2$SO$_4$, filtered and concentrated to dryness under reduced pressure to give the title compound as a yellow solid (1.10 g, 59%). LCMS (Method C): $R_T$=0.51 min, m/z=266 [M+H]$^+$.

Step 2: 4-(4-(2-methoxyethyl)piperazin-1-yl)aniline

A solution of 1-(2-methoxyethyl)-4-(4-nitrophenyl)piperazine (1 g, 3.77 mmol) in ethanol (20 mL) was heated to 50° C. Under stirring, ammonium formate (1.188 g, 18.85 mmol) was added portionwise. The reaction mixture was heated at 50° C. for a further 30 minutes. The reaction mixture was allowed to cool to room temperature, filtered through Celite® and concentrated to dryness under reduced pressure to give the title compound as a brown oil (650 mg, 73%). LCMS (Method C): $R_T$=0.13 min, m/z=236 [M+H]$^+$.

Step 3: 3-(2,6-dichlorophenyl)-7-((4-(4-(2-methoxyethyl)piperazin-1-yl)phenyl)amino)-1-methyl-2,3-dihydropyrimido[4,5-d]pyrimidin-4(1H)-one 3-(2,6-dichlorophenyl)-1-methyl-7-(methylthio)-2,3-dihydropyrimido[4,5-d]pyrimidin-4(1H)-one (100 mg, 0.283 mmol) was reacted with 4-(4-(2-methoxyethyl)piperazin-1-yl)aniline (67 mg, 0.283 mmol) following the procedure for Example 31 to give the title compound as a pale yellow solid (53 mg, 35%). $^1$H NMR (400 MHz, DMSO-d$_6$): δ 9.70 (br s, 1H), 8.45 (s, 1H), 7.65 (d, 2H), 7.62 (br d, 2H), 7.48 (dd, 1H), 6.91 (d, 2H), 4.96 (s, 2H), 3.47 (t, 2H), 3.25 (s, 3H), 3.02-3.15 (m, 7H), 2.51-2.62 (m, 6H). LCMS (Method C): $R_T$=0.78 min, m/z=542 [M+H]$^+$.

Example 121: 3-(2,6-dichlorophenyl)-1-methyl-7-((3-methyl-4-((1R,4R)-5-methyl-2,5-diazabicyclo[2.2.1]heptan-2-yl)phenyl)amino)-2,3-dihydropyrimido[4,5-d]pyrimidin-4(1H)-one

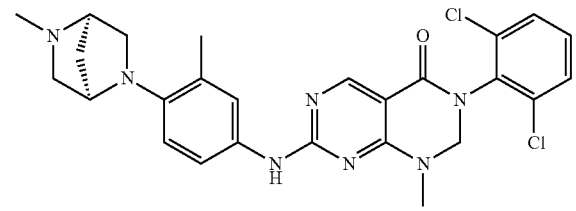 [SMILES: Cc1cc(Nc2ncc3c(n2)N(C)CN(c2c(Cl)cccc2Cl)C3=O)ccc1N1C[C@H]2C[C@@H]1CN2C]

7-((4-((1R,4R)-2,5-diazabicyclo[2.2.1]heptan-2-yl)-3-methylphenyl)amino)-3-(2,6-dichlorophenyl)-1-methyl-2,3-dihydropyrimido[4,5-d]pyrimidin-4(1H)-one (32 mg, 0.063 mmol) was methylated following the procedure for Example 35 to give the title compound as a yellow solid (17 mg, 52%). $^1$H NMR (400 MHz, DMSO-d$_6$): δ 9.63 (br s, 1H), 8.43 (s, 1H), 7.64 (d, 2H), 7.35-7.57 (br m, 3H), 6.73 (d, 1H), 4.95 (s, 2H), 3.92 (s, 1H), 3.32 (s, 1H), 3.20 (s, 2H), 3.09 (s, 3H), 2.75 (dd, 1H), 2.68 (d, 1H), 2.27 (s, 3H), 2.19 (s, 3H), 1.78 (d, 1H), 1.69 (d, 1H). LCMS (Method C): $R_T$=0.80 min, m/z=524 [M+H]$^+$.

Example 122: 3-(2,6-dichlorophenyl)-7-((4-(4-ethylpiperazin-1-yl)phenyl)amino)-1-methyl-2,3-dihydropyrimido[4,5-d]pyrimidin-4(1H)-one

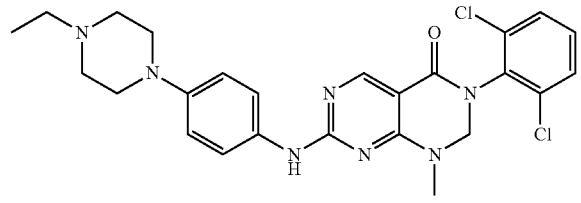 [SMILES: CCN1CCN(c2ccc(Nc3ncc4c(n3)N(C)CN(c3c(Cl)cccc3Cl)C4=O)cc2)CC1]

To a suspension of 3-(2,6-dichlorophenyl)-1-methyl-7-((4-(piperazin-1-yl)phenyl)amino)-2,3-dihydropyrimido[4,5-d]pyrimidin-4(1H)-one (60 mg, 0.124 mmol) and potassium carbonate (51.4 mg, 0.372 mmol) in anhydrous DMF (2 mL) was added iodoethane (0.012 mL, 0.149 mmol) and the mixture was heated at 90° C. for 21 hours. The reaction mixture was allowed to cool to room temperature and partitioned between brine/water (20 mL) and ethyl acetate (5 mL). The aqueous phase was separated and extracted with ethyl acetate (3×5 mL). The combined organic phases were washed with 1:1 brine:water (4×5 mL), dried over Na$_2$SO$_4$, filtered and concentrated to dryness under reduced pressure. The residue was purified by silica gel chromatography (gradient 50-100% ethyl acetate in cyclohexane, KP-NH) and freeze-dried overnight to give the title compound as a pale yellow solid (28 mg, 44%). $^1$H NMR (400 MHz, DMSO-d$_6$): δ 9.70 (br s, 1H), 8.44 (s, 1H), 7.64 (d, 2H), 7.61 (br d, 2H), 7.47 (dd, 1H), 6.90 (d, 2H), 4.95 (s, 2H), 3.01-3.15 (m, 7H), 2.45-2.50 (m, 4H), 2.36 (q, 2H), 1.03 (t, 3H). LCMS (Method C): R$_T$=0.75 min, m/z=512 [M+H]$^+$.

Example 123: 3-(2,6-dichlorophenyl)-7-((4-(4-(2-(dimethylamino)acetyl)piperazin-1-yl)phenyl)amino)-1-methyl-2,3-dihydropyrimido[4,5-d]pyrimidin-4(1H)-one

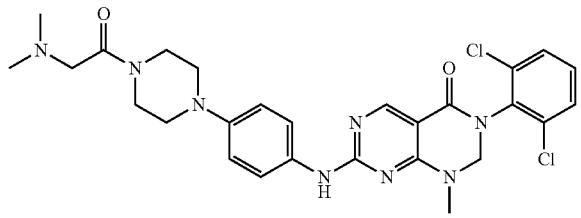 [SMILES: CN(C)CC(=O)N1CCN(c2ccc(Nc3ncc4c(n3)N(C)CN(c3c(Cl)cccc3Cl)C4=O)cc2)CC1]

To a solution of 3-(2,6-dichlorophenyl)-1-methyl-7-((4-(piperazin-1-yl)phenyl)amino)-2,3-dihydropyrimido[4,5-d]pyrimidin-4(1H)-one (40 mg, 0.083 mmol), 2-(dimethylamino)acetic acid (8.52 mg, 0.083 mmol) and N-methylmorpholine (0.036 mL, 0.330 mmol) in anhydrous DMF (1 mL) was added HBTU (37.6 mg, 0.099 mmol) and the resulting mixture was stirred overnight. The reaction mixture was diluted with water (8 mL) and extracted into ethyl acetate (3×4 mL). The combined organic phases were washed with 50:50 water:brine (3×8 mL), dried over Na$_2$SO$_4$, filtered and concentrated to dryness under reduced pressure. The residue was purified by Biotage chromatography (KP-NH 11 g cartridge, cyclohexane:ethyl acetate:methanol, gradient elution from 90:10:0 to 0:100:0 to 0:80:20), slurried in diethyl ether and freeze-dried overnight to give the title compound as a yellow solid (30 mg, 64%). $^1$H NMR (400 MHz, DMSO-d$_6$): δ 9.73 (br s, 1H), 8.45 (s, 1H), 7.54-7.74 (m, 4H), 7.48 (t, 1H), 6.94 (d, 2H), 4.95 (s, 2H), 3.68 (t, 2H), 3.59 (t, 2H), 2.97-3.17 (m, 9H), 2.19 (s, 6H). LCMS (Method C): R$_T$=0.75 min, m/z=569 [M+H]$^+$.

Example 124: 3-(2,6-dichlorophenyl)-1-methyl-7-((4-(4-(2-(methylamino)acetyl)piperazin-1-yl)phenyl)amino)-2,3-dihydropyrimido[4,5-d]pyrimidin-4(1H)-one

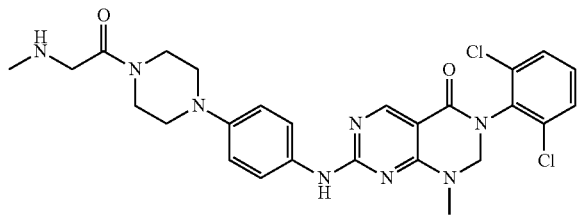 [SMILES: CNCC(=O)N1CCN(c2ccc(Nc3ncc4c(n3)N(C)CN(c3c(Cl)cccc3Cl)C4=O)cc2)CC1]

Step 1: tert-butyl (2-(4-(4-((6-(2,6-dichlorophenyl)-8-methyl-5-oxo-5,6,7,8-tetrahydropyrimido[4,5-d]pyrimidin-2-yl)amino)phenyl)piperazin-1-yl)-2-oxoethyl)(methyl)carbamate 3-(2,6-dichlorophenyl)-1-methyl-7-((4-(piperazin-1-yl)phenyl)amino)-2,3-dihydropyrimido[4,5-d]pyrimidin-4(1H)-one (40 mg, 0.083 mmol) was reacted with 2-((tert-butoxycarbonyl)(methyl)amino)acetic acid (15.62 mg, 0.083 mmol) following the procedure for Example 123 to give the title compound as a yellow solid (35 mg, 65%). $^1$H NMR (400 MHz, CDCl$_3$): δ 8.70 (s, 1H), 7.58 (br s, 1H), 7.54 (br d, 2H), 7.43 (d, 2H), 7.28 (dd, 1H), 6.93 (br d, 2H), 4.87 (s, 2H), 4.06 (br d, 2H), 3.74-3.83 (m, 2H), 3.54-3.65 (m, 2H), 3.16 (s, 3H), 3.13 (t, 4H), 2.94 (s, 3H), 1.41-1.50 (m, 9H). LCMS (Method C): R$_T$=1.31 min, m/z=655 [M+H]$^+$.

Step 2

3-(2,6-dichlorophenyl)-1-methyl-7-((4-(4-(2-(methylamino)acetyl)piperazin-1-yl)phenyl)amino)-2,3-dihydropyrimido[4,5-d]pyrimidin-4(1H)-one tert-butyl (2-(4-(4-((6-(2,6-dichlorophenyl)-8-methyl-5-oxo-5,6,7,8-tetrahydropyrimido[4,5-d]pyrimidin-2-yl)amino)phenyl)piperazin-1-yl)-2-oxoethyl)(methyl)carbamate (35 mg, 0.053 mmol) was deprotected following the procedure for Example 31 to give the title compound as a pale yellow solid (25 mg, 84%). $^1$H NMR (400 MHz, DMSO-d$_6$): δ 9.73 (br s, 1H), 8.45 (s, 1H), 7.54-7.77 (m, 4H), 7.48 (t, 1H), 6.94 (d, 2H), 4.95 (s, 2H), 3.60 (br s, 2H), 3.55 (br s, 2H), 3.34 (s, 2H), 2.97-3.17 (m, 7H), 2.28 (s, 3H), 1.95 (br s, 1H). LCMS (Method C): R$_T$=0.73 min, m/z=555 [M+H]$^+$.

Example 125: 7-((4-(4-acetylpiperazin-1-yl)phenyl)amino)-3-(2,6-dichlorophenyl)-1-methyl-2,3-dihydropyrimido[4,5-d]pyrimidin-4(1H)-one

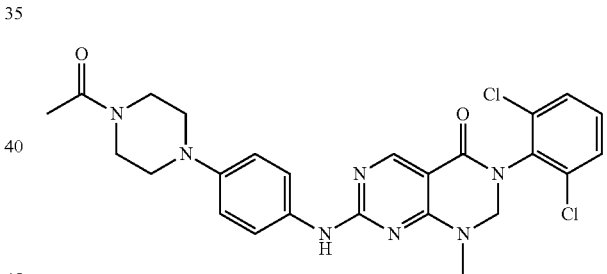

A suspension of 3-(2,6-dichlorophenyl)-1-methyl-7-((4-(piperazin-1-yl)phenyl)amino)-2,3-dihydropyrimido[4,5-d]pyrimidin-4(1H)-one (43 mg, 0.089 mmol) and triethylamine (0.062 mL, 0.444 mmol) in anhydrous dichloromethane (1 mL) was cooled to 0° C. Acetic anhydride (0.017 mL, 0.178 mmol) was added and the resulting solution was allowed to warm to room temperature and stirred for 3 hours. The mixture was washed with saturated sodium bicarbonate solution (3×1 mL), dried over Na$_2$SO$_4$, filtered and concentrated to dryness under reduced pressure. The residue was chromatographed (KP-NH 11 g cartridge, cyclohexane:ethyl acetate:methanol, gradient elution from 90:10:0 to 0:100:0 to 0:80:20), slurried in diethyl ether and freeze-dried overnight to give the title compound as a white solid (29 mg, 62%). $^1$H NMR (400 MHz, DMSO-d$_6$): δ 9.73 (br s, 1H), 8.45 (s, 1H), 7.53-7.77 (m, 4H), 7.48 (t, 1H), 6.94 (d, 2H), 4.95 (s, 2H), 3.57 (br s, 4H), 2.95-3.16 (m, 7H), 2.04 (s, 3H). LCMS (Method C): R$_T$=1.02 min, m/z=526 [M+H]$^+$.

Example 126: (R)-3-(2-chloro-6-fluorophenyl)-7-((4-(3-(methoxymethyl)piperazin-1-yl)phenyl)amino)-1-methyl-2,3-dihydropyrimido[4,5-d]pyrimidin-4(1H)-one

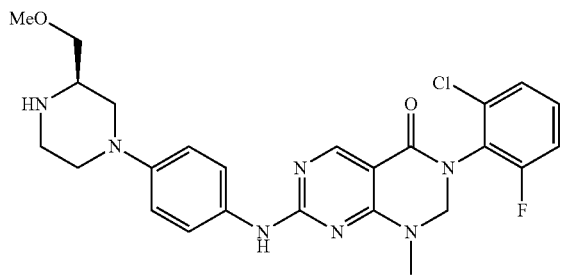 [SMILES: COC[C@H]1CN(c2ccc(Nc3ncc4c(n3)N(C)CN(c3c(F)cccc3Cl)C4=O)cc2)CCN1]

3-(2-chloro-6-fluorophenyl)-1-methyl-7-(methylthio)-2,3-dihydropyrimido[4,5-d]pyrimidin-4(1H)-one (67 mg, 0.197 mmol) was reacted with (R)-tert-butyl 4-(4-aminophenyl)-2-(methoxymethyl)piperazine-1-carboxylate (60 mg, 0.186 mmol) following the procedure for example 31 to give the title compound (37 mg, 39%). $^1$H NMR (400 MHz, DMSO-d$_6$): δ 9.73 (s, 1H), 8.45 (s, 1H), 7.60 (d, 2H), 7.51 (m, 2H), 7.42-7.37 (m, 1H), 6.88 (d, 1H), 4.98 (d, 1H), 4.93 (d, 1H), 3.54 (m, 1H), 3.42 (m, 1H), 3.38 (s, 3H), 3.14 (s, 3H), 3.05 (m, 2H), 2.93 (m, 1H), 2.75 (m, 2H), 2.42 (m, 2H). LCMS (Method C): R$_T$=0.73 min, m/z=482 [M+H]$^+$.

Example 127: (S)-3-(2,6-dichlorophenyl)-7-((4-(2-(hydroxymethyl)piperazin-1-yl)phenyl)amino)-1-methyl-2,3-dihydropyrimido[4,5-d]pyrimidin-4(1H)-one

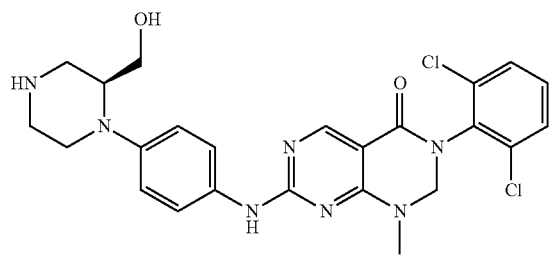 [SMILES: CN1CN(c2c(Cl)cccc2Cl)C(=O)c2cnc(Nc3ccc(N4CCNC[C@H]4CO)cc3)nc21]

Step 1: (S)-tert-butyl 3-(hydroxymethyl)-4-(4-nitrophenyl)piperazine-1-carboxylate 1-fluoro-4-nitrobenzene (1.460 g, 10.4 mmol) and potassium carbonate (4.29 g, 31.0 mmol) were suspended in anhydrous DMF (10 mL). (S)-tert-butyl 3-(hydroxymethyl)piperazine-1-carboxylate (2.35 g, 10.9 mmol) was added and the mixture was heated at 90° C. for 21 h. After cooling the mixture was partitioned between brine/water (100 mL) and ethyl acetate (25 mL). The aqueous layer was separated and further extracted with ethyl acetate (3×25 mL). The combined ethyl acetate fractions were washed with brine/water (1:1, 4×25 mL), dried (anhydrous sodium sulfate), filtered and reduced in vacuo. The resulting residue was purified by silica gel chromatography (gradient 25-100% ethyl acetate in cyclohexane) to afford the title compound (0.99 g, 28.4%). $^1$H NMR (400 MHz, CDCl$_3$): δ 8.12 (d, 2H), 6.83 (d, 2H), 4.20-4.46 (m, 1H), 4.02-4.14 (m, 2H), 3.48-3.76 (m, 3H), 3.08-3.30 (m, 3H), 2.86 (br s, 1H), 1.50 (s, 9H). LCMS (Method C): R$_T$=1.38 min, m/z=338 [M+H]$^+$.

Step 2: (S)-tert-butyl 4-(4-aminophenyl)-3-(hydroxymethyl)piperazine-1-carboxylate (S)-tert-butyl 3-(hydroxymethyl)-4-(4-nitrophenyl)piperazine-1-carboxylate (450 mg, 1.33 mmol) was subjected to continuous flow hydrogenation (ThalesNano H-cube apparatus, 10% Pd/C cartridge, room temperature, Full H$_2$ mode, MeOH solvent). The crude product was chromatographed (10 g Si cartridge, eluted 0-20% MeOH/DCM) to give the title compound as a glass (95 mg, 23%). LCMS (Method C): R$_T$=0.62 min, m/z=308 [M+H]$^+$.

Step 3: (S)-3-(2,6-dichlorophenyl)-7-((4-(2-(hydroxymethyl)piperazin-1-yl)phenyl)amino)-1-methyl-2,3-dihydropyrimido[4,5-d]pyrimidin-4(1H)-one (S)-tert-butyl 4-(4-aminophenyl)-3-(hydroxymethyl)piperazine-1-carboxylate (88 mg, 0.42 mmol) was reacted with 3-(2,6-dichlorophenyl)-1-methyl-7-(methylthio)-2,3-dihydropyrimido[4,5-d]pyrimidin-4(1H)-one (150 mg, 0.42 mmol) as described in Example 1 to give the title compound as a yellow solid (6 mg, 3%). $^1$H NMR (300 MHz, DMSO-d$_6$): δ 9.68 (br s, 1H), 8.44 (s, 1H), 7.60 (m, 4H), 7.48 (t, 1H), 6.85 (d, 2H), 4.95 (s, 2H), 3.71 (t, 1H), 3.55 (m, 1H), 3.25 (dd, 1H), 3.13 (m, 5H), 2.94 (m, 1H), 2.81 (m, 2H), 2.71 (m, 1H). LCMS (Method C): R$_T$=0.72 min, m/z=514 [M+H]$^+$.

Example 128: (S)-3-(2,6-dichlorophenyl)-7-((4-(2-(hydroxymethyl)-4-methylpiperazin-1-yl)phenyl)amino)-1-methyl-2,3-dihydropyrimido[4,5-d]pyrimidin-4(1H)-one

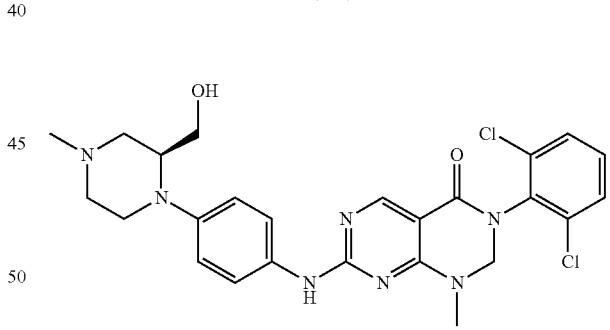

(S)-3-(2,6-dichlorophenyl)-7-((4-(2-(hydroxymethyl)piperazin-1-yl)phenyl)amino)-1-methyl-2,3-dihydropyrimido[4,5-d]pyrimidin-4(1H)-one (52 mg, 0.101 mmol) was dissolved in methanol (1 mL) and aqueous formaldehyde (0.015 mL, 0.20 mmol) was added followed by sodium triacetoxyborohydride (107 mg, 0.51 mmol). The mixture was stirred for 3 h, then added to a 2 g SCX cartridge. The cartridge was washed with methanol then eluted with 2 M NH3/MeOH to give a glass. This was suspended in ether and the resulting solid collected by filtration to give the title compound as a yellow solid (29 mg, 54%). $^1$H NMR (300 MHz, DMSO-d$_6$): δ 9.67 (br s, 1H), 8.44 (s, 1H), 7.60 (m, 4H), 7.48 (t, 1H), 6.86 (d, 2H), 4.95 (s, 2H), 4.59 (br s, 1H), 3.66 (s, 2H), 3.27 (m, 2H), 3.09 (s, 3H), 2.96 (m, 2H), 2.75

(m, 1H), 2.22 (s, 3H), 2.10 (m, 2H). LCMS (Method C): $R_T$=0.74 min, m/z=528 [M+H]$^+$.

Example 129: (R)-3-(2,6-dichlorophenyl)-7-((4-(2-(methoxymethyl)piperazin-1-yl)phenyl)amino)-1-methyl-2,3-dihydropyrimido[4,5-d]pyrimidin-4(1H)-one

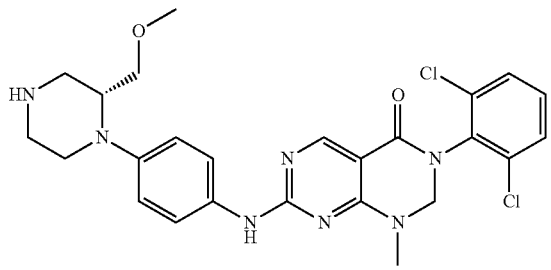 [SMILES: COC[C@H]1CNCCN1c1ccc(Nc2ncc3c(n2)N(C)CN(c2c(Cl)cccc2Cl)C3=O)cc1]

Step 1: (R)-tert-butyl 3-(hydroxymethyl)-4-(4-nitrophenyl)piperazine-1-carboxylate 1-fluoro-4-nitrobenzene (1.056 g, 7.49 mmol) and potassium carbonate (3.10 g, 22.5 mmol) were suspended in anhydrous DMF (10 mL). (R)-tert-butyl 3-(hydroxymethyl)piperazine-1-carboxylate (1.70 g, 7.86 mmol) was added and the mixture was heated at 90° C. for 21 h. After cooling the mixture was partitioned between brine/water (100 mL) and ethyl acetate (25 mL). The aqueous layer was separated and further extracted with ethyl acetate (3×25 mL). The combined ethyl acetate fractions were washed with brine/water (1:1, 4×25 mL), dried ($Na_2SO_4$), filtered and reduced in vacuo. The resulting residue was purified by silica gel chromatography (gradient 20-100% ethyl acetate in cyclohexane) to afford the title compound (0.69 g, 27.3%). LCMS (Method C): $R_T$=1.38 min, m/z=338 [M+H]$^+$.

Step 2: (R)-tert-butyl 3-(methoxymethyl)-4-(4-nitrophenyl)piperazine-1-carboxylate (R)-tert-butyl 3-(hydroxymethyl)-4-(4-nitrophenyl)piperazine-1-carboxylate (430 mg, 1.28 mmol) was dissolved in THF (10 mL) and cooled to 0° C. Sodium hydride (61.3 mg, 1.53 mmol) was added and the mixture was stirred for 5 min. Iodomethane (0.105 mL, 1.67 mmol) was added and the mixture was stirred overnight. The mixture was then concentrated in vacuo and chromatographed (Isolera 25 g Si cartridge; eluted 0-50% EtOAc/c-hex) to give the title compound as a yellow oil (281 mg, 63%). LCMS (Method C): $R_T$=1.67 min, m/z=352 [M+H]$^+$.

Step 3: (R)-tert-butyl 4-(4-aminophenyl)-3-(methoxymethyl)piperazine-1-carboxylate (R)-tert-butyl 3-(methoxymethyl)-4-(4-nitrophenyl)piperazine-1-carboxylate (270 mg, 0.77 mmol mmol) was subjected to continuous flow hydrogenation (H-cube, 10% Pd/C cartridge, room temperature, Full $H_2$, MeOH solvent). The mixture was concentrated to give the crude title compound as a yellow glass (280 mg, 113%), which was used without further purification. LCMS (Method C): $R_T$=0.83 min, m/z=322 [M+H]$^+$.

Step 4: (R)-3-(2,6-dichlorophenyl)-7-((4-(2-(methoxymethyl)piperazin-1-yl)phenyl)amino)-1-methyl-2,3-dihydropyrimido[4,5-d]pyrimidin-4(1H)-one (R)-tert-butyl 4-(4-aminophenyl)-3-(methoxymethyl)piperazine-1-carboxylate (90 mg, 0.28 mmol) was reacted with 3-(2,6-dichlorophenyl)-1-methyl-7-(methylthio)-2,3-dihydropyrimido[4,5-d]pyrimidin-4(1H)-one (100 mg, 0.28 mmol) as described in Example 1 to give the title compound as a yellow solid (45 mg, 30%). $^1$H NMR (300 MHz, DMSO-$d_6$): δ 9.69 (br s, 1H), 8.45 (s, 1H), 7.60 (m, 4H), 7.48 (m, 1H), 6.86 (d, 2H), 4.96 (s, 2H), 3.72 (m, 2H), 3.19 (s, 3H), 3.13 (m, 5H), 2.98 (m, 2H), 2.83 (m, 2H), 2.70 (m, 1H). LCMS (Method C): $R_T$ 0.81 min, m/z=528 [M+H]$^+$.

Example 130: (S)-3-(2,6-dichlorophenyl)-7-((4-(2-(methoxymethyl)piperazin-1-yl)phenyl)amino)-1-methyl-2,3-dihydropyrimido[4,5-d]pyrimidin-4(1H)-one

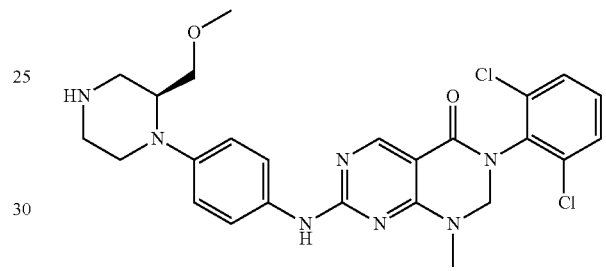

Step 1: (S)-tert-butyl 3-(methoxymethyl)-4-(4-nitrophenyl)piperazine-1-carboxylate (S)-tert-butyl 3-(hydroxymethyl)-4-(4-nitrophenyl)piperazine-1-carboxylate (470 mg, 1.39 mmol) was dissolved in THF (10 mL) and cooled to 0° C. Sodium hydride (61.3 mg, 1.53 mmol) was added and the mixture was stirred for 5 min. Iodomethane (0.105 mL, 1.67 mmol) was added and the mixture was stirred overnight. The mixture was then concentrated in vacuo and chromatographed (25 g Si cartridge; eluted 0-50% EtOAc/c-hex) to give the title compound as a yellow oil (380 mg, 78%). LCMS (Method C): $R_T$=1.67 min, m/z=352 [M+H]$^+$.

Step 2: (S)-tert-butyl 4-(4-aminophenyl)-3-(methoxymethyl)piperazine-1-carboxylate (S)-tert-butyl 3-(methoxymethyl)-4-(4-nitrophenyl)piperazine-1-carboxylate (450 mg, 1.28 mmol) was subjected to continuous flow hydrogenation (H-cube, 10% Pd/C cartridge, room temperature, Full $H_2$ mode, MeOH solvent). The crude product was chromatographed (Isolera 10 g Si cartridge; eluted 0-20% MeOH/DCM) to give the title compound as a glass (90 mg, 22%). LCMS (Method C): $R_T$=0.82 min, m/z=322 [M+H]$^+$.

Step 3: (S)-3-(2,6-dichlorophenyl)-7-((4-(2-(methoxymethyl)piperazin-1-yl)phenyl)amino)-1-methyl-2,3-dihydropyrimido[4,5-d]pyrimidin-4(1H)-one (S)-tert-butyl 4-(4-aminophenyl)-3-(methoxymethyl)piperazine-1-carboxylate (62 mg, 0.28 mmol) was reacted with 3-(2,6-dichlorophenyl)-1-methyl-7-(methylthio)-2,3-dihydropyrimido[4,5-d]pyrimidin-4(1H)-one (100 mg, 0.28 mmol) as described in Example 1 to give the title compound as a yellow solid (12 mg, 6%). $^1$H NMR (300 MHz, DMSO-$d_6$): δ 9.68 (br s, 1H), 8.45 (s, 1H), 7.60 (m, 4H), 7.48 (m, 1H), 6.86 (d, 2H), 4.96 (s, 2H), 3.72 (m, 2H), 3.19 (s, 3H), 3.13 (m, 5H), 2.98 (m, 2H), 2.83 (m, 2H), 2.70 (m, 1H). LCMS (Method C): $R_T$=0.81 min, m/z=528 [M+H]$^+$.

Example 131: 3-(2,6-dichlorophenyl)-7-((3-(hydroxymethyl)-4-(piperidin-1-yl)phenyl)amino)-1-methyl-2,3-dihydropyrimido[4,5-d]pyrimidin-4(1H)-one

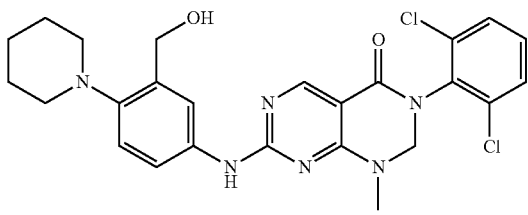 [SMILES: CN1CN(c2c(Cl)cccc2Cl)C(=O)c2cnc(Nc3ccc(N4CCCCC4)c(CO)c3)nc21]

Step 1: (5-amino-2-(piperidin-1-yl)phenyl)methanol 2-fluoro-5-nitrobenzaldehyde (1 g, 5.91 mmol) was dissolved in DMF (10 mL) and piperidine (0.644 mL, 6.50 mmol) was added followed by DIPEA (2.272 mL, 13.0 mmol). The mixture was stirred overnight at room temperature. Water was added and the resulting yellow precipitate was collected by filtration. This was dissolved in ethanol (10.0 mL) and sodium borohydride (0.336 g, 8.87 mmol) was added. The resulting solution was stirred for 30 min, then concentrated in vacuo. The residue was partitioned between DCM and saturated aqueous NH$_4$Cl. The organic layer was separated, washed with brine then concentrated in vacuo. The residue was dissolved in methanol and filtered through cotton wool then subjected to continuous flow hydrogenation (H-cube, 10% Pd/C cartridge, room temperature, 50 bar, methanol solvent) to give the title compound as an orange oil (410 mg, 34%), which was used without further purification. LCMS (Method C): $R_T$=0.25 min, m/z=207 [M+H]$^+$.

Step 2: 3-(2,6-dichlorophenyl)-7-((3-(hydroxymethyl)-4-(piperidin-1-yl)phenyl)amino)-1-methyl-2,3-dihydropyrimido[4,5-d]pyrimidin-4(1H)-one 3-(2,6-Dichlorophenyl)-1-methyl-7-(methylthio)-2,3-dihydropyrimido[4,5-d]pyrimidin-4(1H)-one (300 mg, 0.084 mmol) was suspended in toluene (5 mL) and mCPBA (291 mg, 0.93 mmol) was added as a solution in DCM (3 mL) at RT. After 15 minutes DIPEA (0.44 mL, 2.53 mmol) was added, followed by (5-amino-2-(piperidin-1-yl)phenyl)methanol (174 mg, 0.84 mmol). The resulting mixture was heated at 70° C. for 16 h, then concentrated in vacuo and azeotroped with ethyl acetate. The residue was chromatographed (10 g Si cartridge; eluted 0-100% EtOAc/c-hex then 0-5% MeOH/EtOAc) to give a glass. This was suspended in diethyl ether and the solid collected by filtration to give the title compound as an off-white solid (271 mg, 63%). $^1$H NMR (300 MHz, DMSO-$d_6$): δ 9.69 (br s, 1H), 8.46 (s, 1H), 7.66 (br s, 1H), 7.65 (d, 2H), 7.55 (dd, 1H), 7.48 (t, 1H), 7.00 (d, 1H), 5.04 (br s, 1H), 4.97 (s, 2H), 4.55 (s, 2H), 3.12 (s, 3H), 2.76 (m, 4H), 1.64 (m, 4H), 1.51 (m, 2H). LCMS (Method C): $R_T$=0.97 min, m/z=513 [M+H]$^+$.

Example 132: (R)-3-(2,6-dichlorophenyl)-7-((3-(difluoromethoxy)-4-(3-methylpiperazin-1-yl)phenyl)amino)-1-methyl-2,3-dihydropyrimido[4,5-d]pyrimidin-4(1H)-one

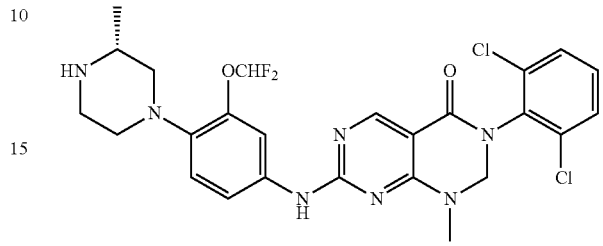

Step 1: 1-bromo-2-(difluoromethoxy)-4-nitrobenzene

A suspension of 2-bromo-5-nitrophenol (1.00 g, 4.59 mmol), ethyl chlorodifluoroacetate (0.581 mL, 4.59 mmol) and potassium carbonate (0.634 g, 4.59 mmol) in anhydrous DMF (10.35 mL) was heated to 70° C. under a nitrogen atmosphere for 5 hours. The reaction mixture was allowed to cool to room temperature, diluted with water (50 mL) and extracted into ethyl acetate (3×25 mL). The combined organic phases were washed with 50:50 water:brine (3×30 mL), dried over Na$_2$SO$_4$, filtered and concentrated to dryness under reduced pressure. The residue was purified by Biotage chromatography (silica 50 g cartridge, cyclohexane:ethyl acetate, gradient elution from 100:0 to 80:20) to give the title compound as a colourless oil (920 mg, 75%). $^1$H NMR (400 MHz, DMSO-$d_6$): δ 8.10 (d, 1H), 8.00 (dd, 1H), 7.83 (d, 1H), 6.66 (t, 1H).

Step 2: (R)-tert-butyl 4-(2-(difluoromethoxy)-4-nitrophenyl)-2-methylpiperazine-1-carboxylate A suspension of 1-bromo-2-(difluoromethoxy)-4-nitrobenzene (400 mg, 1.492 mmol), (R)-tert-butyl 2-methylpiperazine-1-carboxylate (299 mg, 1.492 mmol), tetrabutylammonium bromide (48.1 mg, 0.149 mmol) and potassium carbonate (309 mg, 2.239 mmol) in anhydrous DMSO (2 mL) was heated to 80° C. under a nitrogen atmosphere for 24 hours, then to 120° C. for a further 24 hours. The reaction mixture was allowed to cool to room temperature, diluted with water (10 mL) and extracted into ethyl acetate (3×10 mL). The combined organic phases were washed with 50:50 water:brine (3×10 mL), dried over Na$_2$SO$_4$, filtered and concentrated to dryness under reduced pressure. The residue was purified by Biotage chromatography (silica 50 g cartridge, cyclohexane:ethyl acetate, gradient elution from 95:5 to 60:40) to give the title compound as an orange oil that solidified upon standing (320 mg, 55%). $^1$H NMR (300 MHz, CDCl$_3$): δ 8.08 (dd, 1H), 7.99 (d, 1H), 6.98 (d, 1H), 6.53 (t, 1H), 4.37 (br s, 1H), 3.98 (br d, 1H), 3.51 (ddd, 1H), 3.44 (dt, 1H), 3.28 (td, 1H), 2.99 (dd, 1H), 2.85 (td, 1H), 1.48 (s, 9H), 1.31 (d, 3H). LCMS (Method C): $R_T$=1.87 min, m/z=410 [M+Na]$^1$.

Step 3: (R)-tert-butyl 4-(4-amino-2-(difluoromethoxy)phenyl)-2-methylpiperazine-1-carboxylate A solution of (R)-tert-butyl 4-(2-(difluoromethoxy)-4-nitrophenyl)-2-methylpiperazine-1-carboxylate (320 mg, 0.826 mmol) in methanol (50 mL) was hydrogenated by H-Cube (10% Pd/C cartridge, 40 bar, room temperature, 1 mL/min). The reaction mixture was concentrated to dryness under reduced pressure to give the title compound as a pale yellow solid (262 mg, 89%). $^1$H NMR (400 MHz, CDCl$_3$): δ 6.75-6.83 (m, 1H), 6.37-3.60 (m, 3H), 4.30 (br s, 1H), 3.89 (d, 1H), 3.58 (s, 2H), 3.23 (td, 1H), 3.13 (dd, 1H), 2.98 (dt, 1H), 2.79 (dd, 1H), 2.58 (td, 1H), 1.47 (s, 9H), 1.30 (d, 3H). LCMS (Method C): R$_T$=1.54 min, m/z=358 [M+H]$^+$.

Step 4: (R)-tert-butyl 4-(4-((6-(2,6-dichlorophenyl)-8-methyl-5-oxo-5,6,7,8-tetrahydropyrimido[4,5-d]pyrimidin-2-yl)amino)-2-(difluoromethoxy)phenyl)-2-methylpiperazine-1-carboxylate 3-(2,6-dichlorophenyl)-1-methyl-7-(methylthio)-2,3-dihydropyrimido[4,5-d]pyrimidin-4(1H)-one (100 mg, 0.283 mmol) was reacted with (R)-tert-butyl 4-(4-amino-2-(difluoromethoxy)phenyl)-2-methylpiperazine-1-carboxylate (101 mg, 0.283 mmol) following the procedure for Example 31 to give the title compound as a pale yellow solid (88 mg, 47%). $^1$H NMR (300 MHz, CDCl$_3$): δ 8.70 (s, 1H), 8.13 (br s, 1H), 7.89 (br s, 1H), 7.44 (dd, 2H), 7.29 (dd, 1H), 7.16 (br d, 1H), 6.94 (d, 1H), 6.59 (t, 1H), 4.90 (s, 2H), 4.33 (br s, 1H), 3.93 (d, 1H), 3.08-3.33 (m, 6H), 2.83 (dd, 1H), 2.65 (td, 1H), 1.48 (s, 9H), 1.32 (d, 3H). LCMS (Method C): R$_T$=1.96 min, m/z=664 [M+H]$^+$.

Step 5: (R)-3-(2,6-dichlorophenyl)-7-((3-(difluoromethoxy)-4-(3-methylpiperazin-1-yl)phenyl)amino)-1-methyl-2,3-dihydropyrimido[4,5-d]pyrimidin-4(1H)-one (R)-tert-butyl 4-(4-((6-(2,6-dichlorophenyl)-8-methyl-5-oxo-5,6,7,8-tetrahydropyrimido[4,5-d]pyrimidin-2-yl)amino)-2-(difluoromethoxy)phenyl)-2-methylpiperazine-1-carboxylate (88 mg, 0.132 mmol) was deprotected following the procedure for Example 31 to give the title compound as a pale yellow solid (27 mg, 36%). $^1$H NMR (400 MHz, DMSO-d$_6$): δ 9.95 (br s, 1H), 8.48 (s, 1H), 7.82 (br s, 1H), 7.65 (d, 2H), 7.43-7.53 (m, 2H), 7.05 (d, 1H), 7.02 (t, 1H), 4.98 (s, 2H), 3.11 (s, 3H), 3.07 (d, 2H), 2.75-2.94 (m, 3H), 2.43-2.58 (m, 1H), 2.23 (t, 1H), 0.98 (d, 3H). LCMS (Method C): R$_T$=0.93 min, m/z=564 [M+H]$^+$.

Example 133: (S)-3-(2,6-dichlorophenyl)-7-((4-(hexahydropyrazino[2,1-c][1,4]oxazin-8(1H)-yl)-3-(hydroxymethyl)phenyl)amino)-1-methyl-2,3-dihydropyrimido[4,5-d]pyrimidin-4(1H)-one

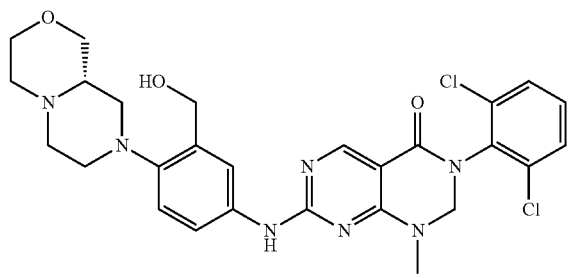 [SMILES: CN1CN(c2c(Cl)cccc2Cl)C(=O)c2cnc(Nc3ccc(N4CCN5CCOC[C@@H]5C4)c(CO)c3)nc21]

Step 1: (S)-2-(hexahydropyrazino[2,1-c][1,4]oxazin-8(1H)-yl)-5-nitrobenzaldehyde A suspension of 2-fluoro-5-nitrobenzaldehyde (400 mg, 2.365 mmol), (S)-octahydropyrazino[2,1-c][1,4]oxazine (336 mg, 2.365 mmol) [prepared as described for the R-enantiomer in J. Med. Chem., 2012, 55(12), 5887-5900, but using the opposite enantiomer of the starting material] and potassium carbonate (490 mg, 3.55 mmol) in anhydrous DMF (2.5 mL) was heated to 50° C. under a nitrogen atmosphere overnight. The reaction mixture was allowed to cool to room temperature, diluted with water (25 mL) and extracted into ethyl acetate (3×10 mL). The combined organic phases were dried over Na$_2$SO$_4$, filtered and concentrated to dryness under reduced pressure. The residue was chromatographed (silica 50 g cartridge, cyclohexane:ethyl acetate:methanol, gradient elution from 90:10:0 to 0:100:0 to 0:80:20) to give the title compound as an orange solid (506 mg, 73%). $^1$H NMR (300 MHz, CDCl$_3$): δ 10.09 (s, 1H), 8.62 (d, 1H), 8.31 (dd, 1H), 7.08 (d, 1H), 3.90 (dd, 1H), 3.65-3.79 (m, 2H), 3.25-3.47 (m, 3H), 3.20 (dt, 1H), 2.79-2.93 (m, 2H), 2.74 (dt, 1H), 2.43-2.68 (m, 3H). LCMS (Method C): R$_T$=0.48 min, m/z=292 [M+H]$^+$.

Step 2: (S)-(2-(hexahydropyrazino[2,1-c][1,4]oxazin-8(1H)-yl)-5-nitrophenyl)methanol A solution of (S)-2-(hexahydropyrazino[2,1-c][1,4]oxazin-8(1H)-yl)-5-nitrobenzaldehyde (506 mg, 1.737 mmol) in anhydrous THF (3217 µl) was cooled to 0° C. followed by the portionwise addition of sodium borohyride (65.7 mg, 1.737 mmol). The mixture was stirred at 0° C. for 90 minutes, then quenched with water (20 mL) and extracted into dichloromethane (3×15 mL). The combined organic phases were dried over Na$_2$SO$_4$, filtered and concentrated to dryness under reduced pressure to give the title compound as a yellow solid (390 mg, 77%). $^1$H NMR (300 MHz, CDCl$_3$): δ 8.29 (d, 1H), 8.14 (dd, 1H), 7.12 (d, 1H), 4.72-4.86 (m, 2H), 3.90 (dd, 1H), 3.65-3.78 (m, 2H), 3.31 (t, 1H), 3.01-3.23 (m, 3H), 2.98 (dt, 1H), 2.89 (dt, 1H), 2.72 (dt, 1H), 2.42-2.67 (m, 4H). LCMS (Method C): R$_T$=0.26 min, m/z=294 [M+H]$^+$.

Step 3: (S)-(5-amino-2-(hexahydropyrazino[2,1-c][1,4]oxazin-8(1H)-yl)phenyl)methanol A solution of (S)-2-(hexahydropyrazino[2,1-c][1,4]oxazin-8(1H)-yl)-5-nitrophenyl)methanol (390 mg, 1.330 mmol) in methanol (40 mL) was hydrogenated by H-Cube (10% Pd/C cartridge, 30 bar H$_2$, room temperature, 1 mL/min) with two-passes. The reaction mixture was concentrated to dryness under reduced pressure to give the title compound as a tan solid (296 mg, 85%). $^1$H NMR (300 MHz, CDCl$_3$): δ 7.03 (d, 1H), 6.57 (dd, 1H), 6.46 (d, 1H), 4.73 (d, 1H), 4.67 (d, 1H), 3.88 (dd, 1H), 3.71 (td, 2H), 3.61 (br s, 2H), 3.29 (dd, 1H), 2.92-3.08 (m, 2H), 2.86 (dt, 1H), 2.78 (dt, 1H), 2.70 (dt, 1H), 2.37-2.61 (m, 4H). LCMS (Method C): R$_T$=0.21 min, m/z=264 [M+H]$^+$.

Step 4: (S)-3-(2,6-dichlorophenyl)-7-((4-(hexahydropyrazino[2,1-c][1,4]oxazin-8(1H)-yl)-3-(hydroxymethyl)phenyl)amino)-1-methyl-2,3-dihydropyrimido[4,5-d]pyrimidin-4(1H)-one 3-(2,6-dichlorophenyl)-1-methyl-7-(methylthio)-2,3-dihydropyrimido[4,5-d]pyrimidin-4(1H)-one (100 mg, 0.283 mmol) was reacted with (S)-(5-amino-2-(hexahydropyrazino[2,1-c] [1,4]oxazin-8(1H)-yl)phenyl)methanol (75 mg, 0.283 mmol) following the procedure for Example 31 to give the title compound as an off-white solid (35 mg, 22%). $^1$H NMR (400 MHz, DMSO-d$_6$): δ 9.81 (br s, 1H), 8.46 (s, 1H), 7.99 (br s, 1H), 7.64 (d, 2H), 7.56 (dd, 1H), 7.48 (t, 1H), 7.00 (d, 1H), 5.06 (t, 1H), 4.96 (s, 2H), 4.48-4.61 (m, 2H), 3.76 (d, 1H), 3.64 (dd, 1H), 3.52 (t, 1H), 3.07-3.18 (m, 4H), 2.90 (d, 1H), 2.70-2.85 (m, 3H), 2.65 (d, 1H), 2.19-2.42 (m, 4H). LCMS (Method C): $R_T$=0.72 min, m/z=570 [M+H]$^+$.

Example 134: 3-(2,6-dichlorophenyl)-7-((3-(2,2-difluoro-1-hydroxyethyl)-4-((R)-3-methylpiperazin-1-yl)phenyl)amino)-1-methyl-2,3-dihydropyrimido[4,5-d]pyrimidin-4(1H)-one

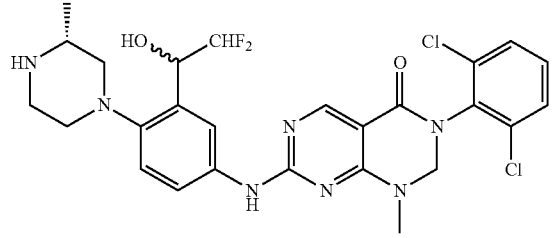

Step 1: (2R)-tert-butyl 4-(2-(2,2-difluoro-1-hydroxyethyl)-4-nitrophenyl)-2-methylpiperazine-1-carboxylate Under N2 atmosphere, CsF (10 mg, 0.07 mmol) was added to a solution of (R)-tert-butyl 4-(2-formyl-4-nitrophenyl)-2-methylpiperazine-1-carboxylate (1 g, 2.86 mmol) and (difluoromethyl)trimethylsilane (0.81 mL, 5.72 mmol) in 10 mL of DMF, then the mixture was stirred at room temperature overnight. A solution of TBAF (5.7 ml, 1 M in THF) was then added, and the whole mixture was stirred for another 1 h. After extraction with Et$_2$O and H$_2$O, the organic phase was washed with brine, and then dried over anhydrous MgSO$_4$. After the solution was filtered and the solvent was evaporated under vacuum, the residue was chromatographed to afford the title compound (0.9 g, 78%).

Step 2: (2R)-tert-butyl 4-(4-amino-2-(2,2-difluoro-1-hydroxyethyl)phenyl)-2-methylpiperazine-1-carboxylate (2R)-tert-butyl 4-(2-(2,2-difluoro-1-hydroxyethyl)-4-nitrophenyl)-2-methylpiperazine-1-carboxylate (0.3 g, 0.747 mol) was hydrogenated with an H-Cube (10% Pd/C cartridge, full H$_2$, 25° C., 1 mL/min). The solution was concentrated in vacuo to give the title compound (0.27 g, 97%).

Step 3: 3-(2,6-dichlorophenyl)-7-((3-(2,2-difluoro-1-hydroxyethyl)-4-((R)-3-methylpiperazin-1-yl)phenyl)amino)-1-methyl-2,3-dihydropyrimido[4,5-d]pyrimidin-4(1H)-one 3-(2,6-Dichlorophenyl)-1-methyl-7-(methylthio)-2,3-dihydropyrimido[4,5-d]pyrimidin-4(1H)-one (191 mg, 0.538 mmol) was reacted with (2R)-tert-butyl 4-(4-amino-2-(2,2-difluoro-1-hydroxyethyl)phenyl)-2-methylpiperazine-1-carboxylate (183 mg, 0.512 mmol) following the procedure for example 31 to give the title compound (154 mg, 52%). LCMS (Method C): $R_T$=0.78 min, m/z=578 [M+H]$^+$.

Example 135: (R)-3-(2,6-dichlorophenyl)-7-((3-(hydroxymethyl)-4-(3-(methoxymethyl)piperazin-1-yl)phenyl)amino)-1-methyl-2,3-dihydropyrimido[4,5-d]pyrimidin-4(1H)-one

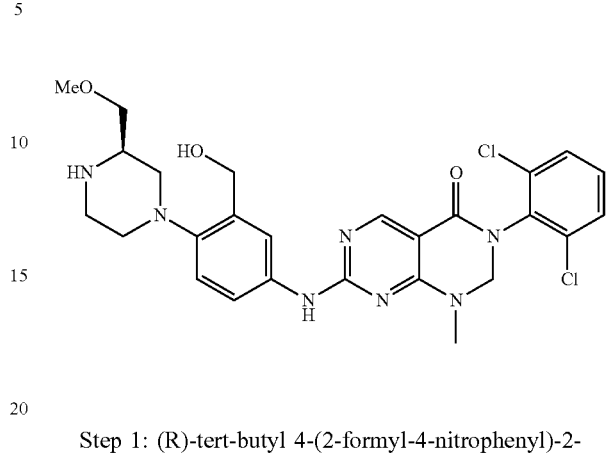

Step 1: (R)-tert-butyl 4-(2-formyl-4-nitrophenyl)-2-(methoxymethyl)piperazine-1-carboxylate 2-fluoro-5-nitrobenzaldehyde (1 g, 5.91 mmol) was reacted with (R)-tert-butyl 2-(methoxymethyl)piperazine-1-carboxylate (1 g, 4.34 mmol) following the procedure for example 21 to give the title compound (1.30 g, 79%).

Step 2: (R)-tert-butyl 4-(2-(hydroxymethyl)-4-nitrophenyl)-2-(methoxymethyl)piperazine-1-carboxylate (R)-tert-butyl 4-(2-formyl-4-nitrophenyl)-2-(methoxymethyl) piperazine-1-carboxylate (0.27 g, 0.712 mol) was reacted with sodium borohydride (0.032 g, 0.854 mmol) following the procedure for example 21 to give the title compound (0.24 g, 88%).

Step 3: (R)-tert-butyl 4-(4-amino-2-(hydroxymethyl)phenyl)-2-(methoxymethyl)piperazine-1-carboxylate (R)-tert-butyl 4-(2-(hydroxymethyl)-4-nitrophenyl)-2-(methoxymethyl)piperazine-1-carboxylate (0.24 g, 0.63 mmol) was hydrogenated using an H-cube apparatus (10% Pd/C cartridge, full H$_2$, 25° C., 1 mL/min). The solution was concentrated in vacuo to give the title compound (0.21 g, 95%).

Step 4: (R)-3-(2,6-dichlorophenyl)-7-((3-(hydroxymethyl)-4-(3-(methoxymethyl)piperazin-1-yl)phenyl)amino)-1-methyl-2,3-dihydropyrimido[4,5-d]pyrimidin-4(1H)-one 3-(2,6-Dichlorophenyl)-1-methyl-7-(methylthio)-2,3-dihydropyrimido [4,5-d]pyrimidin-4(1H)-one (244 mg, 0.687 mmol) was reacted with (R)-tert-butyl 4-(4-amino-2-(hydroxymethyl) phenyl)-2-(methoxymethyl)piperazine-1-carboxylate (230 mg, mmol) following the procedure for Example 31 to give the title compound (190 mg, 52%). $^1$H NMR (400 MHz, MeOD): δ 8.52 (s, 1H), 7.88 (s, 1H), 7.54 (m, 3H), 7.41 (m, 1H), 7.12 (d, 2H), 4.98 (s, 2H), 4.74 (s, 2H), 3.80 (m, 1H), 3.28 (s, 3H), 3.19 (s, 3H), 3.05 (m, 1H), 2.95 (m, 1H), 2.00 (d, 1H), 1.84 (d, 1H). LCMS (Method C): $R_T$=0.70 min, m/z=558 [M+H]$^+$.

Example 136: 3-(2,6-dichlorophenyl)-1-methyl-7-((3-((methylamino)methyl)-4-(piperidin-1-yl)phenyl)amino)-2,3-dihydropyrimido[4,5-d]pyrimidin-4(1H)-one

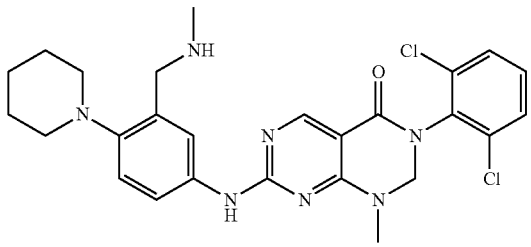 [SMILES: CNCc1cc(Nc2ncc3c(n2)N(C)CN(c2c(Cl)cccc2Cl)C3=O)ccc1N1CCCCC1]

Step 1: 5-nitro-2-(piperidin-1-yl)benzaldehyde 2-fluoro-5-nitrobenzaldehyde (1 g, 5.91 mmol) was dissolved in DMF (10 mL) and piperidine (0.64 mL, 6.50 mmol) was added, followed by DIPEA (2.27 mL, 13.0 mmol). The mixture was stirred overnight at room temperature. Water was added and the resulting precipitate was collected by filtration and dried in vacuo to give the title compound (1.3 g, 94%) as a yellow solid which was used without further purification. LCMS (Method C): $R_T$=1.59 min, m/z=235 [M+H]$^+$.

Step 2: N-methyl-1-(5-nitro-2-(piperidin-1-yl)phenyl)methanamine 5-nitro-2-(piperidin-1-yl)benzaldehyde (250 mg, 1.067 mmol) was dissolved in methanol (1 mL) and sodium bicarbonate (108 mg, 1.281 mmol) was added followed by methylamine (2M in THF, 0.640 mL, 1.281 mmol). The mixture was stirred for 2 h at 70° C., then cooled to 0° C. Sodium borohydride (48.5 mg, 1.281 mmol) was added and the mixture was stirred overnight (allowed to return to room temperature). A drop of water was added and the mixture was concentrated in vacuo. The residue was dissolved in methanol and acidified with HCl. The resulting solution was added to a 5 g SCX cartridge and washed with MeOH, then eluted 2 M NH3/MeOH to give the title compound as a glass (245 mg, 92%). LCMS (Method C): $R_T$=0.70 min, m/z=250 [M+H]$^+$.

Step 3: tert-butyl methyl(5-nitro-2-(piperidin-1-yl)benzyl)carbamate

A solution of di-tert-butyl-dicarbonate (236 mg, 1.081 mmol) in DCM (5 mL) was added to N-methyl-1-(5-nitro-2-(piperidin-1-yl)phenyl)methanamine (245 mg, 0.983 mmol). Triethylamine (0.274 mL, 1.965 mmol) was added and the mixture was stirred at room temperature for 90 min. The mixture was diluted with water and the organic layer was collected using a phase separator cartridge and concentrated to give the title compound (344 mg, 99%) as a glass. LCMS (Method C): $R_T$=2.05 min, m/z=350 [M+H]$^+$.

Step 4: tert-Butyl 5-amino-2-(piperidin-1-yl)benzyl(methyl)carbamate tert-butyl methyl(5-nitro-2-(piperidin-1-yl)benzyl)carbamate (344 mg, 0.98 mmol) was subjected to continuous flow hydrogenation (H-cube, 10% Pd/C cartridge, room temperature, 50 bar, methanol solvent) to give the title compound (306 mg, 96%) as a yellow syrup, which was used without further purification. LCMS (Method C): $R_T$=1.03 min, m/z=320 [M+H]$^+$.

Step 5: 3-(2,6-dichlorophenyl)-1-methyl-7-((3-((methylamino)methyl)-4-(piperidin-1-yl)phenyl)amino)-2,3-dihydropyrimido[4,5-d]pyrimidin-4(1H)-one tert-Butyl 5-amino-2-(piperidin-1-yl)benzyl(methyl)carbamate (71.9 mg, 0.22 mmol) was reacted with 3-(2,6-dichlorophenyl)-1-methyl-7-(methylthio)-2,3-dihydropyrimido[4,5-d]pyrimidin-4(1H)-one (80 mg, 0.22 mmol) as described in example 1 to give the title compound (70 mg, 58%) as a white solid. $^1$H NMR (300 MHz, DMSO-d$_6$): δ 9.76 (br s, 1H), 8.46 (s, 1H), 7.64 (br s, 1H), 7.52 (d, 2H), 7.49 (m, 2H), 7.03 (d, 1H), 4.97 (s, 2H), 3.67 (m, 2H), 3.15 (s, 3H), 2.78 (m, 4H), 2.33 (s, 3H), 1.64 (m, 4H), 1.52 (m, 2H). LCMS (Method C): $R_T$=1.13 min, m/z=526 [M+H]$^+$.

Example 137: 3-(2,6-dichlorophenyl)-1-methyl-7-((3-((methylamino)methyl)-4-(pyrrolidin-1-yl)phenyl)amino)-2,3-dihydropyrimido[4,5-d]pyrimidin-4(1H)-one

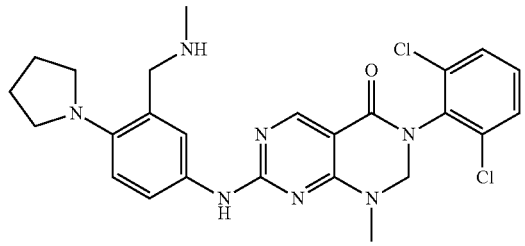 [SMILES: CNCc1cc(Nc2ncc3c(n2)N(C)CN(c2c(Cl)cccc2Cl)C3=O)ccc1N1CCCC1]

Step 1: (5-nitro-2-(pyrrolidin-1-yl)phenyl)methanol 2-fluoro-5-nitrobenzaldehyde (1 g, 5.91 mmol) was dissolved in DMF (10 mL) and pyrrolidine (0.54 mL, 6.50 mmol) was added, followed by DIPEA (2.27 mL, 13.0 mmol). The mixture was stirred overnight at room temperature. Water was added and the resulting precipitate was collected by filtration and dried in vacuo to give the title compound (1.30 g, 99%) as a yellow solid which was used without further purification. LCMS (Method C): $R_T$=1.34 min, m/z=221 [M+H]$^+$.

Step 2: N-methyl-1-(5-nitro-2-(pyrrolidin-1-1)phenyl)methanamine (5-nitro-2-(pyrrolidin-1-yl)phenyl)methanol (235 mg, 1.07 mmol) was dissolved in methanol (1 mL) and sodium bicarbonate (108 mg, 1.281 mmol) was added followed by methylamine (2M in THF, 0.640 mL, 1.281 mmol). The mixture was stirred for 2 h at 70° C., then cooled to 0° C. Sodium borohydride (48.5 mg, 1.28 mmol) was added and the mixture was stirred overnight (allowed to return to room temperature). A drop of water was added and the mixture was concentrated in vacuo. The residue was dissolved in methanol and acidified with HCl. The resulting solution was added to a 5 g SCX cartridge and washed with MeOH, then eluted 2 M NH$_3$/MeOH to give the title compound as a glass (240 mg, 96%). LCMS (Method C): R$_T$=0.61 min, m/z=236 [M+H]$^+$.

Step 3: tert-butyl methyl(5-nitro-2-(pyrrolidin-1-yl)benzyl)carbamate

A solution of di-tert-butyl-dicarbonate (236 mg, 1.08 mmol) in DCM (5 mL) was added to N-methyl-1-(5-nitro-2-(pyrrolidin-1-yl)phenyl)methanamine (235 mg, 1.00 mmol). Triethylamine (0.274 mL, 1.965 mmol) was added and the mixture was stirred at room temperature for 90 min. The mixture was diluted with water and the organic layer was collected using a phase separator cartridge and concentrated to give the title compound (333 mg, 99%) as a glass. LCMS (Method C): R$_T$=1.84 min, m/z=336 [M+H]$^+$.

Step 4: tert-butyl 5-amino-2-(pyrrolidin-1-yl)benzyl(methyl)carbamate tert-Butyl methyl(5-nitro-2-(pyrrolidin-1-yl)benzyl)carbamate (333 mg, 0.99 mmol) was subjected to continuous flow hydrogenation (H-cube, 10% Pd/C cartridge, room temperature, 50 bar, methanol solvent) to give the title compound (312 mg, 102%) as a yellow syrup, which was used without further purification. LCMS (Method C): R$_T$=0.91 min, m/z=306 [M+H]$^+$.

Step 5: 3-(2,6-dichlorophenyl)-1-methyl-7-((3-((methylamino)methyl)-4-(pyrrolidin-1-yl)phenyl)amino)-2,3-dihydropyrimido[4,5-d]pyrimidin-4(1H)-one tert-Butyl 5-amino-2-(pyrrolidin-1-yl)benzyl(methyl)carbamate (69 mg, 0.22 mmol) was reacted with 3-(2,6-dichlorophenyl)-1-methyl-7-(methylthio)-2,3-dihydropyrimido[4,5-d]pyrimidin-4(1H)-one (80 mg, 0.22 mmol) as described in example 1 to give the title compound (51 mg, 50%) as a white solid. $^1$H NMR (300 MHz, DMSO-d$_6$): δ 9.70 (br s, 1H), 8.45 (s, 1H), 7.92 (br s, 1H), 7.65 (m, 2H), 7.48 (t, 2H), 6.91 (d, 1H), 4.96 (s, 2H), 3.65 (s, 2H), 3.12 (s, 3H), 3.06 (m, 4H), 2.32 (s, 3H), 1.86 (m, 4H). LCMS (Method C): R$_T$=0.96 min, m/z=512 [M+H]$^+$.

Example 138: 7-((4-(4-acetylpiperazin-1-yl)-3-(pyrrolidin-1-ylmethyl)phenyl)amino)-3-(2,6-dichlorophenyl)-1-methyl-2,3-dihydropyrimido[4,5-d]pyrimidin-4(1H)-one

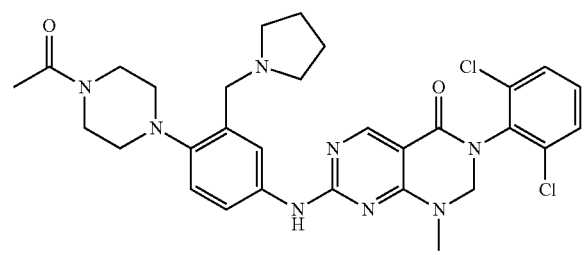 [SMILES: CC(=O)N1CCN(c2ccc(Nc3ncc4c(n3)N(C)CN(c3c(Cl)cccc3Cl)C4=O)cc2CN2CCCC2)CC1]

Step 1: 1-(4-(4-nitro-2-(pyrrolidin-1-ylmethyl)phenyl)piperazin-1-yl)ethanone 2-(4-acetylpiperazin-1-yl)-5-nitrobenzaldehyde (296 mg, 1.07 mmol) was dissolved in methanol (1 mL) and sodium bicarbonate (108 mg, 1.28 mmol) was added followed by pyrrolidine (0.11 mL, 1.28 mmol). The mixture was stirred for 2 h at 70° C., then cooled to 0° C. Sodium borohydride (48.5 mg, 1.28 mmol) was added and the mixture was stirred overnight (allowed to return to room temperature). A drop of water was added and the mixture was concentrated in vacuo. The residue was dissolved in methanol and acidified with HCl. The resulting solution was added to a 5 g SCX cartridge and washed with MeOH, then eluted with 2 M NH$_3$/MeOH to give the title compound as a glass (212 mg, 60%). LCMS (Method C): R$_T$=0.25 min, m/z=333 [M+H]$^+$.

Step 2: 1-(4-(4-amino-2-(pyrrolidin-1-ylmethyl)phenyl)piperazin-1-yl)ethanone 1-(4-(4-nitro-2-(pyrrolidin-1-ylmethyl)phenyl)piperazin-1-yl)ethanone (205 mg, 0.61 mmol) was subjected to continuous flow hydrogenation (H-cube, 10% Pd/C cartridge, room temperature, 50 bar, methanol solvent) to give the title compound (196 mg, 106%) as a yellow syrup, which was used without further purification. LCMS (Method C): R$_T$=0.24 min, m/z=303 [M+H]$^+$.

Step 3: 7-((4-(4-acetylpiperazin-1-yl)-3-(pyrrolidin-1-ylmethyl)phenyl)amino)-3-(2,6-dichlorophenyl)-1-methyl-2,3-dihydropyrimido[4,5-d]pyrimidin-4(1H)-one 1-(4-(4-Amino-2-(pyrrolidin-1-ylmethyl)phenyl)piperazin-1-yl)ethanone (68 mg, 0.22 mmol) was reacted with 3-(2,6-dichlorophenyl)-1-methyl-7-(methylthio)-2,3-dihydropyrimido[4,5-d]pyrimidin-4(1H)-one (80 mg, 0.22 mmol) as described in example 131 to give the title compound (4 mg, 1%) as a yellow solid. $^1$H NMR (300 MHz, DMSO-d$_6$): δ 9.77 (br s, 1H), 8.47 (s, 1H), 7.98 (br s, 1H), 7.66 (d, 2H), 7.50 (m, 2H), 7.03 (d, 1H), 4.98 (s, 2H), 3.65 (s, 2H), 3.57 (m, 4H), 3.14 (s, 3H), 2.80 (m, 4H), 2.04 (s, 3H), 1.70 (m, 4H); one signal mostly obscured by solvent at 2.50, presumed to be 4H. LCMS (Method C): R$_T$=0.90 min, m/z=609 [M+H]$^+$.

Example 139: (R)-3-(2,6-dichlorophenyl)-7-((3-(difluoromethyl)-4-(3-methylpiperazin-1-yl)phenyl)amino)-1-methyl-2,3-dihydropyrimido[4,5-d]pyrimidin-4(1H)-one

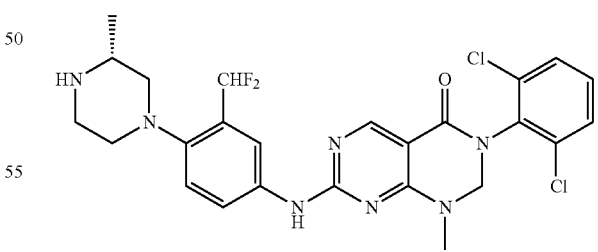

Step 1: (R)-tert-butyl 4-(2-(difluoromethyl)-4-nitrophenyl)-2-methylpiperazine-1-carboxylate A solution of (R)-tert-butyl 4-(2-formyl-4-nitrophenyl)-2-methylpiperazine-1-carboxylate (0.5 g, 1.43 mmol) and DAST (0.6 g, 3.72 mmol) in DCM (20 mL) was stirred at room temperature overnight. It was then diluted with a saturated solution of sodium bicarbonate (5 mL). The organic layer was dried over magnesium sulfate, filtered and concentrated in vacuo. The residue was purified by Biotage chromatography to give the title compound (0.43 g, 81%). LCMS (Method A) $R_T$=0. 1.65 min, m/z=372 [M+H]$^+$.

Step 2: (R)-tert-butyl 4-(4-amino-2-(difluoromethyl) phenyl)-2-methylpiperazine-1-carboxylate A solution of (R)-tert-butyl 4-(2-(difluoromethyl)-4-nitrophenyl)-2-methylpiperazine-1-carboxylate (0.3 g, 0.8 mmol) in methanol (30 mL) was passed through an H-Cube apparatus fitted with a 10% Pd—C cartridge under the following settings [1.0 ml/min flow, 40° C., Full $H_2$ mode)]. The solvent was removed in vacuo to afford the title compound which was used without further purification (270 mg, 97%). LCMS (Method A): $R_T$=1.65 min, m/z=342 [M+H]$^+$.

Step 3: (R)-3-(2,6-dichlorophenyl)-7-((3-(difluoromethyl)-4-(3-methylpiperazin-1-yl)phenyl)amino)-1-methyl-2,3-dihydropyrimido[4,5-d]pyrimidin-4(1H)-one 3-(2,6-Dichlorophenyl)-1-methyl-7-(methylthio)-2,3-dihydropyrimido[4,5-d]pyrimidin-4(1H)-one (183 mg, 0.516 mmol) was reacted with tert-5 butyl 4-(4-amino-2-methoxyphenyl) piperazine-1-carboxylate (160 mg, 0.47 mmol) following the procedure for Example 31 to give the title compound (121 mg, 47%). $^1$H NMR (400 MHz, CDCl$_3$): δ 8.72 (s, 1H), 8.27 (s, 1H), 7.83 (s, 1H), 7.50 (br s, 1H), 7.44 (d, 2H), 7.30 (m, 1H), 7.22 (s, 1H), 7.09 (t, 1H), 5.01 (d, 1H), 4.91 (s, 2H), 3.21 (s, 3H), 3.09 (m, 3H), 2.93 (m, 2H), 2.77 (m, 1H), 2.48 (m, 1H), 1.11 (d, 3H). LCMS (Method C): $R_T$=0.93 min, m/z=548 [M+H]$^+$.

Example 140: (R)-3-(2,6-dichlorophenyl)-7-((3-(2-hydroxypropan-2-yl)-4-(3-methylpiperazin-1-yl) phenyl)amino)-1-methyl-2,3dihydropyrimido [4,5-d] pyrimidin-4(1H)-one

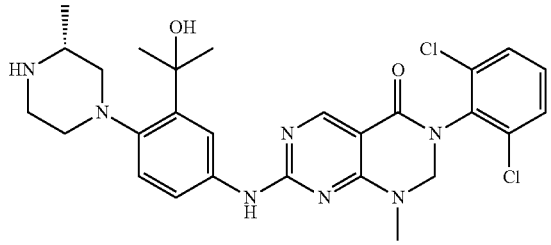 [SMILES: C[C@@H]1CN(c2ccc(Nc3ncc4c(n3)N(C)CN(c3c(Cl)cccc3Cl)C4=O)cc2C(C)(C)O)CCN1]

Step 1: (R)-tert-butyl 4-(2-(ethoxycarbonyl)-4-nitrophenyl)-2-methylpiperazine-1-carboxylate A suspension of ethyl 2-fluoro-5-nitrobenzoate (2.13 g, 10 mmol), (R)-tert-butyl 2-methylpiperazine-1-carboxylate (2 g, 10 mmol) and potassium carbonate (2.1 g, 15 mmol) in anhydrous DMF (20 mL) was heated to 50° C. under a nitrogen atmosphere for 16 h. The reaction mixture was allowed to cool to room temperature, partitioned between water (100 mL) and ethyl acetate (100 mL). The ethyl acetate was separated and washed with water (3×20 ml), dried (anhydrous sodium sulfate), filtered and reduced in vacuo. The residue was purified by flash chromatography (0-100% ethyl acetate in cyclohexane) to afford the title compound (2.8 g, 71%). LCMS (Method A): $R_T$=1.83 min, m/z=394 [M+H]$^+$.

Step 2: (R)-tert-butyl 4-(4-amino-2-(ethoxycarbonyl)phenyl)-2-methylpiperazine-1-carboxylate A solution of (R)-tert-butyl 4-(2-(ethoxycarbonyl)-4-nitrophenyl)-2-methylpiperazine-1-carboxylate (500 mg, 1.27 mmol) in methanol (30 ml) was passed through an H-Cube apparatus fitted with a 10% Pd—C cartridge under the following settings [1.0 ml/min flow, 40° C., Full $H_2$ mode)]. The solvent was removed in vacuo to afford the title compound which was used without further purification (425 mg, 92%). LCMS (Method A) $R_T$=1.2 min, m/z=364 [M+H]$^+$.

Step 3: (R)-tert-butyl 4-(4-amino-2-(2-hydroxypropan-2-yl)phenyl)-2-methylpiperazine-1-carboxylate To a solution of (R)-tert-butyl 4-(4-amino-2-(ethoxycarbonyl)phenyl)-2-methylpiperazine-1-carboxylate (0.8 g, 2.2 mmol) in dry THF (30 mL) at 0° C. under nitrogen was added dropwise a solution of methyl magnesium bromide in THF (1.4M, 7.26 mmol). The resulting was solution was stirred at room temperature overnight then quenched with a saturated solution of ammonium chloride. The resulting solution was diluted with ethyl acetate (100 mL). The organic layer was dried over magnesium sulfate, filtered and concentrated in vacuo. The residue was purified by biotage chromatography to afford the title compound (0.16 g, 20.8%). LCMS (Method A): $R_T$=0.86 min, m/z=350 [M+H]$^+$.

Step 4: (R)-3-(2,6-dichlorophenyl)-7-((3-(2-hydroxypropan-2-yl)-4-(3-methylpiperazin-1-yl)phenyl) amino)-1-methyl-2,3dihydropyrimido [4,5-d] pyrimidin-4(1H)-one 3-(2,6-Dichlorophenyl)-1-methyl-7-(methylthio)-2,3-dihydropyrimido [4,5-d]pyrimidin-4(1H)-one (178 mg, 0.501 mmol) was reacted with (R)-tert-butyl 4-(4-amino-2-(2-hydroxypropan-2-yl)phenyl)-2-methylpiperazine-1-carboxylate (160 mg, 4.77 mmol) following the procedure for example 31 to give the title compound (30 mg, 9.8%). $^1$H NMR (400 MHz, CDCl$_3$): δ 9.18 (s, 1H), 8.72 (s, 1H), 7.60 (s, 1H), 7.52 (dd, 1H), 7.47 (m, 1H), 7.44 (m, 1H), 7.32 (m, 2H), 5.30 (s, 1H), 4.90 (s, 2H), 3.21 (s, 3H), 3.2-3.05 (m, 3H), 2.99 (m, 3H), 2.67 (m, 1H), 1.61 (s, 3H), 1.60 (s, 3H), 1.15 (d, 3H). LCMS (Method C): $R_T$=0.75 min, m/z=556 [M+H]$^+$.

Example 141: 3-(2,6-dichlorophenyl)-1-methyl-7-((4-(piperazin-1-yl)-3-(((2,2,2-trifluoroethyl)amino) methyl)phenyl)amino)-2,3-dihydropyrimido[4,5-d] pyrimidin-4(1H)-one

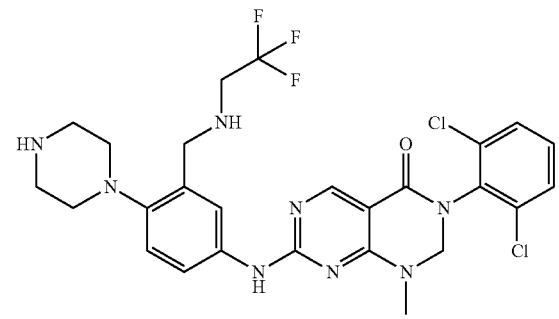 [SMILES: CN1CN(c2c(Cl)cccc2Cl)C(=O)c2cnc(Nc3ccc(N4CCNCC4)c(CNCC(F)(F)F)c3)nc21]

Step 1: tert-butyl 4-(2-(chloromethyl)-4-nitrophenyl)piperazine-1-carboxylate tert-butyl 4-(2-(hydroxymethyl)-4-nitrophenyl)piperazine-1-carboxylate (900 mg, 2.67 mmol) was dissolved in DMF (10 mL). Triethylamine (1.859 mL, 13.3 mmol) was added, followed by methanesulfonyl chloride (0.624 mL, 8.00 mmol), and the mixture was stirred overnight at 60° C. The solvent was removed in vacuo. The residue was diluted with water and extracted with ethyl acetate (×2). The combined organic extracts were dried with MgSO$_4$ and concentrated. The residue was chromatographed (25 g Si; eluted 0-100% EtOAc/cyclohexane) to give the title compound (410 mg, 43%) as a yellow syrup that crystallised (yellow rosettes) on standing. LCMS (Method C): R$_T$=1.86 min, m/z=356 [M+H]$^+$.

Step 2: tert-butyl 4-(4-nitro-2-(((2,2,2-trifluoroethyl)amino)methyl)phenyl)piperazine-1-carboxylate tert-butyl 4-(2-(chloromethyl)-4-nitrophenyl)piperazine-1-carboxylate (200 mg, 0.562 mmol) was suspended in a mixture of 2,2,2-trifluoroethylamine (0.5 mL, 6.37 mmol), DIPEA (0.196 mL, 1.124 mmol) and DMF (0.5 mL). The mixture was heated at 50° C. overnight, then concentrated in vacuo (azeotroped with toluene×3). The residue was dissolved in dichloromethane and the solution was washed with saturated aqueous sodium carbonate solution then concentrated to give the title compound (180 mg, 77%) as a yellow oil, which was used without further purification. LCMS (Method C): R$_T$=1.82 min, m/z=418 [M+H]$^+$.

Step 3: tert-butyl 4-(4-amino-2-(((2,2,2-trifluoroethyl)amino)methyl)phenyl)piperazine-1-carboxylate tert-Butyl 4-(4-nitro-2-(((2,2,2-trifluoroethyl)amino)methyl)phenyl)piperazine-1-carboxylate (180 mg, 0.43 mmol) was subjected to continuous flow hydrogenation (H-cube, 10% Pd/C cartridge, room temperature, 50 bar, methanol solvent) to give the title compound (125 mg, 75%) as a brown glass, which was used without further purification. LCMS (Method C): R$_T$=0.92 min, m/z=389 [M+H]$^+$.

Step 4: 3-(2,6-dichlorophenyl)-1-methyl-7-((4-(piperazin-1-yl)-3-(((2,2,2-trifluoroethyl)amino)methyl)phenyl)amino)-2,3-dihydropyrimido[4,5-d]pyrimidin-4(1H)-one tert-Butyl 4-(4-amino-2-(((2,2,2-trifluoroethyl)amino)methyl)phenyl)piperazine-1-carboxylate (109 mg, 0.28 mmol) was reacted with 3-(2,6-dichlorophenyl)-1-methyl-7-(methylthio)-2,3-dihydropyrimido[4,5-d]pyrimidin-4(1H)-one (100 mg, 0.28 mmol) as described in example 1 to give the title compound (14 mg, 8%) as an off-white solid. $^1$H NMR (300 MHz, DMSO-d$_6$): δ 9.83 (br s, 1H), 8.46 (s, 1H), 7.97 (br s, 1H), 7.65 (d, 2H), 7.49 (m, 2H), 7.05 (d, 1H), 4.97 (s, 2H), 3.81 (d, 2H), 3.26 (m, 2H), 3.11 (s, 3H), 2.76 (m, 8H). LCMS (Method C): R$_T$=0.84 min, m/z=595 [M+H]$^+$.

Example 142: (R)-3-(2,6-dichlorophenyl)-7-((2-fluoro-4-(3-methylpiperazin-1-yl)phenyl)amino)-1-methyl-2,3-dihydropyrimido[4,5-d]pyrimidin-4(1H)-one

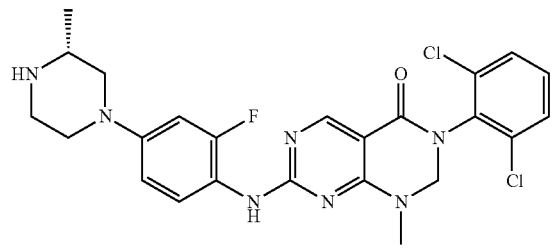 [SMILES: C[C@@H]1CN(c2ccc(Nc3ncc4c(n3)N(C)CN(c3c(Cl)cccc3Cl)C4=O)c(F)c2)CCN1]

Step 1: (R)-tert-butyl 4-(3-fluoro-4-nitrophenyl)-2-methylpiperazine-1-carboxylate A suspension of 2,4-difluoro-1-nitrobenzene (0.827 mL, 7.54 mmol), (R)-tert-butyl 2-methylpiperazine-1-carboxylate (1.511 g, 7.54 mmol) and potassium carbonate (1.564 g, 11.31 mmol) in anhydrous DMSO (6 mL) was heated to 50° C. under a nitrogen atmosphere overnight. The reaction mixture was allowed to cool to room temperature, diluted with water (50 mL) and extracted into ethyl acetate (3×25 mL). The combined organic phases were washed with 50:50 water:brine (3×40 mL), dried over Na$_2$SO$_4$, filtered and concentrated to dryness under reduced pressure. The residue was purified by Biotage chromatography (silica 100 g cartridge, cyclohexane:ethyl acetate, gradient elution from 90:10 to 40:60) to give the title compound as a yellow oil (911 mg, 36%). $^1$H NMR (300 MHz, CDCl$_3$) δ 8.03 (t, 1H), 6.40-6.56 (m, 2H), 4.26-4.40 (m, 1H), 3.93 (dt, 1H), 3.70 (dtd, 1H), 3.57 (ddd, 1H), 3.28-3.41 (m, 2H), 3.16 (ddd, 1H), 1.48 (s, 9H), 1.21 (d, 3H). LCMS (Method C): R$_T$=1.71 min, m/z=340 [M+H]$^+$.

Step 2: (R)-tert-butyl 4-(4-amino-3-fluorophenyl)-2-methylpiperazine-1-carboxylate A solution of (R)-tert-butyl 4-(3-fluoro-4-nitrophenyl)-2-methylpiperazine-1-carboxylate (911 mg, 2.68 mmol) in methanol (60 mL) was hydrogenated by H-Cube (10% Pd/C cartridge, 30 bar H2, room temperature, 1 mL/min) with three-passes. The reaction mixture was concentrated to dryness under reduced pressure to give the title compound as a blue oil (690 mg, 83%). $^1$H NMR (300 MHz, CDCl$_3$) δ 6.72 (dd, 1H), 6.62 (dd, 1H), 6.54 (ddd, 1H), 4.24-4.38 (m, 1H), 3.87-3.97 (m, 1H), 3.46 (br s, 2H), 3.09-3.34 (m, 3H), 2.79 (dd, 1H), 2.61 (td, 1H), 1.48 (s, 9H), 1.30 (d, 3H). LCMS (Method C): R$_T$=1.34 min, m/z=310 [M+H]$^+$.

Step 3: (R)-tert-butyl 4-(4-((6-(2,6-dichlorophenyl)-8-methyl-5-oxo-5,6,7,8-tetrahydropyrimido[4,5-d]pyrimidin-2-yl)amino)-3-fluorophenyl)-2-methylpiperazine-1-carboxylate 3-(2,6-dichlorophenyl)-1-methyl-7-(methylthio)-2,3-dihydropyrimido[4,5-d]pyrimidin-4(1H)-one (200 mg, 0.566 mmol) was reacted with (R)-tert-butyl 4-(4-amino-3-fluorophenyl)-2-methylpiperazine-1-carboxylate (175 mg, 0.566 mmol) following the procedure for Example 31 to give the title compound as a pale brown solid (104 mg, 30%). $^1$H NMR (300 MHz, CDCl$_3$): δ 8.71 (s, 1H), 8.12 (t, 1H), 7.44 (dd, 2H), 7.28 (dd, 1H), 7.24 (br s, 1H), 6.61-6.72 (m, 2H), 4.88 (s, 2H), 4.34 (br s, 1H), 3.95 (td, 1H), 3.46 (br d, 1H), 3.18-3.36 (m, 2H), 3.16 (s, 3H), 2.93 (dd, 1H), 2.74 (td, 1H), 1.48 (s, 9H), 1.29 (d, 3H). LCMS (Method C): R$_T$=1.80 min, m/z=616 [M+H]$^+$.

Step 4: (R)-3-(2,6-dichlorophenyl)-7-((2-fluoro-4-(3-methylpiperazin-1-yl)phenyl)amino)-1-methyl-2,3-dihydropyrimido[4,5-d]pyrimidin-4(1H)-one ((R)-tert-butyl 4-(4-((6-(2,6-dichlorophenyl)-8-methyl-5-oxo-5,6,7,8-tetrahydropyrimido[4,5-d]pyrimidin-2-yl)amino)-3-fluorophenyl)-2-methylpiperazine-1-carboxylate (104 mg, 0.169 mmol) was deprotected following the procedure for Example 31 to give the title compound as a pale yellow solid (55 mg, 63%). $^1$H NMR (300 MHz, DMSO-d$_6$): δ 9.18 (s, 1H), 8.38 (s, 1H), 7.64 (d, 2H), 7.47 (t, 1H), 7.35 (br s, 1H), 6.66-6.86 (m, 2H), 4.91 (s, 2H), 3.52 (t, 2H), 2.86-3.06 (m, 4H), 2.76 (t, 2H), 2.53-2.61 (m, 1H), 2.18 (t, 1H), 1.02 (d, 3H). LCMS (Method C): R$_T$=0.81 min, m/z=516 [M+H]$^+$.

Example 143: 7-((4-(4-acetylpiperazin-1-yl)-3-((methylamino)methyl)phenyl)amino)-3-(2,6-dichlorophenyl)-1-methyl-2,3-dihydropyrimido[4,5-d]pyrimidin-4(1H)-one

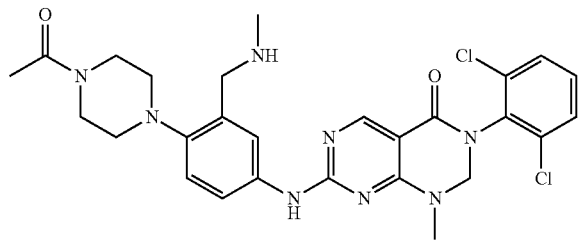 [SMILES: CNCc1cc(Nc2ncc3c(n2)N(C)CN(c2c(Cl)cccc2Cl)C3=O)ccc1N1CCN(C(C)=O)CC1]

Step 1: 2-(4-acetylpiperazin-1-yl)-5-nitrobenzaldehyde

2-Fluoro-5-nitrobenzaldehyde (1.00 g, 5.91 mmol) was dissolved in DMF (10 mL) and 1-(piperazin-1-yl)ethanone (0.83 g, 6.50 mmol) was added, followed by DIPEA (2.27 mL, 13.0 mmol). The mixture was stirred overnight at room temperature. Water was added and the mixture was extracted with ethyl acetate (×2). The combined organic layers were washed with brine and concentrated in vacuo. The residue was dried by toluene azeotrope to give the title compound (1.20 g, 73%) as a yellow syrup that partially crystallised on standing. LCMS (Method C): R$_T$=0.95 min, m/z=278 [M+H]$^+$.

Step 2: 1-(4-(2-((methylamino)methyl)-4-nitrophenyl)piperazin-1-yl)ethanone 2-(4-acetylpiperazin-1-yl)-5-nitrobenzaldehyde (296 mg, 1.07 mmol) was dissolved in methanol (1 mL) and sodium bicarbonate (108 mg, 1.281 mmol) was added followed by methylamine (2M in THF, 0.640 mL, 1.281 mmol). The mixture was stirred for 2 h at 70° C., then cooled to 0° C. Sodium borohydride (48.5 mg, 1.28 mmol) was added and the mixture was stirred overnight (allowed to return to room temperature). A drop of water was added and the mixture was concentrated in vacuo. The residue was dissolved in methanol and acidified with HCl. The resulting solution was added to a 5 g SCX cartridge and washed with MeOH, then eluted with 2 M NH$_3$/MeOH to give the title compound as a glass (256 mg, 82%). LCMS (Method C): R$_T$=0.26 min, m/z=293 [M+H]$^+$.

Step 3: tert-butyl 2-(4-acetylpiperazin-1-yl)-5-nitrobenzyl(methyl)carbamate

A solution of di-tert-butyl-dicarbonate (236 mg, 1.08 mmol) in DCM (5 mL) was added to 1-(4-(2-((methylamino)methyl)-4-nitrophenyl)piperazin-1-yl)ethanone (250 mg, 0.85 mmol). Triethylamine (0.274 mL, 1.965 mmol) was added and the mixture was stirred at room temperature for 90 min. The mixture was diluted with water and the organic layer was collected using a phase separator cartridge and concentrated to give the title compound (334 mg, 92%) as a glass. LCMS (Method C): R$_T$=1.41 min, m/z=393 [M+H]$^+$.

Step 4: tert-butyl 2-(4-acetylpiperazin-1-yl)-5-aminobenzyl(methyl)carbamate tert-butyl 2-(4-acetylpiperazin-1-yl)-5-nitrobenzyl(methyl)carbamate (332 mg, 0.85 mmol) was subjected to continuous flow hydrogenation (H-cube, 10% Pd/C cartridge, room temperature, 50 bar, methanol solvent) to give the title compound (300 mg, 98%) as a yellow syrup, which was used without further purification. LCMS (Method C): R$_T$=0.77 min, m/z=363 [M+H]$^+$.

Step 5: 7-((4-(4-acetylpiperazin-1-yl)-3-((methylamino)methyl)phenyl)amino)-3-(2,6-dichlorophenyl)-1-methyl-2,3-dihydropyrimido[4,5-d]pyrimidin-4(1H)-one tert-Butyl 2-(4-acetylpiperazin-1-yl)-5-aminobenzyl(methyl)carbamate (82 mg, 0.22 mmol) was reacted with 3-(2,6-dichlorophenyl)-1-methyl-7-(methylthio)-2,3-dihydropyrimido[4,5-d]pyrimidin-4(1H)-one (80 mg, 0.22 mmol) as described in example 1 to give the title compound (32 mg, 28%) as a white solid. $^1$H NMR (300 MHz, DMSO-d$_6$): δ 9.87 (br s, 1H), 8.47 (s, 1H), 7.93 (br s, 1H), 7.67 (m, 4H), 7.08 (d, 1H), 4.97 (s, 2H), 3.79 (s, 2H), 3.57 (m, 4H), 3.12 (s, 3H), 2.78 (m, 4H), 2.27 (s, 3H), 2.04 (s, 3H). LCMS (Method C): R$_T$=0.83 min, m/z=569 [M+H]$^+$.

Example 144: 7-((4-(4-acetylpiperazin-1-yl)-3-((dimethylamino)methyl)phenyl)amino)-3-(2,6-dichlorophenyl)-1-methyl-2,3-dihydropyrimido[4,5-d]pyrimidin-4(1H)-one

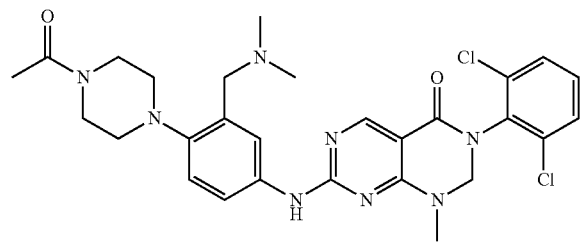 [SMILES: CC(=O)N1CCN(c2ccc(Nc3ncc4c(n3)N(C)CN(c3c(Cl)cccc3Cl)C4=O)cc2CN(C)C)CC1]

Step 1: 1-(4-(2-((dimethylamino)methyl)-4-nitrophenyl)piperazin-1-yl)ethanone 2-(4-acetylpiperazin-1-yl)-5-nitrobenzaldehyde (296 mg, 1.07 mmol) was dissolved in methanol (1 mL) and sodium bicarbonate (108 mg, 1.281 mmol) was added followed by dimethylamine (2M in THF, 0.640 mL, 1.281 mmol). The mixture was stirred for 2 h at 70° C., then cooled to 0° C. Sodium borohydride (48.5 mg, 1.28 mmol) was added and the mixture was stirred overnight (allowed to return to room temperature). A drop of water was added and the mixture was concentrated in vacuo. The residue was dissolved in methanol and acidified with HCl. The resulting solution was added to a 5 g SCX cartridge and washed with MeOH, then eluted with 2 M $NH_3$/MeOH to give the title compound as a glass (198 mg, 61%). LCMS (Method C): $R_T$=0.26 min, m/z=307 $[M+H]^+$.

Step 2: 1-(4-(4-amino-2-((dimethylamino)methyl)phenyl)piperazin-1-yl)ethanone 1-(4-(2-((dimethylamino)methyl)-4-nitrophenyl)piperazin-1-yl)ethanone (190 mg, 0.62 mmol) was subjected to continuous flow hydrogenation (H-cube, 10% Pd/C cartridge, room temperature, 50 bar, methanol solvent) to give the title compound (185 mg, 94%) as a yellow syrup, which was used without further purification. LCMS (Method C): $R_T$=0.23 min, m/z=277 $[M+H]^+$.

Step 3: 7-((4-(4-acetylpiperazin-1-yl)-3-((dimethylamino)methyl)phenyl)amino)-3-(2,6-dichlorophenyl)-1-methyl-2,3-dihydropyrimido[4,5-d]pyrimidin-4(1H)-one 1-(4-(4-Amino-2-((dimethylamino)methyl)phenyl)piperazin-1-yl)ethanone (62 mg, 0.22 mmol) was reacted with 3-(2,6-dichlorophenyl)-1-methyl-7-(methylthio)-2,3-dihydropyrimido[4,5-d]pyrimidin-4(1H)-one (80 mg, 0.22 mmol) as described in example 131 to give the title compound (33 mg, 25%) as a white solid. $^1$H NMR (300 MHz, DMSO-$d_6$): δ 9.85 (br s, 1H), 8.4 (s, 1H), 8.03 (br s, 1H), 7.64 (m, 2H), 7.48 (m, 2H), 7.04 (d, 1H), 4.97 (s, 2H), 3.56 (m, 4H), 3.45 (s, 2H), 3.13 (s, 3H), 2.82 (m, 2H), 2.78 (m, 2H), 2.18 (s, 6H), 2.04 (s, 3H). LCMS (Method C): $R_T$=0.83 min, m/z=583 $[M+H]^+$.

Example 145: N-(5-((6-(2,6-dichlorophenyl)-8-methyl-5-oxo-5,6,7,8-tetrahydropyrimido[4,5-d]pyrimidin-2-yl)amino)-2-(piperazin-1-yl)benzyl)acetamide

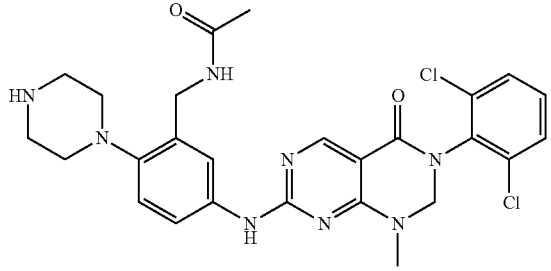 [SMILES: CC(=O)NCc1cc(Nc2ncc3c(n2)N(C)CN(c2c(Cl)cccc2Cl)C3=O)ccc1N1CCNCC1]

Step 1: tert-butyl 4-(2-(aminomethyl)-4-nitrophenyl)piperazine-1-carboxylate tert-butyl 4-(2-(chloromethyl)-4-nitrophenyl)piperazine-1-carboxylate (200 mg, 0.56 mmol) was suspended in a mixture of methanol (2 mL) and ammonium hydroxide (2 mL). The mixture was stirred overnight, then concentrated in vacuo. The residue was chromatographed (10 g Si cartridge; eluted 0-100% ethyl acetate/cyclohexane then 0-10% methanol/ethyl acetate) to give the title compound (95 mg, 50%) as a glass which was used without further purification. LCMS (Method C): $R_T$=0.90 min, m/z=337 $[M+H]^+$.

Step 2: tert-butyl 4-(2-(acetamidomethyl)-4-aminophenyl)piperazine-1-carboxylate tert-Butyl 4-(2-(aminomethyl)-4-nitrophenyl)piperazine-1-carboxylate (90 mg, 0.27 mmol) was dissolved in tetrahydrofuran (2 mL). Triethylamine (0.09 mL, 0.67 mmol) was added, followed by acetic anhydride (0.038 mL, 0.40 mmol). The mixture was stirred at room temperature for 2 h, then diluted with water and extracted with ethyl acetate. The organic layer was dried over anhydrous magnesium sulfate and concentrated. The residue was subjected to continuous flow hydrogenation (H-cube, 10% Pd/C cartridge, room temperature, 50 bar, methanol solvent) to give the title compound (74 mg, 79%) as a yellow oil which was used directly without further purification. LCMS (Method C): $R_T$=0.79 min, m/z=349 $[M+H]^+$.

Step 3: N-(5-((6-(2,6-dichlorophenyl)-8-methyl-5-oxo-5,6,7,8-tetrahydropyrimido[4,5-d]pyrimidin-2-yl)amino)-2-(piperazin-1-yl)benzyl)acetamide tert-Butyl 4-(2-(acetamidomethyl)-4-aminophenyl)piperazine-1-carboxylate (98 mg, 0.28 mmol) was reacted with 3-(2,6-dichlorophenyl)-1-methyl-7-(methylthio)-2,3-dihydropyrimido[4,5-d]pyrimidin-4(1H)-one (100 mg, 0.28 mmol) as described in example 1 to give the title compound (36 mg, 23%) as an off-white solid. $^1$H NMR (300 MHz, DMSO-$d_6$): δ 9.84 (br s, 1H), 8.45 (s, 1H), 8.20 (t, 1H), 7.65 (m, 4H), 7.46 (m, 1H), 7.05 (d, 1H), 4.97 (s, 2H), 4.33 (s, 2H), 3.09 (s, 3H), 2.84 (m, 4H), 2.73 (m, 4H), 1.89 (s, 3H). LCMS (Method C): $R_T$=0.72 min, m/z=556 $[M+H]^+$.

Example 146: 3-(2,6-dichlorophenyl)-7-((4-(1,1-dioxidothiomorpholino)-3-((methylamino)methyl)phenyl)amino)-1-methyl-2,3-dihydropyrimido[4,5-d]pyrimidin-4(1H)-one

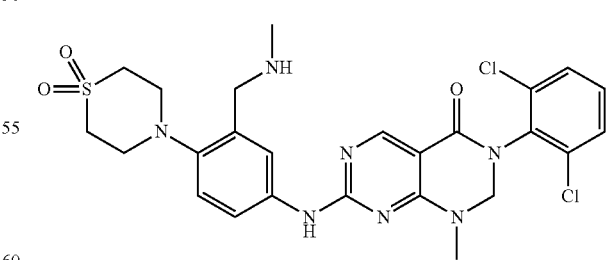

Step 1: 2-(1,1-dioxidothiomorpholino)-5-nitrobenzaldehyde

A suspension of 2-fluoro-5-nitrobenzaldehyde (2 g, 11.83 mmol), thiomorpholine 1,1-dioxide (1.599 g, 11.83 mmol)

and potassium carbonate (2.452 g, 17.74 mmol) in anhydrous DMF (10 mL) was heated to 50° C. under a nitrogen atmosphere overnight. The reaction mixture was allowed to cool to room temperature, diluted with water (70 mL) and stirred at room temperature for 15 minutes. The precipitated solid was isolated by filtration, washed with water, slurried in 1M HCl solution (50 mL), isolated by filtration, sucked dry and freeze-dried overnight to give the title compound as a yellow solid (2.68 g, 80%). $^1$H NMR (300 MHz, DMSO-d$_6$): δ 10.11 (s, 1H), 8.54 (d, 1H), 8.34 (dd, 1H), 7.43 (d, 1H), 3.69-3.80 (m, 4H), 3.36-3.45 (m, 4H). LCMS (Method C): R$_T$=0.95 min, m/z=285 [M+H]$^+$.

Step 2: 4-(2-((methylamino)methyl)-4-nitrophenyl) thiomorpholine 1,1-dioxide

To a suspension of 2-(1,1-dioxidothiomorpholino)-5-nitrobenzaldehyde (800 mg, 2.81 mmol) and sodium bicarbonate (473 mg, 5.63 mmol) in methanol (6 mL) was added methylamine (2M in methanol, 1.688 mL, 3.38 mmol) and the reaction mixture heated to 70° C. for 2 hours. The mixture was then cooled to 0° C. before the addition of sodium borohydride (128 mg, 3.38 mmol) and the mixture stirred at room temperature for 2 hours. Additional methylamine (2M in methanol, 0.492 mL, 0.985 mmol) and sodium borohydride (38.8 mg, 1.688 mmol) were added and the mixture stirred at room temperature for 1 hour. The reaction mixture was quenched with a few drops of water then concentrated to dryness under reduced pressure. The residue was taken up in dichloromethane (20 mL), washed with brine (20 mL) and passed through a phase separator. The organic phase was concentrated to dryness under reduced pressure to give the title compound as a yellow solid (500 mg, 59%). $^1$H NMR (300 MHz, CDCl$_3$): δ 8.30 (d, 1H), 8.12 (dd, 1H), 7.15 (d, 1H), 3.79 (s, 2H), 3.60-3.69 (m, 4H), 3.20-3.29 (m, 4H), 2.50 (s, 3H). LCMS (Method C): R$_T$=0.36 min, m/z=300 [M+H]$^+$.

Step 3: tert-butyl 2-(1,1-dioxidothiomorpholino)-5-nitrobenzyl(methyl)carbamate

To a solution of 4-(2-((methylamino)methyl)-4-nitrophenyl)thiomorpholine 1,1-dioxide (500 mg, 1.670 mmol) and triethylamine (0.512 mL, 3.67 mmol) in anhydrous THF (5 mL) was added di-tert-butyl dicarbonate (0.427 mL, 1.837 mmol) and the resulting solution stirred at room temperature for 2 hours. The reaction mixture was diluted with brine (20 mL) and extracted into ethyl acetate (3×15 mL). The combined organic phases were dried over Na$_2$SO$_4$, filtered, concentrated to dryness under reduced pressure and chromatographed (silica 50 g cartridge, cyclohexane:ethyl acetate, gradient elution from 90:10 to 0:100) to give the title compound as a yellow oil (350 mg, 53%). $^1$H NMR (400 MHz, CDCl$_3$): δ 8.16 (dd, 1H), 8.04 (br s, 1H), 7.23 (d, 1H), 4.53 (br s, 2H), 3.49 (dd, 4H), 3.26 (dd, 4H), 2.88 (s, 3H), 1.52 (br s, 9H). LCMS (Method C): R$_T$=1.43 min, m/z=400 [M+H]$^+$.

Step 4: tert-butyl 5-amino-2-(1,1-dioxidothiomorpholino)benzyl(methyl)carbamate

A solution of tert-butyl 2-(1,1-dioxidothiomorpholino)-5-nitrobenzyl(methyl)carbamate (350 mg, 0.876 mmol) in methanol (40 mL) was hydrogenated by H-Cube (10% Pd/C cartridge, 20 bar H2, room temperature, 1 mL/min). The reaction mixture was concentrated to dryness under reduced pressure to give the title compound as an off-white solid (260 mg, 80%). $^1$H NMR (300 MHz, CDCl$_3$): δ 6.99 (d, 1H), 6.57 (dd, 1H), 6.47 (br s, 1H), 4.47 (br s, 2H), 3.62 (br s, 2H), 3.24-3.36 (m, 4H), 3.11-3.24 (m, 4H), 2.70-2.90 (br m, 3H), 1.39-1.56 (br m, 9H). LCMS (Method C): R$_T$=0.80 min, m/z=370 [M+H]$^+$.

Step 5: tert-butyl 5-((6-(2,6-dichlorophenyl)-8-methyl-5-oxo-5,6,7,8-tetrahydropyrimido[4,5-d] pyrimidin-2-yl)amino)-2-(1,1-dioxidothiomorpholino)benzyl(methyl)carbamate 3-(2,6-Dichlorophenyl)-1-methyl-7-(methylthio)-2,3-dihydropyrimido[4,5-d]pyrimidin-4(1H)-one (150 mg, 0.423 mmol) was reacted with tert-butyl 5-amino-2-(1,1-dioxidothiomorpholino)benzyl(methyl)carbamate (156 mg, 0.423 mmol) following the procedure for Example 31 to give the title compound as an off-white solid (170 mg, 59%). $^1$H NMR (300 MHz, CDCl$_3$): δ 8.68 (s, 1H), 8.10 (br s, 1H), 7.58 (dd, 1H), 7.37-7.47 (m, 3H), 7.27 (dd, 1H), 7.16 (d, 1H), 4.88 (s, 2H), 4.54 (br s, 2H), 3.30-3.43 (m, 4H), 3.15-3.25 (m, 4H), 3.15 (s, 3H), 2.70-2.90 (br m, 3H), 1.47 (br s, 9H). LCMS (Method C): R$_T$=1.46 min, m/z=676 [M+H]$^+$.

Step 6: 3-(2,6-dichlorophenyl)-7-((4-(1,1-dioxidothiomorpholino)-3-((methylamino)methyl)phenyl)amino)-1-methyl-2,3-dihydropyrimido[4,5-d]pyrimidin-4(1H)-one tert-Butyl 5-((6-(2,6-dichlorophenyl)-8-methyl-5-oxo-5,6,7,8-tetrahydropyrimido[4,5-d]pyrimidin-2-yl)amino)-2-(1,1-dioxidothiomorpholino)benzyl(methyl)carbamate (170 mg, 0.251 mmol) was deprotected following the procedure for Example 31 to give the title compound as an off-white solid (121 mg, 84%). $^1$H NMR (400 MHz, DMSO-d$_6$): δ 9.83 (br s, 1H), 8.46 (s, 1H), 7.92 (br s, 1H), 7.65 (d, 2H), 7.56 (dd, 1H), 7.48 (t, 1H), 7.13 (d, 1H), 4.97 (s, 2H), 3.69 (s, 2H), 3.29-3.33 (m, 4H), 3.21-3.29 (m, 4H), 3.12 (s, 3H), 2.33 (s, 3H). LCMS (Method C): R$_T$=0.83 min, m/z=576 [M+H]$^+$.

Example 147: 3-(2,6-dichlorophenyl)-7-((4-(4,4-difluoropiperidin-1-yl)-3-((methylamino)methyl)phenyl)amino)-1-methyl-2,3-dihydropyrimido[4,5-d] pyrimidin-4(1H)-one

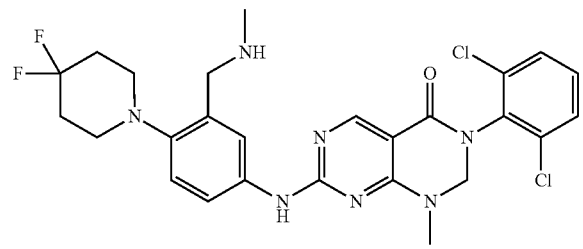

Step 1: 2-(4,4-difluoropiperidin-1-yl)-5-nitrobenzaldehyde

A suspension of 2-fluoro-5-nitrobenzaldehyde (1 g, 5.91 mmol), 4,4-difluoropiperidine hydrochloride (0.932 g, 5.91 mmol) and potassium carbonate (1.635 g, 11.83 mmol) in anhydrous DMF (5 mL) was heated to 50° C. under a nitrogen atmosphere overnight. The reaction mixture was allowed to cool to room temperature, diluted with water (40 mL) and stirred at room temperature for 15 minutes. The precipitated solid was isolated by filtration, washed with water, sucked dry and freeze-dried overnight to give the title compound as a yellow solid (1.52 g, 95%). $^1$H NMR (300 MHz, CDCl$_3$): δ 10.09 (s, 1H), 8.65 (d, 1H), 8.33 (dd, 1H), 7.13 (d, 1H), 3.41 (dd, 4H), 2.17-2.34 (m, 4H). LCMS (Method C): R$_T$=1.47 min, m/z=271 [M+H]$^+$.

Step 2: 1-(2-(4,4-difluoropiperidin-1-yl)-5-nitrophenyl)-N-methylmethanamine

To a suspension of 2-(4,4-difluoropiperidin-1-yl)-5-nitrobenzaldehyde (700 mg, 2.59 mmol) and sodium bicarbonate (435 mg, 5.18 mmol) in methanol (5 mL) was added methylamine (2M in methanol, 1.554 mL, 3.11 mmol) and the reaction mixture heated to 70° C. for 2 hours. The mixture was then cooled to 0° C. before the addition of sodium borohydride (118 mg, 3.11 mmol) and the mixture stirred at room temperature for 2 hours. The reaction mixture was quenched with a few drops of water then concentrated to dryness under reduced pressure. The residue was taken up in dichloromethane (20 mL), washed with brine (20 mL) and passed through a phase separator. The organic phase was concentrated to dryness under reduced pressure to give the title compound as a yellow oil that solidified upon standing (611 mg, 83%). $^1$H NMR (300 MHz, CDCl$_3$): δ 8.32 (d, 1H), 8.09 (dd, 1H), 7.09 (d, 1H), 3.78 (s, 2H), 3.18 (dd, 4H), 2.49 (s, 3H), 2.17 (tt, 4H). LCMS (Method C): R$_T$=0.74 min, m/z=286 [M+H]$^+$.

Step 3: tert-butyl 2-(4,4-difluoropiperidin-1-yl)-5-nitrobenzyl(methyl)carbamate To a solution of 1-(2-(4,4-difluoropiperidin-1-yl)-5-nitrophenyl)-N-methylmethanamine (611 mg, 2.142 mmol) and triethylamine (0.657 mL, 4.71 mmol) in anhydrous THF (6 mL) was added di-tert-butyl dicarbonate (0.547 mL, 2.356 mmol) and the resulting solution stirred at room temperature for 2 hours. The reaction mixture was diluted with brine (20 mL) and extracted into ethyl acetate (3×15 mL). The combined organic phases were dried over Na$_2$SO$_4$, filtered, concentrated to dryness under reduced pressure and purified by Biotage chromatography (silica 50 g cartridge, cyclohexane:ethyl acetate, gradient elution from 95:5 to 70:30) to give the title compound as a yellow oil (850 mg, quantitative yield). $^1$H NMR (400 MHz, CDCl$_3$): δ 8.11 (dd, 1H), 7.99 (br s, 1H), 7.14 (d, 1H), 4.39-4.60 (br m, 2H), 3.08 (t, 4H), 2.75-2.94 (br m, 3H), 2.08-2.26 (m, 4H), 1.38-1.59 (m, 9H). LCMS (Method C): R$_T$=1.85 min, m/z=386 [M+H]$^+$.

Step 4: tert-butyl 5-amino-2-(4,4-difluoropiperidin-1-yl)benzyl(methyl)carbamate A solution of tert-butyl 2-(4,4-difluoropiperidin-1-yl)-5-nitrobenzyl(methyl)carbamate (850 mg, 2.205 mmol) in methanol (60 mL) was hydrogenated by H-Cube (10% Pd/C cartridge, 20 bar H$_2$, room temperature, 1 mL/min). The reaction mixture was concentrated to dryness under reduced pressure to give the title compound as an off-white solid (670 mg, 85%). $^1$H NMR (300 MHz, CDCl$_3$): δ 6.96 (d, 1H), 6.56 (dd, 1H), 6.49 (br d, 1H), 4.48 (d, 2H), 3.55 (s, 2H), 2.88 (t, 4H), 2.80 (d, 3H), 1.98-2.18 (m, 4H), 1.36-1.56 (m, 9H). LCMS (Method C): R$_T$=1.26 min, m/z=356 [M+H]$^+$.

Step 5: tert-butyl 5-((6-(2,6-dichlorophenyl)-8-methyl-5-oxo-5,6,7,8-tetrahydropyrimido[4,5-d]pyrimidin-2-yl)amino)-2-(4,4-difluoropiperidin-1-yl)benzyl(methyl)carbamate 3-(2,6-Dichlorophenyl)-1-methyl-7-(methylthio)-2,3-dihydropyrimido[4,5-d]pyrimidin-4(1H)-one (100 mg, 0.283 mmol) was reacted with tert-butyl 5-amino-2-(4,4-difluoropiperidin-1-yl)benzyl(methyl)carbamate (101 mg, 0.283 mmol) following the procedure for Example 31 to give the title compound as an off-white solid (120 mg, 64%). $^1$H NMR (300 MHz, CDCl$_3$) δ 8.70 (s, 1H), 7.77 (br s, 1H), 7.55 (br d, 1H), 7.43 (dd, 2H), 7.33-7.43 (br m, 1H), 7.28 (dd, 1H), 7.12 (d, 1H), 4.87 (s, 2H), 4.54 (br d, 2H), 3.17 (s, 3H), 2.90-3.00 (m, 4H), 2.71-2.90 (br m, 3H), 2.00-2.21 (m, 4H), 1.35-1.57 (br m, 9H). LCMS (Method C): R$_T$=1.91 min, m/z=662 [M+H]$^+$.

Step 6: 7-((4-((1R,4R)-2,5-diazabicyclo[2.2.1]heptan-2-yl)-3-methylphenyl)amino)-3-(2,6-dichlorophenyl)-1-methyl-2,3-dihydropyrimido[4,5-d]pyrimidin-4(1H)-one tert-Butyl 5-((6-(2,6-dichlorophenyl)-8-methyl-5-oxo-5,6,7,8-tetrahydropyrimido[4,5-d]pyrimidin-2-yl)amino)-2-(4,4-difluoropiperidin-1-yl)benzyl(methyl)carbamate (120 mg, 0.181 mmol) was deprotected following the procedure for Example 31 to give the title compound as an off-white solid (94 mg, 92%). $^1$H NMR (400 MHz, DMSO-d$_6$): δ 9.80 (br s, 1H), 8.46 (s, 1H), 7.93 (br s, 1H), 7.65 (d, 2H), 7.54 (dd, 1H), 7.48 (t, 1H), 7.08 (d, 1H), 4.97 (s, 2H), 3.68 (s, 2H), 3.12 (s, 3H), 2.92-3.02 (m, 4H), 2.33 (s, 3H), 2.02-2.18 (m, 4H). LCMS (Method C): R$_T$=1.05 min, m/z=562 [M+H]$^+$.

Example 148: 3-(2,6-dichlorophenyl)-7-((4-((2S,6R)-2,6-dimethylmorpholino)-3-((methylamino)methyl)phenyl)amino)-1-methyl-2,3-dihydropyrimido[4,5-d]pyrimidin-4(1H)-one

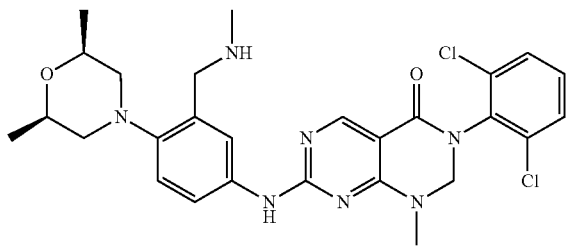 [SMILES: CNCc1cc(Nc2ncc3c(n2)N(C)CN(c2c(Cl)cccc2Cl)C3=O)ccc1N1C[C@@H](C)O[C@@H](C)C1]

Step 1: 2-((2S,6R)-2,6-dimethylmorpholino)-5-nitrobenzaldehyde

A suspension of 2-fluoro-5-nitrobenzaldehyde (2 g, 11.83 mmol), cis-2,6-dimethylmorpholine (1.362 g, 11.83 mmol) and potassium carbonate (2.452 g, 17.74 mmol) in anhydrous DMF (20 mL) was heated to 50° C. under a nitrogen atmosphere overnight. The reaction mixture was allowed to cool to room temperature, diluted with water (70 mL) and stirred at room temperature for 15 minutes. The precipitated solid was isolated by filtration, washed with water, sucked dry and freeze-dried overnight to give the title compound as a yellow solid (2.94 g, 94%). $^1$H NMR (300 MHz, CDCl$_3$):

δ 10.07 (s, 1H), 8.63 (d, 1H), 8.31 (dd, 1H), 7.06 (d, 1H), 3.85-3.99 (m, 2H), 3.30 (d, 2H), 2.82 (dd, 2H), 1.25 (d, 6H). LCMS (Method C): $R_T$=1.43 min, m/z=265 [M+H]$^+$.

Step 2: 1-(2-((2S,6R)-2,6-dimethylmorpholino)-5-nitrophenyl)-N-methylmethanamine To a suspension of 2-((2S,6R)-2,6-dimethylmorpholino)-5-nitrobenzaldehyde (800 mg, 3.03 mmol) and sodium bicarbonate (509 mg, 6.05 mmol) in methanol (6 mL) was added methylamine (2M in methanol, 1.816 mL, 3.63 mmol) and the reaction mixture heated to 70° C. for 2 hours. The mixture was then cooled to 0° C. before the addition of sodium borohydride (137 mg, 3.63 mmol) and the mixture stirred at room temperature for 2 hours. The reaction mixture was quenched with a few drops of water then concentrated to dryness under reduced pressure. The residue was taken up in dichloromethane (20 mL), washed with brine (20 mL) and passed through a phase separator. The organic phase was concentrated to dryness under reduced pressure to give the title compound as a yellow oil (880 mg, quantitative yield). $^1$H NMR (300 MHz, CDCl$_3$): δ 8.29 (d, 1H), 8.08 (dd, 1H), 7.02 (d, 1H), 3.79-3.93 (m, 2H), 3.77 (s, 2H), 3.17 (d, 2H), 2.53 (dd, 2H), 2.46 (s, 3H), 1.23 (d, 6H). LCMS (Method C): $R_T$=0.62 min, m/z=280 [M+H]$^+$.

Step 3: tert-butyl 2-((2S,6R)-2,6-dimethylmorpholino)-5-nitrobenzyl(methyl)carbamate To a solution of 1-(2-((2S,6R)-2,6-dimethylmorpholino)-5-nitrophenyl)-N-methylmethanamine (880 mg, 3.15 mmol) and triethylamine (0.966 mL, 6.93 mmol) in anhydrous THF (9 mL) was added di-tert-butyl dicarbonate (0.805 mL, 3.47 mmol) and the resulting solution stirred at room temperature for 2 hours. The reaction mixture was diluted with brine (40 mL) and extracted into ethyl acetate (3×30 mL). The combined organic phases were dried over Na$_2$SO$_4$, filtered, concentrated to dryness under reduced pressure and purified by Biotage chromatography (silica 50 g cartridge, cyclohexane:ethyl acetate, gradient elution from 95:5 to 70:30) to give the title compound as a yellow oil (1.06 g, 89%). $^1$H NMR (400 MHz, CDCl$_3$): δ 8.11 (dd, 1H), 7.99 (br s, 1H), 7.07 (d, 1H), 4.39-4.58 (m, 2H), 3.85 (br s, 2H), 2.72-3.03 (m, 5H), 2.54 (t, 2H), 1.41-1.59 (m, 9H), 1.23 (d, 6H). LCMS (Method C): $R_T$=1.87 min, m/z=380 [M+H]$^+$.

Step 4: tert-butyl 5-amino-2-((2S,6R)-2,6-dimethylmorpholino)benzyl(methyl)carbamate A solution of tert-butyl 2-((2S,6R)-2,6-dimethylmorpholino)-5-nitrobenzyl(methyl)carbamate (1.06 g, 2.79 mmol) in methanol (60 mL) was hydrogenated by H-Cube (10% Pd/C cartridge, 20 bar H2, room temperature, 1 mL/min). The reaction mixture was concentrated to dryness under reduced pressure to give the title compound as an off-white solid (840 mg, 86%). $^1$H NMR (300 MHz, CDCl$_3$): δ 6.93 (d, 1H), 6.57 (dd, 1H), 6.50 (br d, 1H), 4.40-4.58 (m, 2H), 3.71-3.87 (m, 2H), 3.54 (br s, 2H), 2.61-2.88 (m, 5H), 2.41 (t, 2H), 1.37-1.55 (m, 9H), 1.18 (d, 6H). LCMS (Method C): $R_T$=1.08 min, m/z=350 [M+H]$^+$.

Step 5: tert-butyl 5-((6-(2,6-dichlorophenyl)-8-methyl-5-oxo-5,6,7,8-tetrahydropyrimido[4,5-d]pyrimidin-2-yl)amino)-2-((2S,6R)-2,6-dimethylmorpholino)benzyl(methyl)carbamate 3-(2,6-dichlorophenyl)-1-methyl-7-(methylthio)-2,3-dihydropyrimido[4,5-d]pyrimidin-4(1H)-one (100 mg, 0.283 mmol) was reacted with tert-butyl 5-amino-2-((2S,6R)-2,6-dimethylmorpholino)benzyl(methyl)carbamate (99 mg, 0.283 mmol) following the procedure for Example 31 to give the title compound as a yellow solid (109 mg, 59%). $^1$H NMR (300 MHz, CDCl$_3$): δ 8.69 (s, 1H), 7.78 (br s, 1H), 7.54 (br d, 1H), 7.43 (dd, 2H), 7.32-7.42 (br m, 1H), 7.28 (dd, 1H), 7.08 (br d, 1H), 4.86 (s, 2H), 4.55 (br d, 2H), 3.75-3.90 (m, 2H), 3.16 (s, 3H), 2.67-2.91 (m, 5H), 2.46 (t, 2H), 1.35-1.56 (m, 9H), 1.20 (d, 6H). LCMS (Method C): $R_T$=1.88 min, m/z=656 [M+H]$^+$.

Step 6: 3-(2,6-dichlorophenyl)-7-((4-((2S,6R)-2,6-dimethylmorpholino)-3-((methylamino)methyl)phenyl)amino)-1-methyl-2,3-dihydropyrimido[4,5-d]pyrimidin-4(1H)-one tert-butyl 5-((6-(2,6-dichlorophenyl)-8-methyl-5-oxo-5,6,7,8-tetrahydropyrimido[4,5-d]pyrimidin-2-yl)amino)-2-((2S,6R)-2,6-dimethylmorpholino)benzyl(methyl)carbamate (109 mg, 0.166 mmol) was deprotected following the procedure for Example 31 to give the title compound as an off-white solid (64 mg, 69%). $^1$H NMR (400 MHz, DMSO-d$_6$): δ 9.78 (br s, 1H), 8.46 (s, 1H), 7.90 (br s, 1H), 7.65 (d, 2H), 7.55 (dd, 1H), 7.48 (t, 1H), 7.02 (d, 1H), 4.96 (s, 2H), 3.72 (sep, 2H), 3.66 (s, 2H), 3.12 (s, 3H), 2.94 (d, 2H), 2.24-2.38 (m, 5H), 1.10 (d, 6H). LCMS (Method C): $R_T$=0.97 min, m/z=556 [M+H]$^+$.

Example 149: 3-(2,6-dichlorophenyl)-7-((3-((dimethylamino)methyl)-4-(1,1-dioxidothiomorpholino)phenyl)amino)-1-methyl-2,3-dihydropyrimido[4,5-d]pyrimidin-4(1H)-one

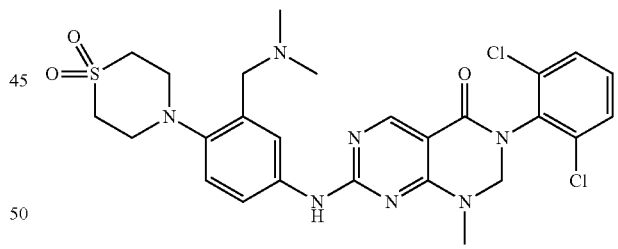

3-(2,6-dichlorophenyl)-7-((4-(1,1-dioxidothiomorpholino)-3-((methylamino)methyl)phenyl)amino)-1-methyl-2,3-dihydropyrimido[4,5-d]pyrimidin-4(1H)-one (66 mg, 0.114 mmol) was methylated following the procedure for Example 35 to give the title compound as a white solid (58 mg, 86%). $^1$H NMR (400 MHz, DMSO-d$_6$): δ 9.85 (br s, 1H), 8.47 (s, 1H), 7.99 (br s, 1H), 7.65 (d, 2H), 7.55 (d, 1H), 7.48 (dd, 1H), 7.15 (d, 1H), 4.97 (s, 2H), 3.44 (s, 2H), 3.32-3.39 (m, 4H), 3.21-3.30 (m, 4H), 3.13 (s, 3H), 2.20 (s, 6H). LCMS (Method C): $R_T$=0.85 min, m/z=590 [M+H]$^+$.

Example 150: 3-(2,6-dichlorophenyl)-7-((4-(4,4-difluoropiperidin-1-yl)-3-((dimethylamino)methyl)phenyl)amino)-1-methyl-2,3-dihydropyrimido[4,5-d]pyrimidin-4(1H)-one

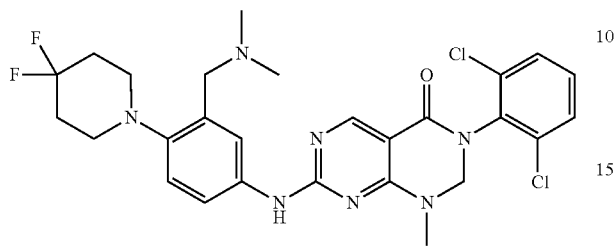

3-(2,6-dichlorophenyl)-7-((4-(4,4-difluoropiperidin-1-yl)-3-((methylamino)methyl)phenyl)amino)-1-methyl-2,3-dihydropyrimido[4,5-d]pyrimidin-4(1H)-one (45 mg, 0.80 mmol) was methylated following the procedure for Example 35 to give the title compound as a white solid (32 mg, 69%). $^1$H NMR (400 MHz, DMSO-d$_6$): δ 9.82 (br s, 1H), 8.46 (s, 1H), 8.03 (br s, 1H), 7.64 (d, 2H), 7.53 (d, 1H), 7.48 (t, 1H), 7.09 (d, 1H), 4.97 (s, 2H), 3.42 (s, 2H), 3.13 (s, 3H), 2.92-3.04 (m, 4H), 2.20 (s, 6H), 2.01-2.17 (m, 4H). LCMS (Method C): R$_T$=1.07 min, m/z=576 [M+H]$^+$.

Example 151: 3-(2,6-dichlorophenyl)-7-((3-((dimethylamino)methyl)-4-((2S,6R)-2,6-dimethylmorpholino)phenyl)amino)-1-methyl-2,3-dihydropyrimido[4,5-d]pyrimidin-4(1H)-one

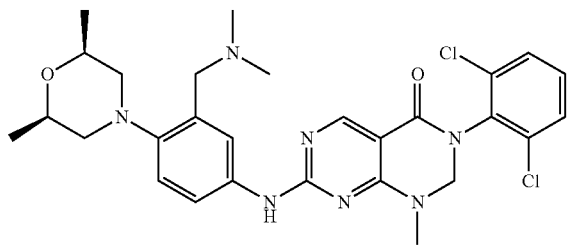 [SMILES: C[C@@H]1CN(c2ccc(Nc3ncc4c(n3)N(C)CN(c3c(Cl)cccc3Cl)C4=O)cc2CN(C)C)C[C@H](C)O1]

3-(2,6-dichlorophenyl)-7-((4-((2S,6R)-2,6-dimethylmorpholino)-3-((methylamino)methyl)phenyl)amino)-1-methyl-2,3-dihydropyrimido[4,5-d]pyrimidin-4(1H)-one (35 mg, 0.63 mmol) was methylated following the procedure for Example 35 to give the title compound as a white solid (12 mg, 33%). $^1$H NMR (400 MHz, DMSO-d$_6$): δ 9.80 (br s, 1H), 8.45 (s, 1H), 8.01 (br s, 1H), 7.65 (d, 2H), 7.54 (dd, 1H), 7.48 (dd, 1H), 7.02 (d, 1H), 4.96 (s, 2H), 3.74 (sep, 2H), 3.41 (s, 2H), 3.13 (s, 3H), 3.02 (d, 2H), 2.32 (t, 2H), 2.19 (s, 6H), 1.10 (d, 6H). LCMS (Method C): R$_T$=0.99 min, m/z=570 [M+H]$^+$.

Example 152: 3-(2,6-dichlorophenyl)-7-((4-fluoro-3-((methylamino)methyl)phenyl)amino)-1-methyl-2,3-dihydropyrimido[4,5-d]pyrimidin-4(1H)-one

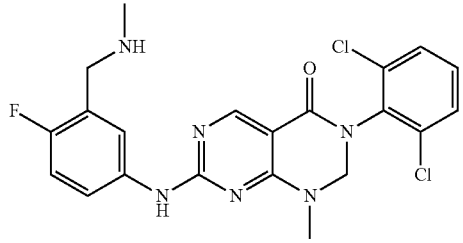 [SMILES: CNCc1cc(Nc2ncc3c(n2)N(C)CN(c2c(Cl)cccc2Cl)C3=O)ccc1F]

Step 1: tert-butyl 2-fluoro-5-nitrobenzyl(methyl)carbamate

2-Fluoro-5-nitrobenzaldehyde (1 g, 5.91 mmol) was dissolved in methylamine (2 M in methanol, 3.25 mL, 6.50 mmol) and Ethanol (7 mL) and the mixture was stirred for 1 h. Sodium borohydride (0.447 g, 11.83 mmol) was added and the mixture was stirred for 1 h, then concentrated in vacuo. The residue was taken up in ethyl acetate and washed with water and brine then concentrated to a yellow oil. This was dissolved in dichloromethane (15 mL) and DIPEA (1.343 mL, 7.69 mmol) was added, followed by di tert-butyl dicarbonate (1.42 g, 6.50 mmol). The mixture was stirred at RT overnight then concentrated in vacuo. The residue was chromatographed (25 g Si cartridge; eluted 0-50% EtOAc/c-hex) to give the title compound (0.90 g, 54%) as a yellow oil. $^1$H NMR (300 MHz, CDCl$_3$): δ 8.17 (m, 2H), 7.24 (m, 1H), 4.50 (m, 2H), 2.93 (m, 3H), 1.49 (s, 9H). LCMS (Method C): R$_T$=1.66 min, m/z=185 [M+H−Boc]$^+$.

Step 2: tert-butyl 5-amino-2-fluorobenzyl(methyl)carbamate tert-Butyl 2-fluoro-5-nitrobenzyl(methyl)carbamate (180 mg, 0.63 mmol) was subjected to continuous flow hydrogenation (H-cube, 10% Pd/C cartridge, room temperature, 50 bar, methanol solvent). The crude product was chromatographed (10 g Si cartridge; eluted 0-100% EtOAc/c-hex) to give the title compound (105 mg, 65%) as a colourless oil. LCMS (Method C): R$_T$=1.05 min, m/z=199 [M+H−tBu]$^+$.

Step 3: 3-(2,6-dichlorophenyl)-7-((4-fluoro-3-((methylamino)methyl)phenyl)amino)-1-methyl-2,3-dihydropyrimido[4,5-d]pyrimidin-4(1H)-one tert-Butyl 5-amino-2-fluorobenzyl(methyl)carbamate (72 mg, 0.28 mmol) was reacted with 3-(2,6-dichlorophenyl)-1-methyl-7-(methylthio)-2,3-dihydropyrimido[4,5-d]pyrimidin-4(1H)-one (100 mg, 0.28 mmol) as described in example 1 to give the title compound (45 mg, 34%) as a white solid. $^1$H NMR (300 MHz, DMSO-d$_6$): δ 9.83 (br s, 1H), 8.48 (s, 1H), 7.98 (br s, 1H), 7.64 (d, 2H), 7.47 (m, 2H), 7.09 (t, 1H), 4.98 (s, 2H), 3.65 (s, 2H), 3.12 (s, 3H), 2.28 (s, 3H), 2.03 (br s, 1H). LCMS (Method C): R$_T$=0.84 min, m/z=461 [M+H]$^+$.

Example 153: 3-(2,6-dichlorophenyl)-7-((4-(dimethylamino)-3-((methylamino)methyl)phenyl)amino)-1-methyl-2,3-dihydropyrimido[4,5-d]pyrimidin-4(1H)-one

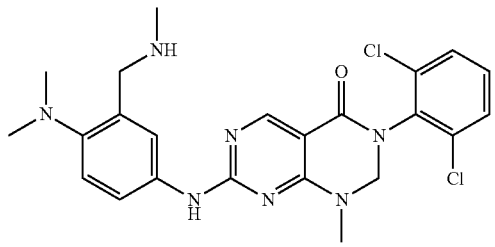

Step 1: tert-butyl 5-amino-2-(dimethylamino)benzyl(methyl)carbamate tert-Butyl 2-fluoro-5-nitrobenzyl(methyl)carbamate (190 mg, 0.668 mmol) was dissolved in a 2 M solution of dimethylamine in THF (3 mL, 6.00 mmol). The mixture was heated at 140° C. for 1 h under microwave irradiation. The solution was concentrated in vacuo, The residue was partitioned between water and DCM and the organic layer was separated using a phase separator cartridge then concentrated in vacuo. The residue was subjected to continuous flow hydrogenation (H-cube, 10% Pd/C cartridge, room temperature, 50 bar, methanol solvent) to give the title compound as a colourless oil (110 mg, 59%), which was used without further purification. LCMS (Method C): $R_T$ 0.76 min, m/z 280 [M+H]$^+$.

Step 2: 3-(2,6-dichlorophenyl)-7-((4-(dimethylamino)-3-((methylamino)methyl)phenyl)amino)-1-methyl-2,3-dihydropyrimido[4,5-d]pyrimidin-4(1H)-one tert-Butyl 5-amino-2-(dimethylamino)benzyl (methyl) carbamate (79 mg, 0.28 mmol) was reacted with 3-(2,6-dichlorophenyl)-1-methyl-7-(methylthio)-2,3-dihydropyrimido[4,5-d]pyrimidin-4(1H)-one (100 mg, 0.28 mmol) as described in example 1 to give the title compound (20 mg, 7%) as an off-white solid. $^1$H NMR (300 MHz, DMSO-d$_6$): δ 9.79 (br s, 1H), 8.46 (s, 1H), 7.64 (br s, 1H), 7.53 (m, 2H), 7.48 (m, 2H), 7.05 (d, 1H), 4.97 (s, 2H), 3.72 (s, 2H), 3.12 (s, 3H), 2.60 (s, 6H), 2.34 (s, 3H). LCMS (Method C): $R_T$=0.92 min, m/z=486 [M+H]$^+$.

Example 154: 3-(2,6-dichlorophenyl)-7-((3-((dimethylamino)methyl)-4-morpholinophenyl)amino)-1-methyl-2,3-dihydropyrimido[4,5-d]pyrimidin-4(1H)-one

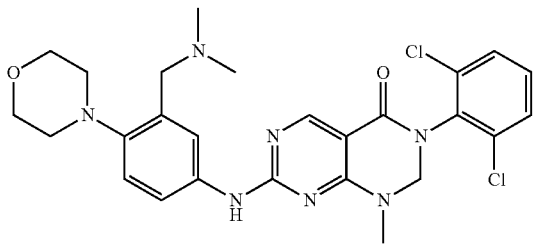 [SMILES: CN(C)Cc1cc(Nc2ncc3c(n2)N(C)CN(c2c(Cl)cccc2Cl)C3=O)ccc1N1CCOCC1]

Step 1: 3-((dimethylamino)methyl)-4-morpholinoaniline

2-Morpholino-5-nitrobenzaldehyde (0.5 g, 2.117 mmol) was suspended in methanol (6 mL). Sodium bicarbonate (0.356 g, 4.23 mmol) was added, followed by a 2 M solution of dimethylamine in methanol (1.270 mL, 2.54 mmol). The mixture was heated at 80° C. for 3 h then cooled to RT. Sodium borohydride (0.096 g, 2.54 mmol) was added and the mixture was stirred at RT for 1 h. The reaction was quenched by addition of a few drops of water and the solution was concentrated in vacuo. The residue was partitioned between water and DCM and the organic layer was separated using a phase separator cartridge and concentrated in vacuo. The residue was subjected to continuous flow hydrogenation (H-cube, 10% Pd/C cartridge, room temperature, 50 bar, methanol solvent) to give the title compound as a white solid (160 mg, 32%) which was used without further purification. LCMS (Method C): $R_T$=0.24 min, m/z=236 [M+H]$^+$.

Step 2: 3-(2,6-dichlorophenyl)-7-((3-((dimethylamino)methyl)-4-morpholinophenyl)amino)-1-methyl-2,3-dihydropyrimido[4,5-d]pyrimidin-4(1H)-one 3-((Dimethylamino)methyl)-4-morpholinoaniline (66 mg, 0.28 mmol) was reacted with 3-(2,6-dichlorophenyl)-1-methyl-7-(methylthio)-2,3-dihydropyrimido[4,5-d]pyrimidin-4(1H)-one (100 mg, 0.28 mmol) as described in example 131 to give the title compound (75 mg, 49%) as a white solid. $^1$H NMR (300 MHz, DMSO-d$_6$): δ 9.84 (br s, 1H), 8.46 (s, 1H), 8.01 (br s, 1H), 7.64 (m, 2H), 7.50 (m, 2H), 7.06 (d, 1H), 4.97 (s, 2H), 3.72 (m, 4H), 3.43 (s, 2H), 3.13 (s, 3H), 2.86 (m, 4H), 2.19 (s, 6H). LCMS (Method C): $R_T$=0.88 min, m/z=542 [M+H]$^+$.

Example 155: 3-(2,6-dichlorophenyl)-1-methyl-7-((3-((methylamino)methyl)-4-(pyridin-4-yl)phenyl)amino)-2,3-dihydropyrimido[4,5-d]pyrimidin-4(1H)-one

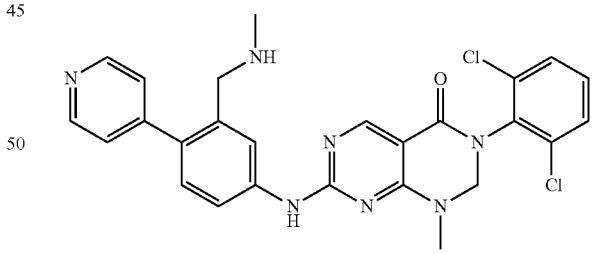

Step 1: 2-bromo-5-nitrobenzaldehyde

A mixture of concentrated sulfuric acid (17.01 mL) and fuming nitric acid (2.250 mL) was cooled to 5° C. followed by the dropwise addition of 2-bromobenzaldehyde (3.15 mL, 27.0 mmol) over a period of 30 minutes. The mixture was then allowed to warm to room temperature and stirred for 60 minutes. The reaction mixture was poured into ice/water (200 mL) and the precipitated solid isolated by filtration, washed with water and sucked dry to give a pale yellow solid. This was recrystallised from 50:50 cyclohexane:ethyl acetate (30 mL) to give the title compound as an off-white solid (3.39 g, 55%). ¹H NMR (300 MHz, CDCl₃): δ 10.39 (s, 1H), 8.72 (d, 1H), 8.29 (dd, 1H), 7.89 (d, 1H).

Step 2: 1-(2-bromo-5-nitrophenyl)-N-methylmethanamine

To a suspension of 2-bromo-5-nitrobenzaldehyde (2.00 g, 8.70 mmol) in methanol (22.53 mL) was added methylamine (2M in methanol, 13.04 mL, 26.1 mmol). The resulting mixture was stirred at room temperature for 60 minutes. After cooling to 0° C., sodium borohydride (0.658 g, 17.39 mmol) was added and the mixture allowed to warm to room temperature and stirred for 2 hours. The reaction mixture was quenched by the addition of a few drops of water and concentrated to dryness under reduced pressure. The residue was taken up in ethyl acetate (30 mL) and washed with water (2×30 mL) and brine (30 mL). The organic phase was dried over MgSO₄, filtered and concentrated to dryness under reduced pressure to give the title compound as an orange solid (1.84 g, 86%). ¹H NMR (400 MHz, CDCl₃): δ 8.31 (d, 1H), 7.98 (dd, 1H), 7.72 (d, 1H), 3.90 (s, 2H), 2.50 (s, 3H). LCMS (Method C): $R_T$=0.33 min, m/z=245 [M+H]⁺.

Step 3: tert-butyl 2-bromo-5-nitrobenzyl(methyl)carbamate

To a solution of 1-(2-bromo-5-nitrophenyl)-N-methylmethanamine (1.84 g, 7.51 mmol) in anhydrous THF (18 mL) was added triethylamine (2.302 mL, 16.52 mmol) and di-tert-butyl dicarbonate (1.917 mL, 8.26 mmol) and the resulting mixture stirred at room temperature for 2 hours. The reaction mixture was diluted with ethyl acetate (50 mL) and washed with saturated sodium bicarbonate solution (50 mL) and brine (50 mL). The organic phase was dried over Na₂SO₄, filtered, concentrated to dryness under reduced pressure and slurried in cyclohexane to give the title compound as a yellow solid. The filtrate was concentrated and chromatographed (silica 50 g cartridge, cyclohexane:ethyl acetate, gradient elution from 100:0 to 80:20) to give a further batch of the title compound. Total yield (2.34 g, 90%). ¹H NMR (300 MHz, CDCl₃): δ 7.92-8.11 (m, 2H), 7.74 (d, 1H), 4.47-4.63 (m, 2H), 2.96 (s, 3H), 1.33-1.61 (m, 9H). LCMS (Method C): $R_T$=1.81 min, m/z=289 [M−ᵗBu+H]⁺.

Step 4: tert-butyl methyl(5-nitro-2-(pyridin-4-yl)benzyl) carbamate

A suspension of tert-butyl 2-bromo-5-nitrobenzyl (methyl)carbamate (200 mg, 0.579 mmol), pyridin-4-ylboronic acid (107 mg, 0.869 mmol) and 2M sodium carbonate solution (869 µl, 1.738 mmol) in 1,4-dioxane (1745 µl) was degassed by bubbling nitrogen for 10 minutes followed by the addition of PdCl₂(dppf)-dichloromethane adduct (47.3 mg, 0.058 mmol). The reaction mixture was heated to 120° C. under microwave irradiation for 15 minutes, diluted with water (10 mL) and extracted into ethyl acetate (3×6 mL). The combined organic phases were dried over Na₂SO₄, filtered and concentrated to dryness under reduced pressure. The residue was purified by Biotage chromatography (GraceResolv silica 24 g cartridge, cyclohexane:ethyl acetate, gradient elution from 90:10 to 0:100) to give the title compound as a yellow oil (161 mg, 81%). ¹H NMR (400 MHz, CDCl₃): δ 8.73 (s, 2H), 8.09-8.28 (m, 2H), 7.39 (d, 1H), 7.23 (s, 2H), 4.32-4.51 (br m, 2H), 2.76 (s, 3H), 1.35-1.55 (br m, 9H). LCMS (Method C): $R_T$=1.25 min, m/z=344 [M+H]⁺.

Step 5: tert-butyl 5-amino-2-(pyridin-4-yl)benzyl(methyl)carbamate

A solution of tert-butyl methyl(5-nitro-2-(pyridin-4-yl) benzyl)carbamate (241 mg, 0.702 mmol) in methanol (25 mL) was hydrogenated by H-Cube (10% Pd/C cartridge, 10 bar H2, room temperature, 1 mL/min). The reaction mixture was concentrated to dryness under reduced pressure to give the title compound as a yellow oil (206 mg, 94%). ¹H NMR (300 MHz, CDCl₃): δ 8.60 (d, 2H), 7.19 (d, 2H), 7.03 (d, 1H), 6.65 (dd, 1H), 6.60 (br s, 1H), 4.38 (br d, 2H), 3.81 (br s, 2H), 2.67 (br d, 3H), 1.44 (s, 9H). LCMS (Method C): $R_T$=0.70 min, m/z=314 [M+H]⁺.

Step 6: tert-butyl 5-((6-(2,6-dichlorophenyl)-8-methyl-5-oxo-5,6,7,8-tetrahydropyrimido[4,5-d] pyrimidin-2-yl)amino)-2-(pyridin-4-yl)benzyl (methyl)carbamate 3-(2,6-Dichlorophenyl)-1-methyl-7-(methylthio)-2,3-dihydropyrimido[4,5-d]pyrimidin-4(1H)-one (100 mg, 0.283 mmol) was reacted with tert-butyl 5-amino-2-(pyridin-4-yl) benzyl(methyl)carbamate (89 mg, 0.283 mmol) following the procedure for Example 31 to give the title compound as an off-white solid (14 mg, 8%). ¹H NMR (300 MHz, CDCl₃): δ 8.74 (s, 1H), 8.64 (br s, 2H), 7.73 (br s, 1H), 7.52 (br s, 2H), 7.45 (d, 2H), 7.29 (dd, 1H), 7.15-7.27 (m, 3H), 4.90 (s, 2H), 4.31-4.56 (m, 2H), 3.20 (s, 3H), 2.51-2.84 (m, 3H), 1.27-1.52 (m, 9H). LCMS (Method C): $R_T$=1.22 min, m/z=620 [M+H]⁺.

Step 7: 3-(2,6-dichlorophenyl)-1-methyl-7-((3-((methylamino)methyl)-4-(pyridin-4-yl)phenyl) amino)-2,3-dihydropyrimido[4,5-d]pyrimidin-4(1H)-one tert-Butyl 5-((6-(2,6-dichlorophenyl)-8-methyl-5-oxo-5,6,7,8-tetrahydropyrimido[4,5-d]pyrimidin-2-yl)amino)-2-(pyridin-4-yl)benzyl(methyl)carbamate (14 mg, 0.023 mmol) was deprotected following the procedure for Example 31 to give the title compound as an off-white solid (5 mg, 43%). ¹H NMR (400 MHz, DMSO-d₆): δ 10.05 (s, 1H), 8.60 (dd, 2H), 8.51 (s, 1H), 8.19 (br s, 1H), 7.72 (d, 1H), 7.65 (d, 2H), 7.45-7.52 (m, 3H), 7.24 (d, 1H), 5.00 (s, 2H), 3.57 (s, 2H), 3.17 (s, 3H), 2.26 (s, 3H). LCMS (Method C): $R_T$=0.71 min, m/z=520 [M+H]⁺.

Example 156: 3-(2,6-dichlorophenyl)-1-methyl-7-((3-((methylamino)methyl)-4-(pyridin-3-yl)phenyl) amino)-2,3-dihydropyrimido[4,5-d]pyrimidin-4(1H)-one

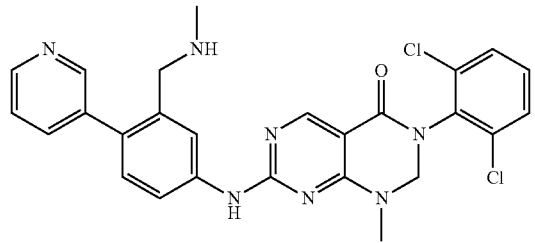 [SMILES: CNCc1cc(Nc2ncc3c(n2)N(C)CN(c2c(Cl)cccc2Cl)C3=O)ccc1-c1cccnc1]

Step 1: tert-butyl methyl(5-nitro-2-(pyridin-3-yl)benzyl)carbamate tert-Butyl 2-bromo-5-nitrobenzyl(methyl)carbamate (300 mg, 0.869 mmol) was reacted with pyridin-3-ylboronic acid (160 mg, 1.30 mmol) following the procedure for Example 155 to give the title compound as a yellow solid (255 mg, 85%). $^1$H NMR (400 MHz, CDCl$_3$): δ 8.70 (d, 1H), 8.57 (d, 1H), 8.10-8.28 (m, 2H), 7.57-7.71 (m, 1H), 7.34-7.49 (m, 2H), 4.33-4.51 (br m, 2H), 2.76 (s, 3H), 1.31-1.57 (br m, 9H). LCMS (Method C): $R_T$=1.30 min, m/z=344 [M+H]$^+$.

Step 2: tert-butyl 5-amino-2-(pyridin-3-yl)benzyl(methyl)carbamate tert-Butyl methyl(5-nitro-2-(pyridin-3-yl)benzyl)carbamate (255 mg, 0.743 mmol) was hydrogenated following the procedure for Example 155 to give the title compound as a yellow oil (243 mg, quantitative yield). LCMS (Method C): $R_T$=0.72 min, m/z=314 [M+H]$^+$.

Step 3: tert-butyl 5-((6-(2,6-dichlorophenyl)-8-methyl-5-oxo-5,6,7,8-tetrahydropyrimido[4,5-d]pyrimidin-2-yl)amino)-2-(pyridin-3-yl)benzyl (methyl)carbamate 3-(2,6-Dichlorophenyl)-1-methyl-7-(methylthio)-2,3-dihydropyrimido[4,5-d]pyrimidin-4(1H)-one (100 mg, 0.283 mmol) was reacted with tert-butyl 5-amino-2-(pyridin-3-yl)benzyl(methyl)carbamate (89 mg, 0.283 mmol) following the procedure for Example 31 to give the title compound as a brown solid (14 mg, 8%). LCMS (Method C): $R_T$=1.36 min, m/z=620 [M+H]$^+$.

Step 4: 3-(2,6-dichlorophenyl)-1-methyl-7-((3-((methylamino)methyl)-4-(pyridin-3-yl)phenyl)amino)-2,3-dihydropyrimido[4,5-d]pyrimidin-4(1H)-one tert-Butyl 5-((6-(2,6-dichlorophenyl)-8-methyl-5-oxo-5,6,7,8-tetrahydropyrimido[4,5-d]pyrimidin-2-yl)amino)-2-(pyridin-3-yl)benzyl(methyl)carbamate (14 mg, 0.23 mmol) was deprotected following the procedure for Example 31 to give the title compound as a pink solid (7 mg, 60%). $^1$H NMR (400 MHz, DMSO-d$_6$): δ 10.03 (s, 1H), 8.62 (d, 1H), 8.55 (dd, 1H), 8.51 (s, 1H), 8.18 (br s, 1H), 7.87 (dt, 1H), 7.70 (dd, 1H), 7.66 (d, 2H), 7.49 (dd, 1H), 7.45 (dd, 1H), 7.22 (d, 1H), 5.00 (s, 2H), 3.54 (s, 2H), 3.17 (s, 3H), 2.24 (s, 3H). LCMS (Method C): $R_T$=0.78 min, m/z=520 [M+H]$^+$.

Example 157: 7-((4-bromo-3-((methylamino)methyl)phenyl)amino)-3-(2,6-dichlorophenyl)-1-methyl-2,3-dihydropyrimido[4,5-d]pyrimidin-4(1H)-one

Step 1: tert-butyl 5-amino-2-bromobenzyl(methyl)carbamate

To a solution of tert-butyl 2-bromo-5-nitrobenzyl(methyl)carbamate (0.72 g, 2.086 mmol) in methanol (11.99 mL) and tetrahydrofuran (2.397 mL) was added zinc dust (1.364 g, 20.86 mmol) followed by the portionwise addition of ammonium chloride (2.231 g, 41.7 mmol). The reaction mixture was stirred at room temperature for 60 minutes, then heated to 40° C. for 4 hours. The reaction mixture was concentrated to dryness under reduced pressure and partitioned between saturated sodium carbonate solution (30 mL) and ethyl acetate (30 mL). The mixture was stirred vigorously for 10 minutes, filtered through Celite® and washed through with ethyl acetate (2×30 mL). The combined organic phases were washed with saturated sodium carbonate solution (2×20 mL), water (2×20 mL) and brine (20 mL), dried over Na$_2$SO$_4$, filtered and concentrated to dryness under reduced pressure to give the title compound as a colourless oil (544 mg, 83%). $^1$H NMR (300 MHz, CDCl$_3$): δ 7.27 (d, 1H), 6.40-6.57 (m, 2H), 4.34-4.52 (m, 2H), 3.37 (br s, 2H), 2.76-2.94 (m, 3H), 1.36-1.54 (m, 9H). LCMS (Method C): $R_T$=1.55 min, m/z=259 [M−$^t$Bu+H]$^+$.

Step 2: tert-butyl 2-bromo-5-((6-(2,6-dichlorophenyl)-8-methyl-5-oxo-5,6,7,8-tetrahydropyrimido[4,5-d]pyrimidin-2-yl)amino)benzyl(methyl)carbamate 3-(2,6-Dichlorophenyl)-1-methyl-7-(methylthio)-2,3-dihydropyrimido[4,5-d]pyrimidin-4(1H)-one (300 mg, 0.846 mmol) was reacted with tert-butyl 5-amino-2-bromobenzyl(methyl)carbamate (267 mg, 0.846 mmol) following the procedure for Example 31 to give the title compound as an off-white solid (223 mg, 42%). $^1$H NMR (300 MHz, CDCl$_3$): δ 8.71 (s, 1H), 7.32-7.61 (m, 6H), 7.29 (dd, 1H), 4.89 (s, 2H), 4.45-4.60 (br m, 2H), 3.18 (s, 3H), 2.80-2.96 (br m, 3H), 1.31-1.57 (br m, 9H). LCMS (Method C): $R_T$=1.98 min, m/z=621 [M+H]$^+$.

Step 3: 7-((4-bromo-3-((methylamino)methyl)phenyl)amino)-3-(2,6-dichlorophenyl)-1-methyl-2,3-dihydropyrimido[4,5-d]pyrimidin-4(1H)-one tert-Butyl 2-bromo-5-((6-(2,6-dichlorophenyl)-8-methyl-5-oxo-5,6,7,8-tetrahydropyrimido[4,5-d]pyrimidin-2-yl)amino)benzyl(methyl)carbamate (25 mg, 0.040 mmol) was deprotected following the procedure for Example 31 to give the title compound as an off-white solid (15 mg, 72%). $^1$H NMR (400 MHz, DMSO-d$_6$): δ 10.01 (s, 1H), 8.49 (s, 1H), 8.15 (br s, 1H), 7.65 (d, 2H), 7.43-7.58 (m, 3H), 4.99 (s, 2H), 3.67 (s, 2H), 3.15 (s, 3H), 2.33 (s, 3H). LCMS (Method C): $R_T$=0.91 min, m/z=521 [M+H]$^+$.

Example 158: 3-(2,6-dichlorophenyl)-7-((4-((3S,5R)-3,5-dimethylpiperazin-1-yl)-3-(hydroxymethyl)phenyl)amino)-1-methyl-2,3-dihydropyrimido[4,5-d]pyrimidin-4(1H)-one

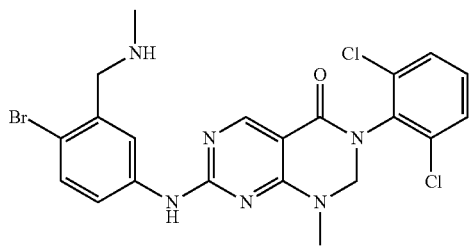 [SMILES: CNCc1cc(Nc2ncc3c(n2)N(C)CN(c2c(Cl)cccc2Cl)C3=O)ccc1Br]

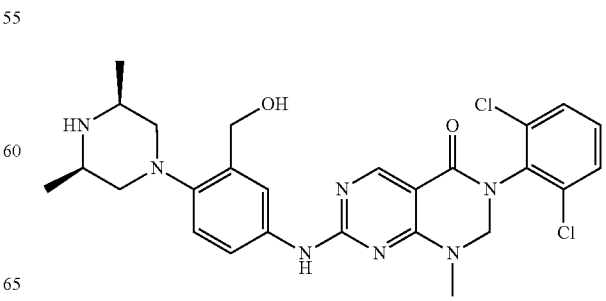

Step 1: 2-((3R,5S)-3,5-dimethylpiperazin-1-yl)-5-nitrobenzaldehyde

To a stirring suspension of 2-fluoro-5-nitrobenzaldehyde (2.69 g, 15.9 mmol) and potassium carbonate (8.80 g, 63.7 mmol) in anhydrous DMF (10 mL) was added (2S,6R)-2,6-dimethylpiperazine (2 g, 17.51 mmol) and the mixture was heated at 90° C. for 16 h. After cooling the mixture was partitioned between brine/water (100 mL) and ethyl acetate (25 mL). The aqueous layer was separated and extracted with ethyl acetate (3×25 mL). The combined ethyl acetate fractions were washed with brine/water (1:1, 4×25 mL), dried (anhydrous sodium sulfate), filtered and reduced in vacuo. The resulting residue was chromatographed (gradient 20-100% ethyl acetate in cyclohexane) to afford the title compound (2.77 g, 66.1%). $^1$H NMR (400 MHz, CDCl$_3$): δ 10.07 (s, 1H), 8.62 (d, 1H), 8.28 (dd, 1H), 7.06 (d, 1H), 3.35 (d, 2H), 3.14-3.17 (m, 2H), 2.72 (dd, 2H), 1.13 (d, 6H). LCMS (Method C): R$_T$=0.43 min, m/z=264 [M+H]$^+$.

Step 2: (2-((3R,5S)-3,5-dimethylpiperazin-1-yl)-5-nitrophenyl)methanol

To a stirring solution of 2-((3R,5S)-3,5-dimethylpiperazin-1-yl)-5-nitrobenzaldehyde (2.77 g, 10.52 mmol) in anhydrous tetrahydrofuran (35 mL) at 0° C. was added portionwise sodium borohydride (0.438 g, 11.57 mmol). Stirring was continued for 1 h. The mixture was reduced in vacuo. The residue was suspended in dichloromethane (40 mL) and stirred for 1 h. The suspension was filtered and the wet cake washed with fresh dichloromethane (2×5 mL). The combined filtrates were concentrated in vacuo to afford the title compound which was used without further purification (2.79 g, 100%). $^1$H NMR (400 MHz, CDCl$_3$): δ 8.25 (d, 1H), 8.12 (dd, 1H), 7.13 (d, 1H), 4.79 (s, 2H), 3.46 (br s, 1H), 3.09 (d, 4H), 2.44 (t, 2H), 1.41 (br s, 1H), 1.12 (d, 6H). LCMS (Method C) R$_T$=0.38 min, m/z=266 [M+H]$^+$.

Step 3: (5-amino-2-((3R,5S)-3,5-dimethylpiperazin-1-yl)phenyl)methanol (2-((3R,5S)-3,5-Dimethylpiperazin-1-yl)-5-nitrophenyl)methanol (1.40 g, 5.28 mmol) was subjected to continuous flow hydrogenation (H-cube, 10% Pd/C cartridge, room temperature, Full H$_2$, 100 ml methanol solvent). The solvent was removed in vacuo to afford the title compound which was used without further purification (1.16 g, 93%). $^1$H NMR (400 MHz, DMSO-d$_6$): δ 6.75 (d, 1H), 6.64 (d, 1H), 6.38 (dd, 1H), 4.97 (br s, 1H), 4.71 (s, 2H), 4.45 (s, 2H), 2.76-2.88 (m, 2H), 2.66 (d, 2H), 2.09 (t, 2H), 1.91 (t, 1H), 0.93 (d, 6H). LCMS (Method C): R$_T$=0.22 min, m/z=236 [M+H]$^+$.

Step 4: 3-(2,6-dichlorophenyl)-7-((4-((3S,5R)-3,5-dimethylpiperazin-1-yl)-3-(hydroxymethyl)phenyl)amino)-1-methyl-2,3-dihydropyrimido[4,5-d]pyrimidin-4(1H)-one (5-Amino-2-((3S,5R)-3,5-dimethylpiperazin-1-yl)phenyl)methanol (66 mg, 0.28 mmol) was reacted with 3-(2,6-dichlorophenyl)-1-methyl-7-(methylthio)-2,3-dihydropyrimido[4,5-d]pyrimidin-4(1H)-one (100 mg, 0.28 mmol) as described in example 131 to give the title compound as a white solid (9 mg, 6%). $^1$H NMR (300 MHz, DMSO-d$_6$): δ 9.83 (s, 1H), 8.46 (s, 1H), 7.99 (br s, 1H), 7.65 (d, 2H), 7.54 (dd, 1H), 7.48 (dd, 1H), 6.96 (d, 1H), 5.07 (t, 1H), 4.96 (s, 2H), 4.54 (d, 2H), 3.11 (s, 3H), 2.83 (m, 4H), 2.16 (t, 2H), 0.97 (d, 6H). LCMS (Method C): R$_T$=0.78 min, m/z=542 [M+H]$^+$.

Example 159: 3-(2,6-dichlorophenyl)-7-((4-methoxy-3-((methylamino)methyl)phenyl)amino)-1-methyl-2,3-dihydropyrimido[4,5-d]pyrimidin-4(1H)-one

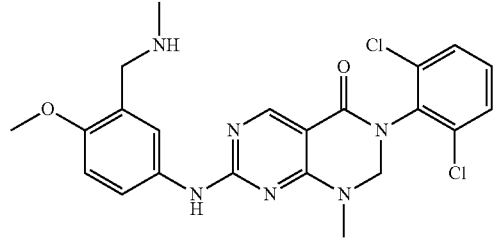 [SMILES: CNCc1cc(Nc2ncc3c(n2)N(C)CN(c2c(Cl)cccc2Cl)C3=O)ccc1OC]

Step 1: tert-butyl 5-amino-2-methoxybenzyl(methyl)carbamate tert-Butyl 2-fluoro-5-nitrobenzyl(methyl)carbamate (185 mg, 0.65 mmol) was dissolved in DMF (4 mL) and a solution of 28% sodium methoxide in methanol (0.16 mL, 0.78 mmol) was added. The mixture was stirred overnight at room temperature. Water was added and the resulting precipitate was collected by filtration to give a solid. This was subjected to continuous flow hydrogenation (H-cube, 10% Pd/C cartridge, room temperature, 50 bar, methanol solvent) to give the title compound (95 mg, 55%) as a colourless oil, which was used without further purification. LCMS (Method C): R$_T$=0.82 min, m/z=267 [M+H]$^+$.

Step 2: 3-(2,6-dichlorophenyl)-7-((4-methoxy-3-((methylamino)methyl)phenyl)amino)-1-methyl-2,3-dihydropyrimido[4,5-d]pyrimidin-4(1H)-one tert-Butyl 5-amino-2-methoxybenzyl(methyl)carbamate (75 mg, 0.28 mmol) was reacted with 3-(2,6-dichlorophenyl)-1-methyl-7-(methylthio)-2,3-dihydropyrimido[4,5-d]pyrimidin-4(1H)-one (100 mg, 0.28 mmol) as described in example 1 to give the title compound (59 mg, 22%) as a white solid. $^1$H NMR (300 MHz, DMSO-d$_6$): δ 9.76 (br s, 1H), 8.45 (s, 1H), 7.78 (br s, 1H), 7.64 (d, 2H), 7.49 (m, 2H), 6.91 (d, 1H), 4.96 (s, 2H), 3.76 (s, 3H), 3.60 (s, 2H), 3.10 (s, 3H), 2.28 (s, 3H). LCMS (Method C): R$_T$=0.78 min, m/z=473 [M+H]$^+$.

Example 160: 3-(2,6-dichlorophenyl)-1-methyl-7-((4-(1-methyl-1H-pyrazol-4-yl)-3-((methylamino)methyl)phenyl)amino)-2,3-dihydropyrimido[4,5-d]pyrimidin-4(1H)-one

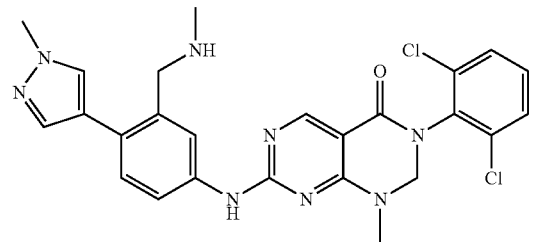 [SMILES: CNCc1cc(Nc2ncc3c(n2)N(C)CN(c2c(Cl)cccc2Cl)C3=O)ccc1-c1cnn(C)c1]

Step 1: tert-butyl 5-((6-(2,6-dichlorophenyl)-8-methyl-5-oxo-5,6,7,8-tetrahydropyrimido[4,5-d]pyrimidin-2-yl)amino)-2-(1-methyl-1H-pyrazol-4-yl)benzyl(methyl)carbamate A suspension of tert-butyl 2-bromo-5-((6-(2,6-dichlorophenyl)-8-methyl-5-oxo-5,6,7,8-tetrahydropyrimido[4,5-d]pyrimidin-2-yl)amino)benzyl(methyl)carbamate (40 mg, 0.064 mmol), 1-methyl-4-(4,4,5,5-tetramethyl-1,3,2-dioxaborolan-2-yl)-1H-pyrazole (20.06 mg, 0.096 mmol) and 2M sodium carbonate solution (193 µl, 0.386 mmol) in 1,4-dioxane (400 µl) was degassed by bubbling nitrogen for 10 minutes. PdCl$_2$(dppf)-dichloromethane adduct (5.25 mg, 6.43 µmol) was added and the reaction mixture was heated to 120° C. under microwave irradiation for 10 minutes, then to 150° C. for 15 minutes then to 180° C. for 10 minutes. The reaction mixture was diluted with water (10 mL) and extracted into ethyl acetate (3×6 mL). The combined organic phases were dried over Na$_2$SO$_4$, filtered and concentrated to dryness under reduced pressure. The residue was chromatographed (KP-NH 11 g cartridge, cyclohexane:ethyl acetate, gradient elution from 90:10 to 0:100) to give the title compound as an off-white solid (17 mg, 42%). $^1$H NMR (400 MHz, CDCl$_3$): δ 8.73 (s, 1H), 7.65 (br s, 1H), 7.53 (s, 1H), 7.36-7.48 (m, 4H), 7.25-7.35 (m, 3H), 4.89 (s, 2H), 4.55 (br s, 2H), 3.96 (s, 3H), 3.20 (s, 3H), 3.64-3.87 (br m, 3H), 1.33-1.56 (br m, 9H). LCMS (Method C): R$_T$=1.50 min, m/z=623 [M+H]$^+$.

Step 2: 3-(2,6-dichlorophenyl)-1-methyl-7-((4-(1-methyl-1H-pyrazol-4-yl)-3-((methylamino)methyl)phenyl)amino)-2,3-dihydropyrimido[4,5-d]pyrimidin-4(1H)-one tert-butyl 5-((6-(2,6-dichlorophenyl)-8-methyl-5-oxo-5,6,7,8-tetrahydropyrimido[4,5-d]pyrimidin-2-yl)amino)-2-(1-methyl-1H-pyrazol-4-yl)benzyl(methyl)carbamate (17 mg, 0.27 mmol) was deprotected following the procedure for Example 31 to give the title compound as an off-white solid (7 mg, 49%). $^1$H NMR (400 MHz, DMSO-d$_6$): δ 9.90 (s, 1H), 8.49 (s, 1H), 8.03 (br s, 1H), 7.90 (s, 1H), 7.55-7.73 (m, 4H), 7.48 (t, 1H), 7.29 (d, 1H), 4.98 (s, 2H), 3.88 (s, 3H), 3.64 (s, 2H), 3.15 (s, 3H), 2.34 (s, 3H). LCMS (Method C): R$_T$=0.85 min, m/z=523 [M+H]$^+$.

Example 161: 3-(2,6-dichlorophenyl)-7-((4-(4-(2-(dimethylamino)acetyl)piperazin-1-yl)-3-(hydroxymethyl)phenyl)amino)-1-methyl-2,3-dihydropyrimido[4,5-d]pyrimidin-4(1H)-one

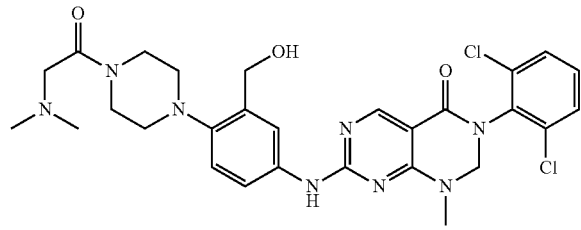 [SMILES: CN(C)CC(=O)N1CCN(c2ccc(Nc3ncc4c(n3)N(C)CN(c3c(Cl)cccc3Cl)C4=O)cc2CO)CC1]

3-(2,6-dichlorophenyl)-7-((3-(hydroxymethyl)-4-(piperazin-1-yl)phenyl)amino)-1-methyl-2,3-dihydropyrimido[4,5-d]pyrimidin-4(1H)-one (47 mg, 0.091 mmol) was dissolved in THF (1 mL) and DIPEA (0.040 mL, 0.23 mmol) was added. 2-chloroacetyl chloride (7.99 µl, 0.101 mmol) was added and the mixture was stirred at RT for 15 min. A 2 M solution of dimethylamine in THF (4.63 µl, 0.091 mmol) was added and the mixture was heated at 150° C. for 30 min under microwave irradiation. The mixture was concentrated in vacuo and the residue was chromatographed (11 g KPNH cartridge; eluted 10-100% EtOAc/c-hex then 0-10% MeOH/EtOAc) to give a colourless glass. This was triturated with ether to give the title compound (12 mg, 22%) as a colourless glass. $^1$H NMR (300 MHz, DMSO-d$_6$): δ 9.87 (br s, 1H), 8.46 (s, 1H), 8.02 (br s, 1H), 7.6 (d, 2H), 7.50 (m, 2H), 7.00 (d, 1H), 4.97 (s, 2), 3.59 (m, 4H), 3.39 (s, 2H), 3.12 (s, 3H), 2.77 (m, 4H), 2.35 (s, 6H). LCMS (Method C): R$_T$=0.76 min, m/z=599 [M+H]$^+$.

Examples 162-163

3-(2,6-dichlorophenyl)-7-((3-((R)-2,2-difluoro-1-hydroxyethyl)-4-((R)-3-(methoxymethyl)piperazin-1-yl)phenyl)amino)-1-methyl-2,3-dihydropyrimido[4,5-d]pyrimidin-4(1H)-one

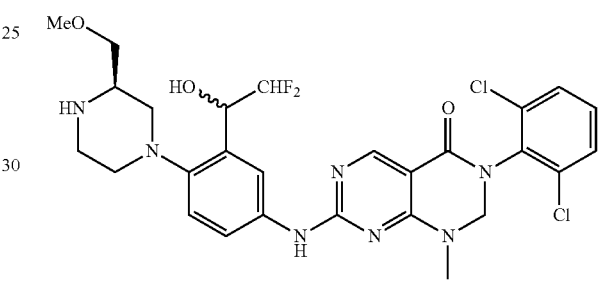

Under an N$_2$ atmosphere, CsF (16 mg, 0.103 mmol) was added to a solution of (R)-tert-butyl 4-(2-formyl-4-nitrophenyl)-2-(methoxymethyl)piperazine-1-carboxylate (300 mg, 0.50 mmol) and (difluoromethyl)trimethylsilane (196 mg, 1.581 mmol) in 5 mL of DMF, then the mixture was stirred at room temperature overnight. A solution of TBAF (2.5 mL, 1 M in THF) was then added, and the whole mixture was stirred for another 1 h. After extraction with ethyl acetate and water, the organic phase was washed with brine, and then dried over anhydrous MgSO$_4$. The solution was filtered and the solvent was evaporated under vacuum. LCMS analysis of the crude residue showed the presence of two diastereoisomers which were separated by biotage chromatography. Each diastereoisomer was then separately hydrogenated using an H-Cube apparatus (10% Pd/C cartridge, Full H$_2$, 25° C., 1 mL/min). Each resulting diastereoisomeric aniline (1 eq) was then coupled with 3-(2,6-dichlorophenyl)-1-methyl-7-(methylthio)-2,3-dihydropyrimido[4,5-d]pyrimidin-4(1H)-one (1.1 eq) following the procedure for example 31 to give each diastereoisomer of the title product. Diastereoisomer 1 (27 mg): $^1$H NMR (400 MHz, DMSO-d$_6$): δ 9.92 (s, 1H), 8.47 (s, 1H), 8.11 (br s, 1H), 7.65 (d, 2H), 7.59 (m, 1H), 7.48 (dd, 1H), 7.21 (d, 1H), 6.12 (d, 1H), 6.03 (dt, 1H), 5.23 (m, 1H), 4.98 (s, 2H), 3.31 (m, 2H), 3.26 (s, 3H), 2.95 (m, 2H), 3.12 (s, 3H), 2.80 (m, 3H), 2.61 (m, 2H). LCMS (Method C): R$_T$=0.87 min, m/z=608 [M+H]$^+$ Diastereoisomer 2 (60 mg): $^1$H NMR (400 MHz, DMSO-d$_6$): δ 9.92 (s, 1H), 8.47 (s, 1H), 8.12 (br s, 1H), 7.65 (d, 2H), 7.58 (m, 1H), 7.48 (dd, 1H), 7.21 (d, 1H), 6.12 (d, 1H), 6.02 (dt, 1H), 5.25 (m, 1H), 4.89 (s, 2H), 3.28 (m, 2H), 3.25 (s, 3H), 3.12 (s, 3H), 3.00-2.60 (m, 7H), 2.37 (m, 2H). LCMS (Method C): R$_T$=0.77 min, m/z=608 [M+H]$^+$.

Example 164: 7-((4-((1S,4S)-2,5-diazabicyclo[2.2.1] heptan-2-yl)-3-(hydroxymethyl)phenyl)amino)-3-(2, 6-dichlorophenyl)-1-methyl-2,3-dihydropyrimido[4, 5-d]pyrimidin-4(1H)-one

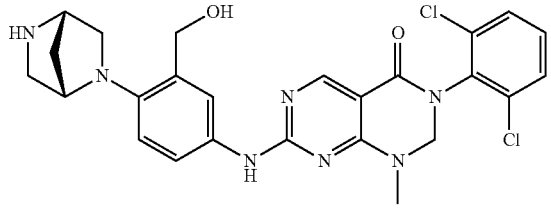 [SMILES: CN1CN(c2c(Cl)cccc2Cl)C(=O)c2cnc(Nc3ccc(N4C[C@@H]5C[C@H]4CN5)c(CO)c3)nc21]

Step 1: (1S,4S)-tert-butyl 5-(2-formyl-4-nitrophenyl)-2,5-diazabicyclo[2.2.1]heptane-2-carboxylate A suspension of 2-fluoro-5-nitrobenzaldehyde (1.00 g, 5.91 mmol), (1S,4S)-tert-butyl 2,5-diazabicyclo[2.2.1]heptane-2-carboxylate (1.172 g, 5.91 mmol) and potassium carbonate (2.452 g, 17.74 mmol) in anhydrous DMF (5 mL) was heated to 50° C. under a nitrogen atmosphere overnight. The reaction mixture was allowed to cool to room temperature, diluted with water (30 mL) and stirred at room temperature for 15 minutes. The precipitated solid was isolated by filtration, washed with water, sucked dry and freeze-dried overnight to give the title compound as a yellow solid (1.82 g, 89%). $^1$H NMR (300 MHz, CDCl$_3$): δ 9.91 (s, 1H), 8.62 (d, 1H), 8.22 (dd, 1H), 6.78 (dd, 1H), 4.50-4.76 (m, 2H), 3.96 (dd, 1H), 3.46-3.66 (m, 2H), 2.91 (dd, 1H), 1.95-2.19 (m, 2H), 1.42 (s, 9H). LCMS (Method C): R$_T$=1.47 min, m/z=348 [M+H]$^+$.

Step 2: (1S,4S)-tert-butyl 5-(2-(hydroxymethyl)-4-nitrophenyl)-2,5-diazabicyclo[2.2.1]heptane-2-carboxylate A suspension of (1S,4S)-tert-butyl 5-(2-formyl-4-nitrophenyl)-2,5-diazabicyclo[2.2.1]heptane-2-carboxylate (1.82 g, 5.24 mmol) in anhydrous THF (9.70 mL) was cooled to 0° C. followed by the portionwise addition of sodium borohydride (0.198 g, 5.24 mmol). The reaction mixture was stirred at 0° C. for 90 minutes. The reaction mixture was quenched with water (30 mL) and extracted into dichloromethane (3×20 mL). The combined organic phases were dried over Na$_2$SO$_4$, filtered and concentrated to dryness under reduced pressure to give the title compound as a yellow solid (1.80 g, 98%). $^1$H NMR (300 MHz, CDCl$_3$): δ 8.18 (dd, 1H), 7.98-8.08 (m, 1H), 6.59 (d, 1H), 4.79 (s, 1H), 4.49-4.73 (m, 3H), 3.81 (d, 1H), 3.36-3.64 (m, 3H), 2.21 (q, 1H), 2.00 (br s, 2H), 1.37-1.53 (m, 9H). LCMS (Method C): R$_T$=1.34 min, m/z=350 [M+H]$^+$.

Step 3: (1S,4S)-tert-butyl 5-(4-amino-2-(hydroxymethyl)phenyl)-2,5-diazabicyclo[2.2.1]heptane-2-carboxylate A solution of (1S,4S)-tert-butyl 5-(2-(hydroxymethyl)-4-nitrophenyl)-2,5-diazabicyclo[2.2.1]heptane-2-carboxylate (1.80 g, 5.15 mmol) in methanol (100 mL) was hydrogenated by H-Cube (10% Pd/C cartridge, 40 bar H$_2$, room temperature, 1 mL/min). The reaction mixture was concentrated to dryness under reduced pressure to give the title compound as a brown solid (1.49 g, 91%). $^1$H NMR (300 MHz, CDCl$_3$): δ 6.86 (d, 1H), 6.51-6.60 (m, 2H), 4.83 (d, 1H), 4.53 (d, 1H), 4.45 (d, 1H), 3.86 (s, 1H), 3.30-3.79 (m, 4H), 3.12-3.29 (m, 2H), 2.02 (d, 1H), 1.91 (t, 1H), 1.65 (br s, 1H), 1.40-1.55 (m, 9H). LCMS (Method C): R$_T$=0.68 min, m/z=320 [M+H]$^+$.

Step 4: (1S,4S)-tert-butyl 5-(4-((6-(2,6-dichlorophenyl)-8-methyl-5-oxo-5,6,7,8-tetrahydropyrimido[4,5-d]pyrimidin-2-yl)amino)-2-(hydroxymethyl)phenyl)-2,5-diazabicyclo[2.2.1]heptane-2-carboxylate 3-(2,6-Dichlorophenyl)-1-methyl-7-(methylthio)-2,3-dihydropyrimido[4,5-d]pyrimidin-4(1H)-one (150 mg, 0.423 mmol) was (1S,4S)-tert-butyl 5-(4-amino-2-(hydroxymethyl)phenyl)-2,5-diazabicyclo[2.2.1]heptane-2-carboxylate (135 mg, 0.423 mmol) following the procedure for Example 31 to give the title compound as a yellow solid (190 mg, 72%). $^1$H NMR (300 MHz, CDCl$_3$): δ 8.71 (s, 1H), 7.59 (br s, 1H), 7.48 (dt, 1H), 7.44 (dd, 2H), 7.35 (br s, 1H), 7.29 (dd, 1H), 6.95 (d, 1H), 4.88 (s, 2H), 4.84 (d, 1H), 4.45-4.67 (m, 2H), 4.06-4.13 (m, 1H), 3.85 (br d, 1H), 3.26-3.63 (m, 4H), 3.18 (s, 3H), 1.86-2.05 (m, 2H), 1.40-1.53 (m, 9H). LCMS (Method C): R$_T$=1.37 min, m/z=626 [M+H]$^+$.

Step 5: 7-((4-((1S,4S)-2,5-diazabicyclo[2.2.1]heptan-2-yl)-3-(hydroxymethyl)phenyl)amino)-3-(2,6-dichlorophenyl)-1-methyl-2,3-dihydropyrimido[4,5-d]pyrimidin-4(1H)-one (1S,4S)-tert-butyl 5-(4-((6-(2,6-dichlorophenyl)-8-methyl-5-oxo-5,6,7,8-tetrahydropyrimido[4,5-d]pyrimidin-2-yl)amino)-2-(hydroxymethyl)phenyl)-2,5-diazabicyclo[2.2.1]heptane-2-carboxylate (190 mg, 0.303 mmol) was deprotected following the procedure for Example 31 to give the title compound as a yellow solid (49 mg, 31%). $^1$H NMR (400 MHz, MeOH-d$_4$): δ 8.51 (s, 1H), 7.83 (br s, 1H), 7.56 (d, 2H), 7.49 (dd, 1H), 7.42 (dd, 1H), 6.97 (d, 1H), 4.97 (s, 2H), 4.70 (d, 1H), 4.61 (d, 1H), 4.15 (s, 1H), 3.88 (s, 1H), 3.42 (dd, 1H), 3.22-3.30 (m, 3H), 3.19 (s, 3H), 3.03 (dd, 1H), 2.05 (d, 1H), 1.80 (d, 1H). LCMS (Method C): R$_T$=0.66 min, m/z=526 [M+H]$^+$.

Example 165: 3-(2,6-dichlorophenyl)-7-((3-(hydroxymethyl)-4-(1-methylpiperidin-4-yl)phenyl) amino)-1-methyl-2,3-dihydropyrimido[4,5-d]pyrimidin-4(1H)-one

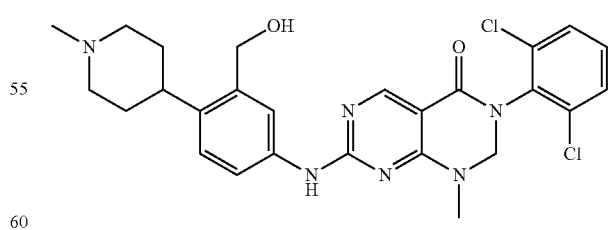

3-(2,6-dichlorophenyl)-7-((3-(hydroxymethyl)-4-(piperidin-4-yl)phenyl)amino)-1-methyl-2,3-dihydropyrimido[4,5-d]pyrimidin-4(1H)-one (31 mg, 0.060 mmol) was methylated following the procedure for Example 35 to give the title compound as a white solid (18 mg, 57%). $^1$H NMR (400 MHz, DMSO-d$_6$): δ 9.83 (br s, 1H), 8.47 (s, 1H), 7.92 (br s, 1H), 7.65 (d, 2H), 7.57 (dd, 1H), 7.48 (t, 1H), 7.18 (d, 1H), 5.07 (t, 1H), 4.97 (s, 2H), 4.53 (d, 2H), 3.12 (s, 3H), 2.85 (d, 2H), 2.57-2.70 (m, 1H), 2.18 (s, 3H), 1.95 (td, 2H), 1.51-1.73 (m, 4H). LCMS (Method C): R$_T$=0.70 min, m/z=527 [M+H]$^+$.

Example 166: 3-(2,6-dichlorophenyl)-1-methyl-7-((1,2,3,4-tetrahydro-1,4-epiminonaphthalen-6-yl)amino)-2,3-dihydropyrimido[4,5-d]pyrimidin-4(1H)-one

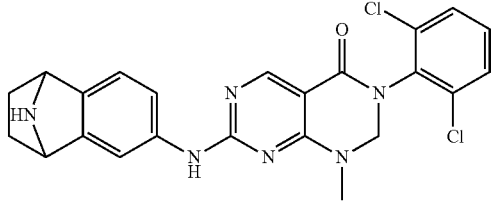 [SMILES: CN1CN(c2c(Cl)cccc2Cl)C(=O)c2cnc(Nc3ccc4c(c3)C3CCC4N3)nc21]

Step 1: tert-butyl 6-amino-1,2,3,4-tetrahydro-1,4-epiminonaphthalene-9-carboxylate A solution of tert-butyl 6-nitro-1,4-dihydro-1,4-epiminonaphthalene-9-carboxylate [Bioorg. Med. Chem., 2011, 19(8), 2726-2741] (500 mg, 1.734 mmol) in methanol (50 mL) was hydrogenated by H-Cube (10% Pd/C cartridge, 40 bar H$_2$, room temperature, 1 mL/min). The reaction mixture was concentrated to dryness under reduced pressure to give the title compound as a white solid (440 mg, 97%). $^1$H NMR (300 MHz, CDCl$_3$): δ 8.06 (d, 1H), 7.97 (dd, 1H), 7.37 (d, 1H), 7.01 (br d, 2H), 5.58 (br s, 2H), 1.37 (s, 9H). LCMS (Method C): R$_T$=1.62 min, m/z=233 [M−$^t$Bu+H]$^+$.

Step 2: tert-butyl 6-((6-(2,6-dichlorophenyl)-8-methyl-5-oxo-5,6,7,8-tetrahydropyrimido[4,5-d]pyrimidin-2-yl)amino)-1,2,3,4-tetrahydro-1,4-epiminonaphthalene-9-carboxylate 3-(2,6-Dichlorophenyl)-1-methyl-7-(methylthio)-2,3-dihydropyrimido[4,5-d]pyrimidin-4(1H)-one (150 mg, 0.423 mmol) was reacted with tert-butyl 6-amino-1,2,3,4-tetrahydro-1,4-epiminonaphthalene-9-carboxylate (110 mg, 0.423 mmol) following the procedure for Example 31 to give the title compound as an off-white solid (143 mg, 60%). $^1$H NMR (300 MHz, CDCl$_3$): δ 8.72 (s, 1H), 7.62 (br s, 1H), 7.44 (dd, 2H), 7.34 (d, 2H), 7.29 (dd, 1H), 7.19 (d, 1H), 5.10 (br s, 2H), 4.89 (s, 2H), 3.18 (s, 3H), 2.12 (d, 2H), 1.40 (s, 9H), 1.32 (d, 2H). LCMS (Method C): R$_T$=1.76 min, m/z=567 [M+H]$^+$.

Step 3: 3-(2,6-dichlorophenyl)-1-methyl-7-((1,2,3,4-tetrahydro-1,4-epiminonaphthalen-6-yl)amino)-2,3-dihydropyrimido[4,5-d]pyrimidin-4(1H)-one tert-Butyl 6-((6-(2,6-dichlorophenyl)-8-methyl-5-oxo-5,6,7,8-tetrahydropyrimido[4,5-d]pyrimidin-2-yl)amino)-1,2,3,4-tetrahydro-1,4-epiminonaphthalene-9-carboxylate (143 mg, 0.252 mmol) was deprotected following the procedure for Example 31 to give the title compound as a pale yellow solid (75 mg, 64%). $^1$H NMR (400 MHz, DMSO-d$_6$): δ 9.79 (br s, 1H), 8.46 (s, 1H), 7.61-7.67 (m, 3H), 7.48 (dd, 1H), 7.42 (d, 1H), 7.12 (d, 1H), 4.96 (s, 2H), 4.41 (dd, 2H), 3.09 (s, 3H), 1.85 (dd, 2H), 1.10 (dd, 2H). LCMS (Method C): R$_T$=0.75 min, m/z=467 [M+H]$^+$.

Example 167: 3-(2,6-dichlorophenyl)-7-((3-(hydroxymethyl)-4-(piperidin-4-yl)phenyl)amino)-1-methyl-2,3-dihydropyrimido[4,5-d]pyrimidin-4(1H)-one

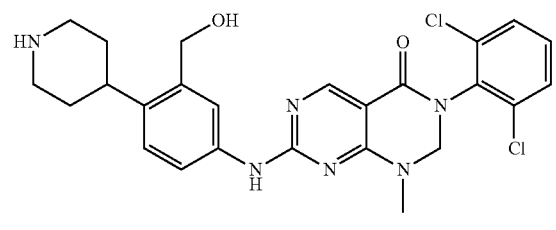 [SMILES: CN1CN(c2c(Cl)cccc2Cl)C(=O)c2cnc(Nc3ccc(C4CCNCC4)c(CO)c3)nc21]

Step 1: tert-butyl 4-(4-amino-2-(hydroxymethyl)phenyl)piperidine-1-carboxylate

A solution of tert-butyl 4-(2-(hydroxymethyl)-4-nitrophenyl)-5,6-dihydropyridine-1(2H)-carboxylate in methanol (15 mL) was hydrogenated by H-Cube (10% Pd/C cartridge, 40 bar H$_2$, room temperature, 1 mL/min; then Pd(OH)$_2$/C cartridge, 40 bar H$_2$, room temperature, 1 mL/min; then Pd(OH)$_2$/C cartridge, 60 bar H$_2$, room temperature, 1 mL/min). The reaction mixture was concentrated to dryness under reduced pressure to give the title compound as an off-white solid (120 mg, 94%). $^1$H NMR (300 MHz, CDCl$_3$): δ 7.01 (d, 1H), 6.70 (d, 1H), 6.62 (dd, 1H), 4.62 (s, 2H), 4.19 (br s, 2H), 3.17 (br s, 2H), 2.64-2.90 (m, 3H), 1.50-1.73 (m, 4H), 1.47 (s, 9H). LCMS (Method C): R$_T$=0.78 min, m/z=314 [M−$^t$Bu-H$_2$O+H]$^+$.

Step 2: tert-butyl 4-(4-((6-(2,6-dichlorophenyl)-8-methyl-5-oxo-5,6,7,8-tetrahydropyrimido[4,5-d]pyrimidin-2-yl)amino)-2-(hydroxymethyl)phenyl)piperidine-1-carboxylate 3-(2,6-Dichlorophenyl)-1-methyl-7-(methylthio)-2,3-dihydropyrimido[4,5-d]pyrimidin-4(1H)-one (150 mg, 0.423 mmol) was reacted with tert-butyl 4-(4-amino-2-(hydroxymethyl)phenyl)piperidine-1-carboxylate (130 mg, 0.423 mmol) following the procedure for Example 31 to give the title compound as an off-white solid (83 mg, 32%). $^1$H NMR (300 MHz, CDCl$_3$): δ 8.73 (s, 1H), 8.38 (br s, 1H), 7.58-7.69 (m, 2H), 7.43 (dd, 2H), 7.28 (dd, 1H), 7.20 (d, 1H), 4.88 (s, 2H), 4.74 (s, 2H), 4.23 (br s, 2H), 3.18 (s, 3H), 3.63-2.97 (m, 4H), 1.52-1.84 (m, 4H), 1.48 (s, 9H). LCMS (Method C): R$_T$=1.54 min, m/z=613 [M+H]$^+$.

Step 3: 3-(2,6-dichlorophenyl)-7-((3-(hydroxymethyl)-4-(piperidin-4-yl)phenyl)amino)-1-methyl-2,3-dihydropyrimido[4,5-d]pyrimidin-4(1H)-one tert-Butyl 4-(4-((6-(2,6-dichlorophenyl)-8-methyl-5-oxo-5,6,7,8-tetrahydropyrimido[4,5-d]pyrimidin-2-yl)amino)-2-(hydroxymethyl)phenyl)piperidine-1-carboxylate (83 mg, 0.135 mmol) was deprotected following the procedure for Example 31 to give the title compound as an off-white solid (56 mg, 81%). $^1$H NMR (400 MHz, DMSO-d$_6$): δ 9.84 (br s, 1H), 8.47 (s, 1H), 7.93 (br s, 1H), 7.65 (d, 2H), 7.58 (dd, 1H), 7.48 (dd, 1H), 7.16 (d, 1H), 5.08 (br s, 1H), 4.97 (s, 2H), 4.54 (s, 2H), 3.13 (s, 3H), 3.05 (d, 2H), 2.80 (tt, 1H), 2.63 (td, 2H), 1.62 (d, 2H), 1.53 (qd, 2H). LCMS (Method C): $R_T$=0.85 min, m/z=513 [M+H]$^+$.

Example 168: 3-(2,6-dichlorophenyl)-1-(3-((methylamino)methyl)phenyl)-7-((4-morpholinophenyl)amino)-2,3-dihydropyrimido[4,5-d]pyrimidin-4(1H)-one

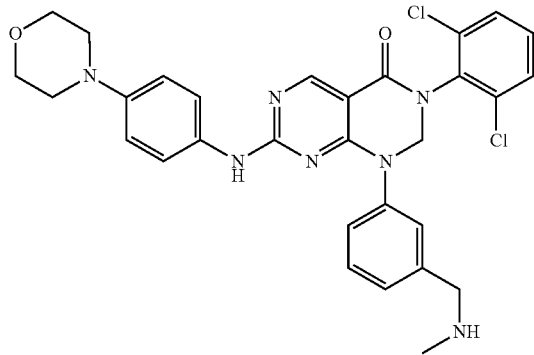 [SMILES: CNCc1cccc(N2CN(c3c(Cl)cccc3Cl)C(=O)c3cnc(Nc4ccc(N5CCOCC5)cc4)nc32)c1]

tert-Butyl 3-(3-(2,6-dichlorophenyl)-7-(methylthio)-4-oxo-3,4-dihydropyrimido[4,5-d]pyrimidin-1(2H)-yl)benzyl(methyl)carbamate (60 mg, 0.107 mmol) was reacted with 4-morpholinoaniline (19 mg, 0.107 mmol) as described in Example 1 to give the title compound (27 mg, 47%) as an off-white solid. $^1$H NMR (300 MHz, DMSO-d$_6$): δ 9.78 (br s, 1H), 8.63 (s, 1H), 7.62 (d, 2H), 7.40 (7H, m), 6.70 (m, 2H), 5.37 (s, 2H), 3.70 (m, 6H), 2.98 (m, 4H). LCMS (Method C): $R_T$=0.81 min, m/z=590 [M+H]$^+$.

Example 169: 3-(2,6-dichlorophenyl)-1-ethyl-7-((4-(piperazin-1-yl)phenyl)amino)-2,3-dihydropyrimido[4,5-d]pyrimidin-4(1H)-one

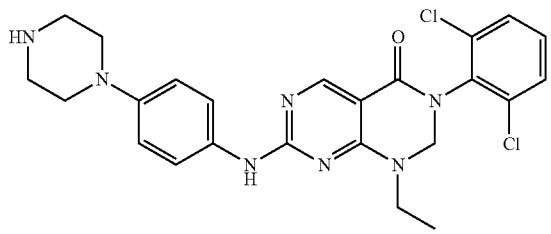 [SMILES: CCN1CN(c2c(Cl)cccc2Cl)C(=O)c2cnc(Nc3ccc(N4CCNCC4)cc3)nc21]

Step 1: N-(2,6-dichlorophenyl)-4-(ethylamino)-2-(methylthio)pyrimidine-5-carboxamide 4-Chloro-N-(2,6-dichlorophenyl)-2-(methylthio)pyrimidine-5-carboxamide (2 g, 5.74 mmol) was suspended in THF (15 mL) and DIPEA (2.00 mL, 11.5 mmol) was added, followed by a 2 M solution of ethylamine in THF (3.16 mL, 6.31 mmol). The mixture was stirred at RT for 30 min. The mixture was concentrated in vacuo, then diluted with water and extracted with ethyl acetate (×3). The combined organic layers were washed with brine, dried (MgSO$_4$) and concentrated in vacuo to give the title compound (2.20 g, 107%) as a white solid which was used without further purification. LCMS (Method C): $R_T$=1.59 min, m/z=357 [M+H]$^+$.

Step 2: 3-(2,6-dichlorophenyl)-1-ethyl-7-(methylthio)-2,3-dihydropyrimido[4,5-d]pyrimidin-4(1H)-one N-(2,6-Dichlorophenyl)-4-(ethylamino)-2-(methylthio)pyrimidine-5-carboxamide (1.50 g, 4.20 mmol) was suspended in acetonitrile (15 mL). Cesium carbonate (6.84 g, 21.0 mmol) was added, followed by dibromomethane (1.17 mL, 16.8 mmol) The mixture was heated at reflux overnight. The mixture was cooled to RT, diluted with water and extracted with dichloromethane (×2). The combined organic layers were washed with brine then dried (MgSO$_4$) and concentrated. The residue was chromatographed (24 g Si cartridge; eluted 0-100% EtOAc/c-hex) to give the title compound (460 mg, 30%) as a colourless glass that crystallised on standing. $^1$H NMR (300 MHz, CDCl$_3$): δ 8.72 (s, 1H), 7.46 (d, 2H), 7.31 (m, 1H), 4.94 (s, 2H), 3.75 (q, 2H), 2.57 (s, 3H), 1.26 (t, 3H). LCMS (Method C): $R_T$=1.57 min, m/z=369 [M+H]$^+$.

Step 3: 3-(2,6-dichlorophenyl)-1-ethyl-7-((4-(piperazin-1-yl)phenyl)amino)-2,3-dihydropyrimido[4,5-d]pyrimidin-4(1H)-one tert-Butyl 4-(4-aminophenyl)piperazine-1-carboxylate (75 mg, 0.27 mmol) was reacted with 3-(2,6-dichlorophenyl)-1-ethyl-7-(methylthio)-2,3-dihydropyrimido[4,5-d]pyrimidin-4(1H)-one (100 mg, 0.27 mmol) as described in Example 1 to give the title compound (60 mg, 45%) as a white solid. $^1$H NMR (300 MHz, DMSO-d$_6$): δ 9.70 (s, 1H), 8.45 (s, 1H), 7.63 (m, 4H), 7.48 (m, 1H), 6.88 (d, 2H), 4.99 (s, 2H), 3.65 (q, 2H), 2.99 (m, 4H), 2.84 (m, 4H), 1.20 (t, 3H). LCMS (Method C): $R_T$=0.80 min, m/z=498 [M+H]$^+$.

Example 170: 3-(2,6-dichlorophenyl)-7-((4-((3S,5R)-3,5-dimethylpiperazin-1-yl)-3-(hydroxymethyl)phenyl)amino)-1-ethyl-2,3-dihydropyrimido[4,5-d]pyrimidin-4(1H)-one

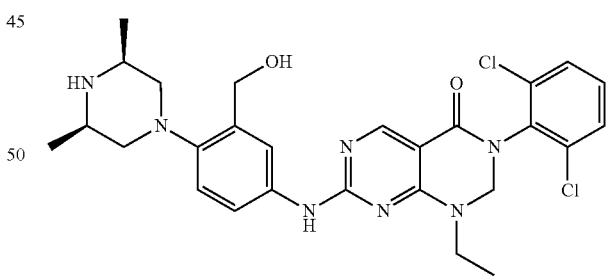

(5-Amino-2-((3S,5R)-3,5-dimethylpiperazin-1-yl)phenyl)methanol (64 mg, 0.27 mmol) was reacted with 3-(2,6-dichlorophenyl)-1-ethyl-7-(methylthio)-2,3-dihydropyrimido[4,5-d]pyrimidin-4(1H)-one (100 mg, 0.27 mmol) as described in Example 131 to give the title compound (60 mg, 45%) as a white solid. $^1$H NMR (300 MHz, DMSO-d$_6$): δ 9.81 (s, 1H), 8.46 (s, 1H), 7.99 (s, 1H), 7.65 (m, 2H), 7.50 (m, 2H), 6.96 (d, 1H), 5.05 (t, 1H), 5.00 (s, 2H), 4.54 (d, 2H), 3.68 (q, 2H), 2.85 (m, 4H), 2.16 (t, 2H), 1.20 (t, 3H), 0.97 (d, 6H). LCMS (Method C): $R_T$=0.84 min, m/z=556 [M+H]$^+$.

Example 171: 3-(2,6-dichlorophenyl)-1-phenyl-7-((4-(piperazin-1-yl)phenyl)amino)-2,3-dihydropyrimido[4,5-d]pyrimidin-4(1H)-one

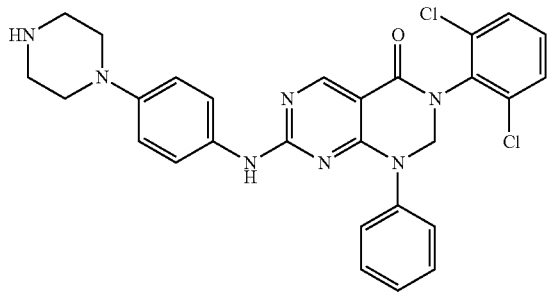 [SMILES: O=C1c2cnc(Nc3ccc(N4CCNCC4)cc3)nc2N(c2ccccc2)CN1c1c(Cl)cccc1Cl]

Step 1: N-(2,6-dichlorophenyl)-2-(methylthio)-4-(phenylamino)pyrimidine-5-carboxamide 4-Chloro-N-(2,6-dichlorophenyl)-2-(methylthio)pyrimidine-5-carboxamide (2 g, 5.74 mmol) was suspended in THF (15 mL). DIPEA (2.00 mL, 11.47 mmol) was added, followed by aniline (0.58 mL, 6.31 mmol). The reaction was stirred at RT for 30 min. The reaction mixture was concentrated in vacuo, then diluted with water and DCM. The organic layer was concentrated to give a solid which was washed with ethyl acetate to give the title compound (2.20 g, 95%) as an off-white solid, which was used without further purification. LCMS (Method C): $R_T$=1.84 min, m/z=405 $[M+H]^+$.

Step 2: 3-(2,6-dichlorophenyl)-7-(methylthio)-1-phenyl-2,3-dihydropyrimido[4,5-d]pyrimidin-4(1H)-one N-(2,6-Dichlorophenyl)-2-(methylthio)-4-(phenylamino)pyrimidine-5-carboxamide (1 g, 2.467 mmol) was dissolved in acetonitrile (10 mL) and dibromomethane (0.69 mL, 9.87 mmol) was added followed by cesium carbonate (4.02 g, 12.34 mmol). The reaction was heated at reflux for 64 h. The mixture was diluted with water and extracted with dichloromethane (×3). The combined organic layers were washed with brine then dried (MgSO4) and concentrated in vacuo. The residue was chromatographed (24 g Si cartridge; eluted 0-50% EtOAc/c-hex) to give the title compound (293 mg, 29%) as an off-white foam. LCMS (Method C): $R_T$=1.72 min, m/z=417 $[M+H]^+$.

Step 3: 3-(2,6-dichlorophenyl)-1-phenyl-7-((4-(piperazin-1-yl)phenyl)amino)-2,3-dihydropyrimido[4,5-d]pyrimidin-4(1H)-one tert-Butyl 4-(4-aminophenyl)piperazine-1-carboxylate (67 mg, 0.24 mmol) was reacted with 3-(2,6-dichlorophenyl)-7-(methylthio)-1-phenyl-2,3-dihydropyrimido[4,5-d]pyrimidin-4(1H)-one (100 mg, 0.24 mmol) as described in Example 1 to give the title compound (60 mg, 45%) as a white solid. $^1$H NMR (300 MHz, DMSO-$d_6$): δ 9.83 (br s, 1), 8.62 (s, 1H), 7.62 (m, 2H), 7.40 (m, 8H), 6.63 (m, 2H), 5.37 (s, 2H), 2.91 (m, 4H), 2.81 (m, 4H). LCMS (Method C): $R_T$=0.95 min, m/z=546 $[M+H]^+$.

Example 172: 3-(2,6-dichlorophenyl)-7-((3-(2-(dimethylamino)-1-hydroxyethyl)phenyl)amino)-1-methyl-2,3-dihydropyrimido[4,5-d]pyrimidin-4(1H)-one

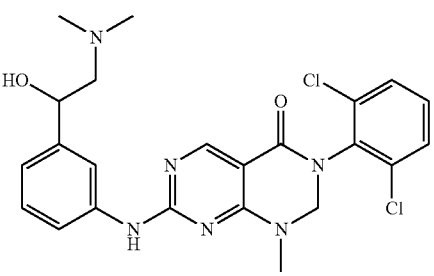

Step 1: 2-(3-nitrophenyl)oxirane 2-(3-nitro-phenyl)-oxirane 5 g of 2-bromo-1-(3-nitro-phenyl)-ethanone was dissolved in 100 mL ethanol, treated with 0.755 g of sodium borohydride and stirred for 1 hour at room temperature. 1.15 g of potassium hydroxide was added and the mixture was stirred for another 15 hours at room temperature. The mixture was diluted with 500 mL of ethyl acetate and the resulting solution was washed twice with 300 mL of half saturated ammonium chloride solution and once with 100 mL of water. The organic phase was dried over sodium sulfate and concentrated in vacuo. The residue was chromatographed to give the title compound (1.50 g, 44%). $^1$H NMR (300 MHz, CDCl$_3$): δ 2.79 (dd, 1H); 3.19 (dd, 1H); 3.93 (dd, 1H); 7.50 (t, 1H); 7.60 (d, 1H); 8.08-8.16 (m, 2H) ppm.

Step 2: tert-butyl (2-hydroxy-2-(3-nitrophenyl) ethyl) (methyl) carbamate 2-(3-Nitrophenyl)oxirane (1.5 g, 9.08 mmol) and methylamine (2N in THF, 20 mL, 40 mmol) were stirred at room temperature overnight. The solution was then concentrated in vacuo. The residue was dissolved in THF. Di-tert-butyl dicarbonate (1.87 g, 8.56 mmol) was then added. The resulting solution was stirred at room temperature overnight then concentrated in vacuo. The residue was purified by Biotage chromatography to afford the title compound (0.57 g, 23.6%).

Step 3: tert-butyl (2-(3-aminophenyl)-2-hydroxyethyl) (methyl)carbamate tert-Butyl (2-hydroxy-2-(3-nitrophenyl) ethyl) (methyl) carbamate (0.3 g, 1.012 mmol) was hydrogenated using an H-Cube following the procedure for example 1 to give the title compound (0.17 g, 63%) that was used directly in the following step.

Step 4: 3-(2,6-dichlorophenyl)-7-((3-(2-(dimethylamino)-1-hydroxyethyl)phenyl)amino)-1-methyl-2,3-dihydropyrimido[4,5-d]pyrimidin-4(1H)-one 3-(2,6-Dichlorophenyl)-1-methyl-7-(methylthio)-2,3-dihydropyrimido [4,5-d]pyrimidin-4(1H)-one (249 mg, 0.702 mmol) was reacted with tert-butyl (2-(3-aminophenyl)-2-hydroxyethyl)(methyl)carbamate (170 mg, 0.638 mmol) following the procedure for example 1 to give the title compound (130 mg, 43%). $^1$H NMR (400 MHz, DMSO-d$_6$): δ 9.92 (s, 1H), 8.49 (s, 1H), 7.97 (s, 1H), 7.67 (d, 2H), 7.55-7.45 (m, 2H), 7.24 (t, 1H), 6.98 (d, 1H), 5.01 (d, 1H), 4.99 (s, 2H), 3.15 (s, 3H), 2.41 (dd, 1H), 2.31 (dd, 1H). LCMS (Method C): R$_T$=0.72 min, m/z=487 [M+H]$^+$.

Example 173: 7-((4-(3-oxa-7,9-diazabicyclo[3.3.1]nonan-7-yl)-3-(hydroxymethyl)phenyl)amino)-3-(2,6-dichlorophenyl)-1-methyl-2,3-dihydropyrimido[4,5-d]pyrimidin-4(1H)-one

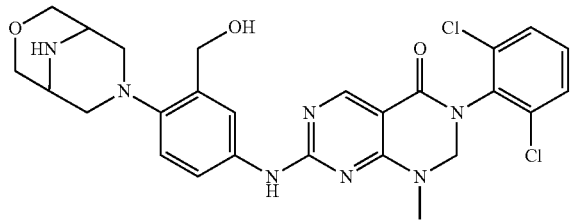 [SMILES: CN1CN(c2c(Cl)cccc2Cl)C(=O)c2cnc(Nc3ccc(N4CC5COCC(C4)N5)c(CO)c3)nc21]

Step 1: tert-butyl 7-(2-formyl-4-nitrophenyl)-3-oxa-7,9-diazabicyclo[3.3.1]nonane-9-carboxylate 2-Fluoro-5-nitrobenzaldehyde (37 mg, 0.219 mol) was reacted with tert-butyl 3-oxa-7,9-diazabicyclo[3.3.1]nonane-9-carboxylate following the procedure for example 21 to give the title compound (85 mg, 93%) that was used directly in the following step.

Step 2: tert-butyl 7-(2-(hydroxymethyl)-4-nitrophenyl)-3-oxa-7,9-diazabicyclo[3.3.1]nonane-9-carboxylate tert-Butyl 7-(2-formyl-4-nitrophenyl)-3-oxa-7,9-diazabicyclo [3.3.1]nonane-9-carboxylate (85 mg, 0.225 mmol) was reacted with sodium borohydride (10.23 mg, 0.27 mmol) following the procedure for example 21 to give the title compound (78 mg, 91%) that was used directly in the following step.

Step 3: tert-butyl 7-(4-amino-2-(hydroxymethyl)phenyl)-3-oxa-7,9-diazabicyclo[3.3.1]nonane-9-carboxylate tert-Butyl 7-(2-(hydroxymethyl)-4-nitrophenyl)-3-oxa-7,9-diazabicyclo[3.3.1]nonane-9-carboxylate (78 mg, 0.206 mmol) was hydrogenated using an H-Cube apparatus (10% Pd/C cartridge, Full H$_2$, 25° C., 1 mL/min). The solution was concentrated in vacuo to give the title compound (66.8 mg, 93%) that was used directly in the following step.

Step 4: 7-((4-(3-oxa-7,9-diazabicyclo[3.3.1]nonan-7-yl)-3-(hydroxymethyl)phenyl)amino)-3-(2,6-dichlorophenyl)-1-methyl-2,3-dihydropyrimido[4,5-d]pyrimidin-4(1H)-one 3-(2,6-Dichlorophenyl)-1-methyl-7-(methylthio)-2,3-dihydropyrimido[4,5-d]pyrimidin-4(1H)-one (84 mg, 0.236 mmol) was reacted with tert-butyl 7-(4-amino-2-(hydroxymethyl)phenyl)-3-oxa-7,9-diazabicyclo[3.3.1]nonane-9-carboxylate (75 mg, 0.215 mmol) following the procedure for example 31 to give the title compound (26 mg, 22%). $^1$H NMR (400 MHz, DMSO-d$_6$): δ 9.80 (s, 1H), 8.46 (s, 1H), 7.86 (br s, 1H), 7.64 (d, 1H), 7.59 (dd, 1H), 7.48 (t, 1H), 7.05 (d, 1H), 5.22 (t, 1H), 4.96 (s, 2H), 4.63 (d, 2H), 3.87 (m, 4H), 3.11 (s, 3H), 3.10 (m, 4H), 2.85 (m, 2H). LCMS (Method C): R$_T$=0.71 min, m/z=556 [M+H]$^+$.

Example 174: 3-(2,6-dichlorophenyl)-7-((3-((ethylamino)methyl)-4-morpholinophenyl)amino)-1-methyl-2,3-dihydropyrimido[4,5-d]pyrimidin-4(1H)-one

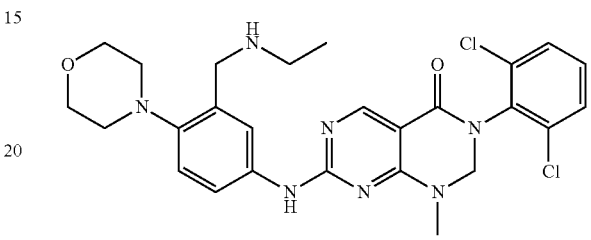

Step 1: tert-butyl ethyl(2-morpholino-5-nitrobenzyl)carbamate

2-Morpholino-5-nitrobenzaldehyde (0.5 g, 2.12 mmol) was suspended in methanol (6 mL). Sodium bicarbonate (0.36 g, 4.23 mmol) was added, followed by a 2 M solution of ethylamine in THF (1.27 mL, 2.54 mmol). The reaction was heated at 80° C. for 3 h. The mixture was cooled to RT. Sodium borohydride (0.096 g, 2.54 mmol) was added and the mixture was stirred at RT for 1 h. The reaction was quenched by addition of water and concentrated in vacuo. The residue was diluted with water and extracted with dichloromethane. The layers were separated using a phase separator cartridge and the organic layer was concentrated. The residue was dissolved in dichloromethane (5 mL) and DIPEA was added (0.481 m, 2.75 mmol), followed by BOC-anhydride (0.54 mL, 2.33 mmol). The reaction was stirred overnight. The mixture was concentrated in vacuo. The residue was chromatographed (10 g Si cartridge; eluted 0-70% EtOAc/c-hex) to give the title compound (680 mg, 88%) as a yellow oil. $^1$H NMR (300 MHz, CDCl$_3$): δ 8.11 (m, 2H), 7.10 (d, 1H), 4.53 (m, 2H), 3.88 (m, 4H), 3.19 (m, 2H), 2.99 (m, 4H), 1.54 (m, 9H), 1.10 (m, 3H). LCMS (Method C): R$_T$=1.73 min, m/z=366 [M+H]$^+$.

Step 2: tert-butyl 5-amino-2-morpholinobenzyl(ethyl)carbamate tert-Butyl ethyl(2-morpholino-5-nitrobenzyl)carbamate (200 mg, 0.55 mmol) was subjected to continuous flow hydrogenation (H-cube, 10% Pd/C cartridge, room temperature, 60 bar, methanol solvent). The crude product was chromatographed (12 g Si cartridge; eluted 0-80% EtOAc/c-hex) to give the title compound as a white solid (85 mg, 46%). LCMS (Method C): R$_T$=1.00 min, m/z=336 [M+H]$^+$.

Step 3: 3-(2,6-dichlorophenyl)-7-((3-((ethylamino)methyl)-4-morpholinophenyl)amino)-1-methyl-2,3-dihydropyrimido[4,5-d]pyrimidin-4(1H)-one tert-Butyl 5-amino-2-morpholinobenzyl(ethyl)carbamate (85 mg, 0.25 mmol) was reacted with with 3-(2,6-dichlorophenyl)-1-methyl-7-(methylthio)-2,3-dihydropyrimido[4,5-d]pyrimidin-4(1H)-one (90 mg, 0.25 mmol) as described in example 1 to give the title compound (35 mg, 26%) as a white solid. $^1$H NMR (300 MHz, DMSO-d$_6$): δ 9.83 (br s, 1H), 8.45 (s, 1H), 7.97 (br s, 1H), 7.65 (m, 2H), 7.53 (dd, 1H), 7.47 (m, 1H), 7.08 (d, 1H), 4.97 (s, 2H), 3.74 (m, 6H), 3.17 (m, 1H), 3.13 (s, 3H), 2.84 (m, 4H), 2.62 (q, 2H), 1.07 (t, 3H). LCMS (Method C): R$_T$=0.91 min, m/z=542 [M+H]$^+$.

Example 175: 3-(2,6-dichlorophenyl)-1-methyl-7-((9-methyl-1,2,3,4-tetrahydro-1,4-epiminonaphthalen-6-yl)amino)-2,3-dihydropyrimido[4,5-d]pyrimidin-4(1H)-one

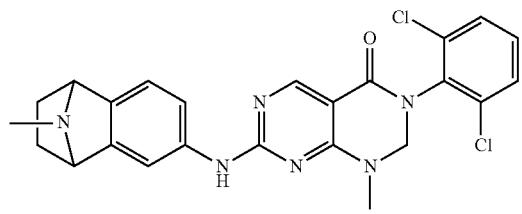

3-(2,6-Dichlorophenyl)-1-methyl-7-((1,2,3,4-tetrahydro-1,4-epiminonaphthalen-6-yl)amino)-2,3-dihydropyrimido[4,5-d]pyrimidin-4(1H)-one (40 mg, 0.086 mmol) was methylated following the procedure for Example 35 to give the title compound as a white solid (18 mg, 44%). $^1$H NMR (400 MHz, DMSO-d$_6$): δ 9.83 (br s, 1H), 8.48 (s, 1H), 7.68 (s, 1H), 7.65 (d, 2H), 7.44-7.56 (m, 2H), 7.18 (d, 1H), 4.96 (s, 2H), 4.01 (d, 2H), 3.10 (s, 3H), 1.86-2.03 (m, 5H), 1.01-1.11 (m, 2H). LCMS (Method C): R$_T$=0.81 min, m/z=481 [M+H]$^+$.

Example 176: 3-(2,6-dichlorophenyl)-7-((3-(hydroxymethyl)-4-((1S,4S)-5-methyl-2,5-diazabicyclo[2.2.1]heptan-2-yl)phenyl)amino)-1-methyl-2,3-dihydropyrimido[4,5-d]pyrimidin-4(1H)-one

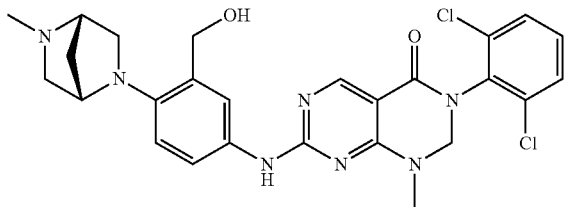 [SMILES: CN1CN(c2c(Cl)cccc2Cl)C(=O)c2cnc(Nc3ccc(N4C[C@@H]5C[C@H]4CN5C)c(CO)c3)nc21]

7-((4-((1S,4S)-2,5-Diazabicyclo[2.2.1]heptan-2-yl)-3-(hydroxymethyl)phenyl)amino)-3-(2,6-dichlorophenyl)-1-methyl-2,3-dihydropyrimido[4,5-d]pyrimidin-4(1H)-one (34 mg, 0.065 mmol) was methylated following the procedure for Example 35 to give the title compound as a yellow solid (12 mg, 34%). $^1$H NMR (400 MHz, DMSO-d$_6$): δ 9.68 (br s, 1H), 8.43 (s, 1H), 7.94 (br s, 1H), 7.64 (d, 2H), 7.44-7.52 (m, 2H), 6.75 (d, 1H), 5.03 (t, 1H), 4.95 (s, 2H), 4.50 (dd, 1H), 4.39 (dd, 1H), 3.93 (s, 2H), 3.23 (d, 1H), 3.28-3.35 (m, 1H), 3.07-3.15 (m, 4H), 2.74 (dd, 1H), 2.64 (d, 1H), 2.28 (s, 3H), 1.77 (d, 1H), 1.69 (d, 1H), peak at 3.28-3.35 ppm partially obscured by solvent. LCMS (Method C): R$_T$=0.70 min, m/z=540 [M+H]$^+$.

Example 177: 3-(2,6-dichlorophenyl)-1-methyl-7-((3-methyl-4-(1,2,3,6-tetrahydropyridin-4-yl)phenyl)amino)-2,3-dihydropyrimido[4,5-d]pyrimidin-4(1H)-one

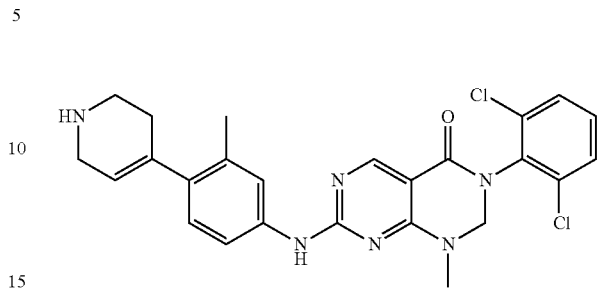

Step 1: tert-butyl 4-(2-methyl-4-nitrophenyl)-5,6-dihydropyridine-1(2H)-carboxylate 1-Iodo-2-methyl-4-nitrobenzene (0.61 g, 2.32 mmol) and tert-butyl 4-(4,4,5,5-tetramethyl-1,3,2-dioxaborolan-2-yl)-5,6-dihydropyridine-1(2H)-carboxylate (0.932 g, 3.01 mmol) were dissolved in 1,4-dioxane (7 mL) and 2M sodium carbonate solution (3.48 mL, 6.96 mmol) was added. The mixture was degassed and placed under nitrogen atmosphere. PdCl$_2$(dppf) dichloromethane adduct (0.189 g, 0.232 mmol) was added and the mixture was heated to 100° C. under microwave irradiation for 20 minutes. The mixture was diluted with water and extracted with ethyl acetate (×3). The combined organic extracts were washed with brine, dried over MgSO$_4$, filtered and concentrated in vacuo. The residue was chromatographed (24 g Si cartridge, eluted 0-50% EtOAc/c-hex) to give the title compound as a brown oil (798 mg, 2.51 mmol, 90% yield). LCMS (Method C): R$_T$=1.89 min, m/z=263 [M+H-tBu]$^+$.

Step 2: tert-butyl 4-(4-amino-2-methylphenyl)-5,6-dihydropyridine-1(2H)-carboxylate tert-Butyl 4-(2-methyl-4-nitrophenyl)-5,6-dihydropyridine-1(2H)-carboxylate (390 mg, 1.23 mmol) was dissolved in ethanol (7 mL). Tin (II) chloride (1.16 g, 6.12 mmol) was added and the mixture was heated at 65° C. for 3 h. The solution was concentrated in vacuo. The residue was taken up in 4 M aqueous sodium hydroxide and extracted with ethyl acetate (×3). The combined organic extracts were washed with brine then dried (MgSO$_4$) and concentrated to give the title compound (246 mg, 70) as a brown syrup which was used directly without further purification. LCMS (Method C): R$_T$=1.24 min, m/z=289 [M+H]$^+$.

Step 3: 3-(2,6-dichlorophenyl)-1-methyl-7-((3-methyl-4-(1,2,3,6-tetrahydropyridin-4-yl)phenyl)amino)-2,3-dihydropyrimido[4,5-d]pyrimidin-4(1H)-one tert-Butyl 4-(4-amino-2-methylphenyl)-5,6-dihydropyridine-1(2H)-carboxylate (179 mg, 0.62 mmol) was reacted with with 3-(2,6-dichlorophenyl)-1-methyl-7-(methylthio)-2,3-dihydropyrimido[4,5-d]pyrimidin-4(1H)-one (200 mg, 0.56 mmol) as described in example 1 to give the title compound (41 mg, 15%) as a white solid. $^1$H NMR (300 MHz, DMSO-d$_6$): δ 9.85 (s, 1H), 8.48 (s, 1H), 7.64 (m, 3H), 7.50 (m, 2H), 6.99 (d, 1H), 5.54 (s, 1H), 4.98 (s, 2H), 3.34 (m, partially obscured by water peak, presumably 2H), 3.12

(s, 3H), 2.87 (t, 3H), 2.24 (s, 3H), 2.14 (m, 2H). LCMS (Method C): $R_T$=0.87 min, m/z=495 [M+H]$^+$.

Example 178: 3-(2,6-dichlorophenyl)-1-methyl-7-((3-methyl-4-(1-methyl-1,2,3,6-tetrahydropyridin-4-yl)phenyl)amino)-2,3-dihydropyrimido[4,5-d]pyrimidin-4(1H)-one

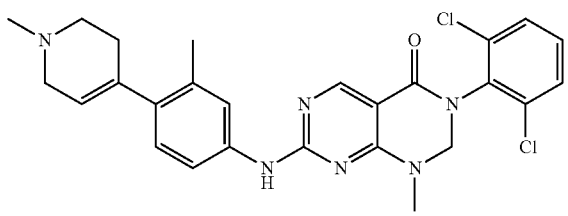 [SMILES: Cc1cc(Nc2ncc3c(n2)N(C)CN(c2c(Cl)cccc2Cl)C3=O)ccc1C1=CCN(C)CC1]

3-(2,6-Dichlorophenyl)-1-methyl-7-((3-methyl-4-(1,2,3,6-tetrahydropyridin-4-yl)phenyl)amino)-2,3-dihydropyrimido[4,5-d]pyrimidin-4(1H)-one (18 mg, 0.036 mmol) was dissolved in methanol (1 mL). Concentrated aqueous formaldehyde (5.41 µl, 0.073 mmol) was added, followed by sodium triacetoxyborohydride (38.5 mg, 0.18 mmol). The mixture was stirred for 16 h. A further portion of aqueous formaldehyde (5.41 µl, 0.073 mmol) was added, followed by sodium triacetoxyborohydride (38.5 mg, 0.18 mmol). The mixture was stirred for 30 min. The reaction was quenched by addition of a few drops of concentrated HCl. The mixture was added to a 2 g SCX cartridge, which was washed with methanol then eluted with 2 M NH$_3$ in methanol to give a white solid. This was suspended in diethyl ether and the solid collected by filtration to give the title compound (8 mg, 43%) as a white solid. $^1$H NMR (300 MHz, DMSO-d$_6$): δ 9.86 (s, 1H), 8.48 (s, 1H), 7.62 (m, 3H), 7.55 (d, 1H), 7.48 (m, 1H), 7.00 (d, 1H), 5.50 (s, 1H), 4.98 (s, 2H), 3.12 (s, 3H), 2.97 (m, 2H), 2.73 (m, 2H), 2.28 (m, 5H). LCMS (Method C): $R_T$=0.90 min, m/z=509 [M+H]$^+$.

Example 179: 3-(2,6-dichlorophenyl)-7-((3-(hydroxymethyl)-4-(1,2,3,6-tetrahydropyridin-4-yl)phenyl)amino)-1-methyl-2,3-dihydropyrimido[4,5-d]pyrimidin-4(1H)-one

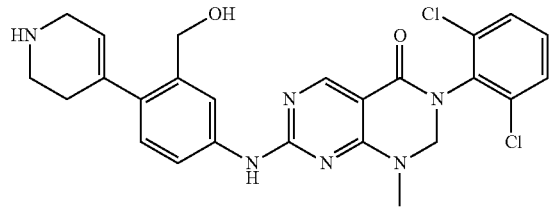

Step 1: (2-bromo-5-nitrophenyl)methanol

A solution of 2-bromo-5-nitrobenzoic acid (2.460 g, 10.00 mmol) in anhydrous THF (50 mL) was cooled to 0° C. followed by the dropwise addition of borane tetrahydrofuran complex (1M in THF, 25 mL, 25.00 mmol). The reaction mixture was allowed to warm to room temperature and stirred overnight. The reaction mixture was cooled to 0° C. and quenched by the addition of brine (50 mL). The layers were separated and the aqueous phase extracted with ethyl acetate (2×50 mL). The combined organic phases were concentrated to dryness under reduced pressure and purified by Biotage chromatography (silica 100 g cartridge, cyclohexane:ethyl acetate, gradient elution from 95:5 to 60:40) to give the title compound as a white solid (1.80 g, 78%). $^1$H NMR (300 MHz, CDCl$_3$): δ 8.43 (d, 1H), 8.02 (dd, 1H), 7.72 (d, 1H), 4.83 (d, 2H), 2.16 (t, 1H).

Step 2: tert-butyl 4-(2-(hydroxymethyl)-4-nitrophenyl)-5,6-dihydropyridine-1(2H)-carboxylate A suspension of (2-bromo-5-nitrophenyl)methanol (500 mg, 2.155 mmol), tert-butyl 4-(4,4,5,5-tetramethyl-1,3,2-dioxaborolan-2-yl)-5,6-dihydropyridine-1(2H)-carboxylate (999 mg, 3.23 mmol) and 2M sodium carbonate solution (3232 µl, 6.46 mmol) in 1,4-dioxane (6491 µl) was degassed by bubbling nitrogen for 10 minutes followed by the addition of PdCl$_2$(dppf)-dichloromethane adduct (88 mg, 0.108 mmol). The reaction mixture was heated to 120° C. under microwave irradiation for 20 minutes. The reaction mixture was diluted with water (20 mL) and extracted into ethyl acetate (3×12 mL). The combined organic phases were dried over Na$_2$SO$_4$, filtered and concentrated to dryness under reduced pressure. The residue was purified by Biotage chromatography (silica 50 g cartridge, cyclohexane:ethyl acetate, gradient elution from 95:5 to 50:50) to give the title compound as a yellow oil (743 mg, quantitative yield). $^1$H NMR (300 MHz, CDCl$_3$) δ 8.41 (d, 1H), 8.11 (dd, 1H), 7.28 (d, 1H), 5.68 (br s, 1H), 4.75 (d, 2H), 4.06 (q, 2H), 3.64 (t, 2H), 2.37 (br s, 2H), 1.50 (s, 9H). LCMS (Method C): $R_T$=1.52 min, m/z=235 [M-Boc+H]$^+$.

Step 3: tert-butyl 4-(4-amino-2-(hydroxymethyl)phenyl)-5,6-dihydropyridine-1(2H)-carboxylate To a solution of tert-butyl 4-(2-(hydroxymethyl)-4-nitrophenyl)-5,6-dihydropyridine-1(2H)-carboxylate (370 mg, 1.107 mmol) in ethanol (7377 µl) was added tin(II) chloride (1049 mg, 5.53 mmol) and the resulting mixture heated to 65° C. for 2.5 hours. The reaction mixture was concentrated to dryness under reduced pressure, diluted with 4M NaOH solution (15 mL) and extracted into ethyl acetate (3×10 mL). The combined organic phases were dried over Na$_2$SO$_4$, filtered, concentrated to dryness under reduced pressure and purified by Biotage chromatography (GraceResolv silica 12 g cartridge, cyclohexane:ethyl acetate:methanol, gradient elution from 90:10:0 to 0:100:0 to 0:90:10) to give the title compound as a white solid (45 mg, 13%). $^1$H NMR (300 MHz, CDCl$_3$): δ 6.92 (d, 1H), 6.79 (d, 1H), 6.58 (dd, 1H), 5.54 (br s, 1H), 4.57 (s, 2H), 3.99 (q, 2H), 3.69 (br s, 2H), 3.58 (t, 2H), 2.32 (br s, 2H), 1.49 (s, 9H). LCMS (Method C): $R_T$=0.92 min, m/z=305 [M+H]$^+$.

Step 4: tert-butyl 4-(4-((6-(2,6-dichlorophenyl)-8-methyl-5-oxo-5,6,7,8-tetrahydropyrimido[4,5-d]pyrimidin-2-yl)amino)-2-(hydroxymethyl)phenyl)-5,6-dihydropyridine-1(2H)-carboxylate 3-(2,6-dichlorophenyl)-1-methyl-7-(methylthio)-2,3-dihydropyrimido[4,5-d]pyrimidin-4(1H)-one (53 mg, 0.148 mmol) was reacted with tert-butyl 4-(4-amino-2-(hydroxymethyl)phenyl)-5,6-dihydropyridine-1(2H)-carboxylate (45 mg, 0.148 mmol) following the procedure for Example 31 to give the title compound as a white solid (58 mg, 64%). $^1$H NMR (300 MHz, CDCl$_3$): δ 8.75 (s, 1H), 7.84 (d, 1H), 7.80 (br s, 1H), 7.57 (dd, 1H), 7.44 (d, 2H), 7.29 (dd, 1H), 7.11 (d, 1H), 5.61 (br s, 1H), 4.90 (s, 2H), 4.68 (d, 2H), 4.03 (d, 2H), 3.62 (t, 2H), 3.21 (s, 3H), 2.37 (br s, 2H), 1.50 (s, 9H). LCMS (Method C): $R_T$=1.58 min, m/z=611 [M+H]$^+$.

Step 5: 3-(2,6-dichlorophenyl)-7-((3-(hydroxymethyl)-4-(1,2,3,6-tetrahydropyridin-4-yl)phenyl)amino)-1-methyl-2,3-dihydropyrimido[4,5-d]pyrimidin-4(1H)-one tert-butyl 4-(4-((6-(2,6-dichlorophenyl)-8-methyl-5-oxo-5,6,7,8-tetrahydropyrimido[4,5-d]pyrimidin-2-yl)amino)-2-(hydroxymethyl)phenyl)-5,6-dihydropyridine-1(2H)-carboxylate (58 mg, 0.095 mmol) was deprotected following the procedure for Example 31 to give the title compound as a white solid (39 mg, 80%). $^1$H NMR (400 MHz, DMSO-d$_6$): δ 9.88 (br s, 1H), 8.48 (s, 1H), 8.07 (br s, 1H), 7.65 (d, 2H), 7.55 (d, 1H), 7.48 (dd, 1H), 7.01 (d, 1H), 5.56 (br s, 1H), 5.04 (t, 1H), 4.97 (s, 2H), 4.48 (d, 2H), 3.13 (s, 3H), 2.89 (t, 2H), 2.50-2.53 (m, 2H), 2.15 (br s, 2H), protons at 2.50-2.53 partially obscured by solvent. LCMS (Method C): $R_T$=0.74 min, m/z=511 [M+H]$^+$.

Example 180: 3-(2,6-dichlorophenyl)-7-((3-(hydroxymethyl)-4-(1-methyl-1,2,3,6-tetrahydropyridin-4-yl)phenyl)amino)-1-methyl-2,3-dihydropyrimido[4,5-d]pyrimidin-4(1H)-one

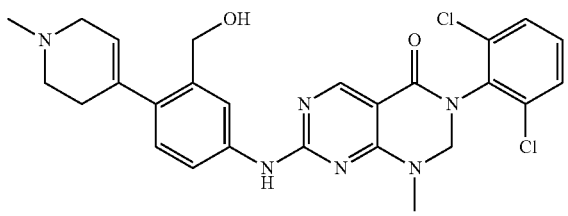 [SMILES: CN1CC=C(c2ccc(Nc3ncc4c(n3)N(C)CN(c3c(Cl)cccc3Cl)C4=O)cc2CO)CC1]

3-(2,6-dichlorophenyl)-7-((3-(hydroxymethyl)-4-(1,2,3,6-tetrahydropyridin-4-yl)phenyl)amino)-1-methyl-2,3-dihydropyrimido[4,5-d]pyrimidin-4(1H)-one (27 mg, 0.91 mmol) was methylated following the procedure for Example 35 to give the title compound as a white solid (27 mg, 91%). $^1$H NMR (400 MHz, DMSO-d$_6$): δ 9.89 (br s, 1H), 8.48 (s, 1H), 8.07 (br s, 1H), 7.65 (d, 2H), 7.55 (d, 1H), 7.48 (t, 1H), 7.02 (d, 1H), 5.52 (br s, 1H), 5.05 (t, 1H), 4.97 (s, 2H), 4.46 (d, 2H), 3.13 (s, 3H), 2.96 (s, 2H), 2.50-2.57 (m, 2H), 2.22-2.35 (m, 5H), protons at 2.50-2.57 partially obscured by solvent. LCMS (Method C): $R_T$=0.75 min, m/z=525 [M+H]$^+$.

Example 181: 7-((4-(1-cyclobutylpiperidin-4-yl)-3-(hydroxymethyl)phenyl)amino)-3-(2,6-dichlorophenyl)-1-methyl-2,3-dihydropyrimido[4,5-d]pyrimidin-4(1H)-one

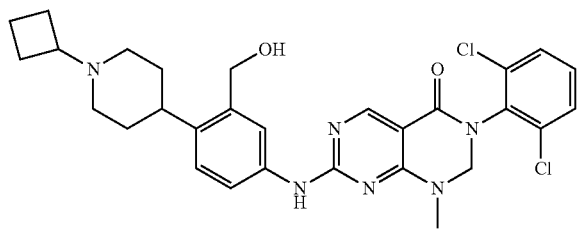 [SMILES: CN1CN(c2c(Cl)cccc2Cl)C(=O)c2cnc(Nc3ccc(C4CCN(C5CCC5)CC4)c(CO)c3)nc21]

A suspension of 3-(2,6-dichlorophenyl)-7-((3-(hydroxymethyl)-4-(piperidin-4-yl)phenyl)amino)-1-methyl-2,3-dihydropyrimido[4,5-d]pyrimidin-4(1H)-one (25 mg, 0.049 mmol), cyclobutanone (10.92 μl, 0.146 mmol) and acetic acid (8.36 μl, 0.146 mmol) in 1,2-dichloroethane (1 mL) was stirred at room temperature for 15 minutes followed by the addition of sodium triacetoxyborohydride (31.0 mg, 0.146 mmol). The reaction mixture was then stirred at room temperature overnight. Further cyclobutanone (10.92 μl, 0.146 mmol) and sodium triacetoxyborohydride (31.0 mg, 0.146 mmol) were added and the mixture heated at 60° C. for 4 hours. The reaction mixture was allowed to cool to room temperature, additional cyclobutanone (10.92 μl, 0.146 mmol), sodium triacetoxyborohydride (31.0 mg, 0.146 mmol) and acetic acid (8.36 μl, 0.146 mmol) added and the mixture stirred at room temperature overnight. The reaction mixture was loaded onto a prewashed 5 g SCX-2 cartridge, allowed to bind for 10 minutes, washed with 80:20 dichloromethane: methanol before the product was eluted with 80:20 dichloromethane: 7M ammonia in methanol. The resulting solution was concentrated to dryness, purified by chromatography (GraceResolv silica 12 g cartridge, dichloromethane:2M ammonia in methanol, gradient elution from 100:0 to 80:20) and freeze-dried overnight to give the title compound as a white solid (10 mg, 36%). $^1$H NMR (300 MHz, DMSO-d$_6$): δ 9.87 (br s, 1H), 8.47 (s, 1H), 7.95 (br s, 1H), 7.65 (d, 2H), 7.56 (br d, 1H), 7.48 (dd, 1H), 7.18 (d, 1H), 5.10 (t, 1H), 4.97 (s, 2H), 4.53 (d, 2H), 3.12 (s, 3H), 2.57-3.05 (br m, 3H), 1.48-2.13 (br m, 13H). LCMS (Method C): $R_T$=0.80 min, m/z=567 [M+H]$^+$.

Example 182: 3-(2,6-dichlorophenyl)-7-((3-methoxy-4-(piperidin-4-yl)phenyl)amino)-1-methyl-2,3-dihydropyrimido[4,5-d]pyrimidin-4(1H)-one

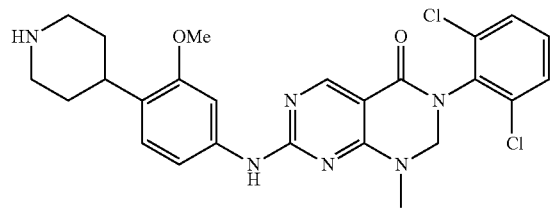 [SMILES: COc1cc(Nc2ncc3c(n2)N(C)CN(c2c(Cl)cccc2Cl)C3=O)ccc1C1CCNCC1]

Step 1: tert-butyl 4-(2-methoxy-4-nitrophenyl)-5,6-dihydropyridine-1(2H)-carboxylate A suspension of 1-iodo-2-methoxy-4-nitrobenzene (600 mg, 2.150 mmol), tert-butyl 4-(4,4,5,5-tetramethyl-1,3,2-dioxaborolan-2-yl)-5,6-dihydropyridine-1(2H)-carboxylate (997 mg, 3.23 mmol) and 2M sodium carbonate solution (3225 μl, 6.45 mmol) in 1,4-dioxane (6477 μl) was degassed by bubbling nitrogen for 10 minutes followed by the addition of PdCl$_2$(dppf)-dichloromethane adduct (88 mg, 0.108 mmol). The reaction mixture was heated to 120° C. under microwave irradiation for 20 minutes. The reaction mixture was diluted with water (20 mL) and extracted into ethyl acetate (3×12 mL). The combined organic phases were dried over Na$_2$SO$_4$, filtered and concentrated to dryness under reduced pressure. The residue was purified by chromatography (silica 50 g cartridge, cyclohexane:ethyl acetate, gradient elution from 95:5 to 70:30) to give the title compound as a yellow oil that solidified upon standing (661 mg, 92%). $^1$H NMR (300 MHz, CDCl$_3$): δ 7.82 (dd, 1H), 7.71 (d, 1H), 7.28 (d, 1H), 5.87 (br s, 1H), 4.07 (q, 2H), 3.91 (s, 3H), 3.60 (t, 2H), 2.48 (br s, 2H), 1.49 (s, 9H). LCMS (Method C): R$_T$=1.85 min, m/z=279 [M−$^t$Bu+H]$^+$.

Step 2: tert-butyl 4-(4-amino-2-methoxyphenyl)piperidine-1-carboxylate

To a suspension of tert-butyl 4-(2-methoxy-4-nitrophenyl)-5,6-dihydropyridine-1(2H)-carboxylate (400 mg, 1.196 mmol) and 10% palladium on carbon (127 mg, 0.120 mmol) in ethanol (5 mL) was added ammonium formate (377 mg, 5.98 mmol) and the resulting mixture heated to 60° C. under a nitrogen atmosphere for 2 hours. The reaction mixture was allowed to cool to room temperature, filtered through Celite® and concentrated to dryness under reduced pressure. The residue was redissolved in dichloromethane (10 mL) and washed with saturated sodium bicarbonate solution (10 mL). The aqueous phase was washed with dichloromethane (2×10 mL). The combined organic phases were dried over Na$_2$SO$_4$, filtered and concentrated to dryness under reduced pressure to give the title compound as a pink solid (270 mg, 74%). $^1$H NMR (300 MHz, CDCl$_3$): δ 6.90 (d, 1H), 6.20-6.30 (m, 2H), 4.20 (br s, 2H), 3.77 (s, 3H), 3.60 (br s, 2H), 2.94 (tt, 1H), 2.79 (br t, 2H), 1.74 (br d, 2H), 1.51 (td, 2H), 1.47 (s, 9H). LCMS (Method C): R$_T$=1.22 min, m/z=251 [M−$^t$Bu+H]$^+$.

Step 3: tert-butyl 4-(4-((6-(2,6-dichlorophenyl)-8-methyl-5-oxo-5,6,7,8-tetrahydropyrimido[4,5-d]pyrimidin-2-yl)amino)-2-methoxyphenyl)piperidine-1-carboxylate 3-(2,6-dichlorophenyl)-1-methyl-7-(methylthio)-2,3-dihydropyrimido[4,5-d]pyrimidin-4(1H)-one (210 mg, 0.590 mmol) was reacted with tert-butyl 4-(4-amino-2-methoxyphenyl)piperidine-1-carboxylate (181 mg, 0.590 mmol) following the procedure for Example 31 to give the title compound as a white solid (210 mg, 58%). $^1$H NMR (300 MHz, CDCl$_3$): δ 8.73 (s, 1H), 7.59 (br s, 1H), 7.39-7.47 (m, 3H), 7.29 (dd, 1H), 7.02-7.12 (m, 2H), 4.89 (s, 2H), 4.22 (br s, 2H), 3.85 (s, 3H), 3.20 (s, 3H), 3.04 (tt, 1H), 2.82 (br t, 2H), 1.79 (br d, 2H), 1.59 (td, 2H), 1.48 (s, 9H). LCMS (Method C): R$_T$=1.89 min, m/z=613 [M+H]$^+$.

Step 4: 3-(2,6-dichlorophenyl)-7-((3-methoxy-4-(piperidin-4-yl)phenyl)amino)-1-methyl-2,3-dihydropyrimido[4,5-d]pyrimidin-4(1H)-one tert-butyl 4-(4-((6-(2,6-dichlorophenyl)-8-methyl-5-oxo-5,6,7,8-tetrahydropyrimido[4,5-d]pyrimidin-2-yl)amino)-2-methoxyphenyl)piperidine-1-carboxylate (210 mg, 0.342 mmol) was deprotected following the procedure for Example 31 to give the title compound as a white solid (168 mg, 96%). $^1$H NMR (300 MHz, DMSO-d$_6$): δ 9.87 (br s, 1H), 8.48 (s, 1H), 7.68 (br s, 1H), 7.65 (d, 2H), 7.48 (dd, 1H), 7.20 (br d, 1H), 7.06 (d, 1H), 4.98 (s, 2H), 3.78 (s, 3H), 3.14 (s, 3H), 2.99 (d, 2H), 2.88 (tt, 1H), 2.49-2.62 (m, 2H), 1.60 (d, 2H), 1.45 (qd, 2H). LCMS (Method C): R$_T$=0.85 min, m/z=513 [M+H]$^+$.

Example 183: 3-(2,6-dichlorophenyl)-7-((3-methoxy-4-(1-methylpiperidin-4-yl)phenyl)amino)-1-methyl-2,3-dihydropyrimido[4,5-d]pyrimidin-4(1H)-one

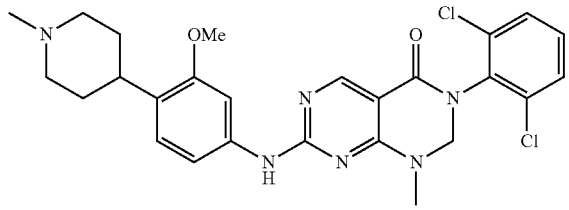 [SMILES: COc1cc(Nc2ncc3c(n2)N(C)CN(c2c(Cl)cccc2Cl)C3=O)ccc1C1CCN(C)CC1]

3-(2,6-dichlorophenyl)-7-((3-methoxy-4-(piperidin-4-yl)phenyl)amino)-1-methyl-2,3-dihydropyrimido[4,5-d]pyrimidin-4(1H)-one (50 mg, 0.97 mmol) was methylated following the procedure for Example 35 to give the title compound as a white solid (42 mg, 82%). $^1$H NMR (300 MHz, DMSO-d$_6$): δ 9.88 (br s, 1H), 8.48 (s, 1H), 7.69 (br s, 1H), 7.65 (d, 2H), 7.48 (dd, 1H), 7.21 (br d, 1H), 7.08 (d, 1H), 4.99 (s, 2H), 3.78 (s, 3H), 3.13 (s, 3H), 2.84 (d, 2H), 2.67-2.79 (m, 1H), 2.17 (s, 3H), 1.84-2.00 (m, 2H), 1.52-1.72 (m, 4H). LCMS (Method C): R$_T$=0.86 min, m/z=527 [M+H]$^+$.

Examples 184-185

3-(2,6-dichlorophenyl)-7-((4-((R)-3-(methoxymethyl)piperazin-1-yl)-3-((R)-2,2,2-trifluoro-1-hydroxyethyl)phenyl)amino)-1-methyl-2,3-dihydropyrimido[4,5-d]pyrimidin-4(1H)-one

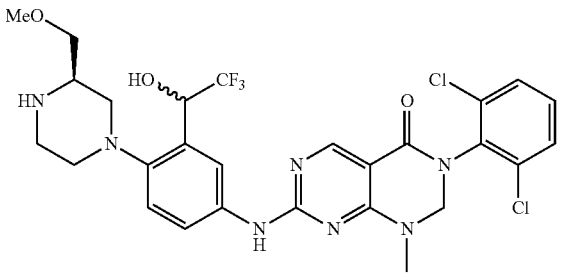 [SMILES: COC[C@H]1CN(c2ccc(Nc3ncc4c(n3)N(C)CN(c3c(Cl)cccc3Cl)C4=O)cc2C(O)C(F)(F)F)CCN1]

(R)-tert-butyl 2-(methoxymethyl)-4-(4-nitro-2-((R)-2,2,2-trifluoro-1-hydroxyethyl)phenyl)piperazine-1-carboxylate and (R)-tert-butyl 2-(methoxymethyl)-4-(4-nitro-2-((S)-2,2,2-trifluoro-1-hydroxyethyl)phenyl)piperazine-1-carboxylate:

Tetrabutylammonium fluoride (2 drops) was added to a solution of 4-(R)-tert-butyl 4-(2-formyl-4-nitrophenyl)-2-(methoxymethyl) piperazine-1-carboxylate (220 mg, 0.58 mmol) and trimethyl(trifluoromethyl)silane (165 mg, 1.160 mmol) in 5 mL of THF, then the mixture was stirred at room temperature overnight. A solution of TBAF (1.7 ml, 1 M in THF) was then added, and the whole mixture was stirred for another 1 h. After extraction with ethyl acetate and water, the organic phase was washed with brine, and then dried over anhydrous MgSO$_4$. The solution was filtered and the solvent was evaporated under vacuum. LCMS analysis (method C) of the crude residue showed the presence of two diastereoisomers (1.69 and 1.74 min, m/z=420) which were separated chromatographically. Each diastereoisomer was then separately hydrogenated using an H-Cube apparatus (10% Pd/C cartridge, Full H₂, 25° C., 1 mL/min). Each resulting diastereoisomeric aniline (1 eq) was then coupled with 3-(2,6-dichlorophenyl)-1-methyl-7-(methylthio)-2,3-dihydropyrimido[4,5-d]pyrimidin-4(1H)-one (1.1 eq) following the procedure for example 31 to give the two diastereoisomers of the title product.

Diastereoisomer 1 (28 mg). ¹H NMR (400 MHz, DMSO-d₆): δ 9.98 (s, 1H), 8.48 (s, 1H),8.26 (br s, 1H), 7.65 (d, 2H), 7.61 (br s, 1H), 7.48 (dd, 1H), 7.27 (d, 1H), 6.75 (d, 1H), 5.69 (m, 1H), 4.98 (s, 2H),3.29 (m, 2H), 3.25 (s, 3H), 3.12 (s, 3H), 2.97 (m, 2H), 2.80 (m, 3H), 2.61 (m, 2H). LCMS (Method C): R$_T$=0.87 min, m/z=626 [M+H]⁺.

Diastereoisomer 2 (18 mg). ¹H NMR (400 MHz, DMSO-d₆): δ 9.98 (s, 1H), 8.48 (s, 1H),8.26 (br s, 1H), 7.65 (d, 2H), 7.61 (br s, 1H),7.48 (dd, 1H), 7.27 (d, 1H), 6.75 (d, 1H), 5.67 (m, 1H), 4.98 (s, 2H),3.32 (m, 2H), 3.25 (s, 3H), 3.12 (s, 3H), 3.00 (m, 2H), 2.9-2.55 (m, 6H), 2.61 (m, 2H). LCMS (Method C): R$_T$=0.91 min, m/z=626 [M+H]⁺.

Comparison of Saturated Compounds with Prior Art:

The compounds herein may have superior physicochemical properties compared with those known in the prior art. For example, kinetic solubility of the examples shown below is higher than the corresponding example claimed in WO2013126656.

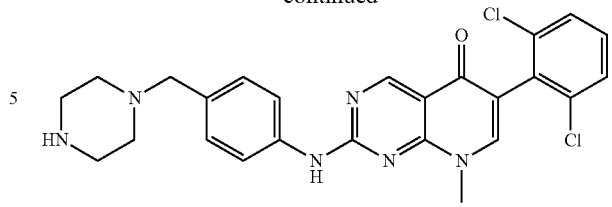

Comparative example under claims
of WO 2013059485
Human microsome Cl$_{int}$ 14 μL/min/mg

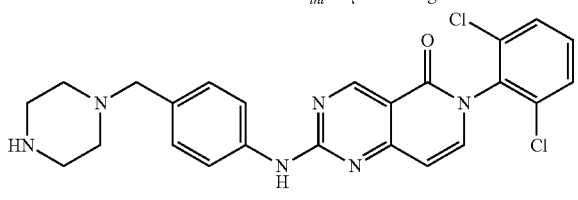

Comparative example under claims
of WO 2013126656
Human microsome Cl$_{int}$ 9 μL/min/mg

| Prior Art | Kinetic Solubility | Present Invention | Kinetic Solubility |
|---|---|---|---|
| | <50 μM | | >150 μM |
| | <50 μM | | >150 μM |

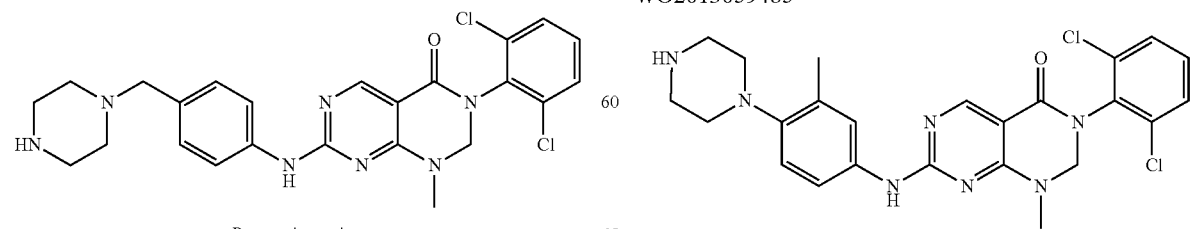

The compounds of the present invention may also have superior metabolic stability compared with those known in the prior art. For example, the intrinsic clearance from human microsomes of the examples shown below is lower than that of the corresponding compounds claimed in WO 2013126656 and WO 2013059485.

Present invention
Human microsome Cl$_{int}$ 3 μL/min/mg

Furthermore, the compounds of the present invention may have lower off-target activity and therefore a greater therapeutic index in vivo. For example, in vitro hERG inhibition is associated with cardiovascular toxicity in vivo. Compounds of the present invention generally have low activity against hERG, e.g. examples 1, 6, 10, 12, 16, 20 all have hERG IC₅₀>10 μM. Furthermore, compounds of the present invention may have lower activity against hERG than those in the prior art, e.g. example 5 of the present invention has lower hERG inhibition than the corresponding analogues from WO2013126656, WO2013013031 and WO2013059485

Example 5 of the present invention
hERG IC50 > 10 μM

-continued

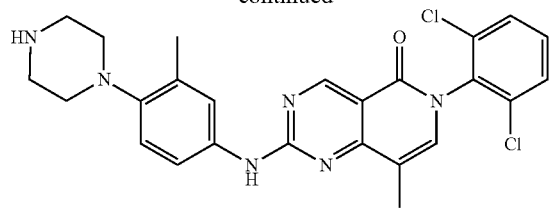

Comparative example from WO2013126656
hERG IC50 = 5.8 μM

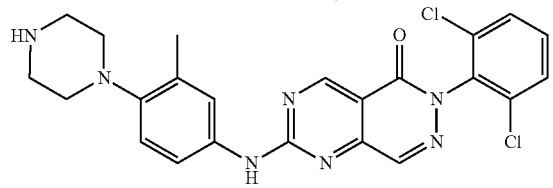

Comparative example from WO2013013031
hERG IC50 = 0.6 μM

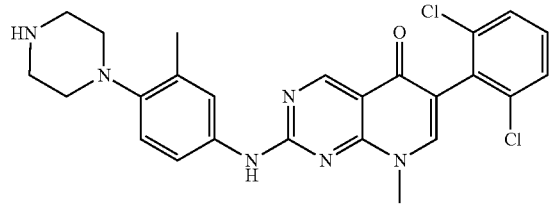

Comparative example from WO 2013059485
hERG IC50 = 7.2 μM

Method 1: Measurement of Wee-1 Kinase Activity

In the measurement of Wee-1 activity, a commercial peptide Poly(Lys Tyr (4:1)) hydrobromide was purchased from Sigma Aldrich and used as the substrate. Activated Wee-1 kinase was purchased from Invitrogen (PV3817) and an ADP-Glo luminescent kit was purchased from Promega.

All reactions took place in 60 μL volumes in reaction buffer containing 40 mM Tris-HCl and 20 mM magnesium chloride, supplemented with 0.1 mg/mL bovine serum albumin and 2 mM DTT. Compounds were serially diluted in buffer and 5 μL of each concentration pipetted into a white 384 well plate (Sigma Aldrich M6186). A 5 μL aliquot of the Wee-1 enzyme was added to each well and the plate centrifuged for 1 min to ensure mixing of the enzyme and inhibitor.

The plate was incubated at room temperature for 30 minutes before the addition of 2.0 μg/mL of substrate and 30 μM ATP in a 5 μL aliquot. The plate was centrifuged for one minute and incubated for 1 h at RT.

15 L of ADP-Glo stop reagent was added to each well to quench the reaction and deplete unconverted ATP. The plate was incubated for a further 40 min in the dark at RT.

30 μL of ADP-Glo kinase detection reagent was added to each well, converting ADP to ATP, catalysing the generation of luciferin by luciferase. The plate was shaken for 1 min, and incubated in the dark for an additional hour.

Luminescence from each well was detected using the Biotek Synergy4 HD plate reader and the percentage inhibition of kinase activity calculated for each inhibitor tested. Positive (kinase only) and negative (no kinase) controls were added to each plate to ensure specific interaction of kinase and inhibitor. The $IC_{50}$ concentration for each inhibitor was calculated by plotting the percentage kinase inhibition against concentration of inhibitor and the curve generated by non-linear regression fitting.

Method 2: Determining the Effect of Compounds on the phosphorylation of cdc2 at Tyr15

The colorectal cancer cell lines HT-29 and HCT-116 were purchased from the ATCC and routinely maintained in McCoy's Medium (Invitrogen) supplemented with 10% Foetal Calf Serum.

The cells were trypsinised from their growing vessel and counted, 100 μL of cell suspension containing 6000 cells was pipetted into black 96 well Co-star plates and incubated overnight to allow adherence to the surface at a temperature of 37° C. and an atmosphere of 5% $CO_2$. Test compounds were formulated in DMSO and diluted in foetal calf serum supplemented medium. Incubating medium was removed by aspiration and diluted drug supplemented medium added to each well.

The plate was returned to the incubator for an additional eight hours at 37° C. and an atmosphere of 5% $CO_2$. Post incubation, the drug supplemented medium was aspirated from each well and the cells were washed once in ice-cold phosphate buffered saline (PBS). 100 μL of cell lysis buffer (Cell Signalling Technologies #9803) containing 20 mM Tris, 150 mM NaCl, 1 mM EDTA, 1 mM EGTA, 1% Triton-X100, 2.5 mM sodium pyrophosphate, 1 mM glycerophosphate, 1 mM $Na_3VO_4$ and 1 μg/mL leupeptin was added to each well of the 96 well plate and incubated at 4° C. for 30 min. The samples on the plate were snap frozen at −80° C. until required. Immediately before the continuation of the assay, the sample plate was thawed and centrifuged at 4° C. for 10 min and the supernatant transferred to secondary tubes or 96 well plate.

Cell supernatant was mixed in a ratio of 1:1 with sample dilutent buffer and vortexed for one minute. 100 μL of diluted sample was pipetted into pre-coated plates containing a rabbit polyclonal antibody for phospho-cdc2 (Tyr15) (Cell Signalling Technologies PathScan kit #7176). The plate was sealed and incubated overnight at 4° C.

The plate seal was removed and the well contents aspirated, followed by 3×5 min washes with 200 μL of diluted wash buffer. Between each wash the plate was tapped firmly onto blotting paper to ensure the removal of all kit solution. 100 μL of kit detection antibody was added to each well and the plate re-sealed and incubated at 37° C. for 1 h. Post incubation the plate was washed and processed in a similar manner to that previously described.

100 μL of horseradish peroxidise-linked secondary antibody was added to each test well, the plate sealed and incubated for thirty minutes at 37° C. Post incubation, the plate was washed as previously stated, followed by the addition of 100 μL of 3,3',5,5' tetramethylbenzidine (TMB reagent). The plate was sealed and incubated at RT for 30 min.

100 μL of stop solution was added to each well and the underside of the plate wiped with a lint-free tissue, prior to spectrophotometric determination. Absorbance from each well was read at 450 nm within 30 min of the addition of the stop solution.

The percentage of phospho-cdc2 was calculated compared to DMSO control and plotted versus the concentration of inhibitor using GraphPad Prism. Data was fitted using non-linear regression analysis and $IC_{50}$ values generated.

Method 3: Determining the Effect of Compounds on the Cdc2 phosphorylation at Tyr15, using a Cell-Based ELISA Base Kit (R&D Systems, KCB001)

The colorectal cancer cell line, HT-29 was purchased from the ATCC and maintained in McCoy's 5 A medium (Gibco®, Life technologies) supplemented with 10% Foetal Calf Serum (FCS).

The cells were trypsinised and counted, 100 µL of 8000 cells was seeded into each well of a clear-bottom black 96-well microplate and incubated overnight to allow adherence to the surface, at 37° C. and 5% $CO_2$ in a cell culture incubator.

Test compounds were formulated in DMSO and diluted in cell culture medium supplemented with FCS. Grow medium was removed from cells and medium containing compounds dilutions was added to each well. The plate was returned to the incubator for an additional eight hours of incubation at 37° C. and 5% $CO_2$.

Post incubation cells were fixed by replacing the compounds supplemented medium with 100 µL of 4% formaldehyde in 1× phosphate buffered saline (PBS), for 20 minutes at room temperature. Formaldehyde solution was removed and cells were washed three times with PBS. The Cell-Based ELISA assay (R&D Systems) was carried out immediately after cell fixation or the plate was sealed and fixed cells were stored in PBS at 4° C. until required (no more than two weeks).

To continue the assay, PBS was removed and cells were washed 3 times for 5 minutes with 200 µL of 1× wash buffer. Each wash step was carried out with gentle shaking. Following washes, 100 µL of 0.6% $H2O2$ in 1× wash buffer (quenching buffer) was added, plate was sealed and incubated for 20 minutes at room temperature. Post incubation cells were washes 3 times for 5 minutes with 200 µL of 1× wash buffer, with gentle shaking. 100 µL of blocking buffer was added to each well, the plate was re-sealed and incubated at room temperature for 1 h.

After blocking, cells were washed as described above. A primary antibody mixture was prepared by mixing the two primary antibodies, a rabbit monoclonal antibody for phospho-cdc2 (Tyr15) (Cell Signaling, #4539) and mouse monoclonal antibody for total cdc2 p34 (Santa Cruz Biotechnology, sc-54), diluted 1:25 and 1:50 in blocking buffer, respectively. 60 µL of primary antibody mixture was added to each well, the plate was sealed and incubated overnight at 4° C.

The primary antibodies were removed and cells were washed as previously described. 100 µL of secondary antibody mixture, containing horseradish-peroxidase (HRP)-conjugated goat anti-rabbit IgG and alkaline phosphatase (AP)-conjugated goat anti-mouse IgG, diluted 1:100 in blocking buffer, was added to each test well. The plate was re-sealed and incubated for 2 hours at room temperature.

The secondary antibodies were removed and cells washed 2 times with wash buffer, followed by 2 washes with PBS. Each wash step was carried out for 5 minutes with gentle shaking. PBS was removed and 75 µL of fluorogenic substrate for HRP (substrate F1) added to each well. The plate was sealed and incubated for 1 h at room temperature, in the dark. 75 µL of fluorogenic substrate for AP (substrate F2) was added directly to each well, plate re-sealed and incubated for additional 40 minutes at room temperature, protected from direct light.

Following incubation fluorescence from each well was read at 600 nm (signal from substrate 1, phosphorylated protein) and then at 450 nm (signal from substrate 2, total protein).

The percentage of phospho-cdc2 was calculated compared to DMSO control, normalized to the total cdc2 and plotted versus the concentration of inhibitor, using Graph-Pad Prism. Data was fitted using a non-linear regression analysis and EC50 values generated.

Method 4: Determination of CLint Estimates Using Human liver microsomes

Test compounds (final concentration=1 µM; final DMSO concentration=0.1%) were incubated in 0.1 M phosphate buffer pH 7.4 with human liver microsomes (0.5 mg of protein/mL) at 37° C. Reactions were started by addition of NADPH in 0.1 M phosphate buffer pH 7.4 (final concentration 1 mM). 40 µL aliquots were removed at 2, 5, 10, 15, 20, 30, 40 and 50 min. Reactions were quenched in 80 µL of ice-cold methanol. Samples were subsequently frozen overnight then centrifuged at 3500 rpm for 20 min at 4° C. The supernatants were removed and transferred into analytical plates and analysed by LC/MS/MS.

LC/MS/MS Method:

All samples were analysed on a Waters Acquity I-Class coupled to a Waters Xevo TQD mass spectrometer. A Waters BEH C18 2.1×50 mm 1.7 µm column was used and mobile phases were water and methanol containing 0.1% formic acid as modifier. Analysis was by multiple reaction monitoring and conditions were optimised for each test compound.

Data Analyses:

From a plot of 1n peak area against time, the gradient of the line is determined. Subsequently, half-life and intrinsic clearance are calculated using the following equations.

$$\text{Eliminated rate constant } (k) = (-\text{gradient})$$

$$\text{Half life } (t_{1/2}) \text{ (min)} = \frac{0.693}{k}$$

$$\text{Intrinsic Clearance } (CL_{int})(\mu L/\text{min/million cells}) = \frac{V \times 0.693}{t_{1/2}}$$

where V=Incubation volume (µL)/number of cells

Method 5: Determination of Kinetic Solubility (in PBS Buffer)

Test compounds (5 µL; 10 mM DMSO stock) were added to 245 µL 10 of PBS buffer pH 7.4 (Dulbecco A) in a Millipore MultiScreen® Solubility Filter plate and mixed at 300 rpm at room temperature on a plate shaker for 90 minutes. Meanwhile 5-points calibration curves for each compound were established in a mixture of acetonitrile/PBS buffer 15 (top concentration 200 µM). After filtration and matrix match, the calibration and assay plates were analysed on a Bioteck Synergy 4 plate reader (240-400 nm). Final concentration of the test compound in the filtrate was calculated using the slope of the calibration curve. All 20 measurements were carried out in triplicate.

Method 6: Determination of hERG Activity

Compounds were tested for inhibition of the human ether a go-go related gene (hERG) K' channel using IonWorks patch clamp electrophysiology at Essen BioScience. 8-Point concentration-response curves of the effect of compound on hERG current as a percentage of pre-compound signal were generated using 3-fold serial dilutions from 11 µM and results are reported as $IC_{50}$ in µM.

The invention claimed is:

1. A compound of Formula (I):

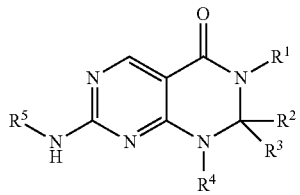

or a pharmaceutically acceptable salt thereof, wherein:
$R^1$ is a phenyl ring substituted with alkyl and/or halogen;
$R^2$ and $R^3$ are independently selected from the group consisting of a hydrogen atom, a deuterium atom, an optionally substituted alkyl group, an optionally substituted cycloalkyl group, an optionally substituted alkoxy group, an optionally substituted amino group, an optionally substituted aryl group and an optionally substituted heteroaryl group; or $R^2$, $R^3$ and the carbon atom to which they are both attached, as taken together, form an optionally substituted cycloalkyl group or an optionally substituted heterocyclyl group;
$R^4$ is a hydrogen atom, an optionally substituted alkyl group, an optionally substituted alkenyl group, an optionally substituted aryl group or an optionally substituted heteroaryl group;
or $R^4$ and $R^2$ or $R^3$ and the ring atoms to which they are attached, as taken together, form an optionally substituted heterocyclyl group; and
$R^5$ is an optionally substituted phenyl ring or a heterocyclic bicyclic ring, wherein the heterocyclic bicyclic ring comprises a phenyl ring that is bound to the amino group.

2. The compound of claim 1, or a pharmaceutically acceptable salt thereof, wherein $R^1$ is a group represented by the formula (a):

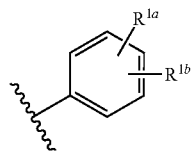

wherein $R^{1a}$ and $R^{1b}$ are each independently selected from the group consisting of a hydrogen atom, a halo group, and a $C_1$-$C_6$ alkyl group.

3. The compound of claim 2, or a pharmaceutically acceptable salt thereof, wherein
$R^{1a}$ is a hydrogen atom, a halo group, or a methyl; and
$R^{1b}$ is a halo group.

4. The compound of claim 1, or a pharmaceutically acceptable salt thereof, wherein $R^1$ is a 2-chlorophenyl group, a 2,6-dichlorophenyl group, or a 2-chloro-6-fluorophenyl group.

5. The compound of claim 4 or a pharmaceutically acceptable salt thereof, wherein $R^1$ is a 2,6-dichlorophenyl group.

6. The compound of claim 1, or a pharmaceutically acceptable salt thereof, wherein $R^2$ and $R^3$ is each independently a hydrogen atom.

7. The compound of claim 1, or a pharmaceutically acceptable salt thereof, wherein $R^2$, $R^3$, or both are a deuterium atom.

8. The compound of claim 1, or a pharmaceutically acceptable salt thereof, wherein $R^4$ is an optionally substituted $C_1$-$C_6$ alkyl group.

9. The compound of claim 8, or a pharmaceutically acceptable salt thereof, wherein $R^4$ is a methyl group.

10. The compound of claim 1, or a pharmaceutically acceptable salt thereof, wherein $R^4$ is an optionally substituted heteroaryl group.

11. The compound of claim 1, or a pharmaceutically acceptable salt thereof, wherein $R^5$ is a group represented by the formula (c):

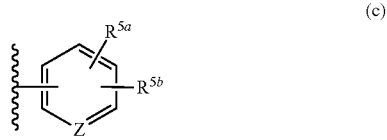

wherein Z is an optionally substituted methine group;
$R^{5a}$ and $R^{5b}$ are independently selected from the group consisting of a hydrogen atom, a halo group, an optionally substituted $C_1$-$C_6$ alkyl group, an optionally substituted $C_1$-$C_6$ nitrile group, an optionally substituted amino group, an optionally substituted $C_1$-$C_6$ alkoxy group, an optionally substituted sulfanyl group, an optionally substituted sulfonyl group, an optionally substituted sulfoximinyl group and an optionally substituted four- to seven-membered nitrogen-containing heterocyclyl group;
wherein the optionally substituted four- to seven-membered nitrogen-containing heterocyclyl group is optionally substituted with one or more substituents selected from the group consisting of a halo group, an optionally substituted $C_1$-$C_6$ alkyl group, an oxo group, a hydroxyl group, an optionally substituted amino group and a group of =N—$R^{5g}$;
or, in formula (c), $R^{5a}$ and $R^{5b}$ exist on adjacent ring atoms and $R^{5a}$ and $R^{5b}$ and the ring atoms to which they are attached may form, as taken together, a three- to seven-membered heterocyclyl group, wherein one or two of the ring atoms constituting the three- to seven-membered heterocyclyl group is optionally independently replaced by an oxygen atom, a nitrogen atom, a group of —N($R^{5c}$)—, a sulfinyl group, a sulfonyl group and a sulfoximinyl group, wherein the three- to seven-membered heterocyclyl group may be substituted with one or more substituents selected from the group consisting of a halo group and a $C_1$-$C_6$ alkyl group;
or $R^{5a}$ and $R^{5b}$ and the ring atoms to which they are attached may form, as taken together, a spirocyclic group or a bicyclic group formed of a five- to seven-membered aliphatic ring and any other three- to seven-membered aliphatic ring, in which one or two or more methylene groups constituting the spirocyclic group or the bicyclic group are each independently replaced by an oxygen atom, a sulphur atom, a sulfinyl group, a sulfonyl, a sulfoximinyl group, an oxo group or a group of —N($R^{5d}$)—, and the spirocyclic group or the bicyclic group may be each independently substituted with a substituent selected from the group consisting of a halo group, a hydroxyl group or a $C_1$-$C_6$ alkyl group; wherein $R^{5c}$, $R^{5d}$ and $R^{5g}$ are each independently a hydrogen atom or a $C_1$-$C_6$ alkyl group optionally substituted with a substituent selected from the group consisting of a halo group, a hydroxyl group, a cyano group, an oxo group, a $C_1$-$C_6$ alkyl group, a $C_1$-$C_6$ alkoxy group, an amino group, a substituted amino group and a nitrogen-containing heterocyclyl group.

12. The compound of claim 1, or a pharmaceutically acceptable salt thereof, wherein $R^5$ is a group represented by the formula (d):

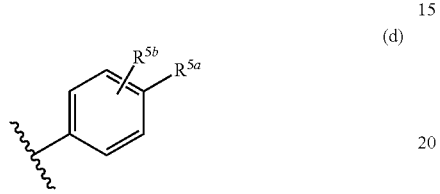

(d)

$R^{5a}$ and $R^{5b}$ are independently selected from the group consisting of a hydrogen atom, a halo group, an optionally substituted $C_1$-$C_6$ alkyl group, an optionally substituted $C_1$-$C_6$ nitrile group, an optionally substituted amino group, an optionally substituted $C_1$-$C_6$ alkoxy group, an optionally substituted sulfanyl group, an optionally substituted sulfonyl group, an optionally substituted sulfoximinyl group and an optionally substituted four- to seven-membered nitrogen-containing heterocyclyl group;

wherein the optionally substituted four- to seven-membered nitrogen-containing heterocyclyl group is optionally substituted with one or more substituents selected from the group consisting of a halo group, an optionally substituted $C_1$-$C_6$ alkyl group, an oxo group, a hydroxyl group, a group of =N—$R^{5g}$ and a group of Q-N($R^{5e}$)$R^{5e'}$;

$R^{5e}$, $R^{5e'}$ and $R^{5g}$ each independently is a hydrogen atom or a $C_1$-$C_6$ alkyl group, or, $R^{5e}$ and $R^{5e'}$ and the nitrogen atom to which they are attached, as taken together, may form an optionally substituted six-membered heterocyclyl group; and Q is a single bond or a $C_1$-$C_3$ alkyl group.

13. The compound of claim 11, wherein the four- to seven-membered nitrogen-containing heterocyclyl group is a four- to seven-membered nitrogen-containing hetercycloalkyl group.

14. The compound of claim 11, or a pharmaceutically acceptable salt thereof, wherein the four- to seven-membered nitrogen-containing heterocyclyl group is selected from the group consisting of an azetidinyl group, a pyrrolidinyl group, a piperidinyl group, a morpholinyl group, a thiomorpholinyl group, a thiomorpholine-S,S-dioxide group, a thiomorpholine-S-Oxo-S-iminyl sulfoximinyl group and a homopiperazinyl group, each of which can be optionally substituted.

15. The compound of claim 11, or a pharmaceutically acceptable salt thereof, wherein $R^{5a}$ is a $C_1$-$C_3$ alkoxy group substituted with an amino group, or $R^{5a}$ is a $C_1$-$C_3$ alkyl group substituted by an optionally substituted five- to seven-membered heterocyclyl group, or $R^{5a}$ is a five- to seven-membered nitrogen-containing heterocyclyl group optionally substituted with one or more substituents selected from the group consisting of a $C_1$-$C_3$ alkyl group and a $C_1$-$C_3$ alkyl group substituted with one or more substituents selected from the group consisting of a hydroxyl group, a carboxyl group, an oxo group and an amino group; and $R^{5b}$ is a hydrogen atom, a halo group, a $C_1$-$C_3$ nitrile group, a $C_1$-$C_3$ alkoxy group or a $C_1$-$C_3$ alkyl group substituted with a substituent selected from the group consisting of an amino group and a hydroxyl group.

16. The compound of claim 1, or a pharmaceutically acceptable salt thereof, wherein $R^5$ is a group represented by the formula (e):

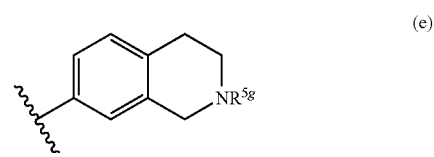

(e)

wherein $R^{5g}$ is selected from the group consisting of a hydrogen atom and an optionally substituted $C_1$-$C_3$ alkyl group.

17. The compound of claim 1, or a pharmaceutically acceptable salt thereof, wherein the compound is selected from the following:

(1) 3-(2,6-dichlorophenyl)-1-methyl-7-((4-(piperazin-1-yl)phenyl)amino)-2,3-dihydropyrimido[4,5-d]pyrimidin-4(1H)-one;

(2) 3-(2,6-dichlorophenyl)-1-methyl-7-((4-(2-(methylamino)ethoxy)phenyl)amino)-2,3-dihydropyrimido[4,5-d]pyrimidin-4(1H)-one;

(3) 3-(2,6-dichlorophenyl)-7-((3-methoxy-4-(piperazin-1-yl)phenyl)amino)-1-methyl-2,3-dihydropyrimido[4,5-d]pyrimidin-4(1H)-one;

(4) 2-(4-(4-((6-(2,6-dichlorophenyl)-8-methyl-5-oxo-5,6,7,8-tetrahydropyrimido[4,5-d]pyrimidin-2-yl)amino)phenyl)piperazin-1-yl)acetic acid hydrochloride;

(5) 3-(2,6-dichlorophenyl)-1-methyl-7-((3-((methylamino)methyl)-4-morpholinophenyl)amino)-2,3-dihydropyrimido[4,5-d]pyrimidin-4(1H)-one;

(6) 3-(2,6-dichlorophenyl)-1-methyl-7-((3-methyl-4-(piperazin-1-yl)phenyl)amino)-2,3-dihydropyrimido[4,5-d]pyrimidin-4(1H)-one;

(7) 3-(2,6-dichlorophenyl)-7-((3-fluoro-4-(piperazin-1-yl)phenyl)amino)-1-methyl-2,3-dihydropyrimido[4,5-d]pyrimidin-4(1H)-one;

(8) 3-(2,6-dichlorophenyl)-1-(4-methoxybenzyl)-7-((4-(piperazin-1-yl)phenyl)amino)-2,3-dihydropyrimido[4,5-d]pyrimidin-4(1H)-one;

(9) 3-(2,6-dichlorophenyl)-7-((4-(piperazin-1-yl)phenyl)amino)-2,3-dihydropyrimido[4,5-d]pyrimidin-4(1H)-one;

(10) 3-(2,6-dichlorophenyl)-7-((3-(hydroxymethyl)-4-(piperazin-1-yl)phenyl)amino)-1-methyl-2,3-dihydropyrimido[4,5-d]pyrimidin-4(1H)-one;

(11) 3-(2,6-dichlorophenyl)-7-((3-cyano-4-(piperazin-1-yl)phenyl)amino)-1-methyl-2,3-dihydropyrimido[4,5-d]pyrimidin-4(1H)-one;

(12) 3-(2,6-dichlorophenyl)-1-methyl-7-((4-(piperazin-1-ylmethyl)phenyl)amino)-2,3-dihydropyrimido[4,5-d]pyrimidin-4(1H)-one;

(13) 7-((4-(4-(2-aminoacetyl)piperazin-1-yl)phenyl)amino)-3-(2,6-dichlorophenyl)-1-methyl-2,3-dihydropyrimido[4,5-d]pyrimidin-4(1H)-one;

(14) 3-(2,6-dichlorophenyl)-1-methyl-7-((1,2,3,4-tetrahydroisoquinolin-7-yl)amino)-2,3-dihydropyrimido[4,5-d]pyrimidin-4(1H)-one;

(15) 3-(2,6-dichlorophenyl)-2,2-dideutero-1-methyl-7-((4-(piperazin-1-yl)phenyl)amino)-2,3-dihydropyrimido[4,5-d]pyrimidin-4(1H)-one;

(16) (R)-3-(2,6-dichlorophenyl)-1-methyl-7-((4-(3-methylpiperazin-1-yl)phenyl)amino)-2,3-dihydropyrimido[4,5-d]pyrimidin-4(1H)-one;

(17) (S)-3-(2,6-dichlorophenyl)-1-methyl-7-((4-(3-methylpiperazin-1-yl)phenyl)amino)-2,3-dihydropyrimido[4,5-d]pyrimidin-4(1H)-one;

(18) 3-(2,6-dichlorophenyl)-1-methyl-7-((3-methyl-4-(piperidin-4-yl)phenyl)amino)-2,3-dihydropyrimido[4,5-d]pyrimidin-4(1H)-one;

(19) (R)-3-(2,6-dichlorophenyl)-7-((4-(3-(hydroxyethyl)piperazin-1-yl)phenyl)amino)-1-methyl-2,3-dihydropyrimido[4,5-d]pyrimidin-4(1H)-one;

(20) (S)-3-(2,6-dichlorophenyl)-7-((4-(3-(hydroxyethyl)piperazin-1-yl)phenyl)amino)-1-methyl-2,3-dihydropyrimido[4,5-d]pyrimidin-4(1H)-one;

(21) 3-(2,6-dichlorophenyl)-7-((3-(hydroxymethyl)-4-(4-isopropylpiperazin-1-yl)phenyl)amino)-1-methyl-2,3-dihydropyrimido[4,5-d]pyrimidin-4(1H)-one;

(22) 3-(2,6-dichlorophenyl)-1-methyl-7-((2-methyl-1,2,3,4-tetrahydroisoquinolin-7-yl)amino)-2,3-dihydropyrimido[4,5-d]pyrimidin-4(1H)-one;

(23) (rac)-3-(2,6-dichlorophenyl)-1-methyl-2-phenyl-7-((1,2,3,4-tetrahydroisoquinolin-7-yl)amino)-2,3-dihydropyrimido[4,5-d]pyrimidin-4(1H)-one;

(24) 3-(2-chlorophenyl)-1-methyl-7-((4-(piperazin-1-yl)phenyl)amino)-2,3-dihydropyrimido[4,5-d]pyrimidin-4(1H)-one;

(25) 3-(2-chloro-6-fluorophenyl)-1-methyl-7-((4-(piperazin-1-yl)phenyl)amino)-2,3-dihydropyrimido[4,5-d]pyrimidin-4(1H)-one;

(26) 3-(2,6-dichlorophenyl)-1,2-dimethyl-7-((4-(piperazin-1-yl)phenyl)amino)-2,3-dihydropyrimido[4,5-d]pyrimidin-4(1H)-one;

(27) 3-(2,6-dichlorophenyl)-7-((4-(morpholinomethyl)phenyl)amino)-2,3-dihydropyrimido[4,5-d]pyrimidin-4(1H)-one;

(28) 6-(2,6-dichlorophenyl)-2-((4-(piperazin-1-yl)phenyl)amino)-6a,7,8,9-tetrahydropyrimido[5,4-e]pyrrolo[1,2-a]pyrimidin-5(6H)-one;

(29) 3-(2,6-dichlorophenyl)-1-methyl-7-((4-((4-methylpiperazin-1-yl)methyl)phenyl)amino)-2,3-dihydropyrimido[4,5-d]pyrimidin-4(1H)-one; and

(30) (rac)-3-(2,6-dichlorophenyl)-1-methyl-7-((4-(S-methylsulfonimidoyl)phenyl)amino)-2,3-dihydropyrimido[4,5-d]pyrimidin-4(1H)-one.

18. The compound of claim 1, or a pharmaceutically acceptable salt thereof, wherein the compound is selected from the following:

(31) 3-(2,6-dichlorophenyl)-7-((3-(methoxymethyl)-4-(piperazin-1-yl)phenyl) amino)-1-methyl-2,3-dihydropyrimido [4,5-d] pyrimidin-4 (1H)-one;

(32) (R)-3-(2,6-dichlorophenyl)-7-((4-(3,4-dimethyl piperazin-1-yl)phenyl) amino)-1-methyl-2,3-dihydropyrimido [4,5-d]pyrimidin-4 (1H)-one;

(33) 3-(2,6-dichlorophenyl)-7-((3-(hydroxymethyl)-4-(4-methylpiperazin-1-yl)phenyl) amino)-1-methyl-2,3-dihydropyrimido [4,5-d]pyrimidin-4 (1H)-one;

(34) (R)-3-(2,6-dichlorophenyl)-7-((4-(3-(hydroxyethyl)-4-methylpiperazin-1-yl)phenyl)amino)-1-methyl-2,3-dihydropyrimido[4,5-d]pyrimidin-4(1H)-one;

(35) 3-(2,6-dichlorophenyl)-1-methyl-7-((4-(5-methylhexahydropyrrolo[3,4-c]pyrrol-2(1H)-yl)phenyl)amino)-2,3-dihydropyrimido[4,5-d]pyrimidin-4(1H)-one;

(36) 3-(2,6-dichlorophenyl)-7-((4-(hexahydropyrrolo[3,4-c]pyrrol-2(1H)-yl)phenyl)amino)-1-methyl-2,3-dihydropyrimido[4,5-d]pyrimidin-4(1H)-one;

(37) 7-((4-(1-aminocyclobutyl)phenyl)amino)-3-(2,6-dichlorophenyl)-1-methyl-2,3-dihydropyrimido[4,5-d]pyrimidin-4(1H)-one;

(38) (R)-3-(2,6-dichlorophenyl)-7-((3-(hydroxymethyl)-4-(3-methylpiperazin-1-yl)phenyl)amino)-1-methyl-2,3-dihydropyrimido[4,5-d]pyrimidin-4(1H)-one;

(39) 7-((4-((1S,4S)-2,5-diazabicyclo[2.2.1]heptan-2-yl)phenyl)amino)-3-(2,6-dichlorophenyl)-1-methyl-2,3-dihydropyrimido[4,5-d]pyrimidin-4(1H)-one;

(40) 3-(2,6-dichlorophenyl)-7-((4-((2R,5S)-2,5-dimethylpiperazin-1-yl)phenyl)amino)-1-methyl-2,3-dihydropyrimido[4,5-d]pyrimidin-4(1H)-one;

(41) 3-(2,6-dichlorophenyl)-1-methyl-7-((4-morpholinophenyl)amino)-2,3-dihydropyrimido[4,5-d]pyrimidin-4(1H)-one;

(42) 3-(2,6-dichlorophenyl)-7-((4-(1,1-dioxidothiomorpholino) phenyl)amino)-1-methyl-2,3-dihydropyrimido[4,5-d]pyrimidin-4(1H)-one;

(43) (R)-3-(2,6-dichlorophenyl)-7-((3-fluoro-4-(3-methylpiperazin-1-yl)phenyl)amino)-1-methyl-2,3-dihydropyrimido[4,5-d]pyrimidin-4(1H)-one;

(44) 3-(2,6-dichlorophenyl)-1-methyl-7-((4-((1S,4S)-5-methyl-2,5-diazabicyclo[2.2.1]heptan-2-yl)phenyl)amino)-2,3-dihydropyrimido[4,5-d]pyrimidin-4(1H)-one;

(45) 3-(2,6-dichlorophenyl)-1-methyl-7-((4-((2R,5S)-2,4,5-trimethylpiperazin-1-yl)phenyl)amino)-2,3-dihydropyrimido[4,5-d]pyrimidin-4(1H)-one;

(46) (R)-3-(2,6-dichlorophenyl)-7-((4-(3,4-dimethylpiperazin-1-yl)-3-(hydroxymethyl)phenyl)amino)-1-methyl-2,3-dihydropyrimido[4,5-d]pyrimidin-4(1H)-one;

(47) (R)-3-(2,6-dichlorophenyl)-7-((4-(3,4-dimethylpiperazin-1-yl)-3-fluorophenyl)amino)-1-methyl-2,3-dihydropyrimido[4,5-d]pyrimidin-4(1H)-one;

(48) (S)-3-(2,6-dichlorophenyl)-7-((3-fluoro-4-(3-(hydroxymethyl)piperazin-1-yl)phenyl)amino)-1-methyl-2,3-dihydropyrimido[4,5-d]pyrimidin-4(1H)-one;

(49) (S)-3-(2,6-dichlorophenyl)-7-((4-(3-(hydroxyethyl)-4-methylpiperazin-1-yl)phenyl)amino)-1-methyl-2,3-dihydropyrimido[4,5-d]pyrimidin-4(1H)-one;

(50) (S)-3-(2,6-dichlorophenyl)-7-((3-fluoro-4-(3-(hydroxymethyl)-4-methylpiperazin-1-yl)phenyl)amino)-1-methyl-2,3-dihydropyrimido[4,5-d]pyrimidin-4(1H)-one;

(51) 7-((4-(2,6-diazaspiro[3.3]heptan-2-yl)phenyl)amino)-3-(2,6-dichlorophenyl)-1-methyl-2,3-dihydropyrimido[4,5-d]pyrimidin-4(1H)-one;

(52) 3-(2,6-dichlorophenyl)-1-methyl-7-((4-((3R,5S)-3,4,5-trimethylpiperazin-1-yl)phenyl)amino)-2,3-dihydropyrimido[4,5-d]pyrimidin-4(1H)-one;

(53) (R)-3-(2-chloro-6-fluorophenyl)-1-methyl-7-((4-(3-methylpiperazin-1-yl)phenyl)amino)-2,3-dihydropyrimido[4,5-d]pyrimidin-4(1H)-one;

(54) 7-((4-((1S,4S)-2,5-diazabicyclo[2.2.1]heptan-2-yl)phenyl)amino)-3-(2-chloro-6-fluorophenyl)-1-methyl-2,3-dihydropyrimido[4,5-d]pyrimidin-4(1H)-one;

(55) 3-(2-chloro-6-fluorophenyl)-1-methyl-7-((3-methyl-4-(piperazin-1-yl)phenyl)amino)-2,3-dihydropyrimido[4,5-d]pyrimidin-4(1H)-one;

(56) 3-(2-chloro-6-fluorophenyl)-7-((3-(hydroxymethyl)phenyl)amino)-1-methyl-2,3-dihydropyrimido[4,5-d]pyrimidin-4(1H)-one;

(57) 3-(2,6-dichlorophenyl)-7-((3-(hydroxymethyl)-4-morpholinophenyl)amino)-1-methyl-2,3-dihydropyrimido[4,5-d]pyrimidin-4(1H)-one;

(58) (R)-3-(2,6-dichlorophenyl)-1-(1-methyl-1H-pyrazol-3-yl)-7-((4-(3-methylpiperazin-1-yl)phenyl)amino)-2,3-dihydropyrimido[4,5-d]pyrimidin-4(1H)-one;

(59) (R)-3-(2,6-dichlorophenyl)-7-((3-(methoxymethyl)-4-(3-methylpiperazin-1-yl)phenyl)amino)-1-methyl-2,3-dihydropyrimido[4,5-d]pyrimidin-4(1H)-one;

(60) (R)-3-(2,6-dichlorophenyl)-7-((4-(3-(methoxymethyl)piperazin-1-yl)phenyl)amino)-1-methyl-2,3-dihydropyrimido[4,5-d]pyrimidin-4(1H)-one;

(61) (S)-3-(2,6-dichlorophenyl)-7-((4-(3-(methoxymethyl)piperazin-1-yl)phenyl)amino)-1-methyl-2,3-dihydropyrimido[4,5-d]pyrimidin-4(1H)-one;

(62) 3-(2,6-dichlorophenyl)-1-methyl-7-((4-(3-(trifluoromethyl)piperazin-1-yl)phenyl)amino)-2,3-dihydropyrimido[4,5-d]pyrimidin-4(1H)-one;

(63) 3-(2,6-dichlorophenyl)-1-methyl-7-((4-(3,3,4-trimethylpiperazin-1-yl)phenyl)amino)-2,3-dihydropyrimido[4,5-d]pyrimidin-4(1H)-one;

(64) 7-((4-(3-oxa-7,9-diazabicyclo[3.3.1]nonan-7-yl)phenyl)amino)-3-(2,6-dichlorophenyl)-1-methyl-2,3-dihydropyrimido[4,5-d]pyrimidin-4(1H)-one;

(65) (R)-3-(2,6-dichlorophenyl)-7-((4-(3-(methoxymethyl)-4-methylpiperazin-1-yl)phenyl)amino)-1-methyl-2,3-dihydropyrimido[4,5-d]pyrimidin-4(1H)-one;

(66) (S)-3-(2,6-dichlorophenyl)-7-((4-(3-(methoxymethyl)-4-methylpiperazin-1-yl)phenyl)amino)-1-methyl-2,3-dihydropyrimido[4,5-d]pyrimidin-4(1H)-one;

(67) (R)-3-(2,6-dichlorophenyl)-7-((4-(3,4-dimethylpiperazin-1-yl)-3-(methoxymethyl)phenyl)amino)-1-methyl-2,3-dihydropyrimido[4,5-d]pyrimidin-4(1H)-one;

(68) 3-(2,6-dichlorophenyl)-1-methyl-7-((4-(4-methyl-3-(trifluoromethyl)piperazin-1-yl)phenyl)amino)-2,3-dihydropyrimido[4,5-d]pyrimidin-4(1H)-one;

(69) 3-(2,6-dichlorophenyl)-7-((3-(methoxymethyl)-4-(piperazin-1-yl)phenyl)amino)-1-methyl-2,3-dihydropyrimido[4,5-d]pyrimidin-4(1H)-one;

(70) 3-(2,6-dichlorophenyl)-1-methyl-7-((6,7,8,9-tetrahydro-5H-5,8-epiminobenzo[7]annulen-3-yl)amino)-2,3-dihydropyrimido[4,5-d]pyrimidin-4(1H)-one;

(71) 3-(2,6-dichlorophenyl)-1-methyl-7-((4-(9-methyl-3-oxa-7,9-diazabicyclo[3.3.1]nonan-7-yl)phenyl)amino)-2,3-dihydropyrimido[4,5-d]pyrimidin-4(1H)-one;

(72) 3-(2,6-dichlorophenyl)-7-((4-(4-ethylpiperazin-1-yl)-3-(hydroxymethyl)phenyl)amino)-1-methyl-2,3-dihydropyrimido[4,5-d]pyrimidin-4(1H)-one;

(73) 3-(2,6-dichlorophenyl)-7-((3-(hydroxymethyl)-4-morpholinophenyl)amino)-1-methyl-2,3-dihydropyrimido[4,5-d]pyrimidin-4(1H)-one;

(74) 7-((4-(3,8-diazabicyclo[3.2.1]octan-3-yl)phenyl)amino)-3-(2,6-dichlorophenyl)-1-methyl-2,3-dihydropyrimido [4,5-d]pyrimidin-4(1H)-one;

(75) 7-((4-((1S,4S)-2,5-diazabicyclo[2.2.1]heptan-2-yl)-3-methylphenyl)amino)-3-(2,6-dichlorophenyl)-1-methyl-2,3-dihydropyrimido [4,5-d]pyrimidin-4(1H)-one;

(76) 3-(2,6-dichlorophenyl)-1-methyl-7-((2'-methyl-2',3'-dihydro-1'H-spiro[cyclopropane-1,4'-isoquinolin]-7'-yl)amino)-2,3-dihydropyrimido[4,5-d]pyrimidin-4(1H)-one;

(77) 3-(2,6-dichlorophenyl)-1-methyl-7-((3-methyl-4-((1S,4S)-5-methyl-2,5-diazabicyclo[2.2.1]heptan-2-yl)phenyl)amino)-2,3-dihydropyrimido[4,5-d]pyrimidin-4(1H)-one;

(78) (R)-3-(2,6-dichlorophenyl)-1-d3-methyl-7-((4-(3-methylpiperazin-1-yl)phenyl)amino)-2,3-dihydropyrimido[4,5-d]pyrimidin-4(1H)-one;

(79) 3-(2,6-dichlorophenyl)-7-((4-((2R,5R)-2,5-dimethylpiperazin-1-yl)phenyl)amino)-1-methyl-2,3-dihydropyrimido[4,5-d]pyrimidin-4(1H)-one;

(80) 3-(2,6-dichlorophenyl)-7-((4-((2S,5R)-2,5-dimethylpiperazin-1-yl)phenyl)amino)-1-methyl-2,3-dihydropyrimido[4,5-d]pyrimidin-4(1H)-one;

(81) 3-(2,6-dichlorophenyl)-7-((4-((2R,5S)-2,5-dimethylpiperazin-1-yl)-3-fluorophenyl)amino)-1-methyl-2,3-dihydropyrimido[4,5-d]pyrimidin-4(1H)-one;

(82) 7-((4-((1S,4S)-2,5-diazabicyclo[2.2.1]heptan-2-yl)-3-methoxyphenyl)amino)-3-(2,6-dichlorophenyl)-1-methyl-2,3-dihydropyrimido[4,5-d]pyrimidin-4(1H)-one;

(83) 3-(2,6-dichlorophenyl)-7-((4-((3R,5S)-3,5-dimethylpiperazin-1-yl)phenyl)amino)-1-methyl-2,3-dihydropyrimido[4,5-d]pyrimidin-4(1H)-one;

(84) 3-(2,6-dichlorophenyl)-7-((3-methoxy-4-((1S,4S)-5-methyl-2,5-diazabicyclo[2.2.1]heptan-2-yl)phenyl)amino)-1-methyl-2,3-dihydropyrimido[4,5-d]pyrimidin-4(1H)-one;

(85) (R)-1-cyclopropyl-3-(2,6-dichlorophenyl)-7-((4-(3-methylpiperazin-1-yl)phenyl)amino)-2,3-dihydropyrimido[4,5-d]pyrimidin-4(1H)-one;

(86) 3-(2,6-dichlorophenyl)-7-((3-(hydroxymethyl)-4-(8-methyl-3,8-diazabicyclo[3.2.1]octan-3-yl)phenyl)amino)-1-methyl-2,3-dihydropyrimido[4,5-d]pyrimidin-4(1H)-one;

(87) 3-(2,6-dichlorophenyl)-1-methyl-7-((4-(piperidin-4-yloxy)phenyl)amino)-2,3-dihydropyrimido[4,5-d]pyrimidin-4(1H)-one;

(88) 3-(2,6-dichlorophenyl)-1-methyl-7-((4-(8-methyl-3,8-diazabicyclo[3.2.1]octan-3-yl)phenyl)amino)-2,3-dihydropyrimido[4,5-d]pyrimidin-4(1H)-one;

(89) 3-(2-chloro-6-fluorophenyl)-7-((3-(hydroxymethyl)-4-(4-isopropylpiperazin-1-yl)phenyl)amino)-1-methyl-2,3-dihydropyrimido[4,5-d]pyrimidin-4(1H)-one;

(90) 3-(2,6-dichlorophenyl)-1-methyl-7-((4-((1-methylpiperidin-4-yl)oxy)phenyl)amino)-2,3-dihydropyrimido[4,5-d]pyrimidin-4(1H)-one;

(91) 3-(2,6-dichlorophenyl)-1-methyl-7-((3-((1-methylpiperidin-4-yl)amino)phenyl)amino)-2,3-dihydropyrimido[4,5-d]pyrimidin-4(1H)-one;

(92) 3-(2-chloro-6-methylphenyl)-1-methyl-7-((4-(piperazin-1-yl)phenyl)amino)-2,3-dihydropyrimido[4,5-d]pyrimidin-4(1H)-one;

(93) 3-(2-chloro-6-fluorophenyl)-7-((4-((2R,5S)-2,5-dimethylpiperazin-1-yl)phenyl)amino)-1-methyl-2,3-dihydropyrimido[4,5-d]pyrimidin-4(1H)-one;

(94) (R)-3-(2-chlorophenyl)-1-methyl-7-((4-(3-methylpiperazin-1-yl)phenyl)amino)-2,3-dihydropyrimido[4,5-d]pyrimidin-4(1H)-one;

(95) 3-(2,6-dichlorophenyl)-1-methyl-7-((4-(1-methylpiperidin-4-yl)phenyl)amino)-2,3-dihydropyrimido[4,5-d]pyrimidin-4(1H)-one;
(96) 3-(2,6-dichlorophenyl)-7-((4-(3,3-dimethylpiperazin-1-yl)phenyl)amino)-1-methyl-2,3-dihydropyrimido[4,5-d]pyrimidin-4(1H)-one;
(97) 3-(2-chlorophenyl)-7-((3-(hydroxymethyl)-4-(8-methyl-3,8-diazabicyclo[3.2.1]octan-3-yl)phenyl)amino)-1-methyl-2,3-dihydropyrimido[4,5-d]pyrimidin-4(1H)-one;
(98) 3-(2-chlorophenyl)-7-((4-((2R,5S)-2,5-dimethylpiperazin-1-yl)phenyl)amino)-1-methyl-2,3-dihydropyrimido[4,5-d]pyrimidin-4(1H)-one;
(99) (R)-3-(2-chlorophenyl)-7-((3-fluoro-4-(3-methylpiperazin-1-yl)phenyl)amino)-1-methyl-2,3-dihydropyrimido[4,5-d]pyrimidin-4(1H)-one;
(100) (R)-3-(2-chloro-6-methylphenyl)-1-methyl-7-((4-(3-methylpiperazin-1-yl)phenyl)amino)-2,3-dihydropyrimido[4,5-d]pyrimidin-4(1H)-one;
(101) (R)-3-(2-chloro-6-methylphenyl)-7-((3-(methoxymethyl)-4-(3-methylpiperazin-1-yl)phenyl)amino)-1-methyl-2,3-dihydropyrimido[4,5-d]pyrimidin-4(1H)-one;
(102) 3-(2-chloro-6-methylphenyl)-7-((4-((2R,5S)-2,5-dimethylpiperazin-1-yl)phenyl)amino)-1-methyl-2,3-dihydropyrimido[4,5-d]pyrimidin-4(1H)-one;
(103) 3-(2-chlorophenyl)-7-((4-((3S,5R)-3,5-dimethylpiperazin-1-yl)phenyl)amino)-1-methyl-2,3-dihydropyrimido[4,5-d]pyrimidin-4(1H)-one;
(104) 7-((4-((1S,4R)-2,5-diazabicyclo[2.2.1]heptan-2-yl)phenyl)amino)-3-(2-chlorophenyl)-1-methyl-2,3-dihydropyrimido[4,5-d]pyrimidin-4(1H)-one;
(105) 7-((4-(4,7-diazaspiro[2.5]octan-7-yl)phenyl)amino)-3-(2-chlorophenyl)-1-methyl-2,3-dihydropyrimido[4,5-d]pyrimidin-4(1H)-one;
(106) 3-(2-chlorophenyl)-7-((4-(3,3-dimethylpiperazin-1-yl)phenyl)amino)-1-methyl-2,3-dihydropyrimido[4,5-d]pyrimidin-4(1H)-one;
(107) 7-((4-((1S,4S)-2,5-diazabicyclo[2.2.1]heptan-2-yl)-3-methoxyphenyl)amino)-3-(2-chlorophenyl)-1-methyl-2,3-dihydropyrimido[4,5-d]pyrimidin-4(1H)-one;
(108) 3-(2-chlorophenyl)-7-((3-(methoxymethyl)-4-(piperazin-1-yl)phenyl)amino)-1-methyl-2,3-dihydropyrimido[4,5-d]pyrimidin-4(1H)-one;
(109) 7-((4-((1S,4S)-2,5-diazabicyclo[2.2.1]heptan-2-yl)-3-methylphenyl)amino)-3-(2-chlorophenyl)-1-methyl-2,3-dihydropyrimido[4,5-d]pyrimidin-4(1H)-one;
(110) 3-(2-chlorophenyl)-7-((4-((2R,5S)-2,5-dimethylpiperazin-1-yl)-3-fluorophenyl)amino)-1-methyl-2,3-dihydropyrimido[4,5-d]pyrimidin-4(1H)-one;
(111) 3-(2-chlorophenyl)-7-((4-((2S,5R)-2,5-dimethylpiperazin-1-yl)phenyl)amino)-1-methyl-2,3-dihydropyrimido[4,5-d]pyrimidin-4(1H)-one;
(112) 7-((4-((1S,4S)-2,5-diazabicyclo[2.2.1]heptan-2-yl)-3-methylphenyl)amino)-3-(2-chloro-6-methylphenyl)-1-methyl-2,3-dihydropyrimido[4,5-d]pyrimidin-4(1H)-one;
(113) 3-(2-chlorophenyl)-7-((4-(4-ethylpiperazin-1-yl)-3-(hydroxymethyl)phenyl)amino)-1-methyl-2,3-dihydropyrimido[4,5-d]pyrimidin-4(1H)-one;
(114) 3-(2-chloro-6-methylphenyl)-7-((3-(hydroxymethyl)-4-(8-methyl-3,8-diazabicyclo[3.2.1]octan-3-yl)phenyl)amino)-1-methyl-2,3-dihydropyrimido[4,5-d]pyrimidin-4(1H)-one;
(115) 7-((4-(4-cyclopropylpiperazin-1-yl)phenyl)amino)-3-(2,6-dichlorophenyl)-1-methyl-2,3-dihydropyrimido[4,5-d]pyrimidin-4(1H)-one;
(116) 3-(2,6-dichlorophenyl)-7-((4-(4-(2-hydroxyethyl)piperazin-1-yl)phenyl)amino)-1-methyl-2,3-dihydropyrimido[4,5-d]pyrimidin-4(1H)-one;
(117) 3-(2,6-dichlorophenyl)-1-methyl-7-((4-(4-methylpiperazin-1-yl)phenyl)amino)-2,3-dihydropyrimido[4,5-d]pyrimidin-4(1H)-one;
(118) 7-((4-((1R,4R)-2,5-diazabicyclo[2.2.1]heptan-2-yl)-3-methylphenyl)amino)-3-(2,6-dichlorophenyl)-1-methyl-2,3-dihydropyrimido[4,5-d]pyrimidin-4(1H)-one;
(119) 3-(2,6-dichlorophenyl)-1-methyl-7-((4-(piperidin-4-yl)phenyl)amino)-2,3-dihydropyrimido[4,5-d]pyrimidin-4(1H)-one;
(120) 3-(2,6-dichlorophenyl)-7-((4-(4-(2-methoxyethyl)piperazin-1-yl)phenyl)amino)-1-methyl-2,3-dihydropyrimido[4,5-d]pyrimidin-4(1H)-one;
(121) 3-(2,6-dichlorophenyl)-1-methyl-7-((3-methyl-4-((1R,4R)-5-methyl-2,5-diazabicyclo[2.2.1]heptan-2-yl)phenyl)amino)-2,3-dihydropyrimido[4,5-d]pyrimidin-4(1H)-one;
(122) 3-(2,6-dichlorophenyl)-7-((4-(4-ethylpiperazin-1-yl)phenyl)amino)-1-methyl-2,3-dihydropyrimido[4,5-d]pyrimidin-4(1H)-one;
(123) 3-(2,6-dichlorophenyl)-7-((4-(4-(2-(dimethylamino)acetyl)piperazin-1-yl)phenyl)amino)-1-methyl-2,3-dihydropyrimido[4,5-d]pyrimidin-4(1H)-one;
(124) 3-(2,6-dichlorophenyl)-1-methyl-7-((4-(4-(2-(methylamino)acetyl)piperazin-1-yl)phenyl)amino)-2,3-dihydropyrimido[4,5-d]pyrimidin-4(1H)-one;
(125) 7-((4-(4-acetylpiperazin-1-yl)phenyl)amino)-3-(2,6-dichlorophenyl)-1-methyl-2,3-dihydropyrimido[4,5-d]pyrimidin-4(1H)-one;
(126) (R)-3-(2-chloro-6-fluorophenyl)-7-((4-(3-(methoxymethyl)piperazin-1-yl)phenyl)amino)-1-methyl-2,3-dihydropyrimido[4,5-d]pyrimidin-4(1H)-one;
(127) (S)-3-(2,6-dichlorophenyl)-7-((4-(2-(hydroxymethyl)piperazin-1-yl)phenyl)amino)-1-methyl-2,3-dihydropyrimido[4,5-d]pyrimidin-4(1H)-one;
(128) (S)-3-(2,6-dichlorophenyl)-7-((4-(2-(hydroxymethyl)-4-methylpiperazin-1-yl)phenyl)amino)-1-methyl-2,3-dihydropyrimido[4,5-d]pyrimidin-4(1H)-one;
(129) (R)-3-(2,6-dichlorophenyl)-7-((4-(2-(methoxymethyl)piperazin-1-yl)phenyl)amino)-1-methyl-2,3-dihydropyrimido[4,5-d]pyrimidin-4(1H)-one;
(130) (S)-3-(2,6-dichlorophenyl)-7-((4-(2-(methoxymethyl)piperazin-1-yl)phenyl)amino)-1-methyl-2,3-dihydropyrimido[4,5-d]pyrimidin-4(1H)-one;
(131) 3-(2,6-dichlorophenyl)-7-((3-(hydroxymethyl)-4-(piperidin-1-yl)phenyl)amino)-1-methyl-2,3-dihydropyrimido[4,5-d]pyrimidin-4(1H)-one;
(132) (R)-3-(2,6-dichlorophenyl)-7-((3-(difluoromethoxy)-4-(3-methylpiperazin-1-yl)phenyl)amino)-1-methyl-2,3-dihydropyrimido[4,5-d]pyrimidin-4(1H)-one;
(133) (S)-3-(2,6-dichlorophenyl)-7-((4-(hexahydropyrazino[2,1-c][1,4]oxazin-8(1H)-yl)-3-(hydroxymethyl)phenyl)amino)-1-methyl-2,3-dihydropyrimido[4,5-d]pyrimidin-4(1H)-one;
(134) 3-(2,6-dichlorophenyl)-7-((3-(2,2-difluoro-1-hydroxyethyl)-4-((R)-3-methylpiperazin-1-yl)phenyl)amino)-1-methyl-2,3-dihydropyrimido[4,5-d]pyrimidin-4(1H)-one;

(135) (R)-3-(2,6-dichlorophenyl)-7-((3-(hydroxymethyl)-4-(3-(methoxymethyl)piperazin-1-yl)phenyl)amino)-1-methyl-2,3-dihydropyrimido[4,5-d]pyrimidin-4(1H)-one;

(136) 3-(2,6-dichlorophenyl)-1-methyl-7-((3-((methylamino)methyl)-4-(piperidin-1-yl)phenyl)amino)-2,3-dihydropyrimido[4,5-d]pyrimidin-4(1H)-one;

(137) 3-(2,6-dichlorophenyl)-1-methyl-7-((3-((methylamino)methyl)-4-(pyrrolidin-1-yl)phenyl)amino)-2,3-dihydropyrimido[4,5-d]pyrimidin-4(1H)-one;

(138) 7-((4-(4-acetylpiperazin-1-yl)-3-(pyrrolidin-1-ylmethyl)phenyl)amino)-3-(2,6-dichlorophenyl)-1-methyl-2,3-dihydropyrimido[4,5-d]pyrimidin-4(1H)-one;

(139) (R)-3-(2,6-dichlorophenyl)-7-((3-(difluoromethyl)-4-(3-methylpiperazin-1-yl)phenyl)amino)-1-methyl-2,3-dihydropyrimido[4,5-d]pyrimidin-4(1H)-one;

(140) (R)-3-(2,6-dichlorophenyl)-7-((3-(2-hydroxypropan-2-yl)-4-(3-methylpiperazin-1-yl)phenyl)amino)-1-methyl-2,3dihydropyrimido [4,5-d]pyrimidin-4(1H)-one;

(141) 3-(2,6-dichlorophenyl)-1-methyl-7-((4-(piperazin-1-yl)-3-(((2,2,2-trifluoroethyl)amino)methyl)phenyl)amino)-2,3-dihydropyrimido[4,5-d]pyrimidin-4(1H)-one;

(142) (R)-3-(2,6-dichlorophenyl)-7-((2-fluoro-4-(3-methylpiperazin-1-yl)phenyl)amino)-1-methyl-2,3-dihydropyrimido[4,5-d]pyrimidin-4(1H)-one;

(143) 7-((4-(4-acetylpiperazin-1-yl)-3-((methylamino)methyl)phenyl)amino)-3-(2,6-dichlorophenyl)-1-methyl-2,3-dihydropyrimido[4,5-d]pyrimidin-4(1H)-one;

(144) 7-((4-(4-acetylpiperazin-1-yl)-3-((dimethylamino)methyl)phenyl)amino)-3-(2,6-dichlorophenyl)-1-methyl-2,3-dihydropyrimido[4,5-d]pyrimidin-4(1H)-one;

(145) N-(5-((6-(2,6-dichlorophenyl)-8-methyl-5-oxo-5,6,7,8-tetrahydropyrimido[4,5-d]pyrimidin-2-yl)amino)-2-(piperazin-1-yl)benzyl)acetamide;

(146) 3-(2,6-dichlorophenyl)-7-((4-(1,1-dioxidothiomorpholino)-3-((methylamino)methyl)phenyl)amino)-1-methyl-2,3-dihydropyrimido[4,5-d]pyrimidin-4(1H)-one;

(147) 3-(2,6-dichlorophenyl)-7-((4-(4,4-difluoropiperidin-1-yl)-3-((methylamino)methyl)phenyl)amino)-1-methyl-2,3-dihydropyrimido[4,5-d]pyrimidin-4(1H)-one;

(148) 3-(2,6-dichlorophenyl)-7-((4-((2S,6R)-2,6-dimethylmorpholino)-3-((methylamino)methyl)phenyl)amino)-1-methyl-2,3-dihydropyrimido[4,5-d]pyrimidin-4(1H)-one;

(149) 3-(2,6-dichlorophenyl)-7-((3-((dimethylamino)methyl)-4-(1,1-dioxidothiomorpholino)phenyl)amino)-1-methyl-2,3-dihydropyrimido[4,5-d]pyrimidin-4(1H)-one;

(150) 3-(2,6-dichlorophenyl)-7-((4-(4,4-difluoropiperidin-1-yl)-3-((dimethylamino)methyl)phenyl)amino)-1-methyl-2,3-dihydropyrimido[4,5-d]pyrimidin-4(1H)-one;

(151) 3-(2,6-dichlorophenyl)-7-((3-((dimethylamino)methyl)-4-((2S,6R)-2,6-dimethylmorpholino)phenyl)amino)-1-methyl-2,3-dihydropyrimido[4,5-d]pyrimidin-4(1H)-one;

(152) 3-(2,6-dichlorophenyl)-7-((4-fluoro-3-((methylamino)methyl)phenyl)amino)-1-methyl-2,3-dihydropyrimido[4,5-d]pyrimidin-4(1H)-one;

(153) 3-(2,6-dichlorophenyl)-7-((4-(dimethylamino)-3-((methylamino)methyl)phenyl)amino)-1-methyl-2,3-dihydropyrimido[4,5-d]pyrimidin-4(1H)-one;

(154) 3-(2,6-dichlorophenyl)-7-((3-((dimethylamino)methyl)-4-morpholinophenyl)amino)-1-methyl-2,3-dihydropyrimido[4,5-d]pyrimidin-4(1H)-one;

(155) 3-(2,6-dichlorophenyl)-1-methyl-7-((3-((methylamino)methyl)-4-(pyridin-4-yl)phenyl)amino)-2,3-dihydropyrimido[4,5-d]pyrimidin-4(1H)-one;

(156) 3-(2,6-dichlorophenyl)-1-methyl-7-((3-((methylamino)methyl)-4-(pyridin-3-yl)phenyl)amino)-2,3-dihydropyrimido[4,5-d]pyrimidin-4(1H)-one;

(157) 7-((4-bromo-3-((methylamino)methyl)phenyl)amino)-3-(2,6-dichlorophenyl)-1-methyl-2,3-dihydropyrimido[4,5-d]pyrimidin-4(1H)-one;

(158) 3-(2,6-dichlorophenyl)-7-((4-((3S,5R)-3,5-dimethylpiperazin-1-yl)-3-(hydroxymethyl)phenyl)amino)-1-methyl-2,3-dihydropyrimido[4,5-d]pyrimidin-4(1H)-one;

(159) 3-(2,6-dichlorophenyl)-7-((4-methoxy-3-((methylamino)methyl)phenyl)amino)-1-methyl-2,3-dihydropyrimido[4,5-d]pyrimidin-4(1H)-one;

(160) 3-(2,6-dichlorophenyl)-1-methyl-7-((4-(1-methyl-1H-pyrazol-4-yl)-3-((methylamino)methyl)phenyl)amino)-2,3-dihydropyrimido[4,5-d]pyrimidin-4(1H)-one;

(161) 3-(2,6-dichlorophenyl)-7-((4-(4-(2-(dimethylamino)acetyl)piperazin-1-yl)-3-(hydroxymethyl)phenyl)amino)-1-methyl-2,3-dihydropyrimido[4,5-d]pyrimidin-4(1H)-one;

(162, 163) 3-(2,6-dichlorophenyl)-7-((3-((R)-2,2-difluoro-1-hydroxyethyl)-4-((R)-3-(methoxymethyl)piperazin-1-yl)phenyl)amino)-1-methyl-2,3-dihydropyrimido[4,5-d]pyrimidin-4(1H)-one;

(164) 7-((4-((1S,4S)-2,5-diazabicyclo[2.2.1]heptan-2-yl)-3-(hydroxymethyl)phenyl)amino)-3-(2,6-dichlorophenyl)-1-methyl-2,3-dihydropyrimido[4,5-d]pyrimidin-4(1H)-one;

(165) 3-(2,6-dichlorophenyl)-7-((3-(hydroxymethyl)-4-(1-methylpiperidin-4-yl)phenyl)amino)-1-methyl-2,3-dihydropyrimido[4,5-d]pyrimidin-4(1H)-one;

(166) 3-(2,6-dichlorophenyl)-1-methyl-7-((1,2,3,4-tetrahydro-1,4-epiminonaphthalen-6-yl)amino)-2,3-dihydropyrimido[4,5-d]pyrimidin-4(1H)-one;

(167) 3-(2,6-dichlorophenyl)-7-((3-(hydroxymethyl)-4-(piperidin-4-yl)phenyl)amino)-1-methyl-2,3-dihydropyrimido[4,5-d]pyrimidin-4(1H)-one;

(168) 3-(2,6-dichlorophenyl)-1-(3-((methylamino)methyl)phenyl)-7-((4-morpholinophenyl)amino)-2,3-dihydropyrimido [4,5-d]pyrimidin-4(1H)-one;

(169) 3-(2,6-dichlorophenyl)-1-ethyl-7-((4-(piperazin-1-yl)phenyl)amino)-2,3-dihydropyrimido [4,5-d]pyrimidin-4(1H)-one;

(170) 3-(2,6-dichlorophenyl)-7-((4-((3S,5R)-3,5-dimethylpiperazin-1-yl)-3-(hydroxymethyl)phenyl)amino)-1-ethyl-2,3-dihydropyrimido [4,5-d]pyrimidin-4(1H)-one;

(171) 3-(2,6-dichlorophenyl)-1-phenyl-7-((4-(piperazin-1-yl)phenyl)amino)-2,3-dihydropyrimido [4,5-d]pyrimidin-4(1H)-one;

(172) 3-(2,6-dichlorophenyl)-7-((3-(2-(dimethylamino)-1-hydroxyethyl)phenyl)amino)-1-methyl-2,3-dihydropyrimido [4,5-d]pyrimidin-4(1H)-one;

(173) 7-((4-(3-oxa-7,9-diazabicyclo [3.3.1]nonan-7-yl)-3-(hydroxymethyl)phenyl)amino)-3-(2,6-dichlorophenyl)-1-methyl-2,3-dihydropyrimido [4,5-d]pyrimidin-4(1H)-one;

(174) 3-(2,6-dichlorophenyl)-7-((3-((ethylamino)methyl)-4-morpholinophenyl)amino)-1-methyl-2,3-dihydropyrimido [4,5-d]pyrimidin-4(1H)-one;

(175) 3-(2,6-dichlorophenyl)-1-methyl-7-((9-methyl-1,2,3,4-tetrahydro-1,4-epiminonaphthalen-6-yl)amino)-2,3-dihydropyrimido [4,5-d]pyrimidin-4(1H)-one;

(176) 3-(2,6-dichlorophenyl)-7-((3-(hydroxymethyl)-4-((1S,4S)-5-methyl-2,5-diazabicyclo [2.2.1]heptan-2-yl)phenyl)amino)-1-methyl-2,3-dihydropyrimido [4,5-d]pyrimidin-4(1H)-one;

(177) 3-(2,6-dichlorophenyl)-1-methyl-7-((3-methyl-4-(1,2,3,6-tetrahydropyridin-4-yl)phenyl)amino)-2,3-dihydropyrimido [4,5-d]pyrimidin-4(1H)-one;

(178) 3-(2,6-dichlorophenyl)-1-methyl-7-((3-methyl-4-(1-methyl-1,2,3,6-tetrahydropyridin-4-yl)phenyl)amino)-2,3-dihydropyrimido [4,5-d]pyrimidin-4(1H)-one;

(179) 3-(2,6-dichlorophenyl)-7-((3-(hydroxymethyl)-4-(1,2,3,6-tetrahydropyridin-4-yl)phenyl)amino)-1-methyl-2,3-dihydropyrimido [4,5-d]pyrimidin-4(1H)-one;

(180) 3-(2,6-dichlorophenyl)-7-((3-(hydroxymethyl)-4-(1-methyl-1,2,3,6-tetrahydropyridin-4-yl)phenyl)amino)-1-methyl-2,3-dihydropyrimido [4,5-d]pyrimidin-4(1H)-one;

(181) 7-((4-(1-cyclobutylpiperidin-4-yl)-3-(hydroxymethyl)phenyl)amino)-3-(2,6-dichlorophenyl)-1-methyl-2,3-dihydropyrimido [4,5-d]pyrimidin-4(1H)-one;

(182) 3-(2,6-dichlorophenyl)-7-((3-methoxy-4-(piperidin-4-yl)phenyl)amino)-1-methyl-2,3-dihydropyrimido [4,5-d]pyrimidin-4(1H)-one;

(183) 3-(2,6-dichlorophenyl)-7-((3-methoxy-4-(1-methylpiperidin-4-yl)phenyl)amino)-1-methyl-2,3-dihydropyrimido[4,5-d]pyrimidin-4(1H)-one; and (184, 185) 3-(2,6-dichlorophenyl)-7-((4-((R)-3-(methoxymethyl)piperazin-1-yl)-3-((R)-2,2,2-trifluoro-1-hydroxyethyl)phenyl)amino)-1-methyl-2,3-dihydropyrimido[4,5-d]pyrimidin-4(1H)-one.

19. A pharmaceutical composition comprising the compound of claim 1, or a pharmaceutically acceptable salt thereof, and at least one pharmaceutically acceptable excipient.

20. A method of treating cancer in a human or animal patient comprising administering to a patient in need thereof an effective amount of a compound according to claim 1, wherein the cancer is selected from the group consisting of cardiac cancer, lung cancer, gastrointestinal cancer, genitourinary tract cancer, liver cancer, bone cancer, nervous system cancer, gynecological cancer, hematologic cancer, skin cancer, and adrenal gland cancer.

* * * * *